(12) United States Patent
Suzuki et al.

(10) Patent No.: US 8,642,782 B2
(45) Date of Patent: Feb. 4, 2014

(54) CARBAZOLE DERIVATIVE, LIGHT-EMITTING ELEMENT MATERIAL AND ORGANIC SEMICONDUCTOR MATERIAL

(75) Inventors: Hiroki Suzuki, Kanagawa (JP); Kyoko Takeda, Kanagawa (JP); Sachiko Kawakami, Kanagawa (JP); Tsunenori Suzuki, Kanagawa (JP); Satoshi Seo, Kanagawa (JP); Nobuharu Ohsawa, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 13/228,672

(22) Filed: Sep. 9, 2011

(65) Prior Publication Data

US 2012/0071668 A1 Mar. 22, 2012

(30) Foreign Application Priority Data

Sep. 21, 2010 (JP) ................................ 2010-211184
Aug. 24, 2011 (JP) ................................ 2011-182368

(51) Int. Cl.
*C07D 209/82* (2006.01)
*C07D 209/86* (2006.01)

(52) U.S. Cl.
USPC .......................................... 548/440; 548/445

(58) Field of Classification Search
None
See application file for complete search history.

(56) References Cited

U.S. PATENT DOCUMENTS

| | | | |
|---|---|---|---|
| 5,061,569 A | 10/1991 | Vanslyke et al. | |
| 7,897,964 B2 | 3/2011 | Kawakami et al. | |
| 7,989,644 B2 | 8/2011 | Tanabe et al. | |
| 2003/0129448 A1 | 7/2003 | Lin et al. | |
| 2004/0151943 A1 | 8/2004 | Lee et al. | |
| 2004/0161633 A1 | 8/2004 | Seo et al. | |
| 2005/0067951 A1 | 3/2005 | Richter et al. | |
| 2005/0221124 A1 | 10/2005 | Hwang et al. | |
| 2006/0073357 A1 | 4/2006 | Brunner et al. | |
| 2007/0145888 A1 | 6/2007 | Yabunouchi et al. | |
| 2007/0231503 A1 | 10/2007 | Hwang et al. | |
| 2008/0014464 A1 | 1/2008 | Kawamura et al. | |
| 2008/0124572 A1 | 5/2008 | Mizuki et al. | |
| 2008/0268282 A1 | 10/2008 | Spindler et al. | |
| 2008/0284328 A1 | 11/2008 | Nakashima et al. | |
| 2009/0015140 A1 | 1/2009 | Kawakami et al. | |
| 2009/0058261 A1 | 3/2009 | Kawakami et al. | |
| 2009/0131673 A1 | 5/2009 | Tanabe et al. | |
| 2009/0160323 A1 | 6/2009 | Nomura et al. | |
| 2010/0069647 A1 | 3/2010 | Suzuki et al. | |
| 2010/0133519 A1 | 6/2010 | Chen et al. | |
| 2010/0244008 A1 | 9/2010 | Lee et al. | |
| 2011/0006670 A1 | 1/2011 | Katakura et al. | |
| 2011/0042654 A1 | 2/2011 | Jung et al. | |
| 2011/0127495 A1 | 6/2011 | Hong et al. | |
| 2011/0147728 A1 | 6/2011 | Kawakami et al. | |
| 2011/0248217 A1 | 10/2011 | Tanabe et al. | |
| 2011/0297924 A1 | 12/2011 | Yabunouchi et al. | |
| 2012/0074390 A1 | 3/2012 | Seo et al. | |
| 2012/0211736 A1* | 8/2012 | Kim et al. ........................ 257/40 |

FOREIGN PATENT DOCUMENTS

| | | |
|---|---|---|
| EP | 1 862 524 A1 | 12/2007 |
| EP | 1 950 194 A1 | 7/2008 |
| JP | 62-280850 | 12/1987 |
| JP | 63-14156 | 1/1988 |
| JP | 9-310066 | 12/1997 |
| JP | 3210481 | 7/2001 |
| JP | 2002-241352 | 8/2002 |
| JP | 2003-89682 | 3/2003 |
| JP | 2004-103467 | 4/2004 |
| JP | 2004-178896 | 6/2004 |
| JP | 2007-15933 | 1/2007 |
| JP | 2007-110093 | 4/2007 |
| JP | 2007-520470 | 7/2007 |
| JP | 2008-21687 | 1/2008 |
| JP | 2008-545729 | 12/2008 |
| JP | 2009-267255 | 11/2009 |
| JP | 2010-114180 | 5/2010 |
| KR | 10-2008-0018218 | 2/2008 |
| WO | WO 2005/090512 A1 | 9/2005 |
| WO | WO 2006/128800 A1 | 12/2006 |
| WO | WO 2007/013537 A1 | 2/2007 |
| WO | WO 2007/043354 A1 | 4/2007 |
| WO | WO 2007/148660 A1 | 12/2007 |
| WO | WO 2008/062636 A1 | 5/2008 |

(Continued)

OTHER PUBLICATIONS

International Search Report re application No. PCT/JP2011/069973, dated Sep. 27, 2011.
Written Opinion re application No. PCT/JP2011/069973, dated Sep. 27, 2011.
Ho et al., "P-131: Novel Deep Blue Dopants for Organic Light Emitting Devices," Sid 05 Digest '05, May 24, 2005, vol. 36, pp. 802-805.
Promarak et al., "Synthesis and Properties of Stable Amorphous Hole-Transporting Molecules for Electroluminescent Devices," Tetrahedron Letters, 2006, vol. 47, pp. 8949-8952.
Shen et al., "Ambipolar Conductive 2,7-Carbazole Derivatives for Electroluminescent Devices," Adv. Funct. Mater., 2007, vol. 17, pp. 983-995.
Goldsmith et al., C-H Bond Activation by a Ferric Methoxide Complex: Modeling the Rate-Determining Step in the Mechanism of Lipoxygenase, J. Am. Chem. Soc., 2002, pp. 83-96, vol. 124, No. 1.
Ohnishi et al., A Method of Measuring an Energy Level, High Molecular EL Materials—Development of Light-Emitting High Molecular Compounds, Kyoritsu Shuppan, Dec. 25, 2004, pp. 64-67 (English translation).

*Primary Examiner* — Nyeemah A Grazier
(74) *Attorney, Agent, or Firm* — Husch Blackwell LLP

(57) ABSTRACT

An object is to provide a novel carbazole derivative that has an excellent carrier-transport property and can be suitably used for a transport layer or as a host material of a light-emitting element. Another object is to provide an organic semiconductor material and a light-emitting element material each using the carbazole derivative. As the carbazole derivative that can achieve the above objects, a carbazole derivative in which a carbazolyl group whose either 2- or 3-position of carbazole is substituted by the 4-position of a dibenzothiophene skeleton or a dibenzofuran skeleton is bonded to aromatic hydrocarbon that has 14 to 70 carbon atoms and includes a condensed tricyclic ring, a condensed tetracyclic ring, a condensed pentacyclic ring, a condensed hexacyclic ring, or a condensed heptacyclic ring has been able to be synthesized.

13 Claims, 47 Drawing Sheets

(56) References Cited

FOREIGN PATENT DOCUMENTS

| WO | WO 2008/069756 A1 | 6/2008 |
| WO | WO 2009/035296 A2 | 3/2009 |
| WO | WO 2009/061145 A1 | 5/2009 |
| WO | WO 2009/061156 A1 | 5/2009 |
| WO | WO 2009/096202 A1 | 8/2009 |
| WO | WO 2010/004877 A1 | 1/2010 |
| WO | WO 2011/004639 A1 | 1/2011 |
| WO | WO 2011/052250 A1 | 5/2011 |
| WO | WO 2011055934 A2 * | 5/2011 |

* cited by examiner

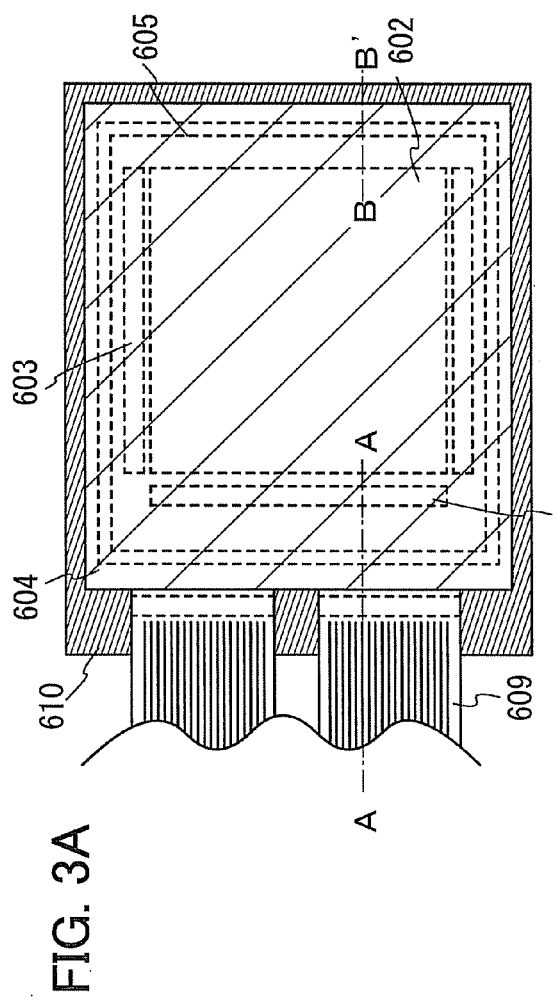
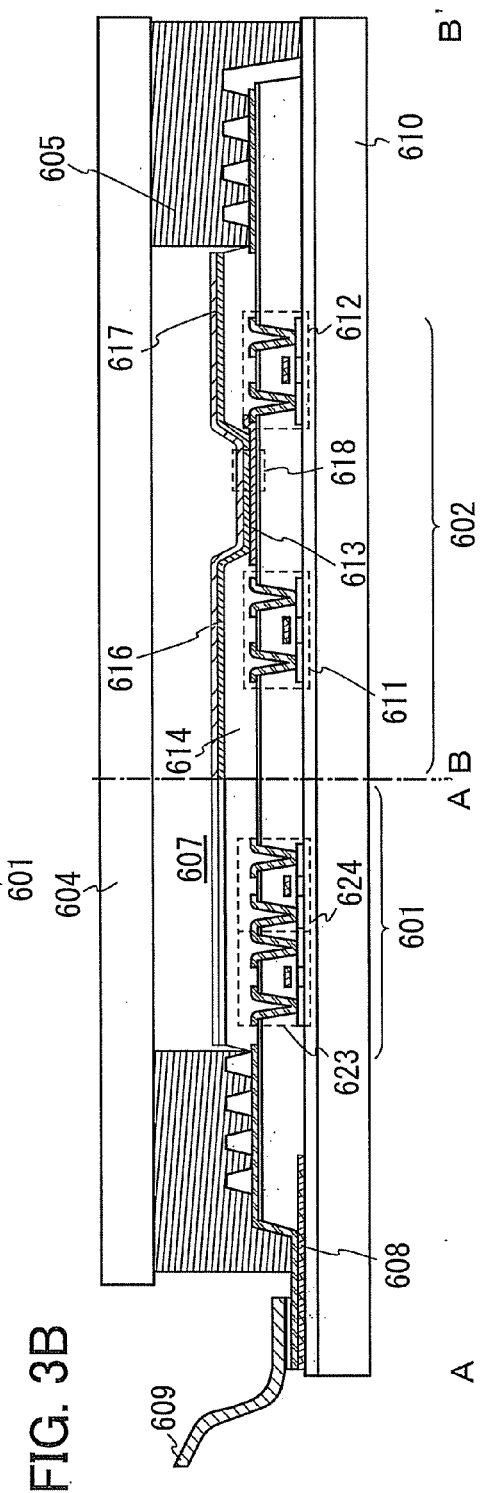
FIG. 3A
FIG. 3B

FIG. 5A
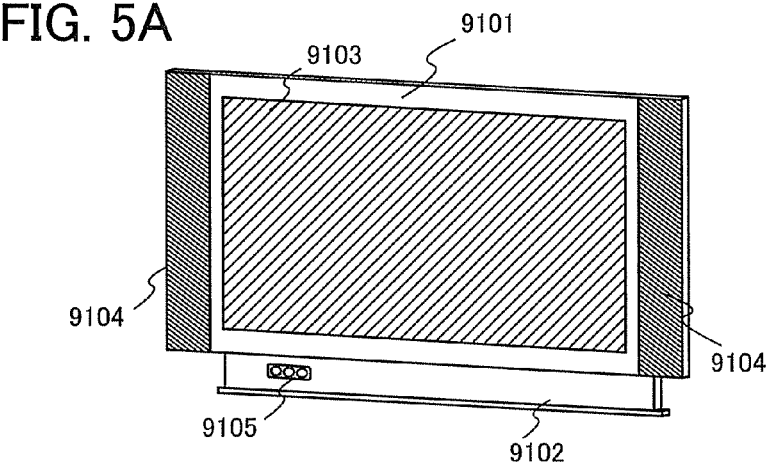
FIG. 5B
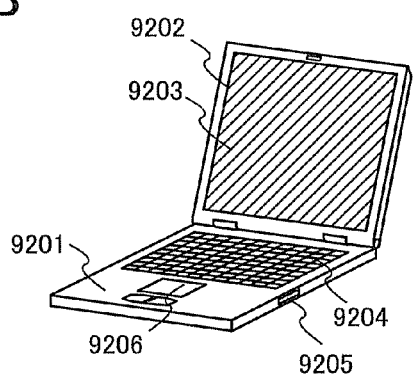
FIG. 5C
FIG. 5D
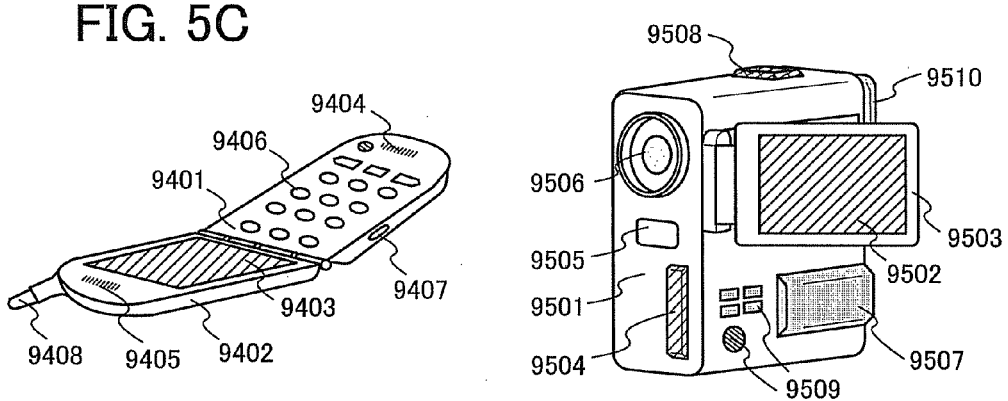

CARBAZOLE DERIVATIVE, LIGHT-EMITTING ELEMENT MATERIAL AND ORGANIC SEMICONDUCTOR MATERIAL

TECHNICAL FIELD

The present invention relates to carbazole derivatives. The present invention further relates to light-emitting element materials and organic semiconductor materials each using the carbazole derivative.

BACKGROUND ART

A display device using a light-emitting element (organic EL element) in which an organic compound is used as a light-emitting substance has been developed rapidly as a next generation lighting device or display device because it has advantages that such a light-emitting element can be manufactured to be thin and lightweight, has very high response speed with respect to an input signal, and has low power consumption.

In an organic EL element, when a voltage is applied between a pair of electrodes between which a light-emitting layer is interposed, electrons and holes are injected from the electrodes. The injected electrons and holes are recombined to form an excited state of a light-emitting substance contained in the light-emitting layer, and when the excited state relaxes to a ground state, light is emitted. A wavelength of light emitted from a light-emitting substance is peculiar to the light-emitting substance; thus, by using different types of organic compounds as light-emitting substances, light-emitting elements which exhibit various wavelengths, i.e., various colors can be obtained.

In a case of a display device which is expected to display images, such as a display, at least three colors of light, i.e., red, green, and blue are required to be obtained in order to reproduce full-color images. In the case of a lighting device, in order to obtain high color rendering property, light having wavelength components thoroughly in the visible light region is ideally obtained. Actually, two or more kinds of light having different wavelengths are mixed to be used for lighting application in many cases. Note that it is known that by mixing light of three colors, red, green, and blue, white light emission having high color rendering property can be obtained.

Light emitted from a light-emitting substance is peculiar to the substance, as described above. However, important performances as a light-emitting element, such as lifetime or power consumption, are not only dependent on a light-emitting substance but also greatly dependent on layers other than a light-emitting layer, an element structure, properties of the light-emitting substance and a host, compatibility between them, or the like. Therefore, it is true that many kinds of light-emitting element materials are necessary in order to show the growth of this field. For the above-described reasons, light-emitting element materials which have a variety of molecular structures have been proposed (for example, see Patent Document 1).

REFERENCE

Patent Document

[Patent Document 1] Japanese Published Patent Application No. 2007-15933

DISCLOSURE OF INVENTION

In view of the above, an object of one embodiment of the present invention is to provide a novel carbazole derivative that can be used for a transport layer or as a host material or a light-emitting material of a light-emitting element.

Another object of one embodiment of the present invention is to provide a light-emitting element material using the above novel carbazole derivative.

Another object of one embodiment of the present invention is to provide an organic semiconductor material using the above novel carbazole derivative.

Another object of one embodiment of the present invention is to provide a synthetic intermediate to synthesize the above novel carbazole derivative.

Note that in one embodiment of the present invention, it is only necessary that at least one of the above-described objects is achieved.

The present inventors have been able to synthesize a carbazole derivative in which a carbazolyl group whose 2- or 3-position of carbazole is substituted by the 4-position of dibenzothiophene or dibenzofuran is bonded to aromatic hydrocarbon that has 14 to 70 carbon atoms and includes a condensed tricyclic ring, a condensed tetracyclic ring, a condensed pentacyclic ring, a condensed hexacyclic ring, or a condensed heptacyclic ring. Further, the present inventors have found out that the carbazole derivative has a moderate carrier-transport property, the film quality is favorable, and the carbazole derivative can be suitably used as a material of a light-emitting element and an organic semiconductor material.

That is, one embodiment of the present invention is a carbazole derivative in which a carbazolyl group whose 2- or 3-position of carbazole is substituted by the 4-position of a dibenzothiophene skeleton or a dibenzofuran skeleton is bonded to aromatic hydrocarbon that has 14 to 70 carbon atoms and includes a condensed tricyclic ring, a condensed tetracyclic ring, a condensed pentacyclic ring, a condensed hexacyclic ring, or a condensed heptacyclic ring.

In addition, another embodiment of the present invention is a carbazole derivative in which a carbazolyl group whose either 2- or 3-position and either 6- or 7-position of carbazole is substituted by the 4-position of a dibenzothiophene skeleton or a dibenzofuran skeleton is bonded to aromatic hydrocarbon that has 14 to 70 carbon atoms and includes a condensed tricyclic ring, a condensed tetracyclic ring, a condensed pentacyclic ring, a condensed hexacyclic ring, or a condensed heptacyclic ring.

Note that the dibenzothiophene or dibenzofuran bonded to the carbazolyl group may have a substituent.

Another embodiment of the present invention is a carbazole derivative represented by the following general formula (G0).

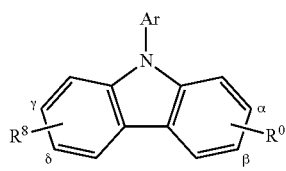

(G0)

In the formula, Ar represents an aryl group that has 14 to 70 carbon atoms and includes a condensed tricyclic ring, a condensed tetracyclic ring, a condensed pentacyclic ring, a condensed hexacyclic ring, or a condensed heptacyclic ring. In addition, $R^0$ represents a group represented by the following general formula (g1), and $R^8$ represents any one of hydrogen, an alkyl group having 1 to 4 carbon atoms, an aryl group having 6 to 15 carbon atoms, and a group represented by the following general formula (g2). Note that the substitution site of $R^0$ is a carbon atom represented by either α or β, and the substitution site of $R^8$ is a carbon atom represented by either γ or δ.

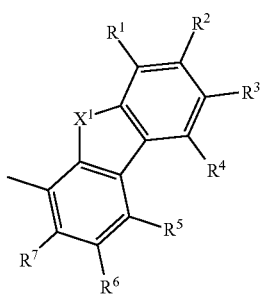

(g1)

(In the formula, $X^1$ represents oxygen or sulfur, and $R^1$ to $R^7$ individually represent any one of hydrogen, an alkyl group having 1 to 4 carbon atoms, and an aryl group having 6 to 15 carbon atoms.)

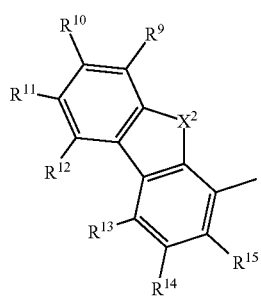

(g2)

(In the formula, $X^2$ represents oxygen or sulfur, and $R^9$ to $R^{15}$ individually represent any one of hydrogen, an aryl group having 6 to 15 carbon atoms, and an alkyl group having 1 to 4 carbon atoms.)

In addition, another embodiment of the present invention is a carbazole derivative represented by the general formula (G0) in which $R^8$ is a substituent represented by the general formula (g2). In the case where $R^0$ is bonded to the position of α, $R^8$ is bonded to the position of γ, and in the case where $R^0$ is bonded to the position of β, $R^8$ is bonded to the position of δ.

Another embodiment of the present invention is a carbazole derivative represented by the following general formula (G1).

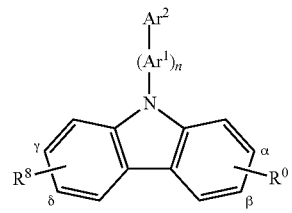

(G1)

In the formula, $Ar^1$ represents any one of a phenylene group, a naphthylene group, and a biphenylene group, and $Ar^2$ represents a group that has 14 to 30 carbon atoms and includes a condensed tricyclic ring, a condensed tetracyclic ring, a condensed pentacyclic ring, a condensed hexacyclic ring, or a condensed heptacyclic ring. In addition, n is either 0 or 1. Note that $Ar^1$ may or may not have a substituent, and in the case where $Ar^1$ has a substituent, the substituent is an alkyl group having 1 to 4 carbon atoms. Note also that $Ar^2$ may or may not have a substituent, and in the case where $Ar^2$ has a substituent, the substituent is any of an alkyl group having 1 to 4 carbon atoms and an aryl group having 6 to 15 carbon atoms. Further, $R^0$ represents a group represented by the following general formula (g1), and $R^8$ represents any one of hydrogen, an aryl group having 6 to 15 carbon atoms, an alkyl group having 1 to 4 carbon atoms, and a group represented by the following general formula (g2). Note that the substitution site of $R^0$ is a carbon atom represented by either α or β, and the substitution site of $R^8$ is a carbon atom represented by either γ or δ.

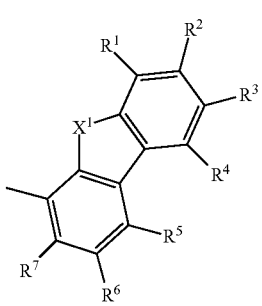

(g1)

(In the formula, $X^1$ represents oxygen or sulfur, and $R^1$ to $R^7$ individually represent any one of hydrogen, an alkyl group having 1 to 4 carbon atoms, and an aryl group having 6 to 15 carbon atoms.)

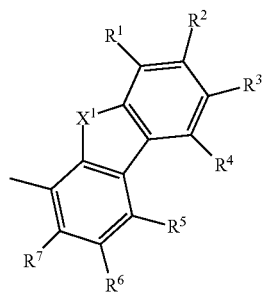

(g1)

(In the formula, $X^2$ represents oxygen or sulfur, and $R^9$ to $R^{15}$ individually represent any one of hydrogen, an aryl group having 6 to 15 carbon atoms, and an alkyl group having 1 to 4 carbon atoms.)

In addition, another embodiment of the present invention is a carbazole derivative represented by the general formula (G1) in which $R^8$ is a substituent represented by the general formula (g2). In the case where $R^0$ is bonded to the position of α, $R^8$ is bonded to the position of γ, and in the case where $R^0$ is bonded to the position of β, $R^8$ is bonded to the position of δ.

Another embodiment of the present invention is a carbazole derivative represented by the following general formula (G1).

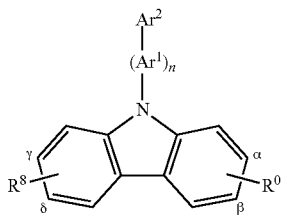

(G1)

In the formula, $Ar^1$ represents any one of a phenylene group, a naphthylene group, and a biphenylene group, and $Ar^2$ represents a group that has 14 to 30 carbon atoms and includes a condensed tricyclic ring, a condensed tetracyclic ring, a condensed pentacyclic ring, a condensed hexacyclic ring, or a condensed heptacyclic ring. In addition, n is either 0 or 1. Note that $Ar^1$ may or may not have a substituent, and in the case where $Ar^1$ has a substituent, the substituent is an alkyl group having 1 to 4 carbon atoms. Note also that $Ar^2$ may or may not have a substituent, and in the case where $Ar^2$ has a substituent, the substituent is any of an alkyl group having 1 to 4 carbon atoms and an aryl group having 6 to 15 carbon atoms. Further, $R^0$ represents a group represented by the following general formula (g3), and $R^8$ represents any one of hydrogen, an aryl group having 6 to 15 carbon atoms, an alkyl group having 1 to 4 carbon atoms, and a group represented by the following general formula (g4). Note that the substitution site of $R^0$ is a carbon atom represented by either α or β, and the substitution site of $R^8$ is a carbon atom represented by either γ or δ.

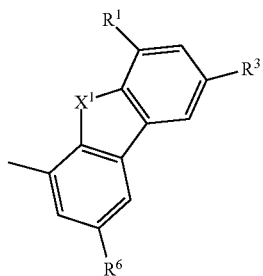

(g3)

In the formula, $X^1$ represents oxygen or sulfur, and $R^1$, $R^3$, and $R^6$ individually represent any one of hydrogen, an aryl group having 6 to 15 carbon atoms, and an alkyl group having 1 to 4 carbon atoms.

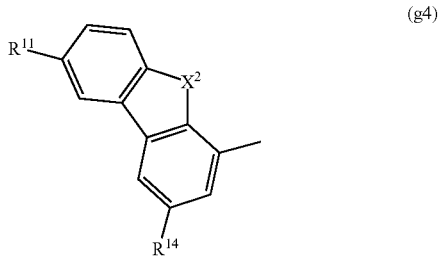

(g4)

Note that in the formula, $X^2$ represents oxygen or sulfur, and $R^9$, $R^{11}$, and $R^{14}$ individually represent any one of hydrogen, an aryl group having 6 to 15 carbon atoms, and an alkyl group having 1 to 4 carbon atoms.

Another embodiment of the present invention is a carbazole derivative having any of the above structures in which $R^8$ is hydrogen or a group represented by the following general formula (g4).

In addition, another embodiment of the present invention is a carbazole derivative that has any of the above structures and is represented by the general formula (G1) in which $R^8$ is a substituent represented by the general formula (g4). In the case where $R^0$ is bonded to the position of α, $R^8$ is bonded to the position of γ, and in the case where $R^0$ is bonded to the position of β, $R^8$ is bonded to the position of δ.

Another embodiment of the present invention is a carbazole derivative represented by the following general formula (G1).

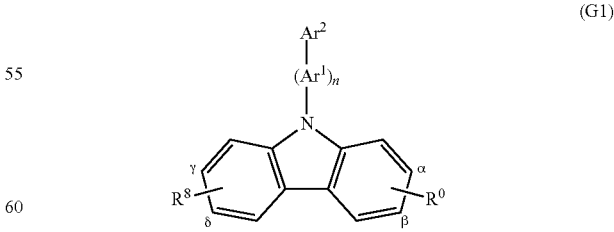

(G1)

In the formula, $Ar^1$ represents any one of a phenylene group, a naphthylene group, and a biphenylene group, and $Ar^2$ represents a group that has 14 to 30 carbon atoms and includes a condensed tricyclic ring, a condensed tetracyclic ring, a condensed pentacyclic ring, a condensed hexacyclic ring, or a condensed heptacyclic ring. In addition, n is either 0 or 1. Note that $Ar^1$ may or may not have a substituent, and in the case where $Ar^1$ has a substituent, the substituent is an alkyl group having 1 to 4 carbon atoms. Note also that $Ar^2$ may or may not have a substituent, and in the case where $Ar^2$ has a substituent, the substituent is any of an alkyl group having 1 to 4 carbon atoms and an aryl group having 6 to 15 carbon atoms. Further, $R^0$ represents a group represented by the following general formula (g5), and $R^8$ represents hydrogen or a group represented by the following general formula (g6). Note that the substitution site of $R^0$ is a carbon atom represented by either α or β, and the substitution site of $R^8$ is a carbon atom represented by either γ or δ.

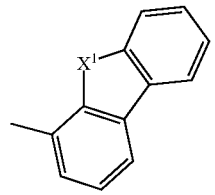

(g5)

In the formula, $X^1$ represents oxygen or sulfur.

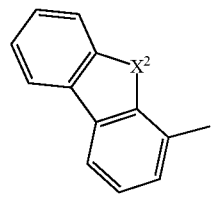

(g6)

(In the Formula, $X^2$ Represents Oxygen or Sulfur.)

In addition, another embodiment of the present invention is a carbazole derivative that has any of the above structures and is represented by the general formula (G1) in which $R^8$ is a substituent represented by the general formula (g6). In the case where $R^0$ is bonded to the position of α, $R^8$ is bonded to the position of γ, and in the case where $R^0$ is bonded to the position of β, $R^8$ is bonded to the position of δ.

Another embodiment of the present invention is a carbazole derivative represented by the following general formula (G2).

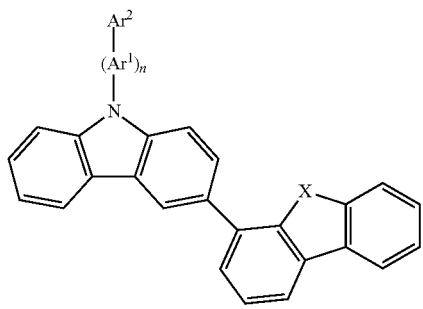

(G2)

Note that in the formula, X represents oxygen or sulfur, $Ar^1$ represents any one of a phenylene group, a naphthylene group, and a biphenylene group, and $Ar^2$ represents a group that has 14 to 30 carbon atoms and includes a condensed tricyclic ring, a condensed tetracyclic ring, a condensed pentacyclic ring, a condensed hexacyclic ring, or a condensed heptacyclic ring. In addition, n is either 0 or 1. Note that $Ar^1$ may or may not have a substituent, and in the case where $Ar^1$ has a substituent, the substituent is an alkyl group having 1 to 4 carbon atoms. Note also that $Ar^2$ may or may not have a substituent, and in the case where $Ar^2$ has a substituent, the substituent is any of an alkyl group having 1 to 4 carbon atoms and an aryl group having 6 to 15 carbon atoms.

Another embodiment of the present invention is a carbazole derivative represented by the following general formula (G3).

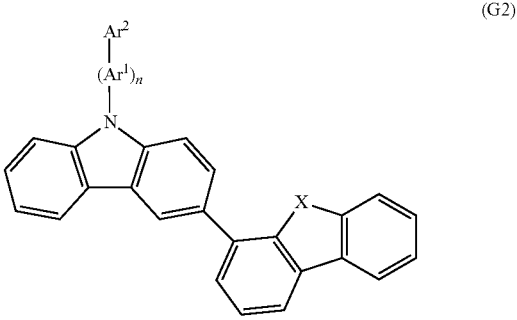

(G2)

Note that in the formula, $X^1$ and $X^2$ individually represent oxygen or sulfur, $Ar^1$ represents any one of a phenylene group, a naphthylene group, and a biphenylene group, and $Ar^2$ represents a group that has 14 to 30 carbon atoms and includes a condensed tricyclic ring, a condensed tetracyclic ring, a condensed pentacyclic ring, a condensed hexacyclic ring, or a condensed heptacyclic ring. In addition, n is either 0 or 1. Note that $Ar^1$ may or may not have a substituent, and in the case where $Ar^1$ has a substituent, the substituent is an alkyl group having 1 to 4 carbon atoms. Note also that $Ar^2$ may or may not have a substituent, and in the case where $Ar^2$ has a substituent, the substituent is any of an alkyl group having 1 to 4 carbon atoms and an aryl group having 6 to 15 carbon atoms.

Another embodiment of the present invention is a carbazole derivative represented by the following general formula (G4).

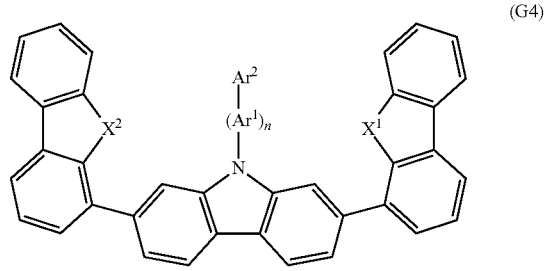

(G4)

Note that in the formula, $X^1$ and $X^2$ individually represent oxygen or sulfur, $Ar^1$ represents any one of a phenylene group, a naphthylene group, and a biphenylene group, and $Ar^2$ represents a group that has 14 to 30 carbon atoms and includes a condensed tricyclic ring, a condensed tetracyclic ring, a condensed pentacyclic ring, a condensed hexacyclic ring, or a condensed heptacyclic ring. In addition, n is either 0 or 1. Note that $Ar^1$ may or may not have a substituent, and in the case where $Ar^1$ has a substituent, the substituent is an alkyl group having 1 to 4 carbon atoms. Note also that $Ar^2$ may or may not have a substituent, and in the case where $Ar^2$ has a substituent, the substituent is any of an alkyl group having 1 to 4 carbon atoms and an aryl group having 6 to 15 carbon atoms.

Another embodiment of the present invention is a carbazole derivative represented by the following structural formula.

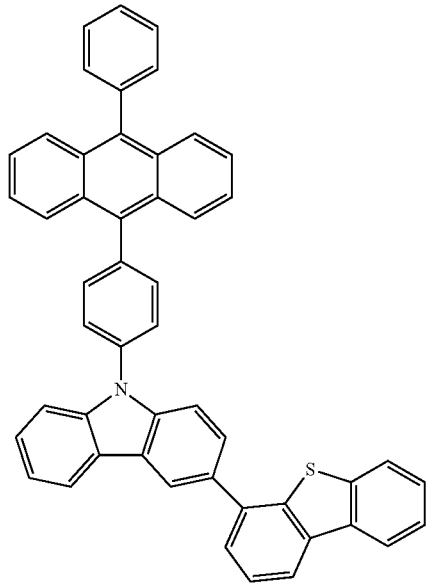

Another embodiment of the present invention is a carbazole derivative represented by the following structural formula.

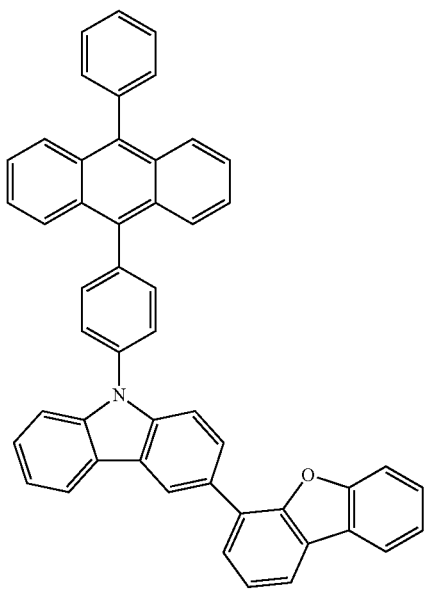 [SMILES: c1ccc(-c2c3ccccc3c(-c3ccc(-n4c5ccccc5c5cc(-c6cccc7c6oc6ccccc67)ccc54)cc3)c3ccccc23)cc1]

Another embodiment of the present invention is a carbazole derivative represented by the following structural formula.

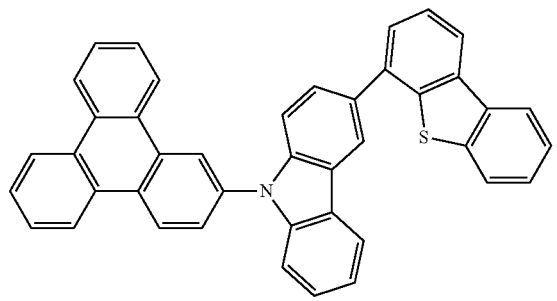 [SMILES: c1ccc2c(c1)sc1c(-c3ccc4c(c3)c3ccccc3n4-c3ccc4c5ccccc5c5ccccc5c4c3)cccc12]

Another embodiment of the present invention is a carbazole derivative represented by the following structural formula.

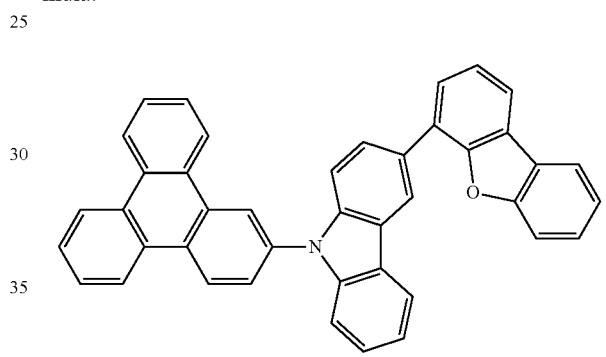

Another embodiment of the present invention is a carbazole derivative represented by the following structural formula.

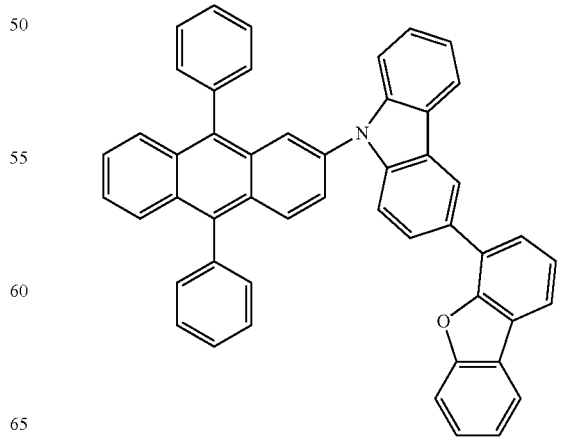

Another embodiment of the present invention is a carbazole derivative represented by the following structural formula.

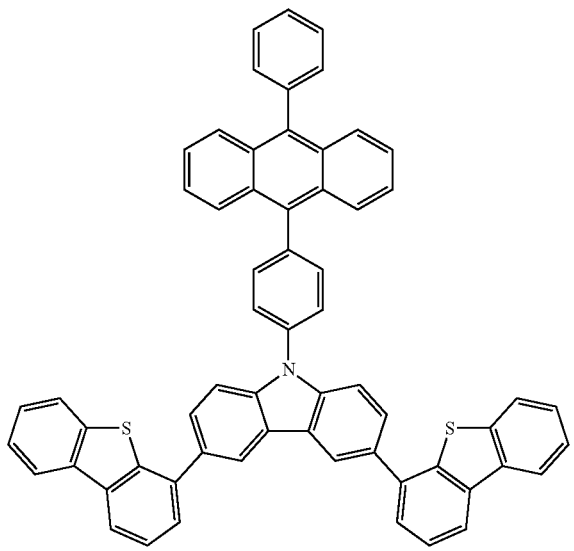 [SMILES: c1ccc(-c2c3ccccc3c(-c3ccc(-n4c5ccc(-c6cccc7c6sc6ccccc67)cc5c5cc(-c6cccc7c6sc6ccccc67)ccc54)cc3)c3ccccc23)cc1]

In addition, another embodiment of the present invention is a synthetic intermediate to synthesize any of the above carbazole derivatives. That is, another embodiment of the present invention is a carbazole derivative represented by the following general formula (G5).

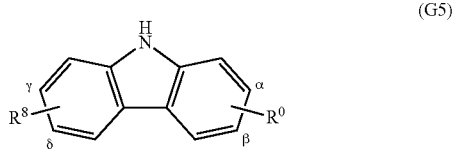

(G5)

(In the formula, $R^0$ represents a group represented by the following general formula (g1), and $R^8$ represents any one of hydrogen, an alkyl group having 1 to 4 carbon atoms, an aryl group having 6 to 15 carbon atoms, and a group represented by the following general formula (g2). Note that the substitution site of $R^0$ is a carbon atom represented by either α or β, and the substitution site of $R^8$ is a carbon atom represented by either γ or δ.)

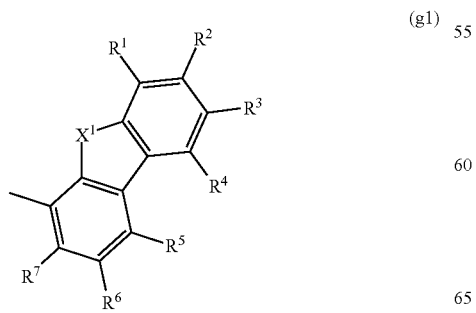

(g1)

(In the formula, $X^1$ represents oxygen or sulfur, and $R^1$ to $R^7$ individually represent any one of hydrogen, an alkyl group having 1 to 4 carbon atoms, and an aryl group having 6 to 15 carbon atoms.)

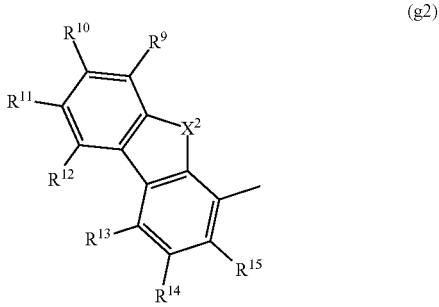

(g2)

(In the formula, $X^2$ represents oxygen or sulfur, and $R^9$ to $R^{15}$ individually represent any one of hydrogen, an aryl group having 6 to 15 carbon atoms, and an alkyl group having 1 to 4 carbon atoms.)

In addition, another embodiment of the present invention is a carbazole derivative that has any of the above structures and is represented by the general formula (G5) in which $R^8$ is a substituent represented by the general formula (g2). In the case where $R^0$ is bonded to the position of α, $R^8$ is bonded to the position of γ, and in the case where $R^0$ is bonded to the position of β, $R^8$ is bonded to the position of δ.

Another embodiment of the present invention is a carbazole derivative represented by the following general formula (G5).

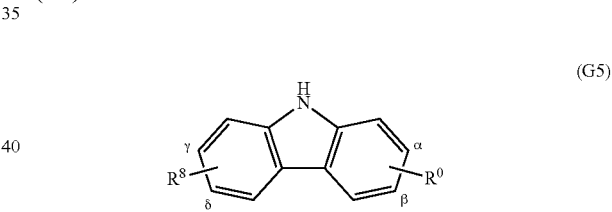

(G5)

(In the formula, $R^0$ represents a group represented by the following general formula (g3), and $R^8$ represents any one of hydrogen, an aryl group having 6 to 15 carbon atoms, an alkyl group having 1 to 4 carbon atoms, and a group represented by the following general formula (g4). Note that the substitution site of $R^0$ is a carbon atom represented by either α or β, and the substitution site of $R^8$ is a carbon atom represented by either γ or δ.)

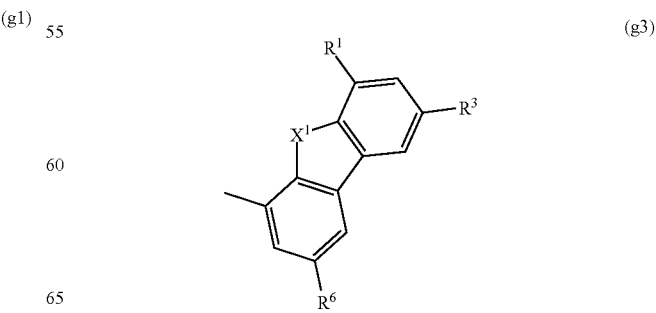

(g3)

(In the formula, $X^1$ represents oxygen or sulfur, and $R^1$, $R^3$, and $R^6$ individually represent any one of hydrogen, an aryl group having 6 to 15 carbon atoms, and an alkyl group having 1 to 4 carbon atoms.)

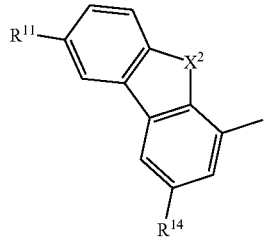

(g4)

(Note that in the formula, $X^2$ represents oxygen or sulfur, and $R^9$, $R^{11}$, and $R^{14}$ individually represent any one of hydrogen, an aryl group having 6 to 15 carbon atoms, and an alkyl group having 1 to 4 carbon atoms.)

In addition, another embodiment of the present invention is a carbazole derivative that has any of the above structures and is represented by the general formula (G5) in which $R^8$ is a substituent represented by the general formula (g4). In the case where $R^0$ is bonded to the position of α, $R^8$ is bonded to the position of γ, and in the case where $R^0$ is bonded to the position of β, $R^8$ is bonded to the position of δ.

Another embodiment of the present invention is a carbazole derivative represented by the following general formula (G5).

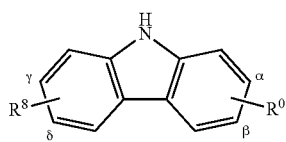

(G5)

(In the formula, $R^0$ represents a group represented by the following general formula (g3), and $R^8$ represents hydrogen or a group represented by the following general formula (g4). Note that the substitution site of $R^0$ is a carbon atom represented by either α or β, and the substitution site of $R^8$ is a carbon atom represented by either γ or δ.)

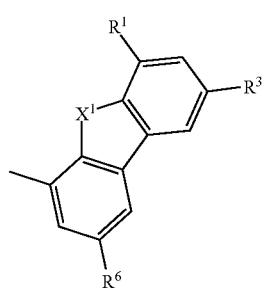

(g3)

(In the formula, $X^1$ represents oxygen or sulfur, and $R^1$, $R^3$, and $R^6$ individually represent any one of hydrogen, an aryl group having 6 to 15 carbon atoms, and an alkyl group having 1 to 4 carbon atoms.)

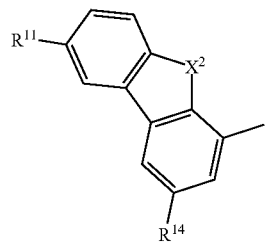

(g4)

(Note that in the formula, $X^2$ represents oxygen or sulfur, and $R^9$, $R^{11}$, and $R^{14}$ individually represent any one of hydrogen, an aryl group having 6 to 15 carbon atoms, and an alkyl group having 1 to 4 carbon atoms.)

In addition, another embodiment of the present invention is a carbazole derivative that has any of the above structures and is represented by the general formula (G5) in which $R^8$ is a substituent represented by the general formula (g4). In the case where $R^0$ is bonded to the position of α, $R^8$ is bonded to the position of γ, and in the case where $R^0$ is bonded to the position of β, $R^8$ is bonded to the position of δ.

Another embodiment of the present invention is a carbazole derivative represented by the following general formula (G5).

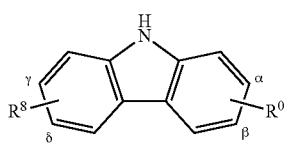

(G5)

(In the formula, $R^0$ represents a group represented by the following general formula (g5), and $R^8$ represents hydrogen or a group represented by the following general formula (g6). Note that the substitution site of $R^0$ is a carbon atom represented by either α or β, and the substitution site of $R^8$ is a carbon atom represented by either γ or δ.)

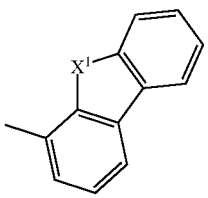

(g5)

(In the Formula, $X^1$ Represents Oxygen or Sulfur.)

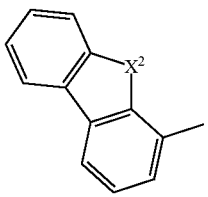

(g6)

(In the Formula, $X^2$ Represents Oxygen or Sulfur.)

In addition, another embodiment of the present invention is a carbazole derivative that has any of the above structures and is represented by the general formula (G5) in which $R^8$ is a substituent represented by the general formula (g6). In the case where $R^0$ is bonded to the position of α, $R^8$ is bonded to the position of γ, and in the case where $R^0$ is bonded to the position of β, $R^8$ is bonded to the position of δ.

Another embodiment of the present invention is a carbazole derivative represented by the following general formula (G6).

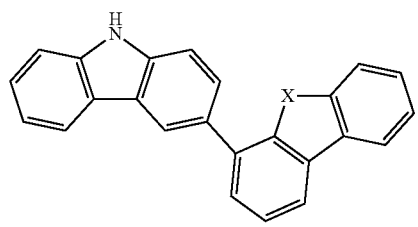
(G6)

(Note that in the Formula, X Represents Oxygen or Sulfur.)

Another embodiment of the present invention is a carbazole derivative represented by the following general formula (G7).

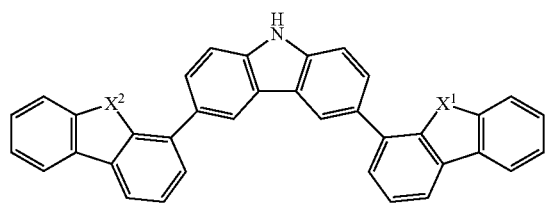
(G7)

(Note that in the Formula, $X^1$ and $X^2$ Individually Represent Oxygen or Sulfur.)

Another embodiment of the present invention is a carbazole derivative represented by the following general formula (G8).

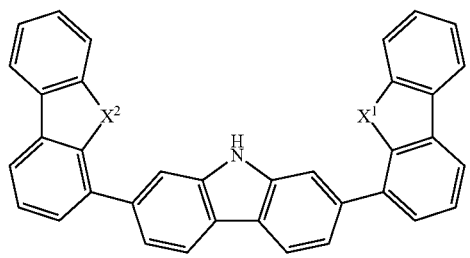
(G8)

(Note that in the Formula, $X^1$ and $X^2$ Individually Represent Oxygen or Sulfur.)

Another embodiment of the present invention is a carbazole derivative represented by the following structural formula.

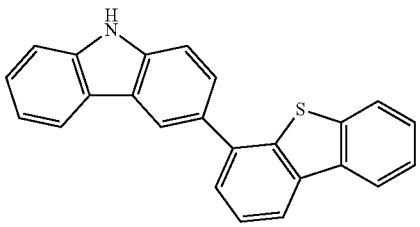

Another embodiment of the present invention is a carbazole derivative represented by the following structural formula.

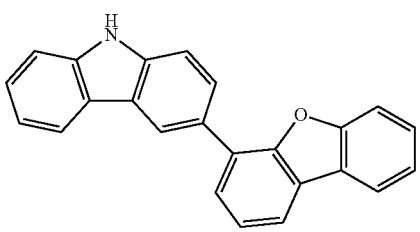 [SMILES: c1ccc2c(c1)[nH]c1ccc(-c3cccc4c3sc3ccccc34)cc12]

Another embodiment of the present invention is a carbazole derivative represented by the following structural formula.

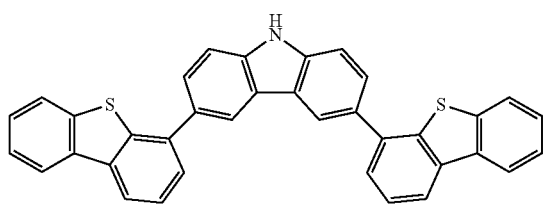 [SMILES: c1ccc2c(c1)sc1c(-c3ccc4[nH]c5ccc(-c6cccc7c6sc6ccccc67)cc5c4c3)cccc12]

Another embodiment of the present invention is a carbazole derivative represented by the following structural formula.

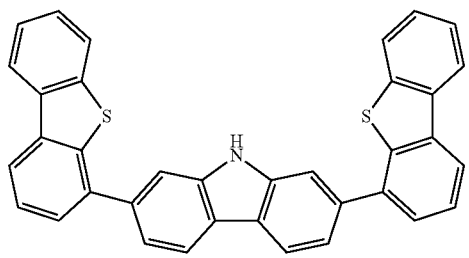 [SMILES: c1ccc2c(c1)sc1c(-c3ccc4c(c3)[nH]c3cc(-c5cccc6c5sc5ccccc56)ccc34)cccc12]

Another embodiment of the present invention is a carbazole derivative represented by the following structural formula.

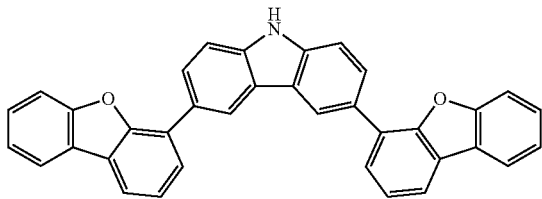 [SMILES: c1ccc2c(c1)oc1c(-c3ccc4[nH]c5ccc(-c6cccc7c6oc6ccccc67)cc5c4c3)cccc12]

A carbazole derivative having any of the above-described structures is a light-emitting element material having a wide energy gap, and can be used for a transport layer or as a host material or a light-emitting substance of the light-emitting element. A light-emitting element using a light-emitting element material containing the carbazole derivative can be a light-emitting element having high emission efficiency. In addition, a light-emitting element using a light-emitting element material containing the carbazole derivative can be a light-emitting element driven with a low driving voltage. Further, a light-emitting element using a light-emitting element material containing the carbazole derivative can be a light-emitting element having a long lifetime. The carbazole derivative can also be used as an organic semiconductor material.

In addition, a synthetic intermediate used for synthesis of the above carbazole derivative can be provided.

BRIEF DESCRIPTION OF DRAWINGS

FIGS. 3A and 3B are conceptual diagrams of an active matrix light-emitting device.
FIGS. 5A to 5D each illustrate an electronic device.

BEST MODE FOR CARRYING OUT THE INVENTION

Figure 1A:
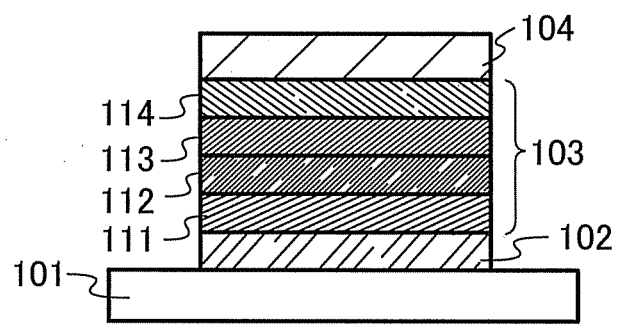
FIGS. 1A and 1B are conceptual diagrams of light-emitting elements.

Hereinafter, embodiments of the present invention are described. It is easily understood by those skilled in the art that modes and details disclosed herein can be modified in various ways without departing from the spirit and the scope of the present invention. Therefore, the present invention is not construed as being limited to description of the embodiments.

Embodiment 1

A carbazole derivative in this embodiment is a substance in which a carbazolyl group whose carbon atom at the 2- or 3-position of carbazole is substituted by a carbon atom at the 4-position of dibenzothiophene or the 4-position of dibenzofuran is bonded to aromatic hydrocarbon having 14 to 70 carbon atoms. Note that the dibenzothiophene or dibenzofuran and the carbazole may or may not have a substituent. In addition, the aromatic hydrocarbon has a structure that includes a condensed tricyclic ring, a condensed tetracyclic ring, a condensed pentacyclic ring, a condensed hexacyclic ring, or a condensed heptacyclic ring, and the number of carbon atoms of the aromatic hydrocarbon indicates the total number of carbon atoms, including those of a substituent such as an alkyl group.

In the case where the dibenzothiophene or dibenzofuran bonded to the carbazolyl group has a substituent, the substituent can be any of an aryl group having 6 to 15 carbon atoms and an alkyl group having 1 to 4 carbon atoms.

In the case where the carbazole in the carbazolyl group has another substituent, the substitution site of the substituent is the 6- or 7-position of the carbazole, and the substituent can be any of an aryl group having 6 to 15 carbon atoms, an alkyl group having 1 to 4 carbon atoms, a dibenzothiophen-4-yl group, and a dibenzofuran-4-yl group. In the case where the dibenzothiophen-4-yl group or dibenzofuran-4-yl group is selected as the substituent that is bonded to the 6- or 7-position of the carbazole, the dibenzothiophen-4-yl group or the dibenzofuran-4-yl group may further have a substituent that can be selected from an aryl group having 6 to 15 carbon atoms and an alkyl group having 1 to 4 carbon atoms. For easier synthesis, in the case where the dibenzothiophen-4-yl group or dibenzofuran-4-yl group is selected as the substituent that is bonded to the 6- or 7-position of the carbazole and the dibenzothiophene or the dibenzofuran is bonded to the 2-position of the carbazole, the dibenzothiophen-4-yl group or the dibenzofuran-4-yl group is preferably substituted at the 7-position of the carbazole; in the case where the dibenzothiophene or the dibenzofuran is bonded to the 3-position of the carbazole, the dibenzothiophen-4-yl group or the dibenzofuran-4-yl group is preferably substituted at the 6-position of the carbazole. Note that for easier synthesis, the dibenzothiophene or dibenzofuran bonded to the 2- or 3-position of the carbazole and the substituent bonded to the 6- or 7-position of the carbazole are preferably of the same type.

The present inventors have found out that the above-described carbazole derivative has a moderate carrier-transport property and can be suitably used as a light-emitting element material. With the use of the light-emitting element material having excellent carrier mobility, a light-emitting element driven with a low driving voltage can be provided.

The above-described carbazole derivative has a rigid group such as dibenzothiophene or dibenzofuran, and thus the morphology is excellent and the film quality is stable. Further, the thermophysical property is also excellent. From the above, a light-emitting element that uses a light-emitting material containing the carbazole derivative can be a light-emitting element having a long lifetime.

Note that with a substance having an electron-transport property selected as the above-described aromatic hydrocarbon that includes a condensed tricyclic ring, a condensed tetracyclic ring, a condensed pentacyclic ring, a condensed hexacyclic ring, or a condensed heptacyclic ring, a material having both the electron-transport property and a hole-transport property, i.e., a bipolar material, can be obtained. With the use of the bipolar material for a light-emitting layer in a light-emitting element, localization of an emission region can be prevented, concentration quenching or triplet-triplet annihilation (T-T annihilation) can be suppressed, and a light-emitting element having high emission efficiency can be obtained. From such a point of view, it is preferable to select anthracene, pyrene, chrysene, naphthacene, pentacene, fluoranthene, perylene, coronene, or triphenylene as the condensed tricyclic ring, the condensed tetracyclic ring, the condensed pentacyclic ring, the condensed hexacyclic ring, or the condensed heptacyclic ring.

In addition, a skeleton whose T1 level is high, such as triphenylene or phenanthrene, can be used as the condensed tricyclic ring, the condensed tetracyclic ring, the condensed pentacyclic ring, the condensed hexacyclic ring, or the condensed heptacyclic ring for suitable application to a phosphorescent element.

The above-described carbazole derivative can be represented by the following general formula (G0) or (G1).

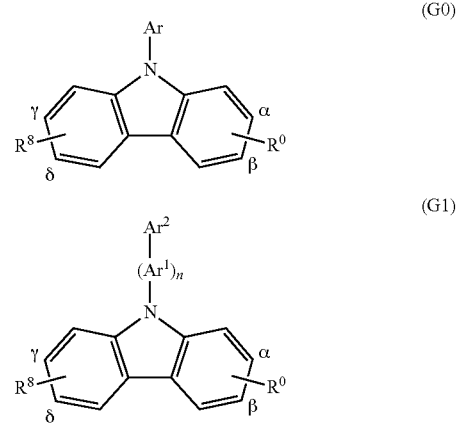

In the formula (G0), Ar represents an aryl group that has 14 to 70 carbon atoms. Note that the aromatic hydrocarbon has a structure that includes a condensed tricyclic ring, a condensed tetracyclic ring, a condensed pentacyclic ring, a condensed hexacyclic ring, or a condensed heptacyclic ring, and the number of carbon atoms of the aromatic hydrocarbon indicates the total number of carbon atoms, including those of a substituent such as an alkyl group.

In the formula (G1), $Ar^1$ represents any one of a phenylene group, a naphthylene group, and a biphenylene group, and $Ar^2$ represents a group that has 14 to 30 carbon atoms and includes a condensed tricyclic ring, a condensed tetracyclic ring, a condensed pentacyclic ring, a condensed hexacyclic ring, or a condensed heptacyclic ring. In addition, n is either 0 or 1. Note that $Ar^1$ may or may not have a substituent, and in the case where $Ar^1$ has a substituent, the substituent is an alkyl group having 1 to 4 carbon atoms. Note also that $Ar^2$ may or may not have a substituent, and in the case where $Ar^2$ has a substituent, the substituent is any of an alkyl group having 1 to 4 carbon atoms and an aryl group having 6 to 15 carbon atoms.

A carbazole derivative represented by the above general formula (G0) or (G1) in which Ar is such a group has excellent morphology and the film quality is stable. Further, the thermophysical property is also excellent.

Note that it is found out that a substance that has a favorable balance of the electron-transport property and the hole-transport property, and can be very effective as a light-emitting element material can be obtained by including anthracene such as diphenylanthracene in Ar in the general formula (G0) or $Ar^2$ in the general formula (G1).

In addition, with a skeleton that has a chromophore, such as anthracene, pyrene, chrysene, naphthacene, pentacene, fluoranthene, perylene, or coronene, as Ar in the general formula (G0) or $Ar^2$ in the general formula (G1), a light-emitting element material having a favorable carrier balance and high efficiency can be obtained. In addition, a skeleton whose T1 level is high, such as triphenylene or phenanthrene, can be used as Ar to obtain a light-emitting element material for suitable application to a phosphorescent element.

$R^0$ represents a group represented by the following general formula (g1). Note that the substitution site of $R^0$ is a carbon atom represented by either α or β.

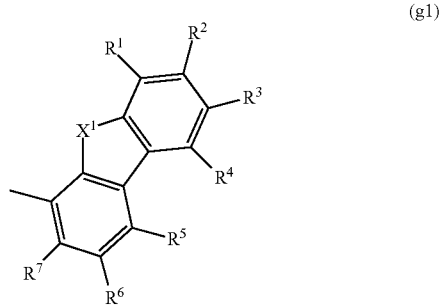
(g1)

In the formula (g1), $X^1$ represents oxygen or sulfur, and $R^1$ to $R^7$ individually represent any one of hydrogen, an alkyl group having 1 to 4 carbon atoms, and an aryl group having 6 to 15 carbon atoms.

Further, a carbazole derivative having the above-described structure has an excellent carrier-transport property, and a light-emitting element using the carbazole derivative can be a light-emitting element driven with a low driving voltage. In addition, the above-described carbazole derivative has a rigid group such as dibenzothiophene or dibenzofuran, and thus the morphology is excellent and the film quality is stable. Further, the thermophysical property is also excellent. From the above, by using a light-emitting material using the carbazole derivative, a light-emitting element having a long lifetime can be provided.

Note that the carbazole derivative represented by the above general formula (G1) may have a substituent represented by $R^8$, as also illustrated in the above general formula (G1). $R^8$ represents any one of hydrogen, an alkyl group having 1 to 4 carbon atoms, an aryl group having 6 to 15 carbon atoms, and a group represented by the following general formula (g2). Note that the substitution site of $R^8$ is a carbon atom represented by either γ or δ.

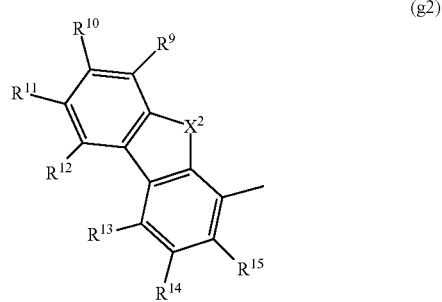
(g2)

In the formula (g2), $X^2$ represents oxygen or sulfur, and $R^9$ to $R^{15}$ individually represent any one of hydrogen, an aryl group having 6 to 15 carbon atoms, and an alkyl group having 1 to 4 carbon atoms.

In the case where $R^8$ is a substituent other than hydrogen, $R^8$ and $R^0$ are preferably the same group for easier synthesis.

In the case where the group represented by the above general formula (g1) further includes a substituent, the substitution site of the substituent is preferably a site represented by $R^1$, $R^3$, or $R^6$ for a reduction in cost of synthesizing the material owing to availability of the material and easiness of the synthesis. From the same point of view, it is further preferable that $R^1$ to $R^7$ be all hydrogen.

In a similar manner, in the case where the group represented by (g2) is applied as $R^8$, the substitution site of the substituent is preferably a site represented by $R^9$, $R^{11}$, or $R^{14}$, and it is further preferable that $R^9$ to $R^{15}$ be all hydrogen.

In the above general formula (G0) or (G1), as an alkyl group having 1 to 4 carbon atoms or an aryl group having 6 to 15 carbon atoms, which can be used as any of $R^1$ to $R^{15}$, any of the groups represented by the following structural formulas (R-1) to (R-23) can be used. Note that as $R^8$, instead of the groups represented by the following structural formulas (R-1) to (R-23), the group represented by the above general formula (g2) can be used.

(R-1)

(R-2)

(R-3)

(R-4)

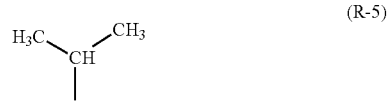
(R-5)

-continued
(R-6) 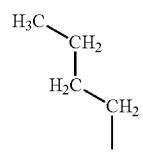
(R-7) 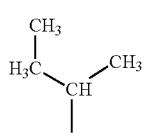
(R-8) 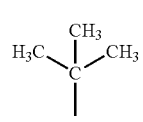
(R-9) 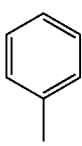
(R-10) 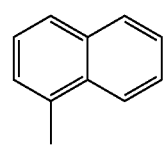
(R-11) 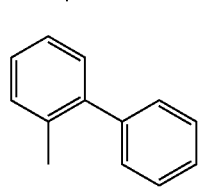
(R-12) 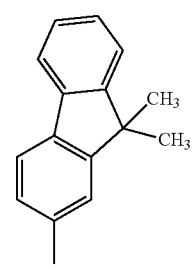
(R-13) 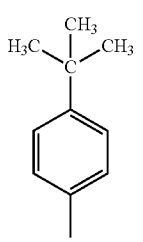
(R-14) 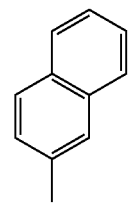
-continued
(R-15) 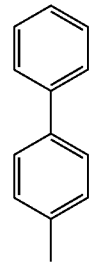
(R-16) 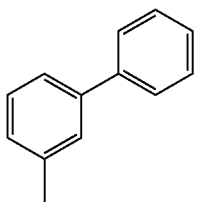
(R-17) 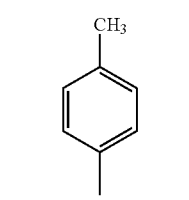
(R-18) 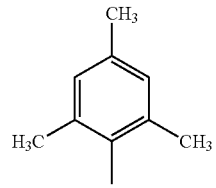
(R-19) 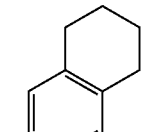
(R-20) 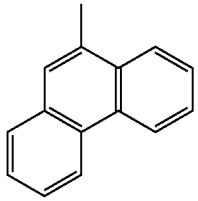
(R-21)

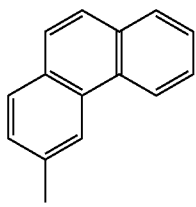
(R-22)

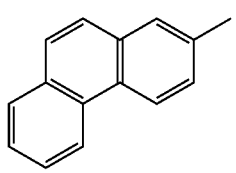
(R-23)

In the above general formula (G0), as an aryl group having 14 to 70 carbon atoms, which can be applied to Ar, any of the groups represented by the following structural formulas (Ar-1) to (Ar-78) can be used. Note that an —Ar group in the general formula (G0) corresponds to an —(Ar$^1$)n-Ar$^2$ group in the general formula (G1) (note that Ar$^1$ is a phenylene group, a naphthylene group, or a biphenylene group, and n is 0 or 1).

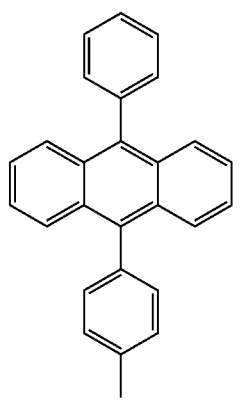
(Ar-1)

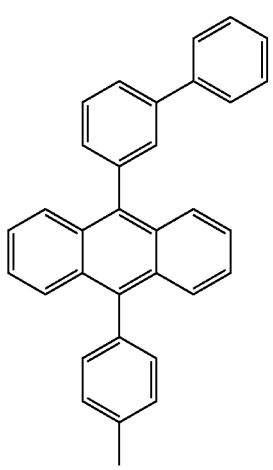
(Ar-2)

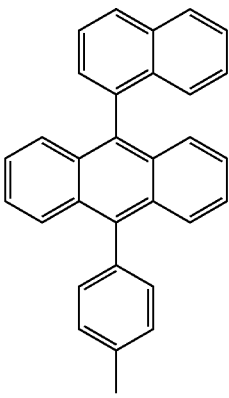
(Ar-3)

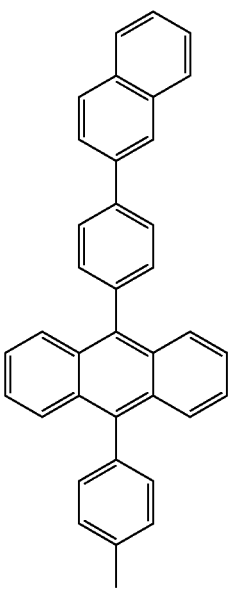
(Ar-4)

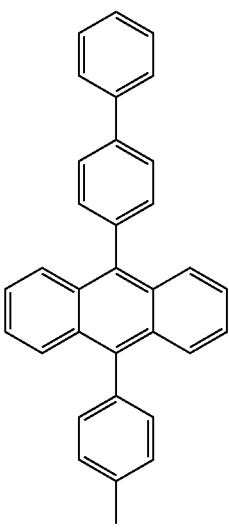
(Ar-5)

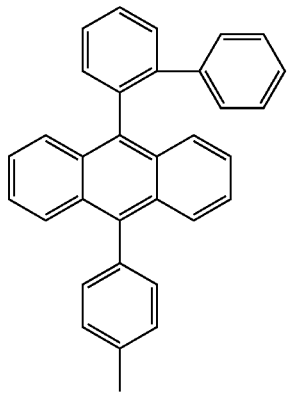 (Ar-6)
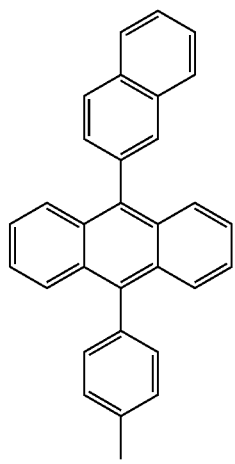 (Ar-7)
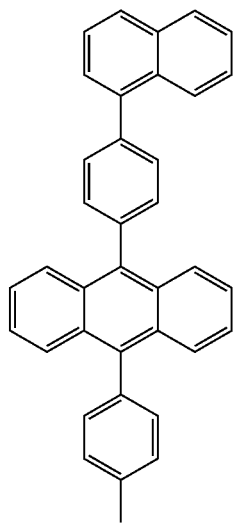 (Ar-8)
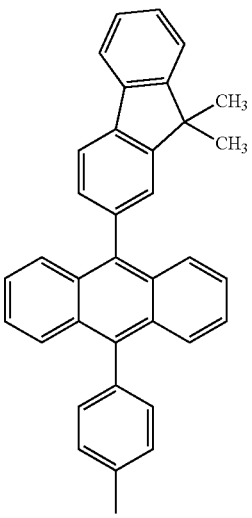 (Ar-9)
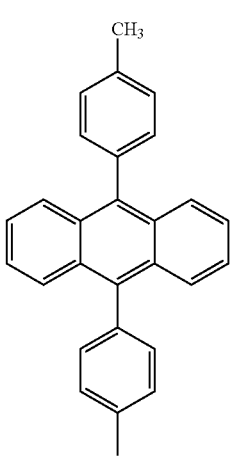 (Ar-10)
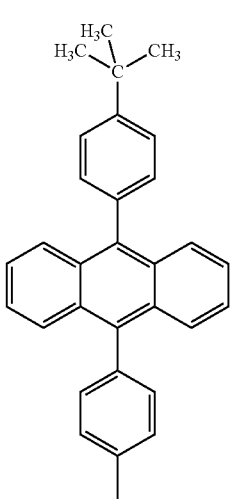 (Ar-11)

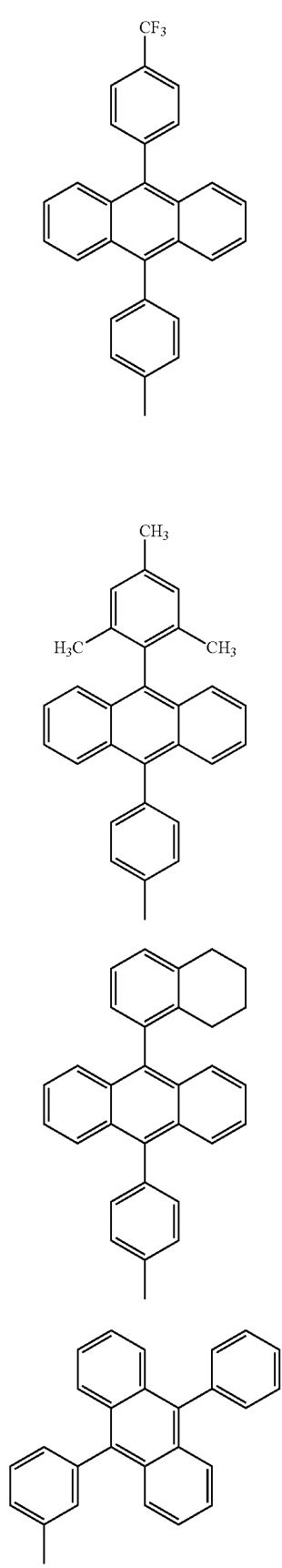 (Ar-12) (Ar-13) (Ar-14) (Ar-15)
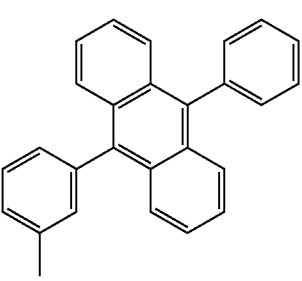 (Ar-16)
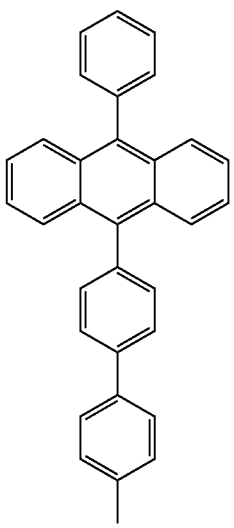 (Ar-17)
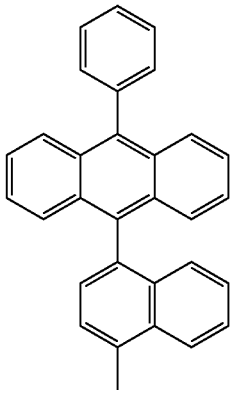 (Ar-18)
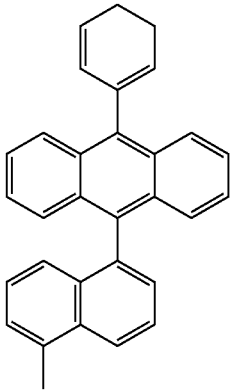 (Ar-19)

-continued
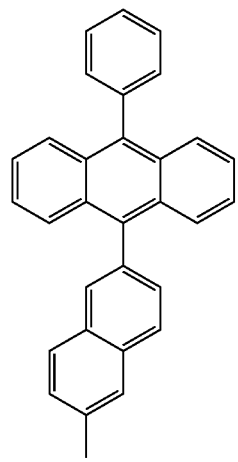
(Ar-20)
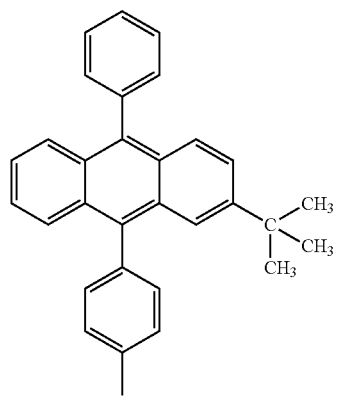
(Ar-21)
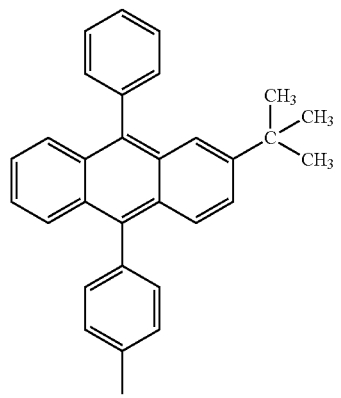
(Ar-22)
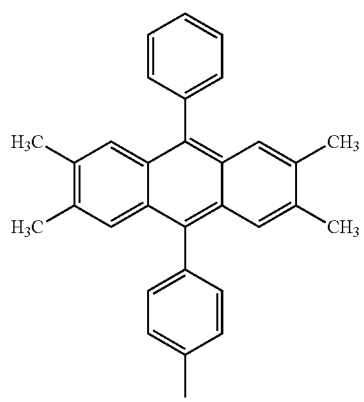
(Ar-23)
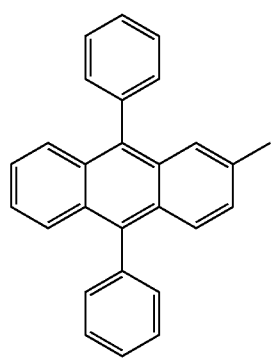
(Ar-24)
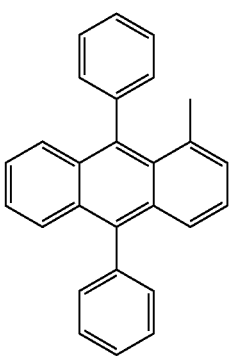
(Ar-25)
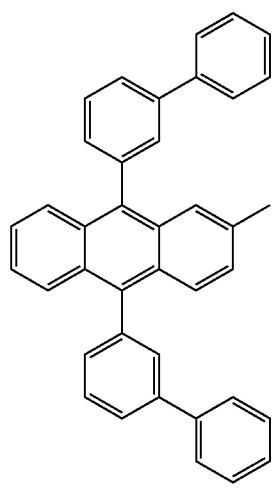
(Ar-26)
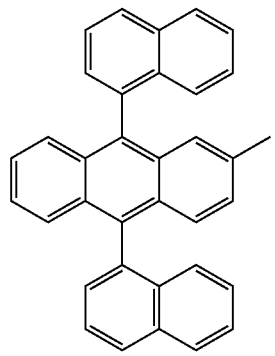
(Ar-27)

(Ar-28)
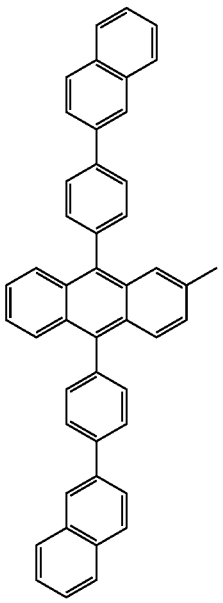
(Ar-29)
(Ar-30)
(Ar-31)
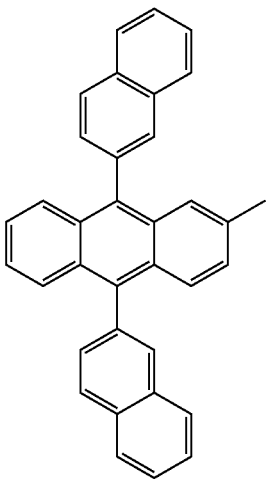
(Ar-32)
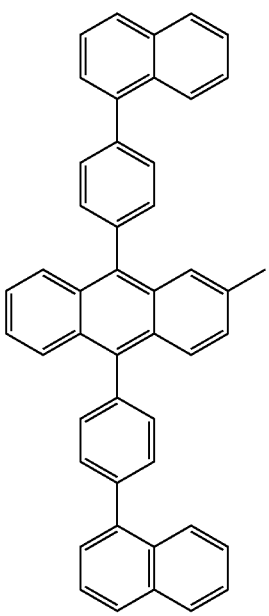
(Ar-33)
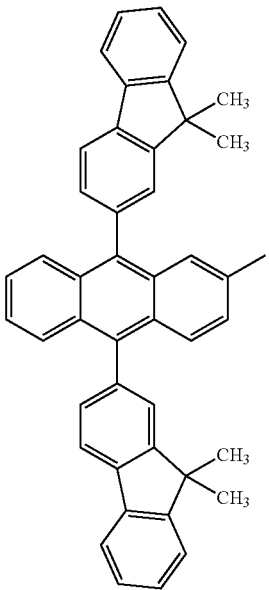

(Ar-34)
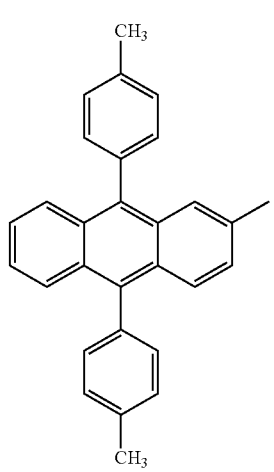
(Ar-35)
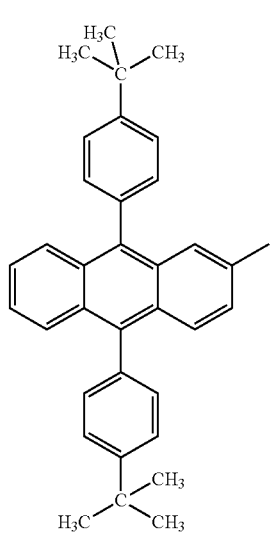
(Ar-36)
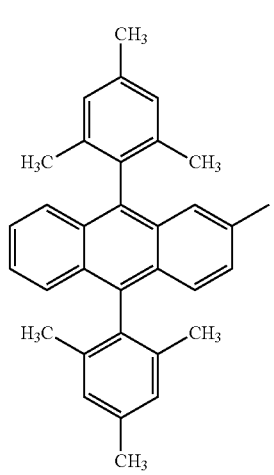
(Ar-37)
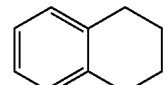
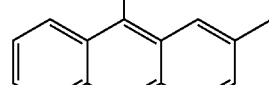
(Ar-38)
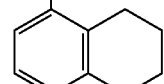
(Ar-39)
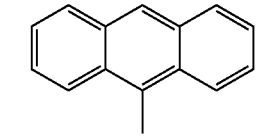
(Ar-40)
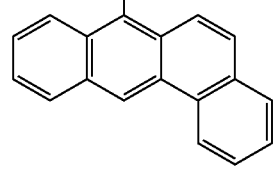
(Ar-41)
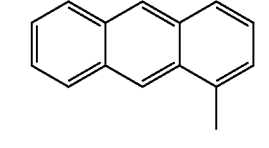
(Ar-42)
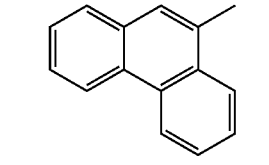
(Ar-43)
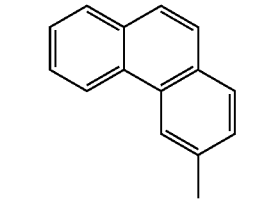
(Ar-44)
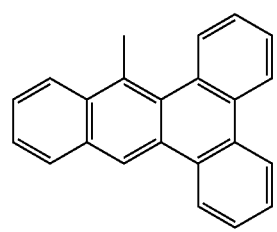

(Ar-45)
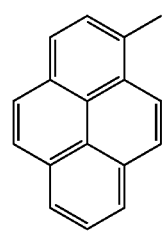
(Ar-46)
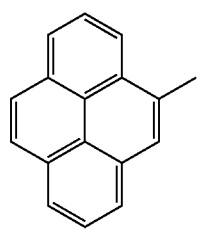
(Ar-47)
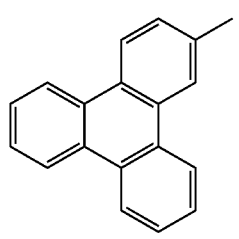
(Ar-48)
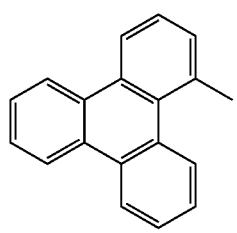
(Ar-49)
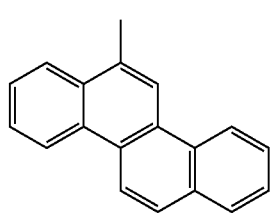
(Ar-50)
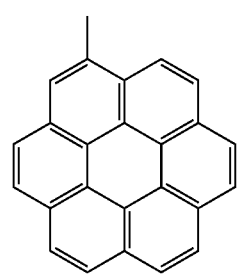
(Ar-51)
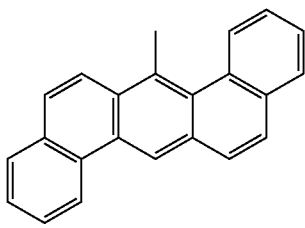
(Ar-52)
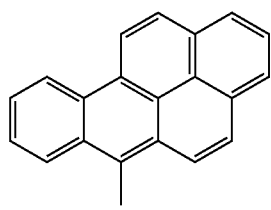
(Ar-53)
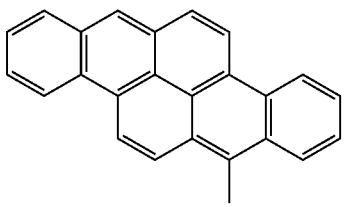
(Ar-54)
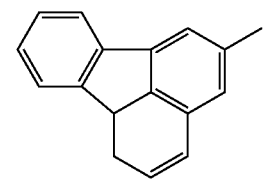
(Ar-55)
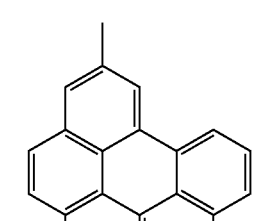
(Ar-56)
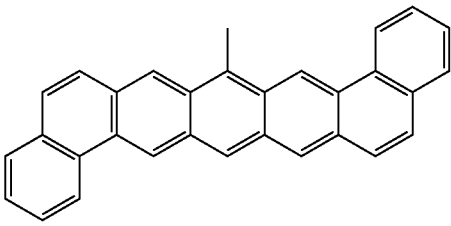

(Ar-57)
(Ar-58)
(Ar-59)
(Ar-60)
(Ar-61)
(Ar-62)
(Ar-63)
(Ar-64)
(Ar-65)
(Ar-66)
(Ar-67)

(Ar-68) 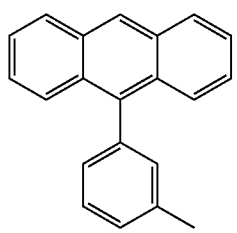
(Ar-69)
(Ar-70)
(Ar-71)
(Ar-72)
(Ar-73)
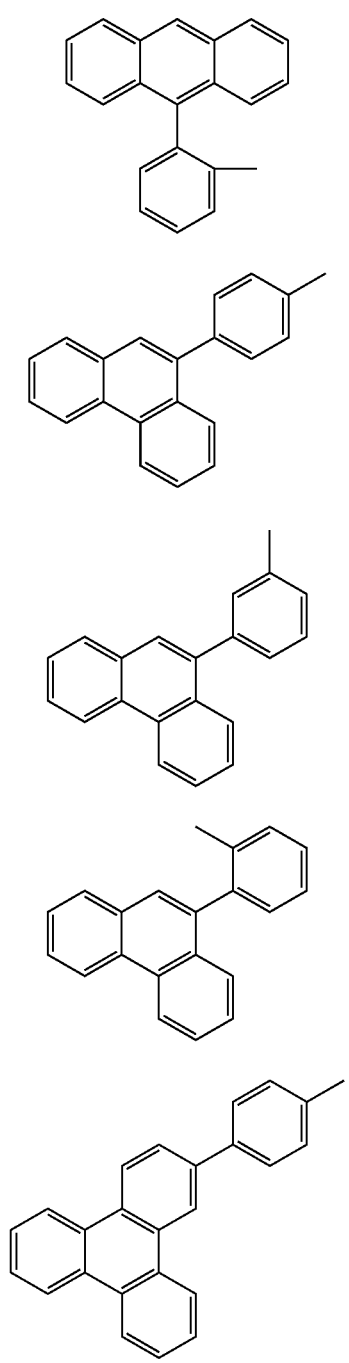
(Ar-74) 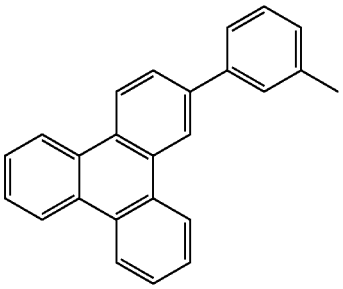
(Ar-75) 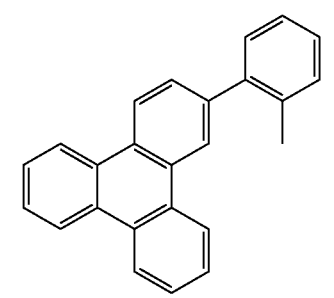
(Ar-76) 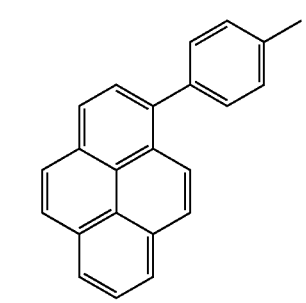
(Ar-77) 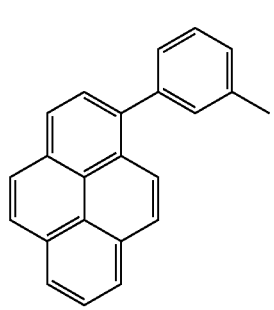
(Ar-78) 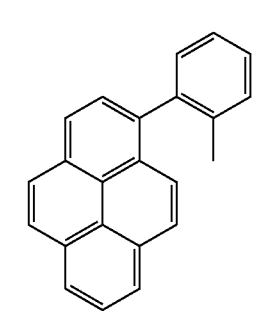
As specific structures of the carbazole derivative represented by the above general formula (G0) or (G1), substances represented by the following structural formulas (100) to (441) and (500) to (841) and the like can be given.

(100) 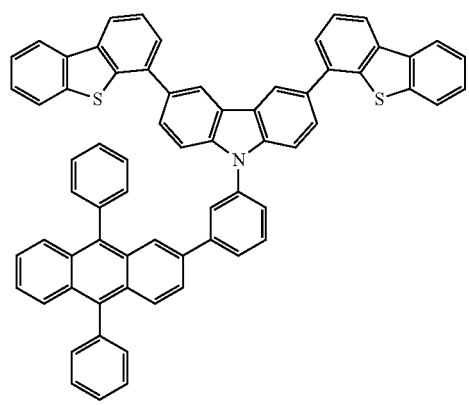 (101) 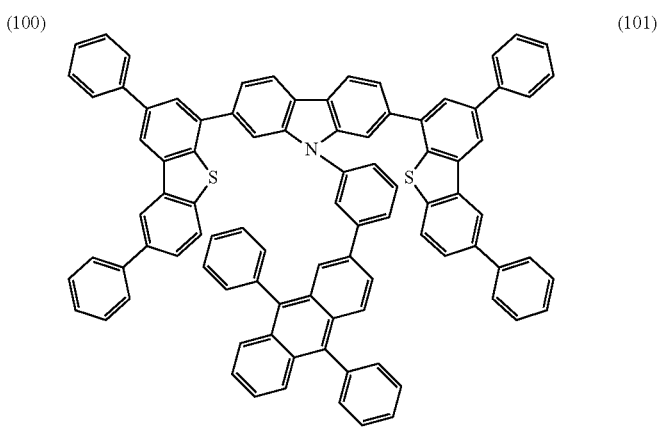
(102) 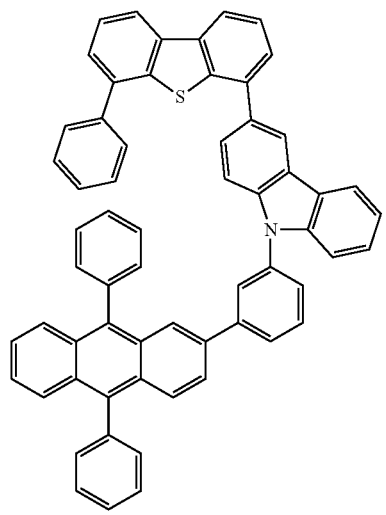 (103) 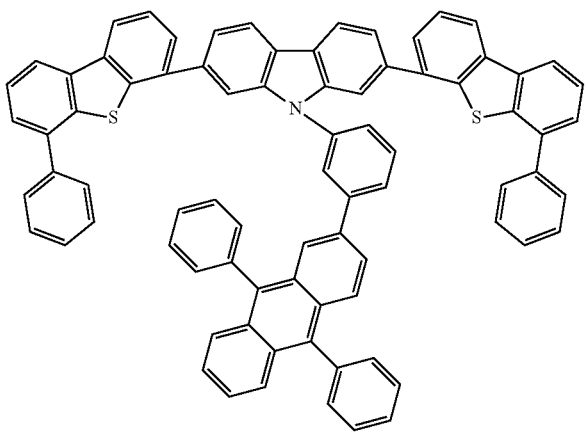
(104) 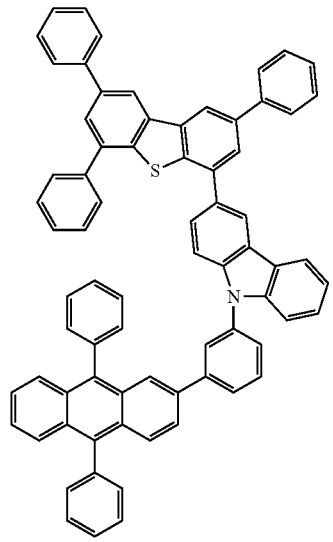 (105) 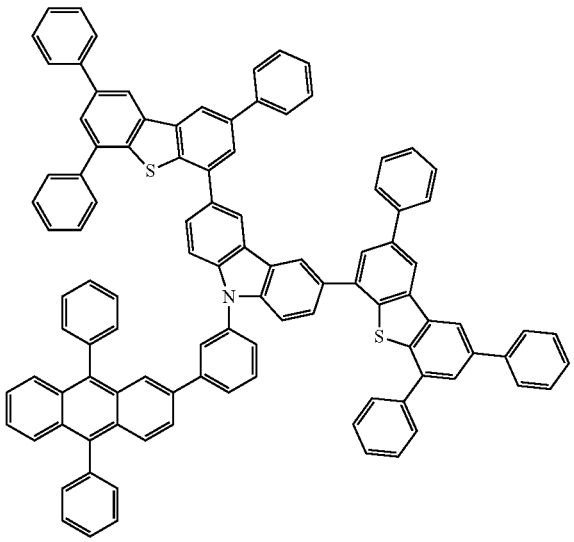

-continued
(106)
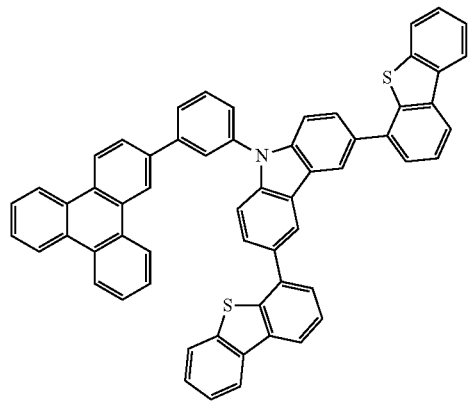
(107)
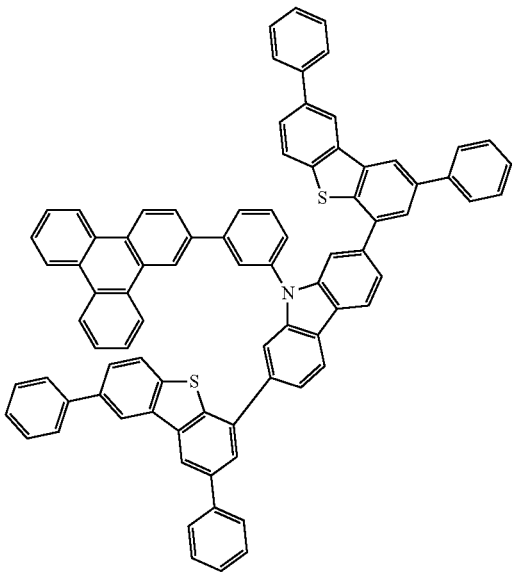
(108)
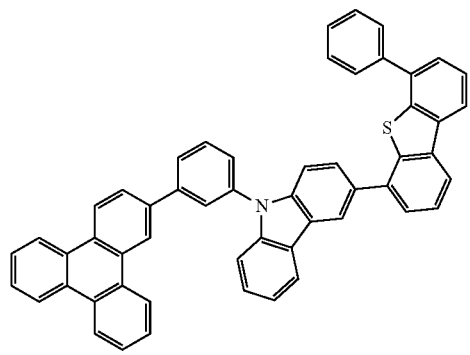
(109)
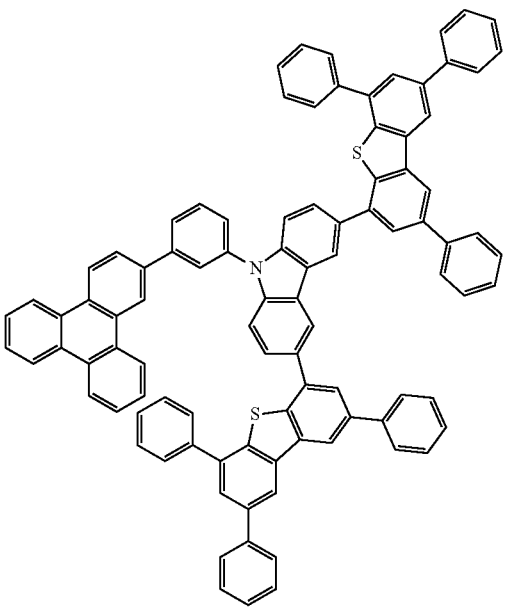
(110)
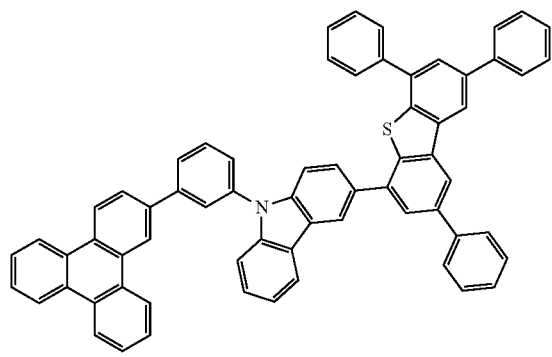
(111)
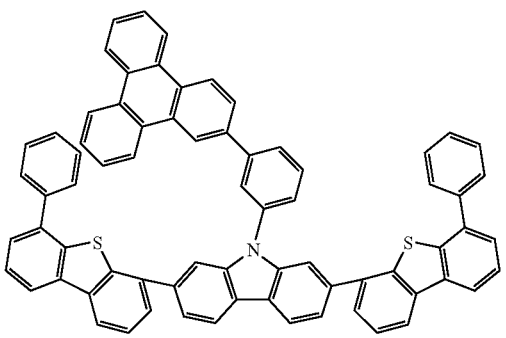

-continued
(112)
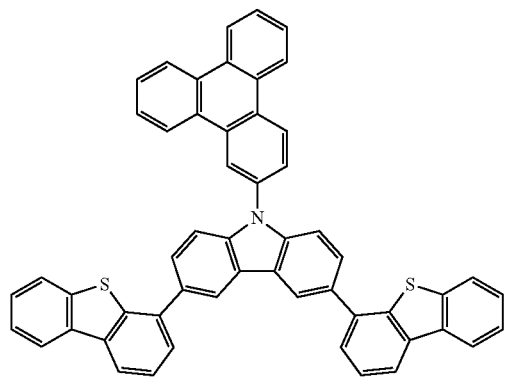
(113)
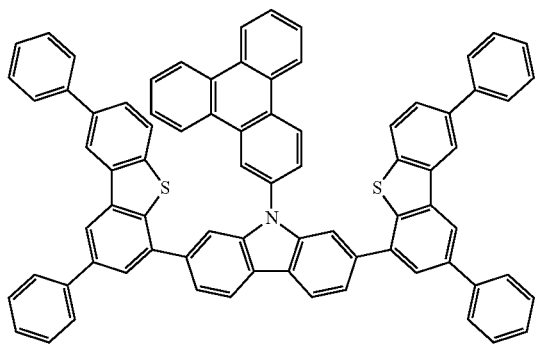
(114)
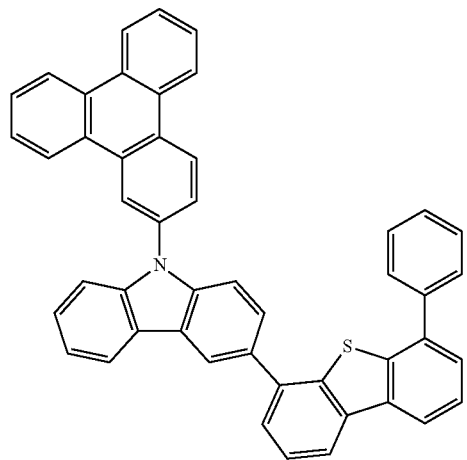
(115)
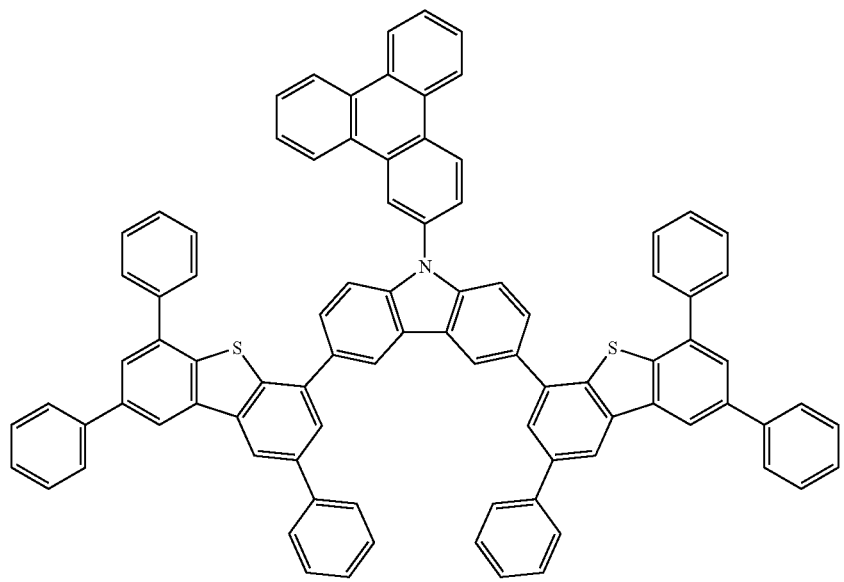

-continued
(116)
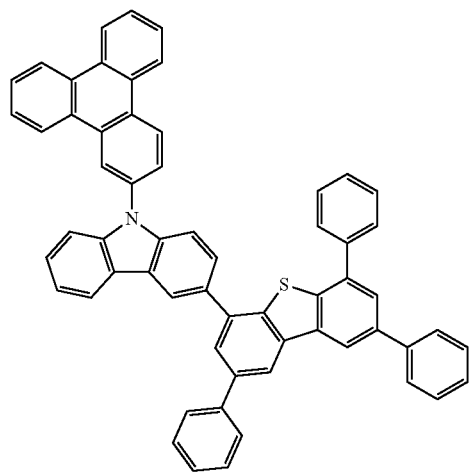
(117)
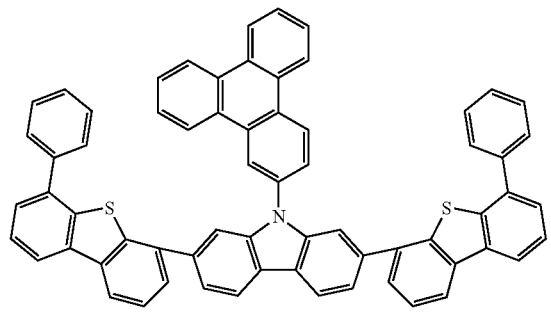
(118)
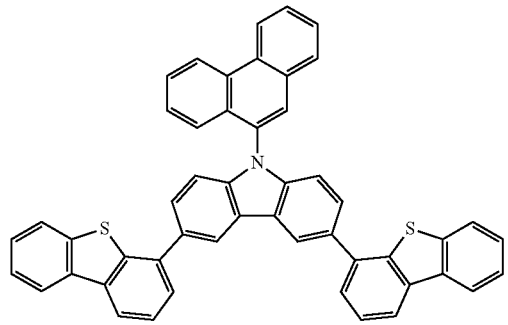
(119)
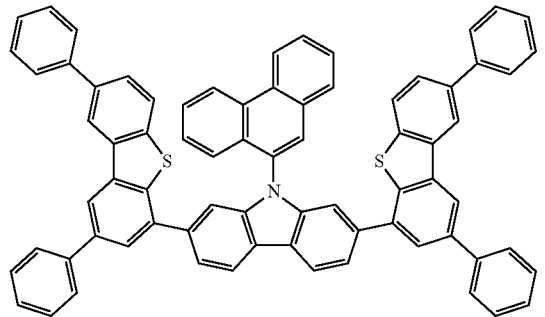
(120)
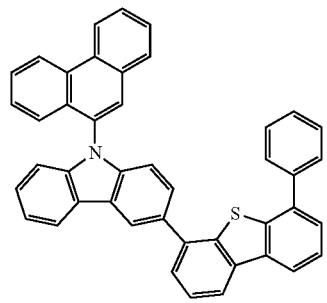
(121)
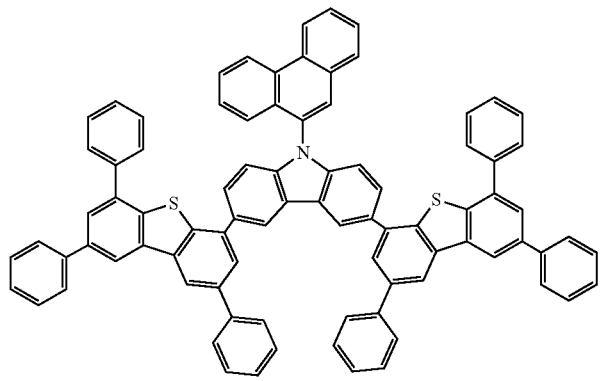

-continued
(122)
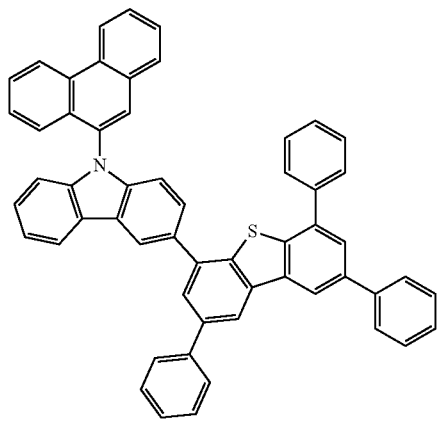
(123)
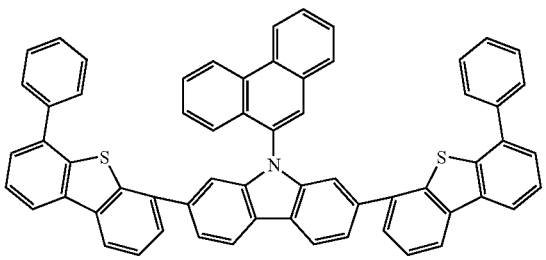
(124)
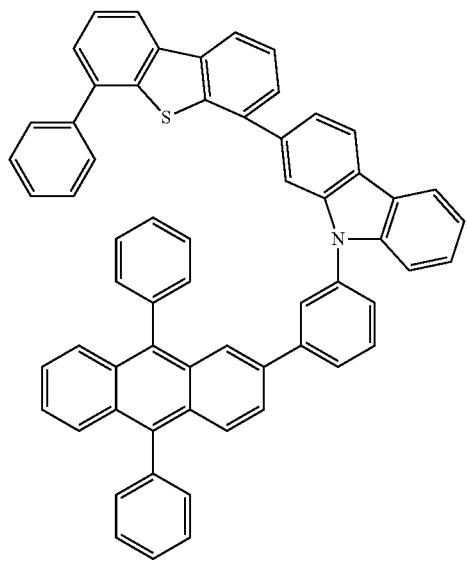
(125)
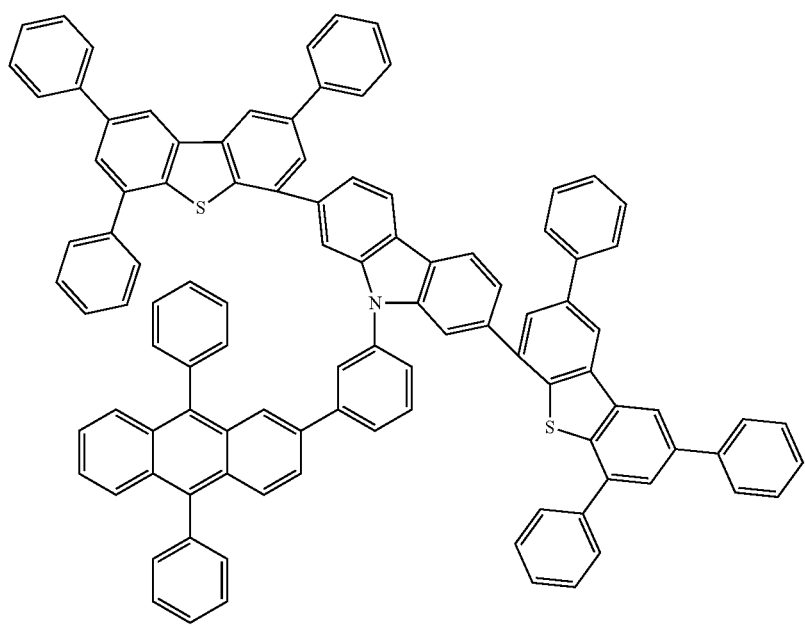

-continued
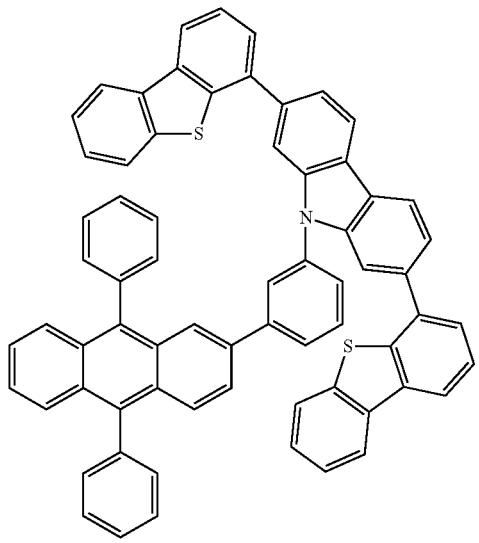
(126)
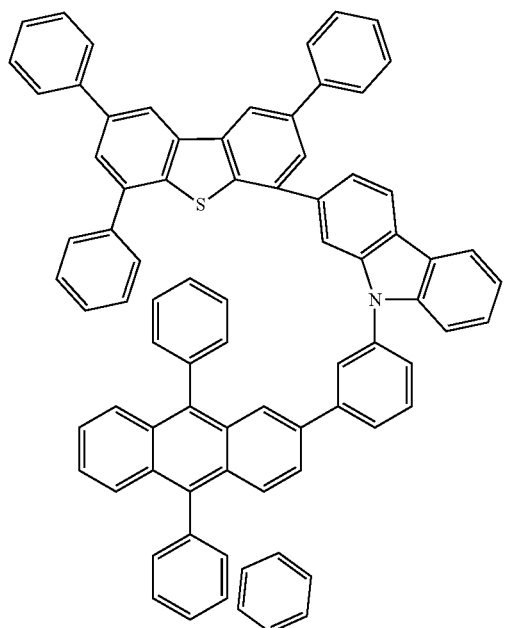
(127)
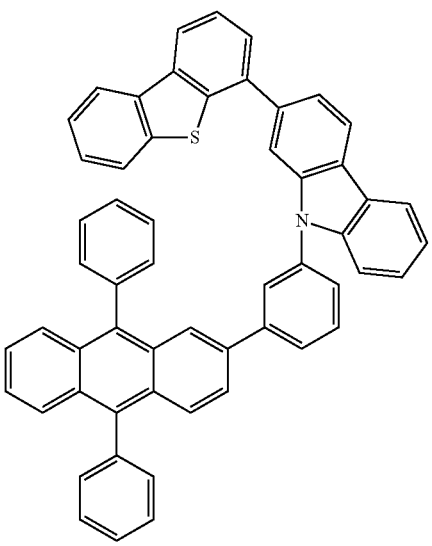
(128)
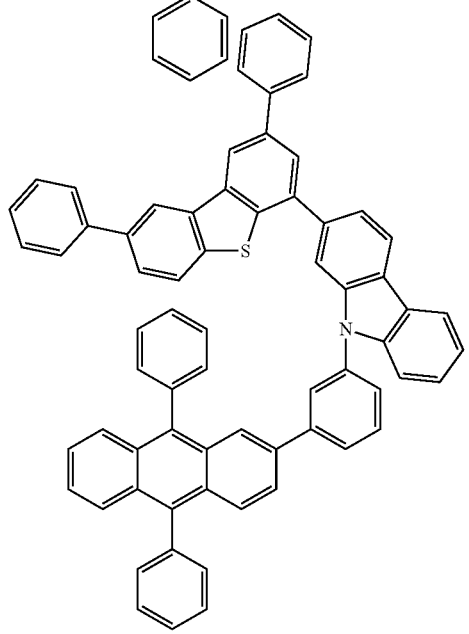
(129)
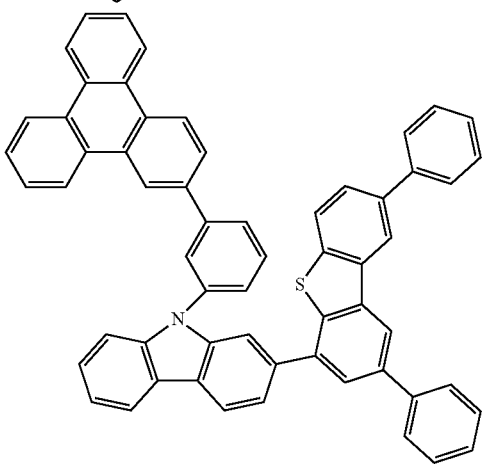
(130)

-continued
(131)
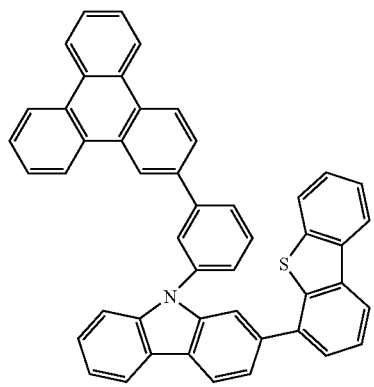
(132)
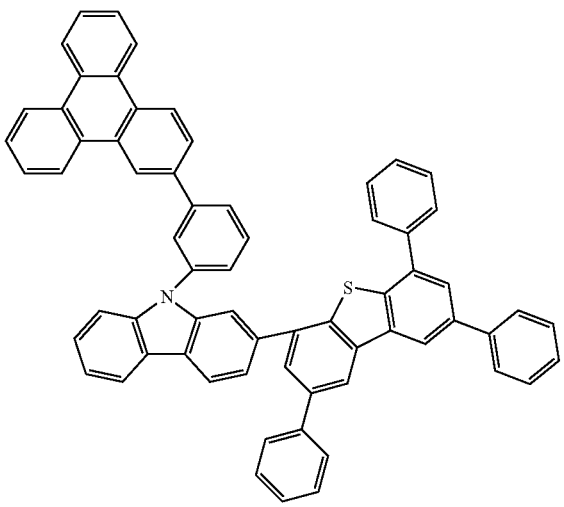
(133)
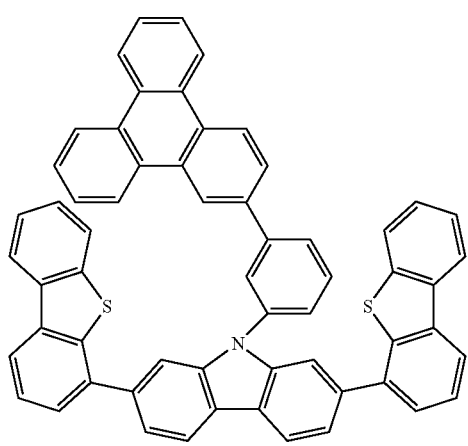
(134)
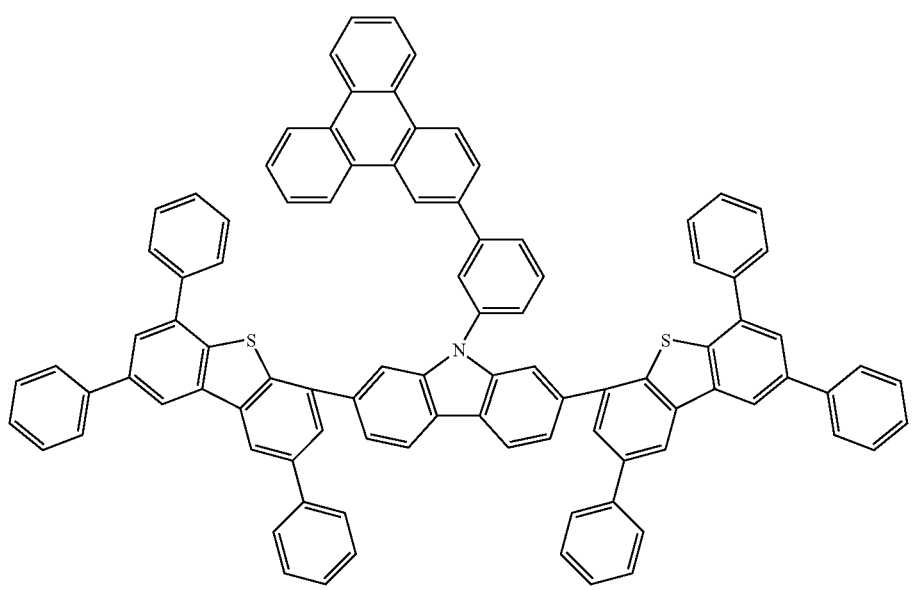

-continued
(135)
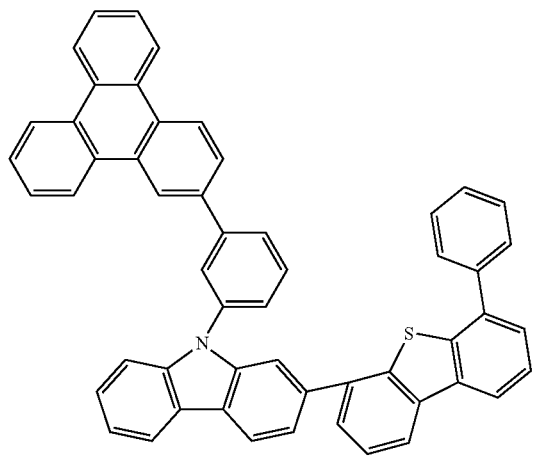
(136)
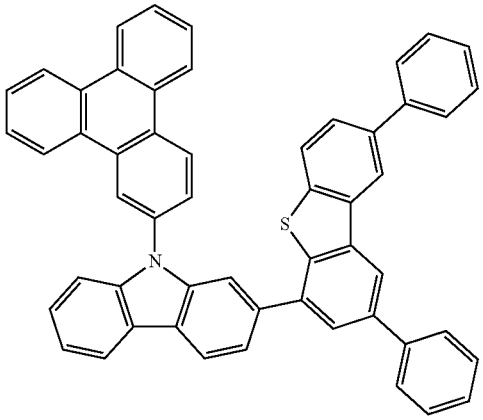
(137)
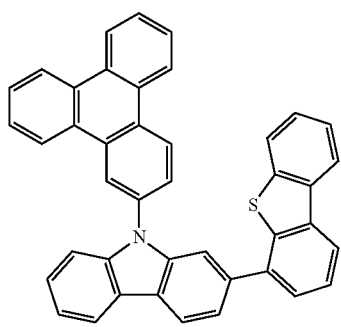
(138)
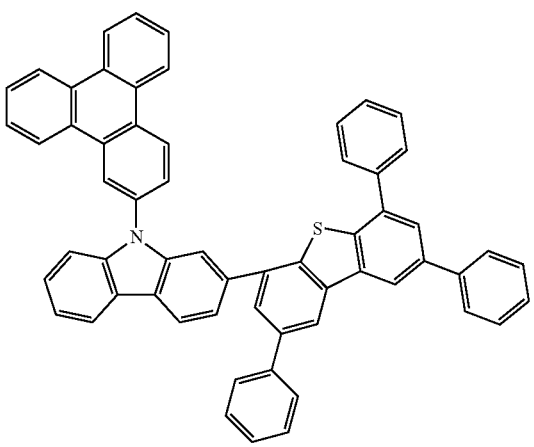
(139)
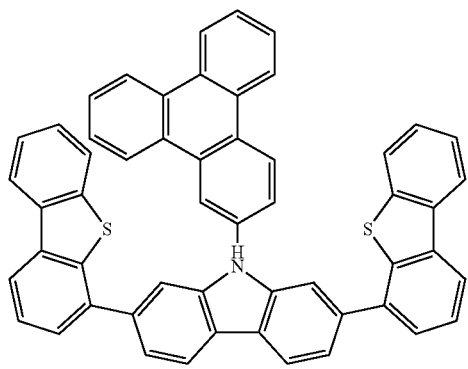

(140)
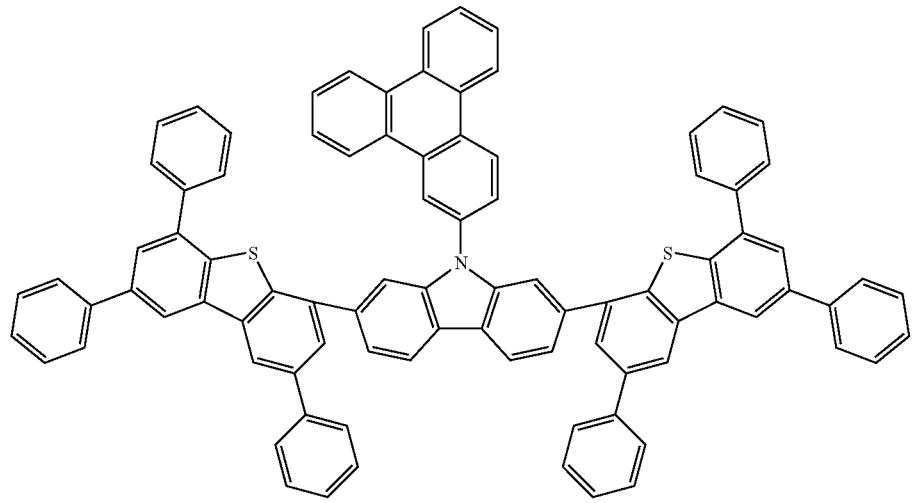
(141)
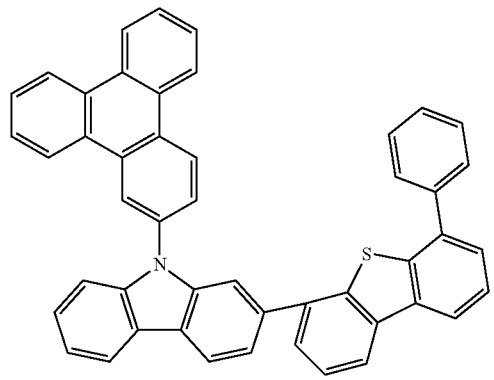
(142)
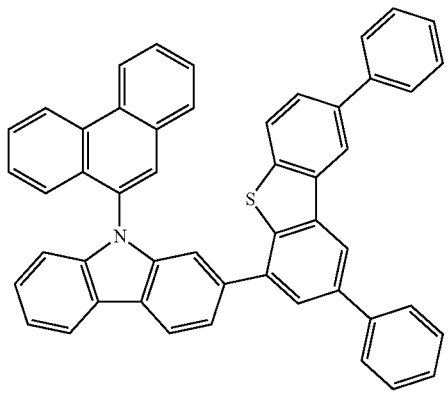
(143)
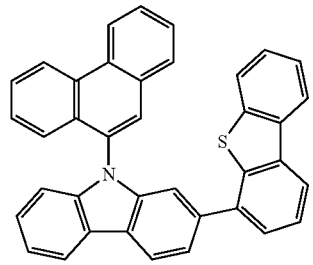
(144)
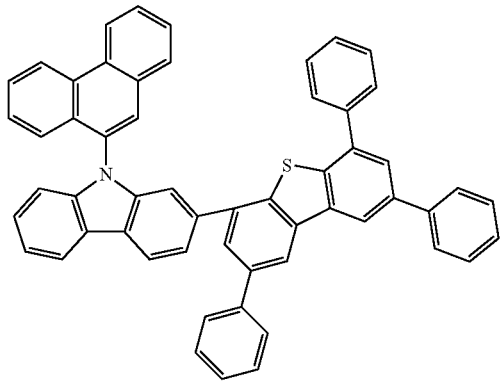
(145)
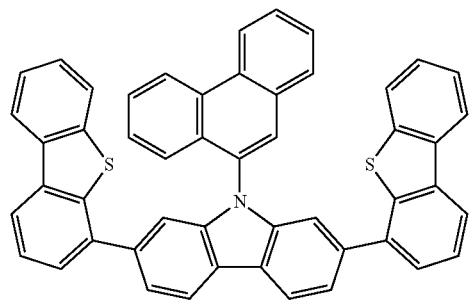

-continued
(146)
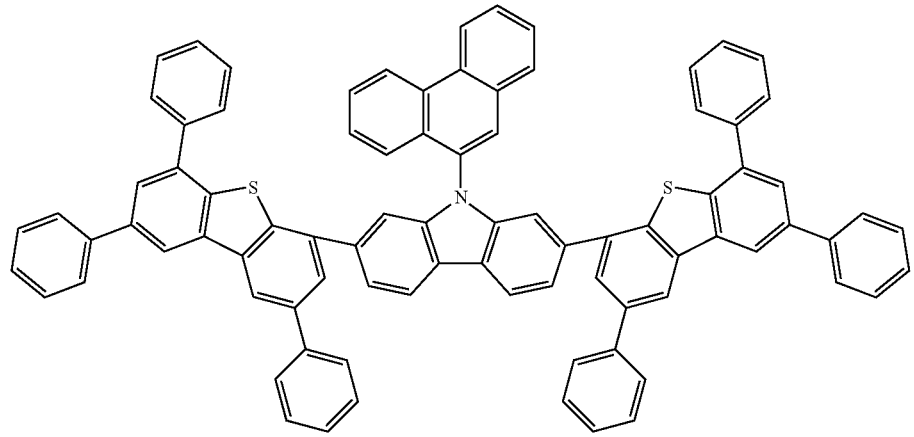
(147)
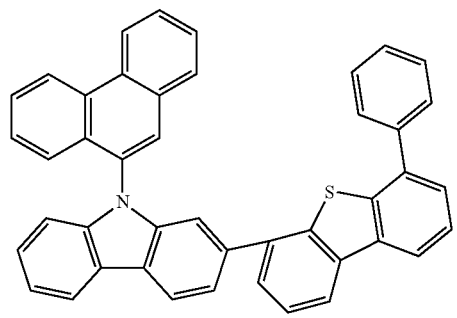
(148)
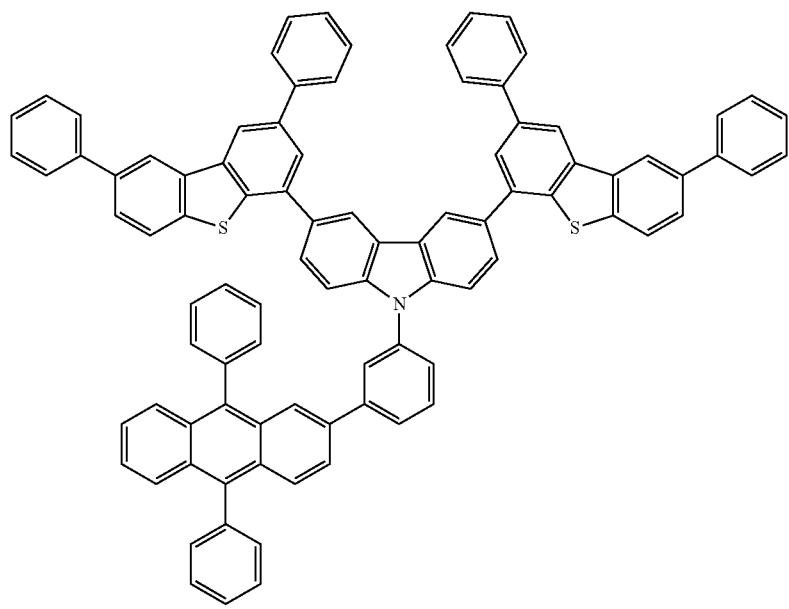

-continued
(149)
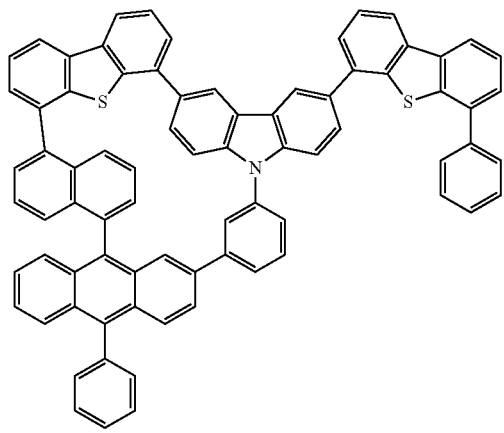
(150)
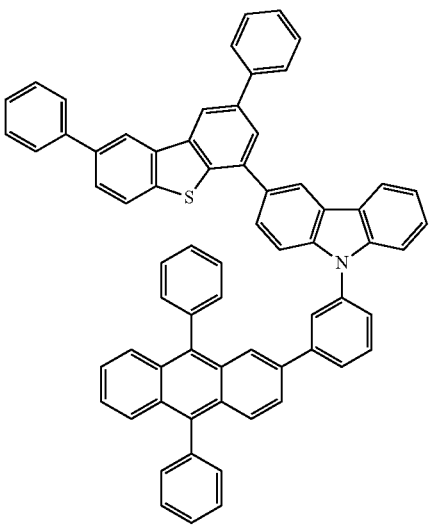
(151)
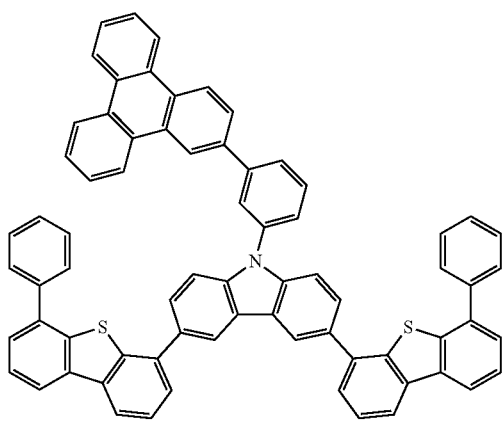
(152)
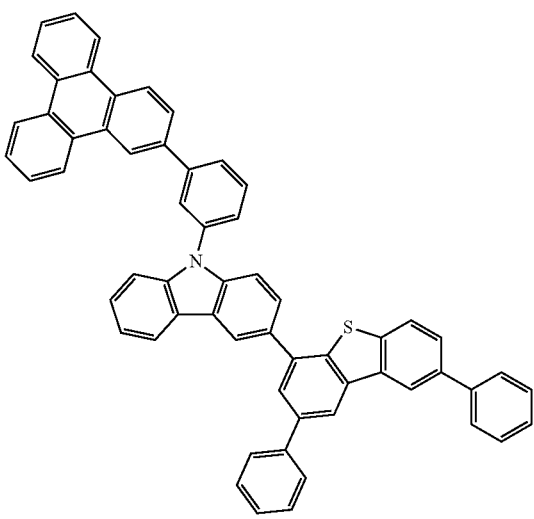
(153)
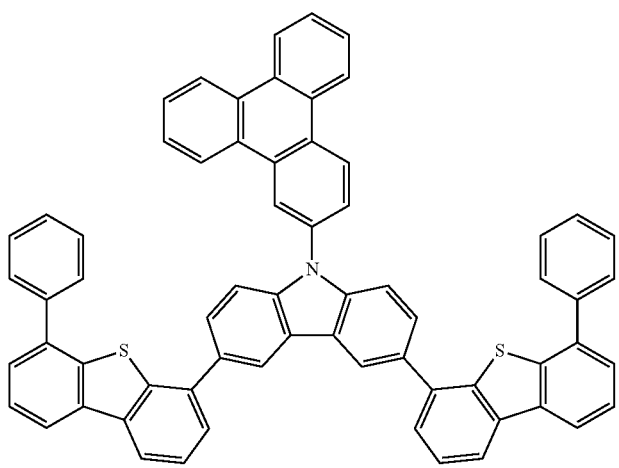

(154)
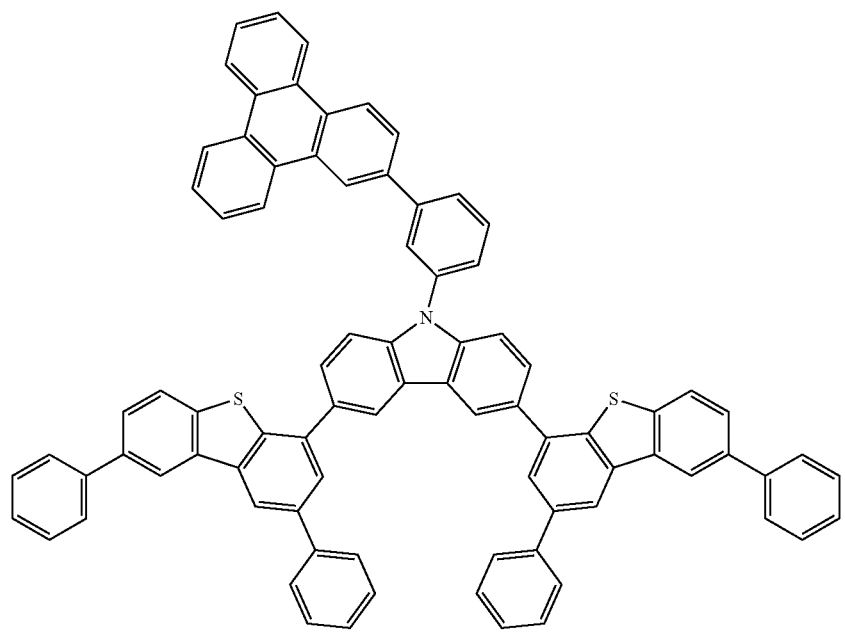
(155)
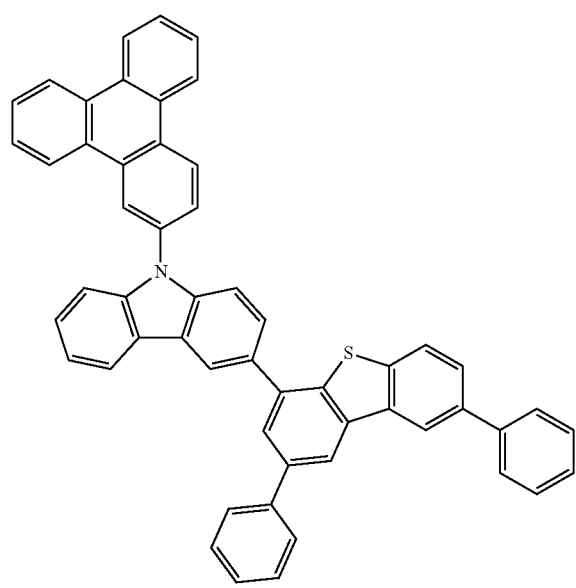

(156)
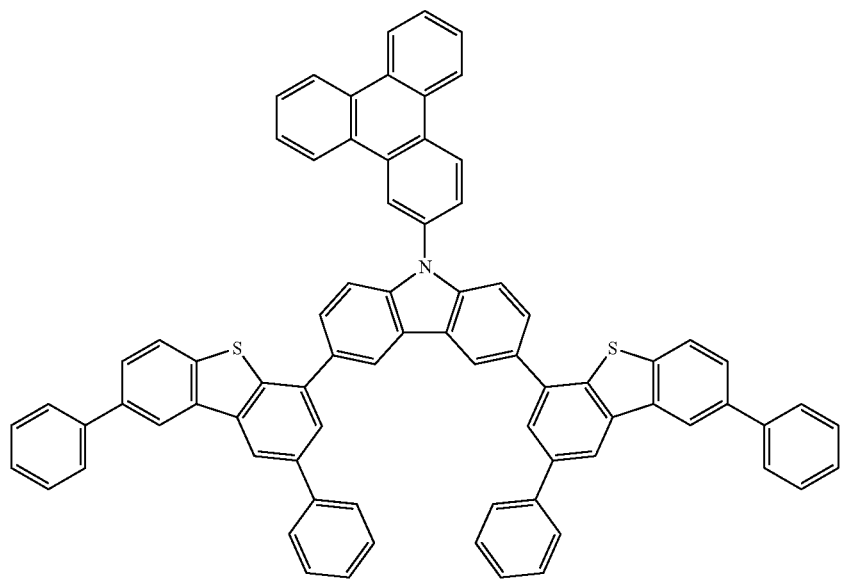
(157)
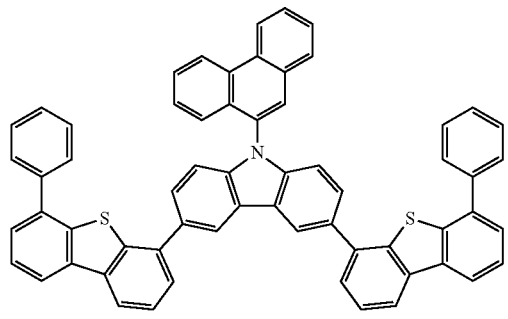
(158)
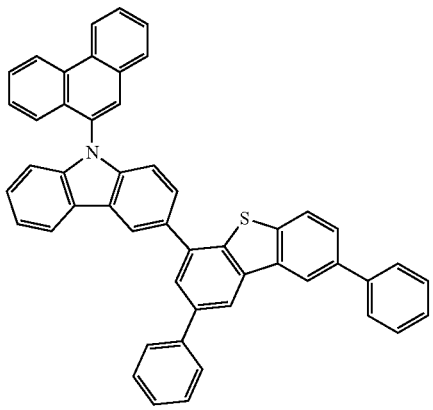
(159)
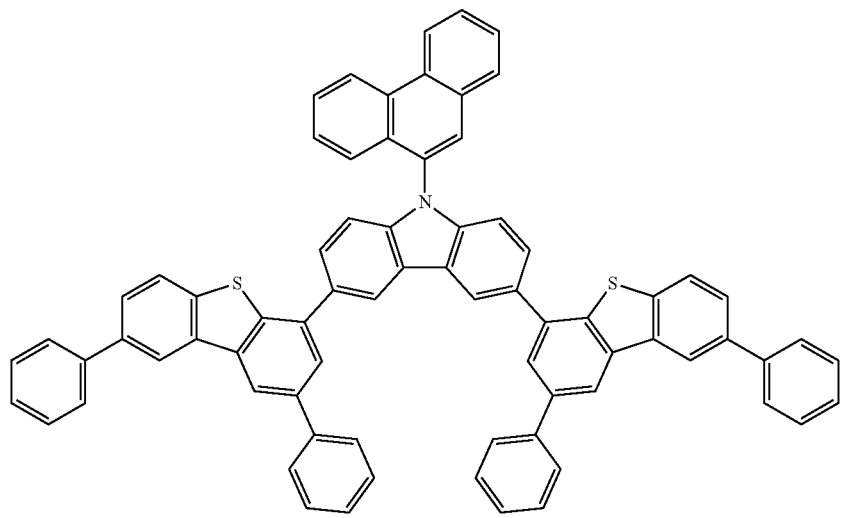

-continued
(160)
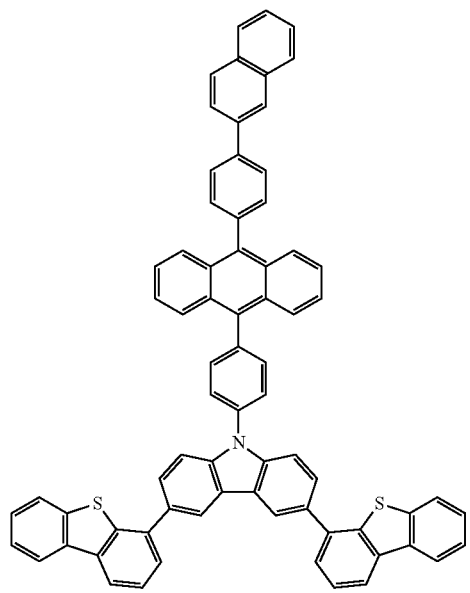
(161)
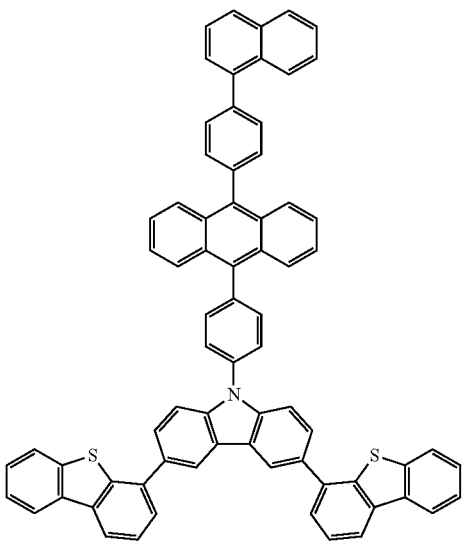
(162)
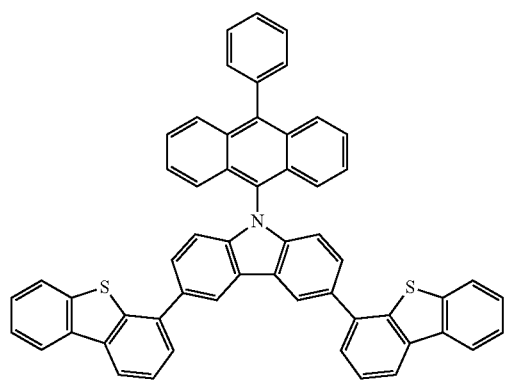
(163)
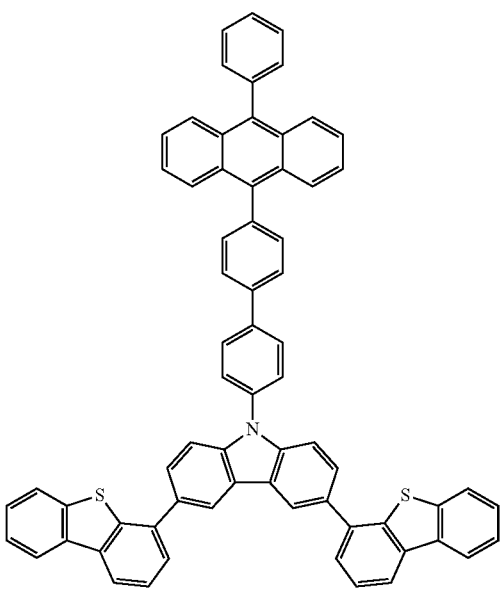
(164)
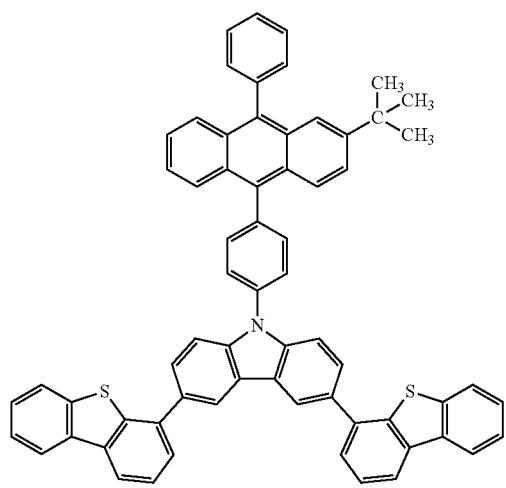
(165)
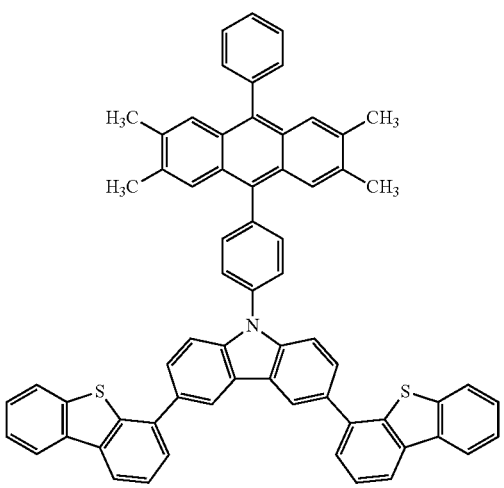

-continued
(166)
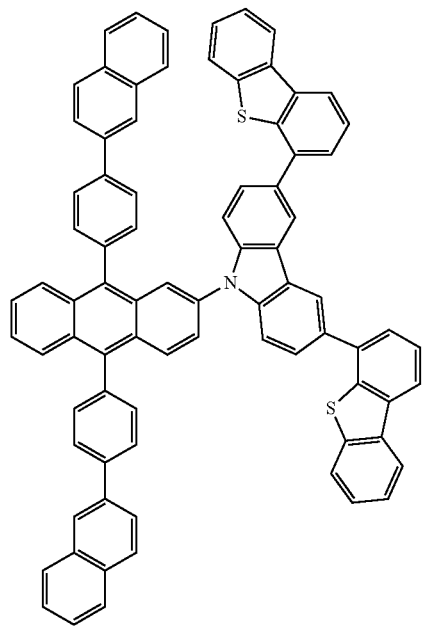
(167)
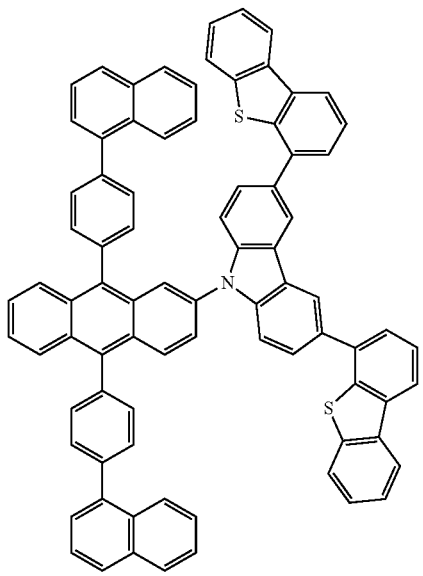
(168)
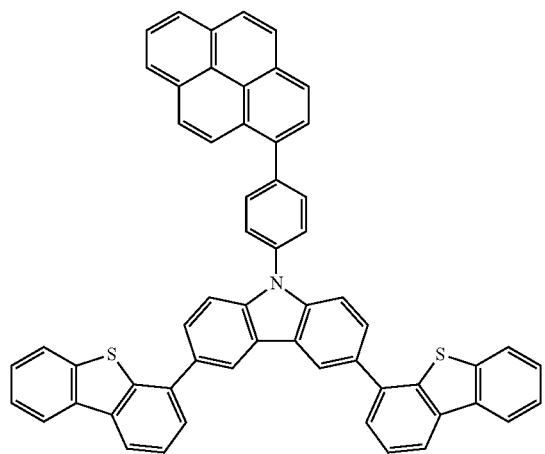
(169)
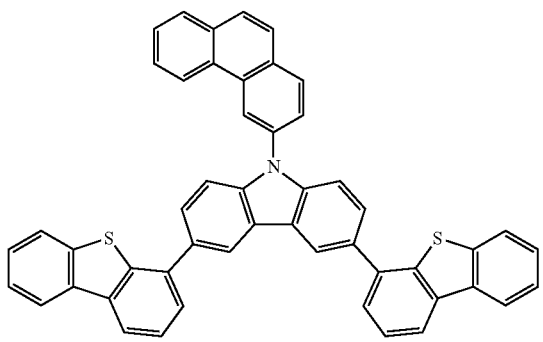
(170)
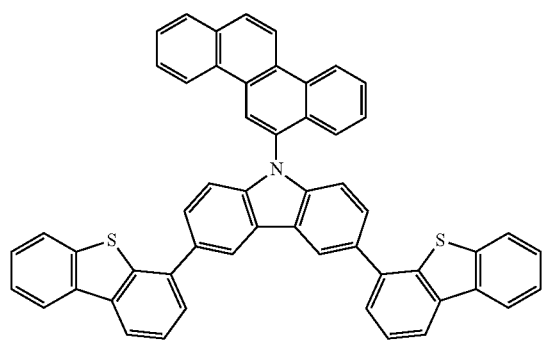
(171)
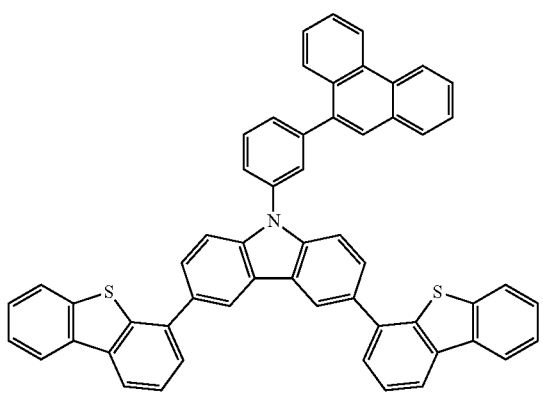

(172)
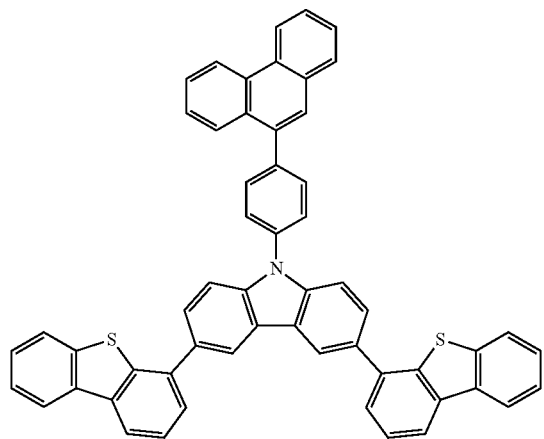
(181)
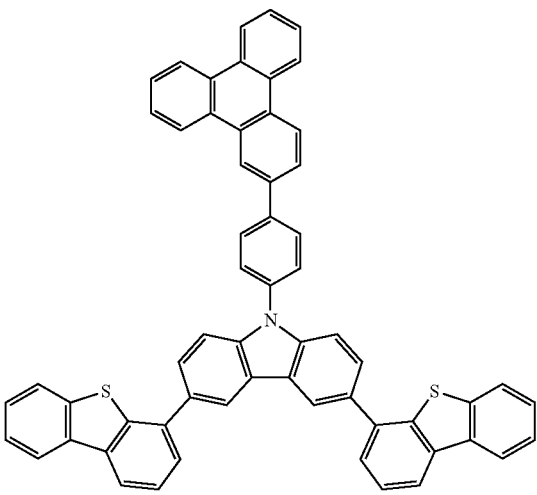
(182)
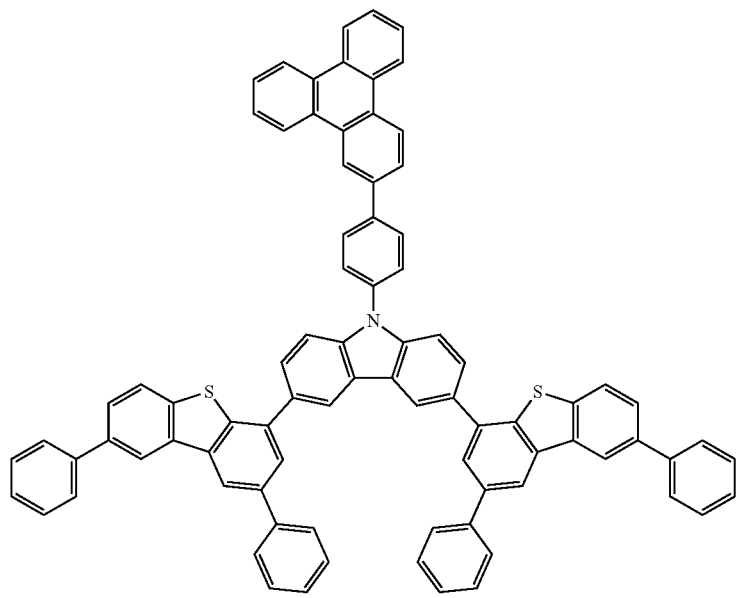

(183)
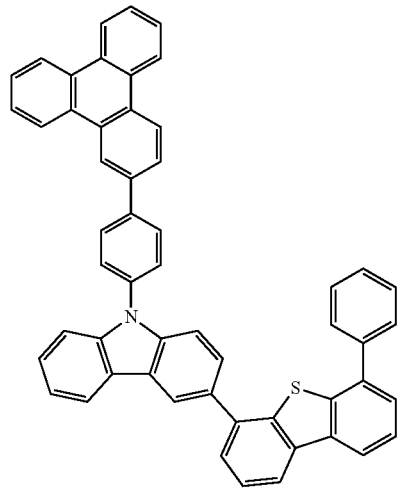
(184)
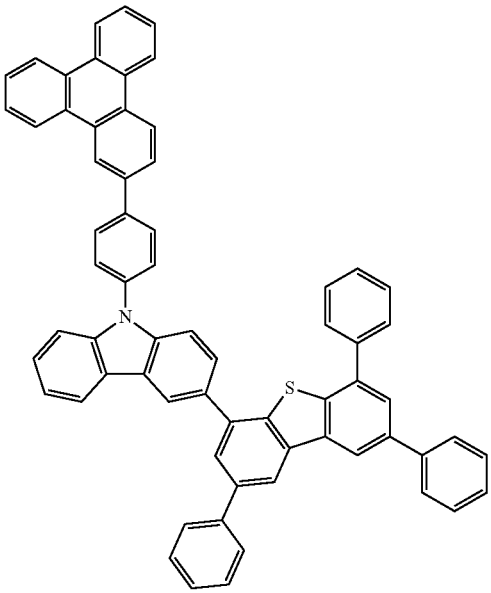
(191)
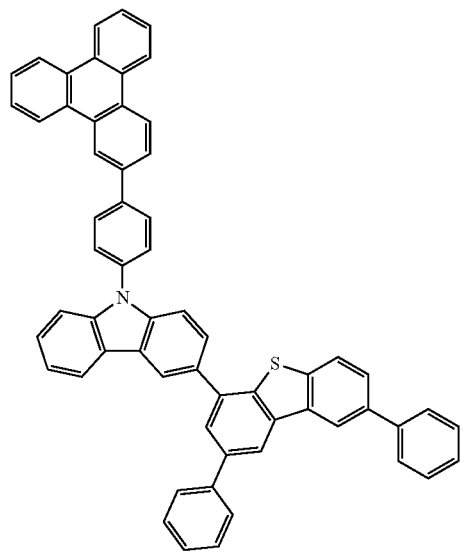
(192)
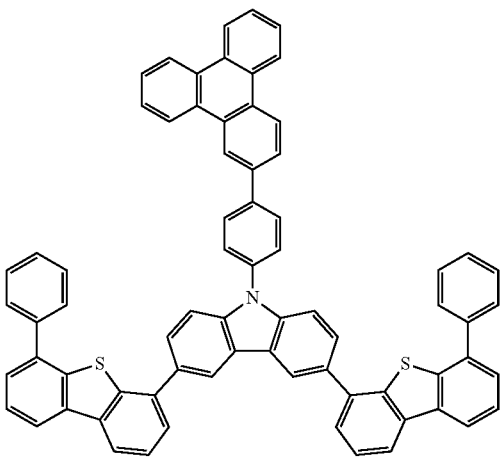

-continued
(193)
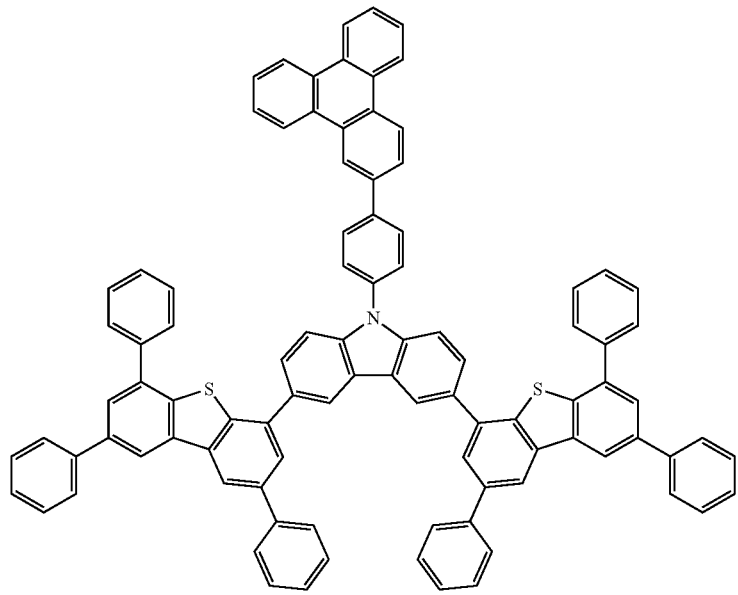
(194)
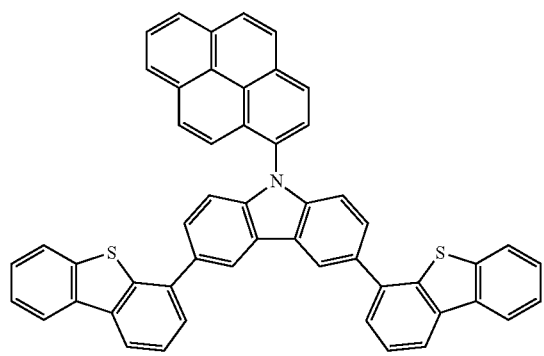
(195)
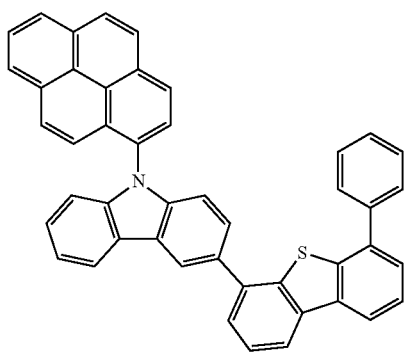
(196)
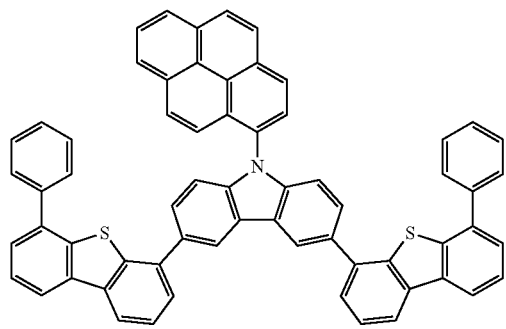
(197)
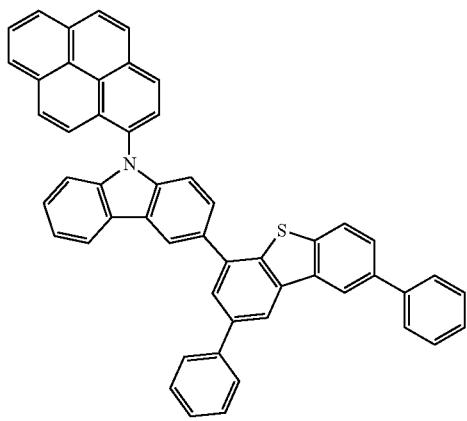

(198)
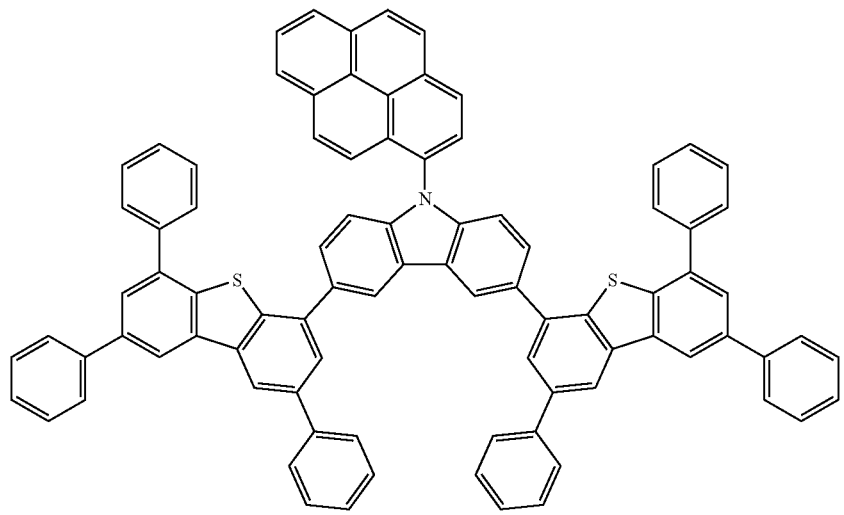
(199)
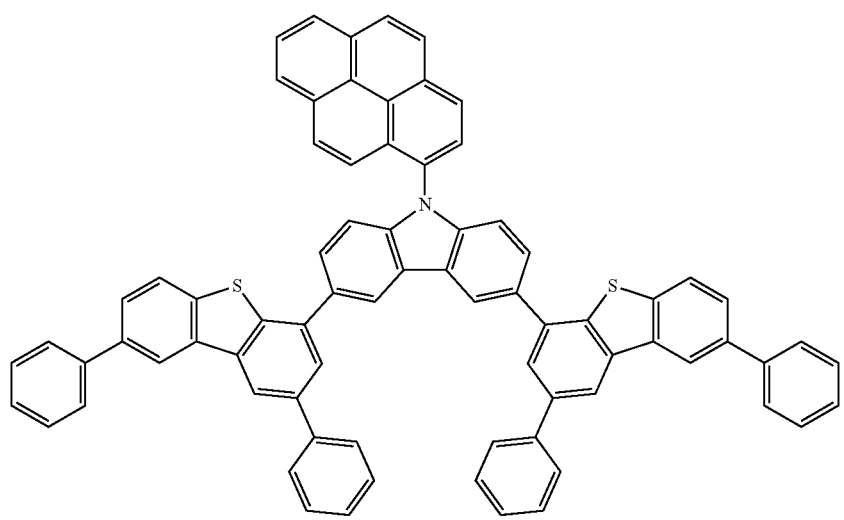
(200)
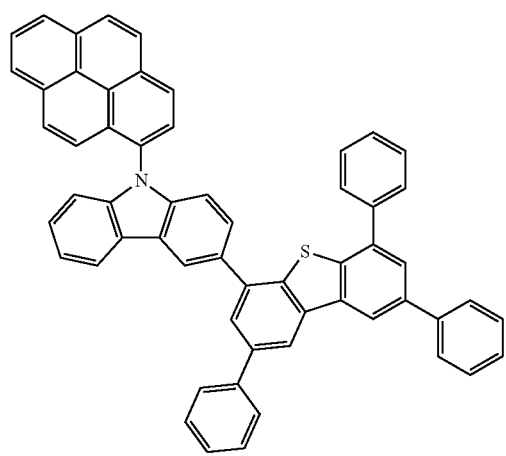
(201)
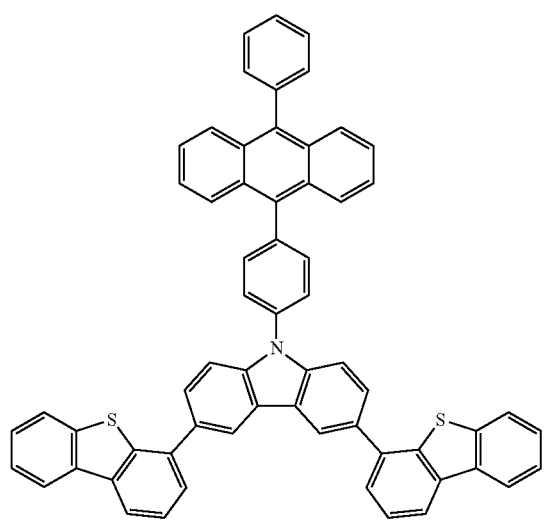

-continued
(202)
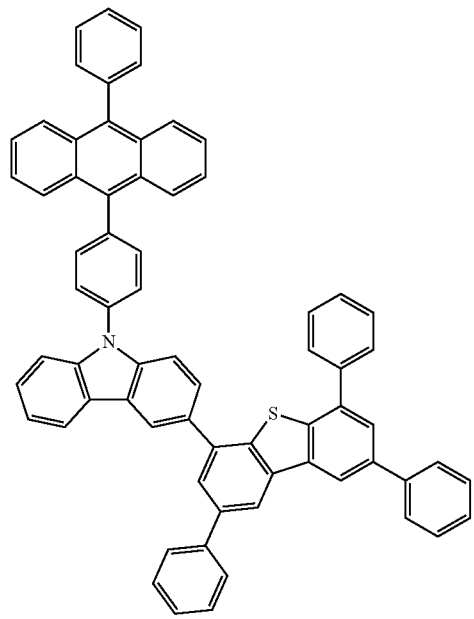
(203)
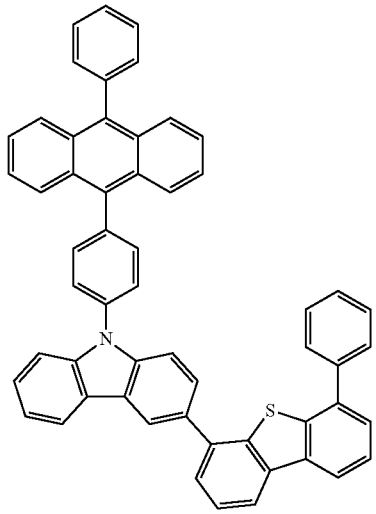
(204)
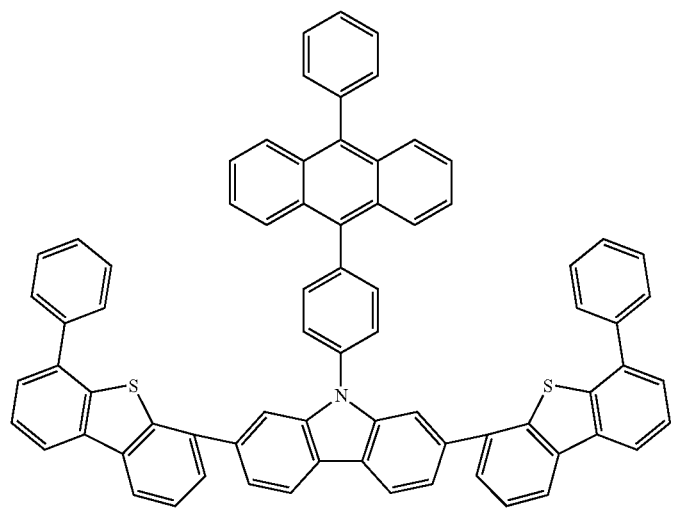

(205)
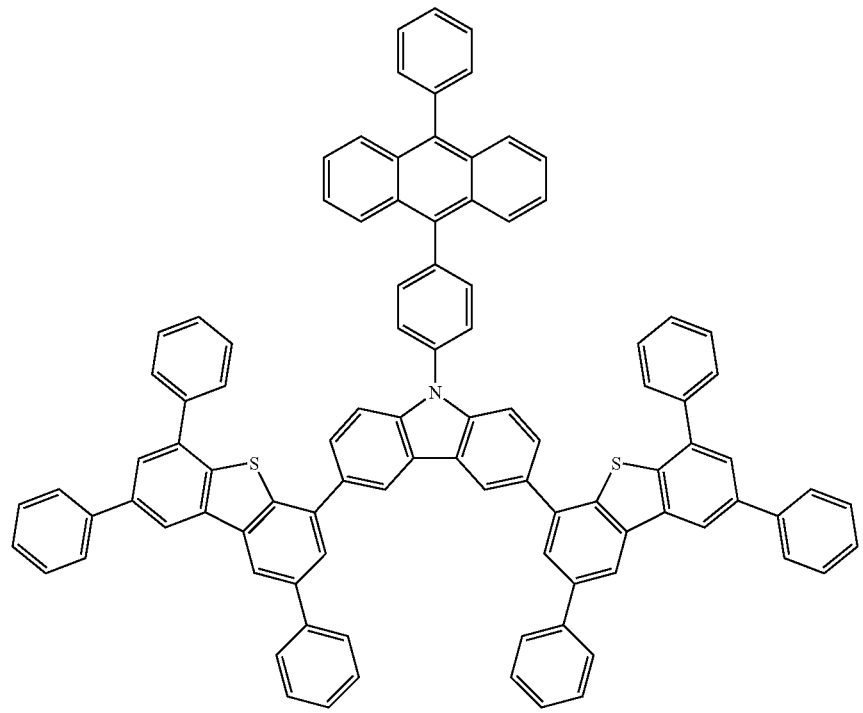
(206)
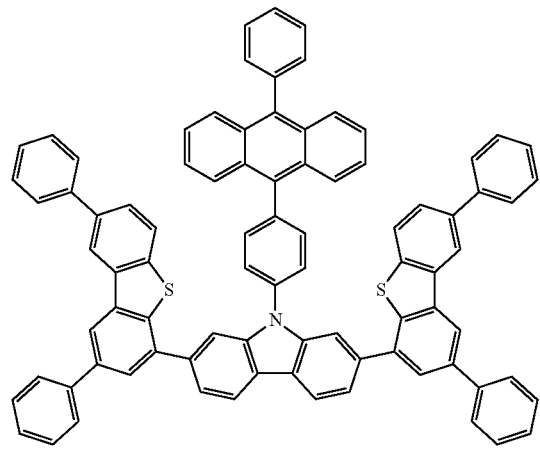
(207)
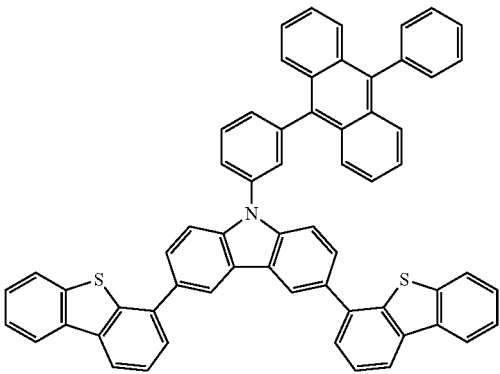
(208)
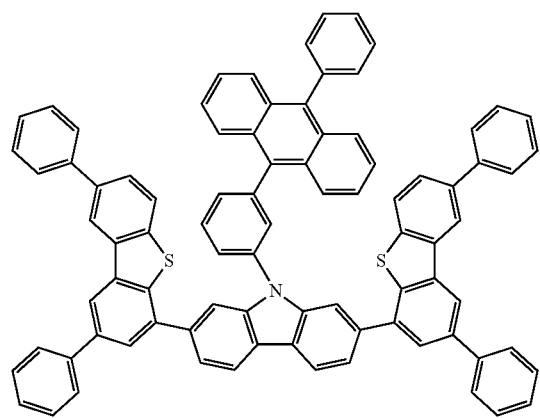
(209)
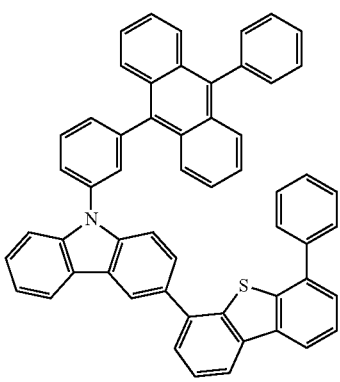

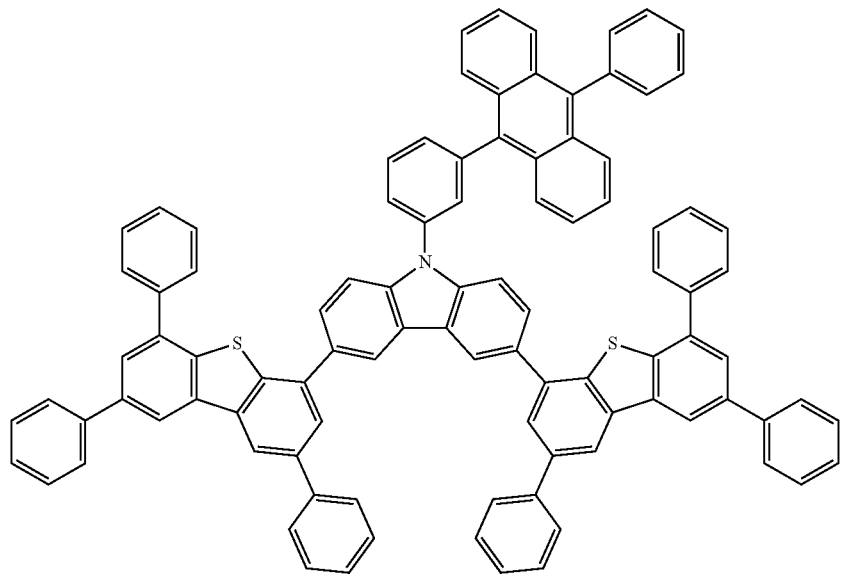
(210)
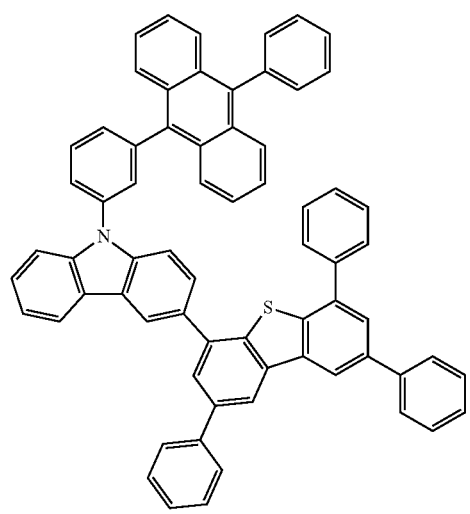
(211)
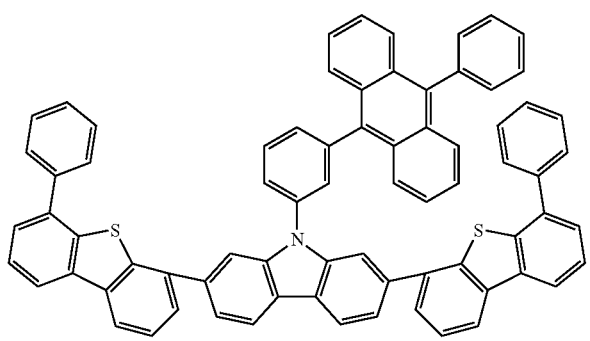
(212)

-continued
(213)
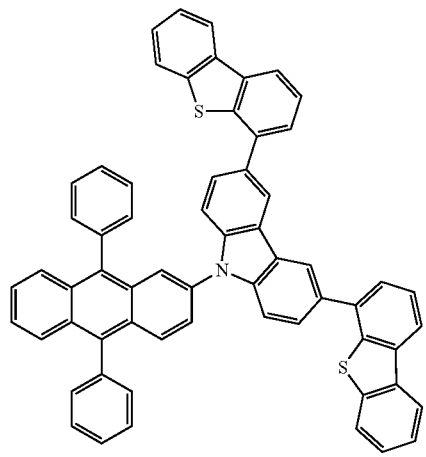
(214)
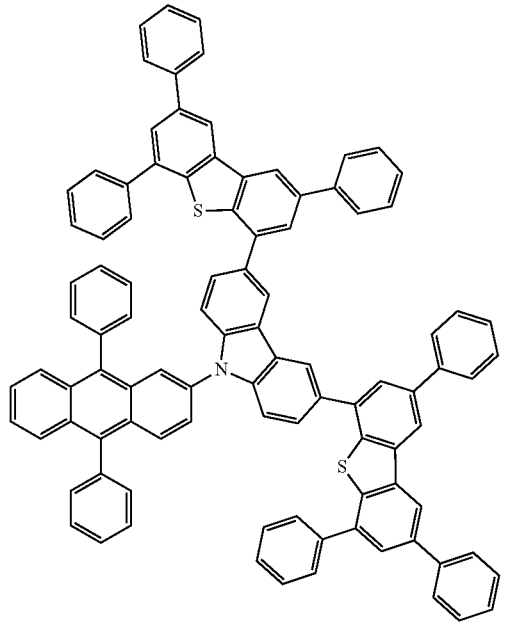
(215)
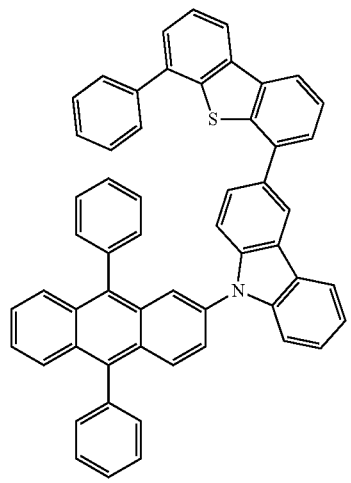
(216)
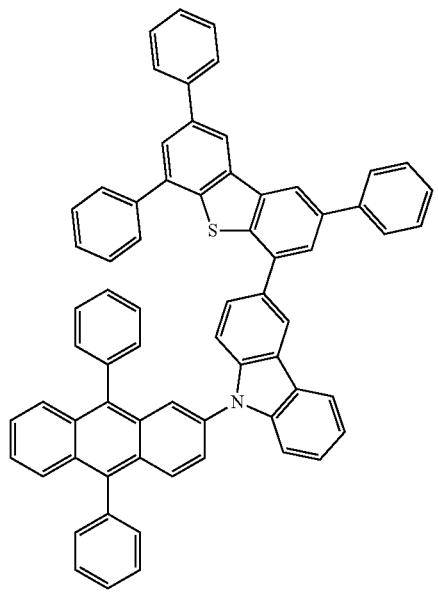

-continued
(217)
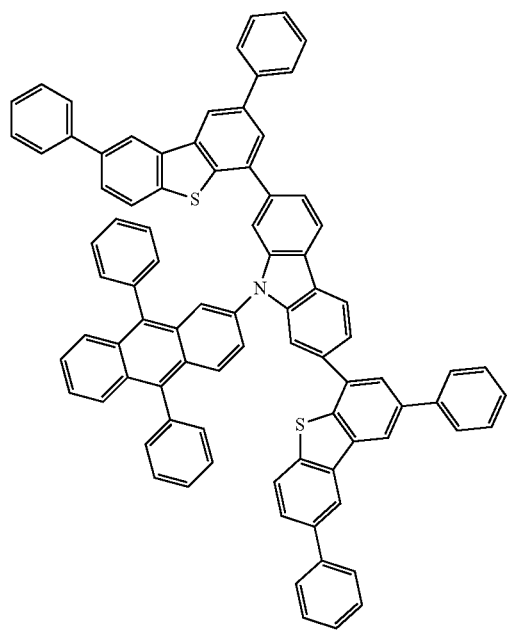
(218)
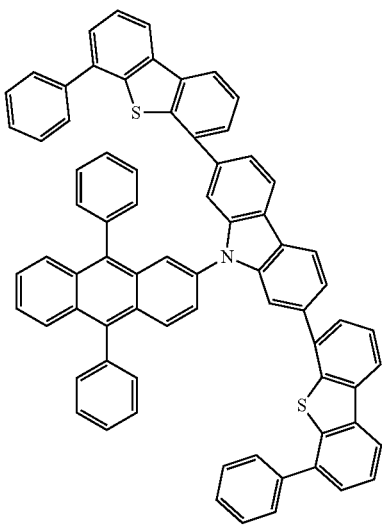
(219)
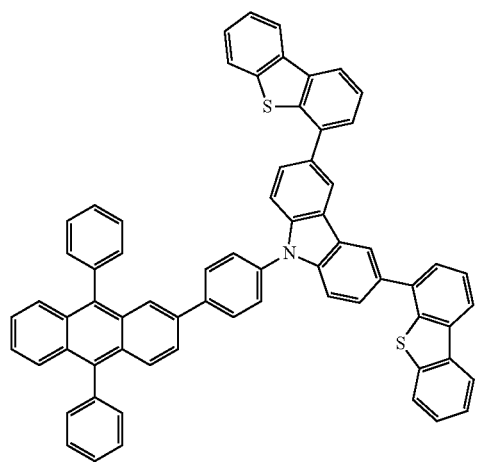
(220)
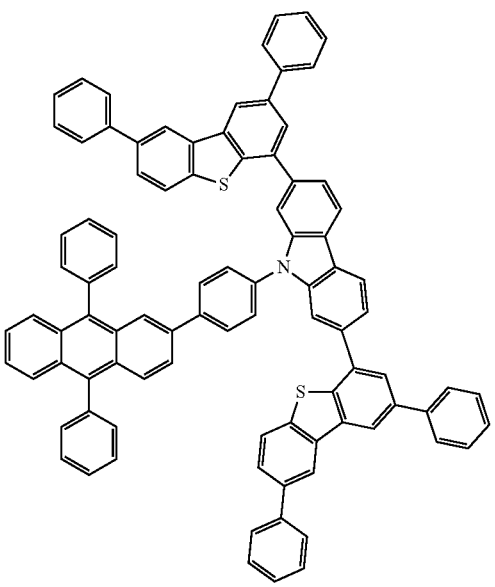

-continued
(221)
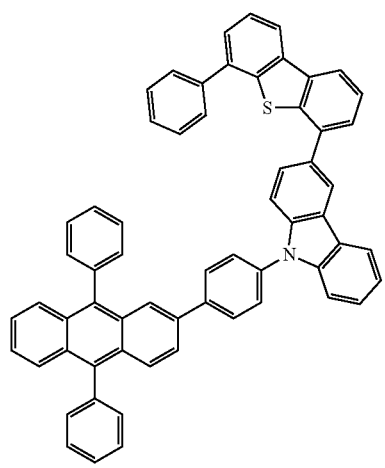
(222)
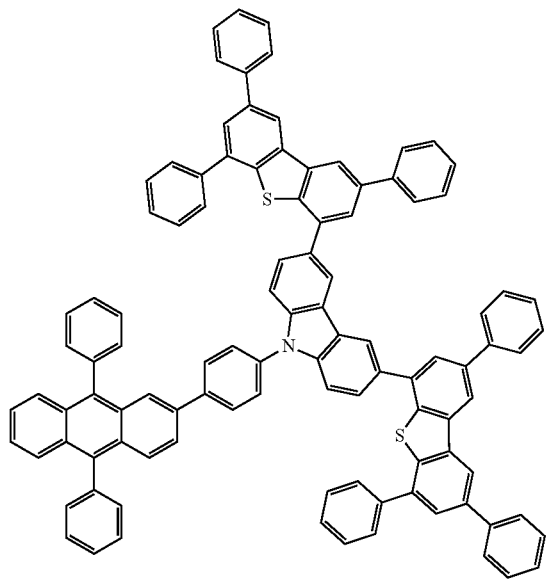
(223)
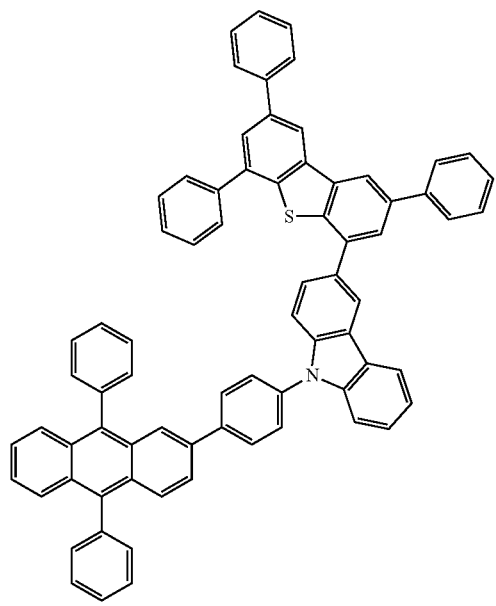
(224)
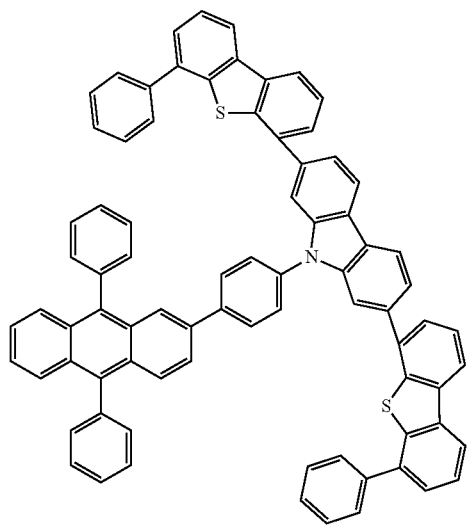

(225)
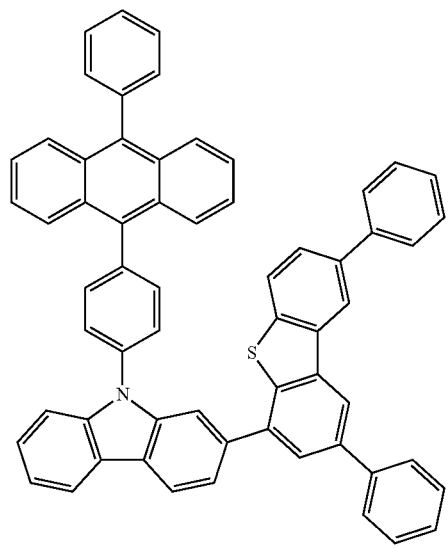
(226)
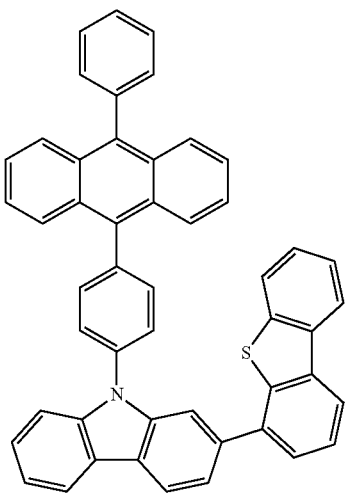
(227)
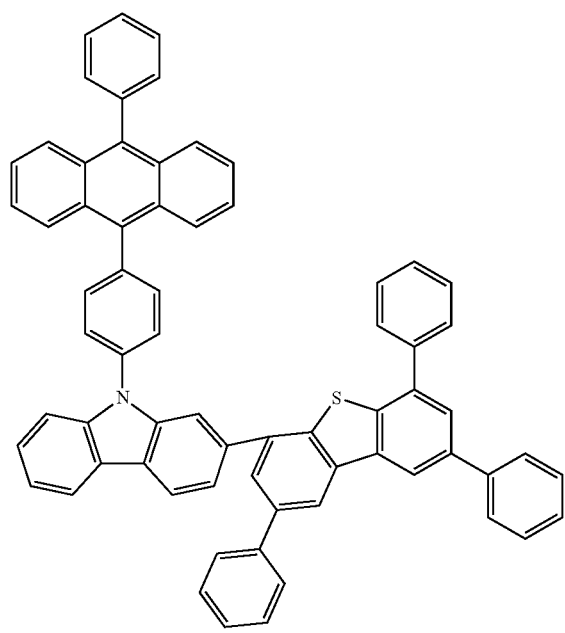
(228)
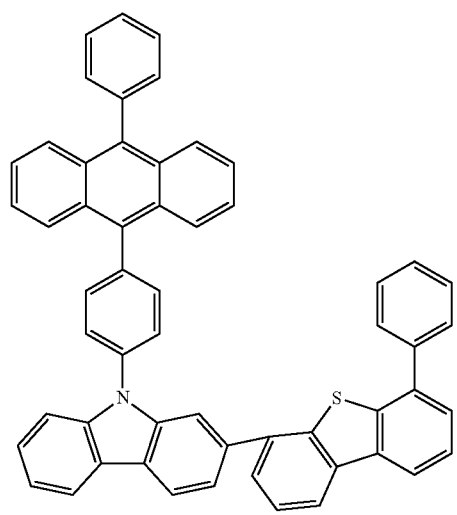

(229)
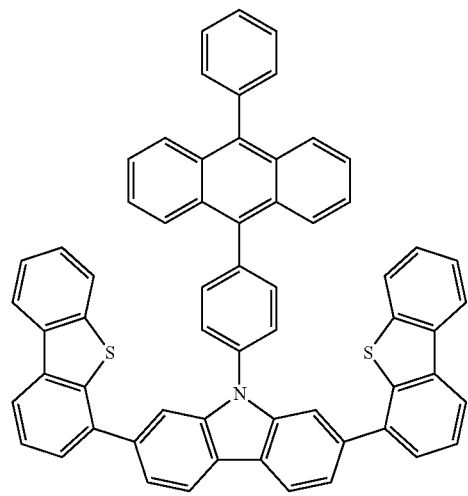
(230)
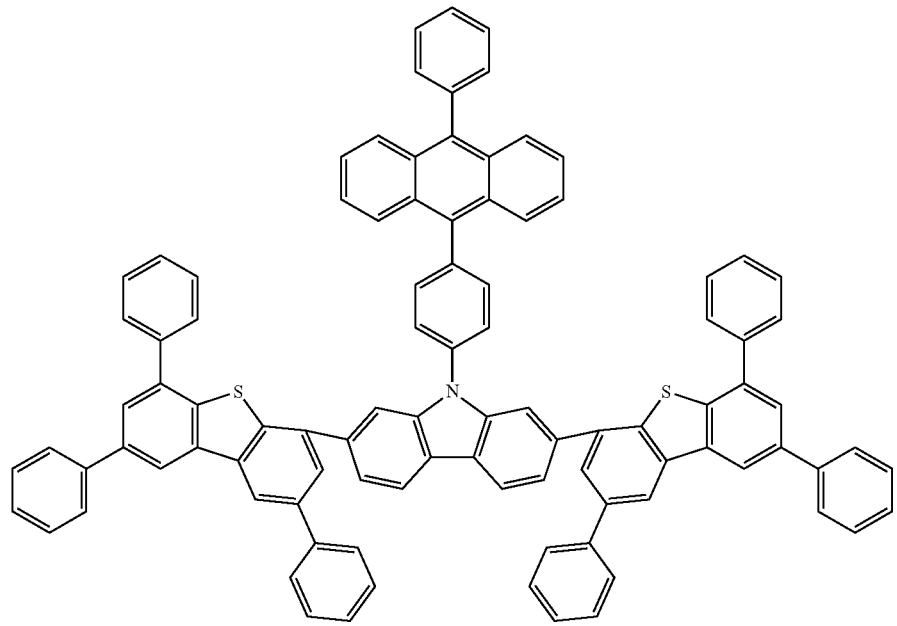
(231)
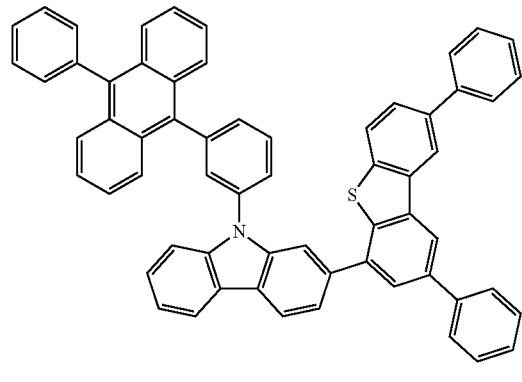
(232)
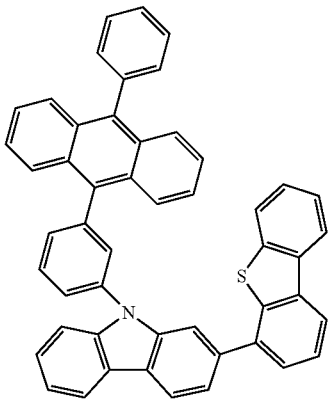

-continued
(233)
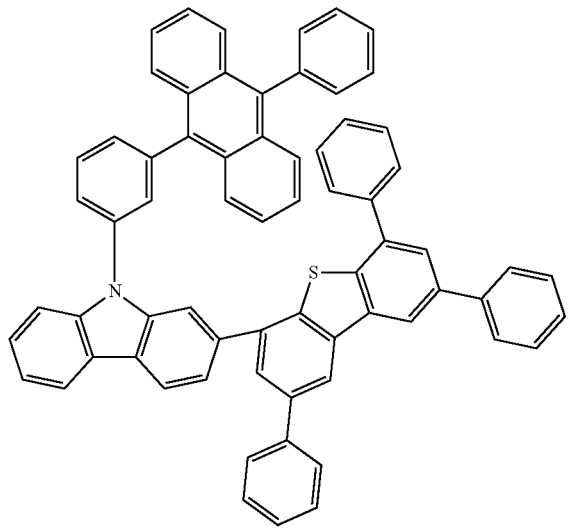
(234)
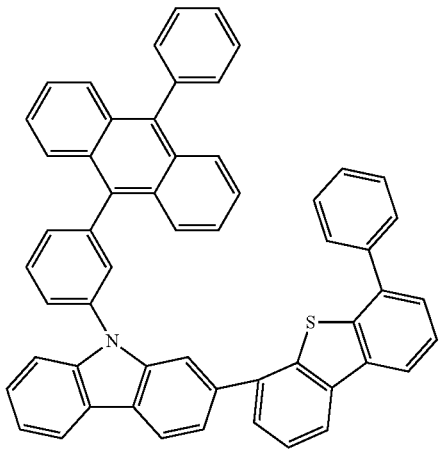
(235)
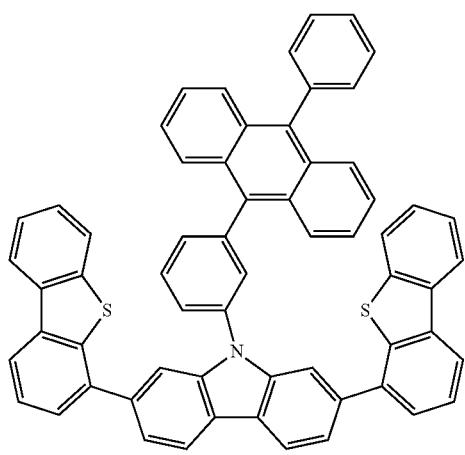
(236)
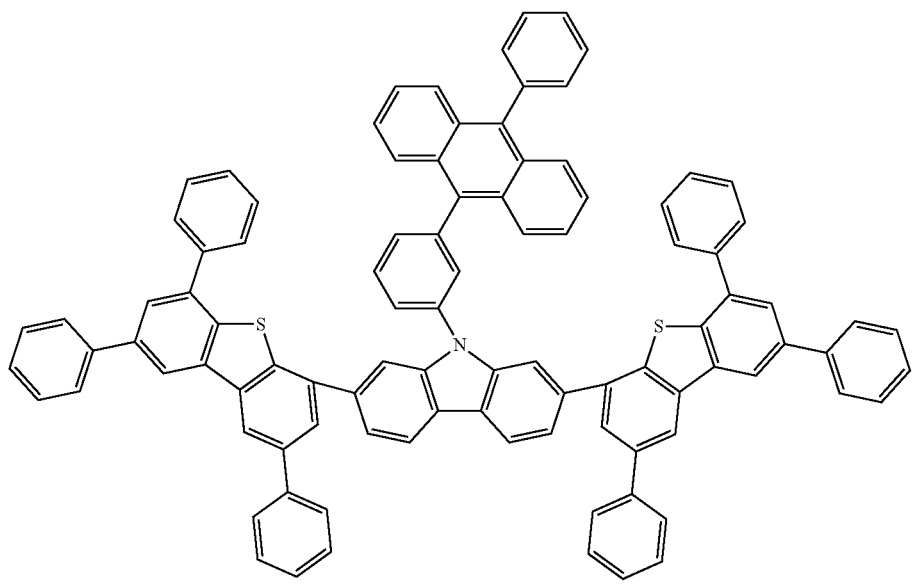

-continued
(237)
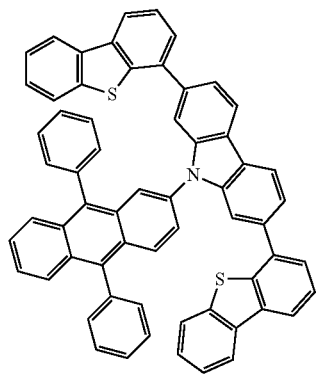
(238)
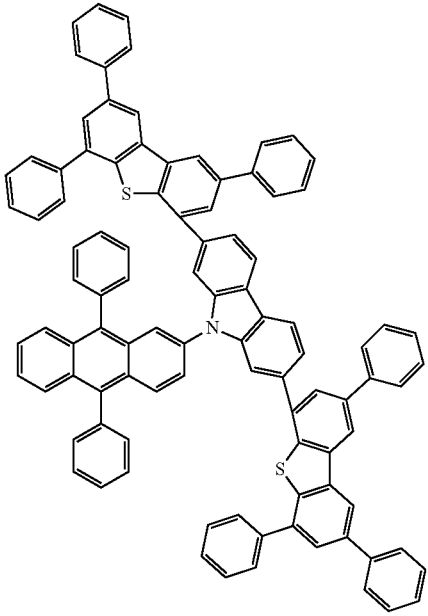
(239)
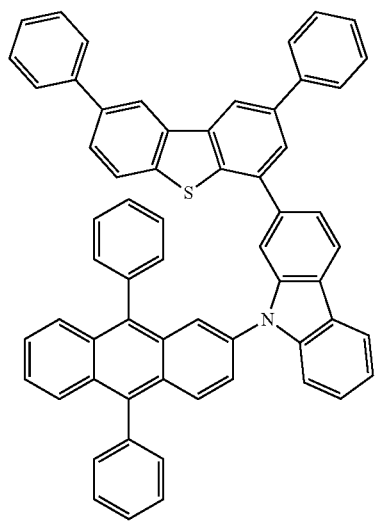
(240)
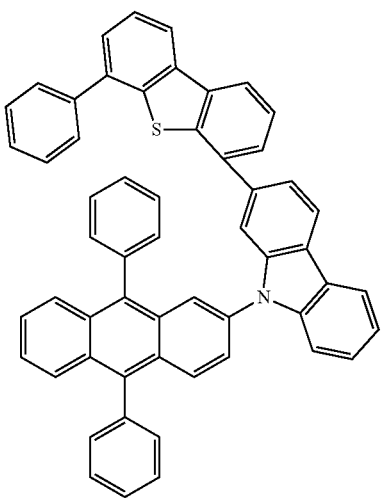

-continued
(241)
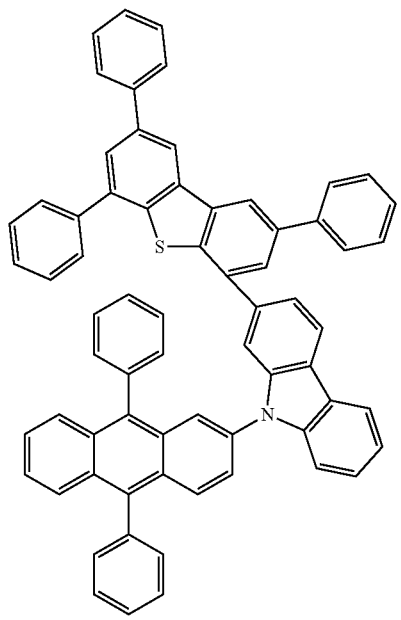
(242)
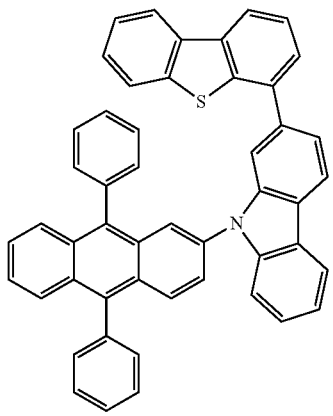
(243)
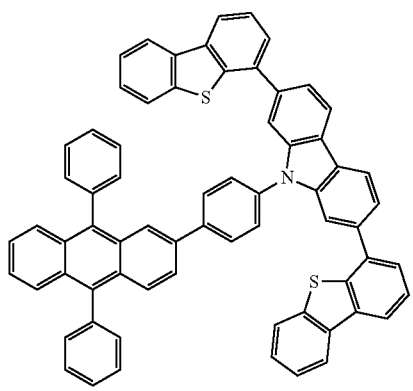
(244)
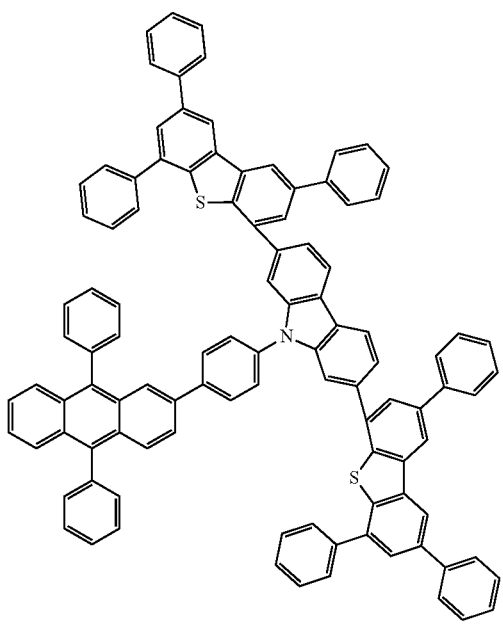

-continued
(245)
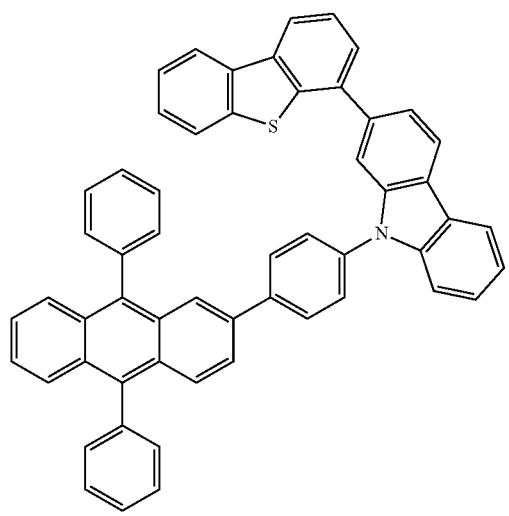
(246)
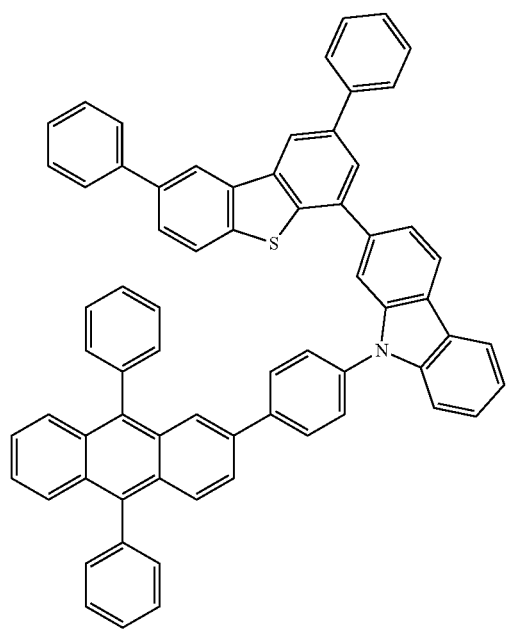
(247)
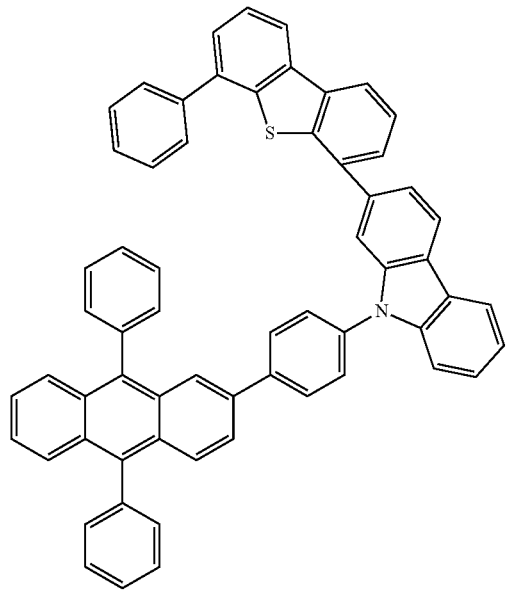
(248)
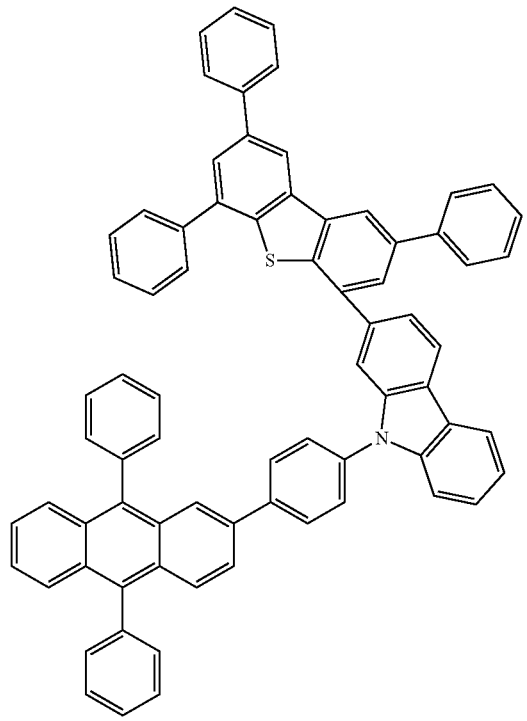

(249)
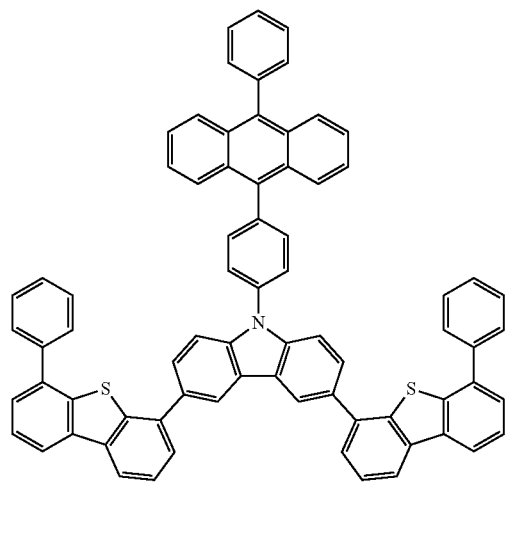
(250)
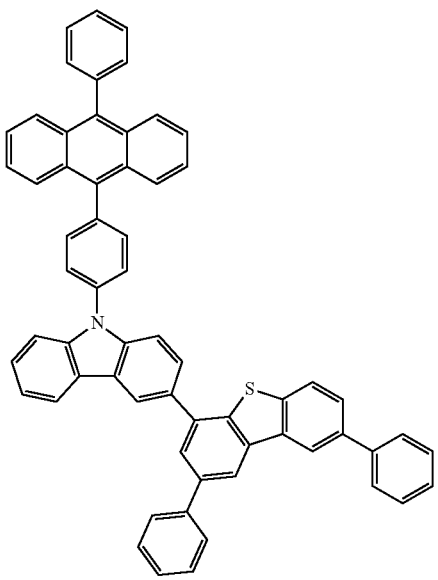
(251)
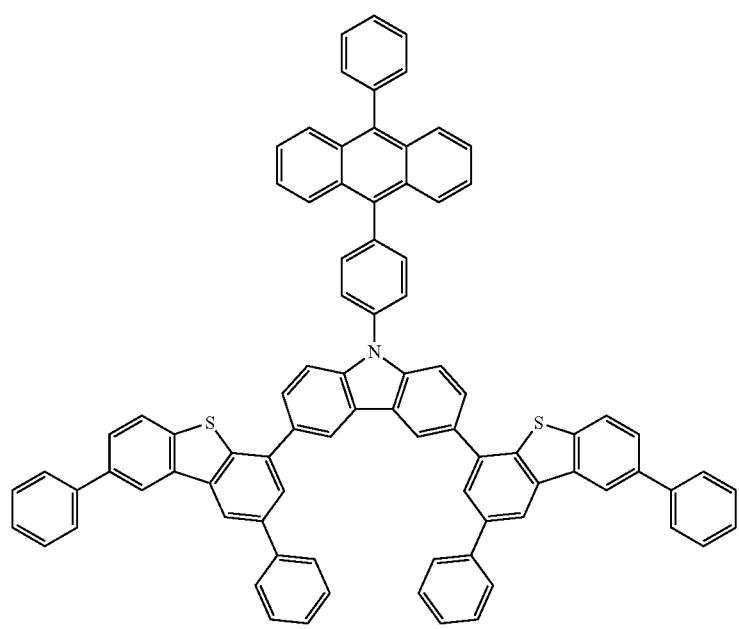

-continued
(252)
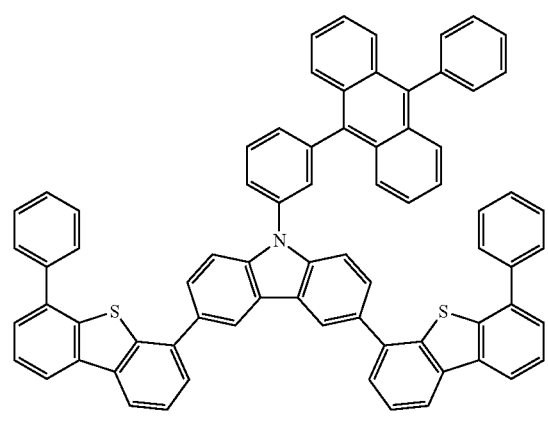
(253)
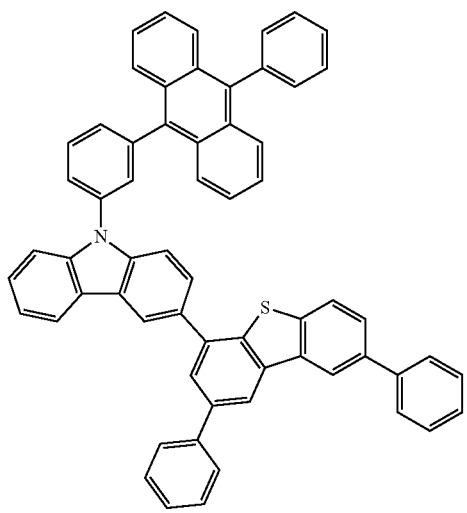
(254)
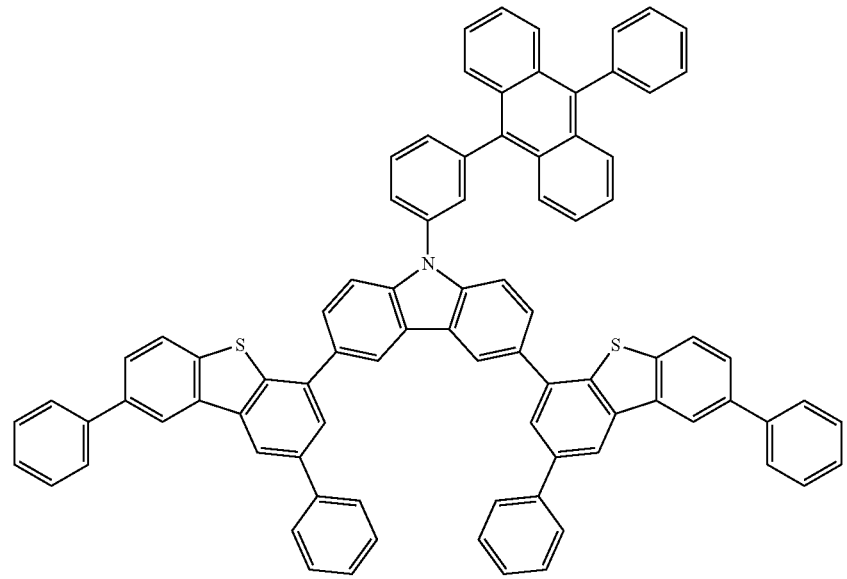

-continued
(255)
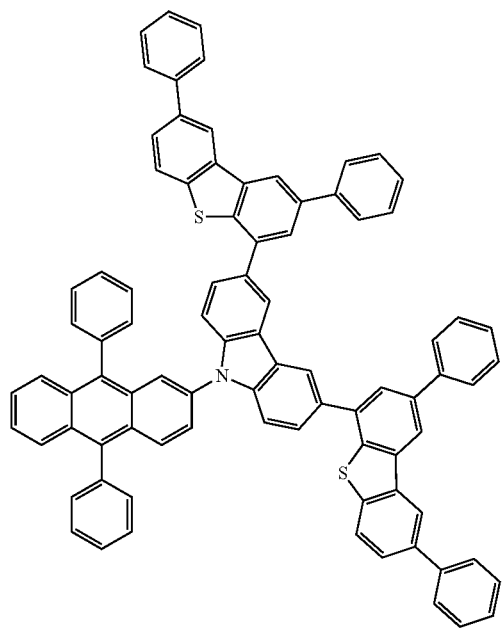
(256)
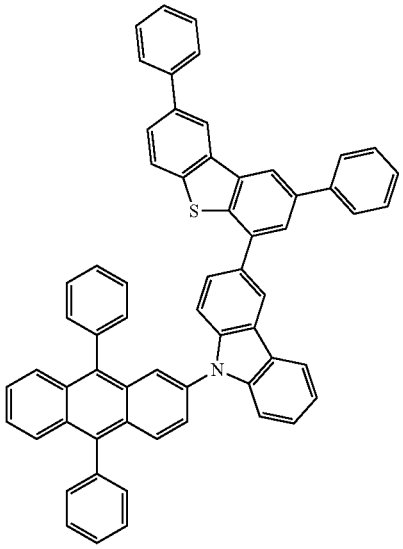
(257)
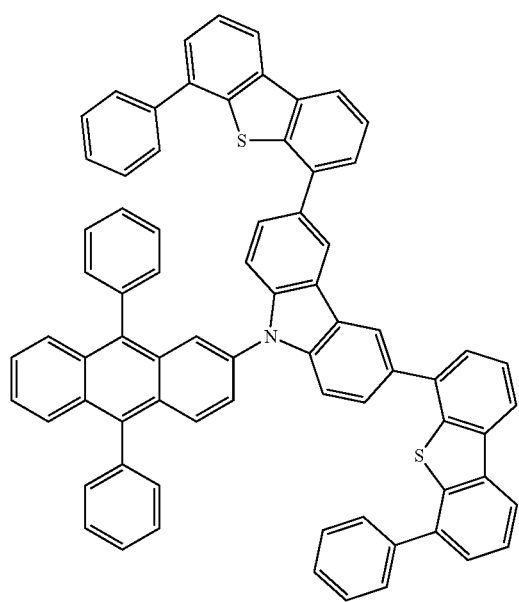

-continued
(258)
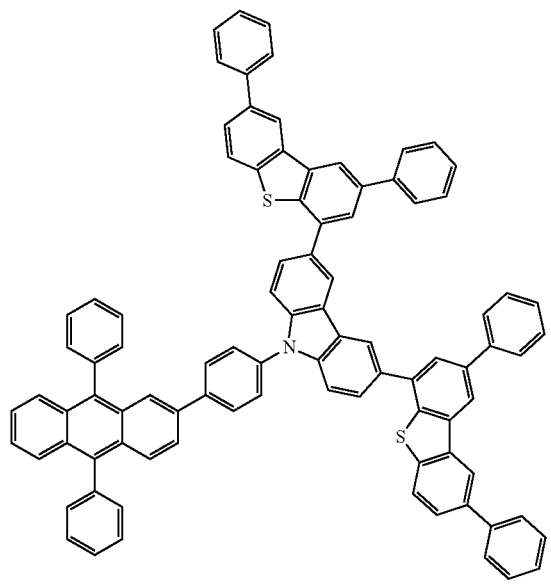
(259)
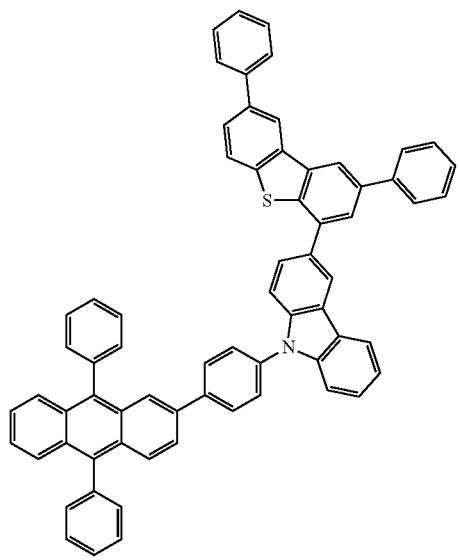
(260)
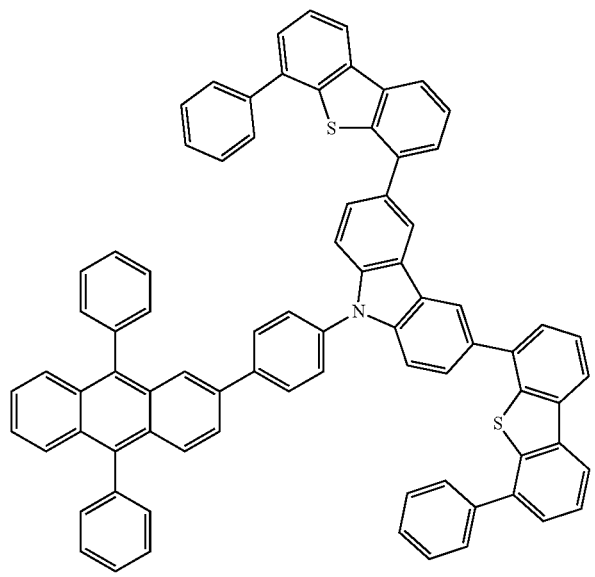
(261)
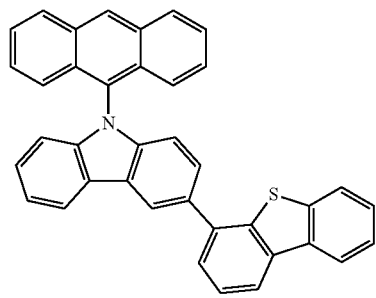

-continued
(262)
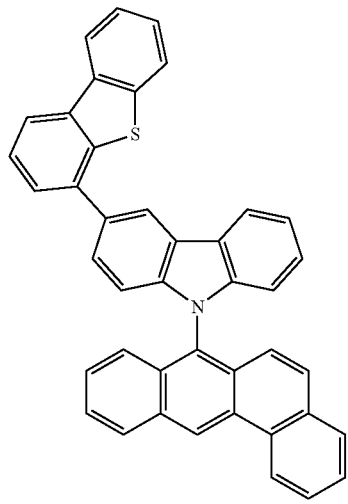
(263)
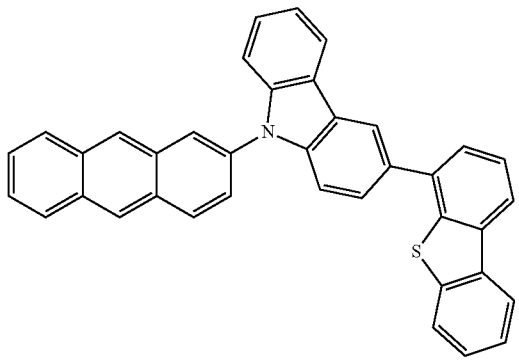
(264)
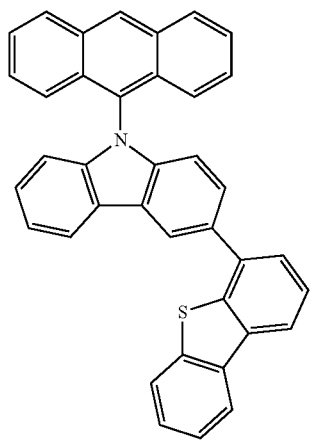
(265)
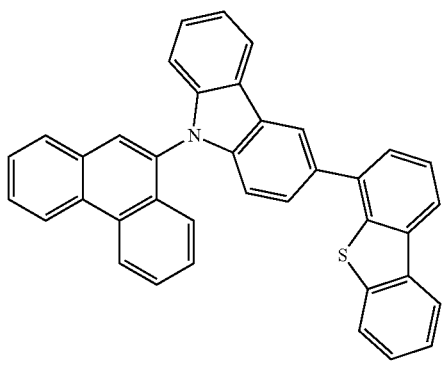
(266)
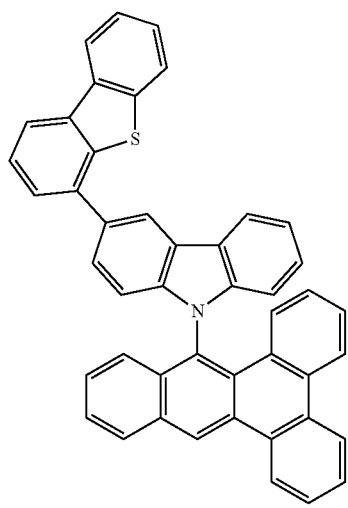
(267)
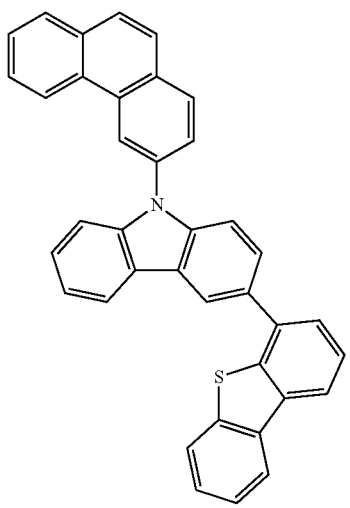

-continued
(268)
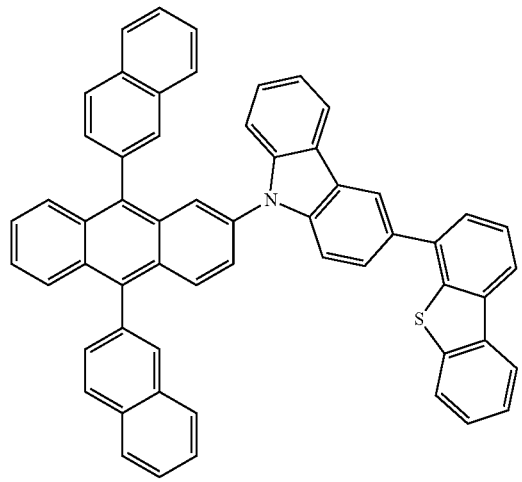
(269)
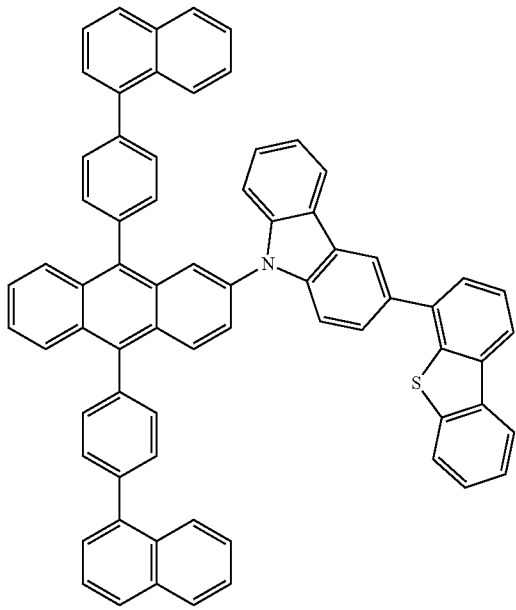
(270)
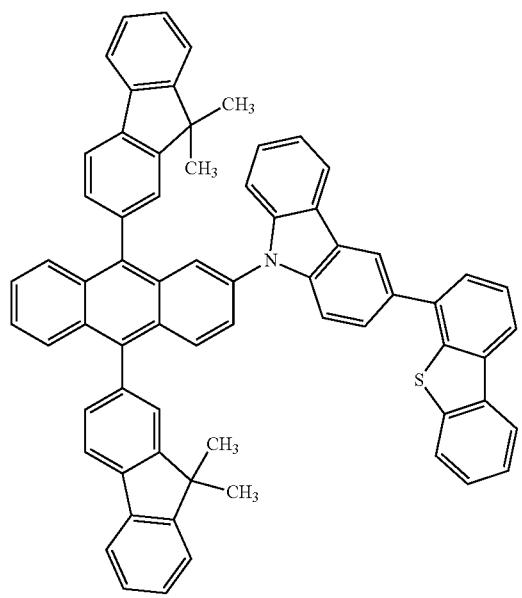
(273)
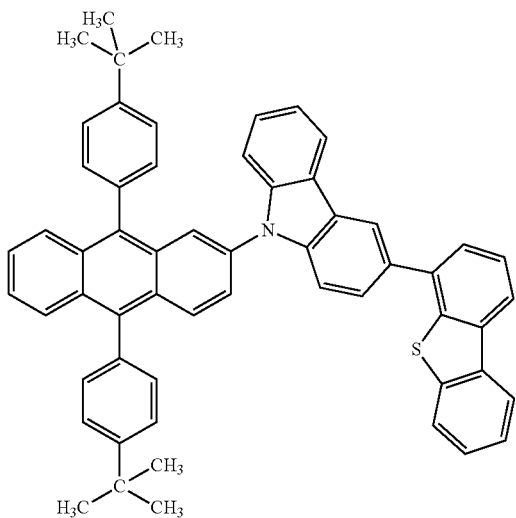
(274)
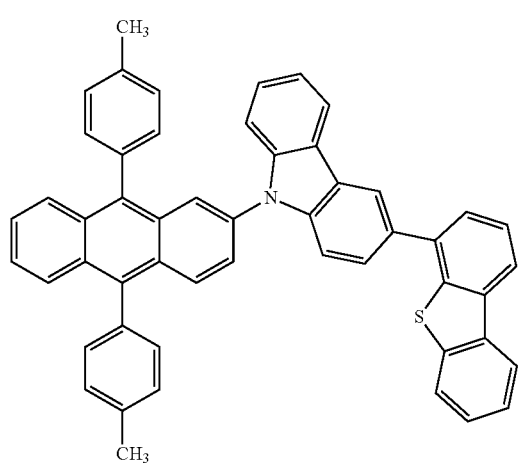
(275)
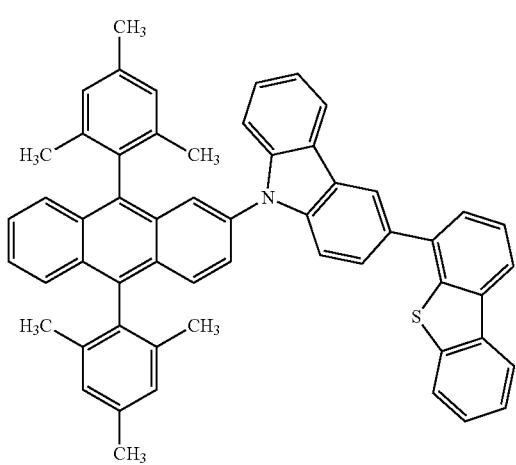

-continued
(279)
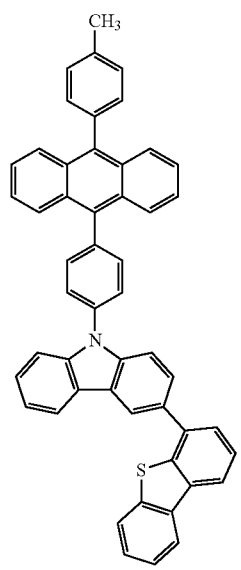
(280)
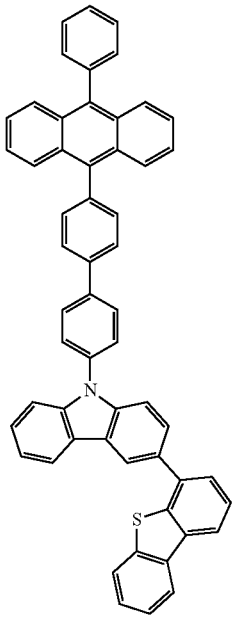
(282)
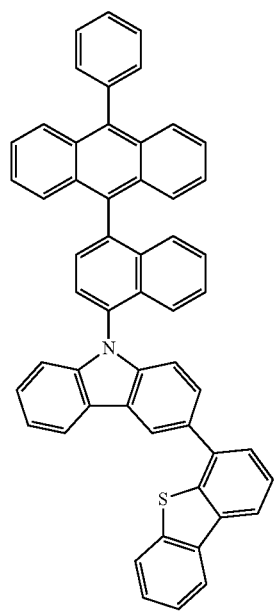
(283)
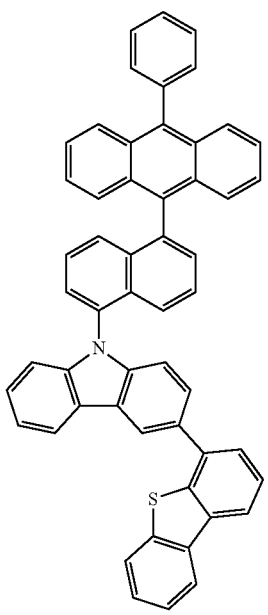
(285)
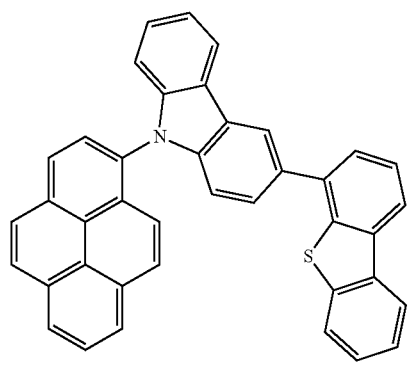
(286)
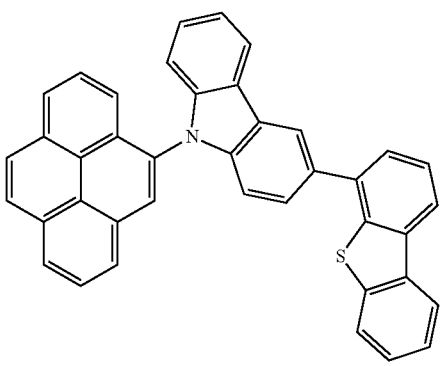

-continued
(287)
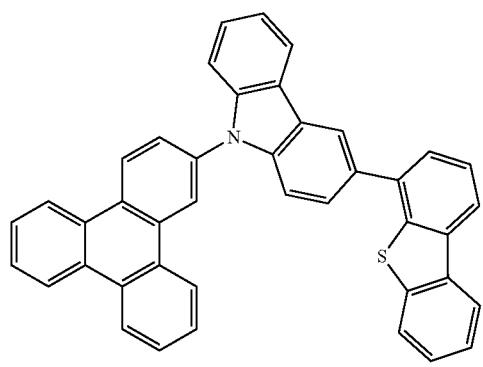
(288)
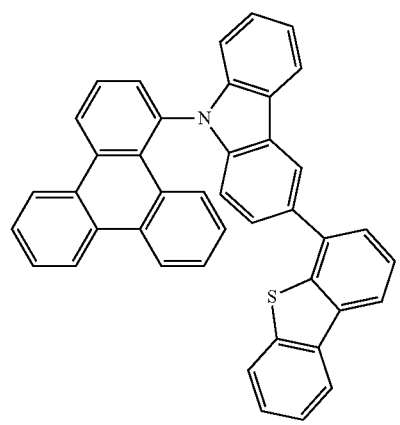
(289)
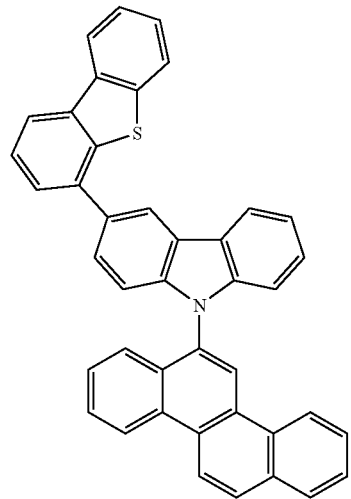
(290)
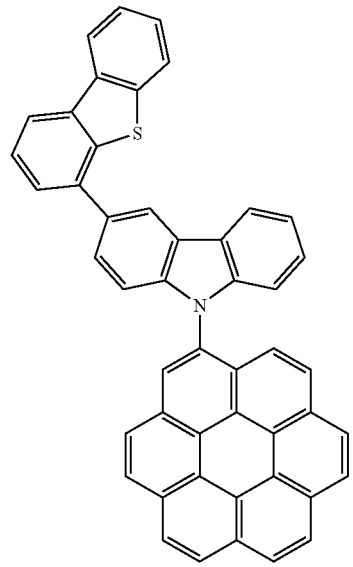
(292)
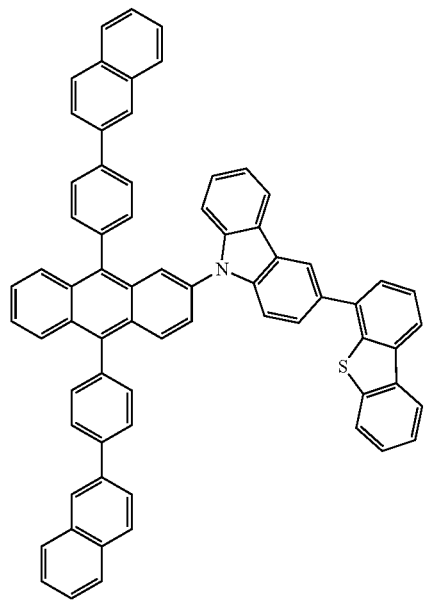
(293)
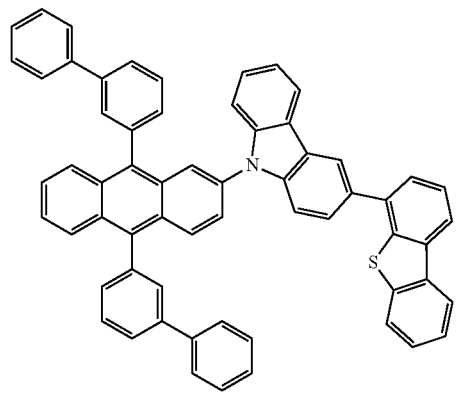

-continued
(294)
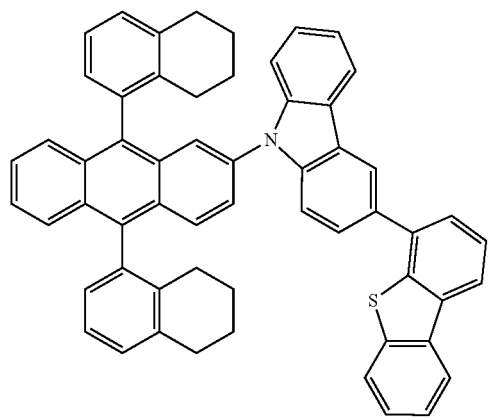
(295)
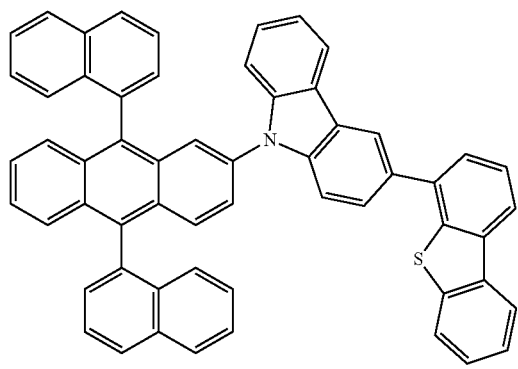
(296)
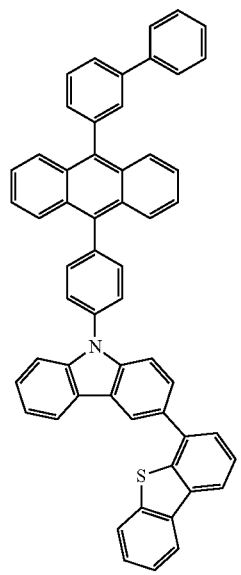
(297)
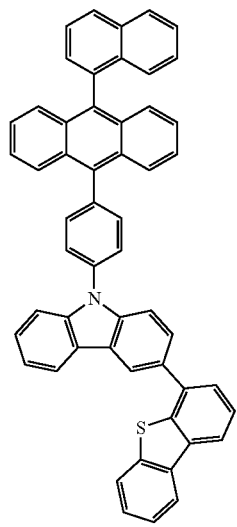
(298)
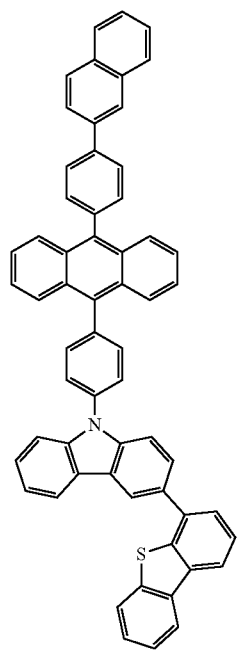
(299)
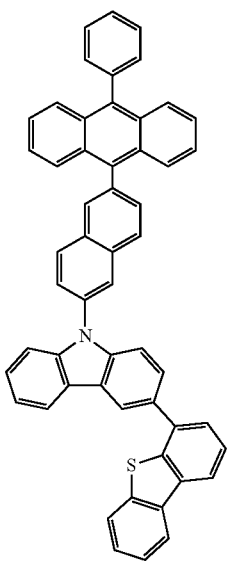

-continued
(302)
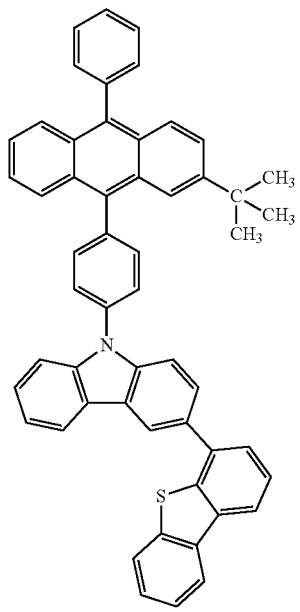
(312)
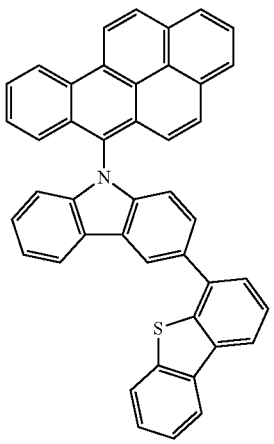
(313)
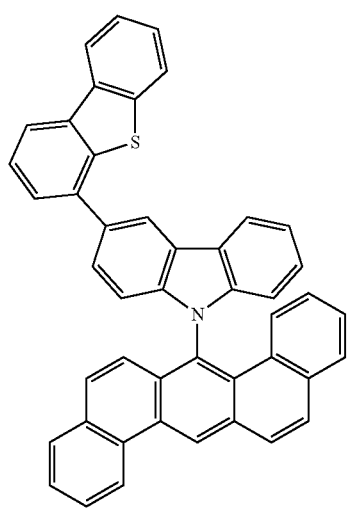
(314)
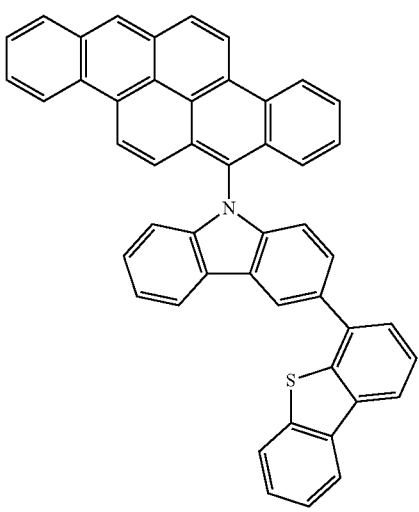

-continued
(315)
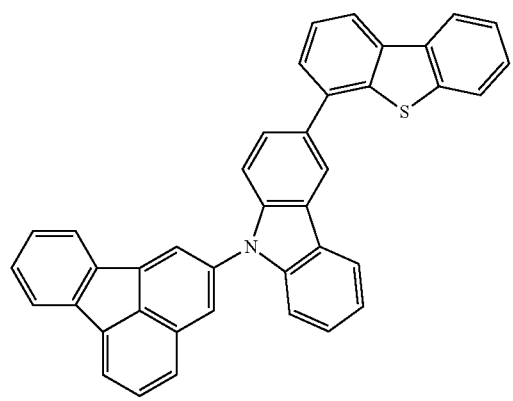
(317)
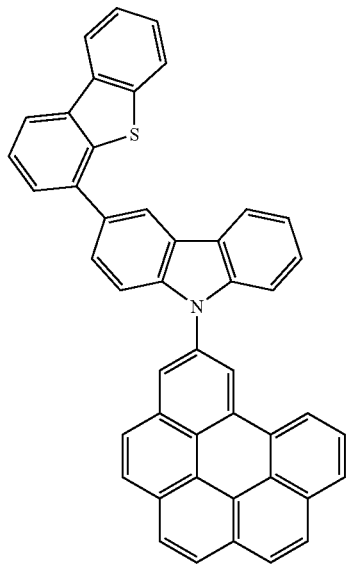
(318)
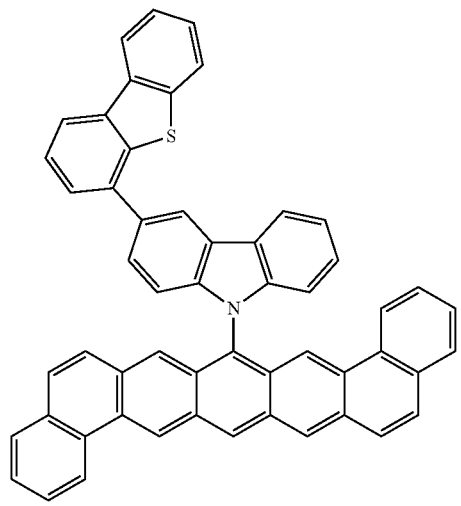
(319)
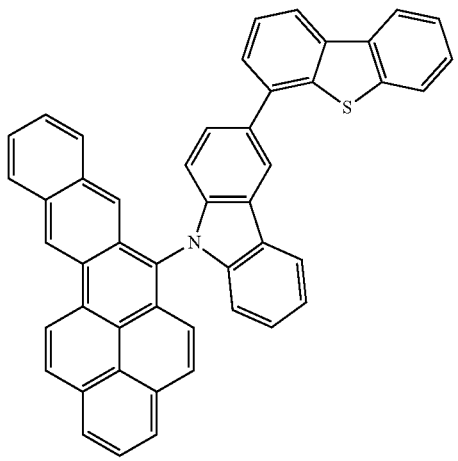
(320)
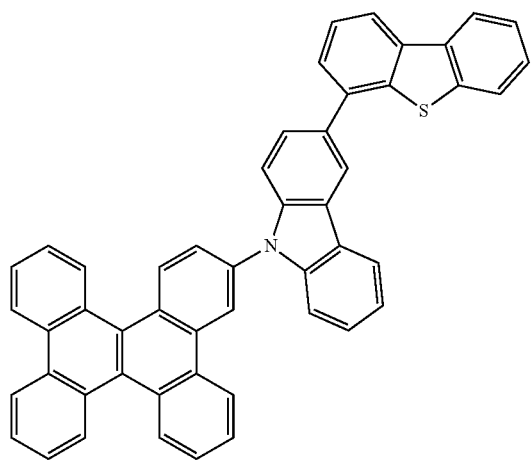
(321)
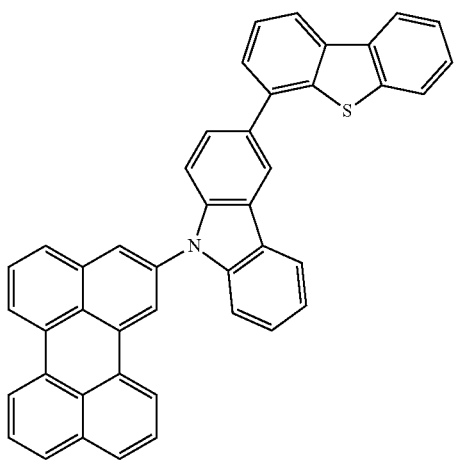

-continued
(322)
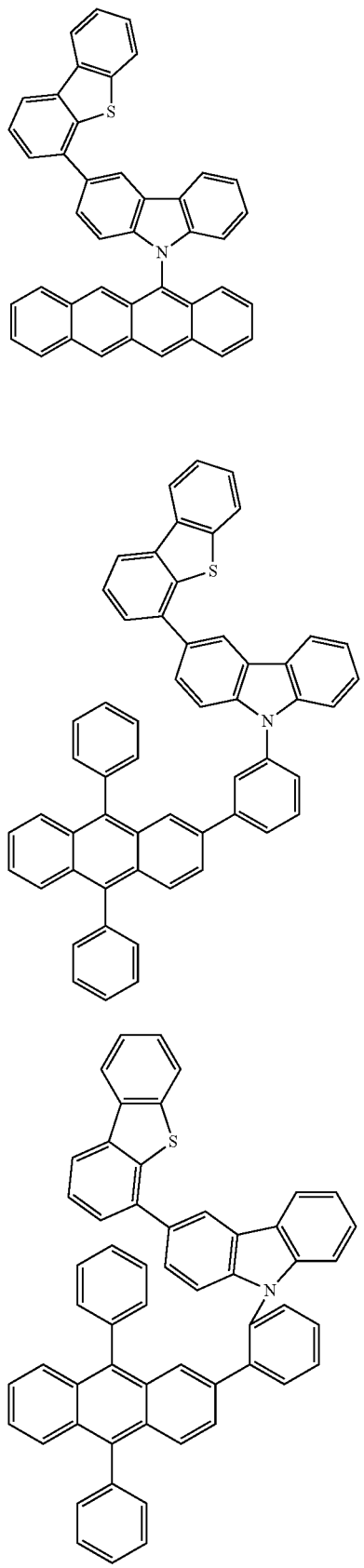
(323)
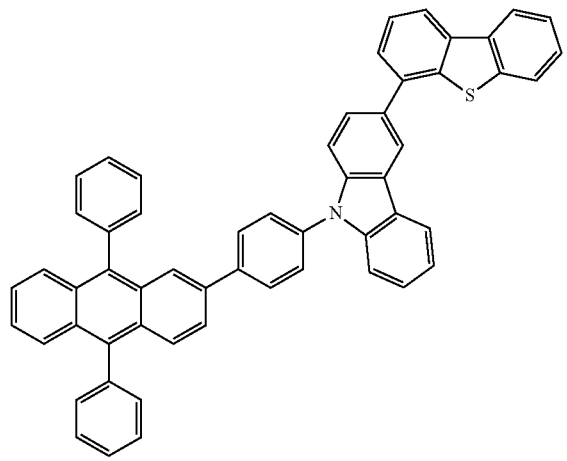
(324)
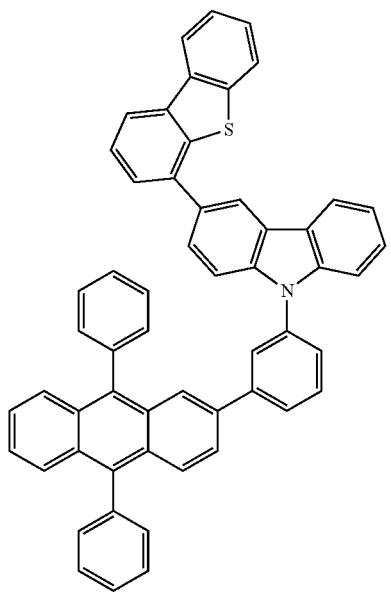
(325)
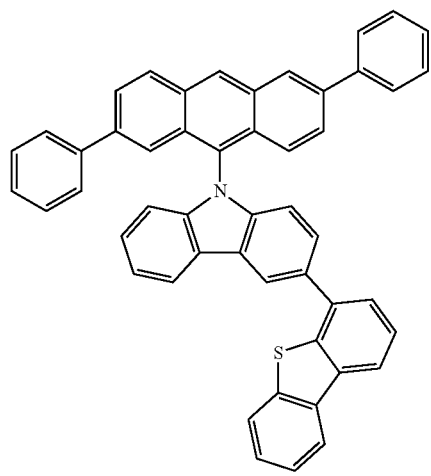
(326)
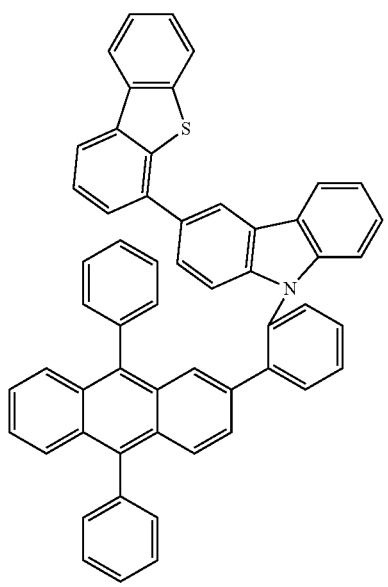
(327)
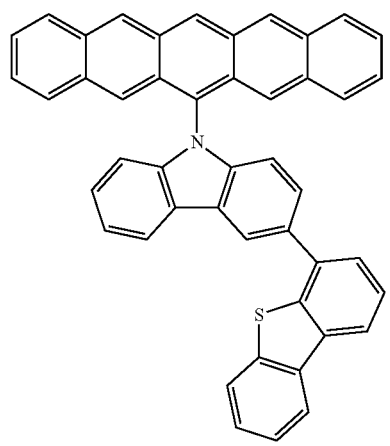

-continued
(328)
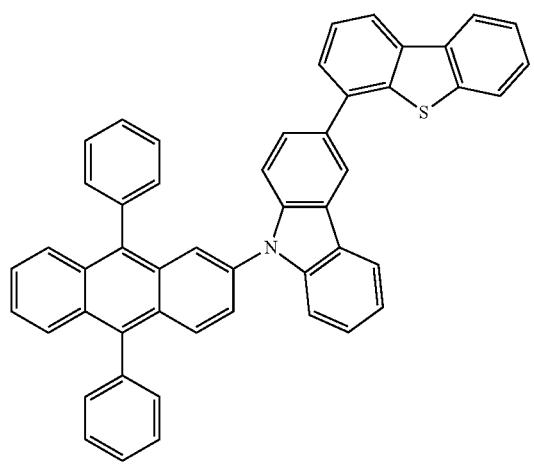
(329)
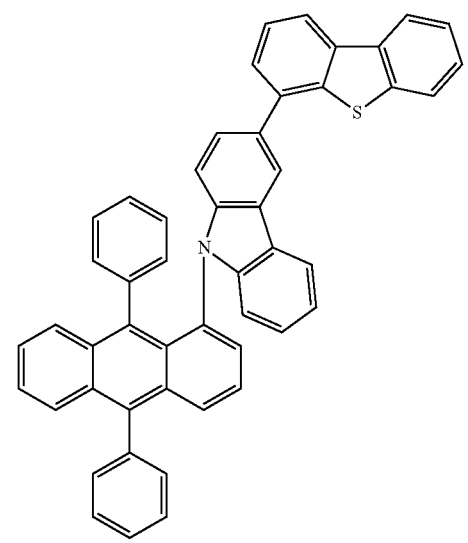
(330)
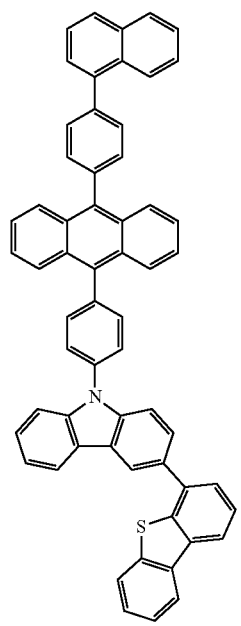
(331)
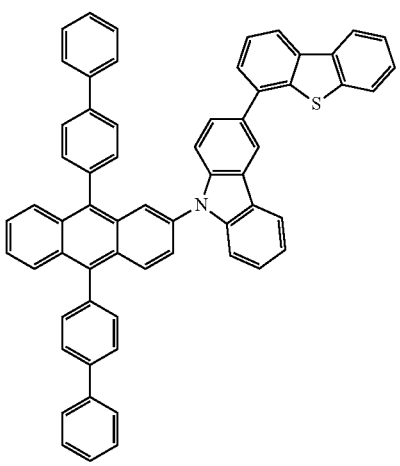

(332)
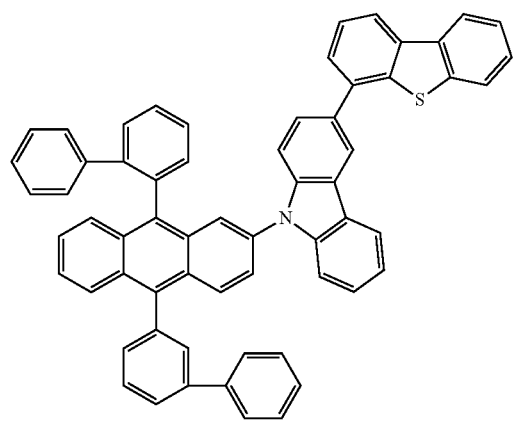
(333)
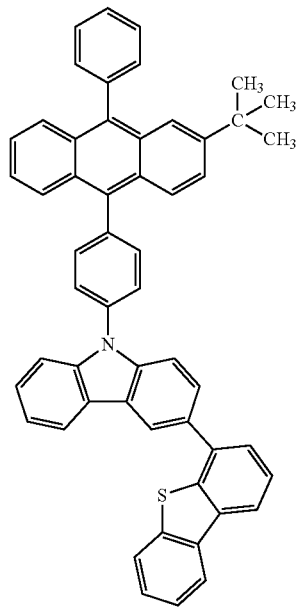
(334)
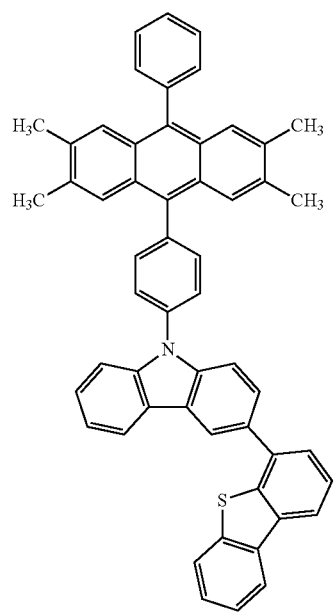
(335)
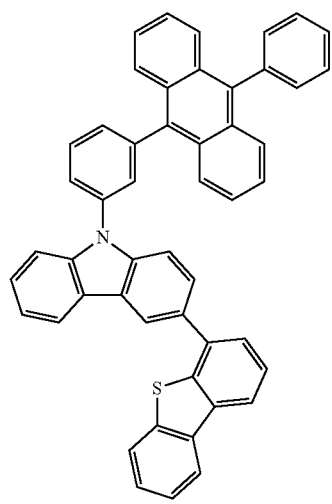

-continued
(336)
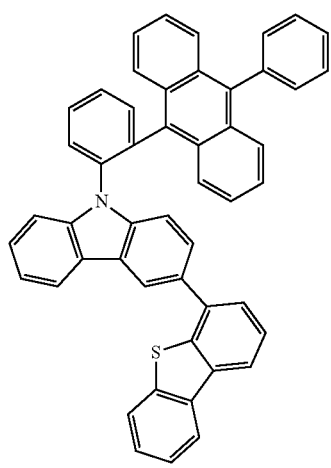
(337)
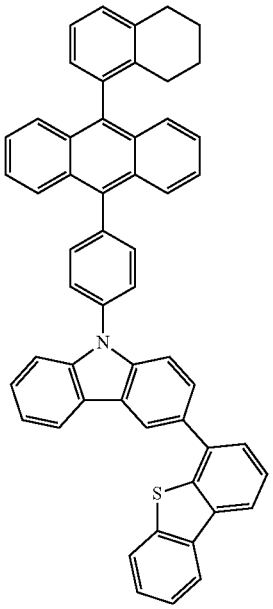
(338)
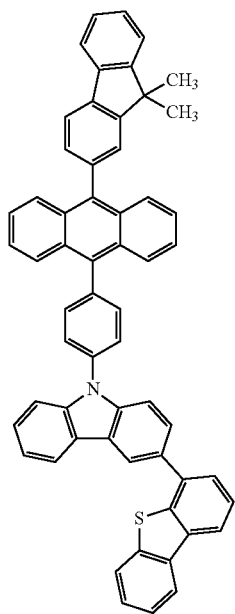
(339)
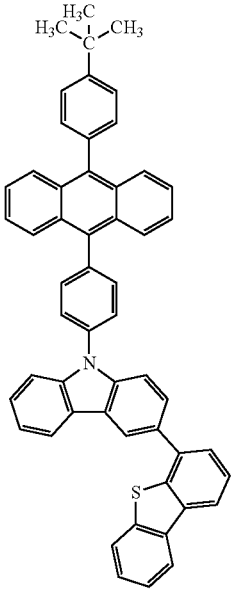

-continued
(340)
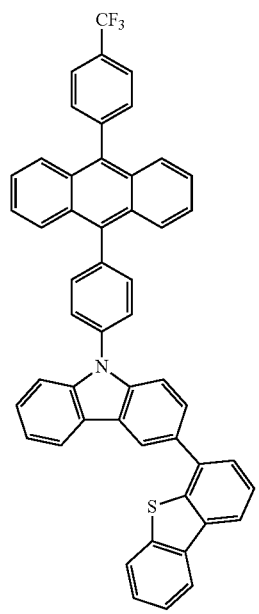
(341)
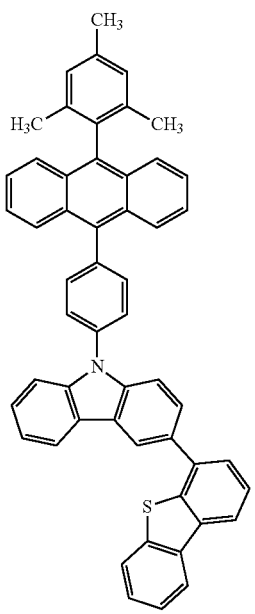
(342)
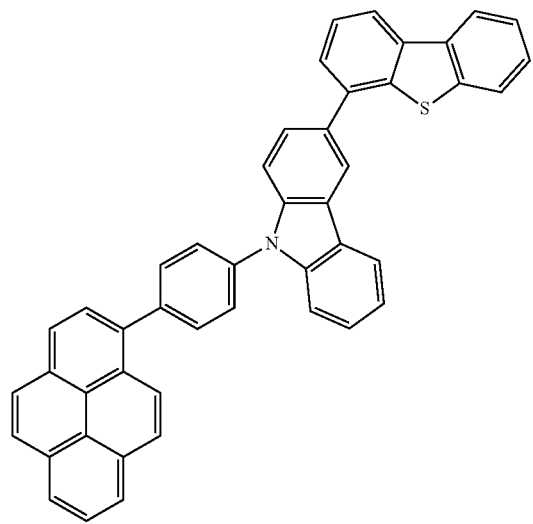
(343)
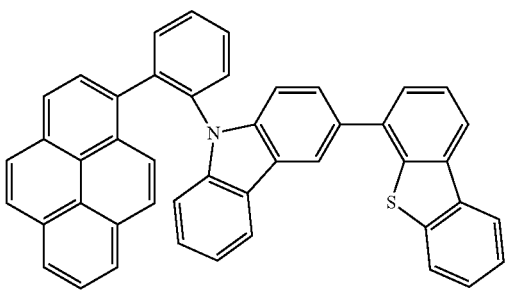

-continued
(344)
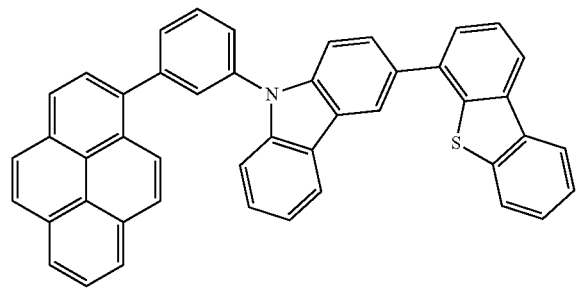
(345)
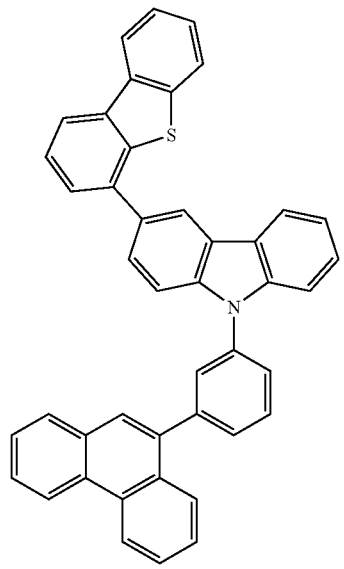
(346)
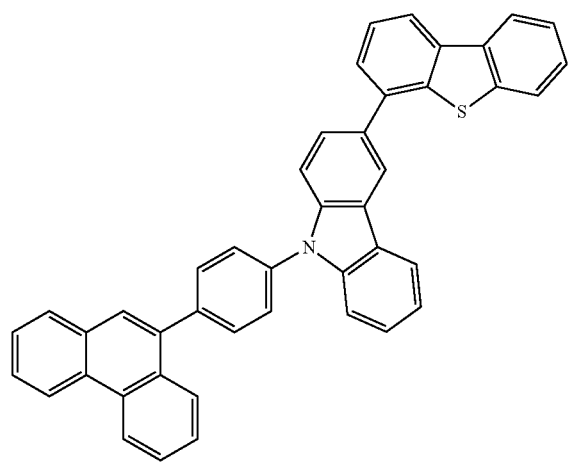
(347)
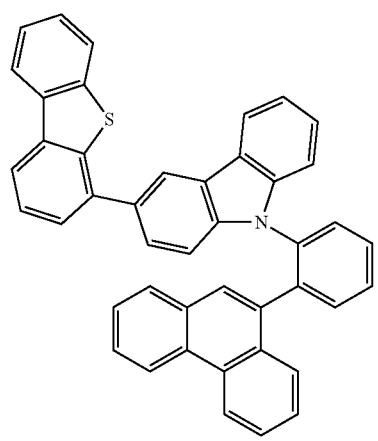
(348)
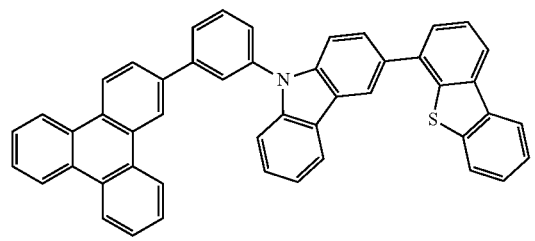
(349)
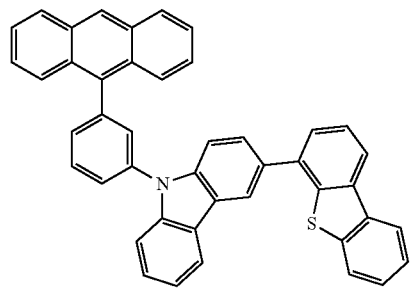

-continued
(350)
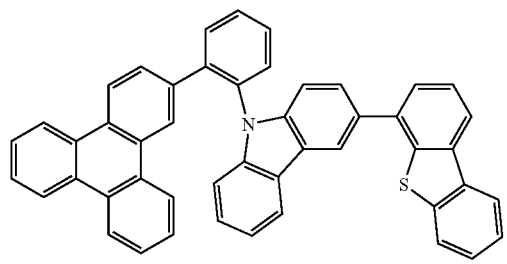
(351)
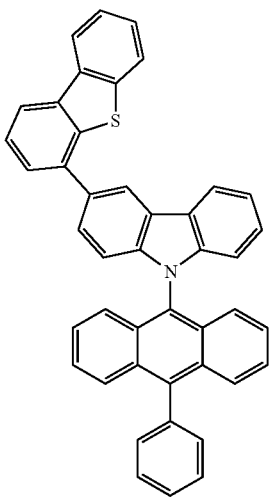
(352)
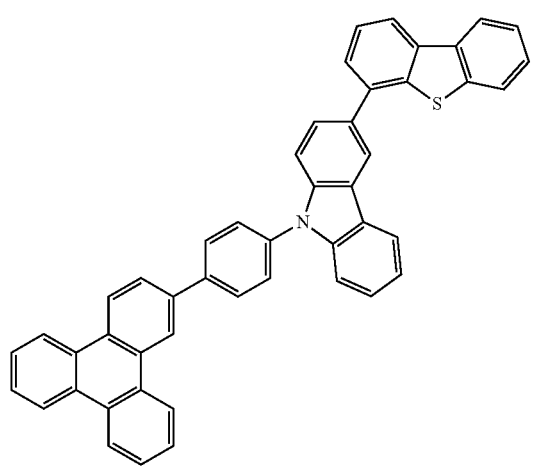
(353)
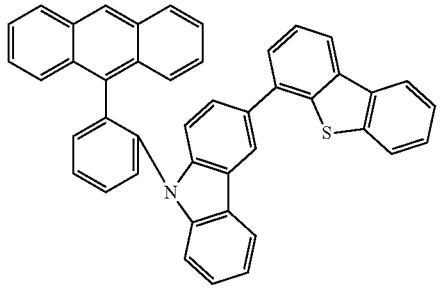
(354)
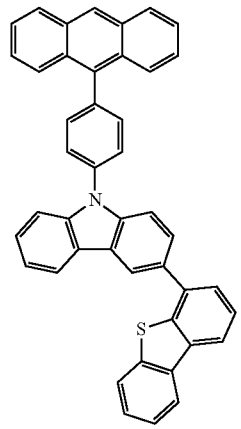
(355)
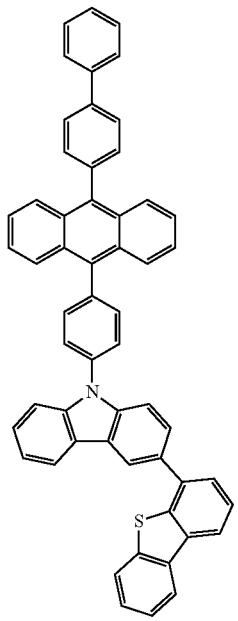

-continued
(356)
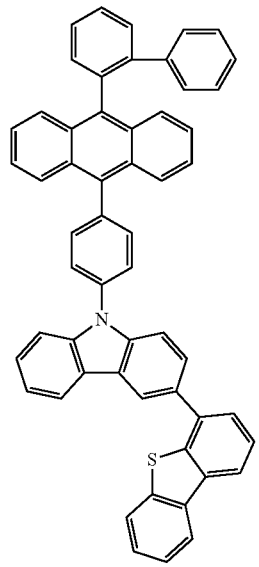
(357)
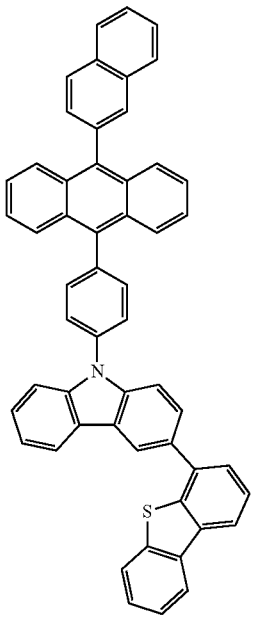
(358)
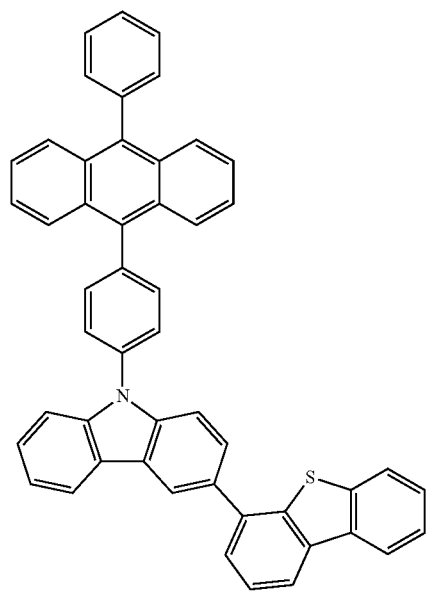
(359)
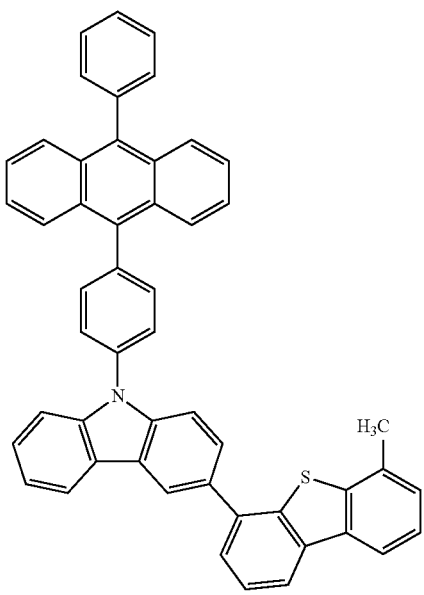

-continued
(360)
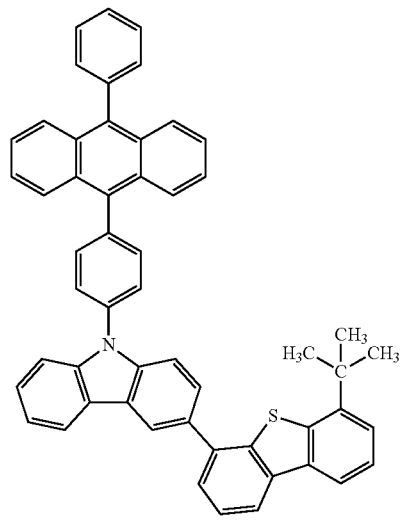
(362)
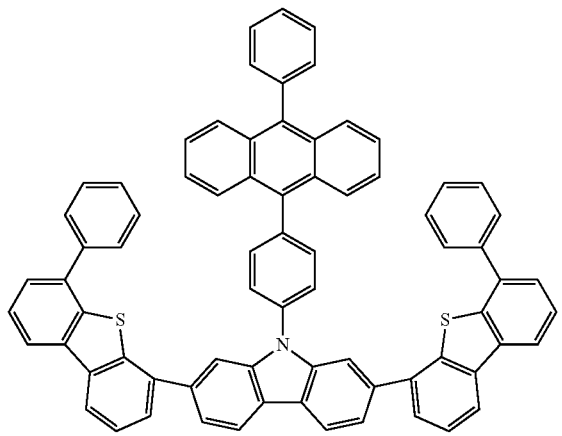
(363)
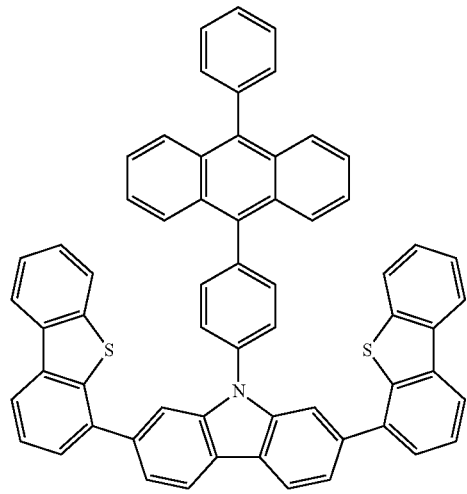
(364)
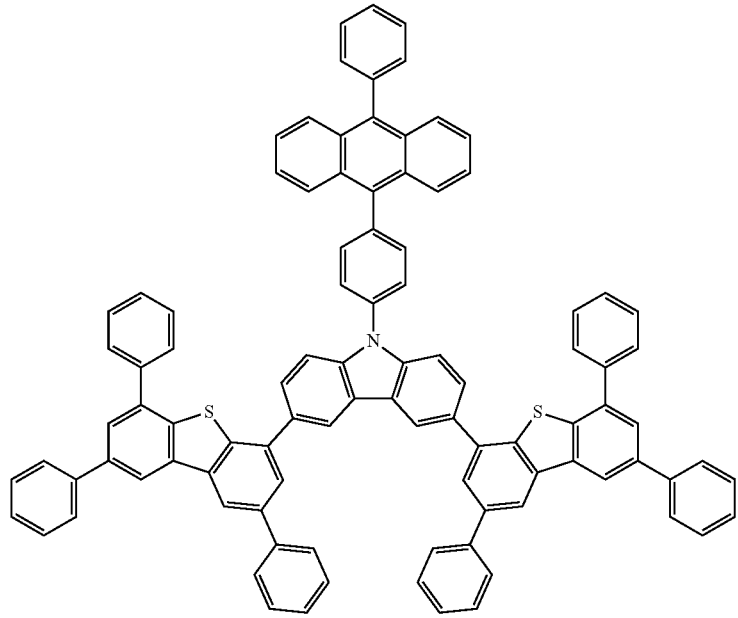

(365)
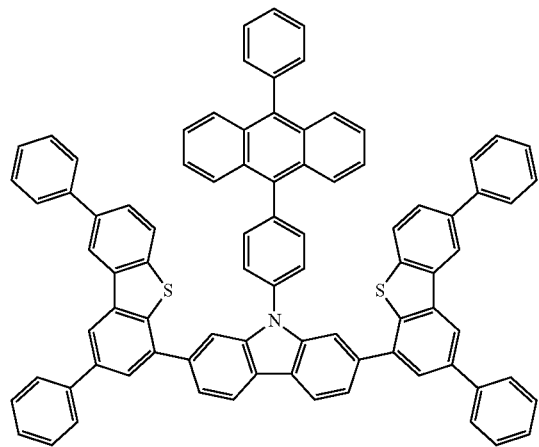
(366)
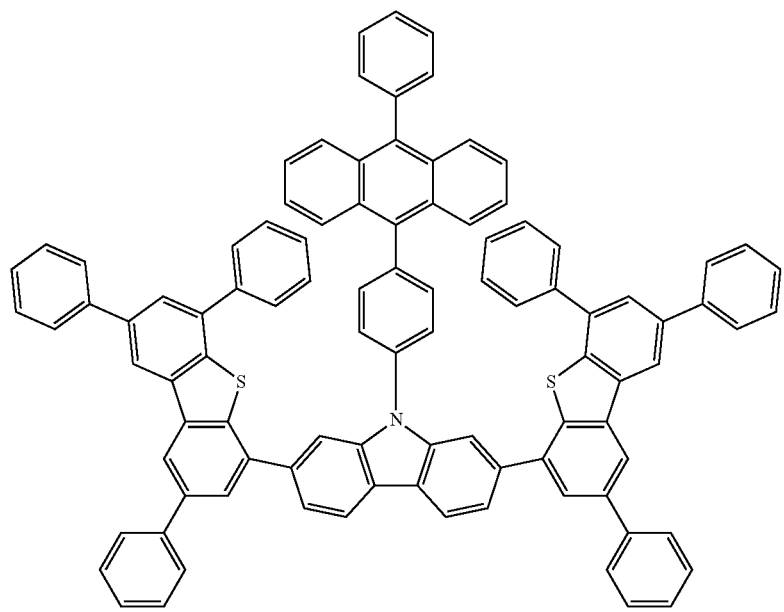
(367)
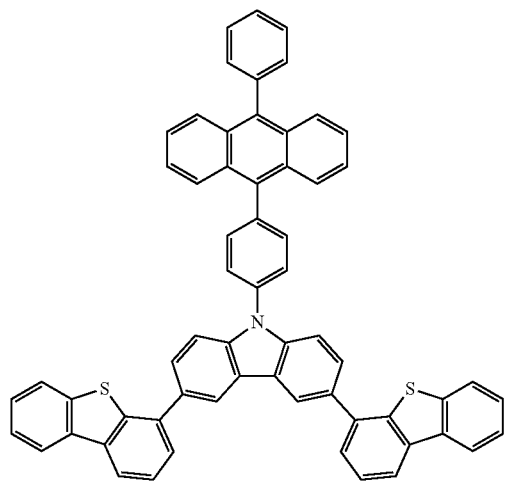
(368)
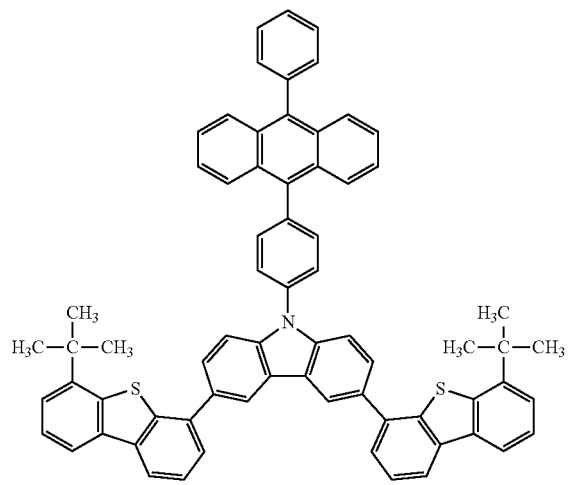

-continued
(369)
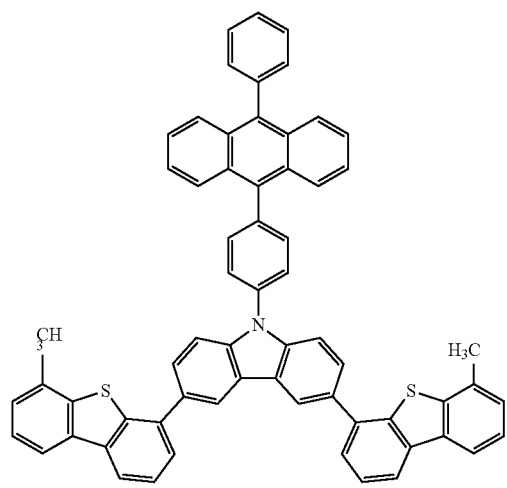
(371)
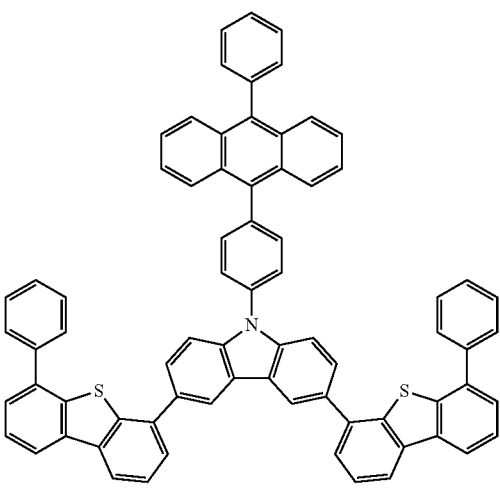
(372)
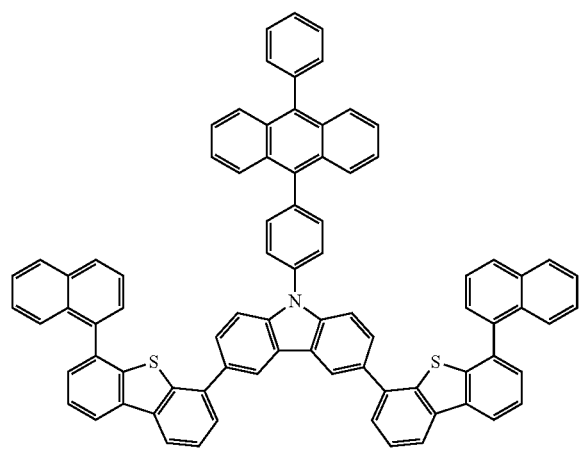
(373)
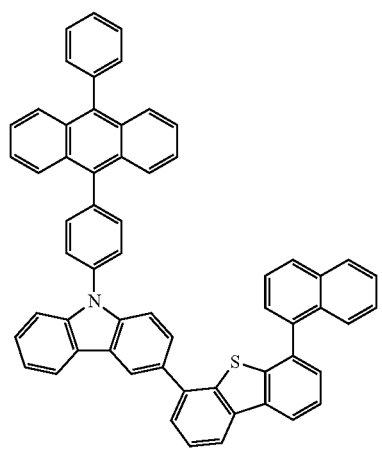
(374)
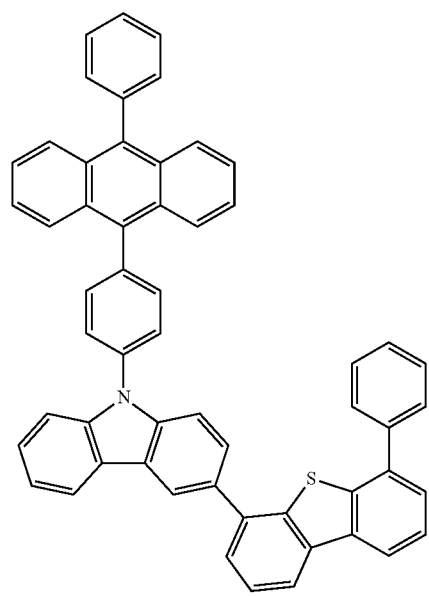
(375)
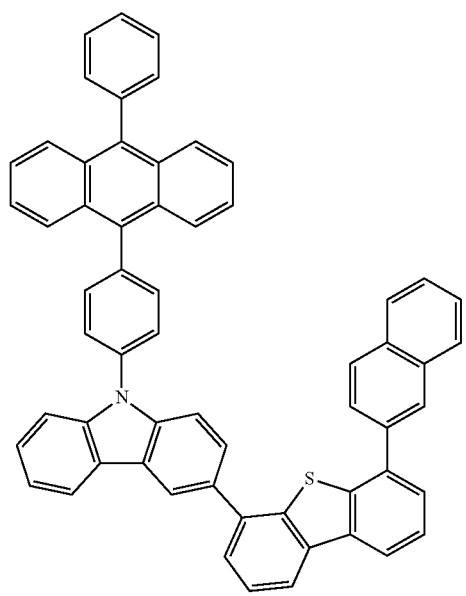

-continued
(376)
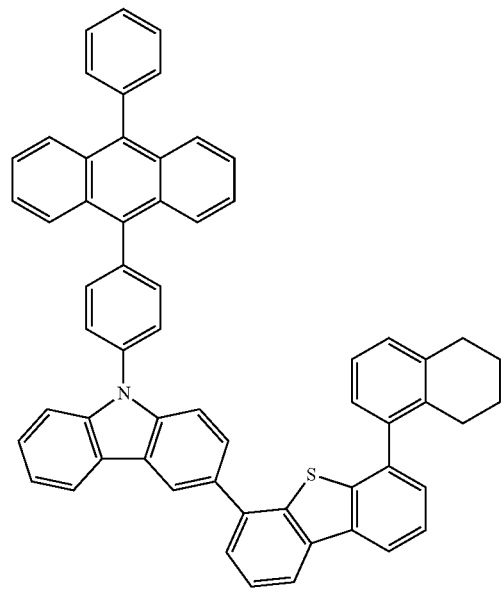
(377)
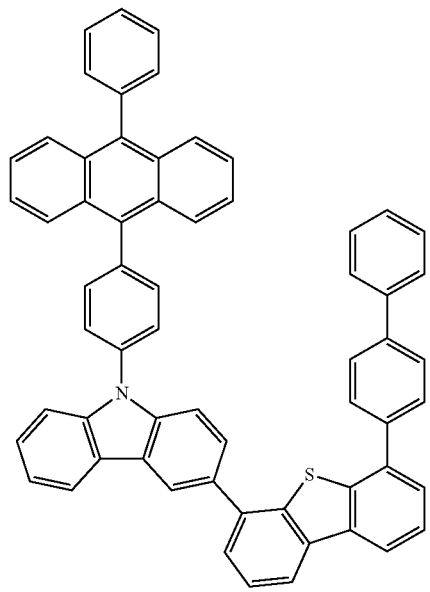
(378)
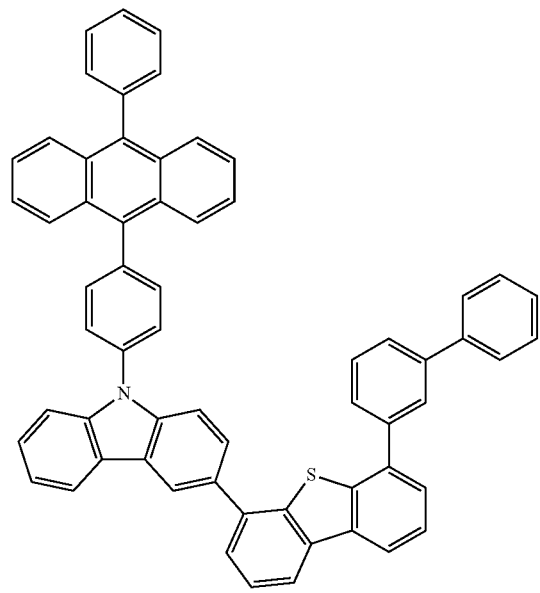
(379)
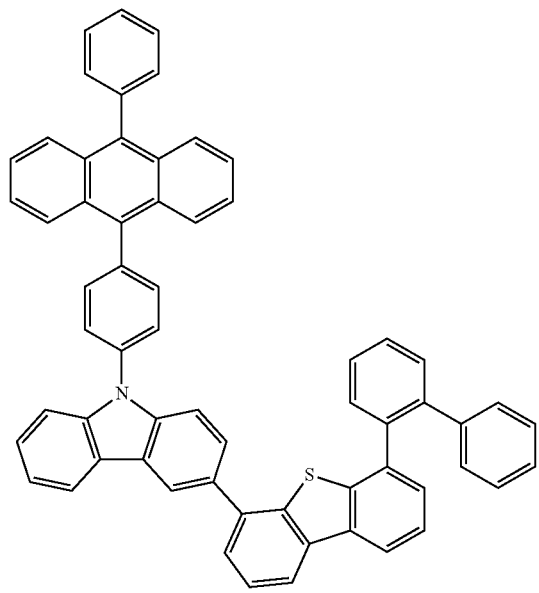

(380)
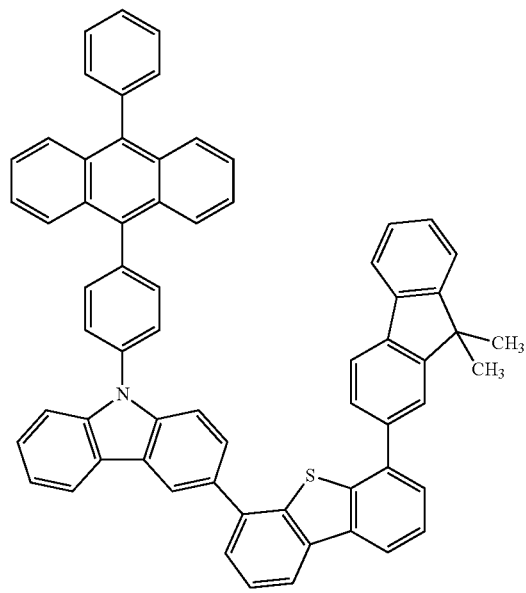
(381)
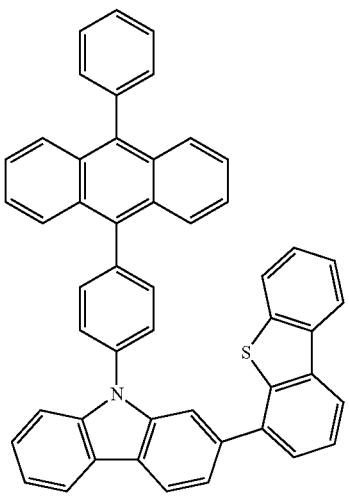
(382)
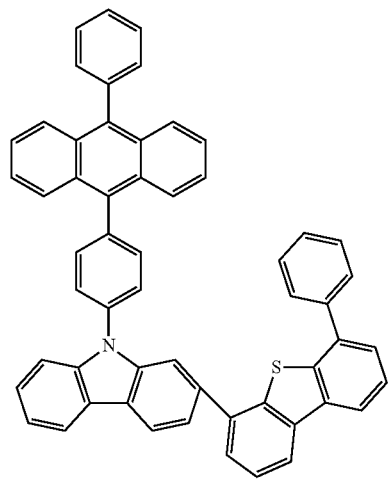
(383)
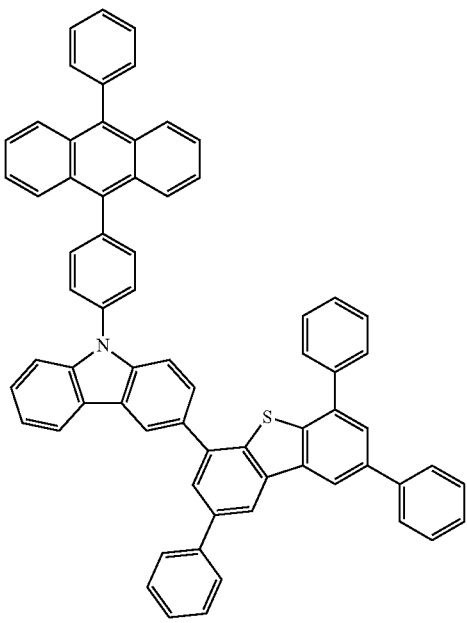

(384)
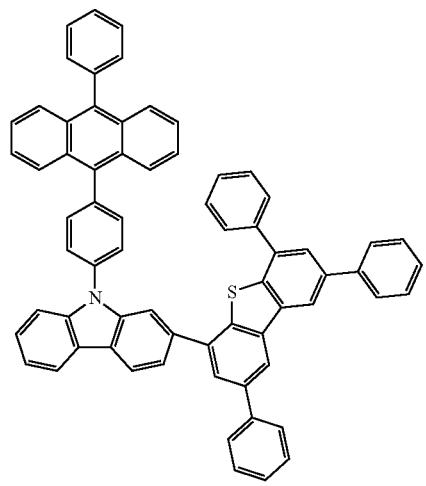
(385)
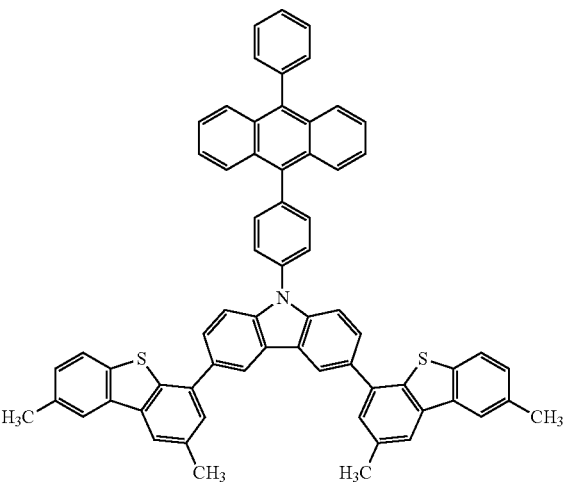
(386)
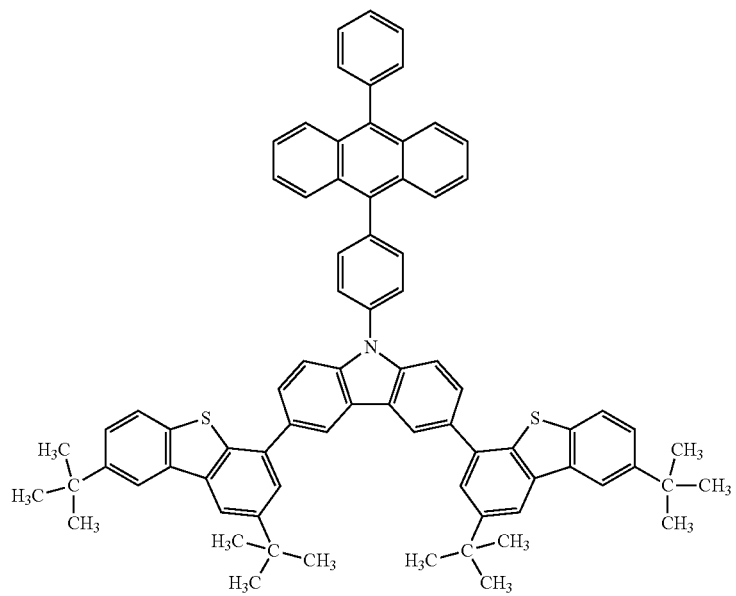

(388)
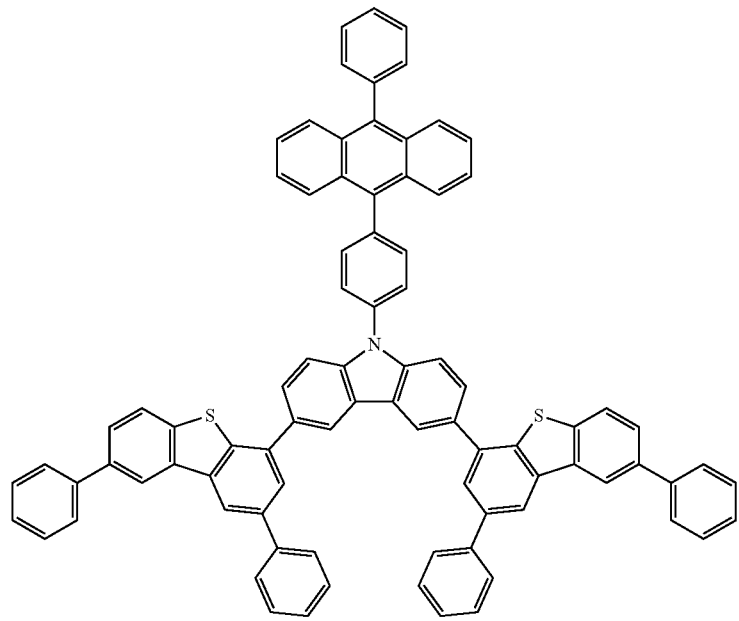
(389)
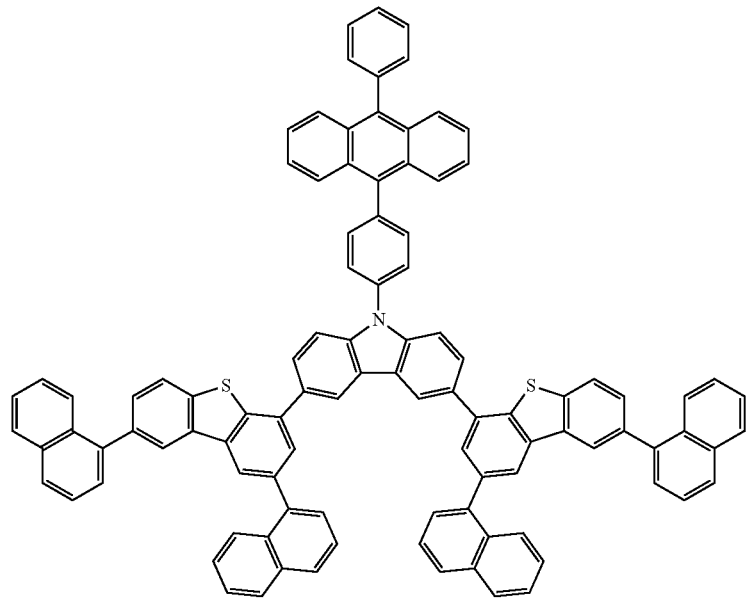

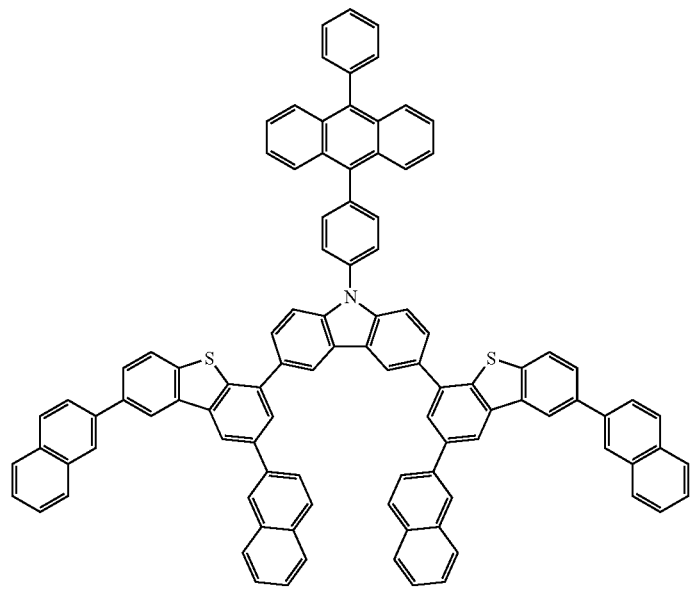
(390)
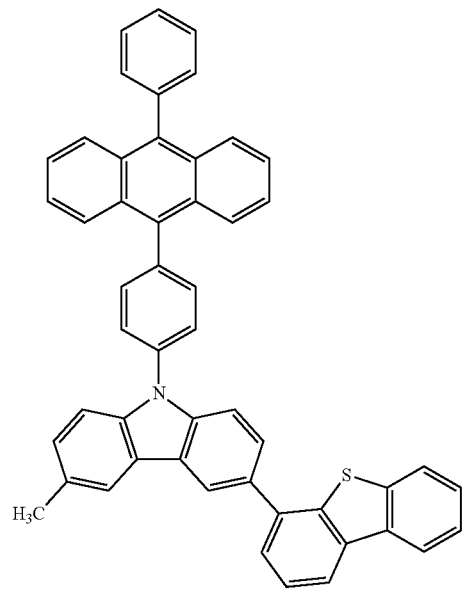
(391)
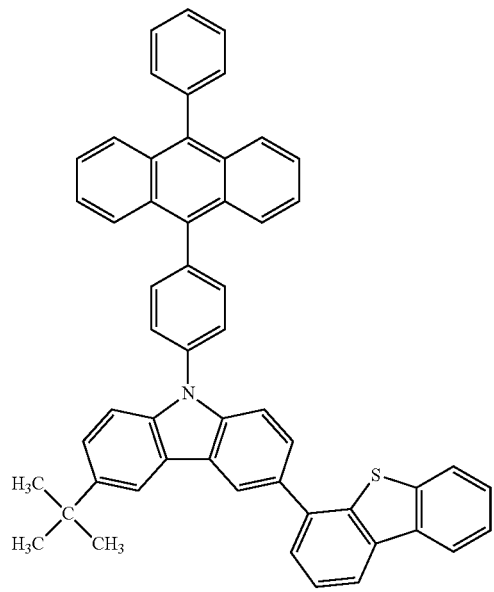
(392)

(393)
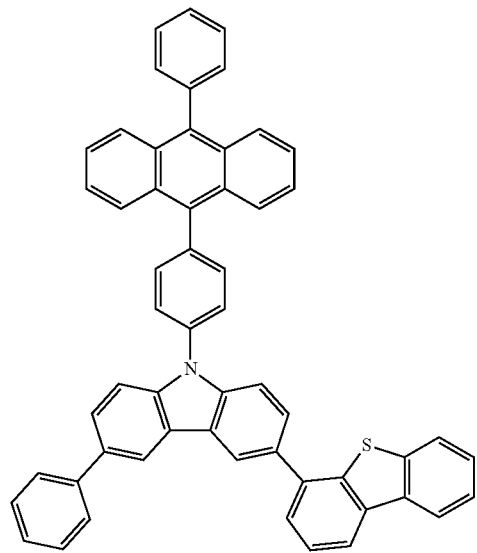
(395)
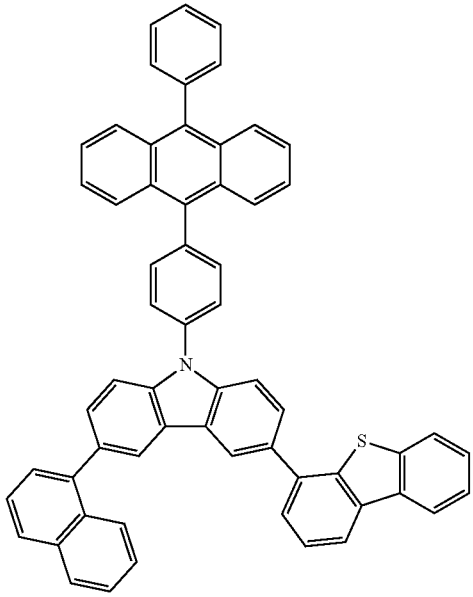
(396)
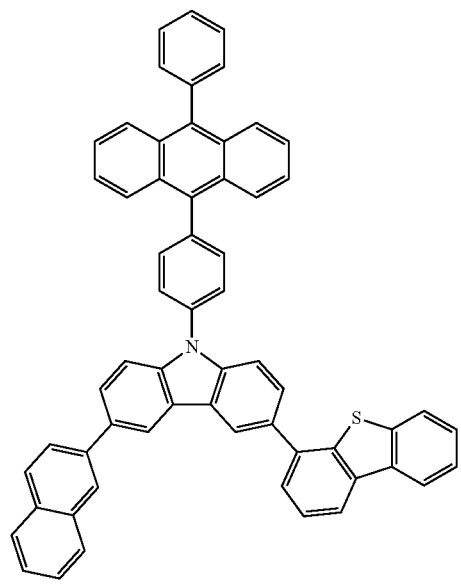
(397)
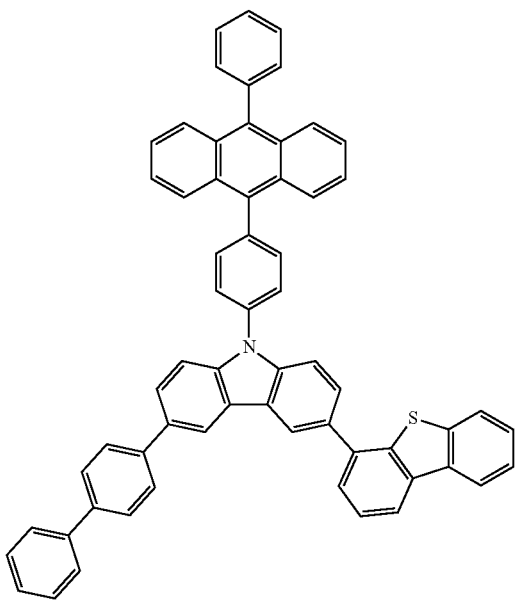

-continued
(398)
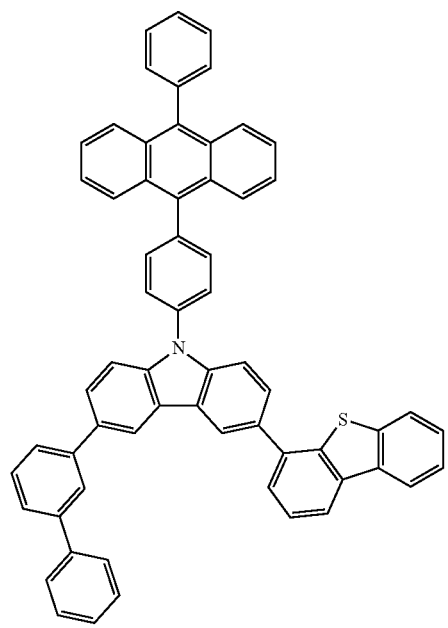
(399)
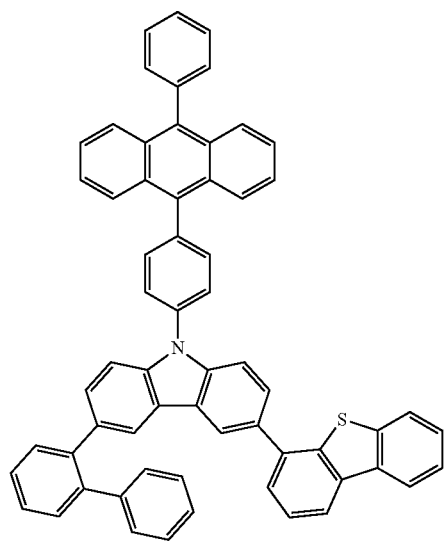
(400)
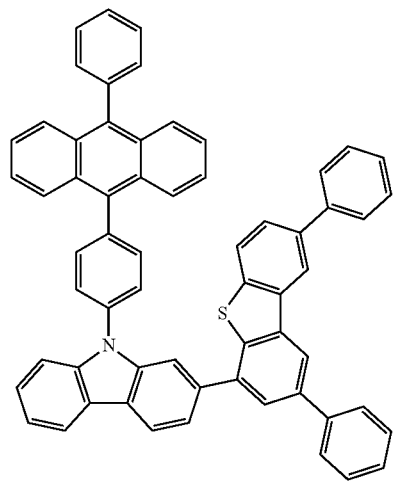
(401)
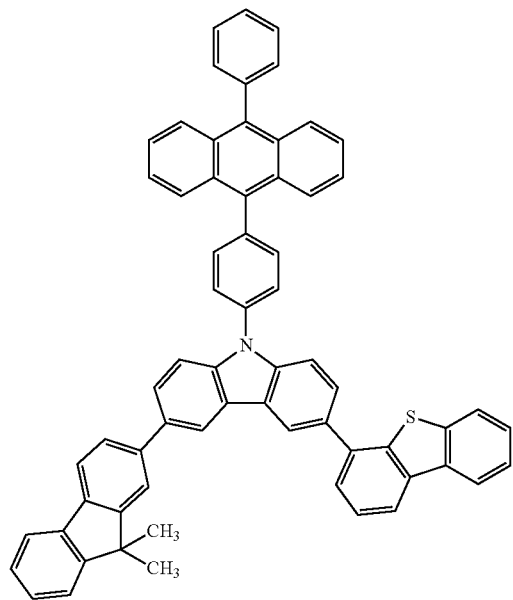

(402)
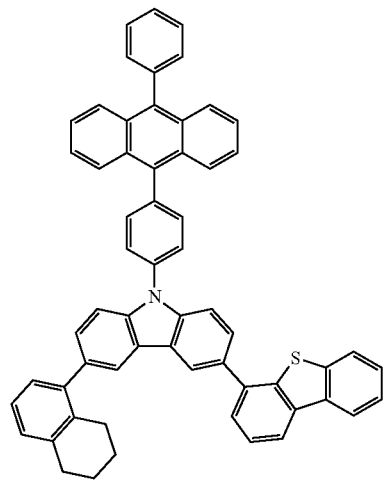
(403)
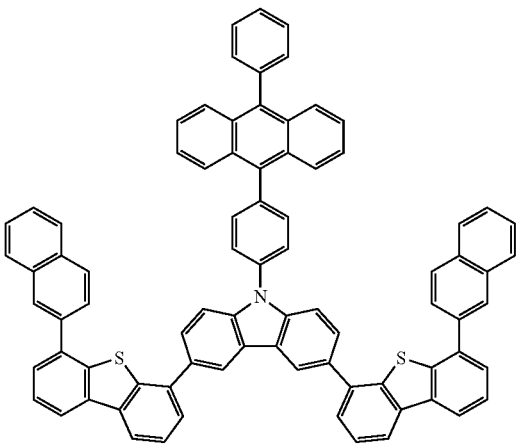
(404)
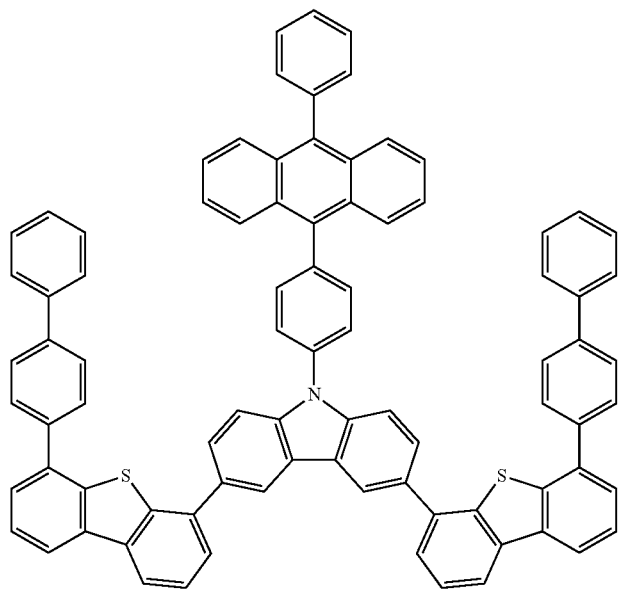
(405)
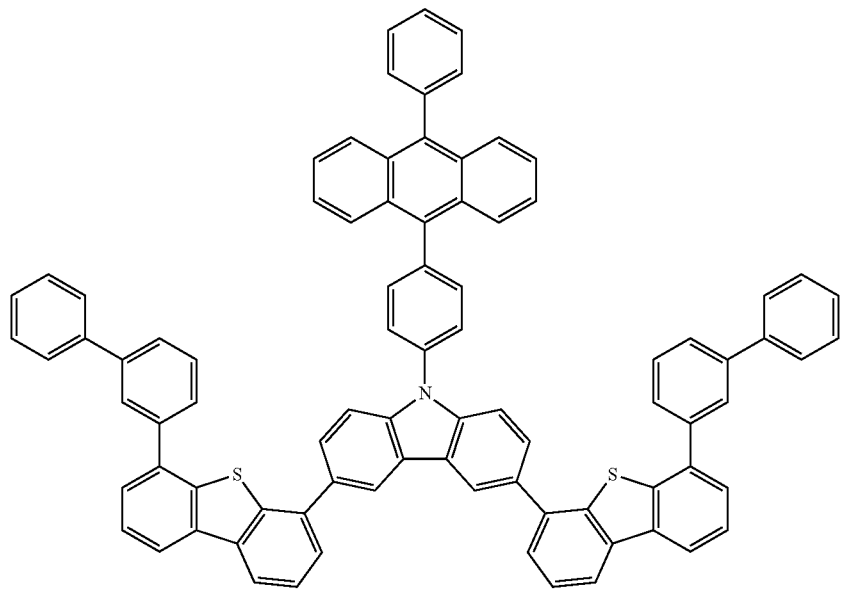

-continued
(406)
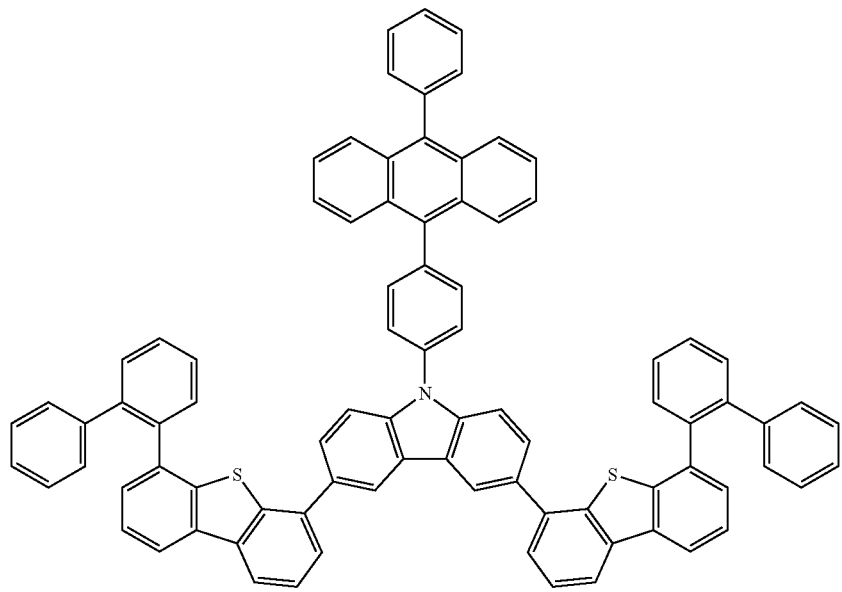
(407)
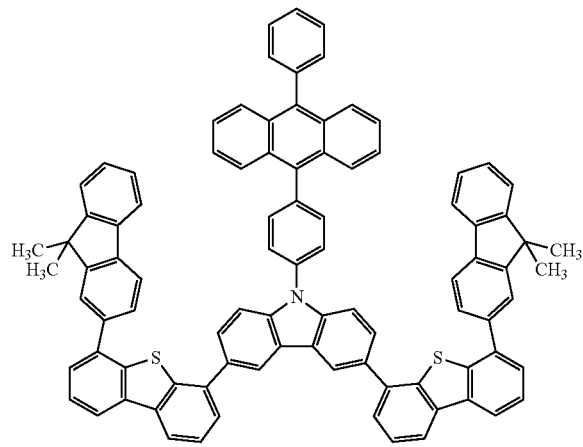
(408)
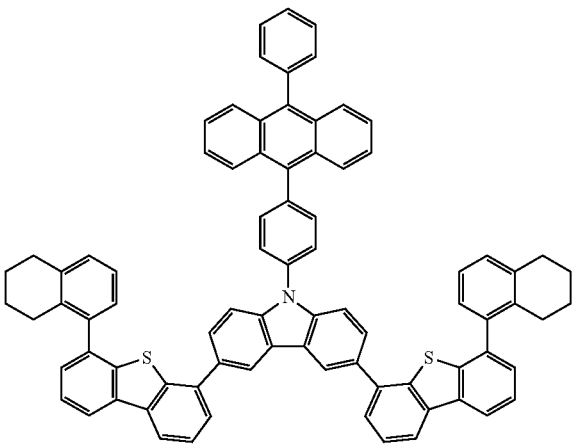
(409)
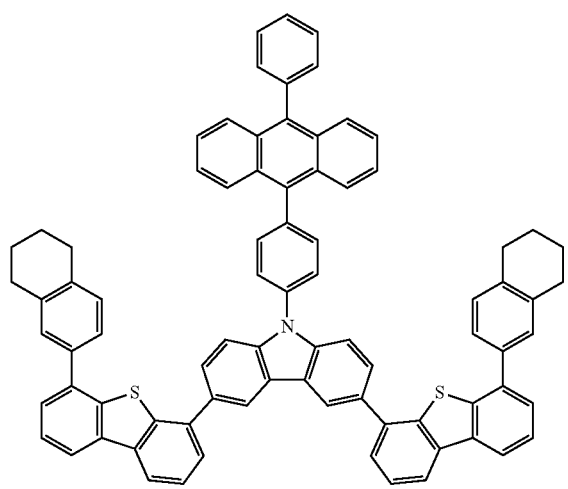
(410)
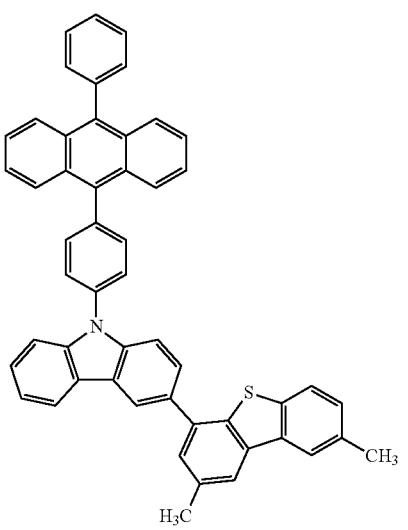

-continued
(411)
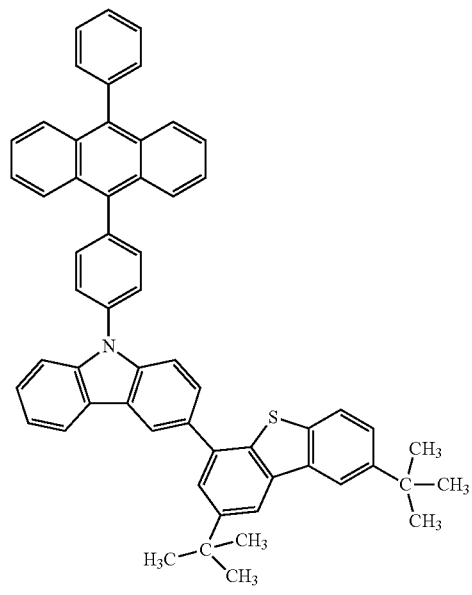
(413)
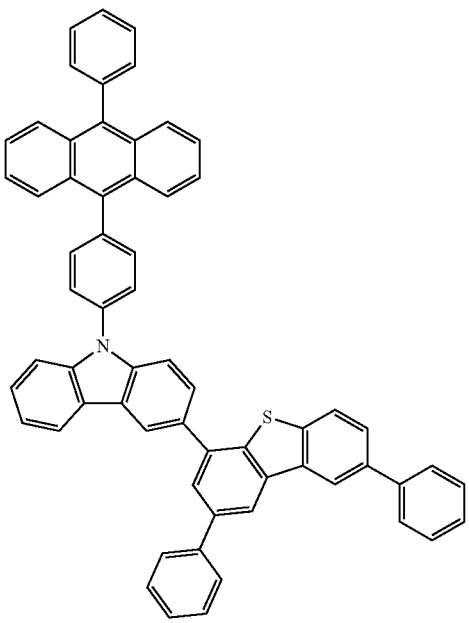
(414)
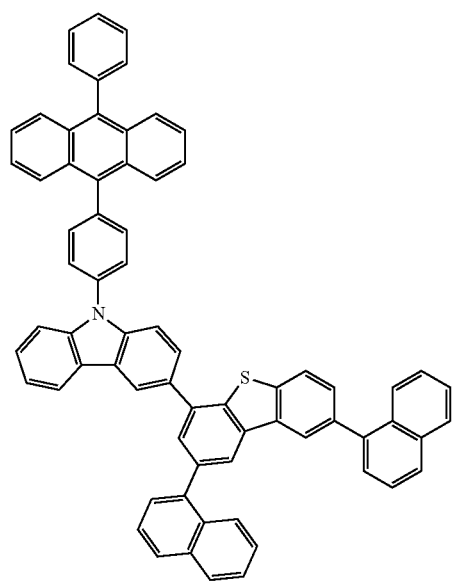
(415)
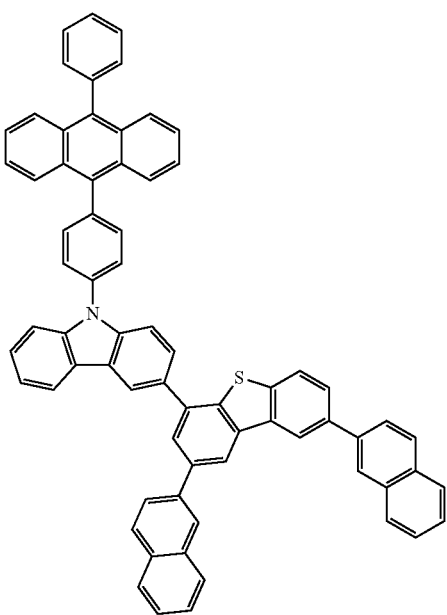

-continued
(416)
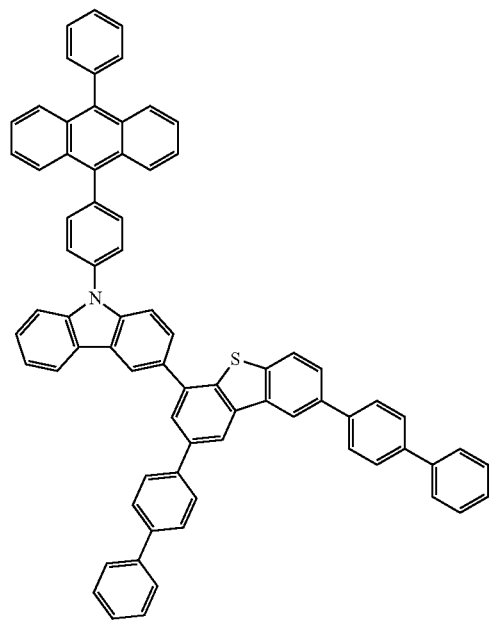
(417)
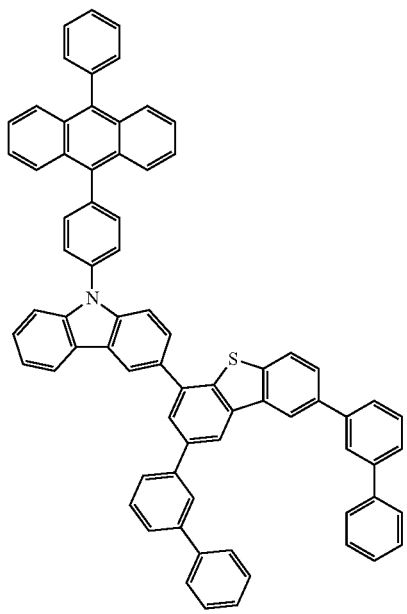
(418)
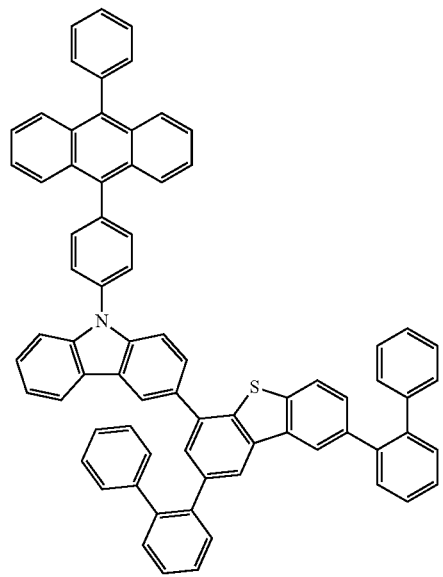
(419)
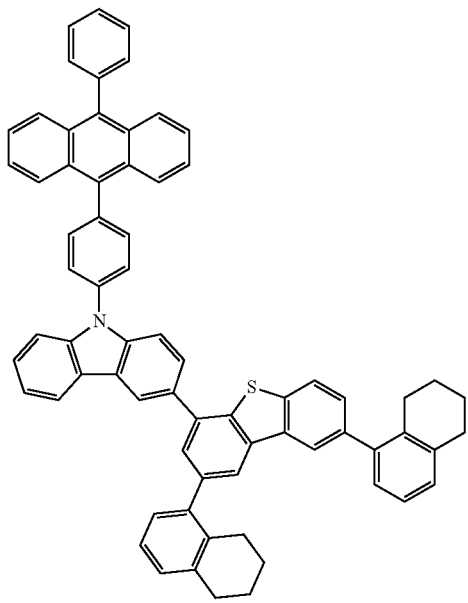

(420)
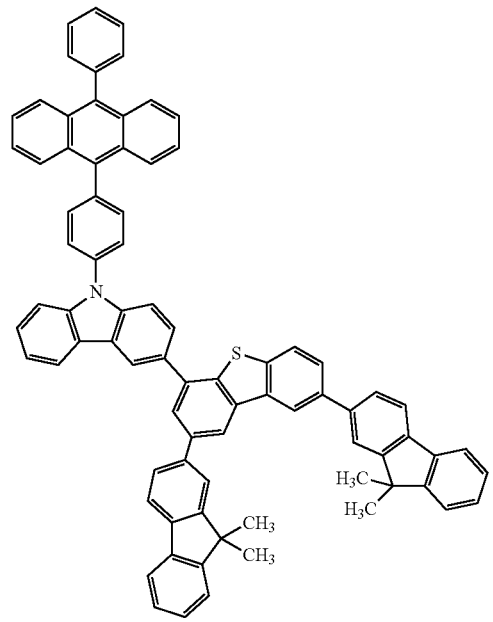
(421)
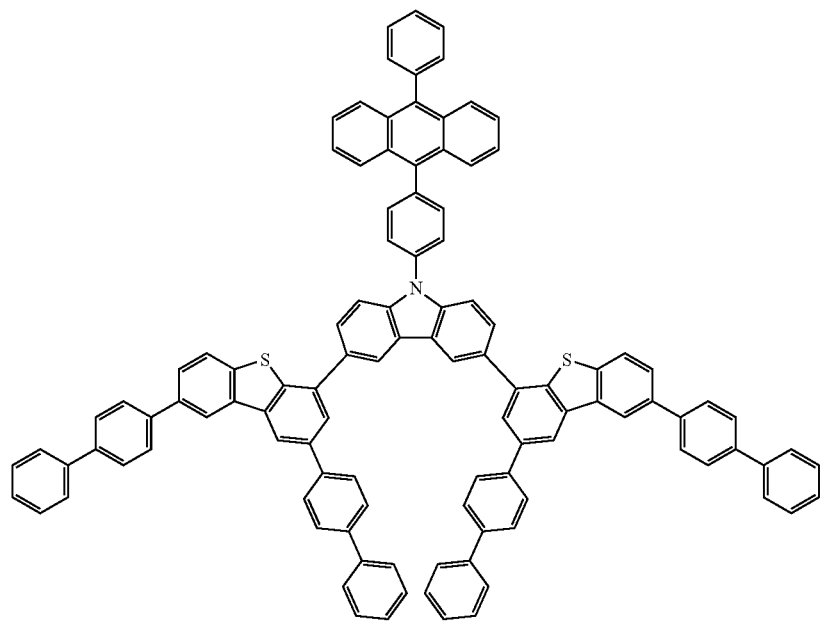

(422)
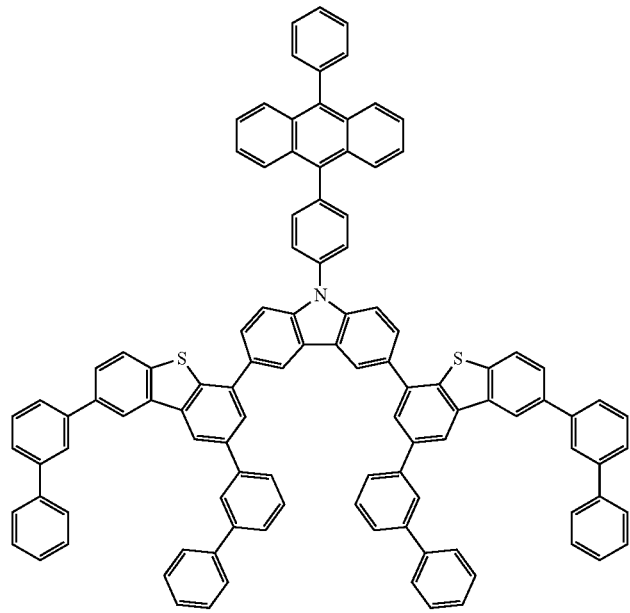
(423)
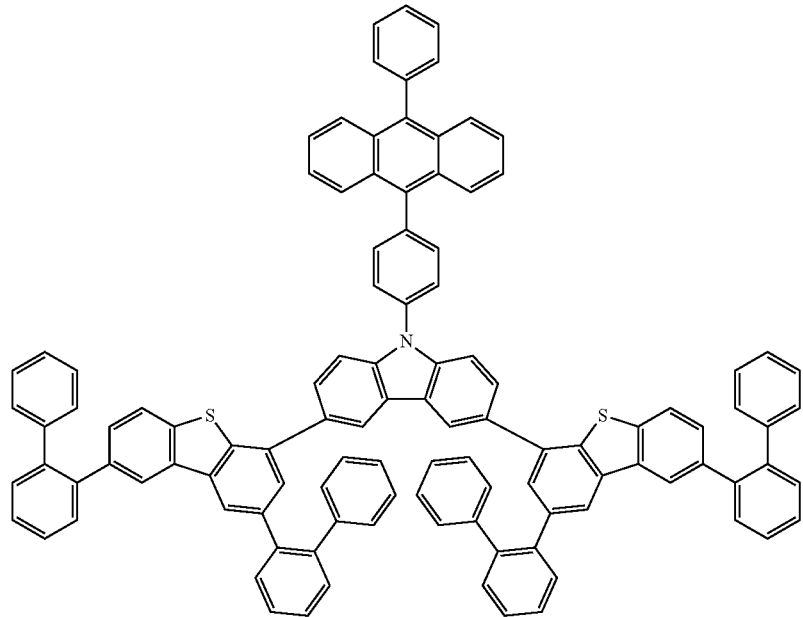

-continued
(424)
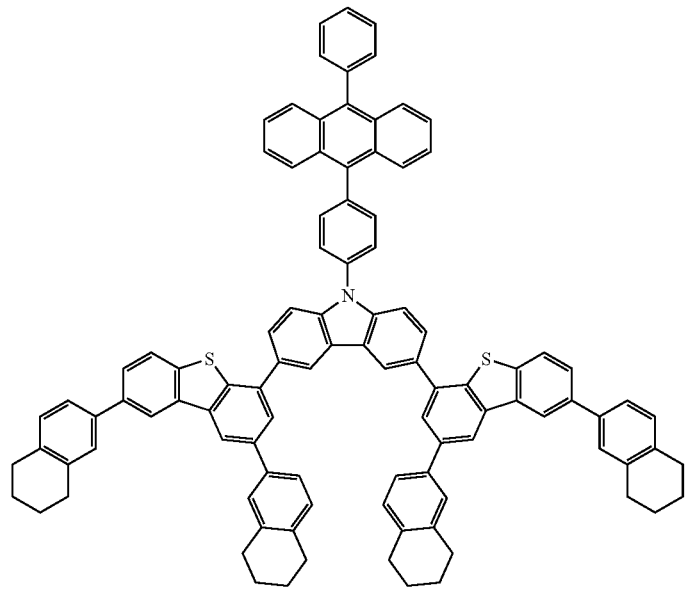
(425)
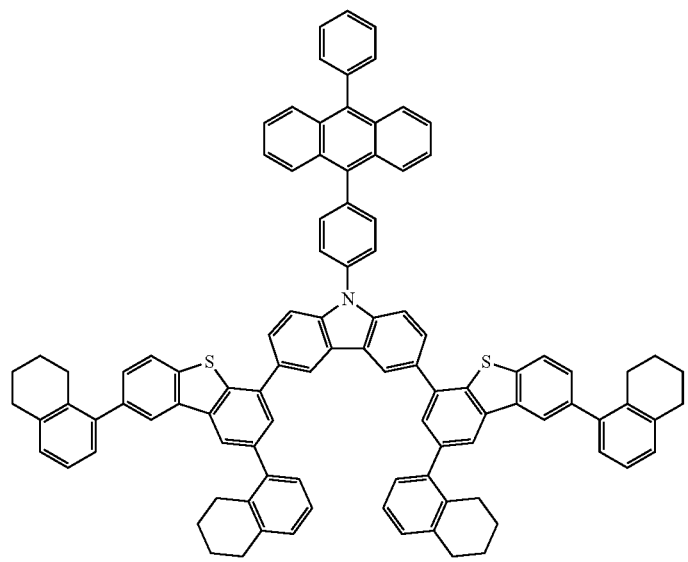

(426)
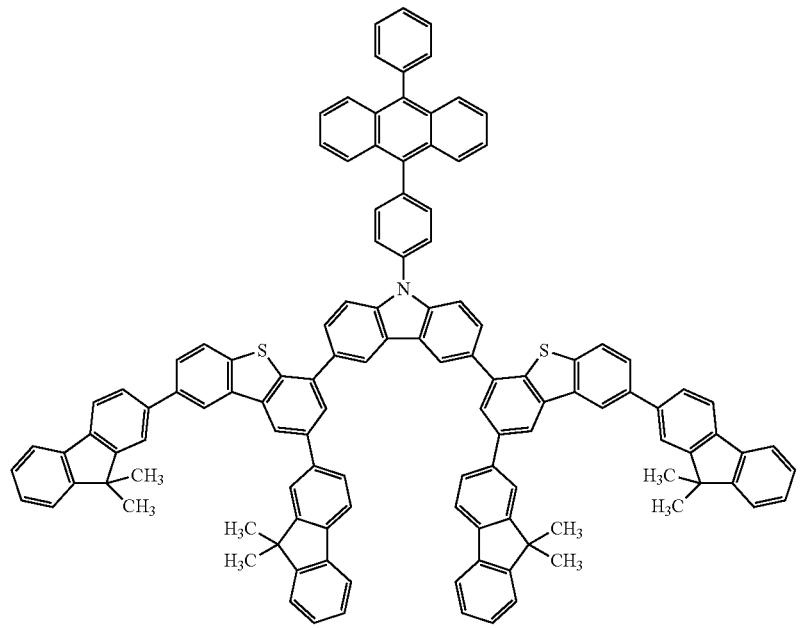
(427)
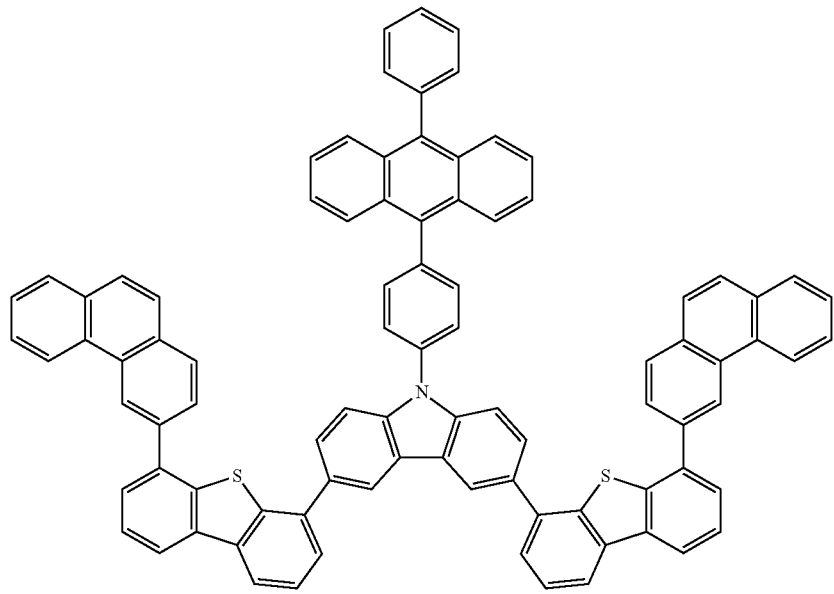

(428)
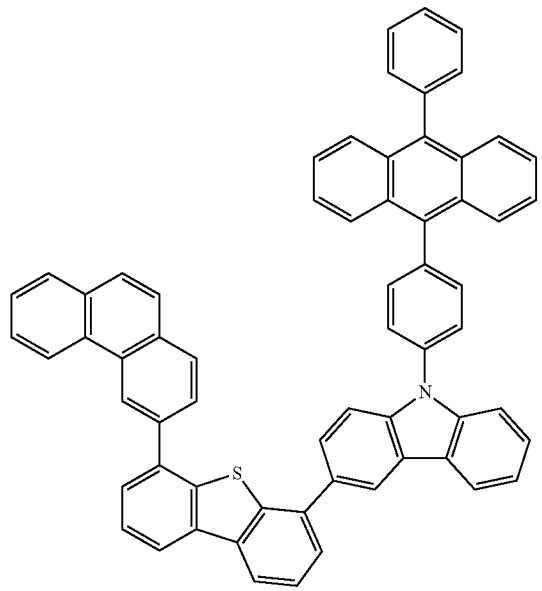
(429)
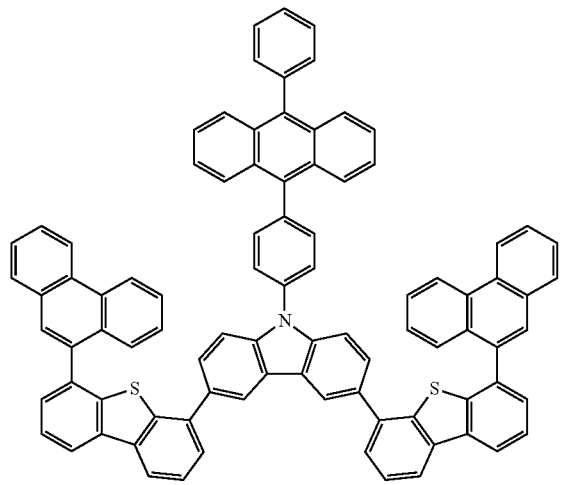
(430)
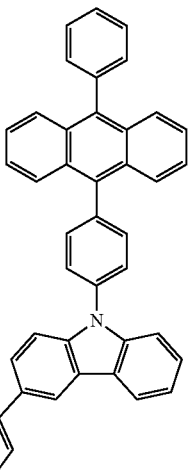
(431)
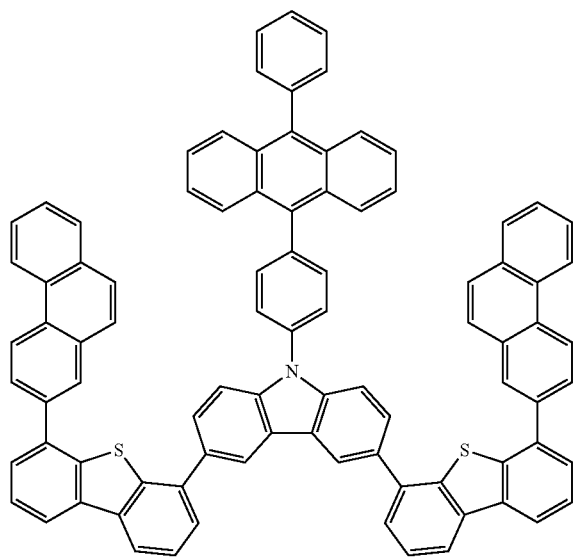
(432)
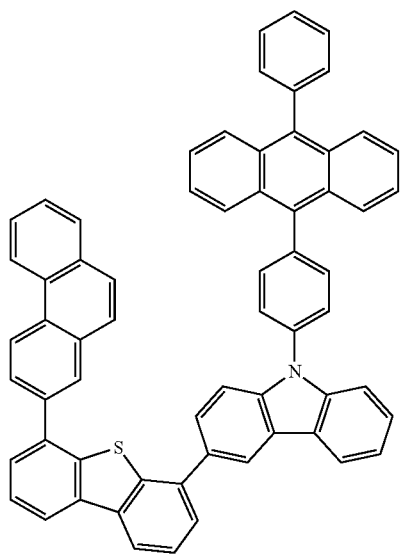

181
-continued
(433)
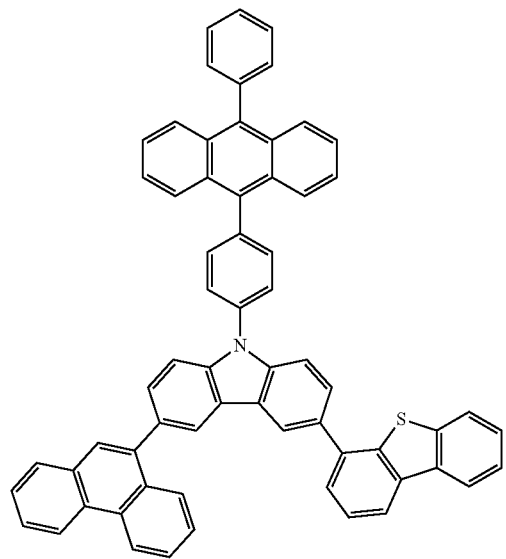
182
(434)
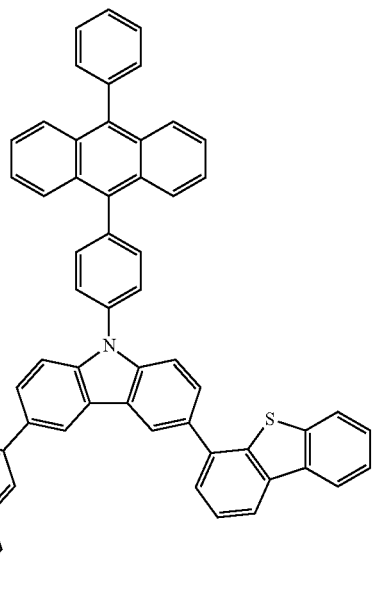
(435)
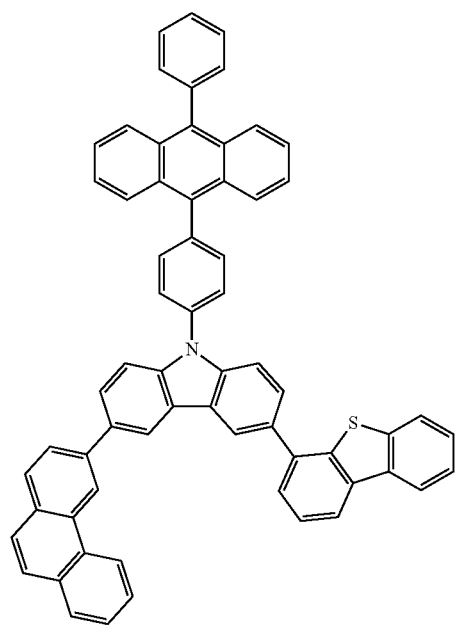

(436)
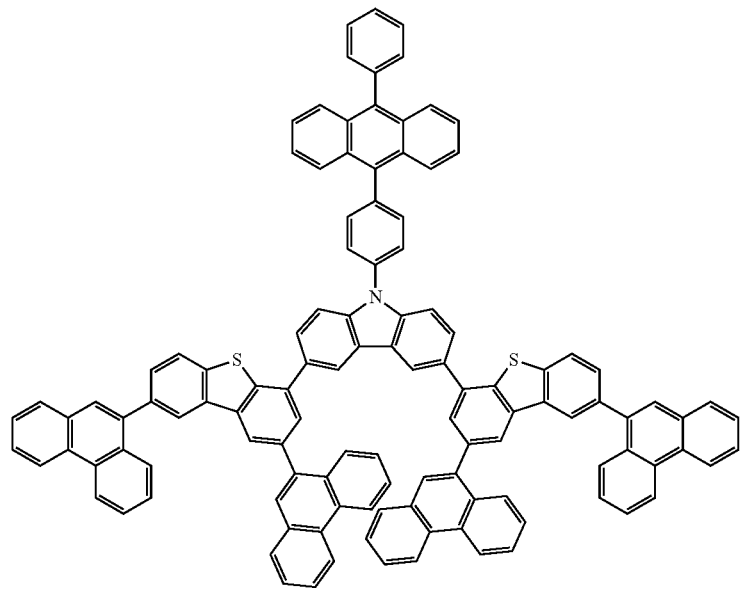
(437)
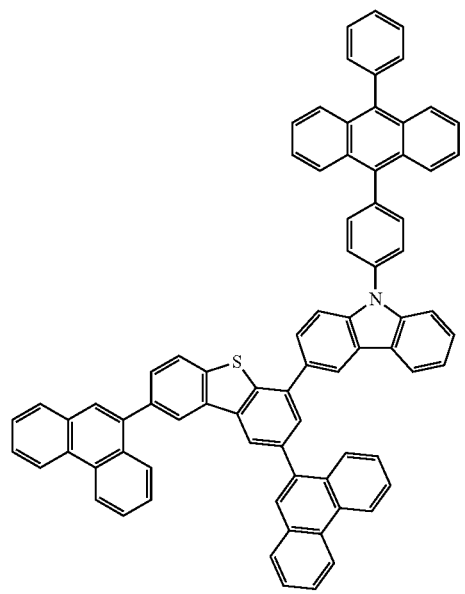

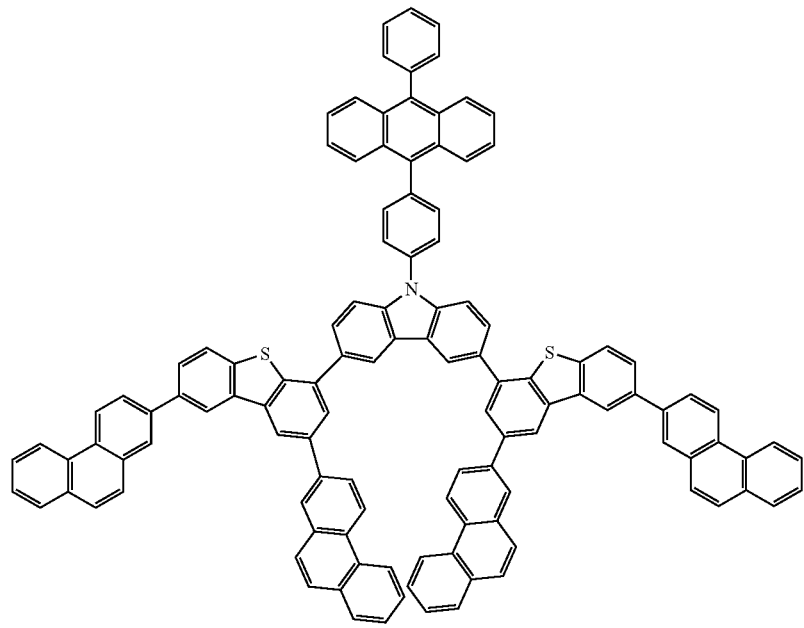
(438)
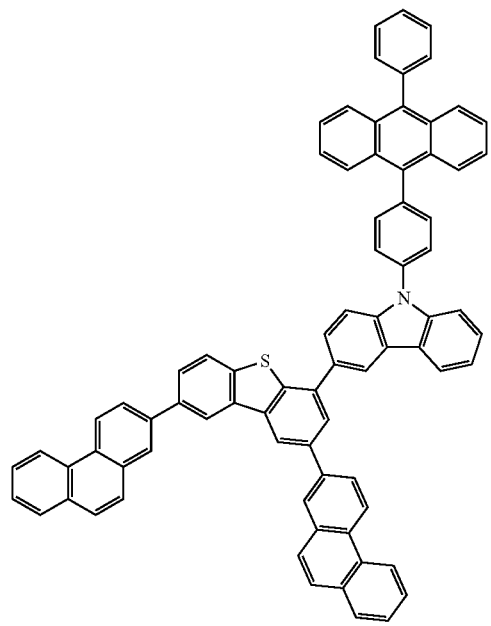
(439)

-continued
(440)
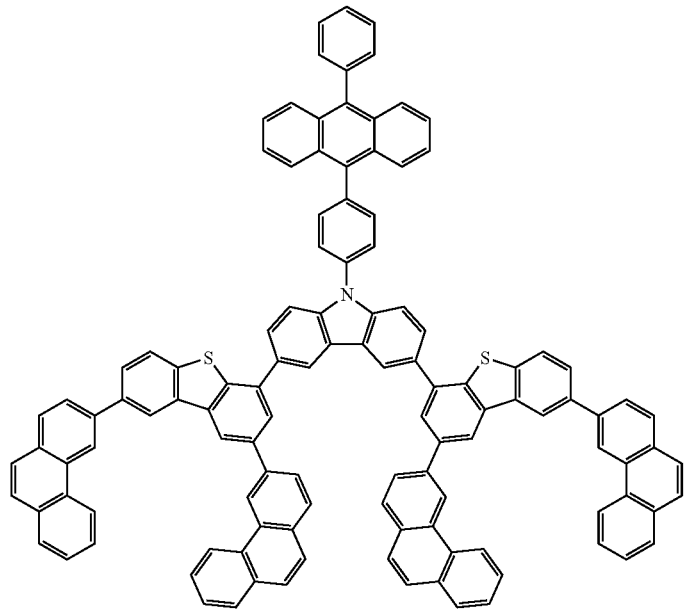
(441)
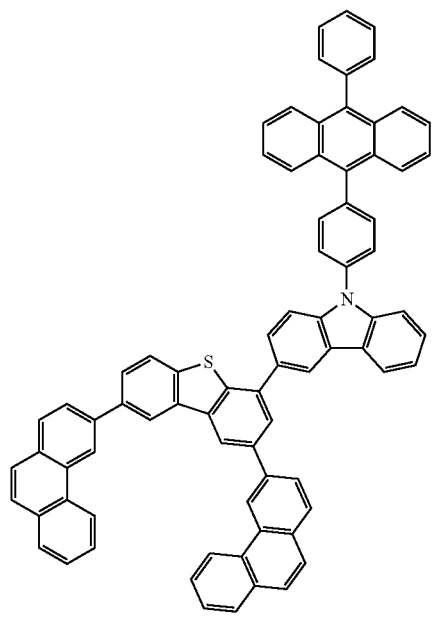
(500)
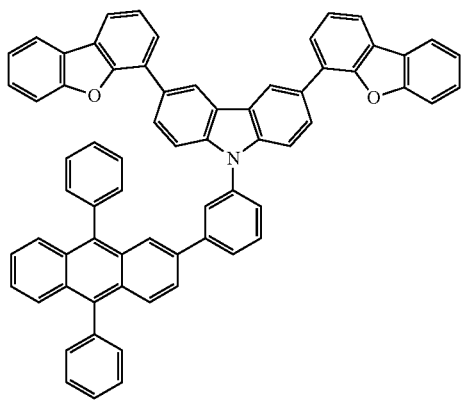
(501)
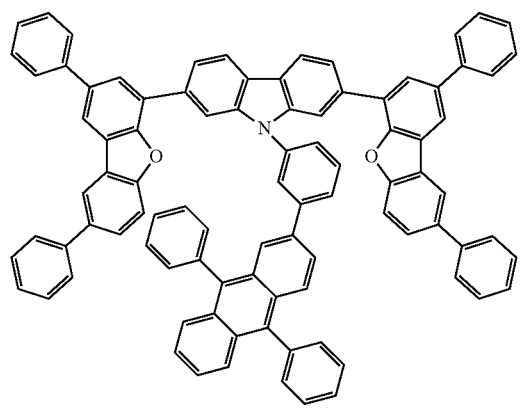
(502)
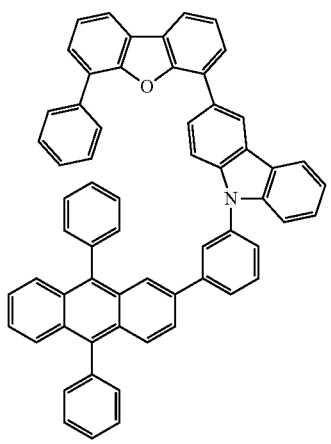

-continued
(503)
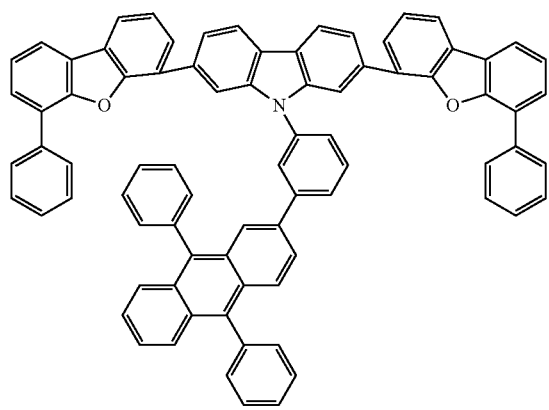
(504)
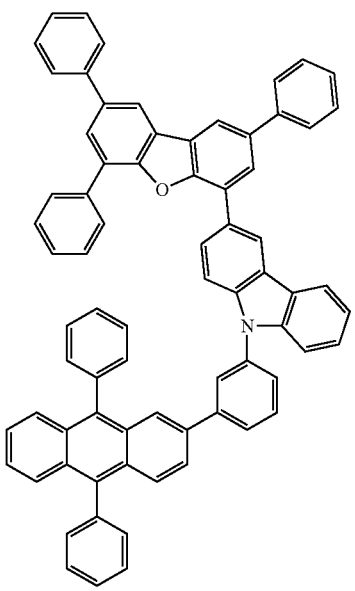
(505)
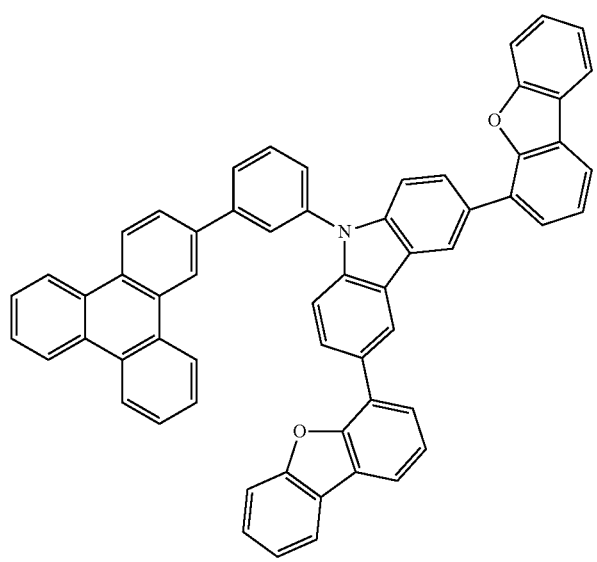

(506)
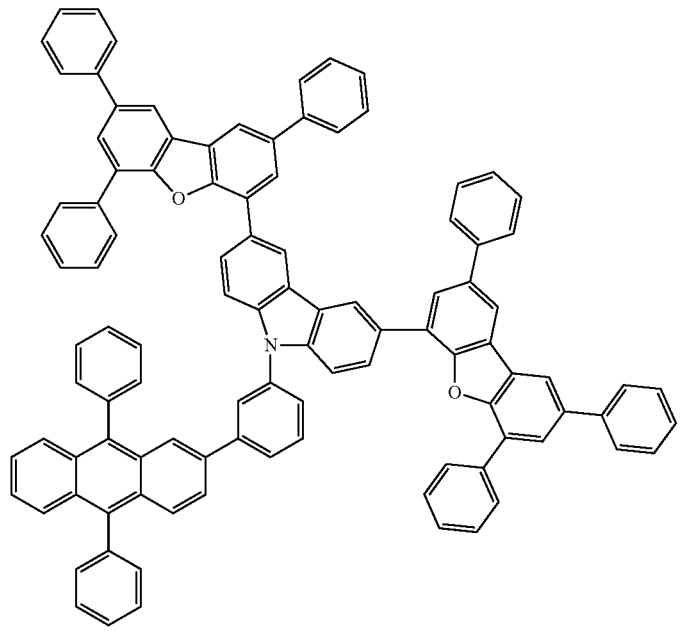
(507)
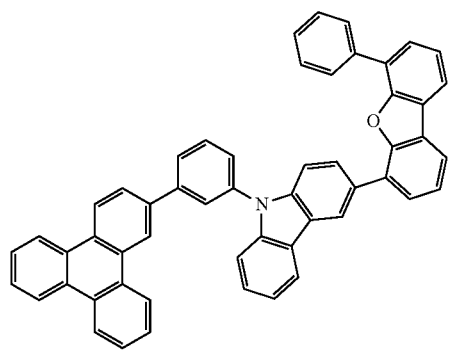
(508)
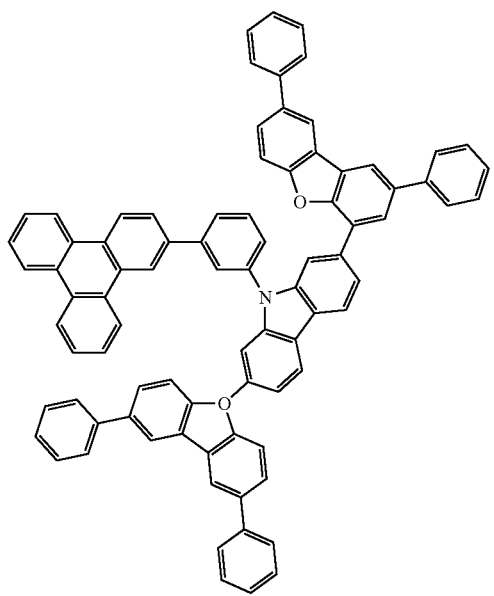

-continued
(509)
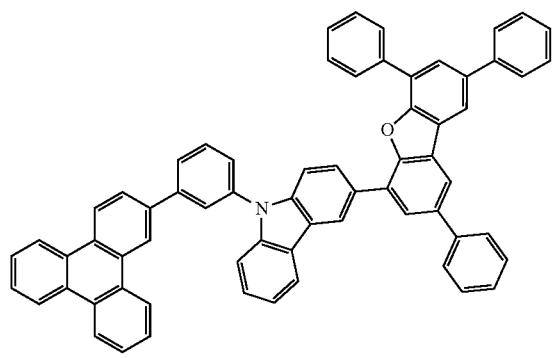
(510)
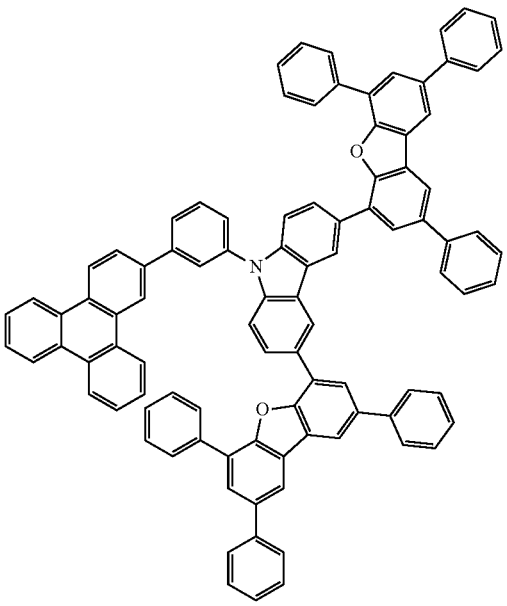
(511)
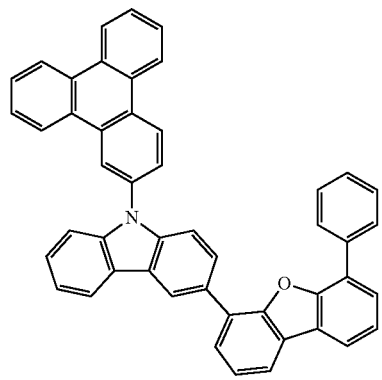
(512)
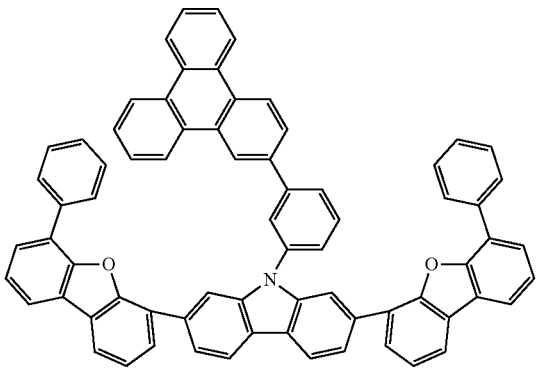
(513)
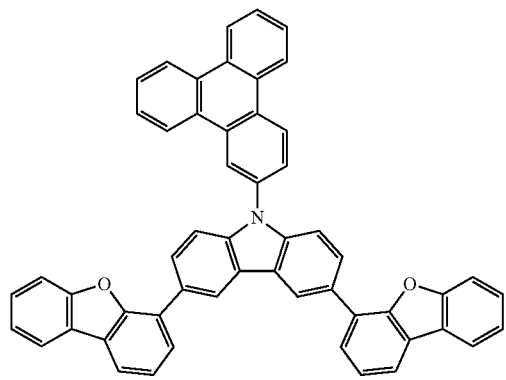
(514)
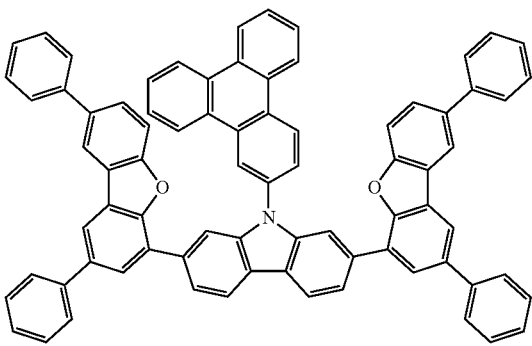

-continued
(515)
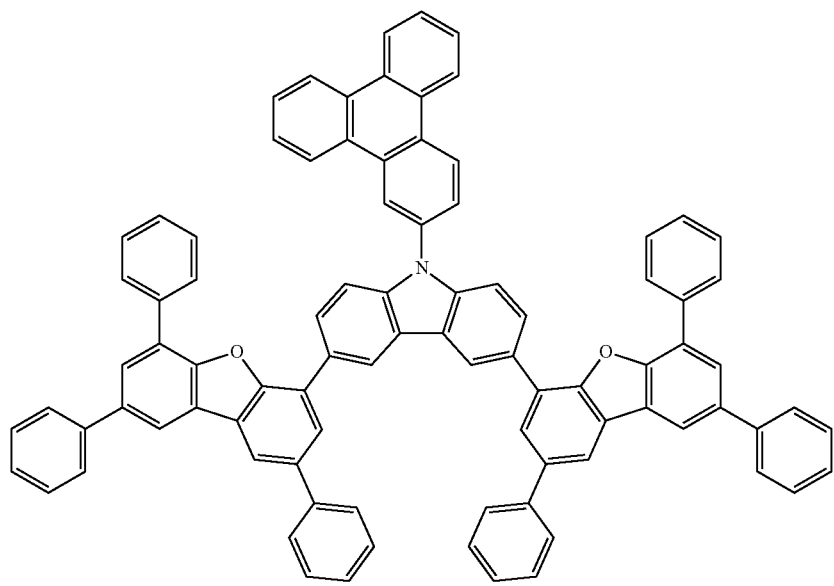
(516)
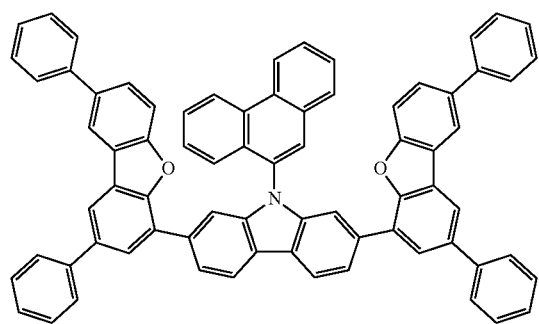
(517)
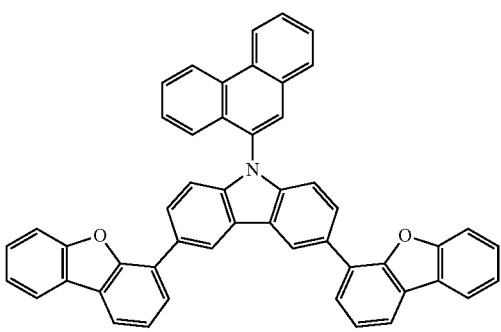
(518)
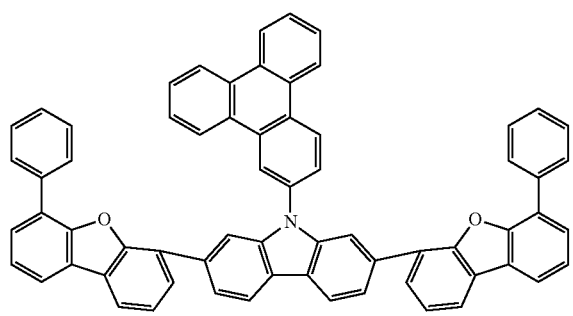
(519)
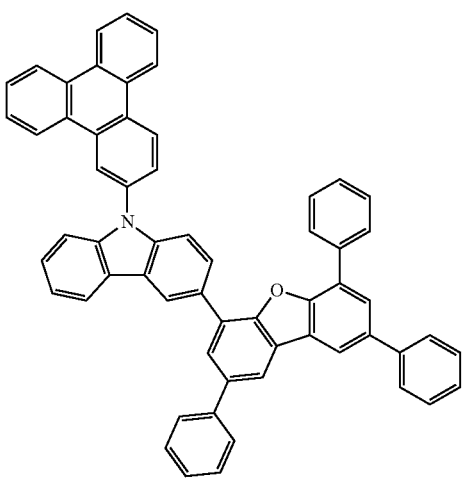

-continued
(520)
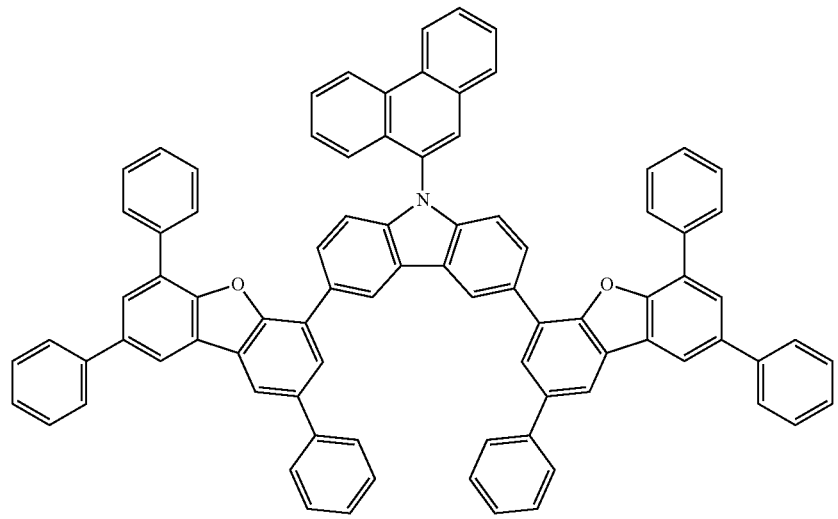
(521)
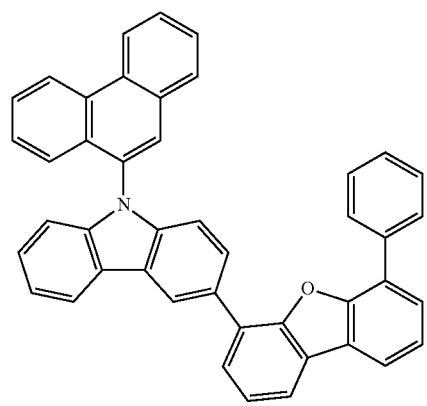
(522)
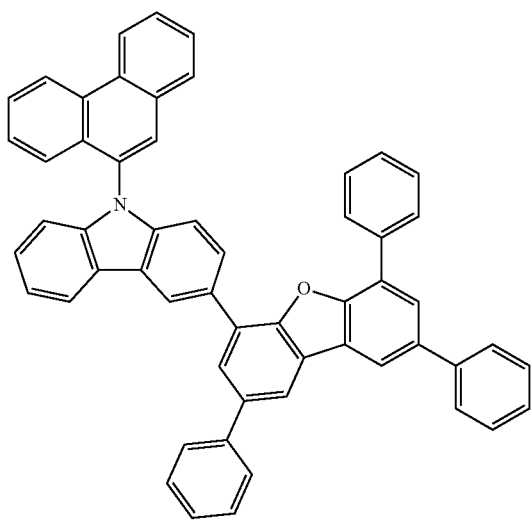
(523)
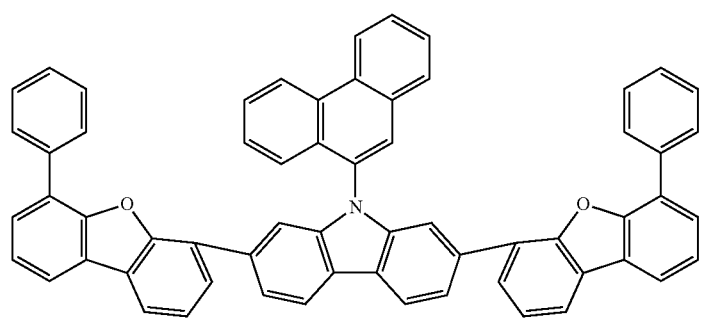

(524)
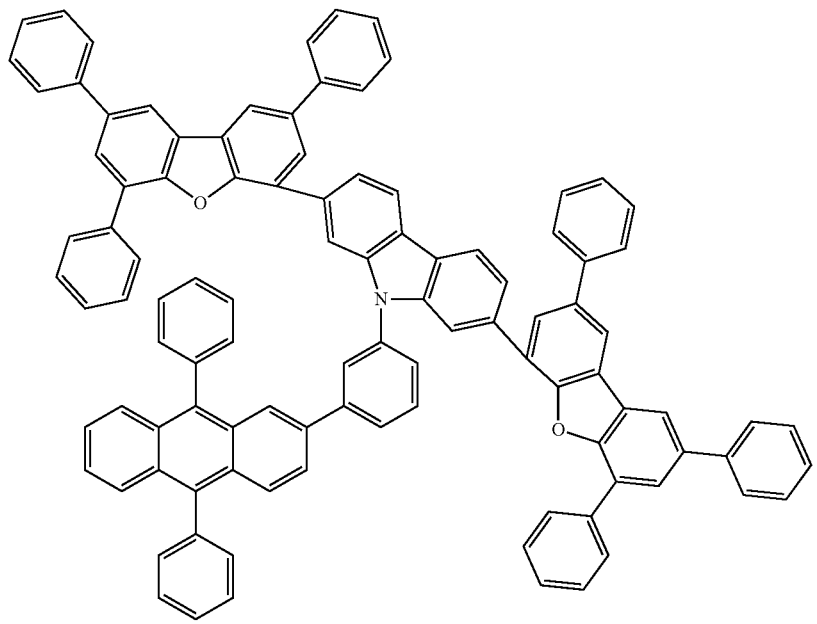
(525)
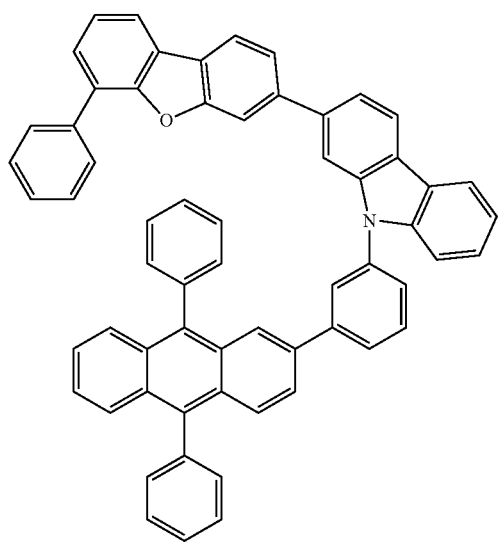
(526)
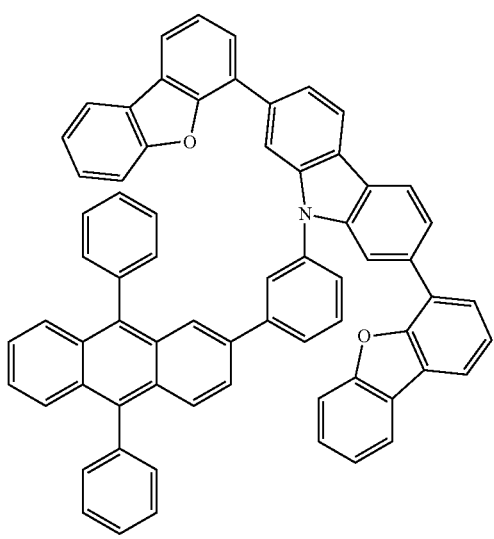

201
(527)
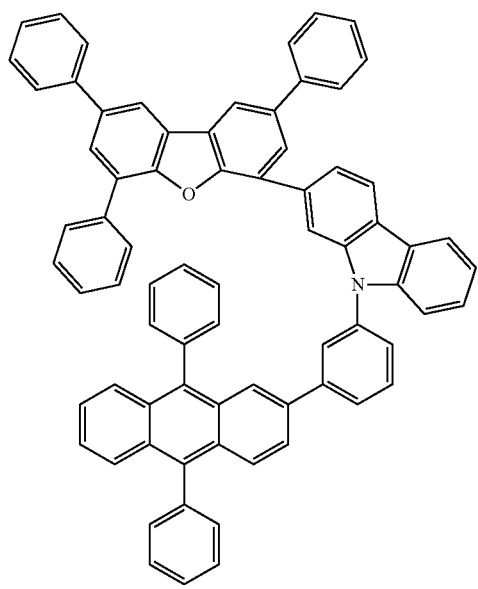
202
(528)
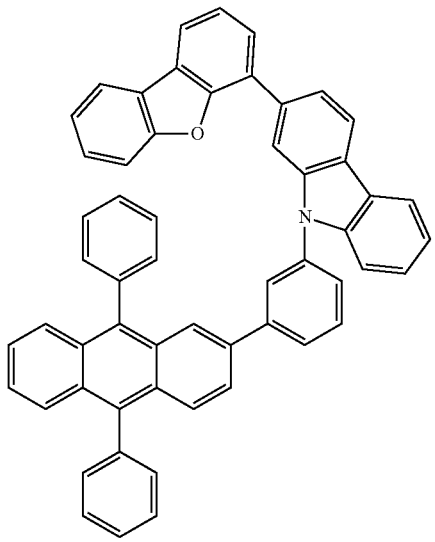
(529)
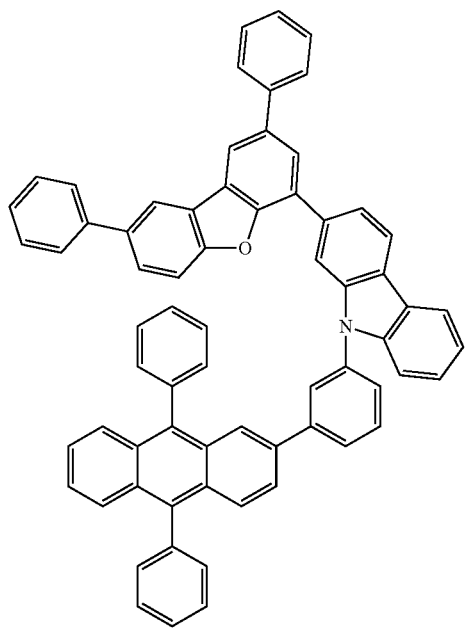
(530)
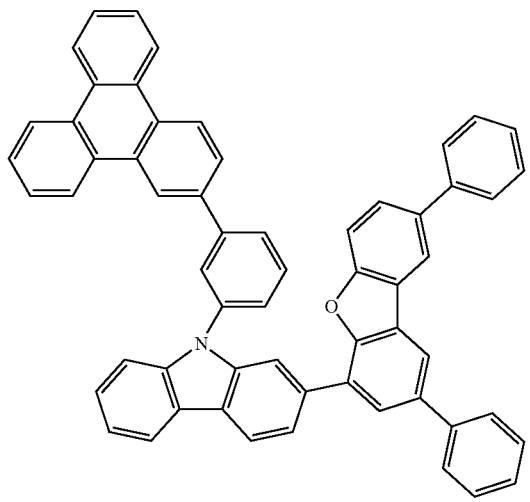

-continued
(531)
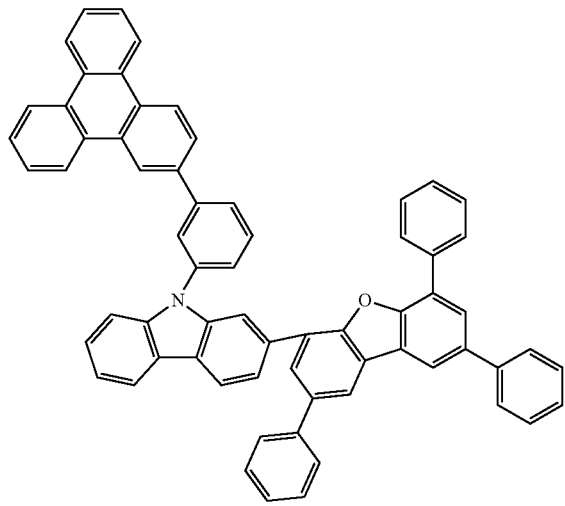
(532)
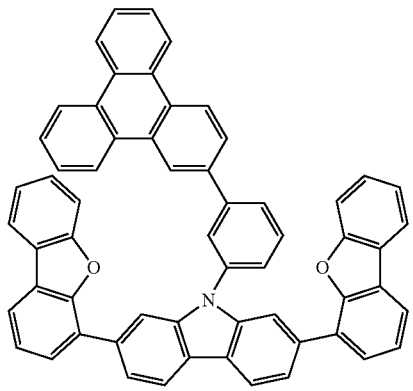
(533)
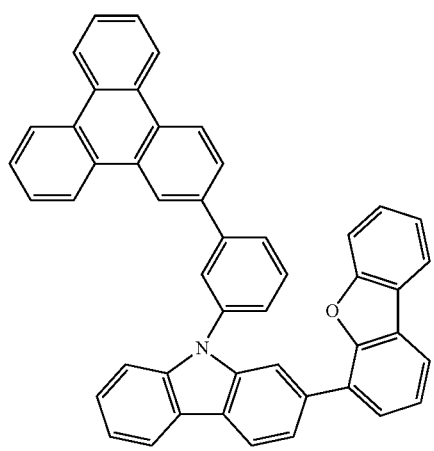
(534)
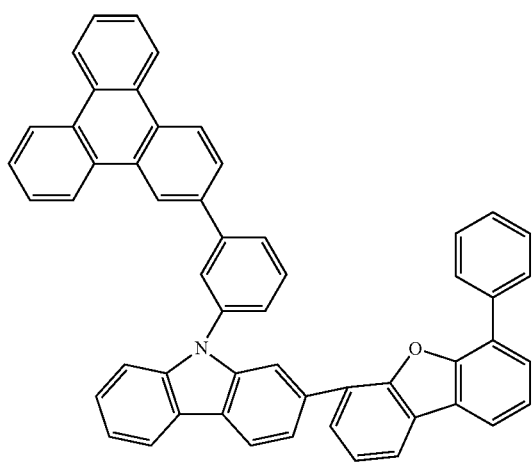
(535)
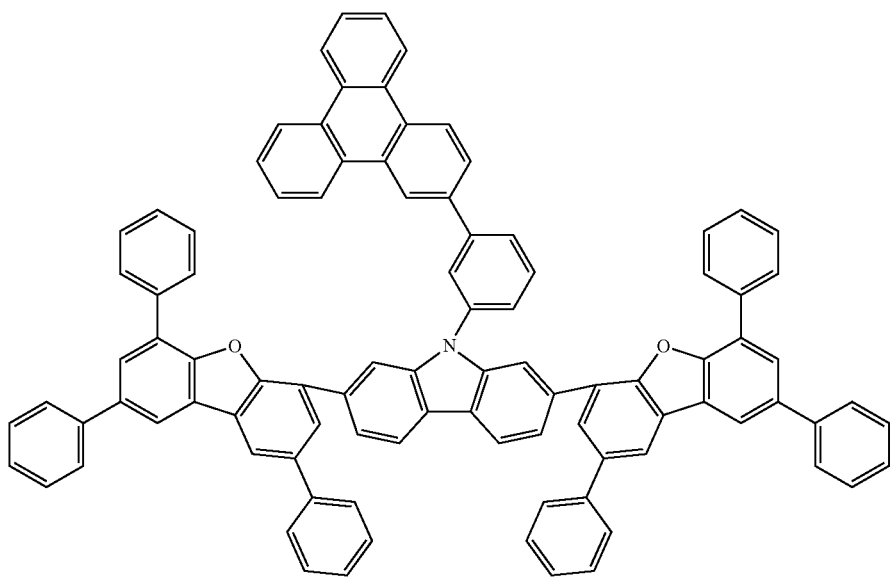

-continued
(536)
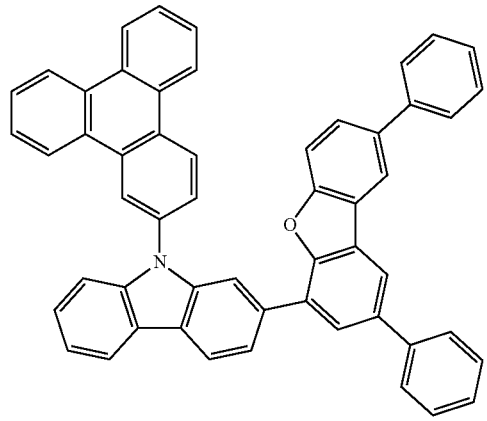
(537)
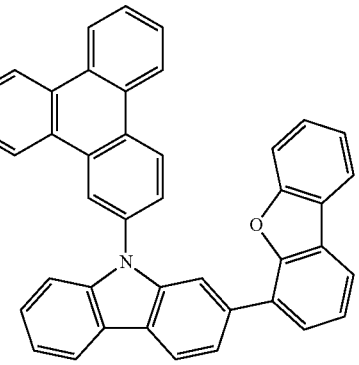
(538)
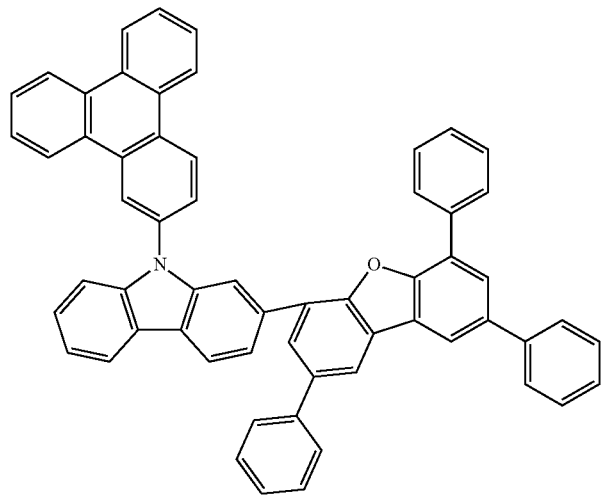
(539)
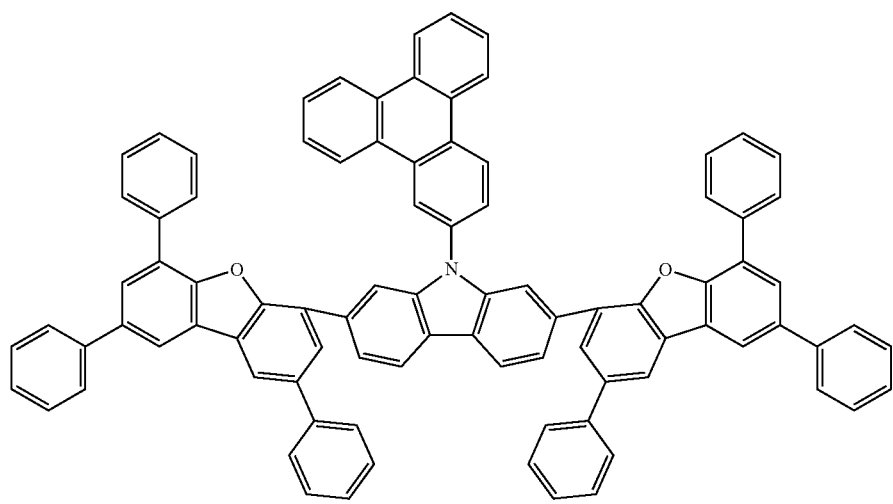

-continued
(540)
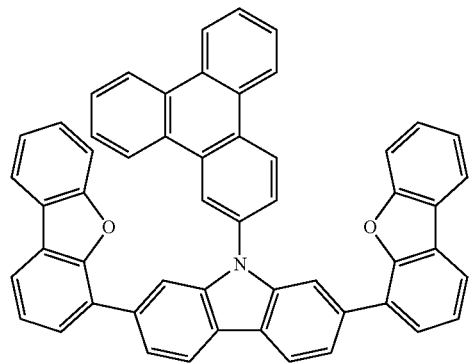
(541)
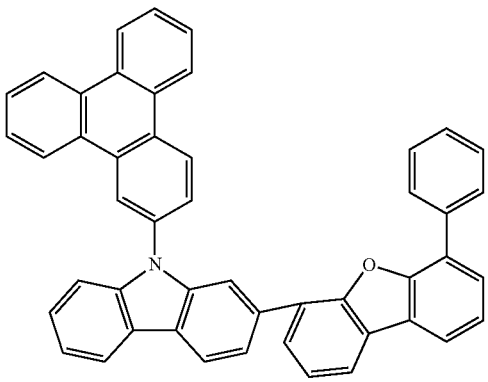
(542)
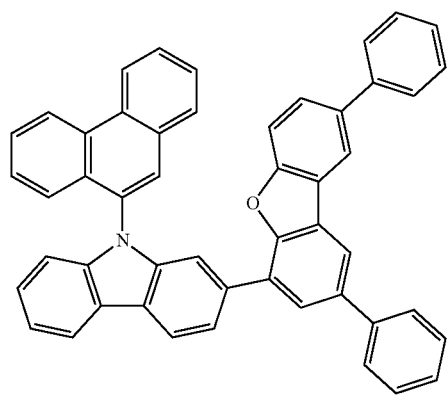
(543)
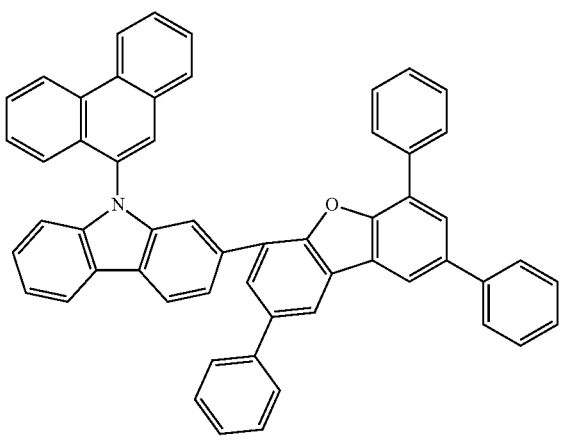
(544)
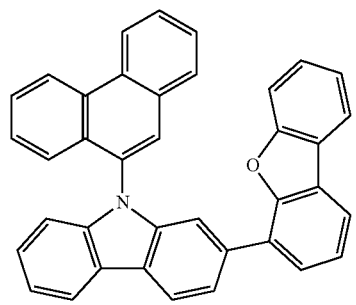
(545)
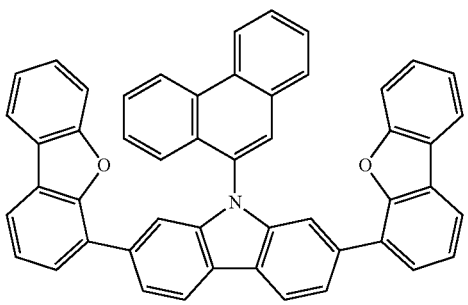
(546)
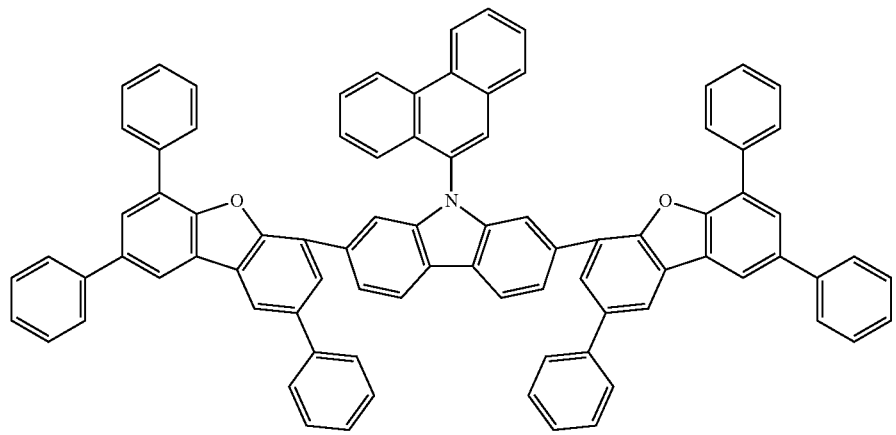

-continued
(547)
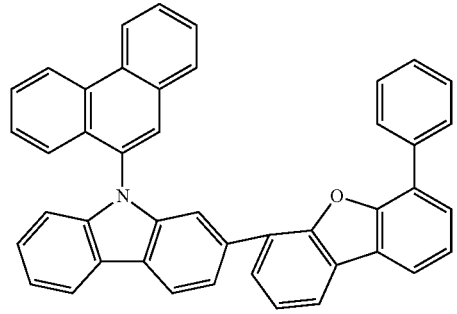
(548)
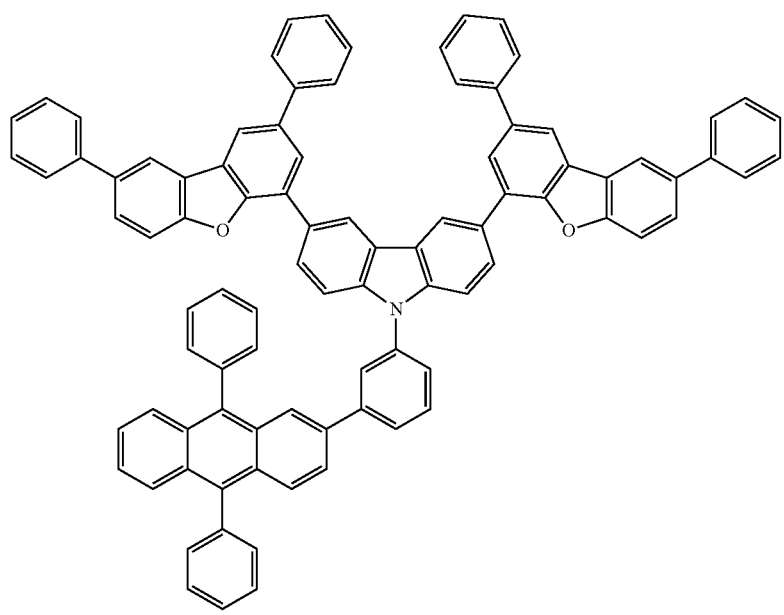
(549)
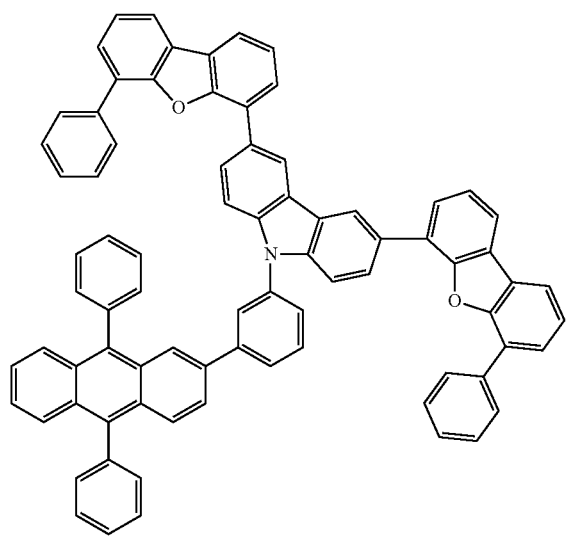
(550)
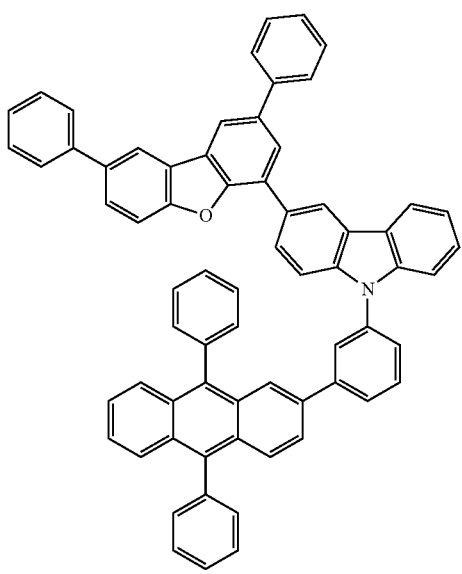

-continued
211 (551)
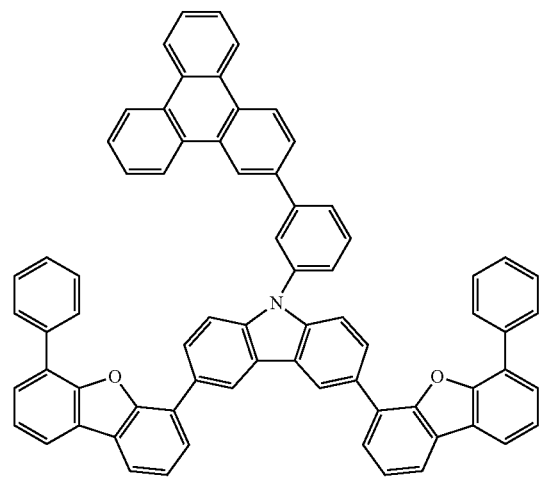
212 (552)
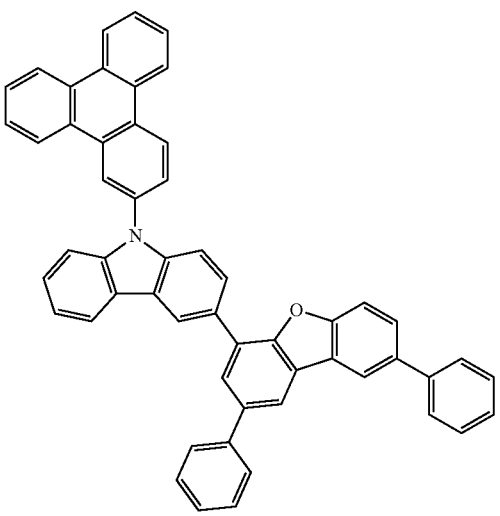
(553)
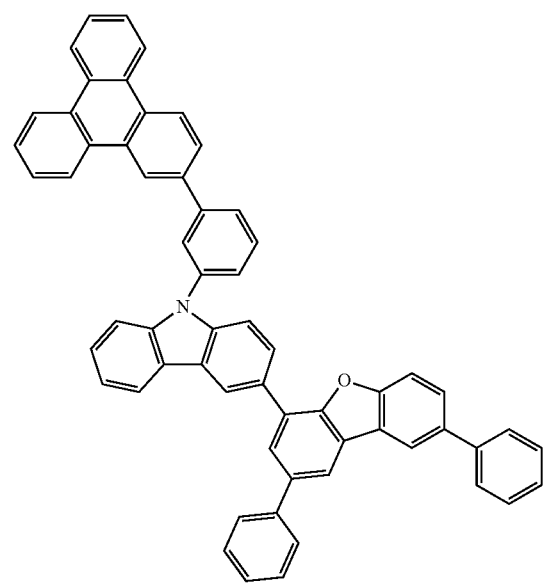

(554)
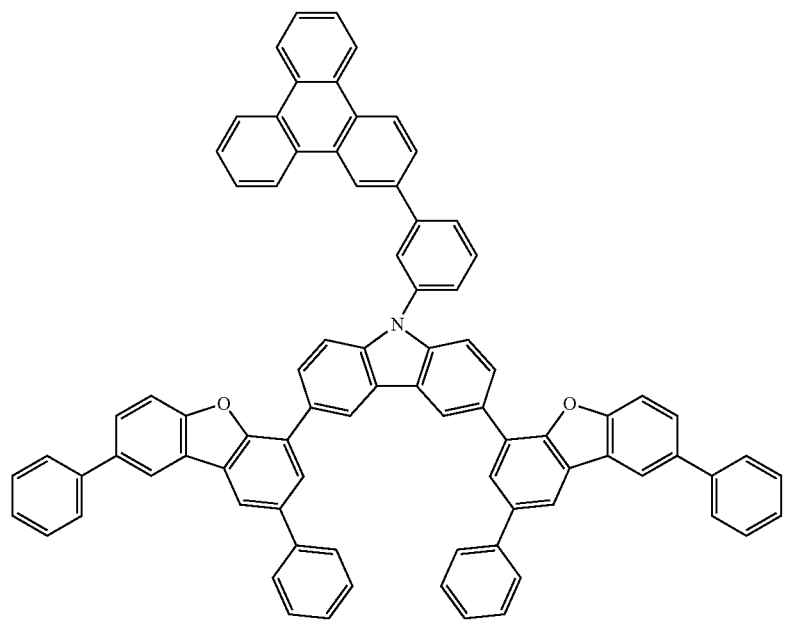
(555)
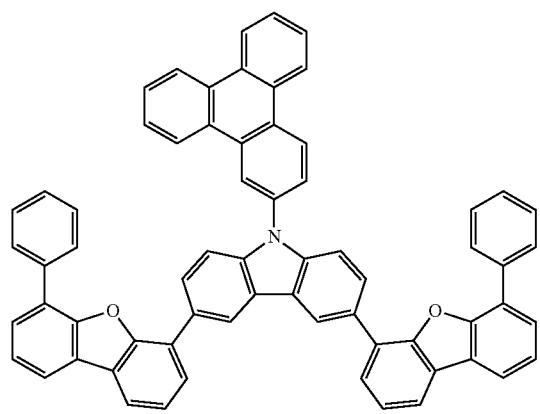
(556)
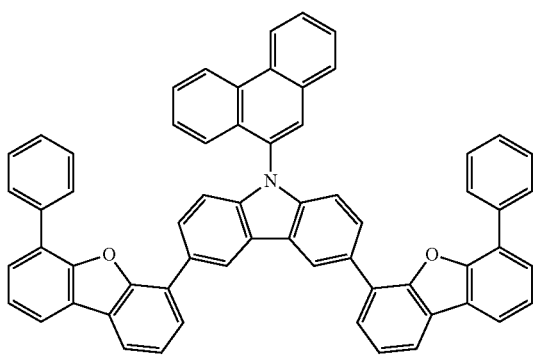
(557)
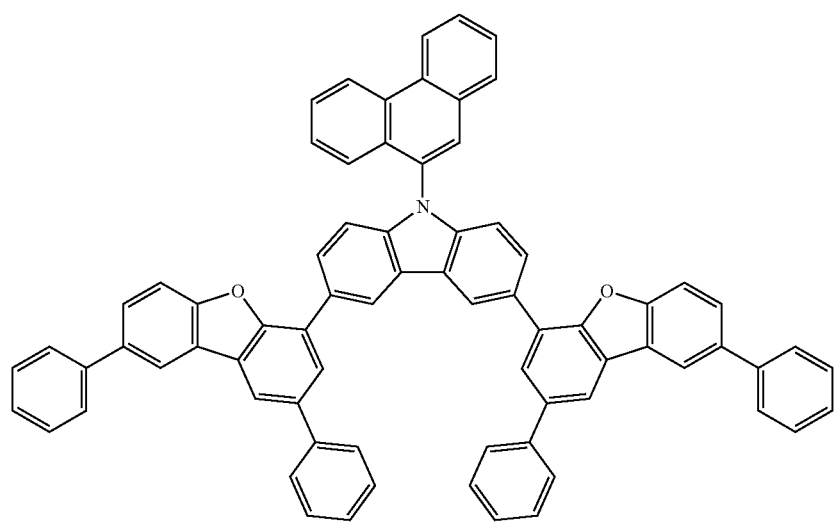

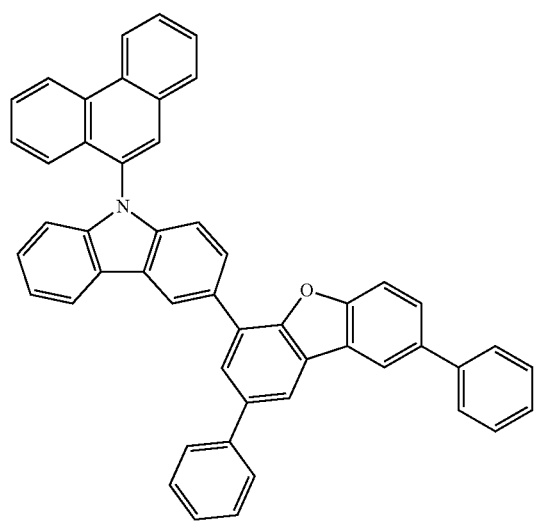
(558)
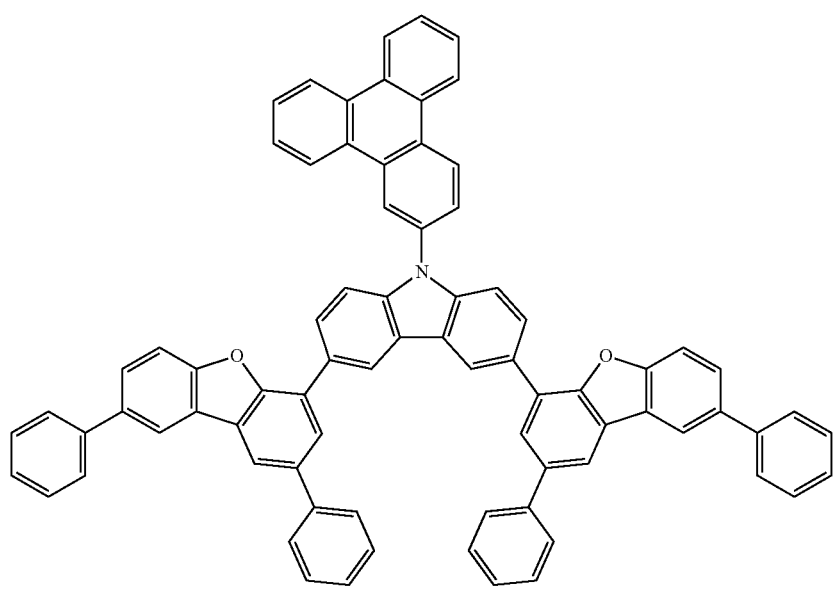
(559)

217
218
-continued
(560)
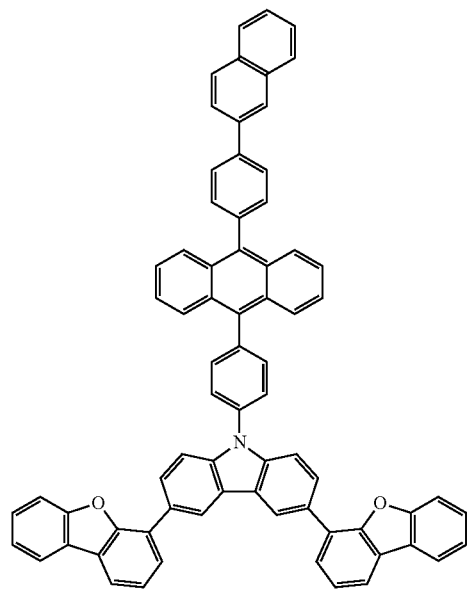
(561)
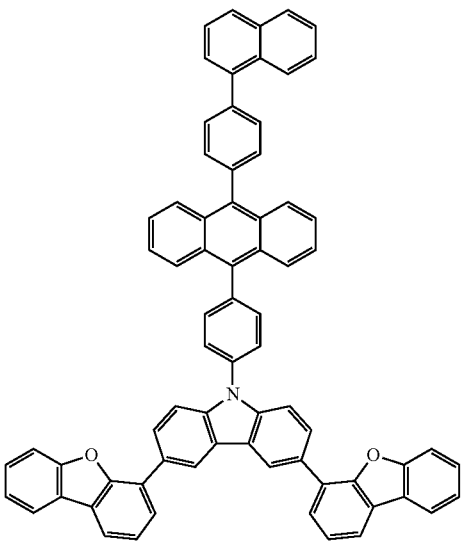
(562)
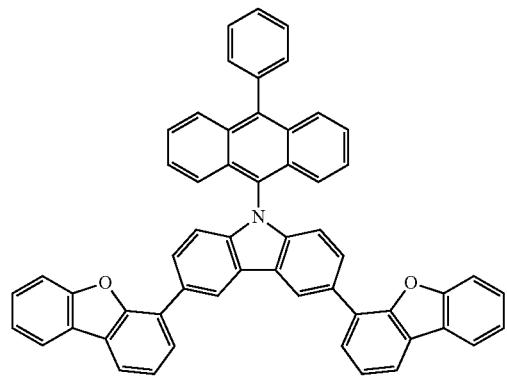
(563)
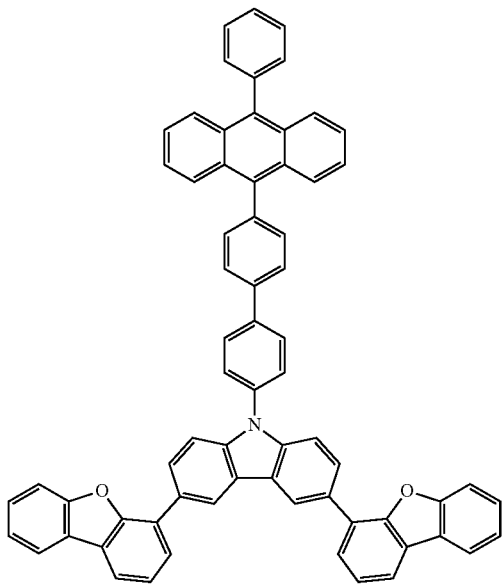

-continued
(564)
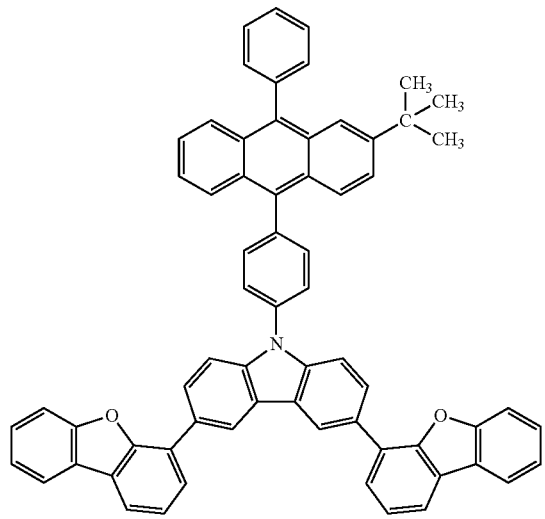
(565)
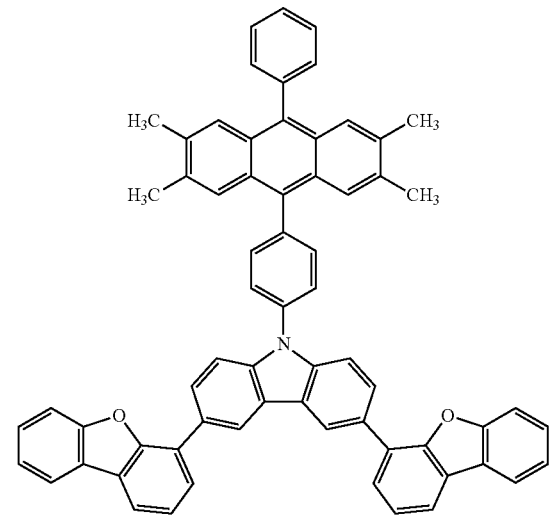
(566)
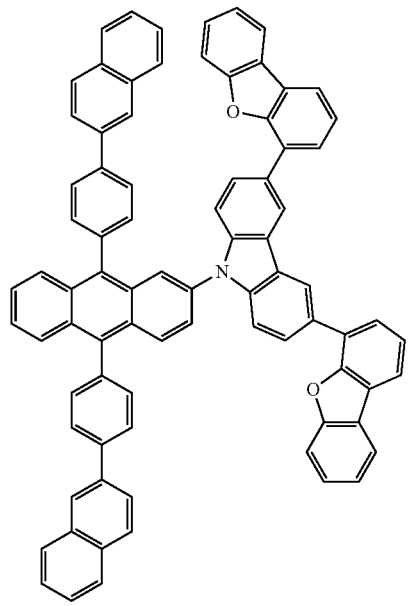
(567)
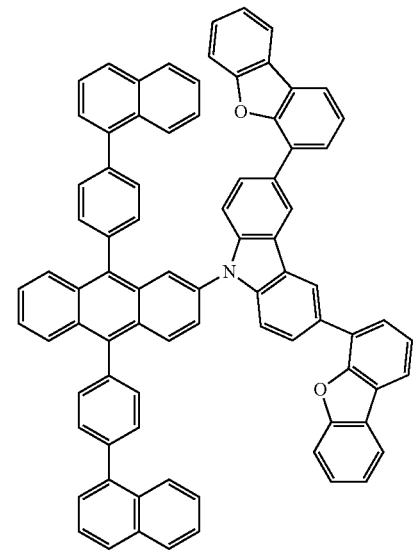
(568)
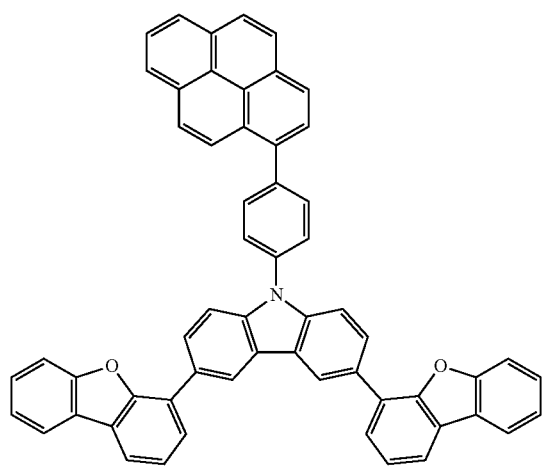
(569)
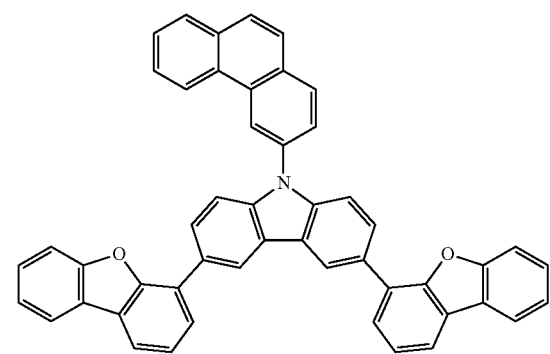

-continued
(570)
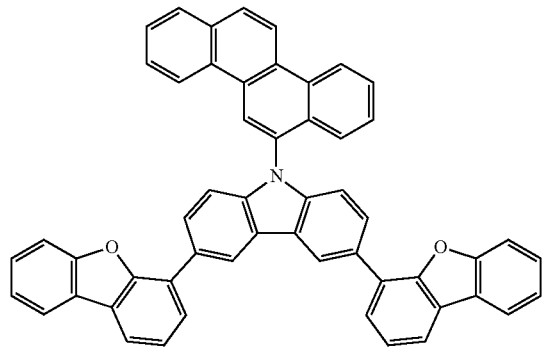
(571)
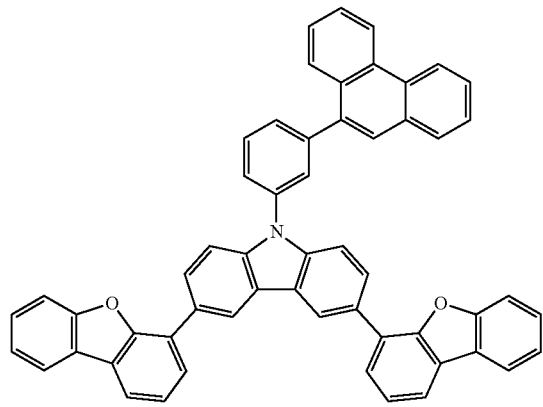
(572)
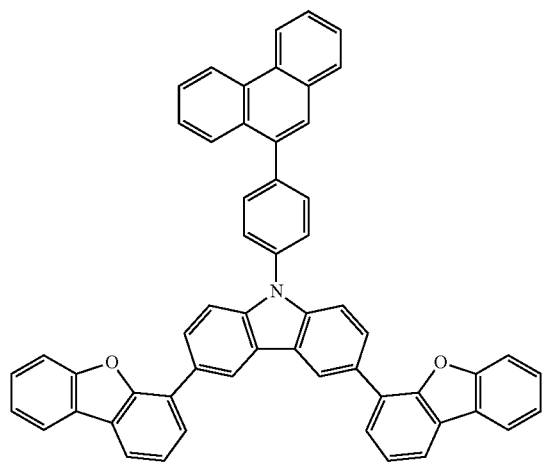
(581)
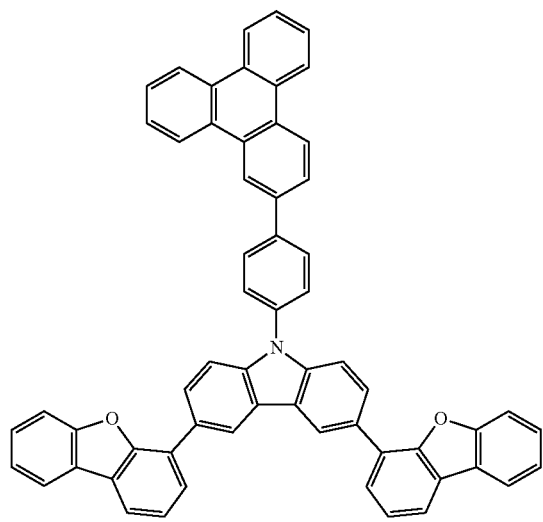
(582)
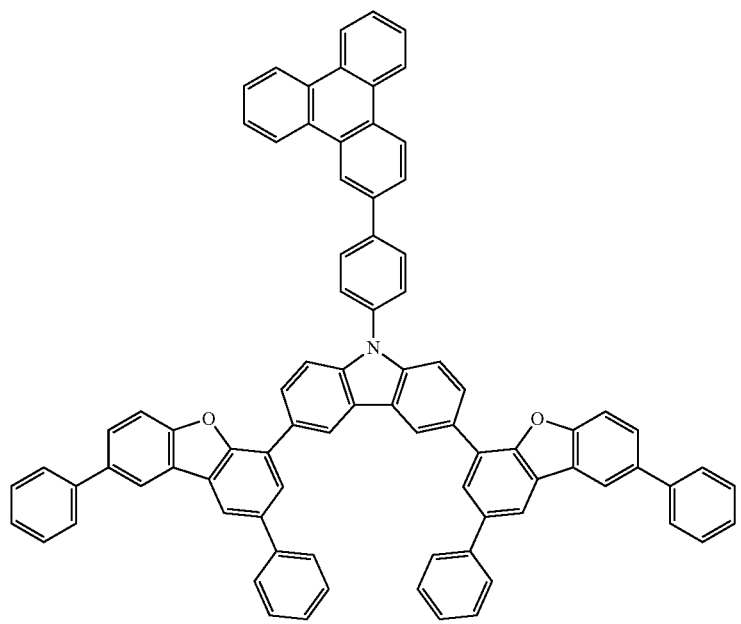

223
224
-continued
(583)
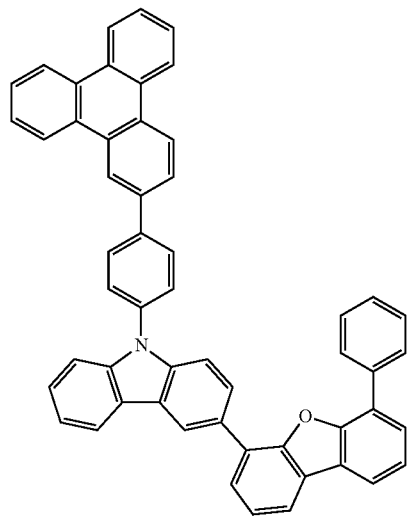
(584)
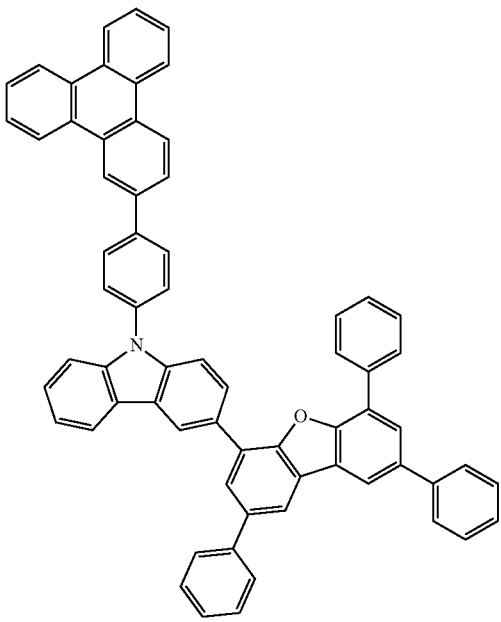
(591)
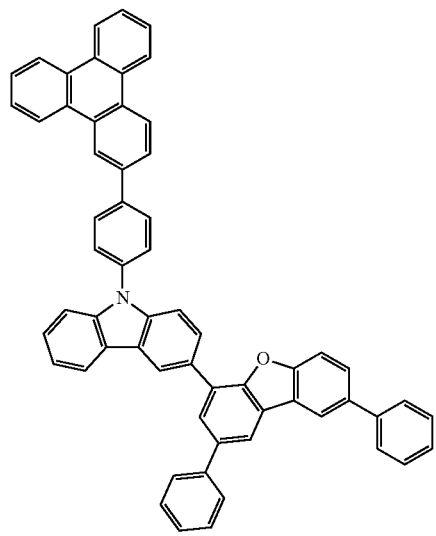
(592)
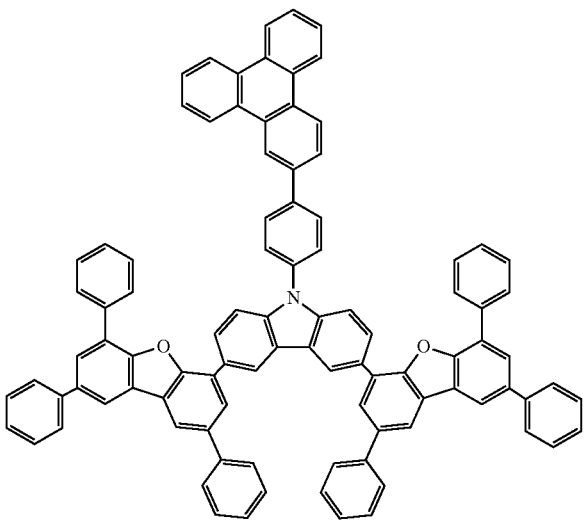

(593)
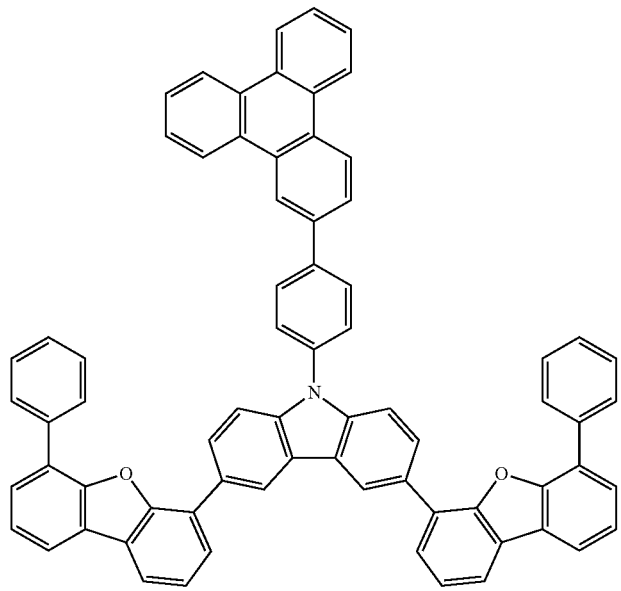
(594)
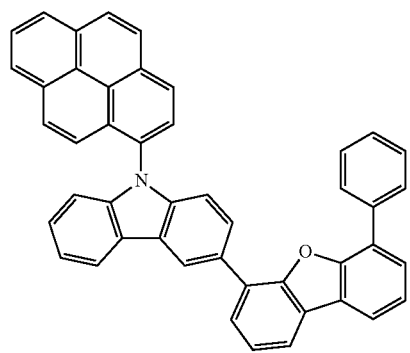
(595)
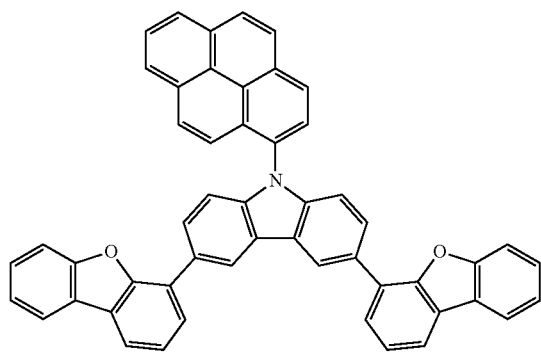
(596)
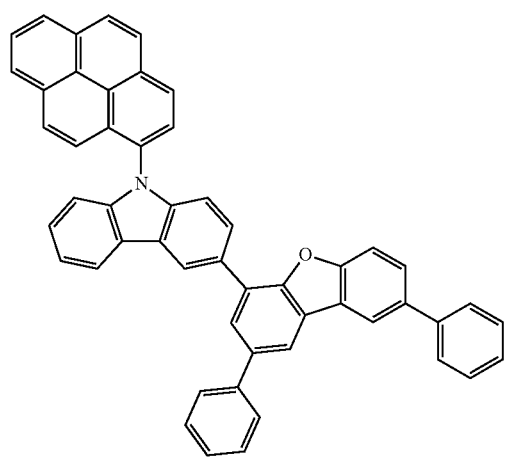
(597)
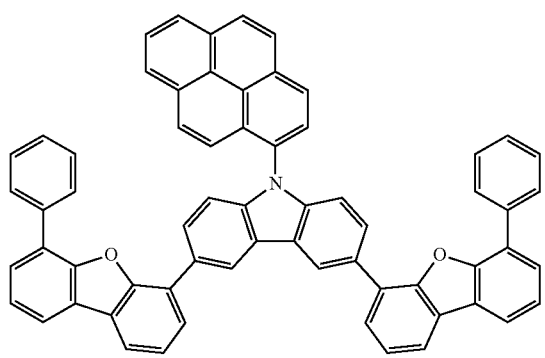

(598)
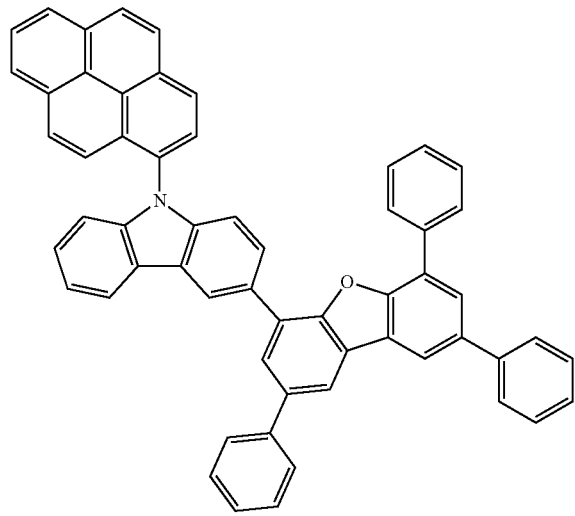
(599)
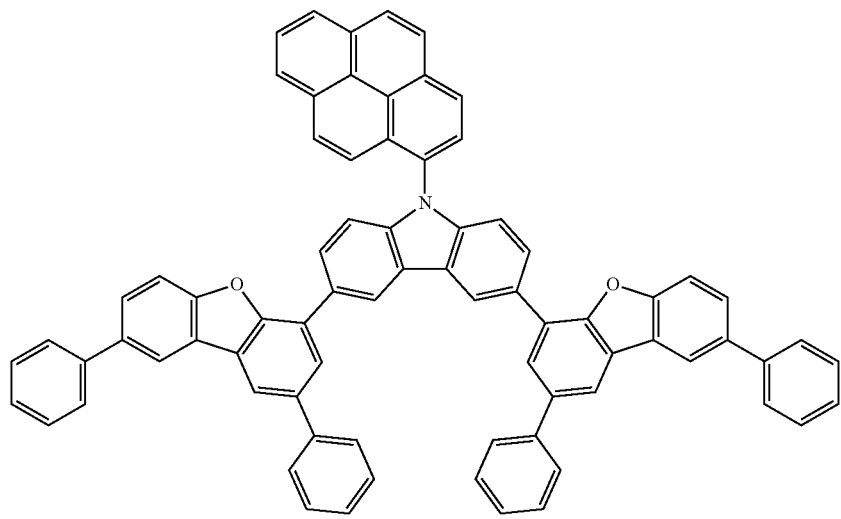
(600)
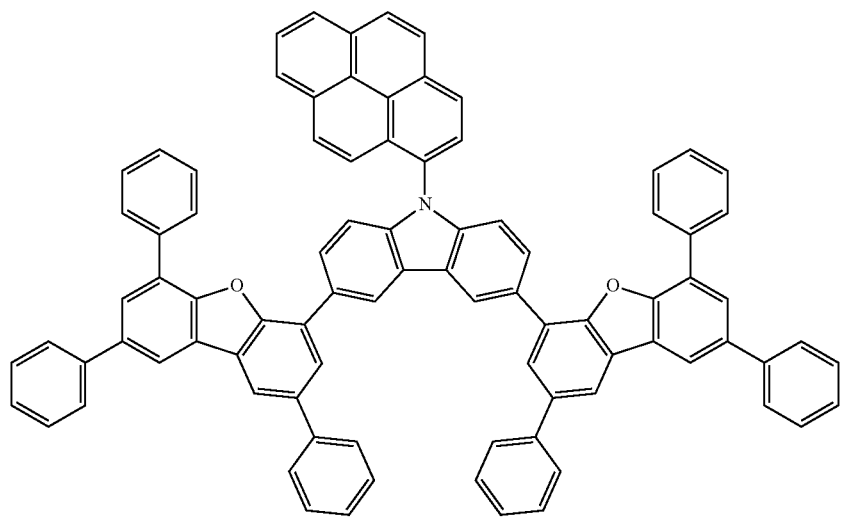

(601)
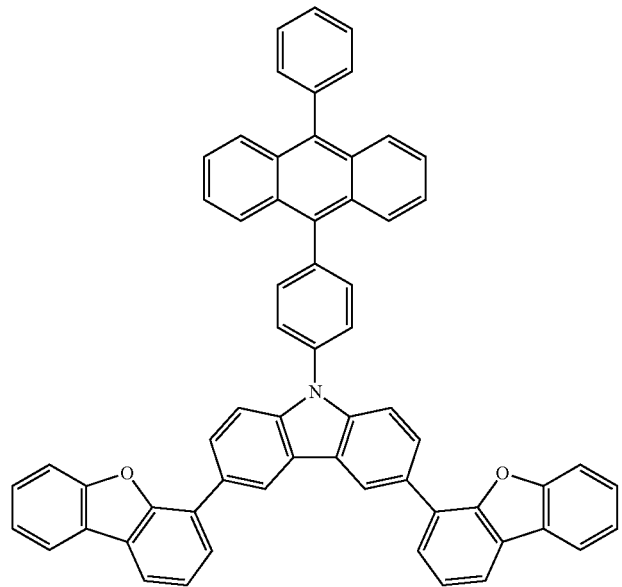
(602)
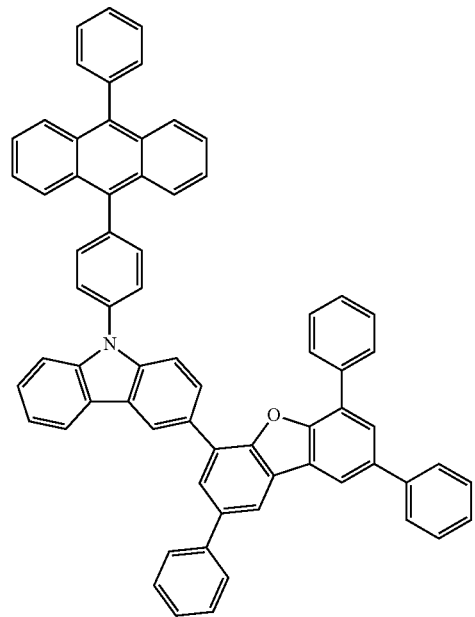
(603)
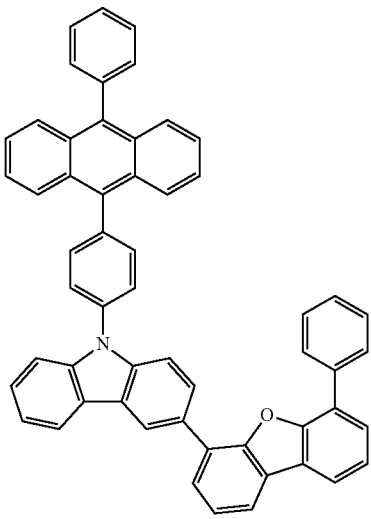

(604)
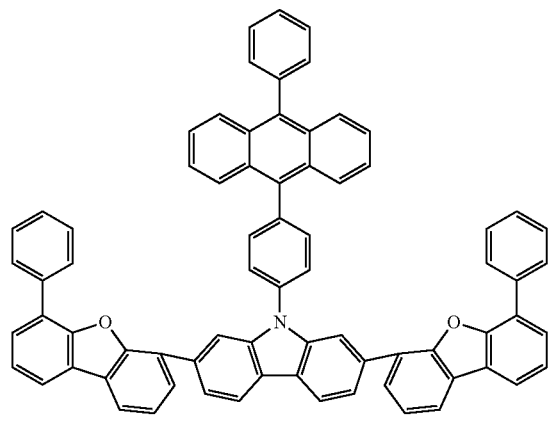
(605)
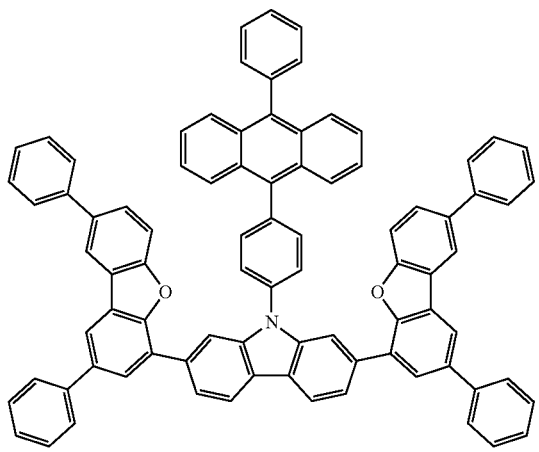
(606)
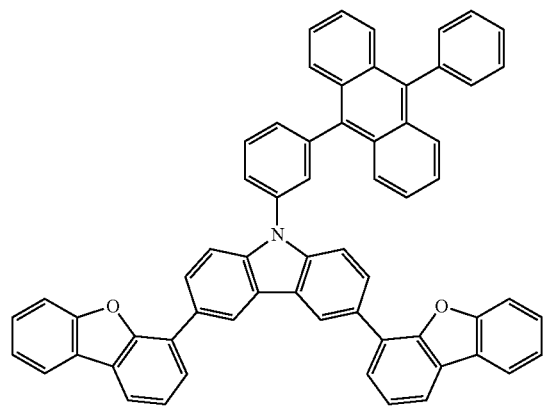
(607)
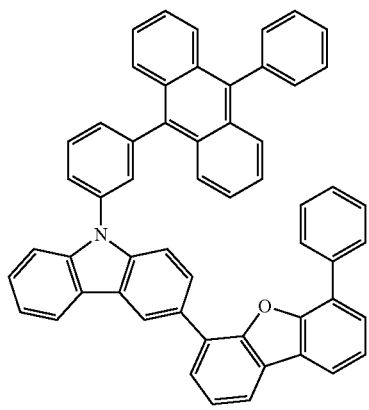
(608)
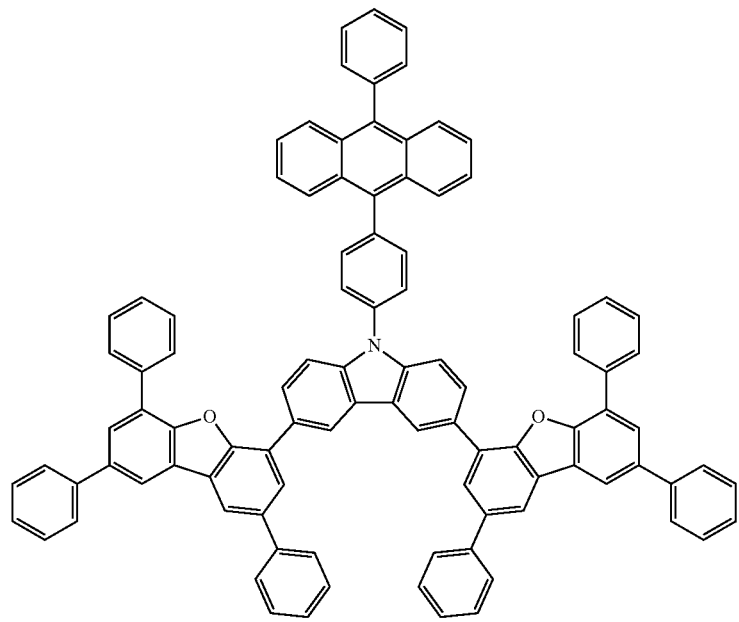

-continued
(609)
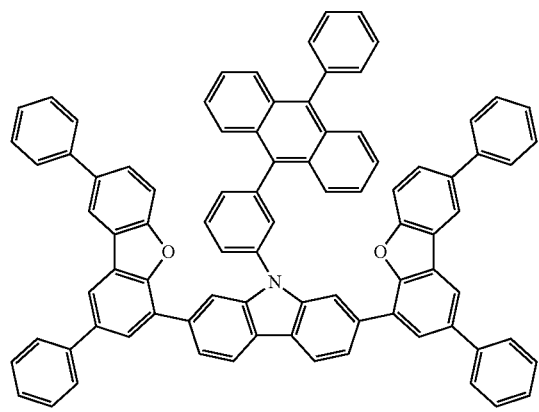
(610)
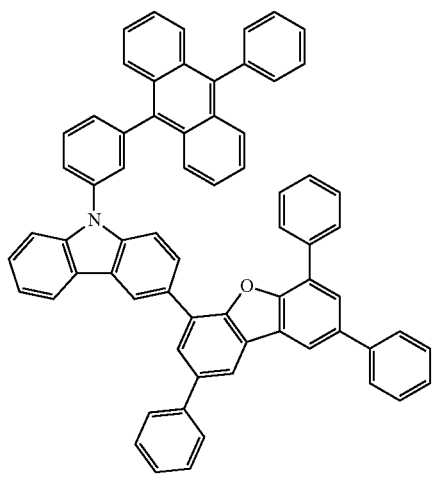
(611)
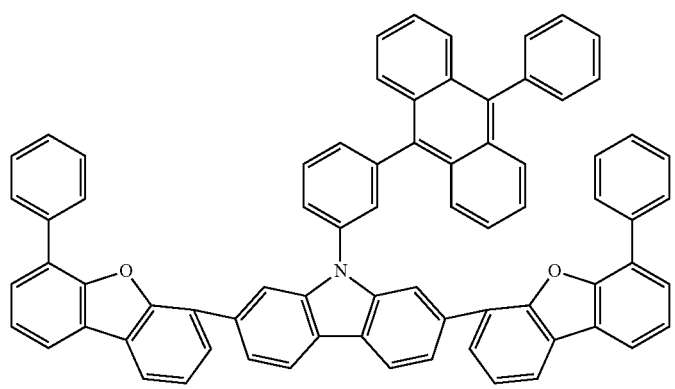
(612)
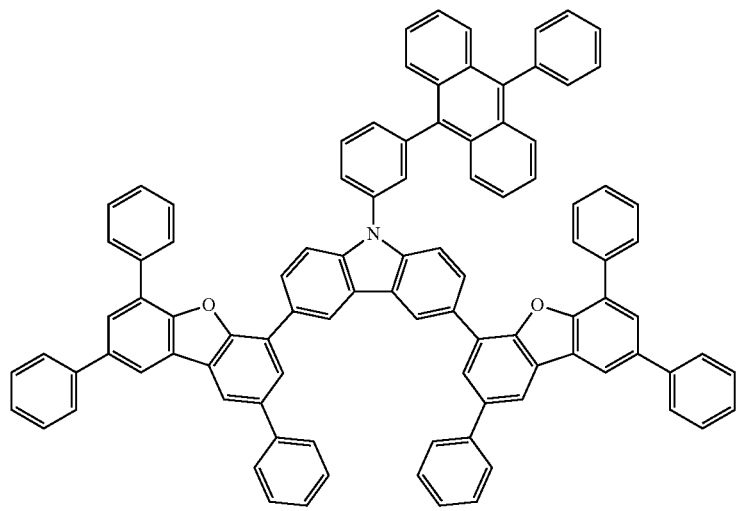

-continued
(613)
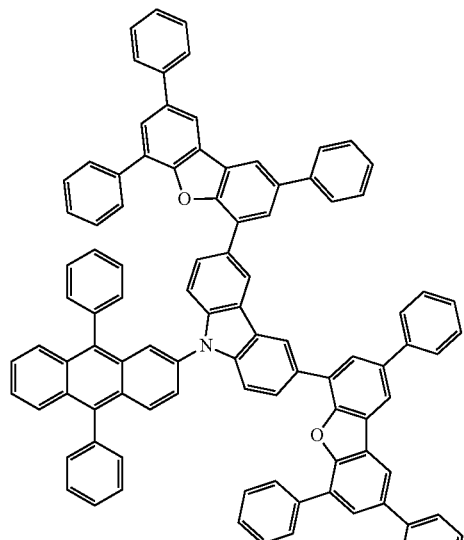
(614)
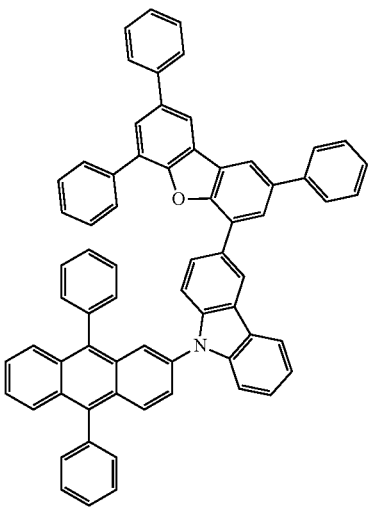
(615)
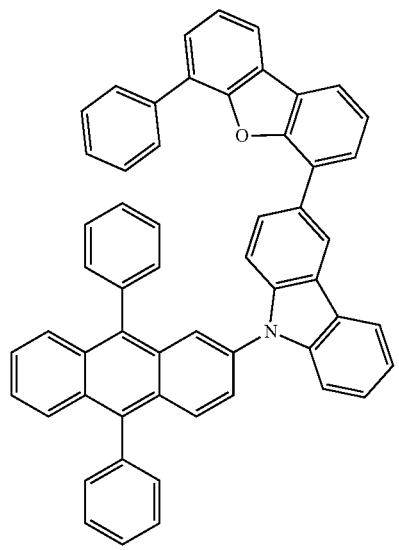
(616)
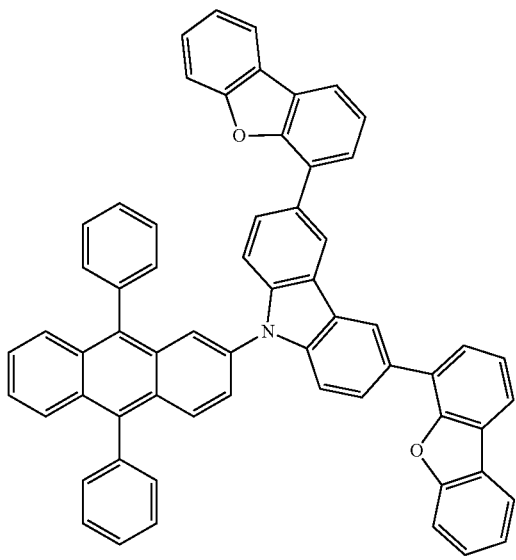
(617)
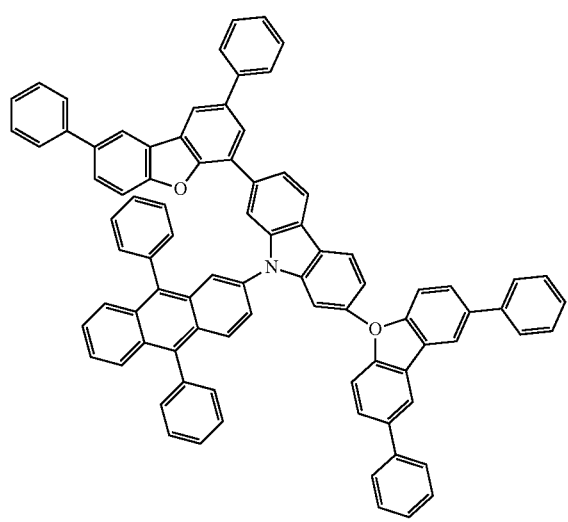
(618)
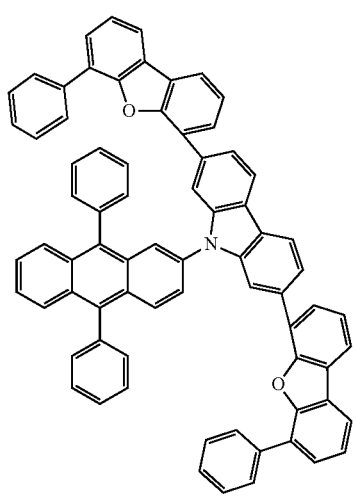

(619)
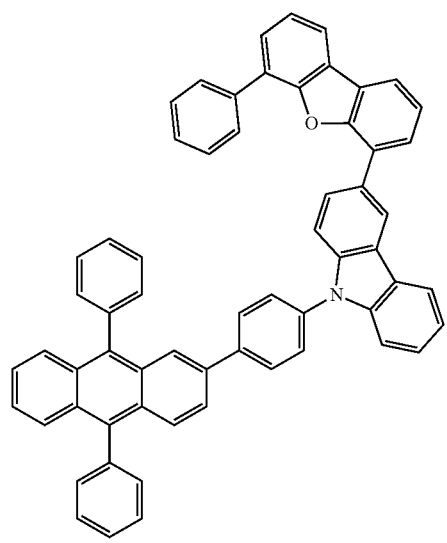
(620)
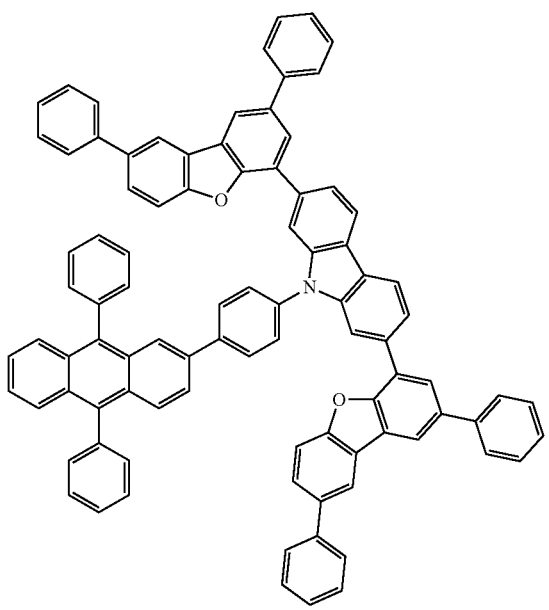
(621)
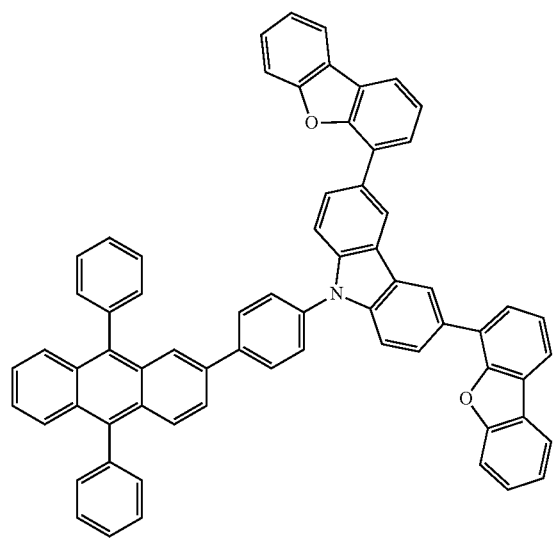
(622)
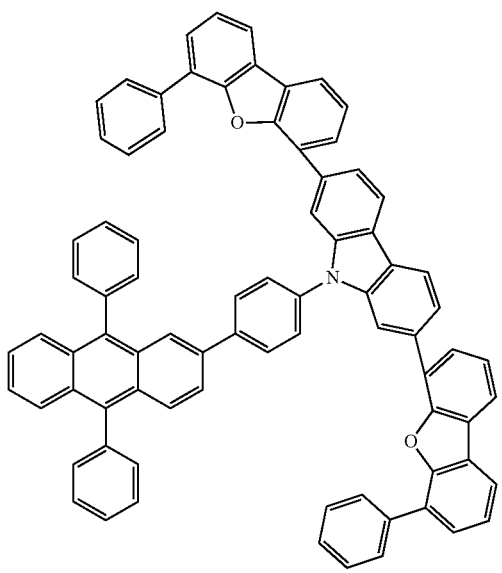

-continued
(623)
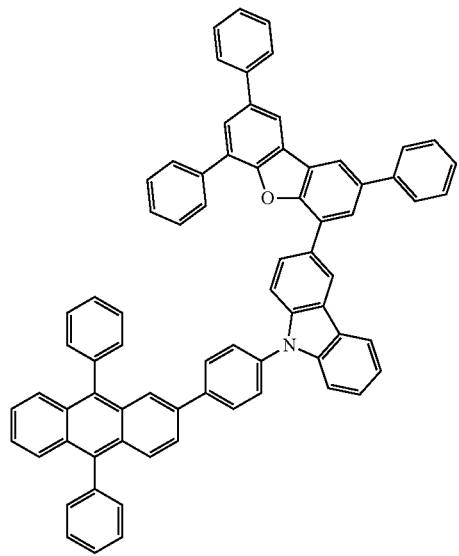
(624)
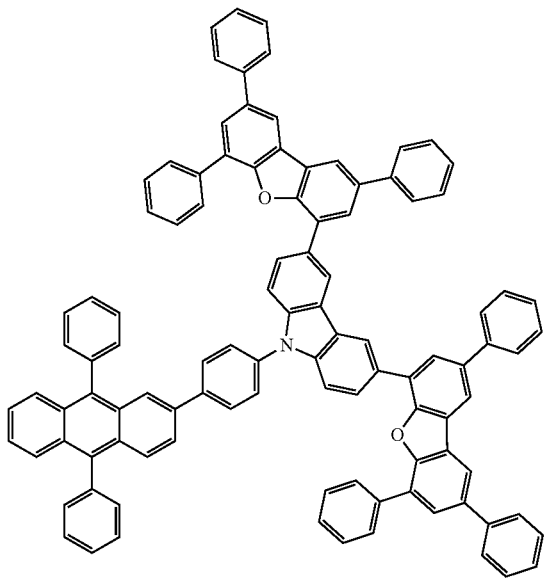
(625)
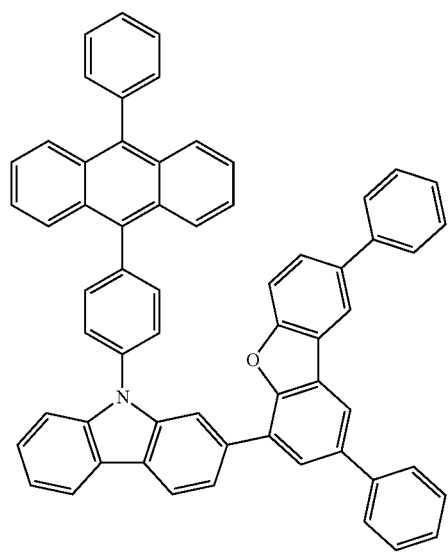
(626)
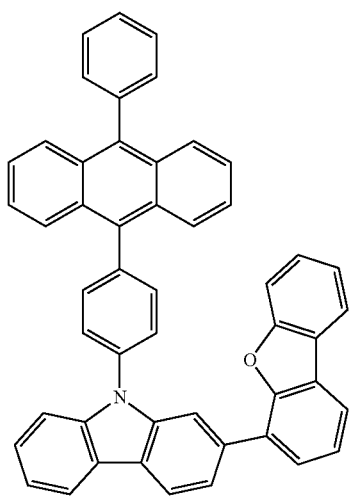

-continued
(627)
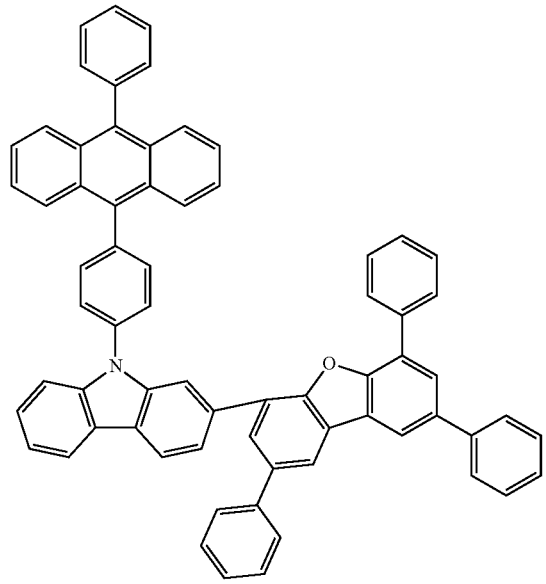
(628)
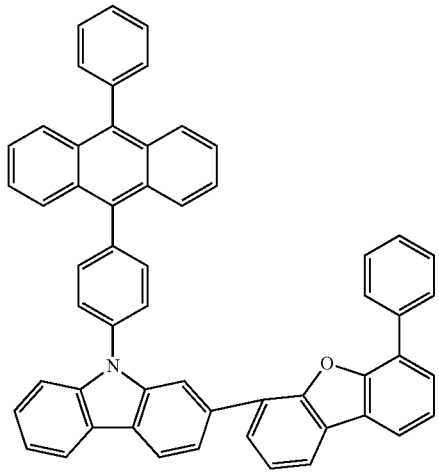
(629)
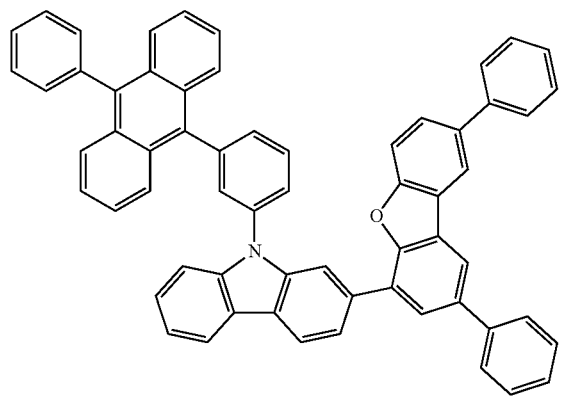
(630)
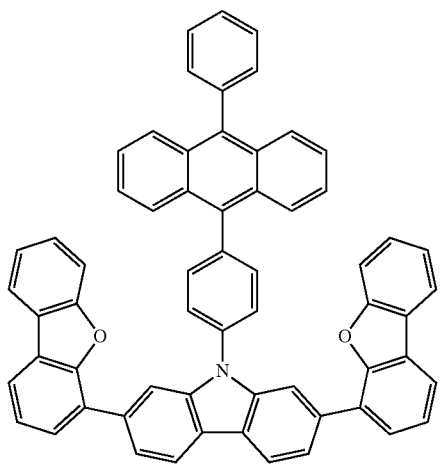
(531)
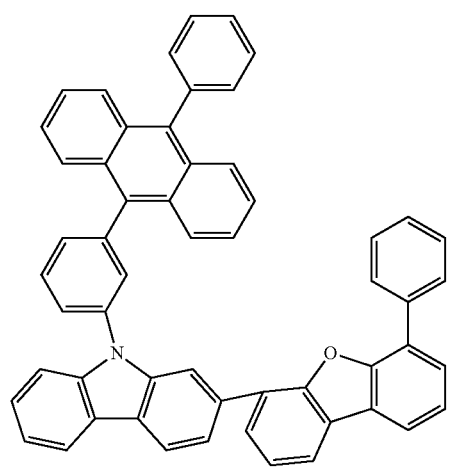

-continued
(532)
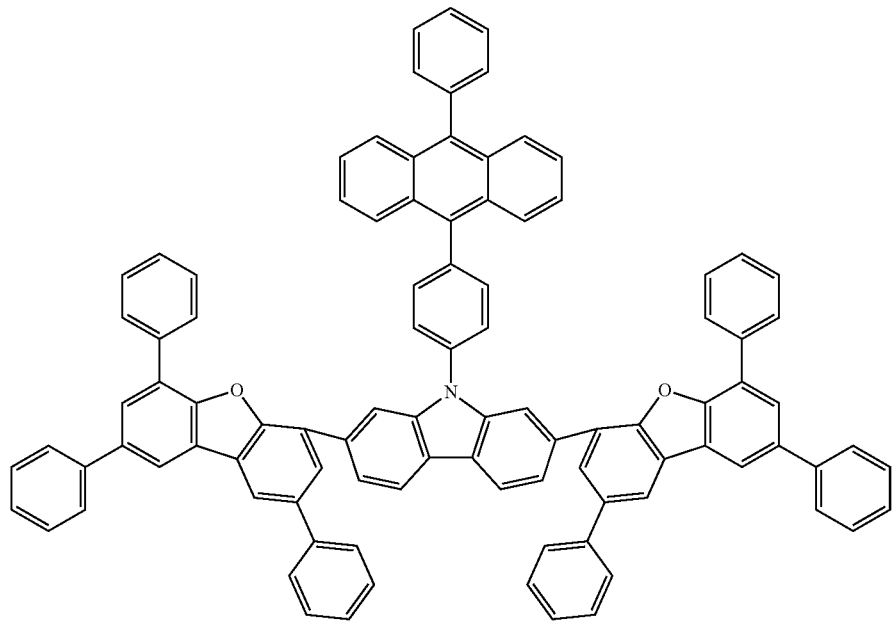
(533)
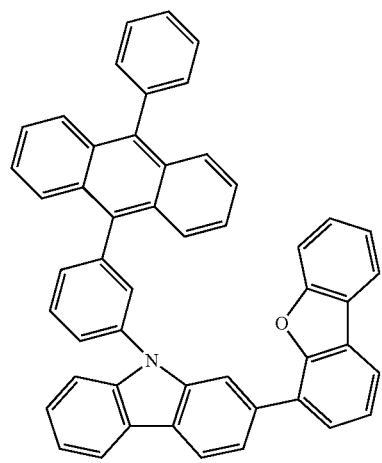
(634)
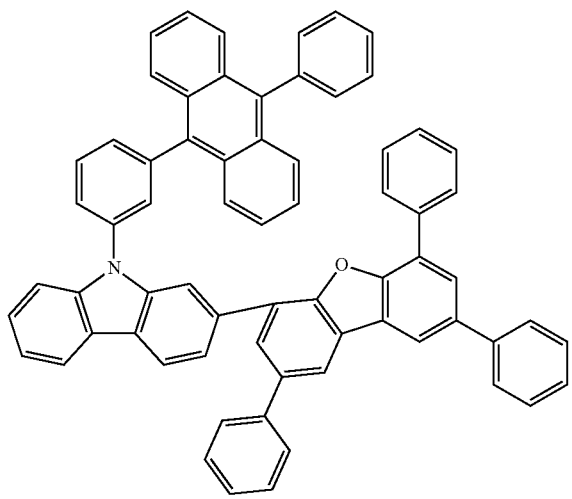
(635)
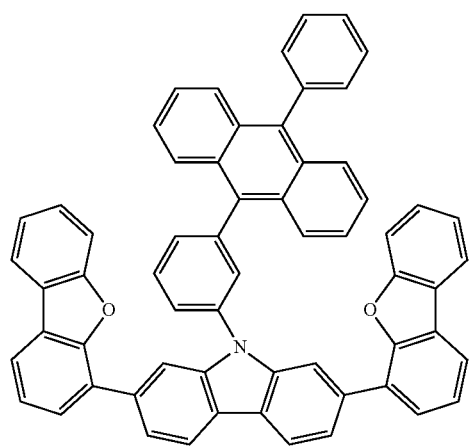

(636)
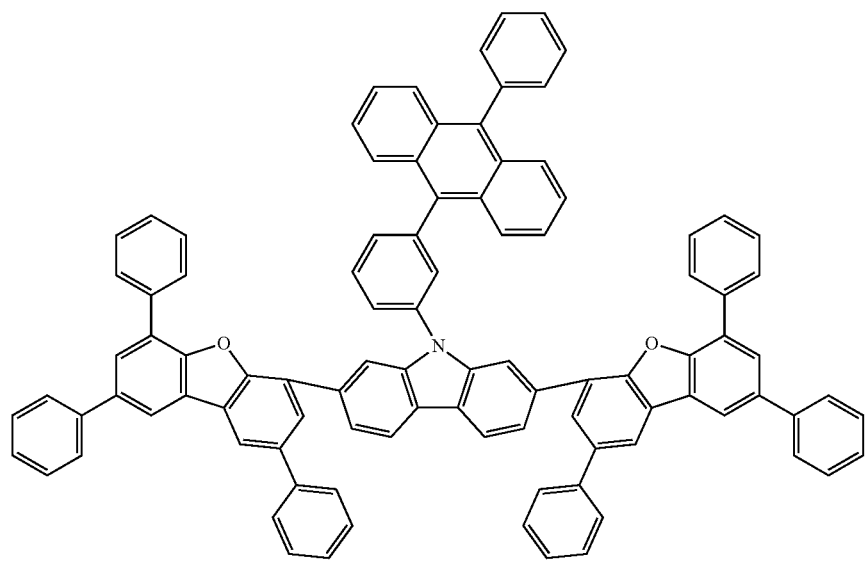
(637)
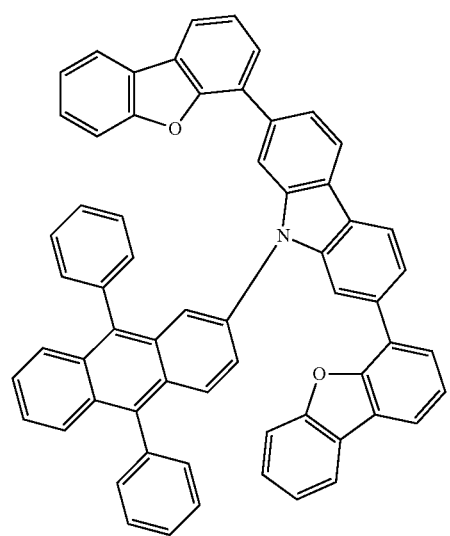
(638)

(639)
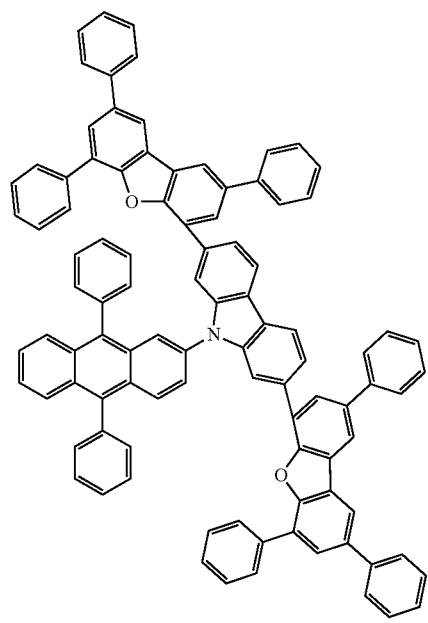
(640)
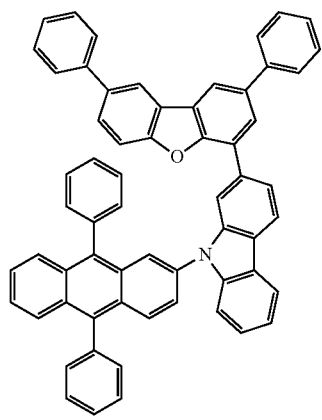
(641)
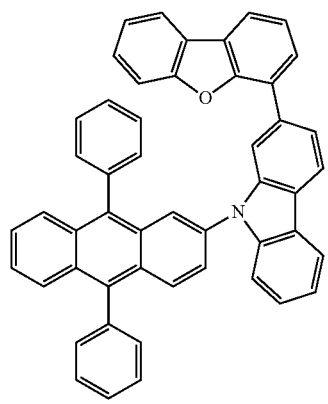
(642)
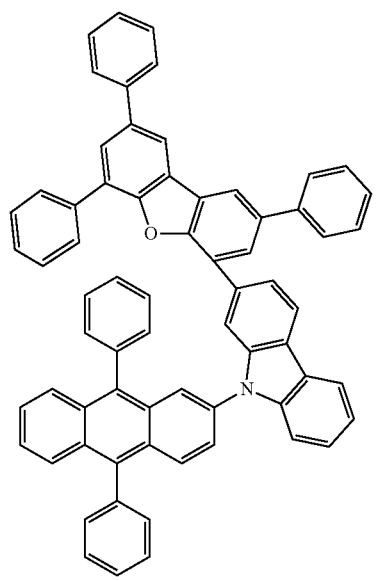

-continued
(643)
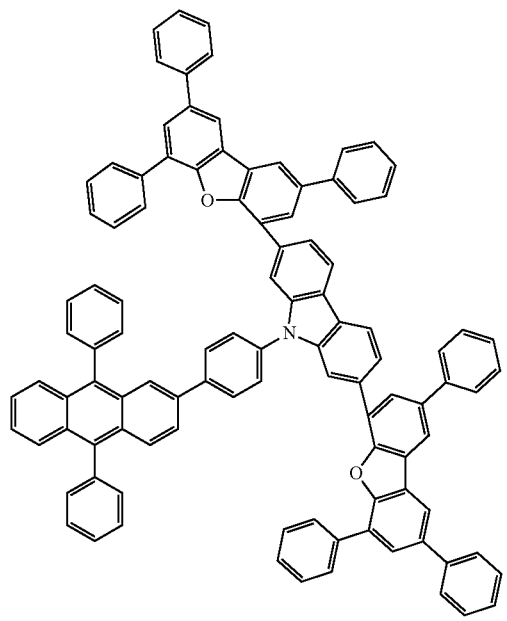
(644)
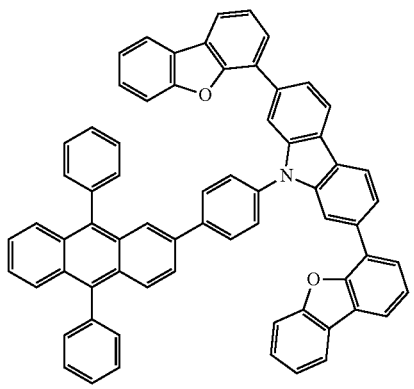
(645)
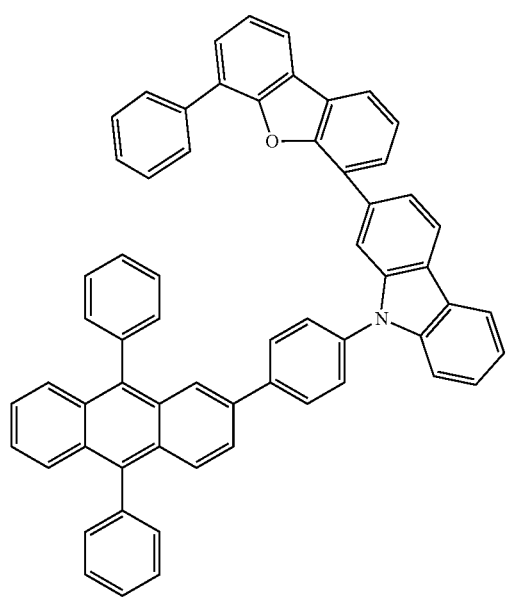
(646)
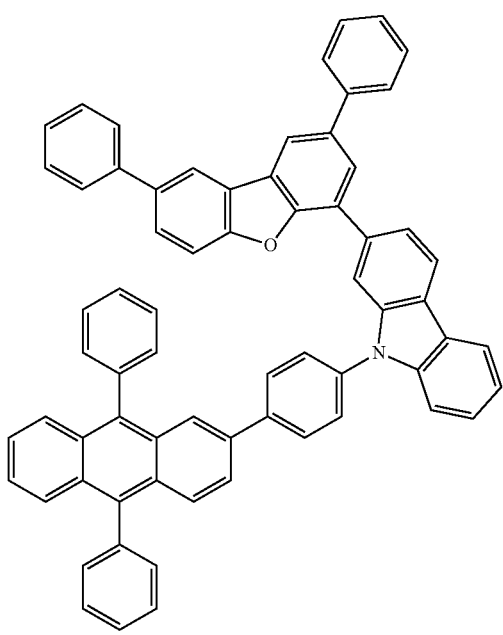

-continued
(647)
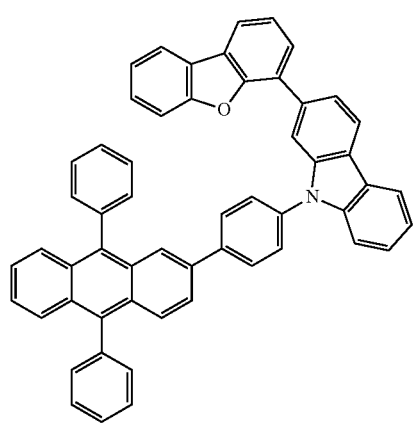
(648)
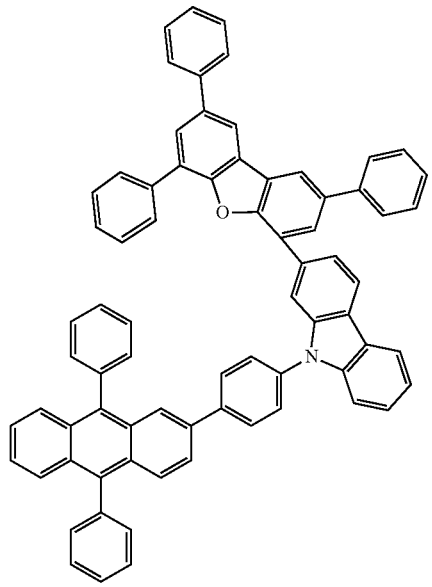
(649)
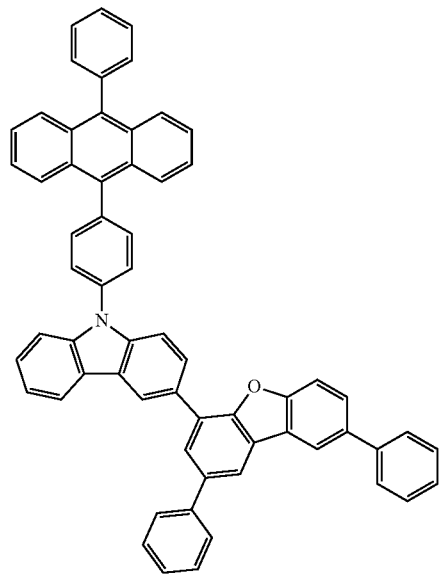
(650)
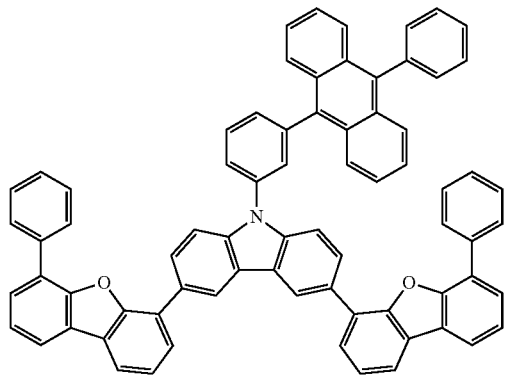

(651)
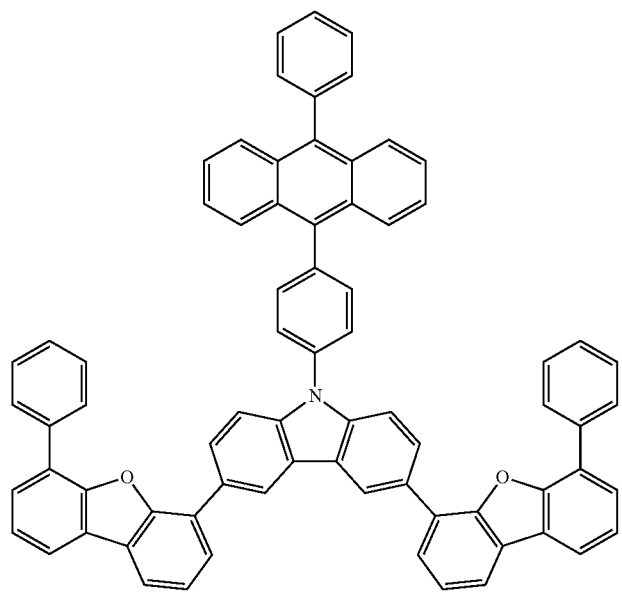
(652)
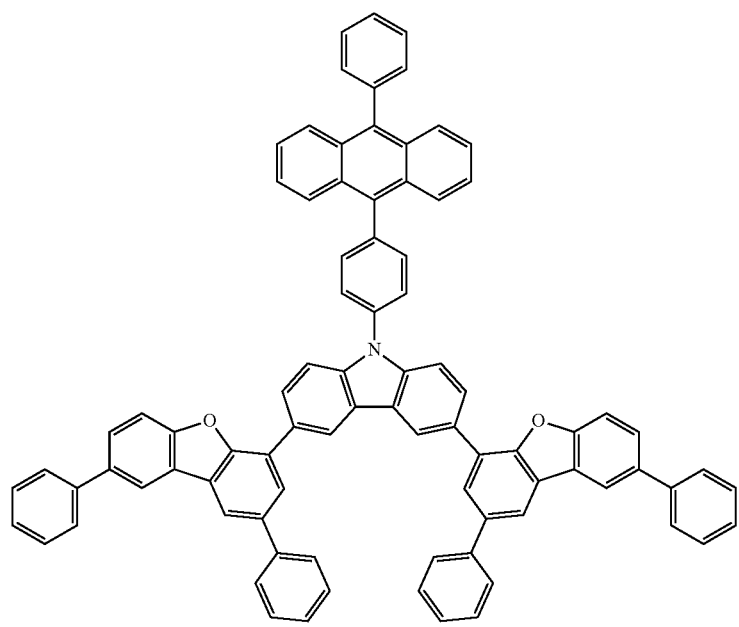

(653)
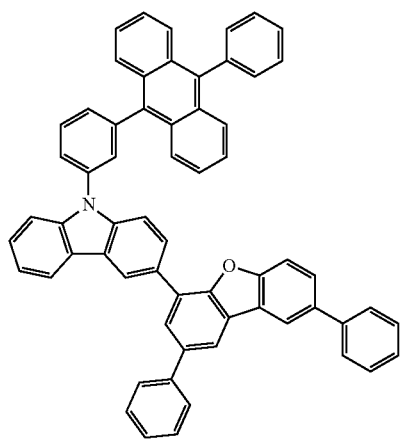
(654)
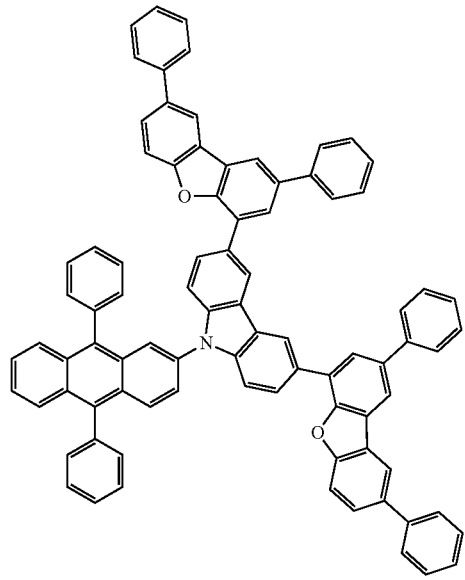
(655)
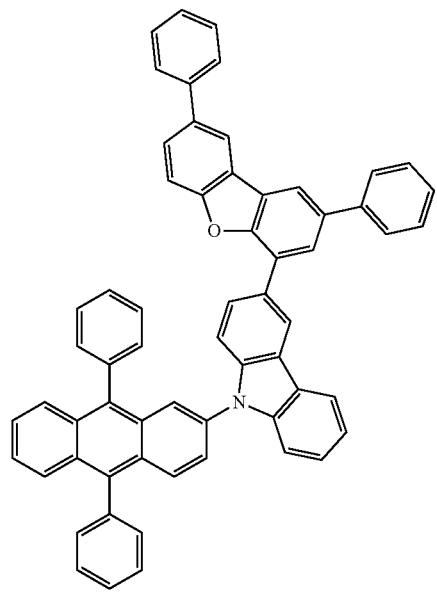

(656)
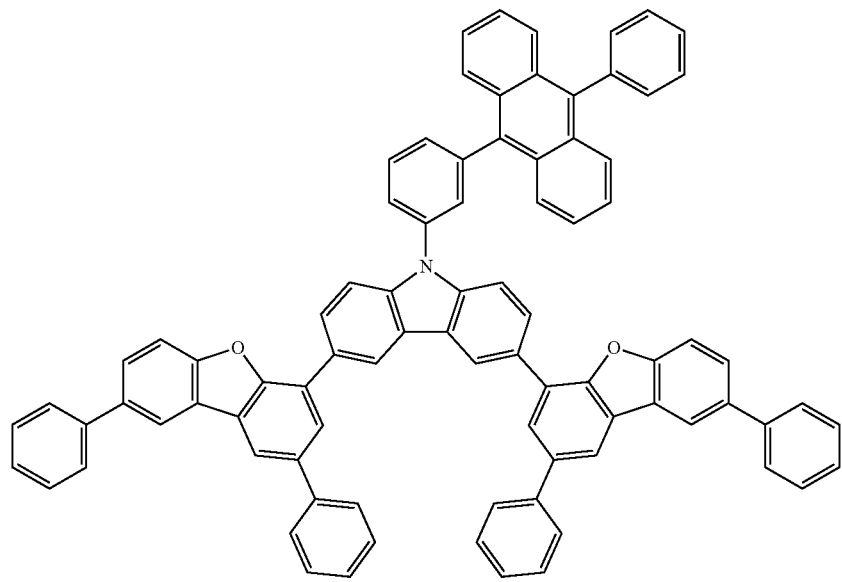
(657)
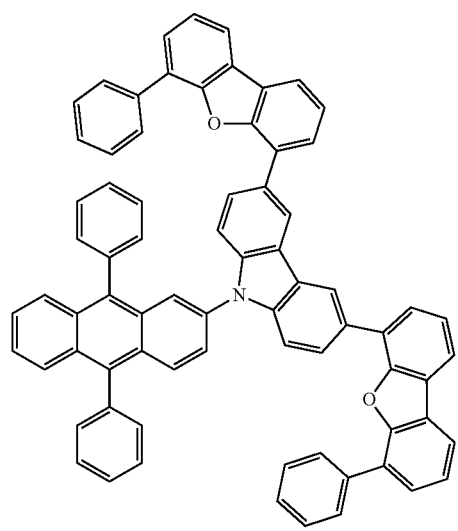
(658)
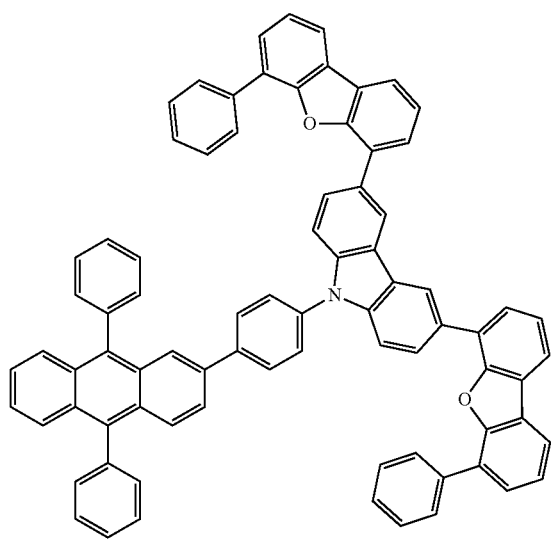

-continued
(659)
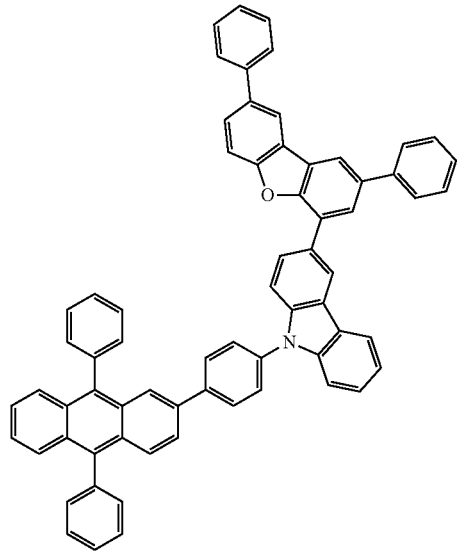
(660)
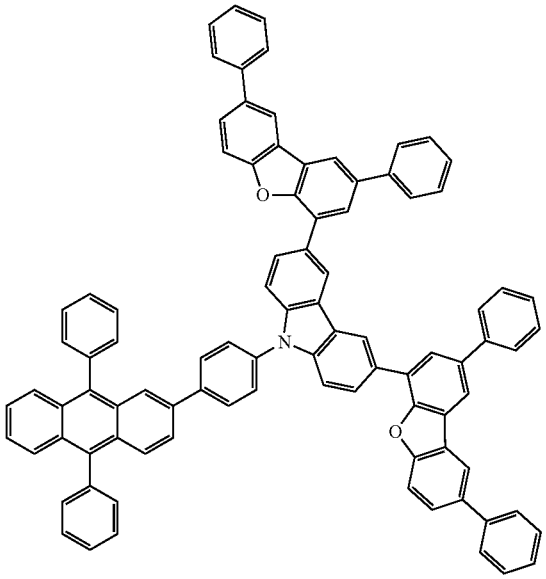
(661)
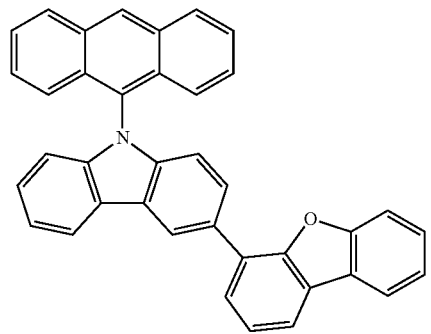
(662)
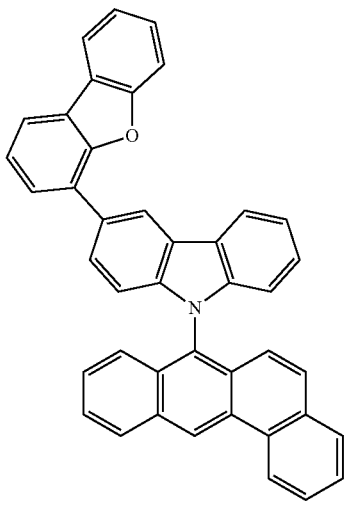
(663)
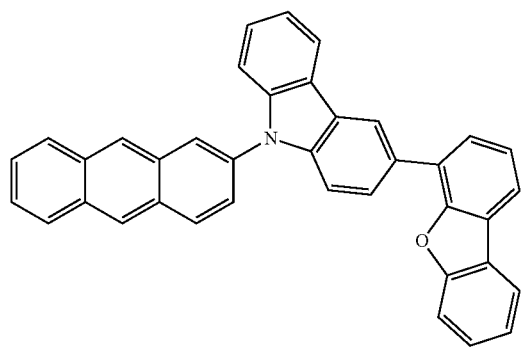
(664)
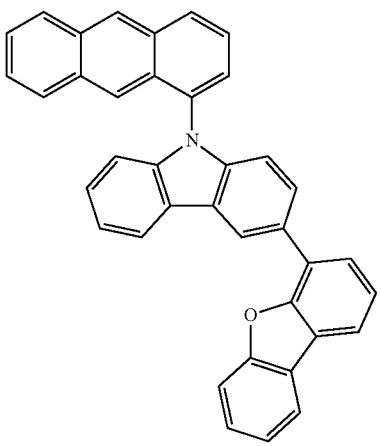

-continued
(665)
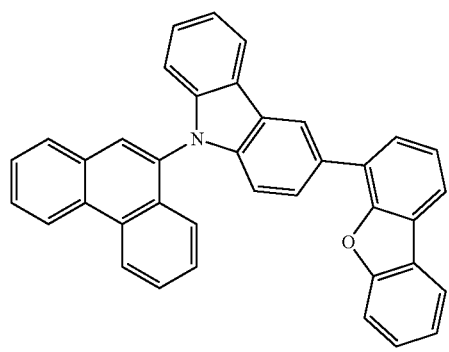
(666)
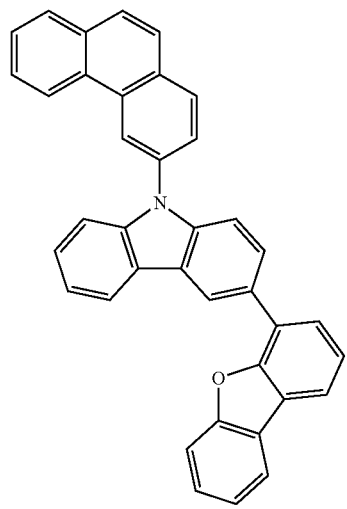
(667)
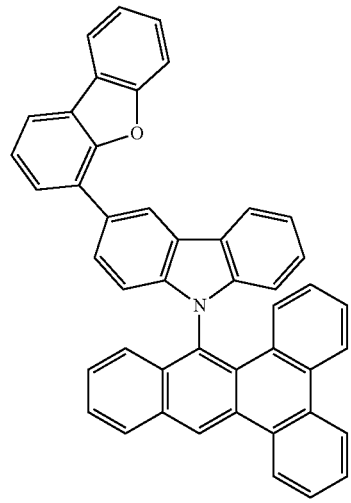
(668)
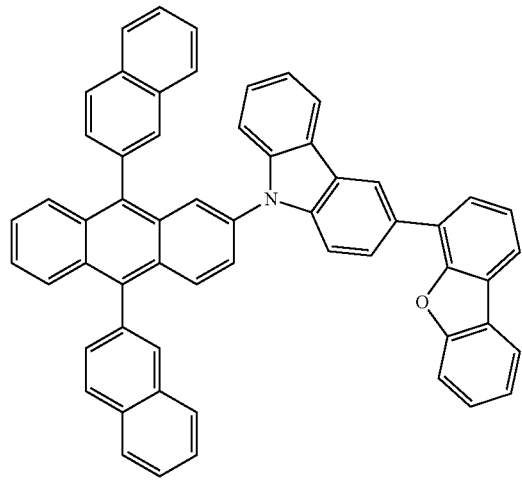
(669)
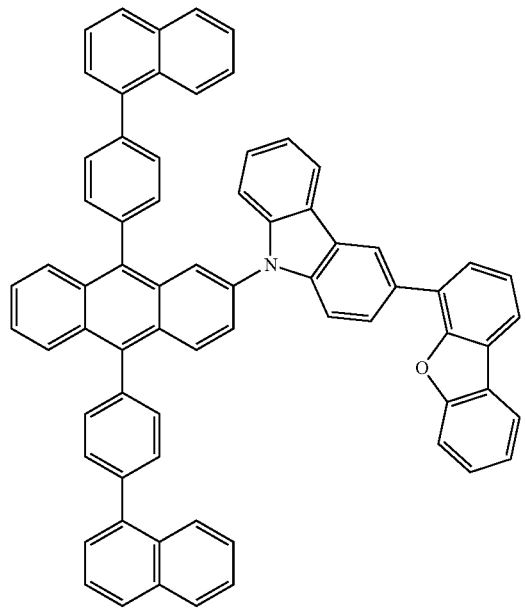
(670)
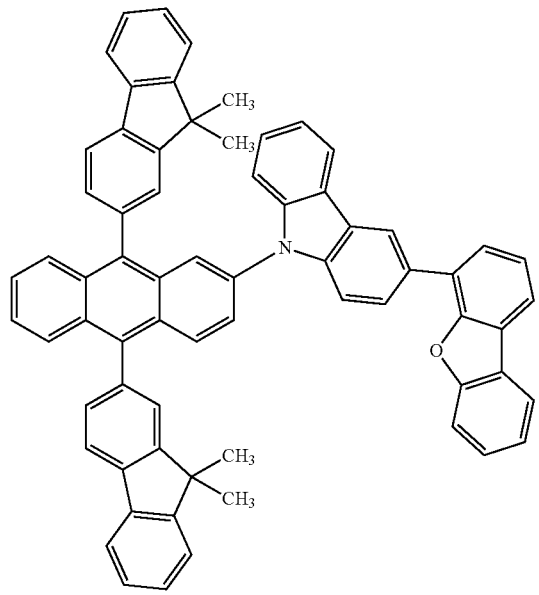

263                                    264
-continued
(673)
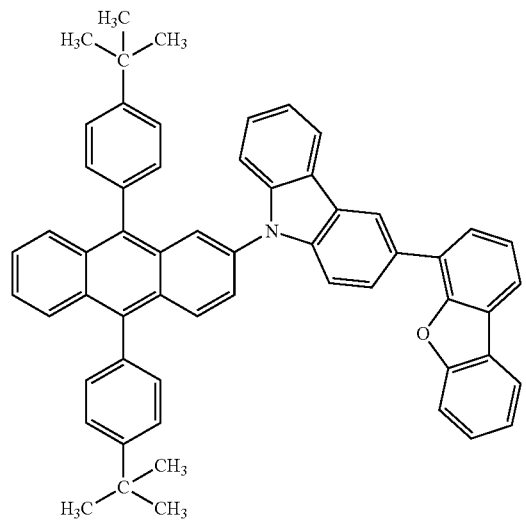
(674)
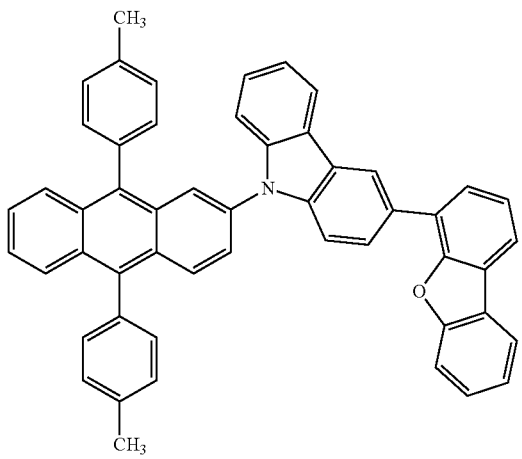
(675)
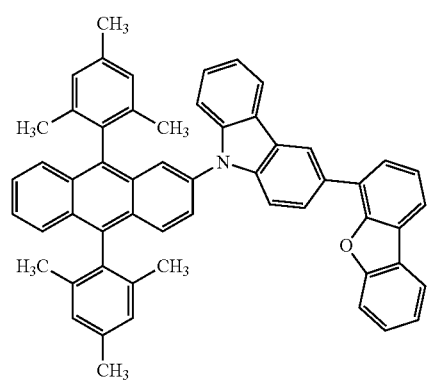
(679)
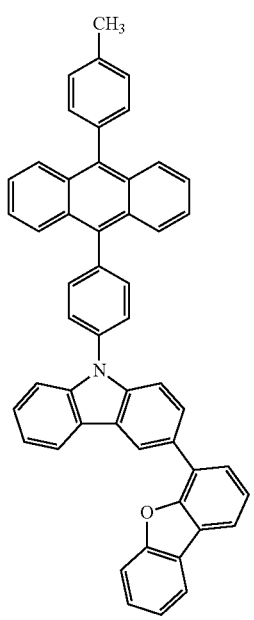

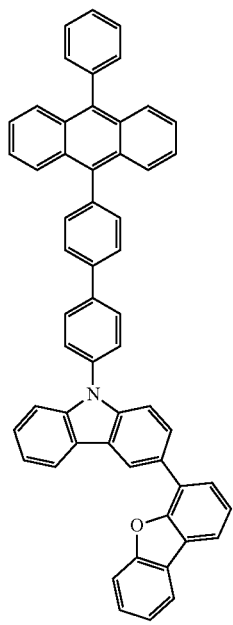
(680)
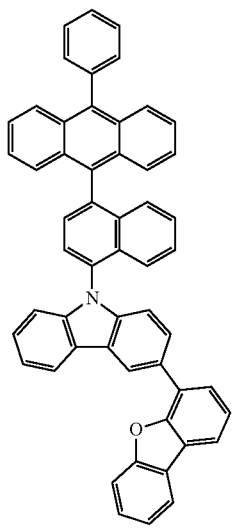
(682)
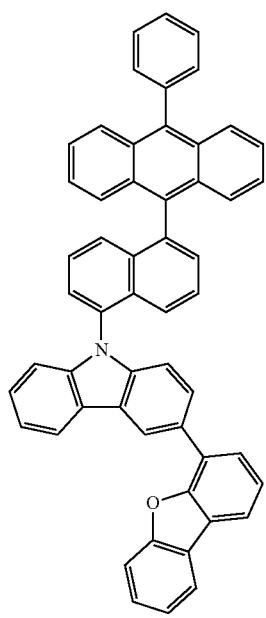
(683)
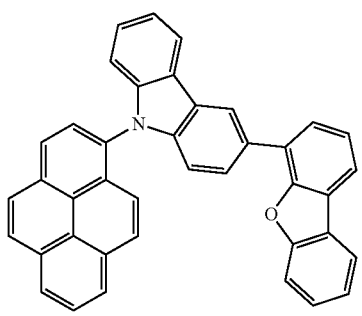
(685)
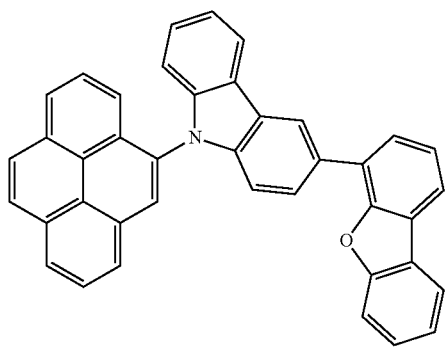
(686)
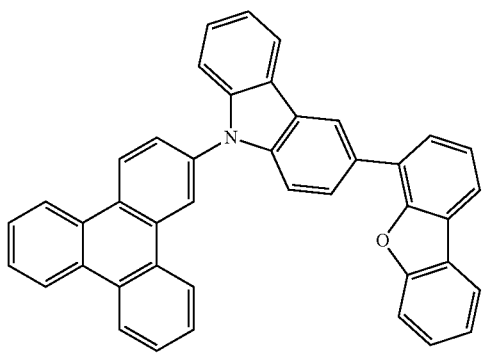
(687)

-continued
(688)
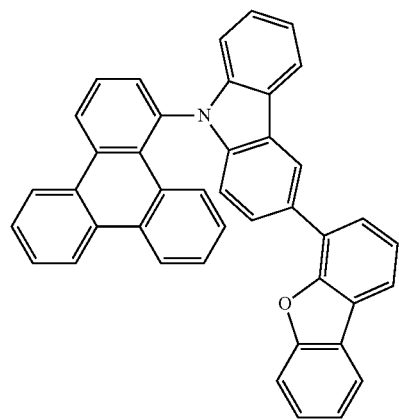
(689)
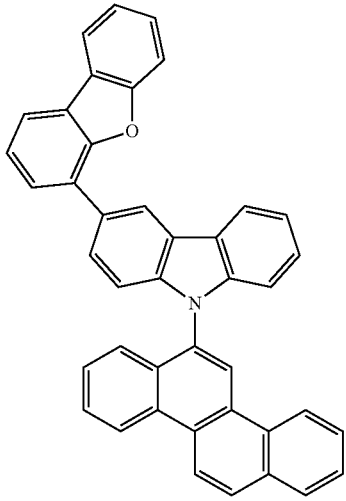
(690)
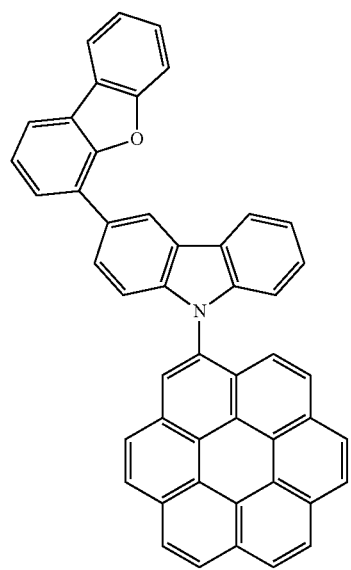
(692)
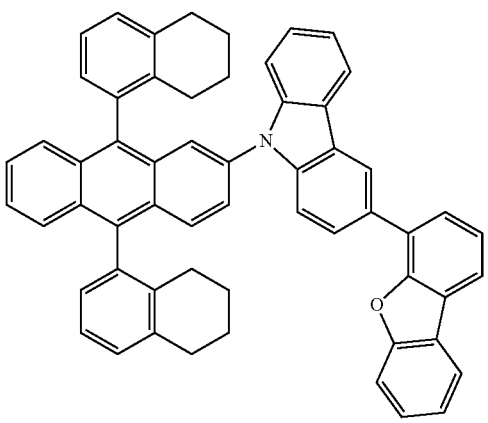

-continued
(693)
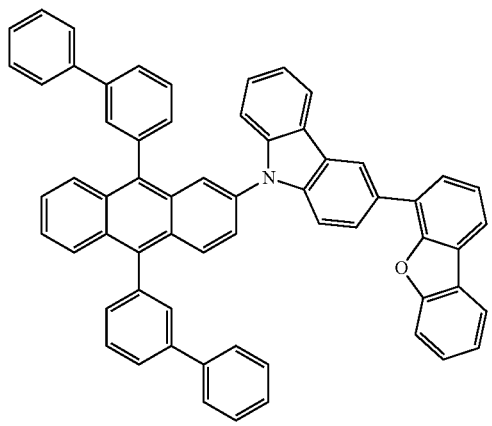
(694)
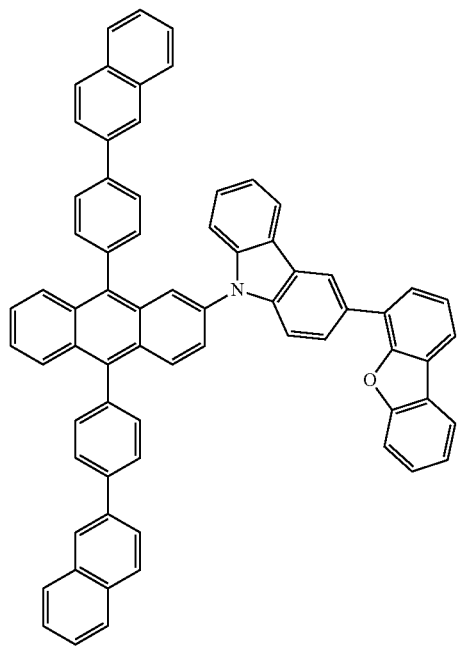
(695)
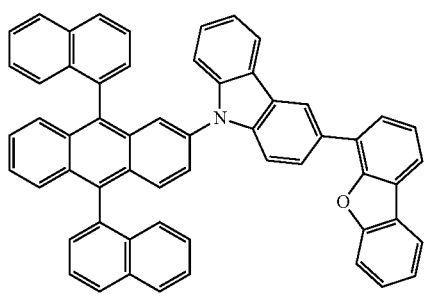
(696)
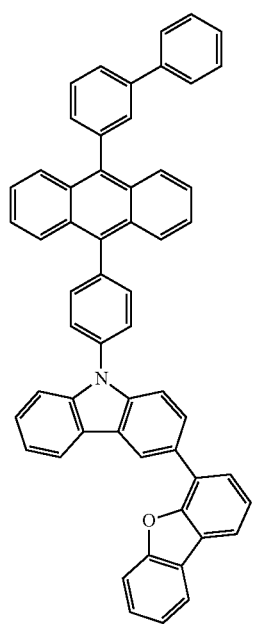
(697)
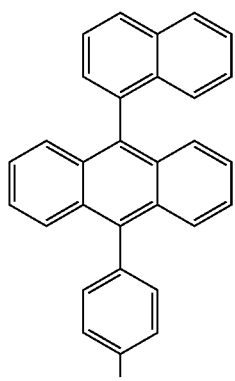
(698)
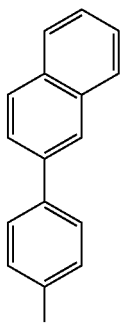

271
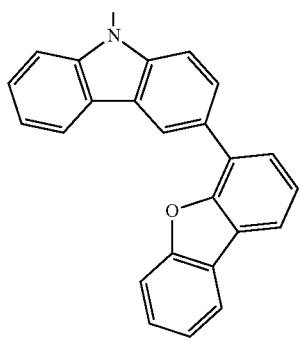
-continued
272
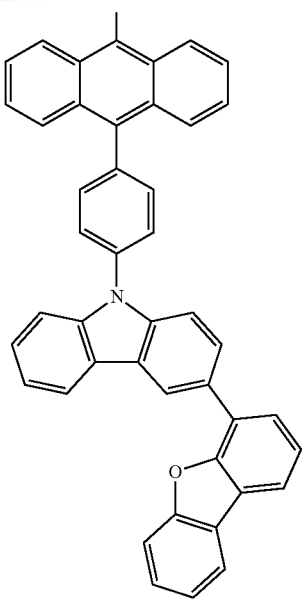
(699)
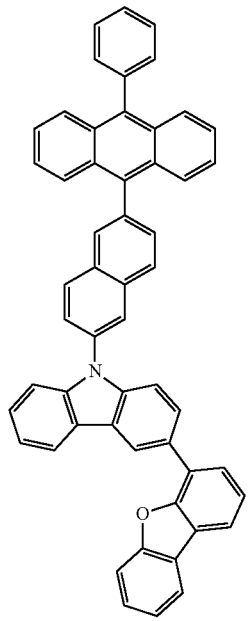
(701)
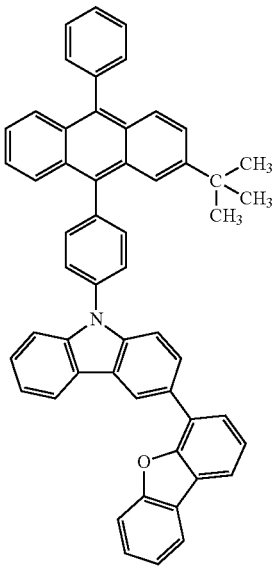

-continued
(712)
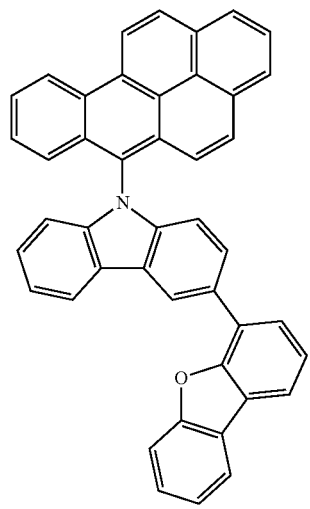
(713)
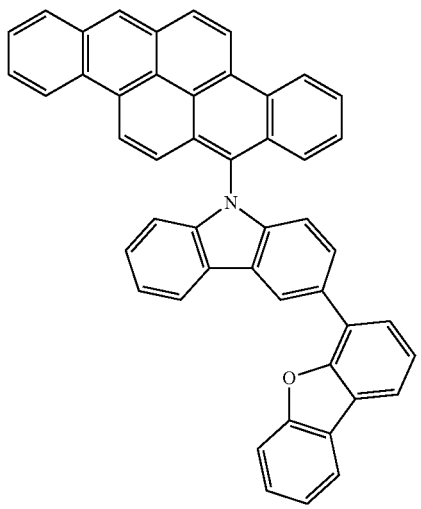
(714)
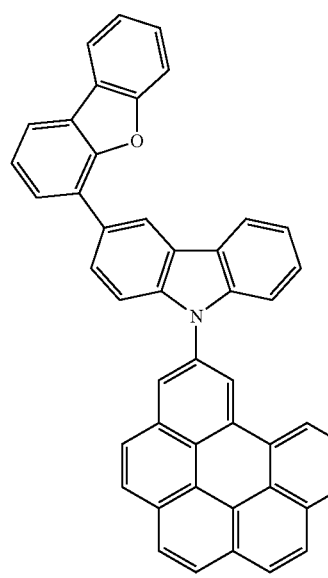
(715)
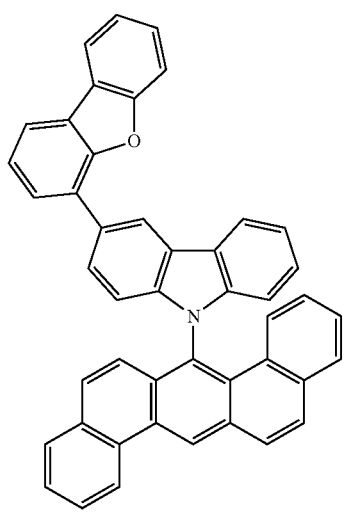
(717)
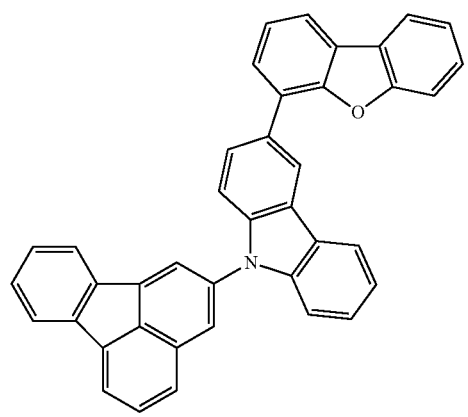
(718)
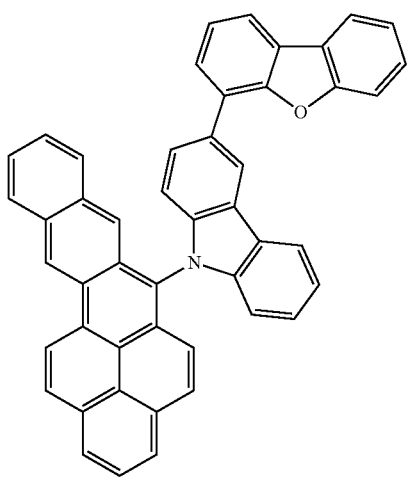

-continued
(719)
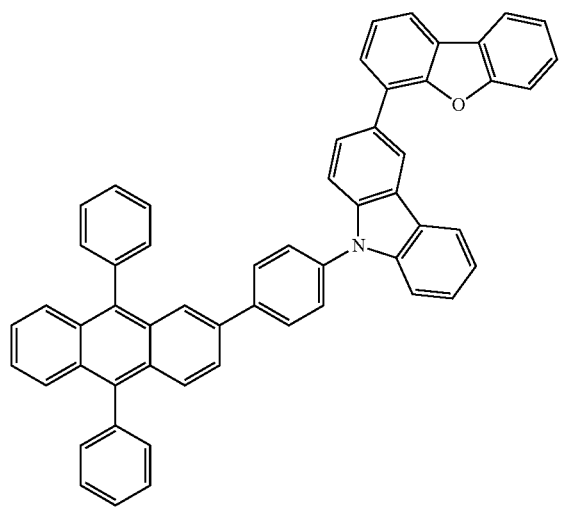
(720)
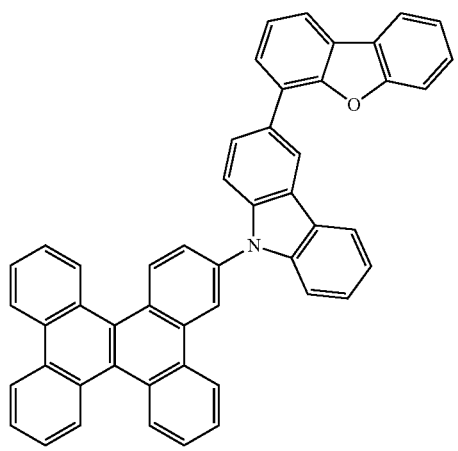
(721)
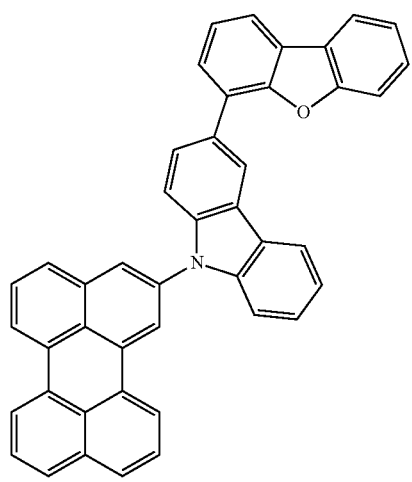
(722)
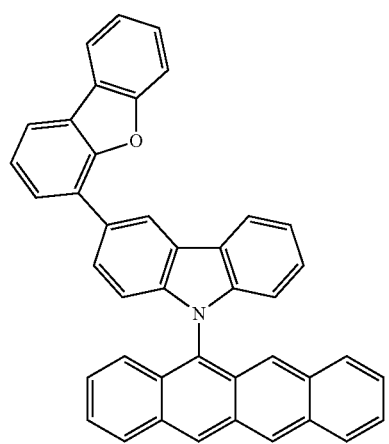
(723)
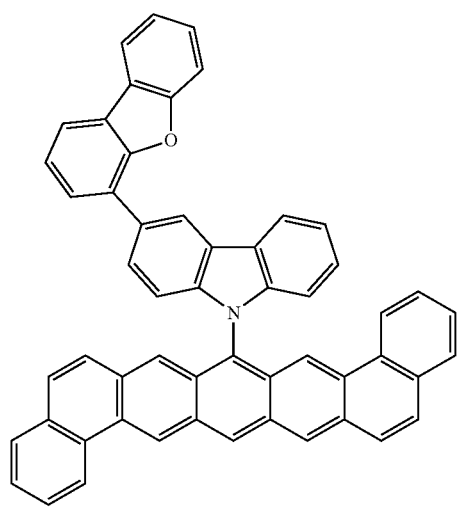
(724)
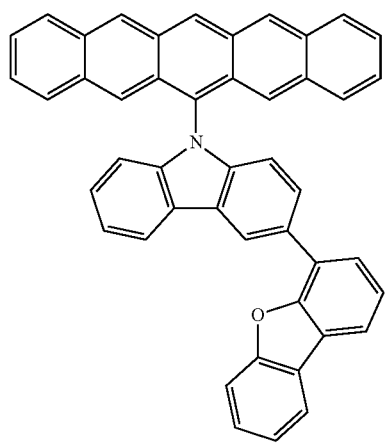

-continued
(725)
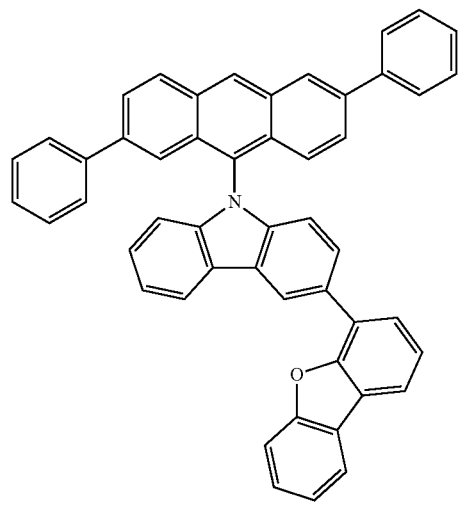
(726)
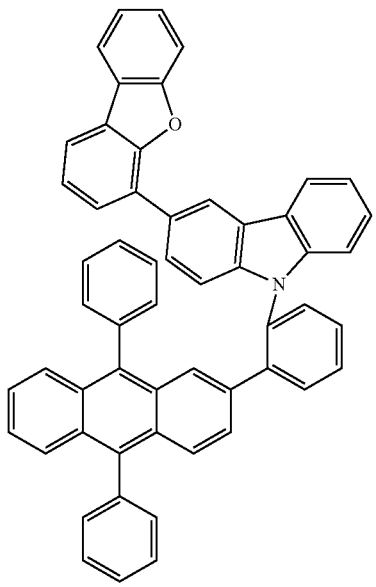
(727)
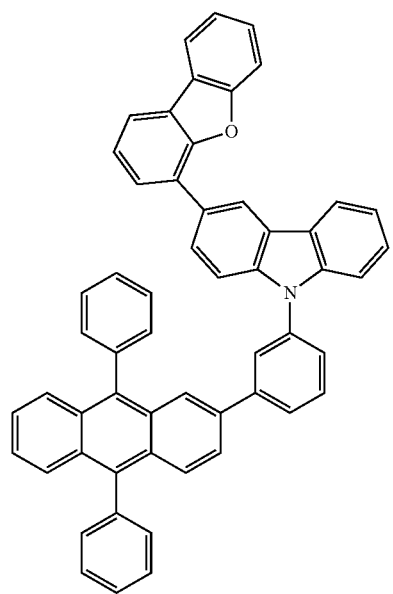
(728)
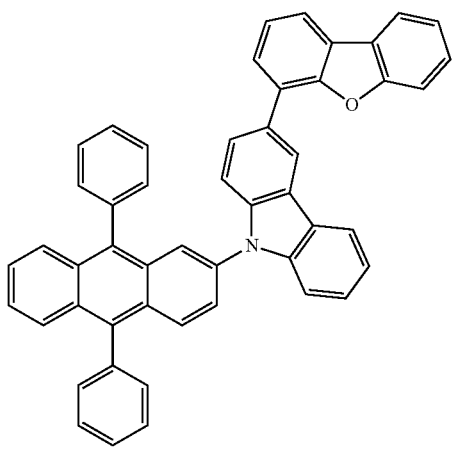

-continued
(729)
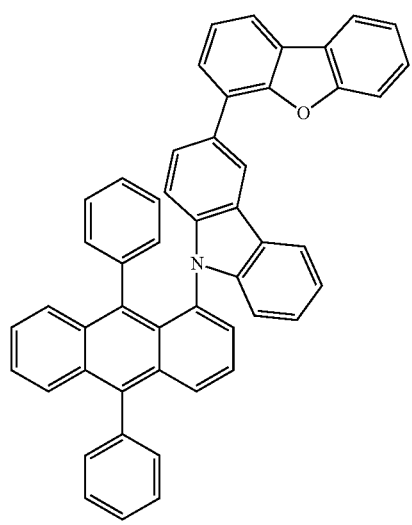
(730)
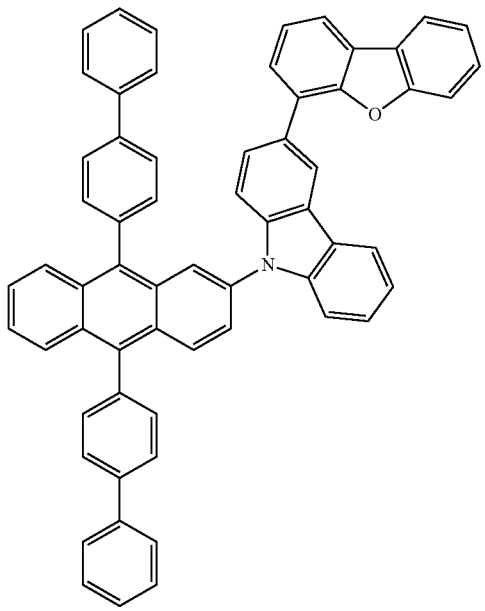
(731)
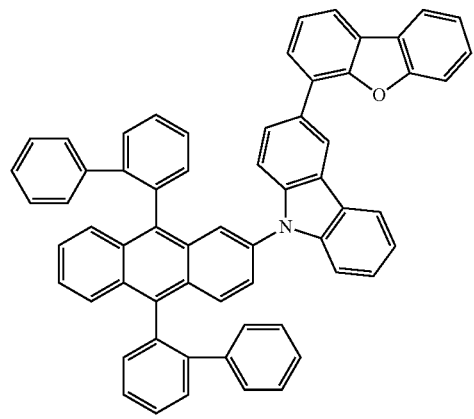
(732)
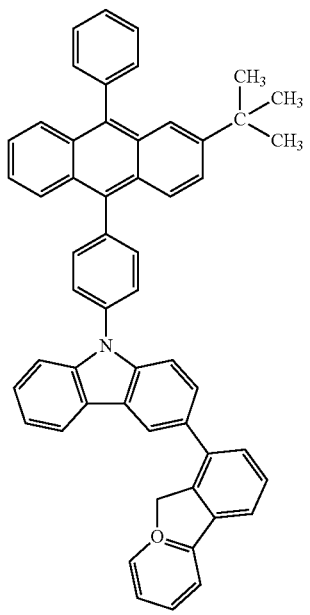

(733)
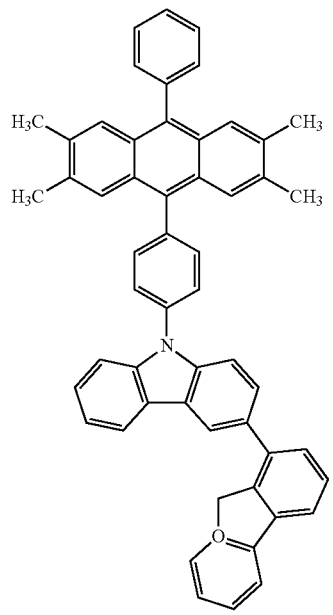
(734)
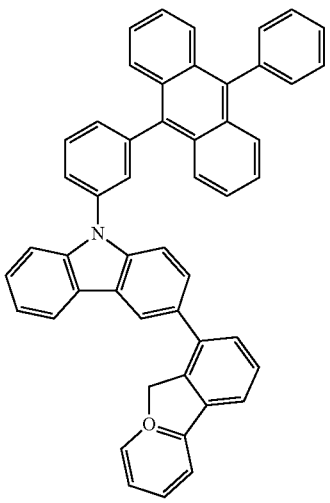
(735)
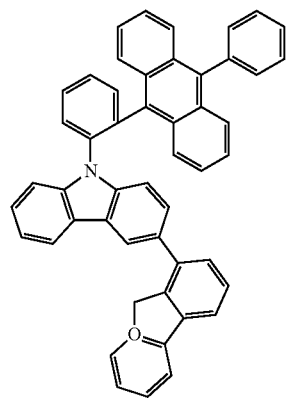
(736)
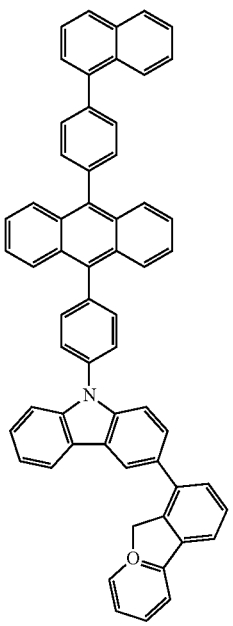

(737)
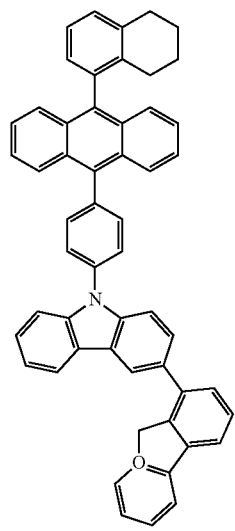
-continued
(738)
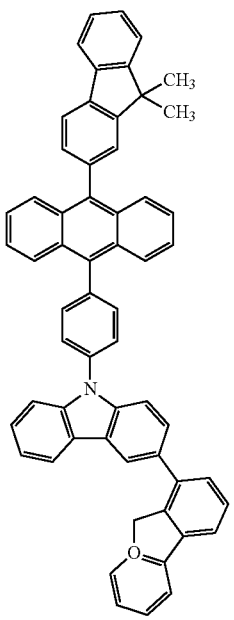
(739)
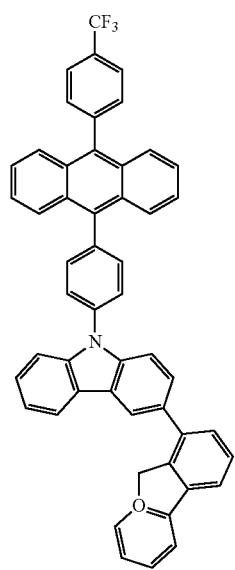
(740)
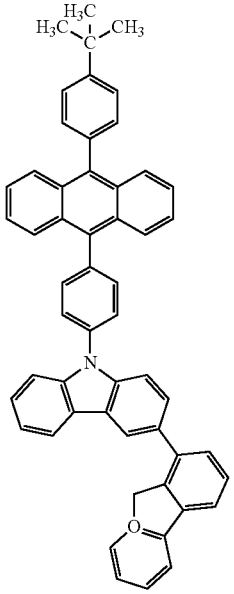

(741) 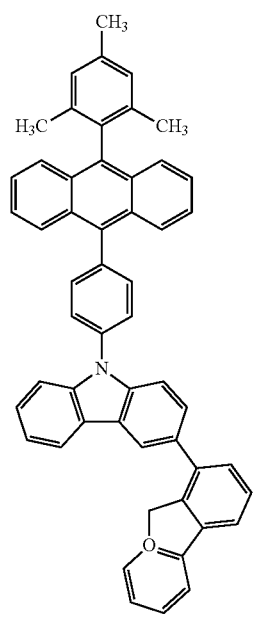
(742) 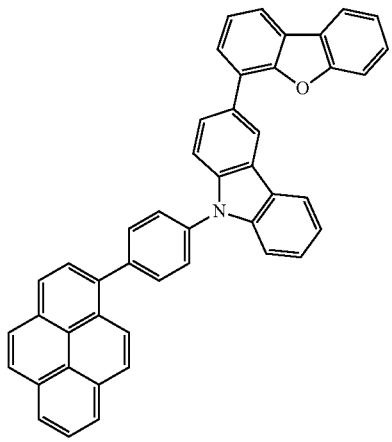
(743) 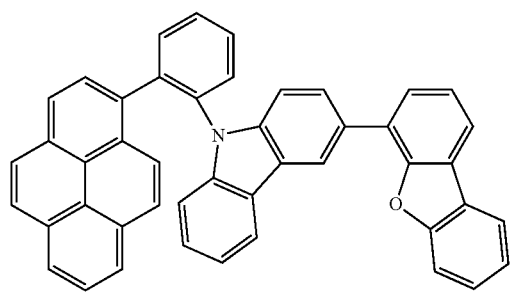
(744) 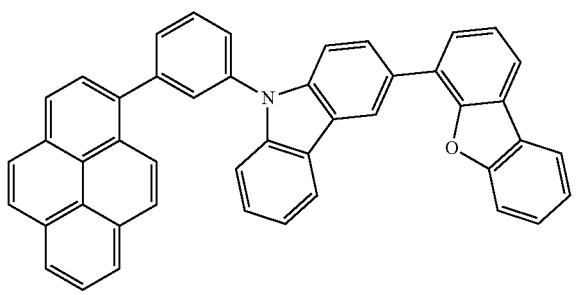
(745) 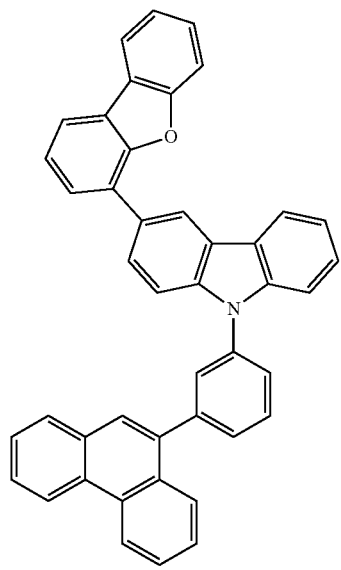
(746) 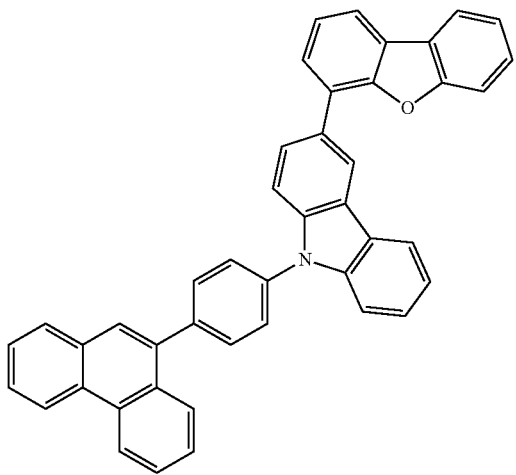

-continued
(747)
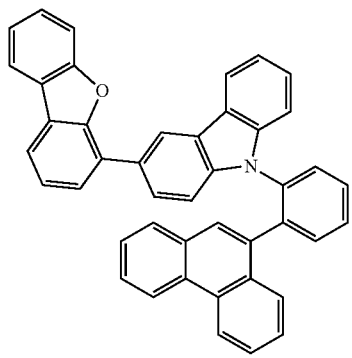
(748)
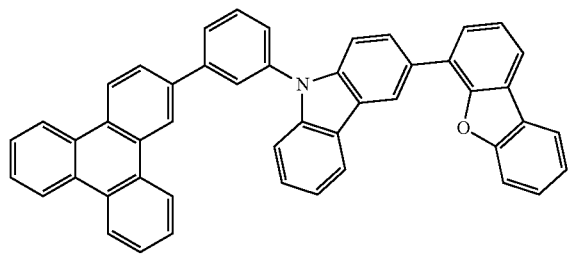
(749)
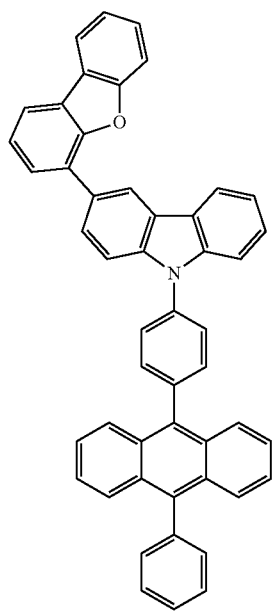
(750)
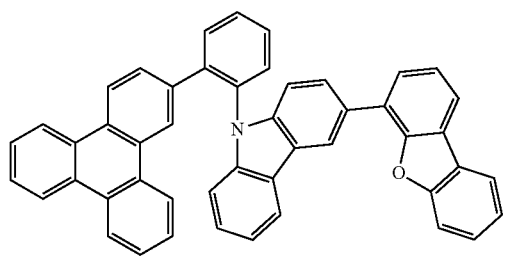
(751)
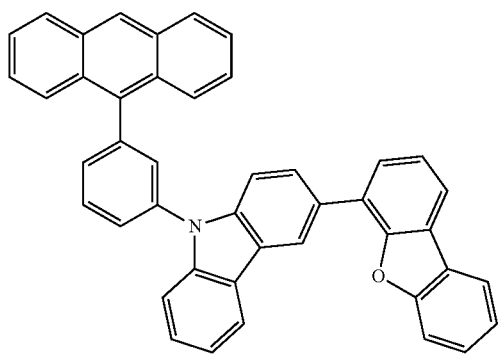
(752)
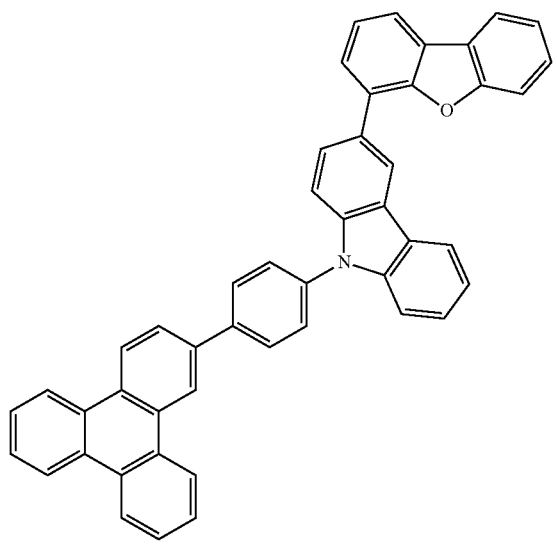

-continued
(753)
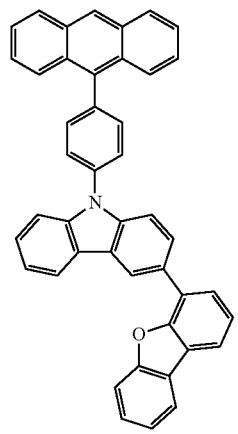
(754)
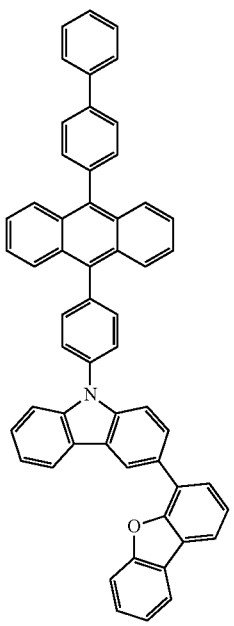
(755)
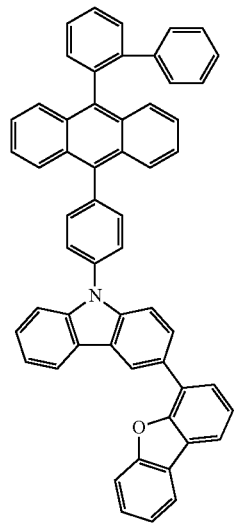
(756)
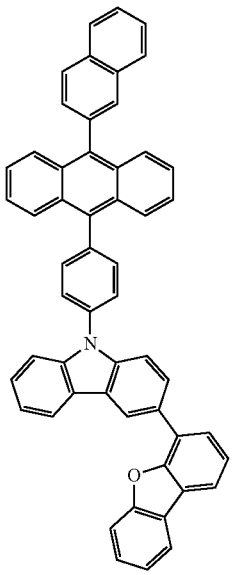

291                                                                                  292
-continued
(757)
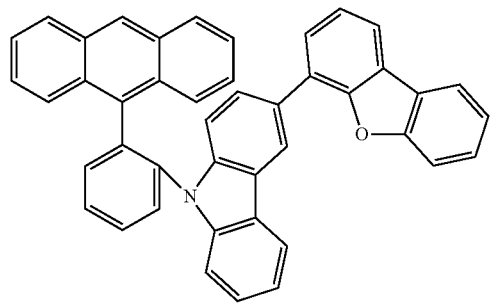
(758)
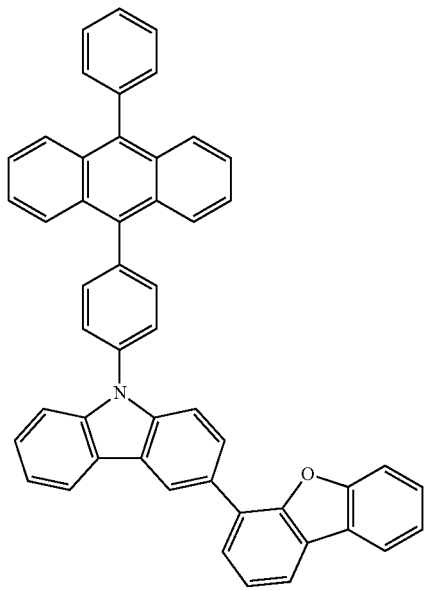
(759)
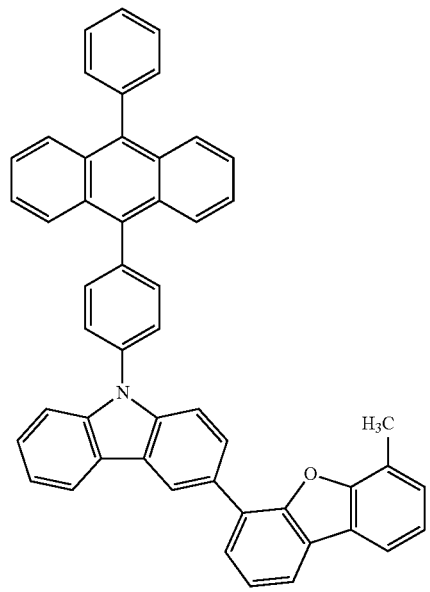
(760)
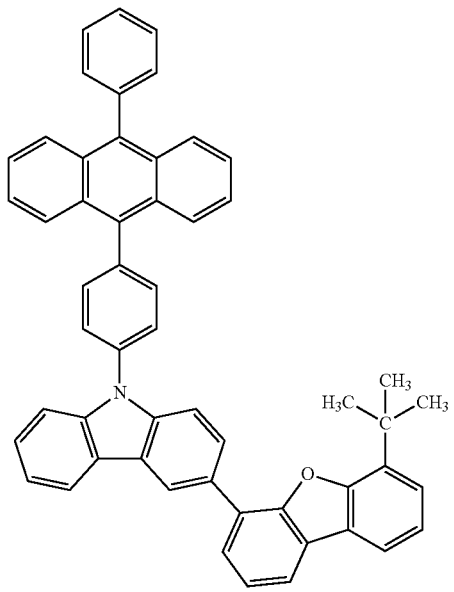
(761)
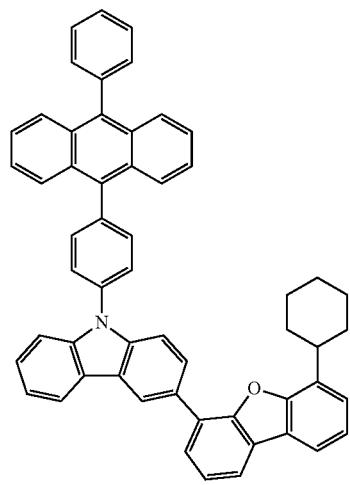
(762)
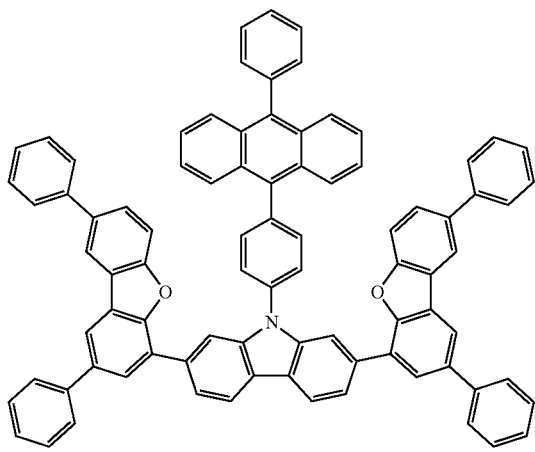

(763)
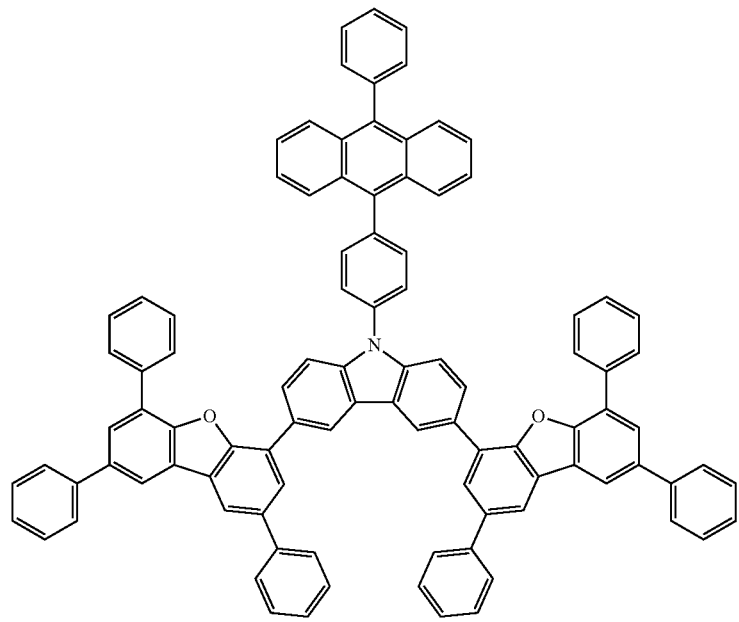
(764)
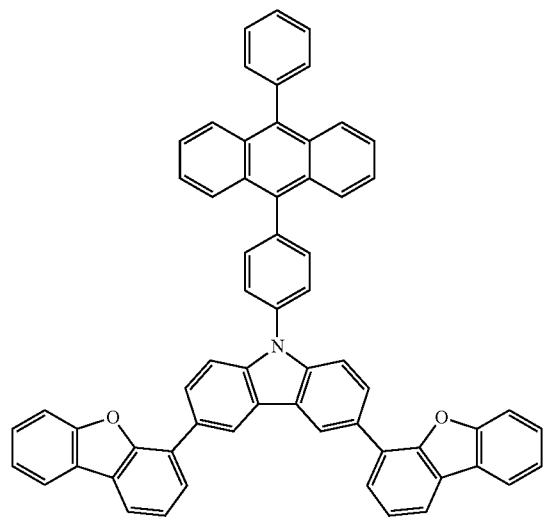
(765)
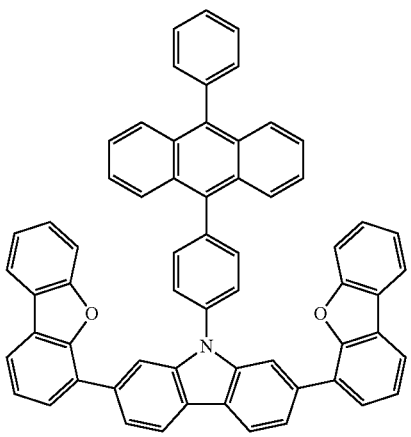

(766)
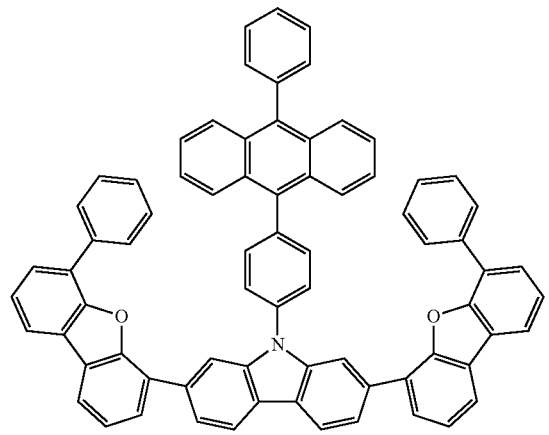
(767)
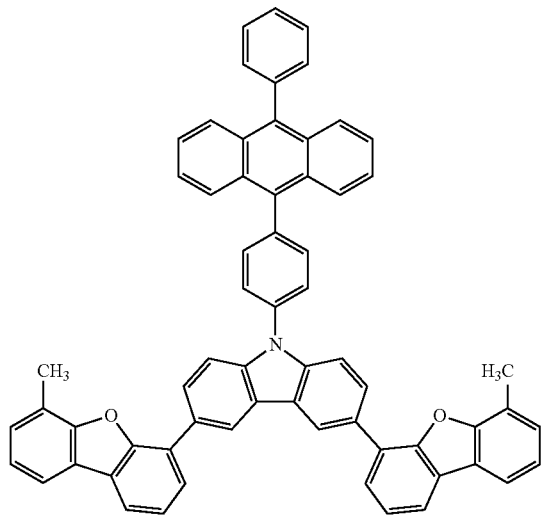
(768)
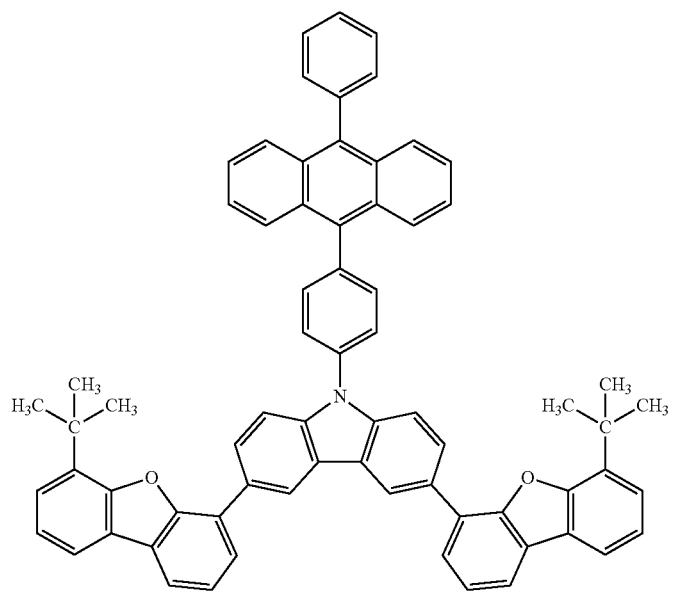

(769)
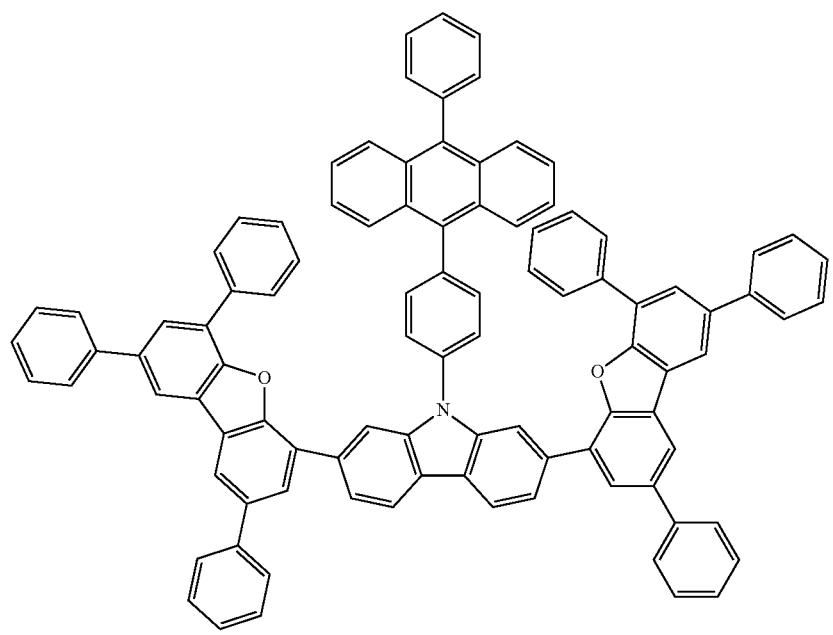
(770)
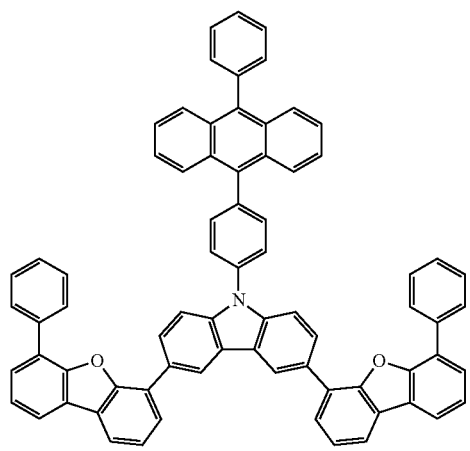
(771)
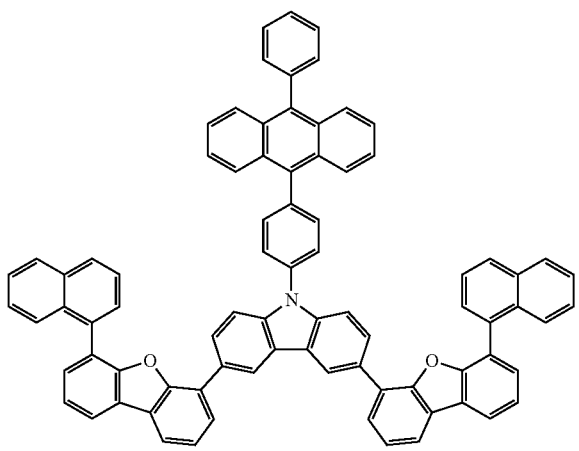

-continued
(773)
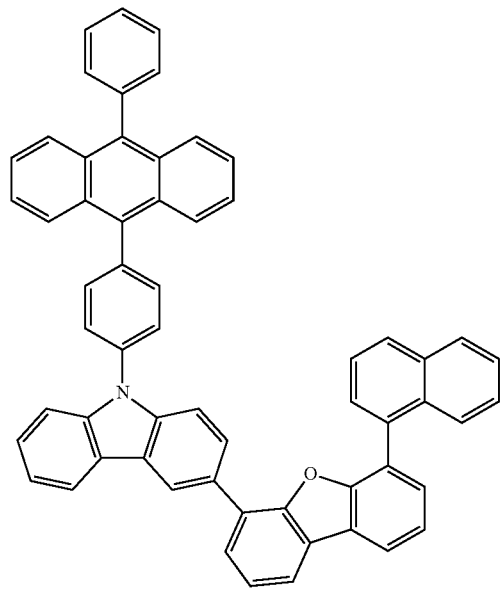
(774)
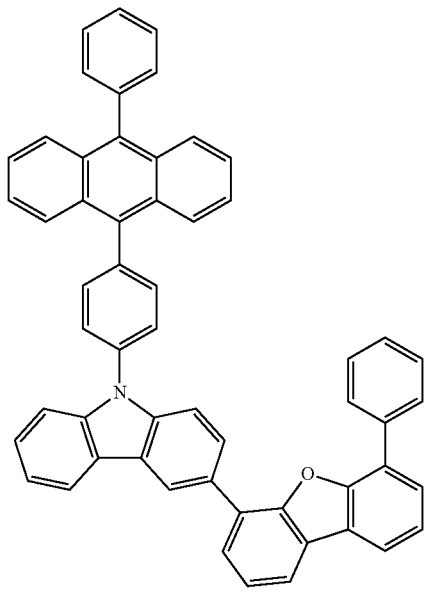
(775)
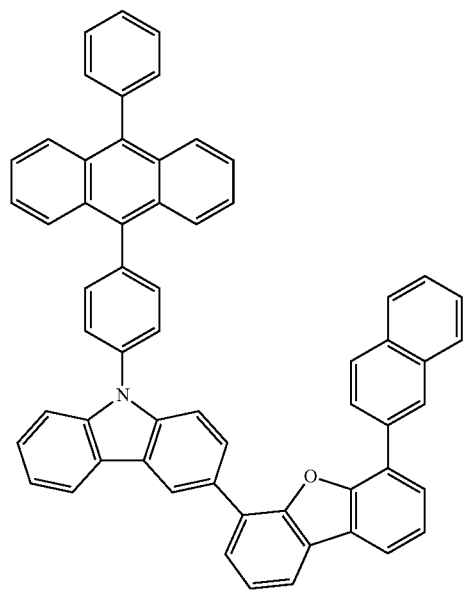
(776)
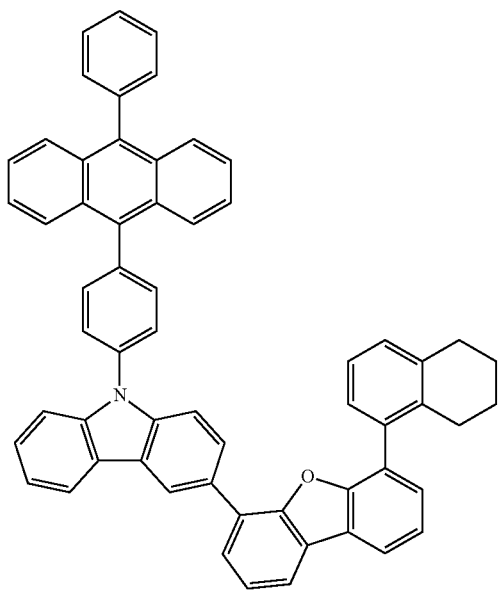

301
-continued
(777)
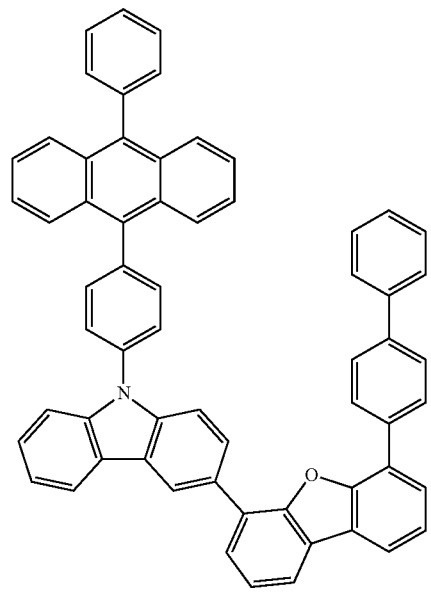
302
(778)
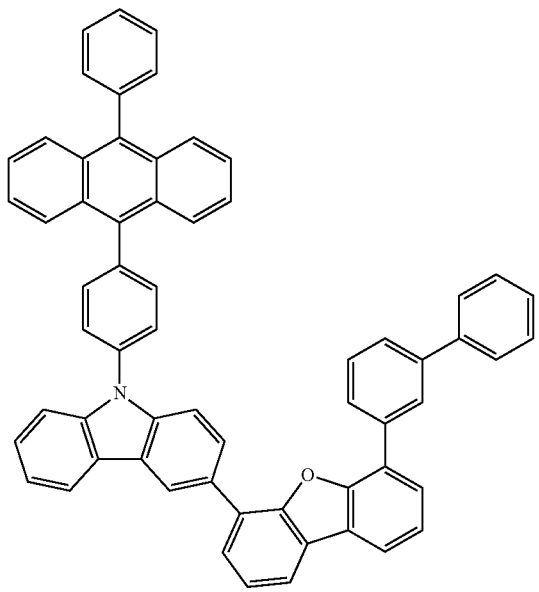
(779)
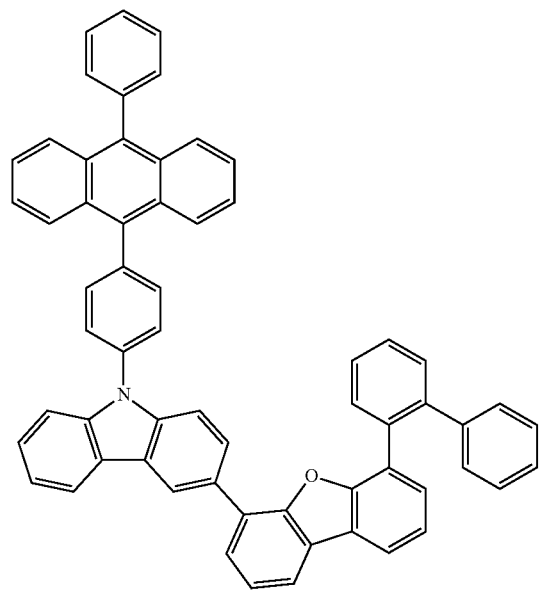
(780)
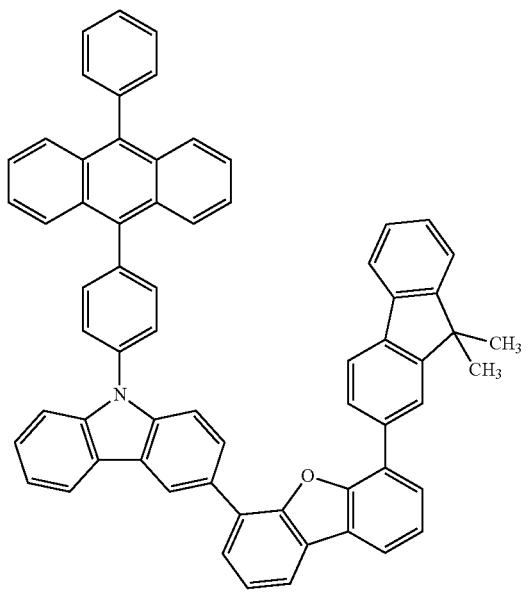

-continued
(781)
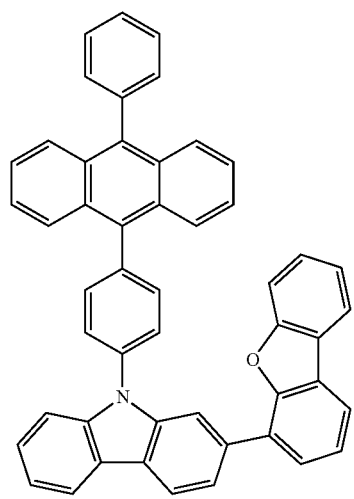
(782)
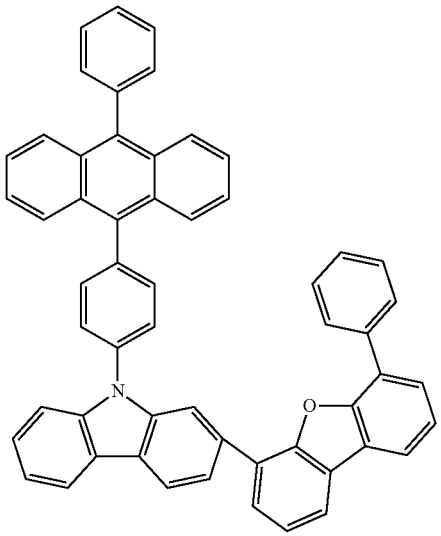
(783)
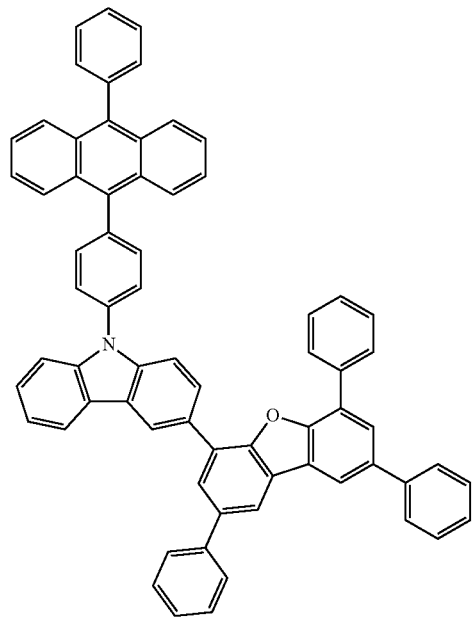
(784)

(785)
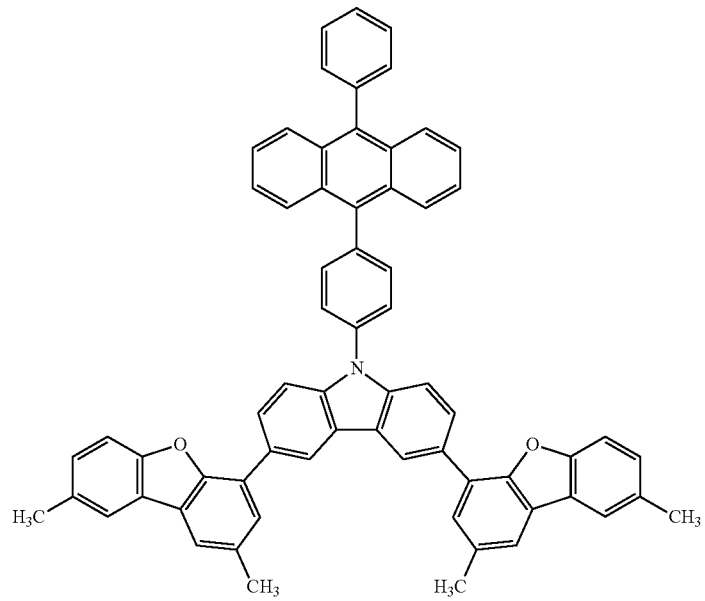
(786)
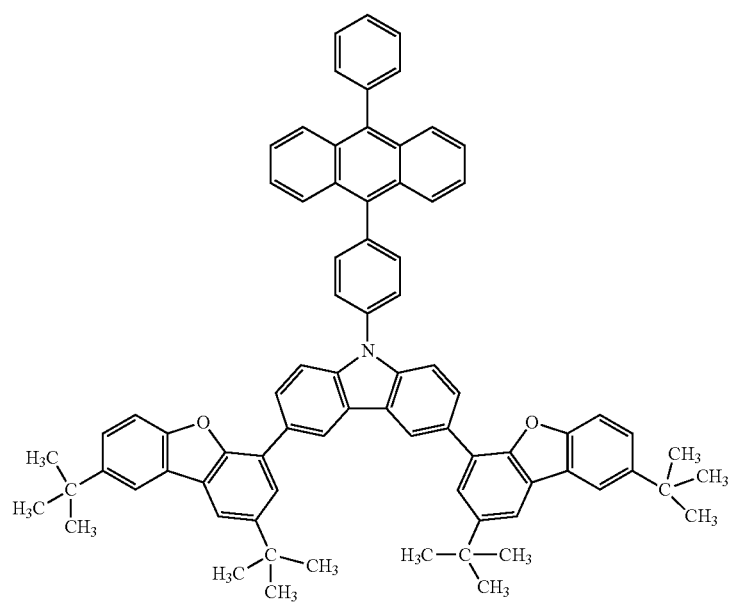

-continued
(788)
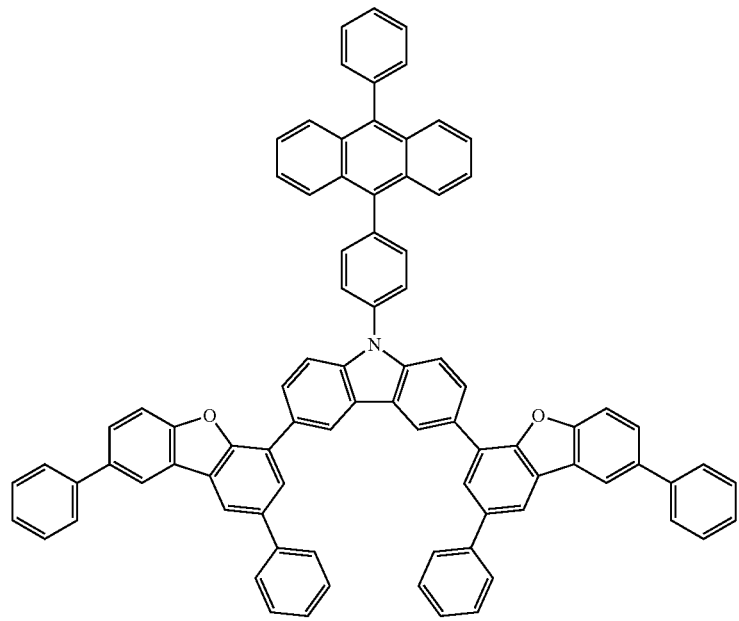
(789)
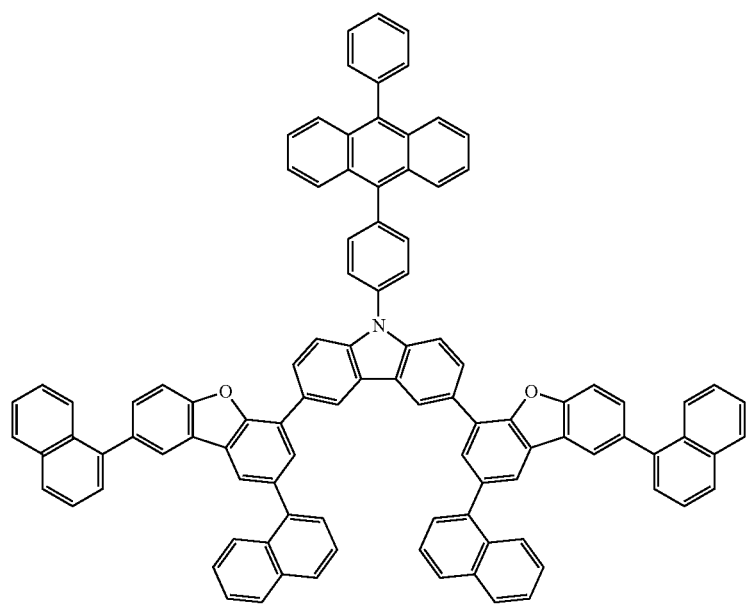

-continued
(790)
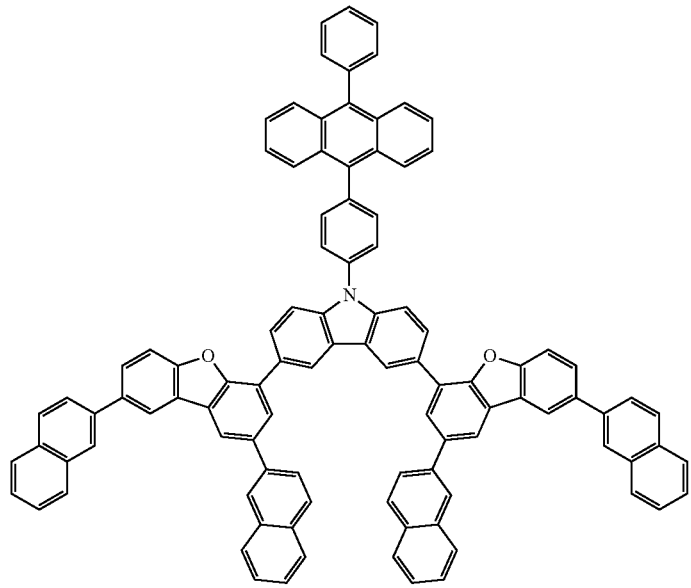
(791)
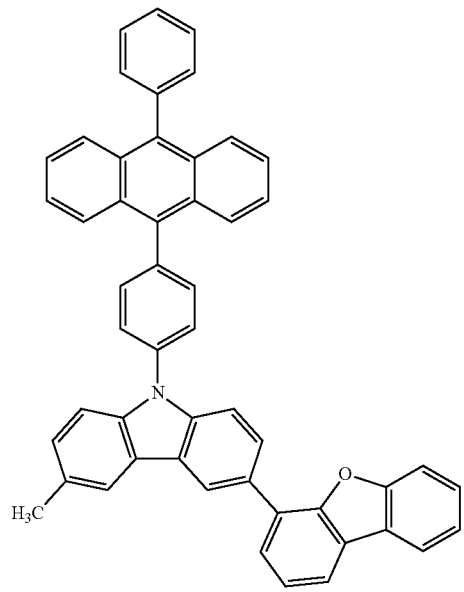
(792)
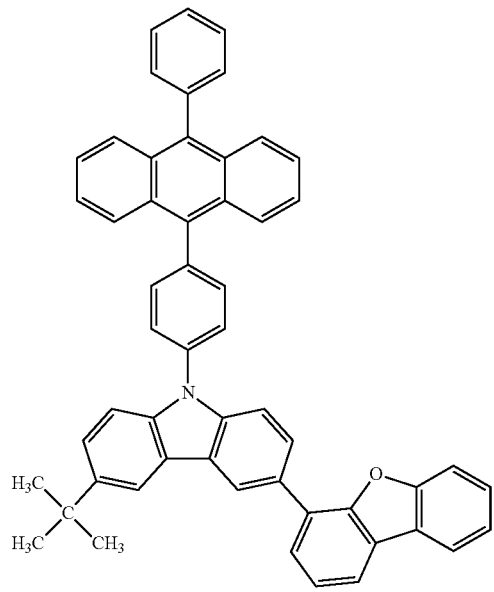

311
312
-continued
(793)
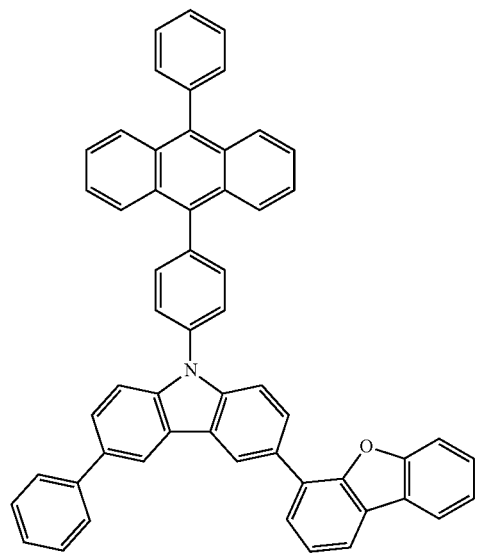
(795)
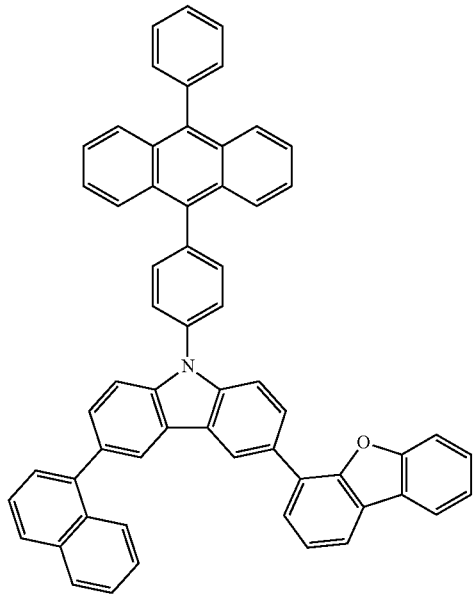
(796)
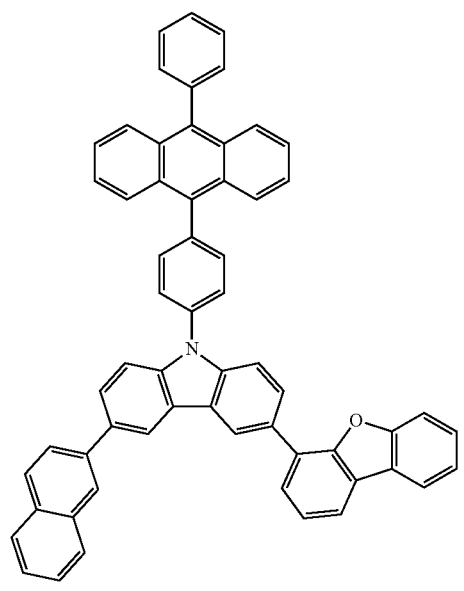
(797)
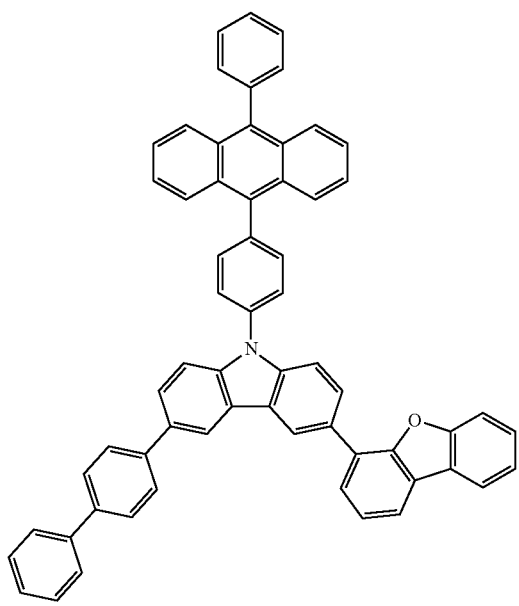

313
314
-continued
(798)
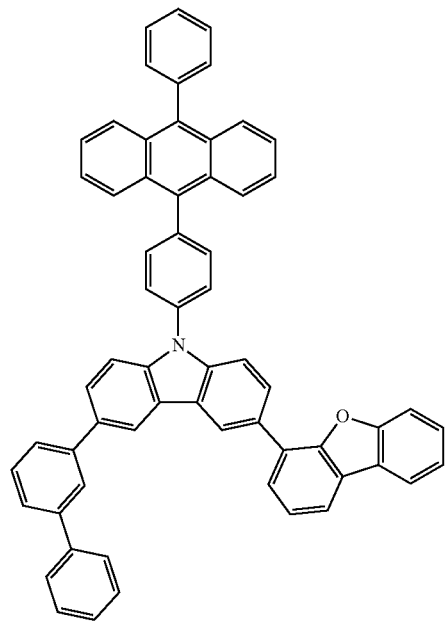
(799)
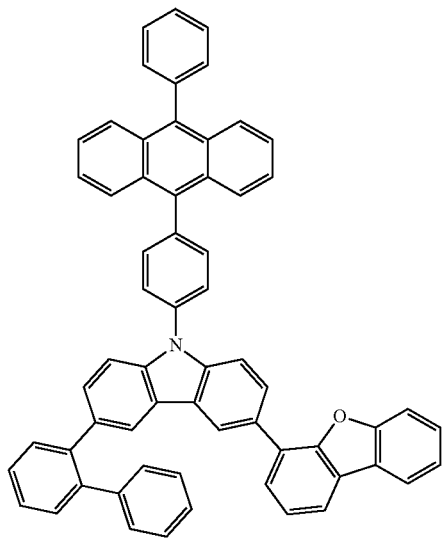
(800)
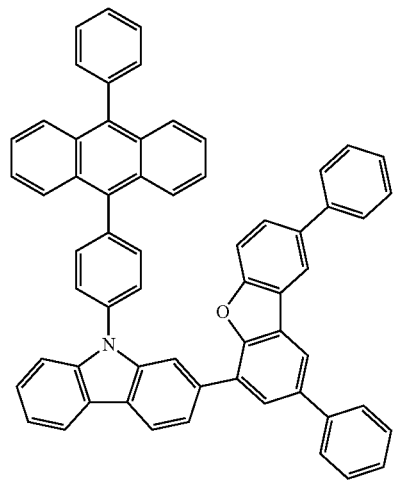
(801)
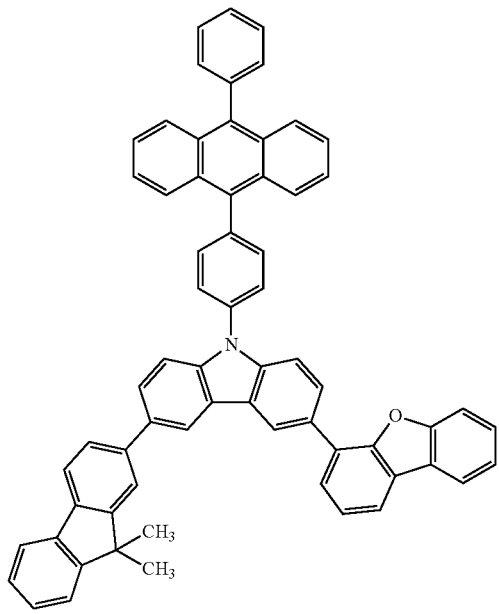

-continued
(802)
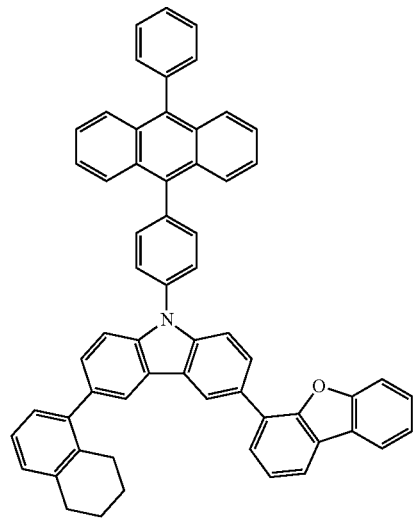
(803)
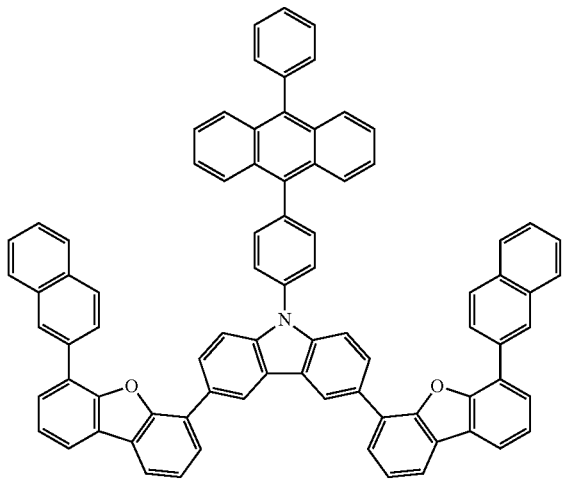
(804)
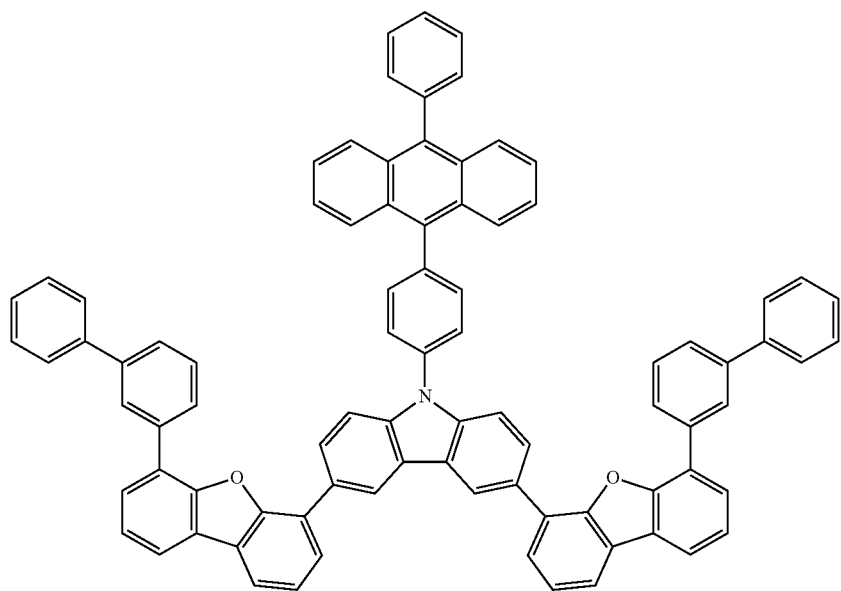

(805)
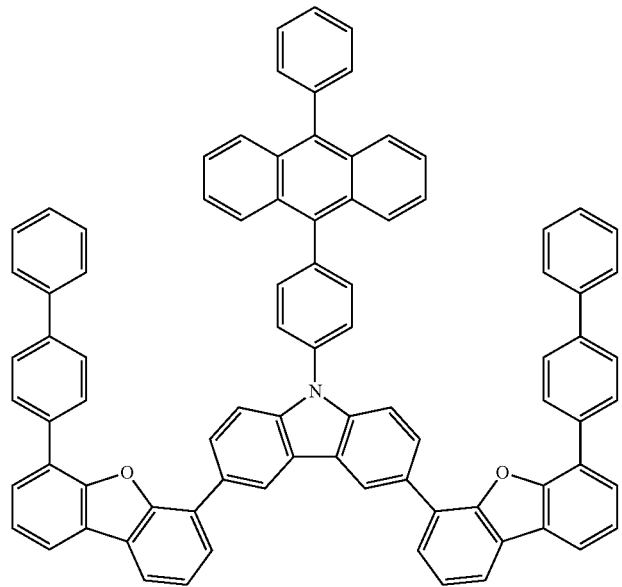
(806)
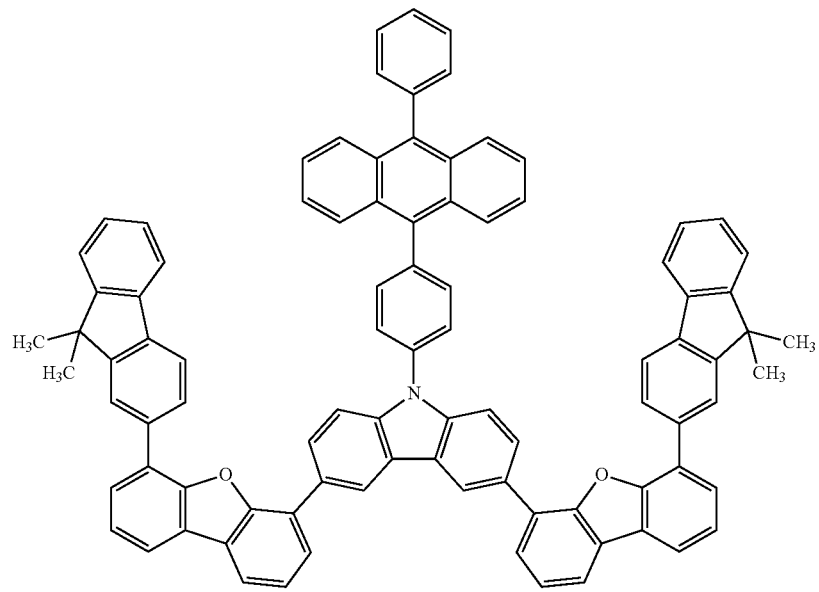

(807)
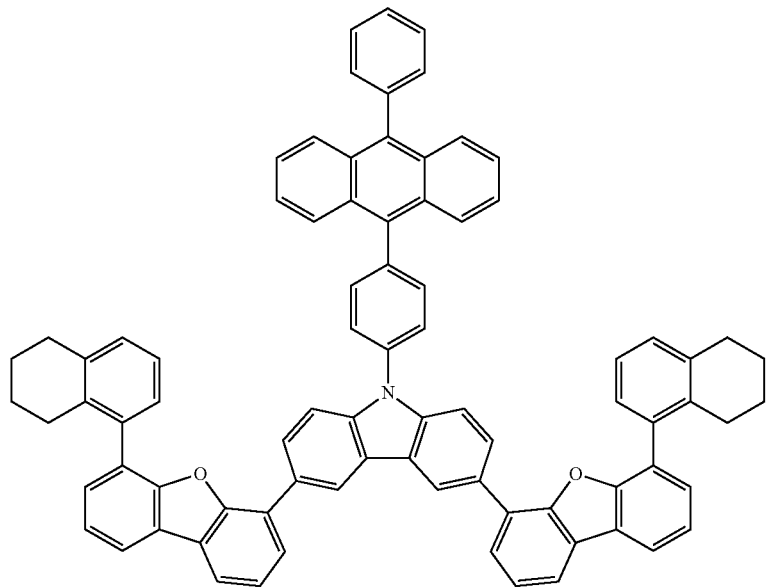
(808)
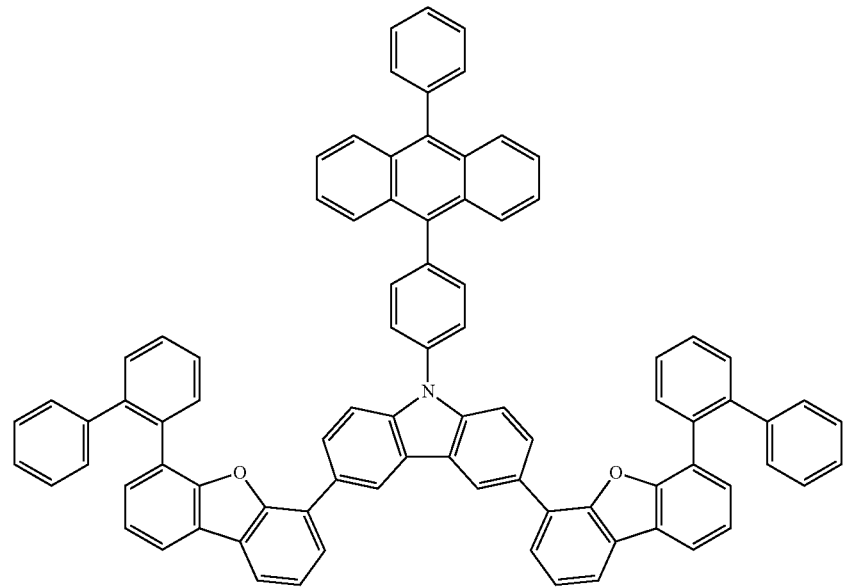

321
(809)
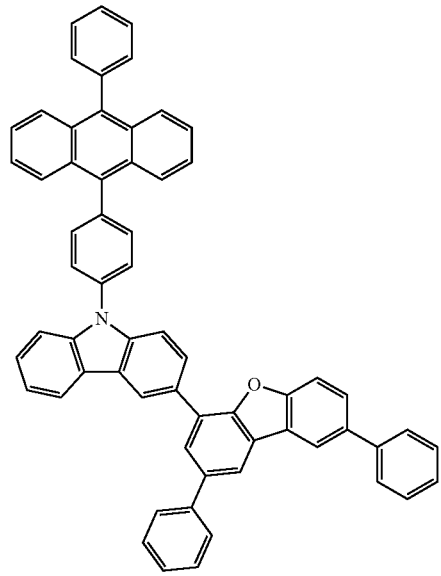
322
(810)
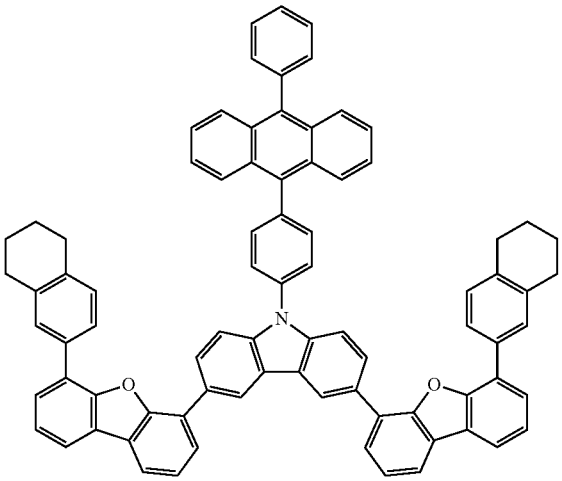
(811)
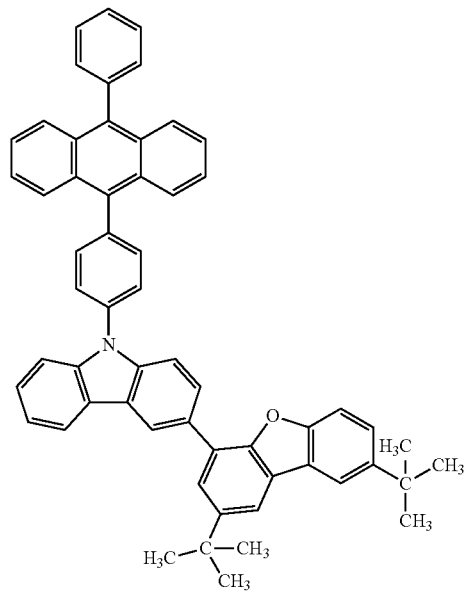
(812)
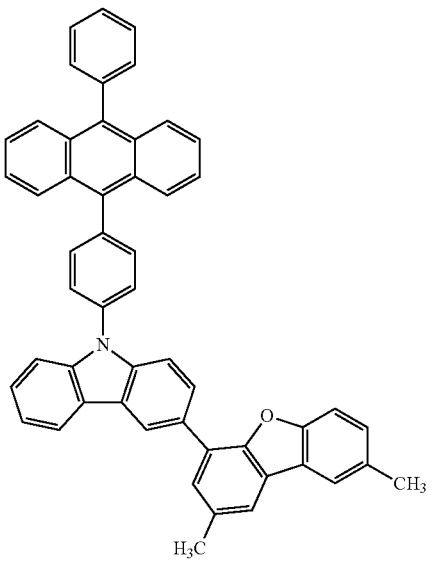

323                                324
-continued
(814)
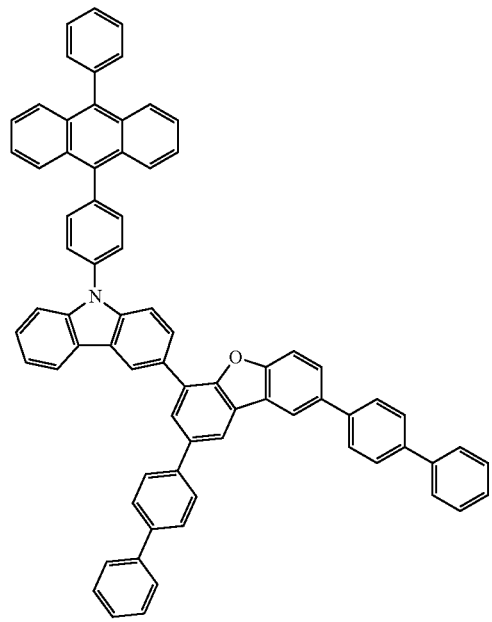
(815)
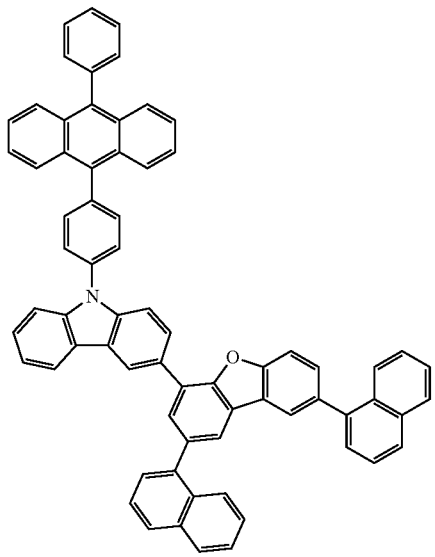
(816)
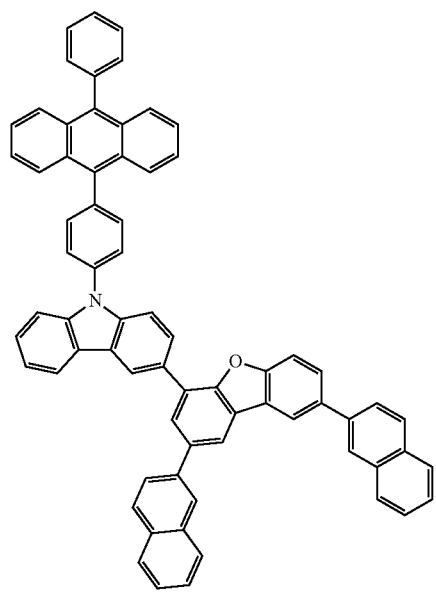
(817)
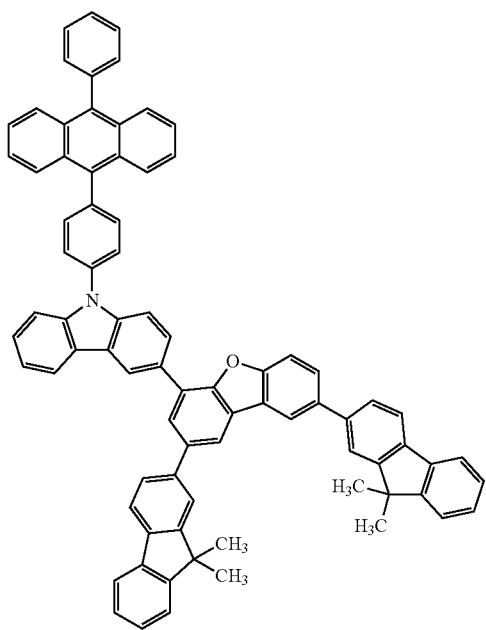

-continued
(818)
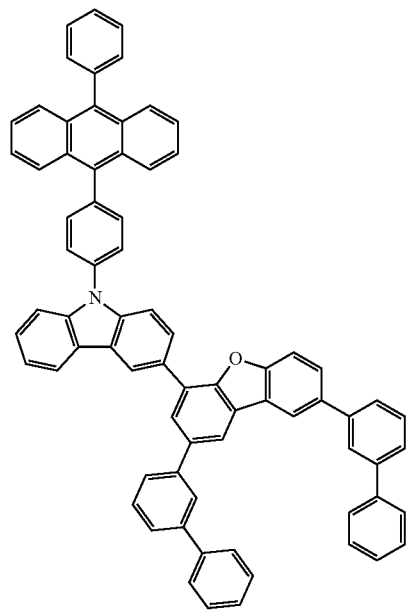
(819)
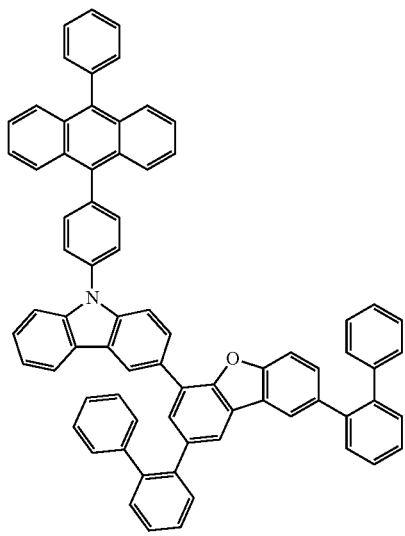
(820)
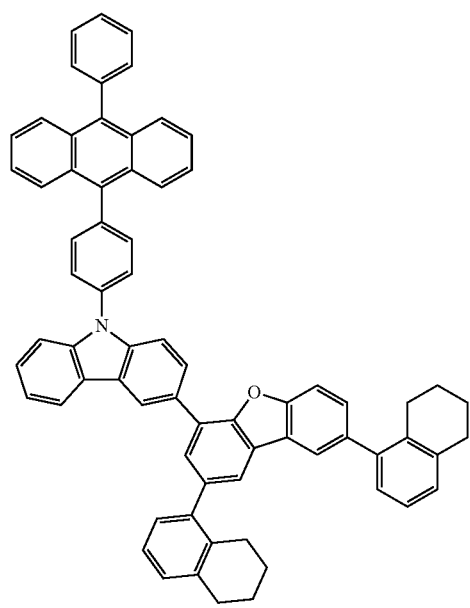

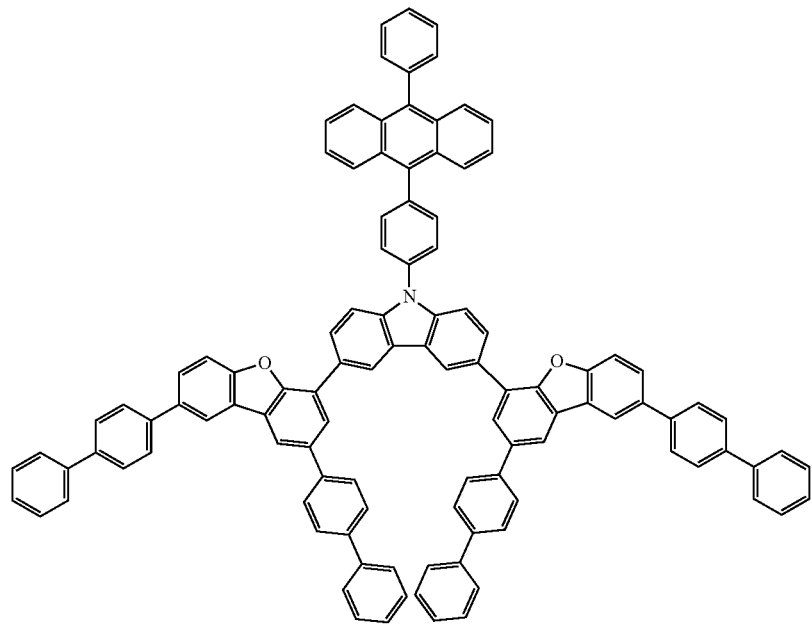
(821)
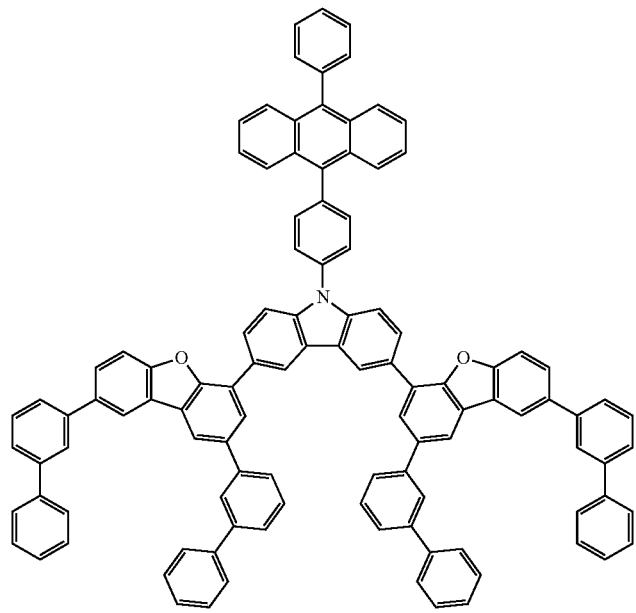
(822)

(823)
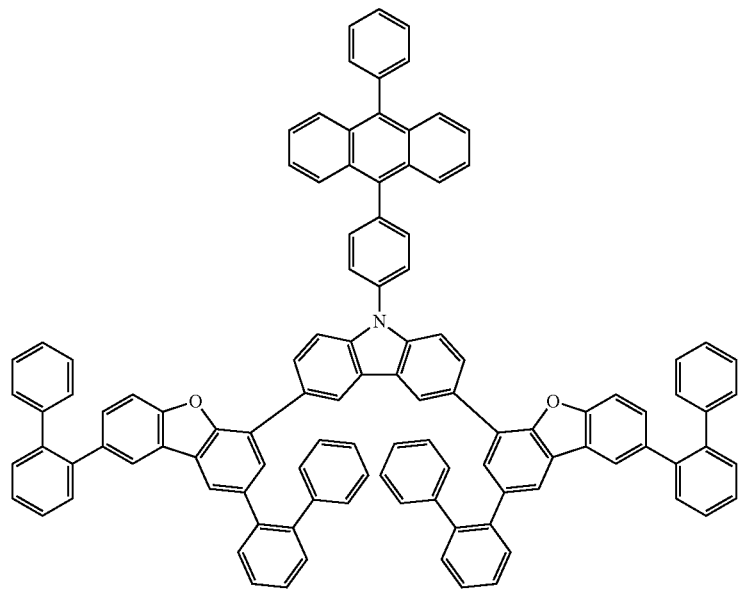
(824)
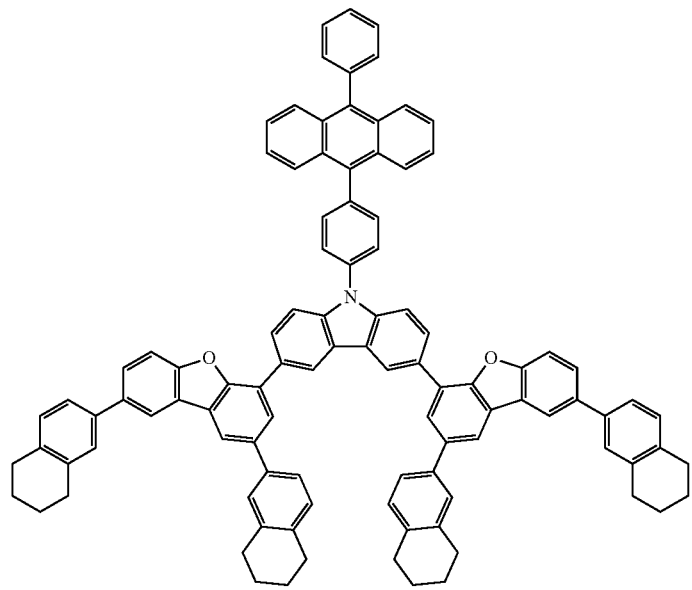

-continued
(825)
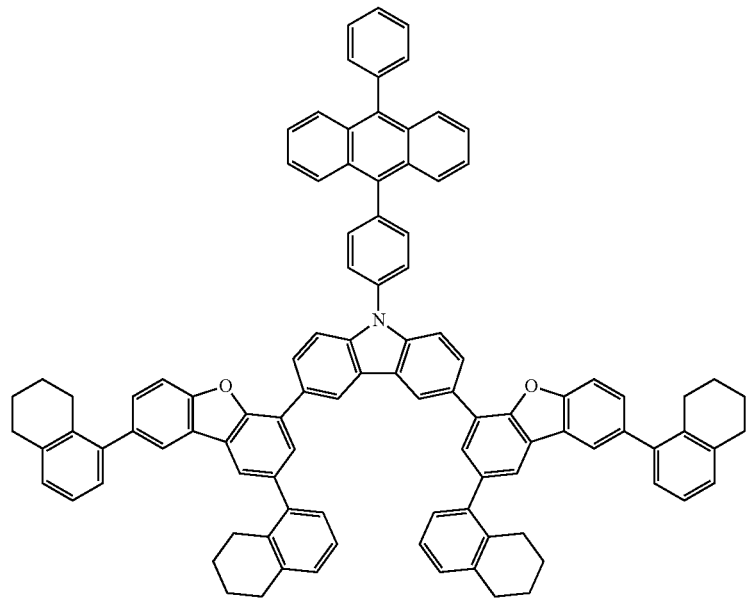
(826)
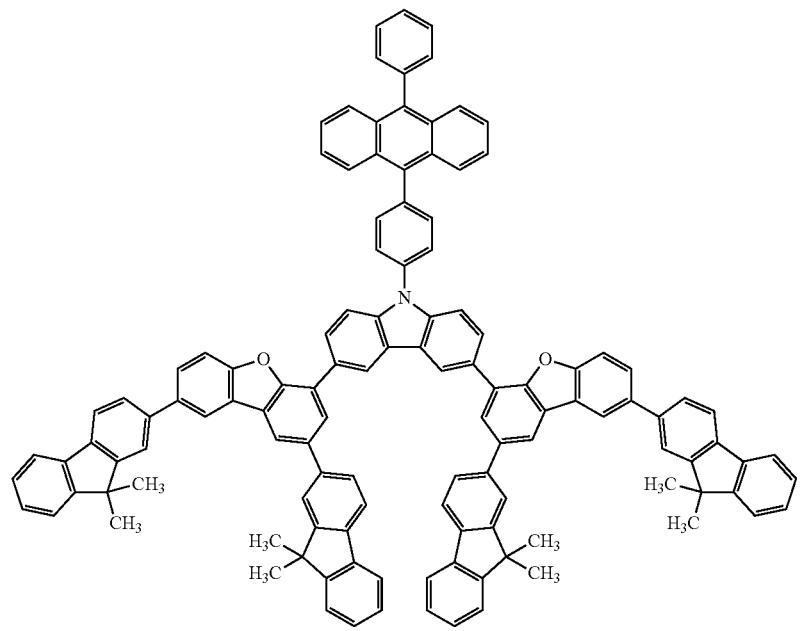

(827)
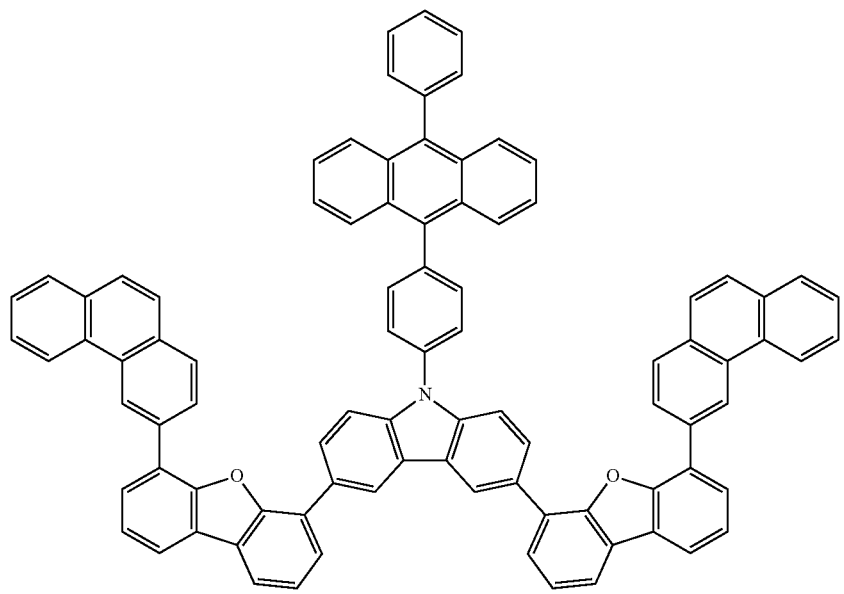
(828)
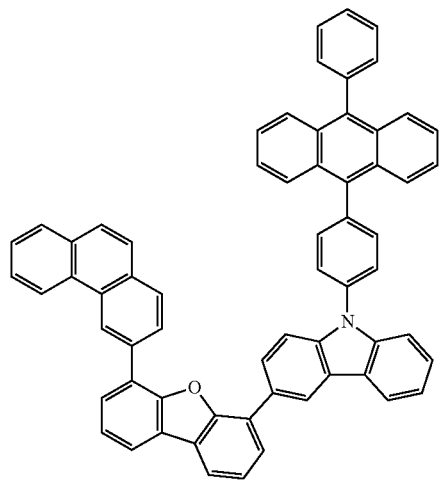
(829)
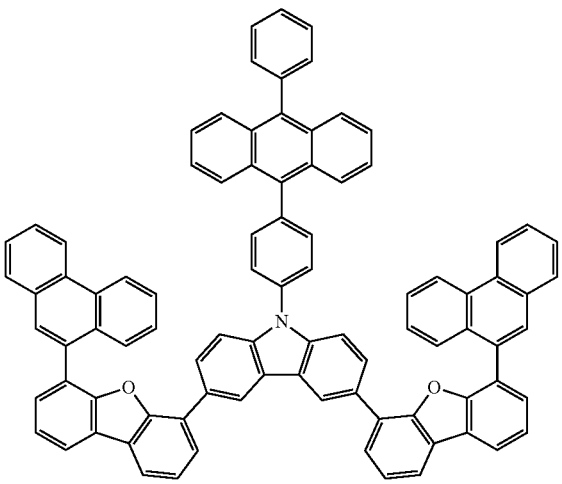
(830)
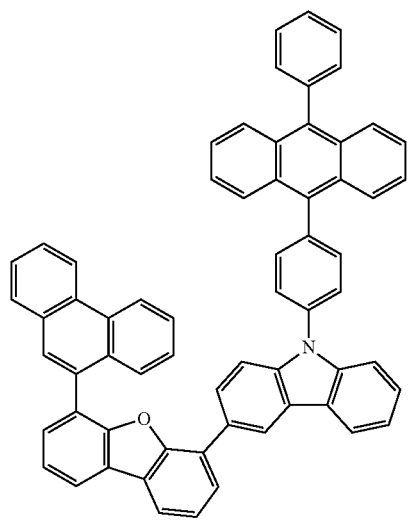
(831)
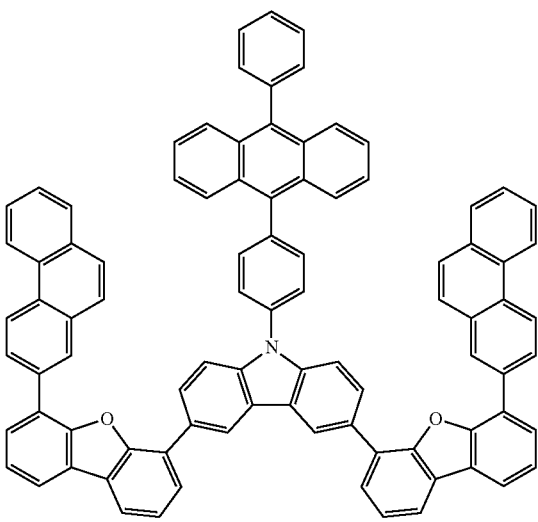

335
-continued
(832)
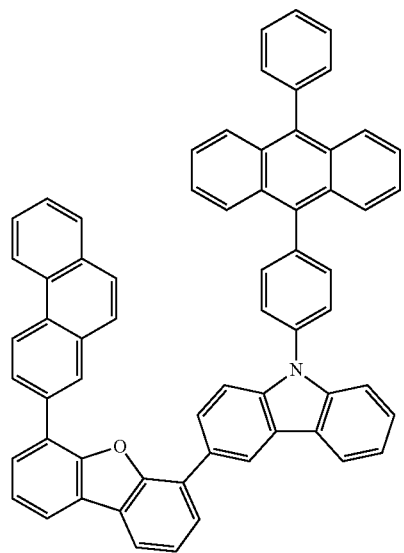
336
(833)
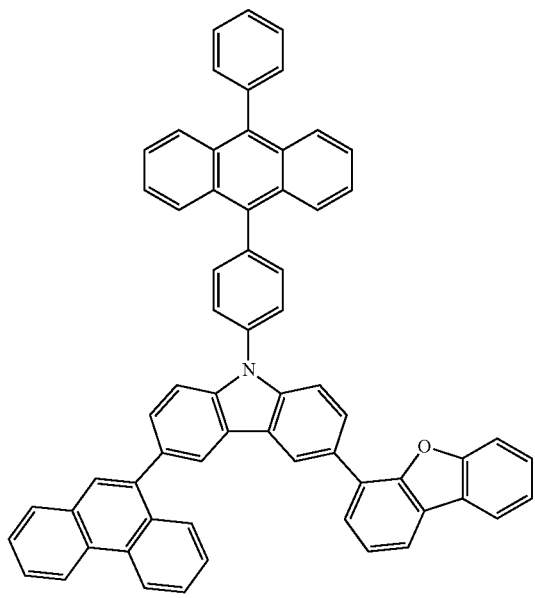
(834)
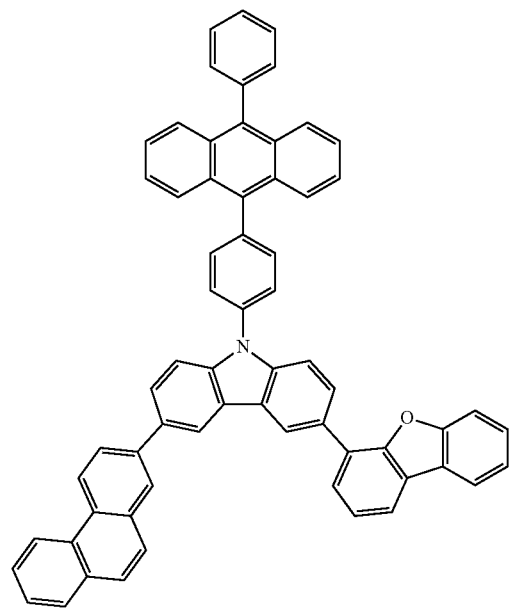
(835)
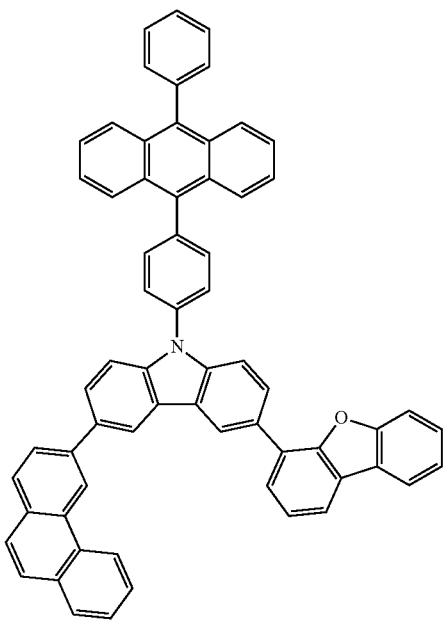

(836)
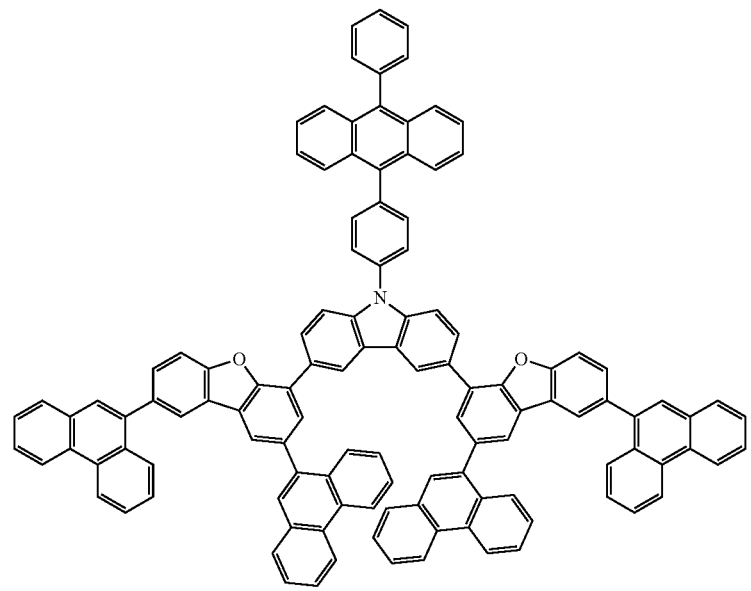
(837)
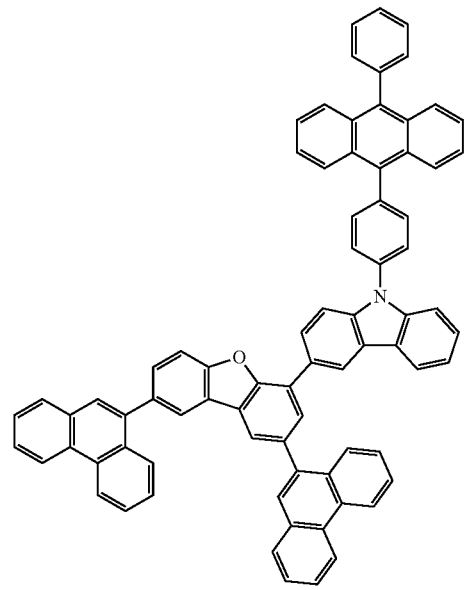

-continued
(838)
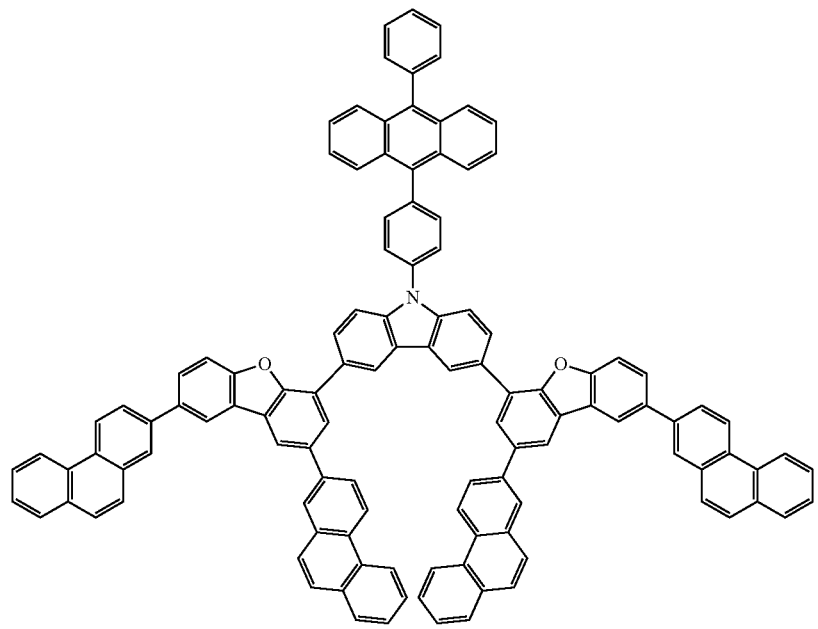
(839)
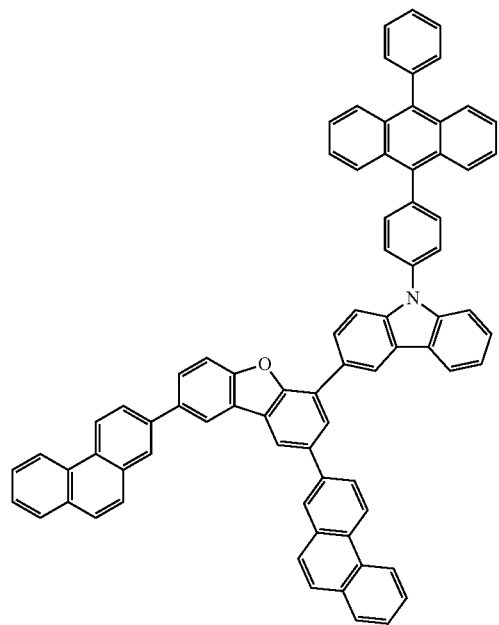

(840)

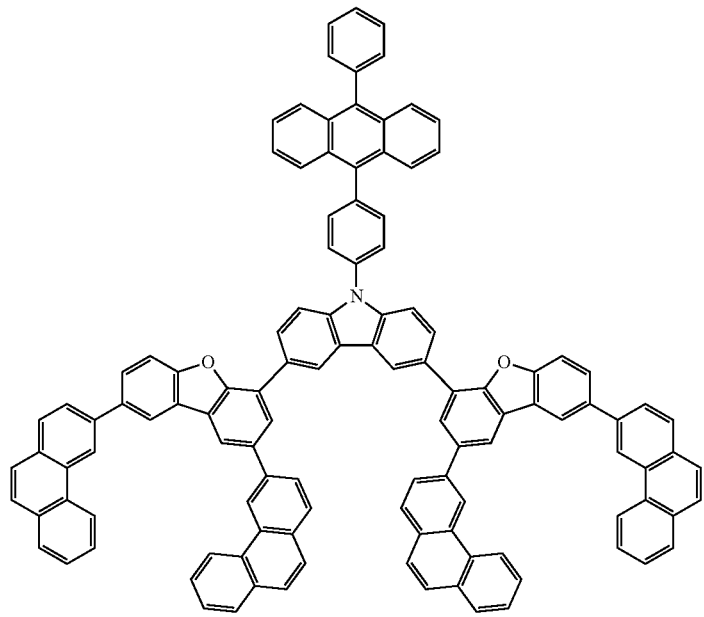

(841)

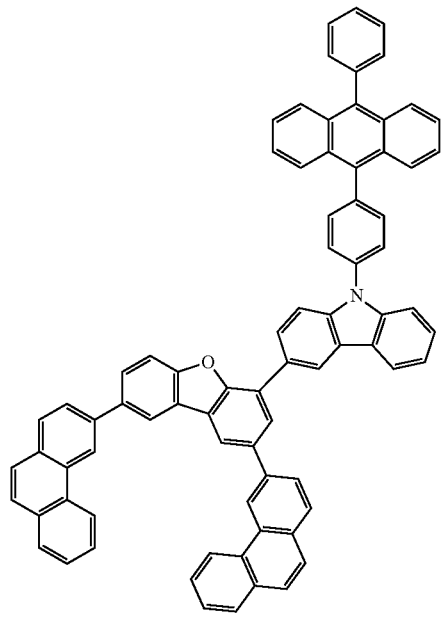

The above-described carbazole derivative is suitable as a carrier-transport material or a host material because the carrier-transport property is excellent. Owing to this, a light-emitting element driven with a low driving voltage can also be provided. In addition, any of the carbazole derivatives in this embodiment has a rigid group such as dibenzothiophene or dibenzofuran, and thus the morphology is excellent and the film quality is stable. Further, the thermophysical property is also excellent. From the above, a light-emitting element using such a carbazole derivative can be a light-emitting element having a long lifetime. In addition, with a skeleton that has a chromophore, such as anthracene, pyrene, chrysene, naphthacene, pentacene, fluoranthene, perylene, or coronene, a light-emitting element material having high efficiency can be obtained. Further, a skeleton whose T1 level is high, such as triphenylene or phenanthrene, can be used as Ar to obtain a light-emitting element material for suitable application to a phosphorescent element.

Embodiment 2

Next, in this embodiment, a method for synthesizing a carbazole derivative represented by the following general formula (G0) or (G1) is described.

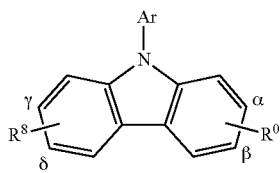
(G0)

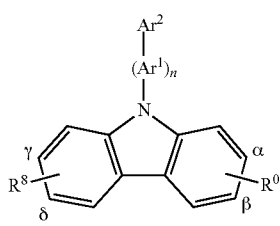
(G1)

In the formula (G0), Ar represents an aryl group that has 14 to 70 carbon atoms and includes a condensed tricyclic ring, a condensed tetracyclic ring, a condensed pentacyclic ring, a condensed hexacyclic ring, or a condensed heptacyclic ring. In addition, in the formula (G1), $Ar^1$ represents any one of a phenylene group, a naphthylene group, and a biphenylene group, and $Ar^2$ represents a group that has 14 to 30 carbon atoms and includes a condensed tricyclic ring, a condensed tetracyclic ring, a condensed pentacyclic ring, a condensed hexacyclic ring, or a condensed heptacyclic ring. In addition, n is either 0 or 1. Note that $Ar^1$ may or may not have a substituent, and in the case where $Ar^1$ has a substituent, the substituent is an alkyl group having 1 to 4 carbon atoms. Note also that $Ar^2$ may or may not have a substituent, and in the case where $Ar^2$ has a substituent, the substituent is any of an alkyl group having 1 to 4 carbon atoms and an aryl group having 6 to 15 carbon atoms. Further, in the carbazole derivative represented by the general formula (G1), the Ar group in the general formula (G0) is represented by an $(Ar^1)n\text{-}Ar^2$ group.

In addition, $R^0$ is a substituent represented by the following general formula (g1) which is bonded to a carbon atom represented by either α or β. $R^8$ represents any one of hydrogen, an alkyl group having 1 to 4 carbon atoms, an aryl group having 6 to 15 carbon atoms, and a group represented by the following general formula (g2), which is bonded to a carbon atom represented by either γ or δ.

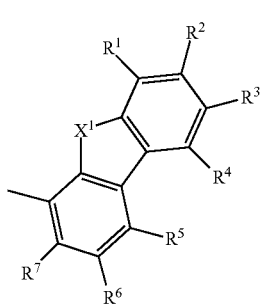
(g1)

In the formula, $X^1$ represents oxygen or sulfur, and $R^1$ to $R^7$ individually represent any one of hydrogen, an alkyl group having 1 to 4 carbon atoms, and an aryl group having 6 to 15 carbon atoms.

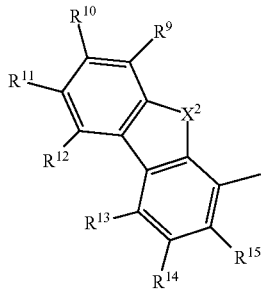
(g2)

In the formula (g2), $X^2$ represents oxygen or sulfur, and $R^9$ to $R^{15}$ individually represent any one of hydrogen, an aryl group having 6 to 15 carbon atoms, and an alkyl group having 1 to 4 carbon atoms.

Here, as described above, the Ar group in the general formula (G0) is the $(Ar^1)n\text{-}Ar^2$ group in the general formula (G1), and $R^0$ in the formulas is a substituent represented by the above general formula (g1); therefore, the above general formulas (G0) and (G1) can also be represented by the following general formula (G1'). In the general formula (G1'), the substitution site of the substituent corresponding to the above general formula (g1) is a carbon atom represented by either α or β in the general formula (G0) or (G1). Hereinafter, the substitution sites of substituents or elements represented by Ar, $R^1$ to $R^{16}$, $X^1$, and $X^2$, and substituents corresponding to $R^8$ and the above general formula (g1) are the same as those in the above explanation unless otherwise explained.

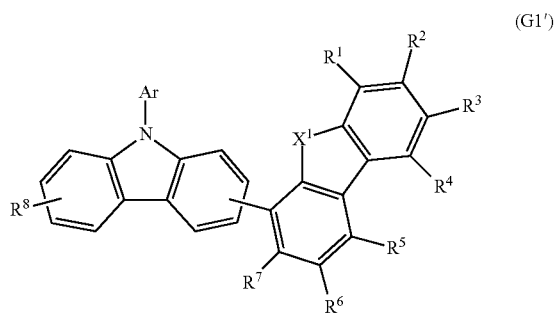
(G1')

In this embodiment, a method for synthesizing substances represented by the above general formula (G1') is described by using the general formula (G1') instead of the general formula (G0) or (G1).

<Synthesis Method 1>

In Synthesis Method 1, a method for synthesizing a substance represented by the general formula (G1') in which $R^8$ is hydrogen (the following general formula (G1'-1)) is described.

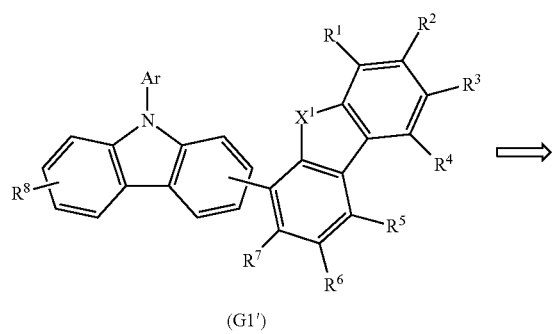

(G1')

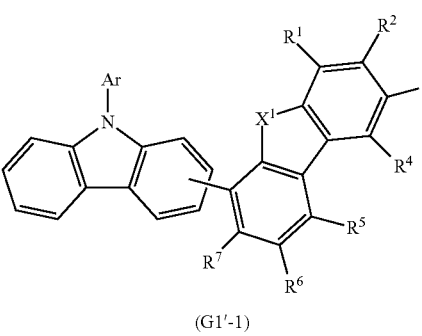

(G1'-1)

R⁸ = H

First, a compound having a halogen group or a triflate group at the 2- or 3-position of 9H-carbazole (a compound 1) is coupled with a boronic acid compound of dibenzothiophene or a boronic acid compound of dibenzofuran (a compound 2), whereby a 9H-carbazole derivative having a structure in which the 2- or 3-position of 9H-carbazole is bonded to the 4-position of dibenzothiophene or the 4-position of dibenzofuran (a compound 3) can be obtained (a reaction formula (A-1)).

(A-1)

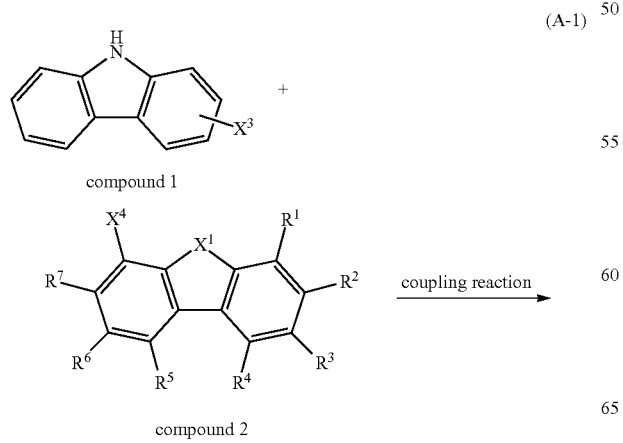

compound 1 compound 2

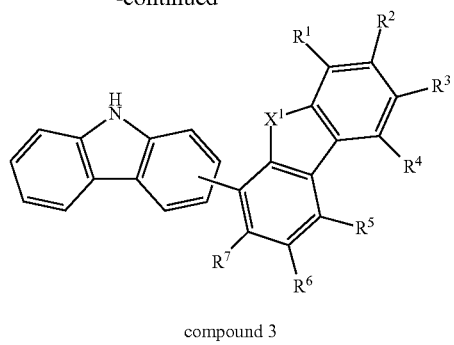

compound 3

In the reaction formula (A-1), $X^1$ represents oxygen or sulfur, $X^3$ represents a halogen group, a triflate group, or the like, $X^4$ represents a boronic acid (the boronic acid may be protected by ethylene glycol or the like), $R^1$ to $R^7$ individually represent any one of hydrogen, an alkyl group having 1 to 4 carbon atoms, and an aryl group having 6 to 15 carbon atoms. As the coupling reaction in the reaction formula (A-1), a Suzuki-Miyaura coupling reaction using a palladium catalyst or the like can be given.

Next, the obtained 9H-carbazole derivative (the compound 3) is coupled with a halogenated aryl (a compound 4), whereby a compound (G1'-1), which is the object of the synthesis, can be obtained (a reaction formula (A-2)).

(A-2)

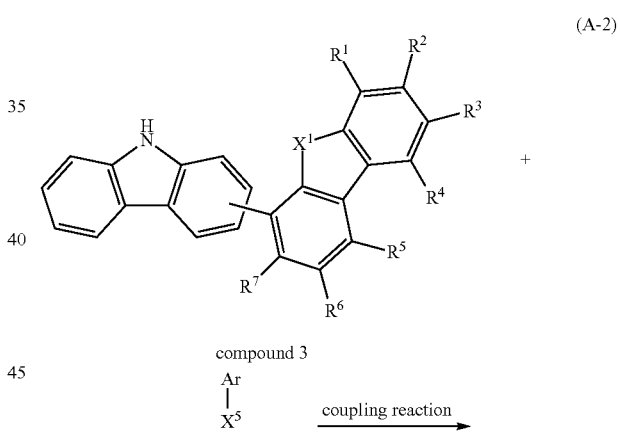

compound 3 compound 4

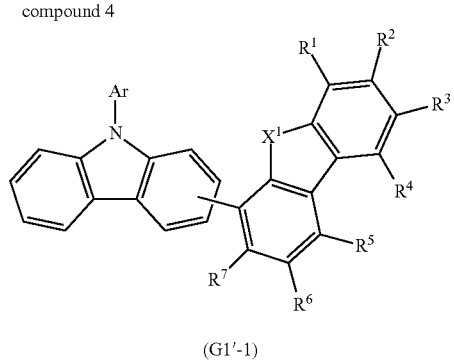

(G1'-1)

In the reaction formula (A-2), $X^1$ represents oxygen or sulfur, $X^5$ represents a halogen group or the like, $R^1$ to $R^7$ individually represent any one of hydrogen, an alkyl group having 1 to 4 carbon atoms, and an aryl group having 6 to 15 carbon atoms, and Ar represents an aryl group that has 14 to 70 carbon atoms and includes a condensed tricyclic ring, a condensed tetracyclic ring, a condensed pentacyclic ring, a condensed hexacyclic ring, or a condensed heptacyclic ring. As the coupling reaction in the reaction formula (A-2), a Buchwald-Hartwig reaction using a palladium catalyst, an Ullmann reaction using copper or a copper compound, or the like can be given.

<Synthesis Method 2>

In Synthesis Method 2, a method for synthesizing a substance in which $R^8$ in the above general formula (G1') is a substituent represented by the above general formula (g2) (the following general formula (G1'-2)) is described.

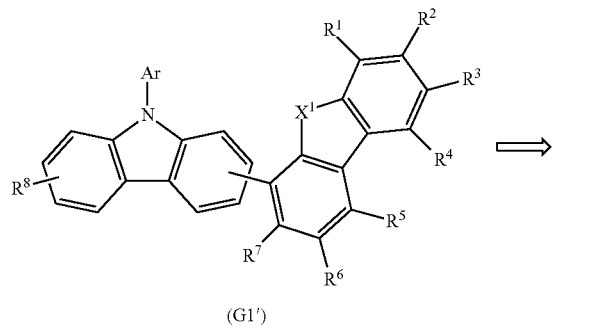

(G1')

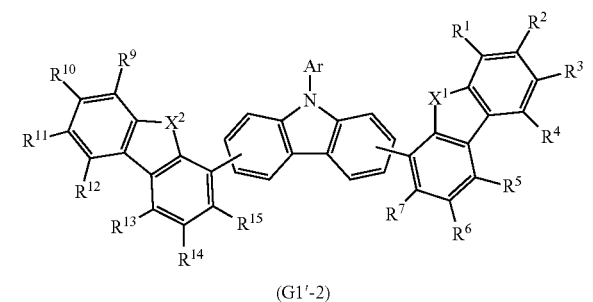

(G1'-2)

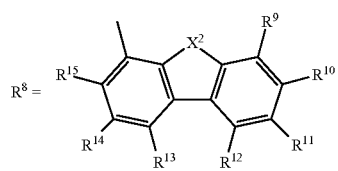

$R^8 =$

First, a carbazole derivative having halogen groups at the 2- and 7-positions of, the 3- and 6-positions of, or the 2- and 6-positions of 9H-carbazole (a compound 5) is coupled with a boronic acid compound of dibenzothiophene or a boronic acid compound of dibenzofuran (a compound 2), whereby a carbazole derivative (a compound 6) can be obtained (a reaction formula (B-1)).

(B-1)

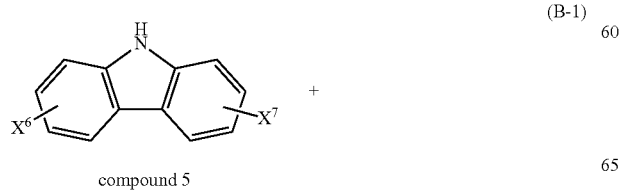

compound 5

+

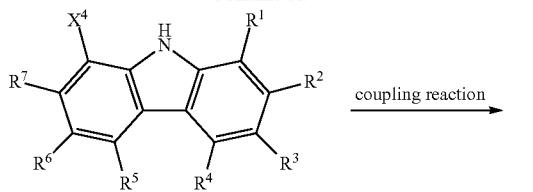

compound 2 coupling reaction

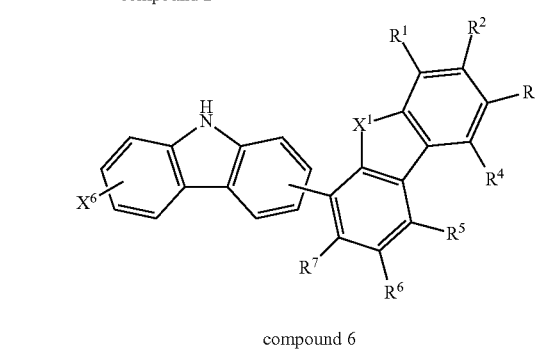

compound 6

In the reaction formula (B-1), $X^6$ and $X^7$ individually represent a halogen group, a triflate group, or the like, $X^4$ represents a boronic acid (the boronic acid may be protected by ethylene glycol or the like), $R^1$ to $R^7$ individually represent any of hydrogen, an alkyl group having 1 to 4 carbon atoms, and an aryl group having 6 to 15 carbon atoms. $X^6$ and $X^7$ may the same or different. As the coupling reaction in the reaction formula (B-1), a Suzuki-Miyaura coupling reaction using a palladium catalyst or the like can be given.

Next, the monohalide of 9H-carbazole (the compound 6) is coupled with a boronic acid compound of dibenzothiophene or a boronic acid compound of dibenzofuran (a compound 7), whereby a carbazole derivative (a compound 8) can be obtained (a reaction formula (B-2)).

(B-2)

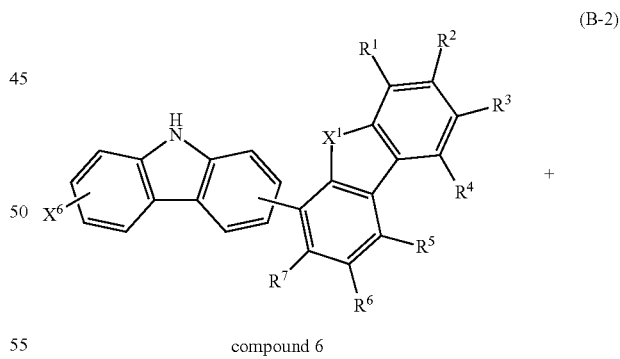

compound 6

+

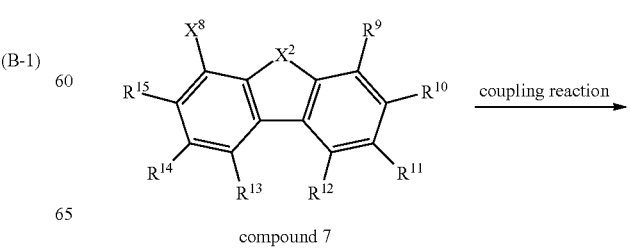

compound 7 coupling reaction

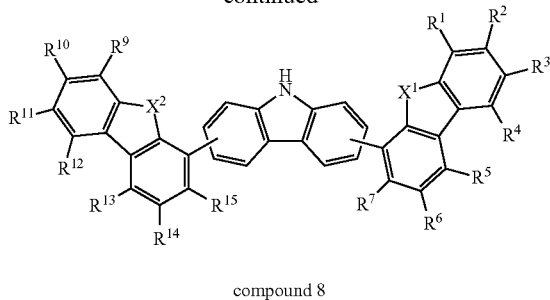

compound 8

In the reaction formula (B-2), $X^6$ represents a halogen group, a triflate group, or the like, $X^8$ represents a boronic acid (the boronic acid may be protected by ethylene glycol or the like), $R^1$ to $R^7$ individually represent any of hydrogen, an alkyl group having 1 to 4 carbon atoms, and an aryl group having 6 to 15 carbon atoms. As the coupling reaction in the reaction formula (B-1), a Suzuki-Miyaura coupling reaction using a palladium catalyst or the like can be given.

Lastly, the 9H-carbazole derivative (the compound 8) is coupled with a halogenated aryl (a compound 4), whereby a compound (G1'-2), which is the object of the synthesis, can be obtained (a reaction formula (B-3)).

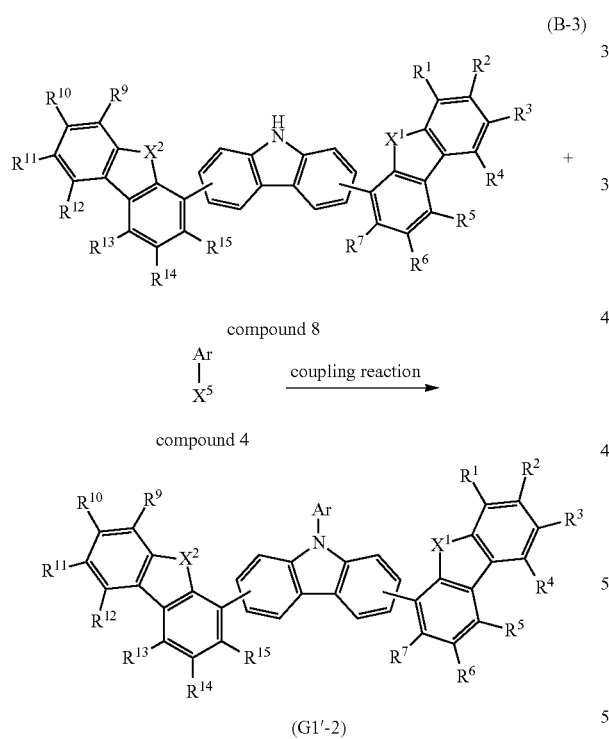

In the reaction formula (B-3), $X^1$ and $X^2$ individually represents oxygen or sulfur, $X^5$ represents a halogen group, $R^1$ to $R^7$ individually represent any one of hydrogen, an alkyl group having 1 to 4 carbon atoms, and an aryl group having 6 to 15 carbon atoms, and Ar represents an aryl group that has 14 to 70 carbon atoms and includes a condensed tricyclic ring, a condensed tetracyclic ring, a condensed pentacyclic ring, a condensed hexacyclic ring, or a condensed heptacyclic ring. As the coupling reaction in the reaction formula (B-3), a Buchwald-Hartwig reaction using a palladium catalyst, an Ullmann reaction using copper or a copper compound, or the like can be given. With the above reaction formulas (B-1) to (B-3), a method in which a dibenzothiophene derivative or a dibenzofuran derivative is coupled by one equivalent is described. However, when the compounds 2 and 7 have the same structure, two equivalents of the dibenzothiophene derivative or dibenzofuran derivative may be coupled with the 9H-carbazole compound at the same time.

<Synthesis Method 3>

In Synthesis Method 3, a method for synthesizing a substance in which $R^8$ in the above general formula (G1') is an aryl group having 6 to 15 carbon atoms or an alkyl group having 1 to 4 carbon atoms (the following general formula (G1'-3)) is described.

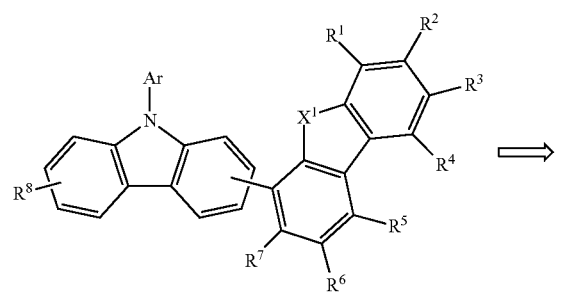

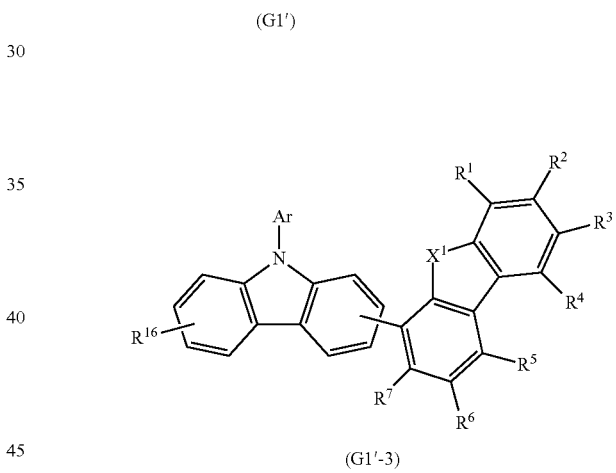

$R^8$ = aryl group or alkyl group

First, a 9H-carbazole compound in which the 2- or 3-position of 9H-carbazole is substituted by an alkyl group or an aryl group and the 3- or 6-position of 9H-carbazole is substituted by a halogen group (a compound 9) is coupled with a boronic acid compound of dibenzothiophene or a boronic acid compound of dibenzofuran (a compound 2), whereby a 9H-carbazole derivative (a compound 10) can be obtained (a reaction formula (C-1)).

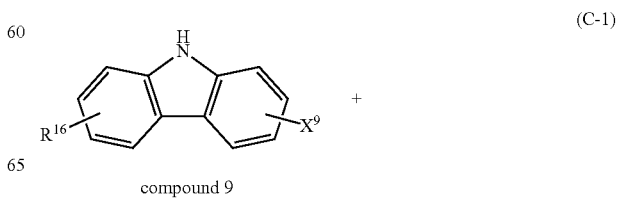

compound 9

-continued

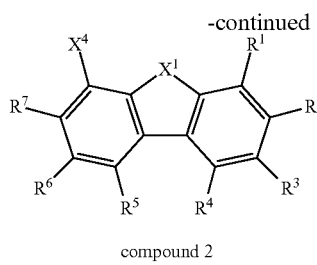

compound 2

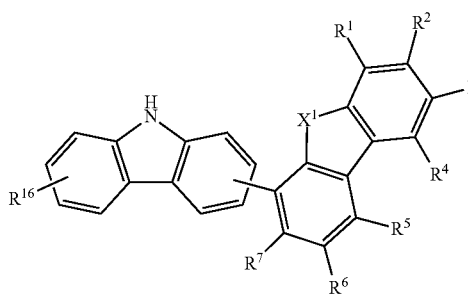

compound 10

In the reaction formula (C-1), $X^1$ represents oxygen or sulfur, $X^9$ represents a halogen group, a triflate group, or the like, $X^4$ represents a boronic acid (the boronic acid may be protected by ethylene glycol or the like), $R^1$ to $R^7$ individually represent any one of hydrogen, an alkyl group having 1 to 4 carbon atoms, and an aryl group having 6 to 15 carbon atoms, and $R^{16}$ represents any of an alkyl group having 1 to 4 carbon atoms and an aryl group having 6 to 15 carbon atoms. As the coupling reaction in the reaction formula (C-1), a Suzuki-Miyaura coupling reaction using a palladium catalyst or the like can be given.

Next, the 9H-carbazole derivative (the compound 10) is coupled with a halogenated aryl (a compound 4), whereby a compound (G1'-3), which is the object of the synthesis, can be obtained (a reaction formula (C-2)).

(C-2)

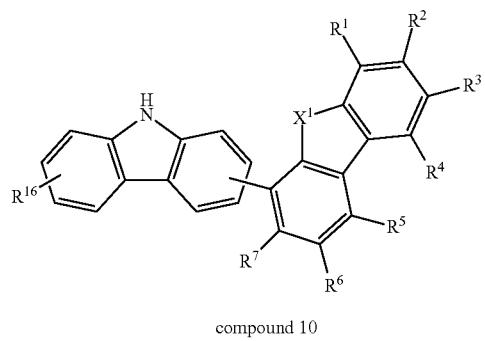

-continued

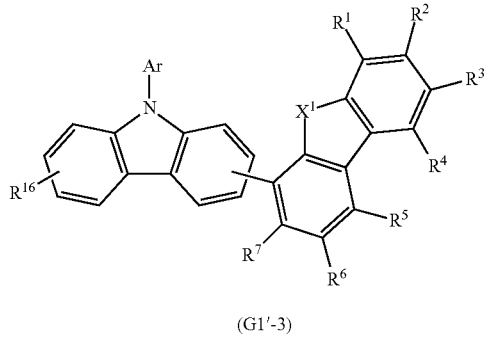

(G1'-3)

In the reaction formula (C-2), $X^1$ represents oxygen or sulfur, $X^5$ represents a halogen group, $R^1$ to $R^7$ individually represent any one of hydrogen, an alkyl group having 1 to 4 carbon atoms, and an aryl group having 6 to 15 carbon atoms, $R^{16}$ represents any of an alkyl group having 1 to 4 carbon atoms and an aryl group having 6 to 15 carbon atoms, and Ar represents an aryl group that has 14 to 70 carbon atoms and includes a condensed tricyclic ring, a condensed tetracyclic ring, a condensed pentacyclic ring, a condensed hexacyclic ring, or a condensed heptacyclic ring.

Here, in the above Synthesis Methods, the compounds 3, 8, and 10 are each a synthetic intermediate of a carbazole derivative described in Embodiment 1. That is, a carbazole derivative represented by the following general formula (G5) is a synthetic intermediate of the carbazole derivative represented by the general formula (G1).

(G5)

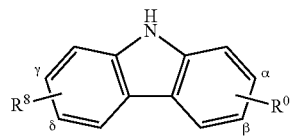

(In the formula, $R^0$ represents a group represented by the following general formula (g1), and $R^8$ represents any one of hydrogen, an alkyl group having 1 to 4 carbon atoms, an aryl group having 6 to 15 carbon atoms, and a group represented by the following general formula (g2). Note that the substitution site of $R^0$ is a carbon atom represented by either α or β, and the substitution site of $R^8$ is a carbon atom represented by either γ or δ.)

(g1)

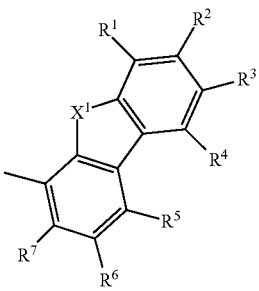

(In the formula, $X^1$ represents oxygen or sulfur, and $R^1$ to $R^7$ individually represent any one of hydrogen, an alkyl group having 1 to 4 carbon atoms, and an aryl group having 6 to 15 carbon atoms.)

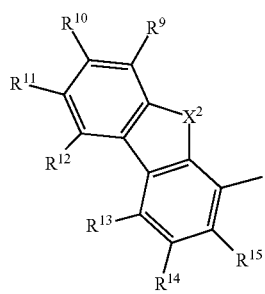

(g2)

(In the formula, $X^2$ represents oxygen or sulfur, and $R^9$ to $R^{15}$ individually represent any one of hydrogen, an aryl group having 6 to 15 carbon atoms, and an alkyl group having 1 to 4 carbon atoms.)

Here, in a carbazole derivative represented by the general formula (G0) or (G1), in the case where the group represented by the above general formula (g1) further includes a substituent, the substitution site of the substituent is preferably a site represented by $R^1$, $R^3$, or $R^6$ for a reduction in cost of synthesizing the material owing to availability of the material and easiness of the synthesis. From the same point of view, it is further preferable that $R^1$ to $R^7$ be all hydrogen. Therefore, also in a carbazole derivative represented by the general formula (G5), which is a synthetic intermediate of the carbazole derivative represented by the general formula (G0) or (G1), in the case where the group represented by the above general formula (g1) further includes a substituent, the substitution site of the substituent is preferably a site represented by $R^1$, $R^3$, or $R^6$, and it is further preferable that $R^1$ to $R^7$ be all hydrogen.

In a similar manner, in the case where the group represented by (g2) is applied as $R^8$, the substitution site of the substituent is preferably a site represented by $R^9$, $R^{10}$ or $R^{14}$, and it is further preferable that $R^9$ to $R^{15}$ be all hydrogen.

Note that the compound 3 having a preferred structure in which $R^1$ to $R^7$ are all hydrogen is a carbazole derivative represented by the following general formula (G6).

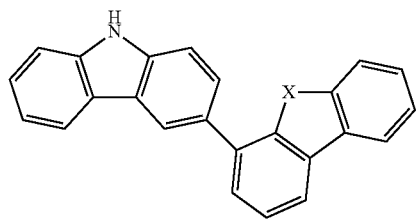

(G6)

Note that the compound 8 having a preferred structure in which $R^1$ to $R^7$ and $R^9$ to $R^{15}$ are all hydrogen is any of carbazole derivatives represented by the following general formulas (G7) and (G8).

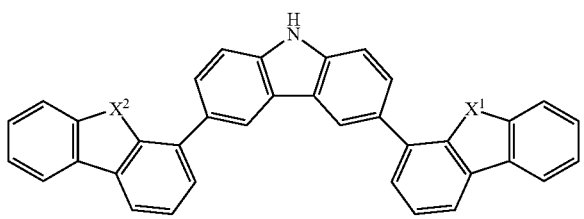

(G7)

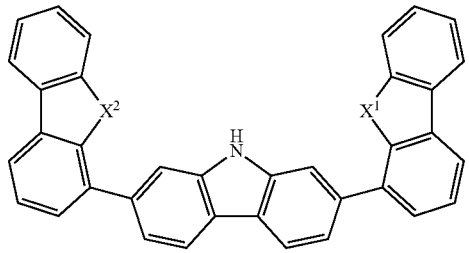

(G8)

As specific examples of an alkyl group having 1 to 4 carbon atoms and an aryl group having 6 to 15 carbon atoms, which can be applied to any of $R^1$ to $R^{15}$ in the carbazole derivative represented by the above general formula (G5), groups represented by the structural formulas (R-1) to (R-23), which are described in Embodiment 1 as groups applicable to any of $R^1$ to $R^{15}$ in the general formula (G0) or (G1), can be applied.

Specific examples of the carbazole derivative represented by the above general formula (G5) are shown by the following structural formulas (UT-1) to (UT-137) and (UF-1) to (UF-137).

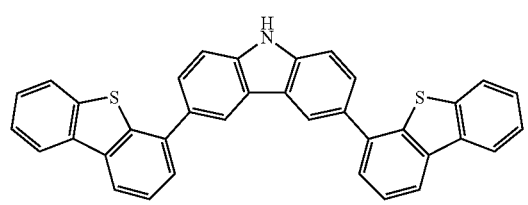

(UT-1)

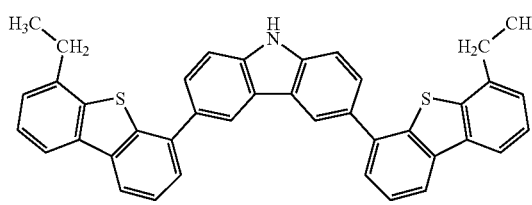

(UT-2)

-continued
(UT-3)
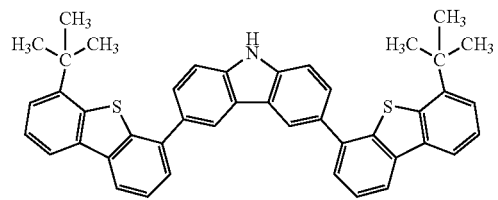
(UT-4)
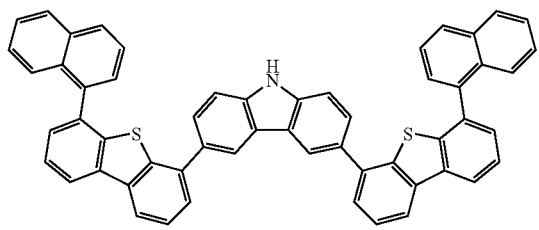
(UT-5)
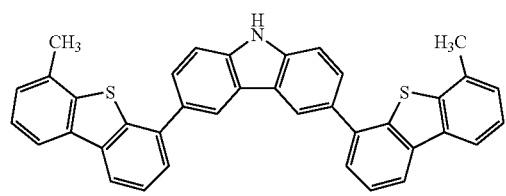
(UT-7)
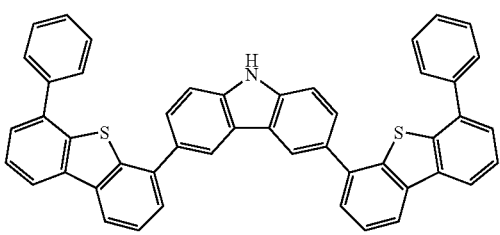
(UT-8)
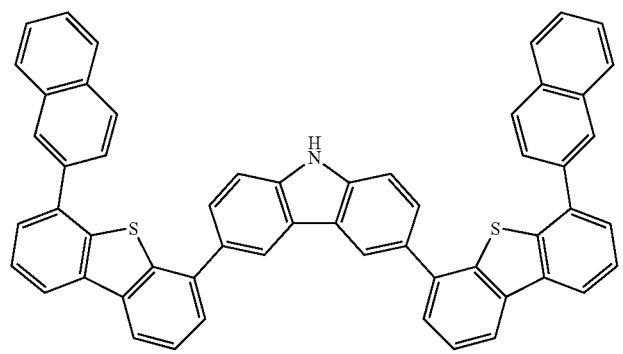
(UT-9)
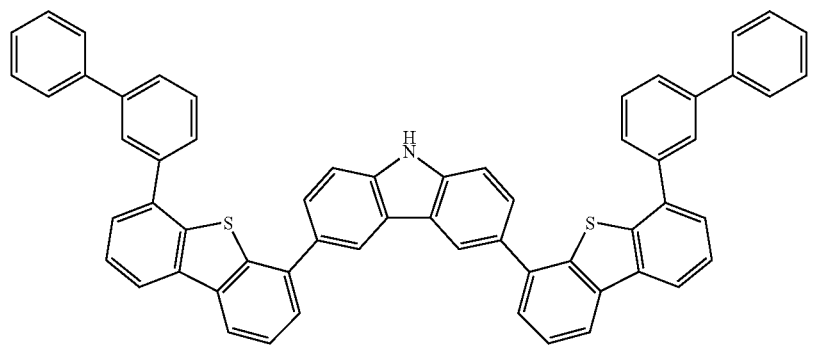
(UT-10)
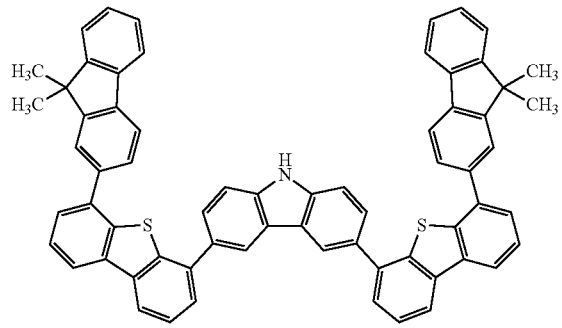
(UT-11)
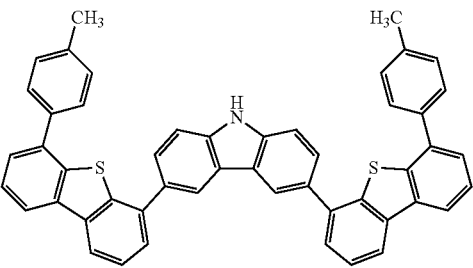

-continued
(UT-12)
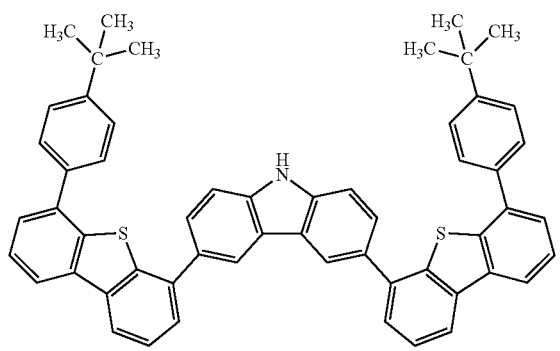
(UT-13)
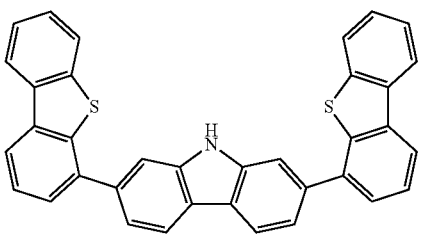
(UT-14)
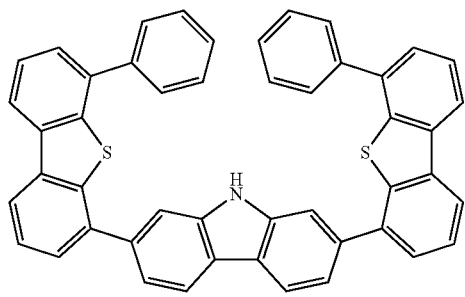
(UT-15)
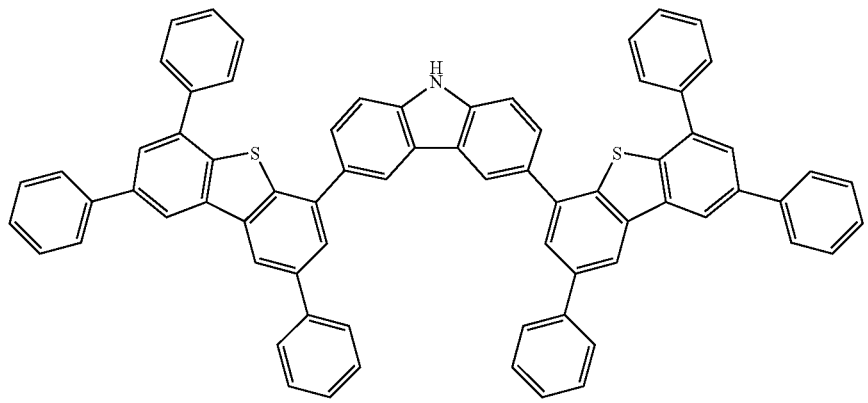
(UT-16)
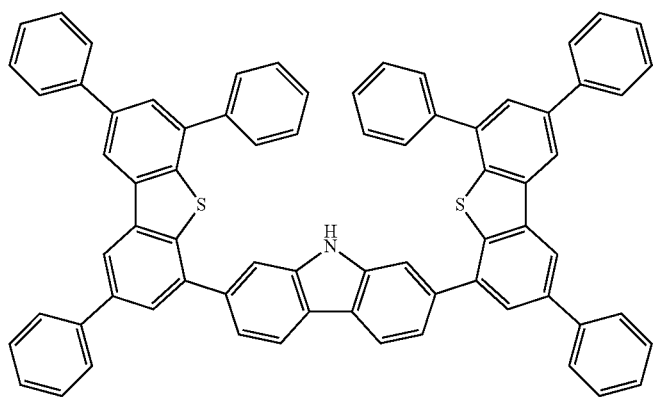

-continued
(UT-17)
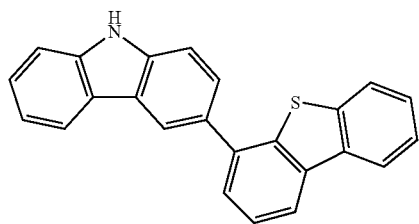
(UT-18)
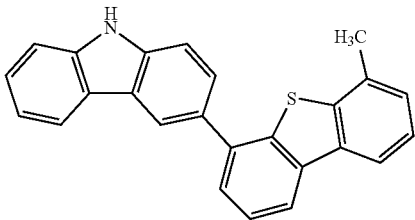
(UT-19)
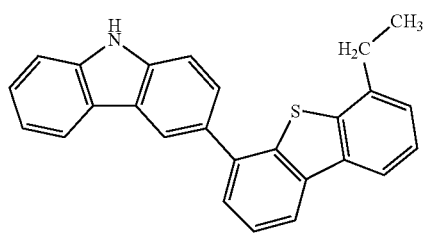
(UT-21)
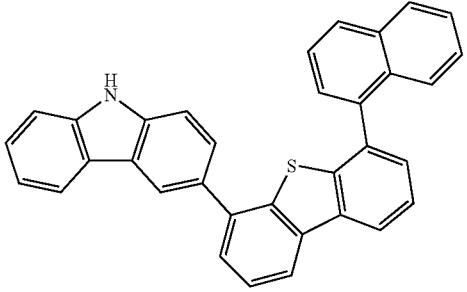
(UT-22)
(UT-23)
(UT-24)
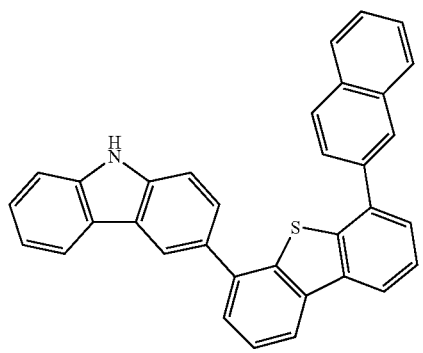
(UT-25)
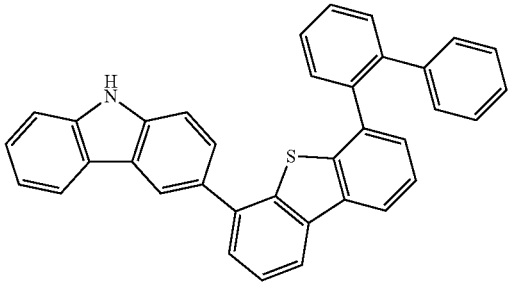
(UT-26)
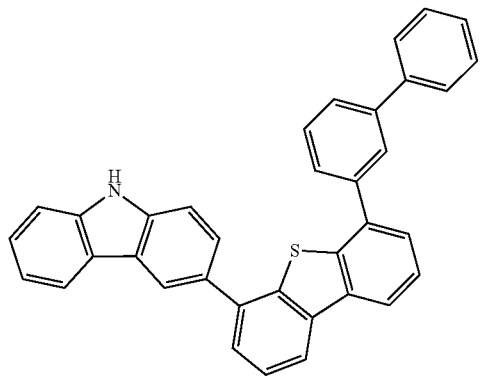
(UT-27)

-continued
(UT-28)
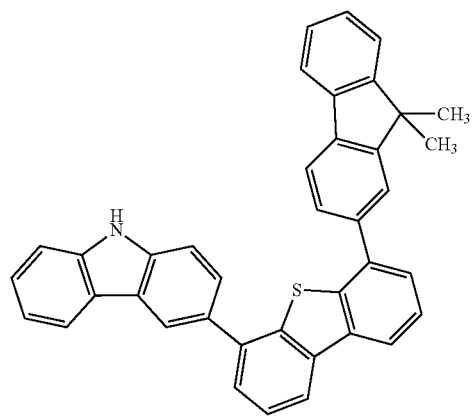
(UT-29)
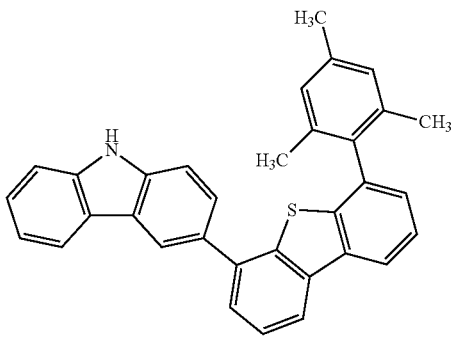
(UT-30)
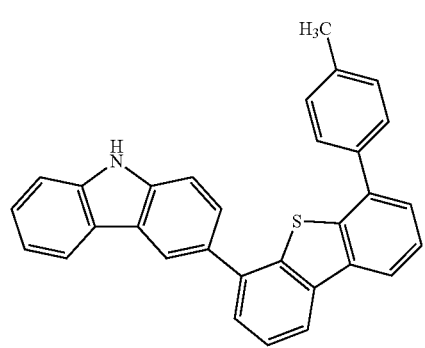
(UT-31)
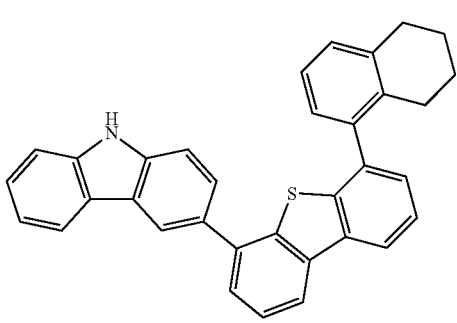
(UT-32)
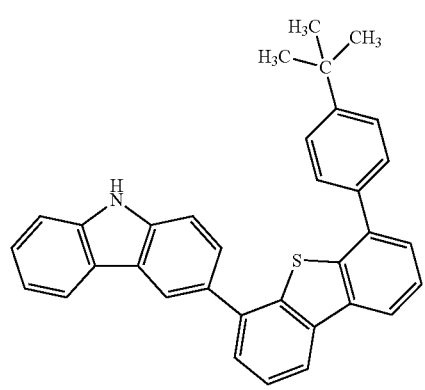
(UT-33)
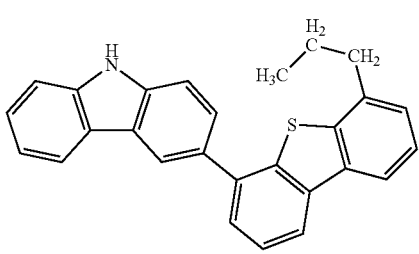
(UT-35)
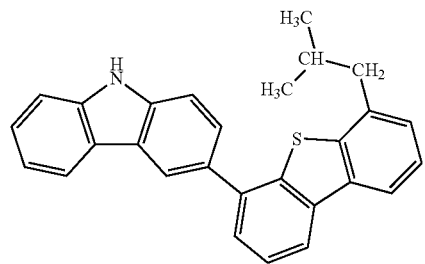
(UT-36)
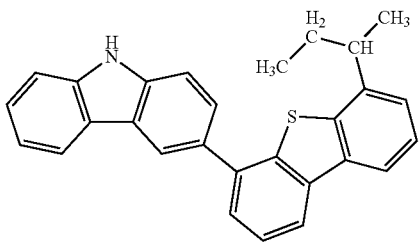

-continued
(UT-37)
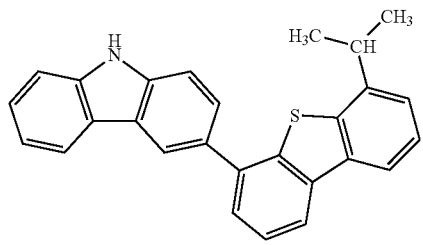
(UT-39)
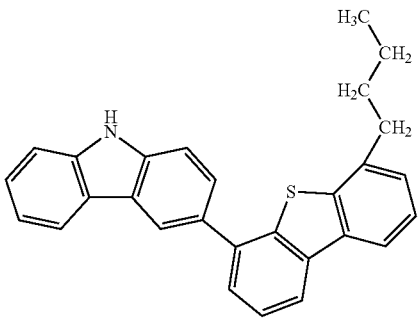
(UT-40)
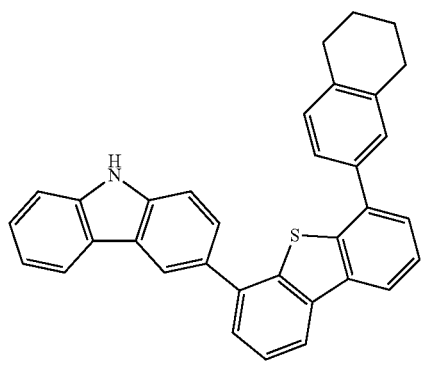
(UT-41)
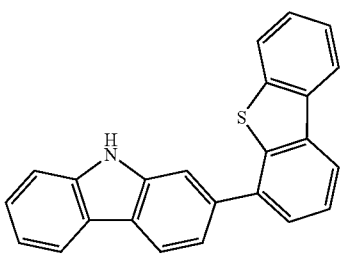
(UT-42)
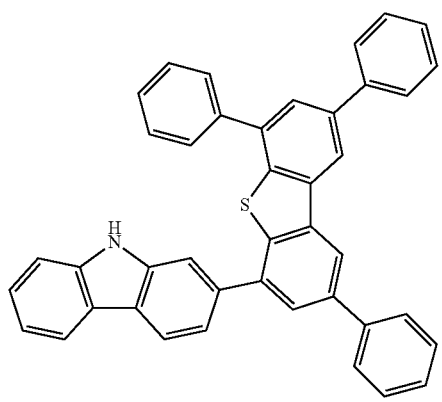
(UT-43)
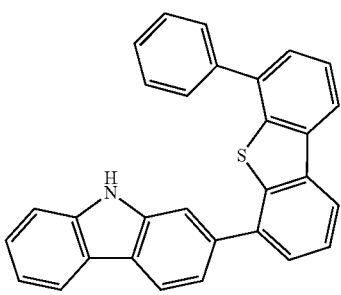
(UT-44)
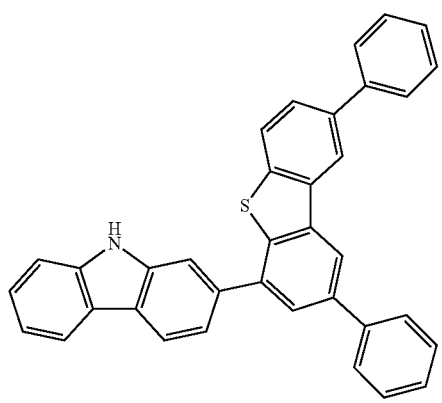
(UT-45)
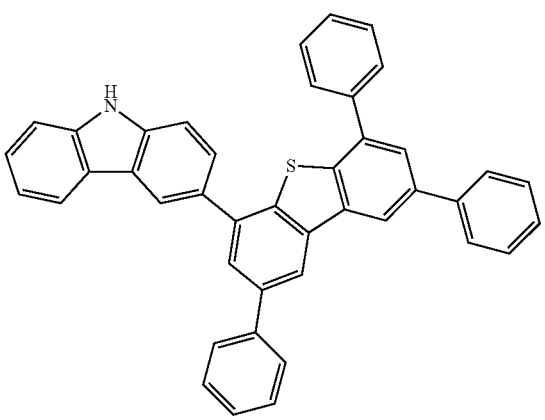

(UT-46)
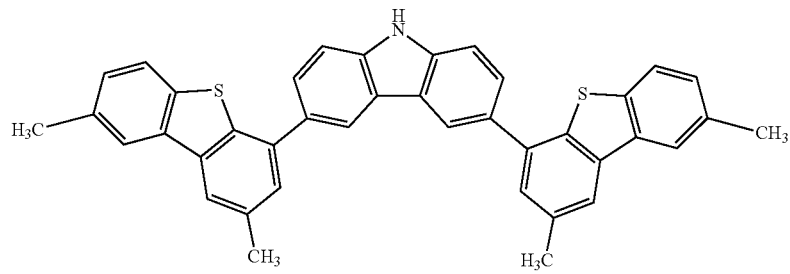
(UT-47)
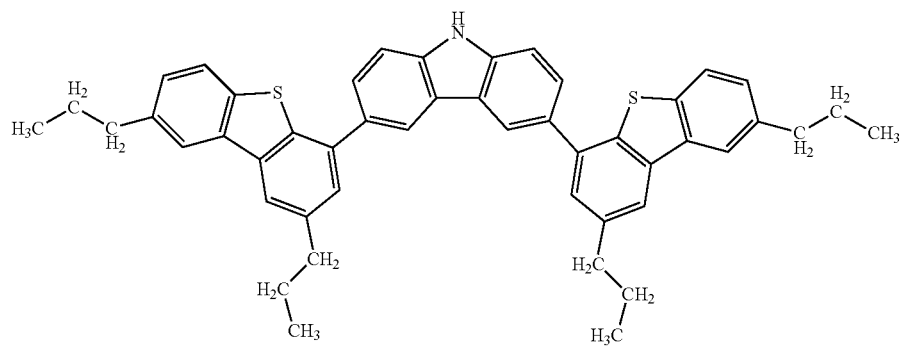
(UT-48)
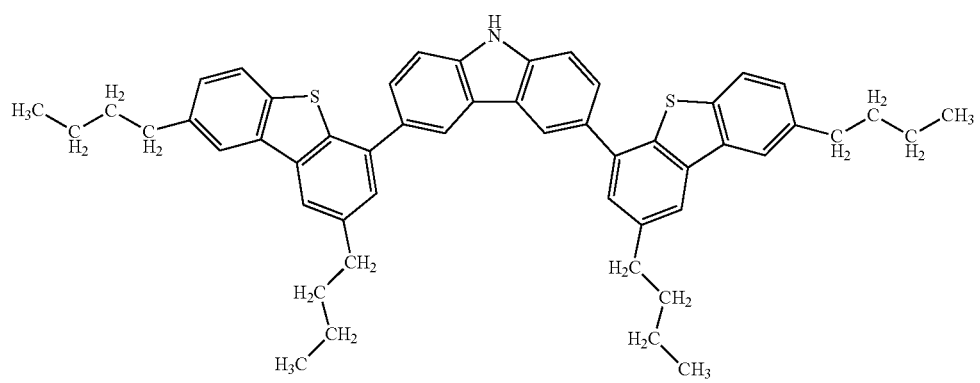
(UT-49)
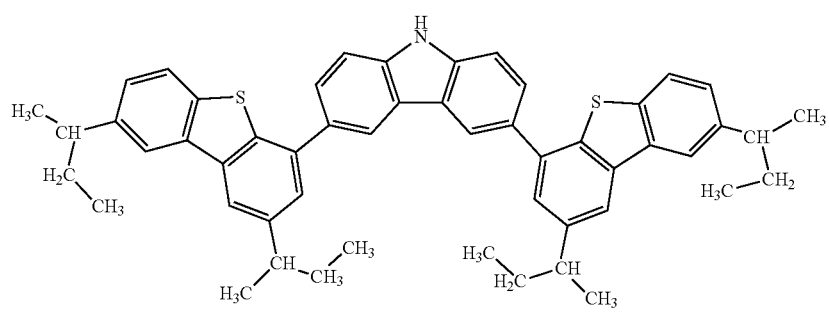
(UT-50)
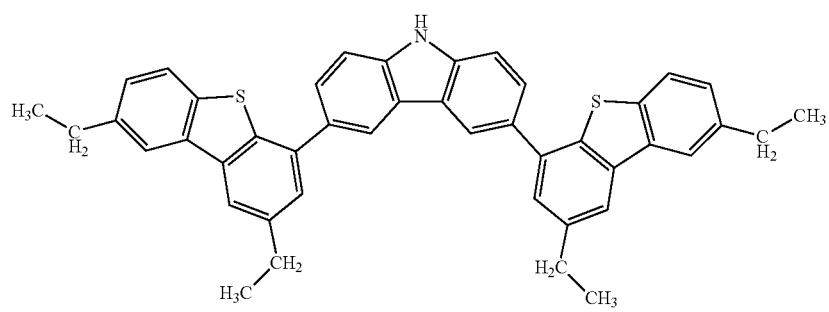

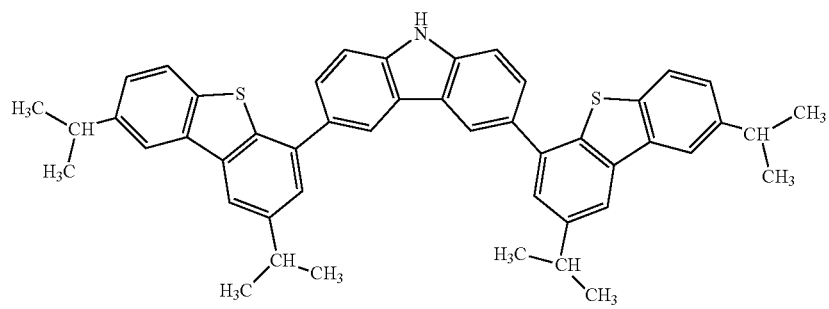
(UT-51)
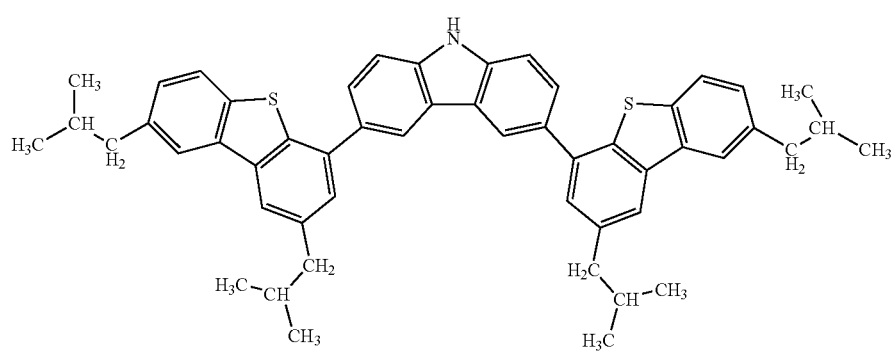
(UT-52)
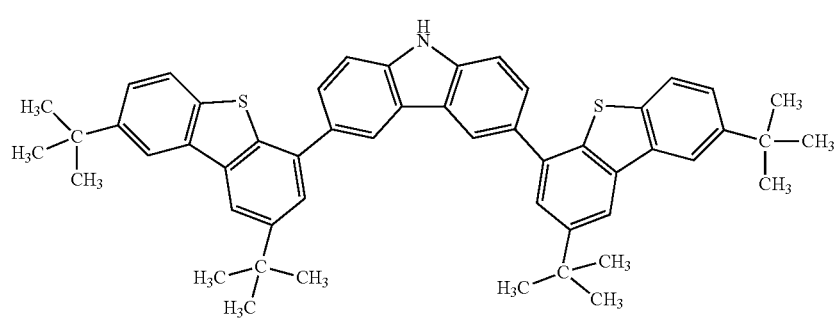
(UT-53)
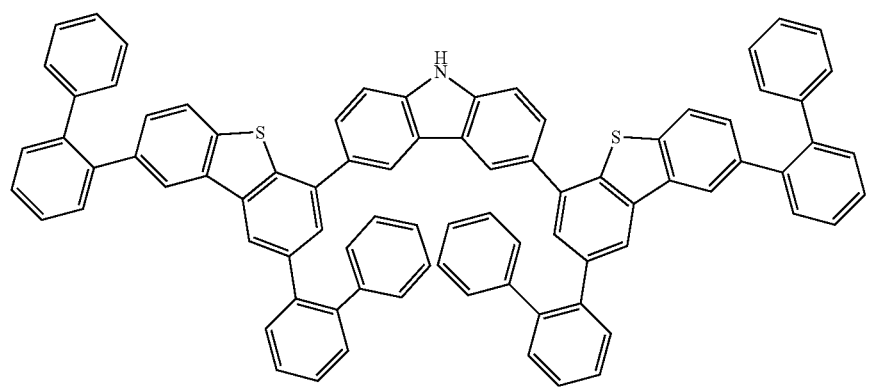
(UT-54)

-continued
(UT-55)
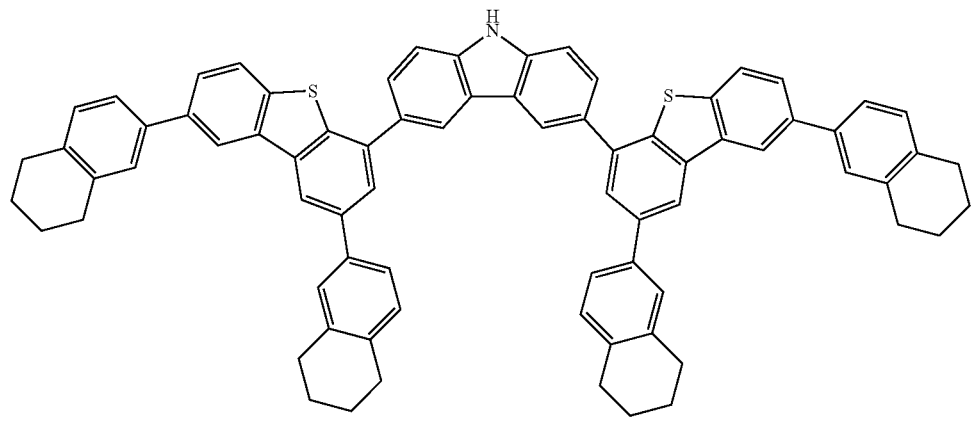
(UT-56)
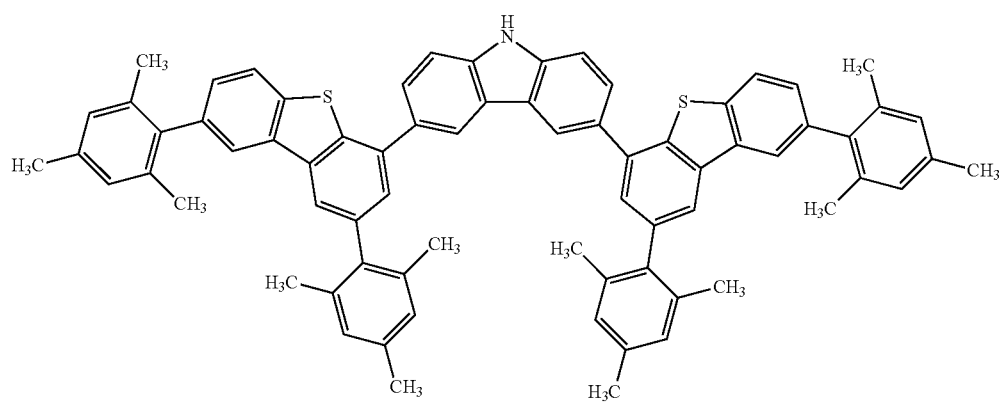
(UT-57)
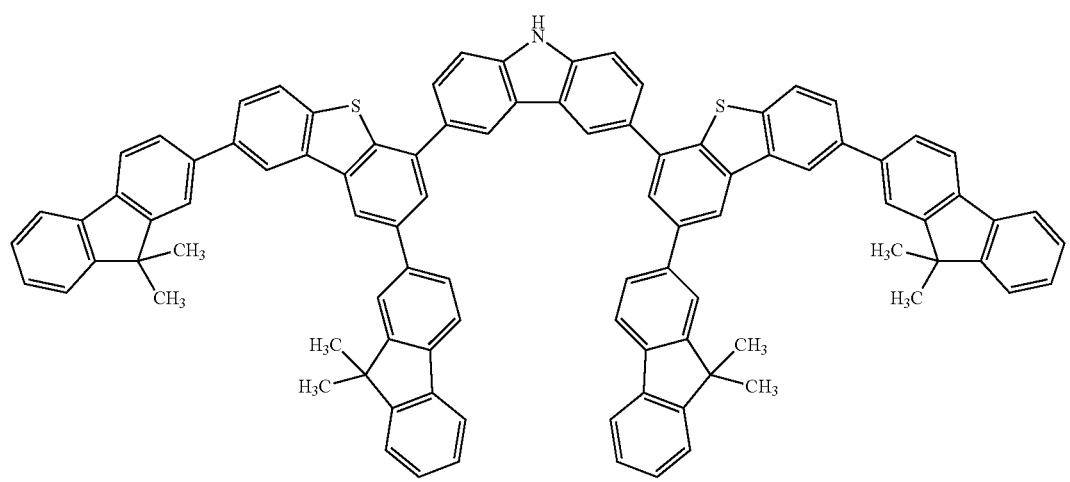
(UT-58)                    (UT-59)
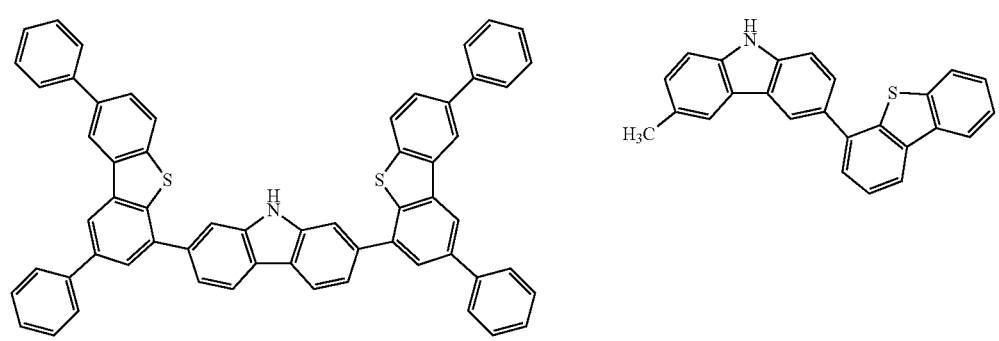

-continued
(UT-60)
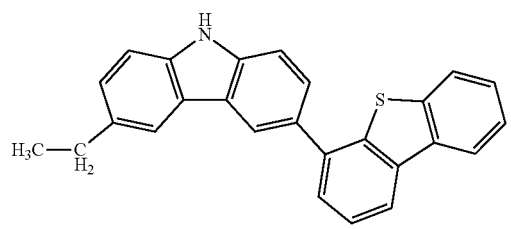
(UT-61)
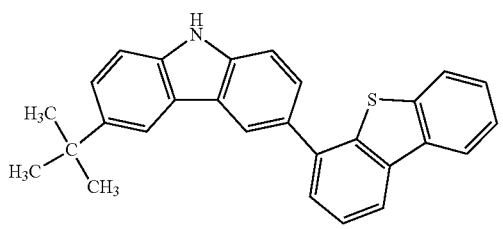
(UT-62)
(UT-63)
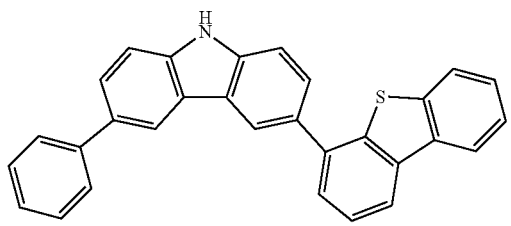
(UT-64)
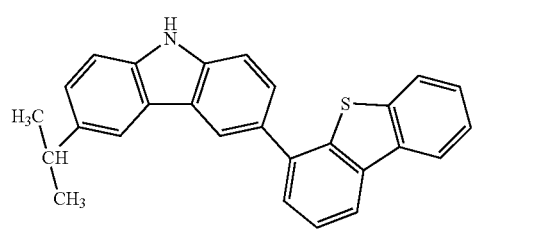
(UT-65)
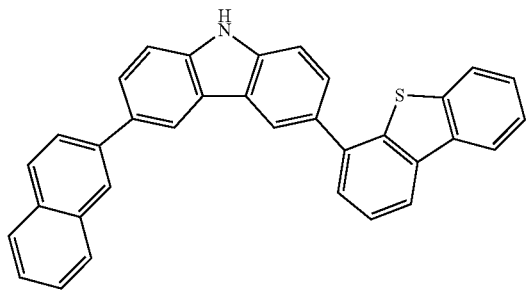
(UT-66)
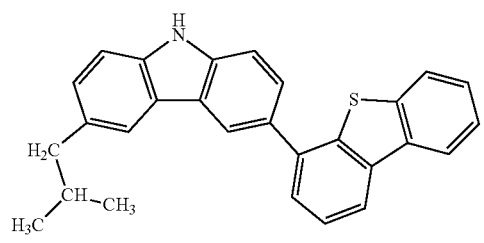
(UT-77)
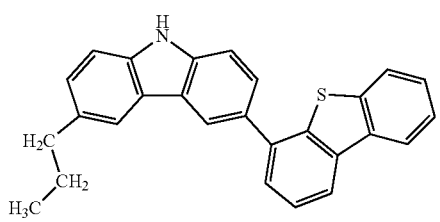
(UT-78)
(UT-79)
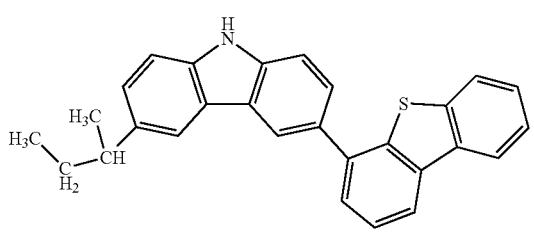
(UT-80)
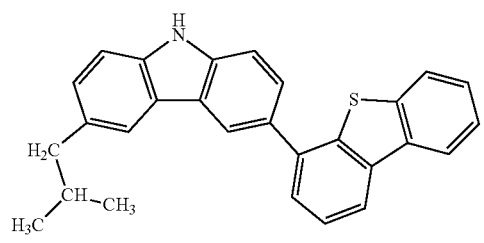
(UT-83)
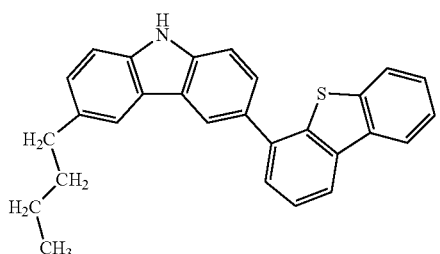

-continued
(UT-84)
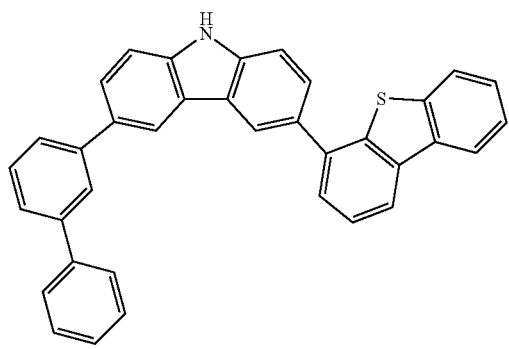
(UT-85)
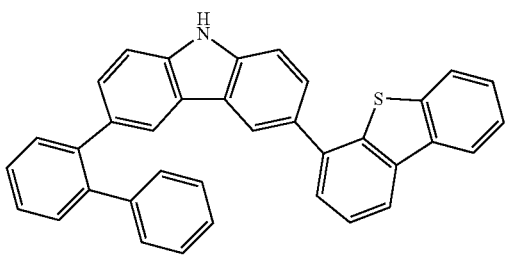
(UT-86)
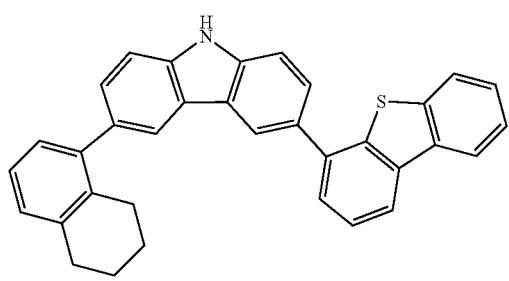
(UT-87)
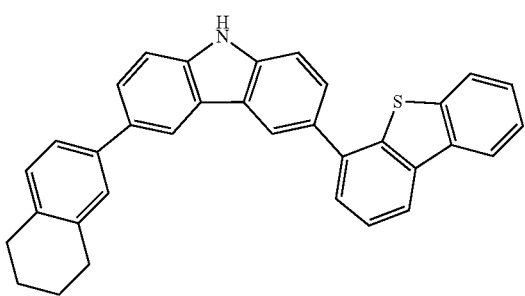
(UT-88)
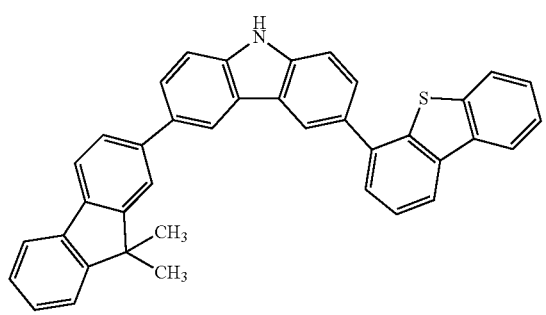
(UT-89)
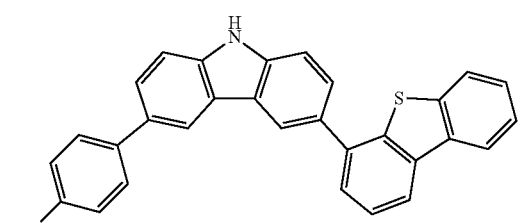
(UT-90)
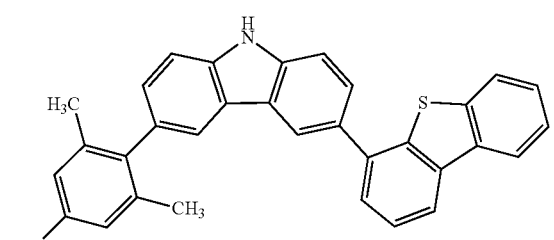
(UT-91)
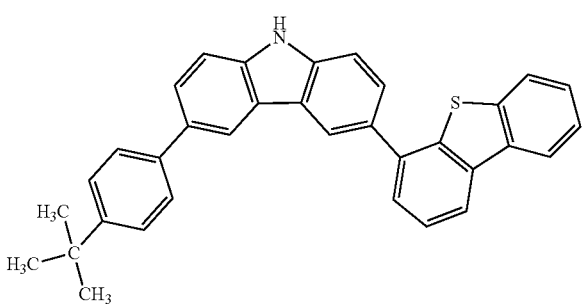

-continued
(UT-92)
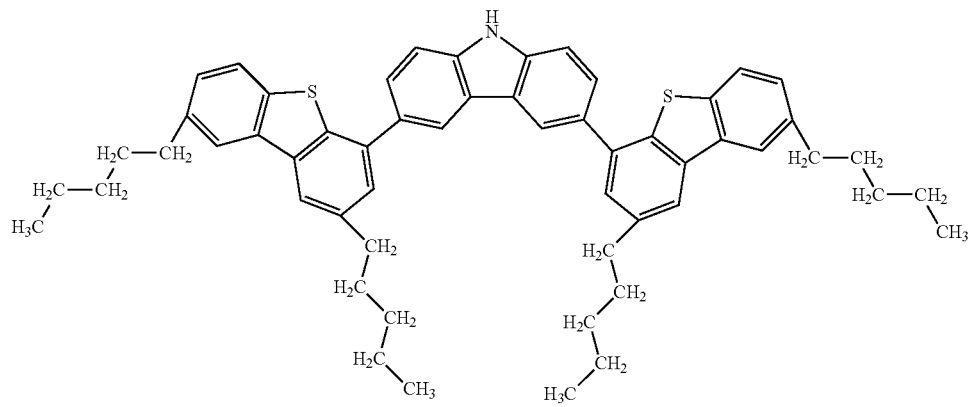
(UT-93)
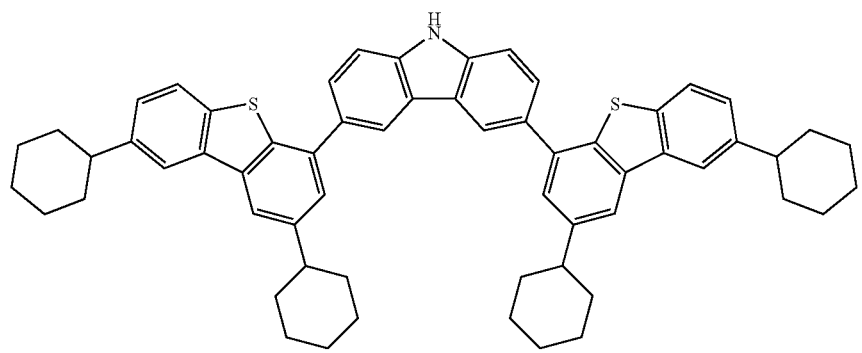
(UT-94)
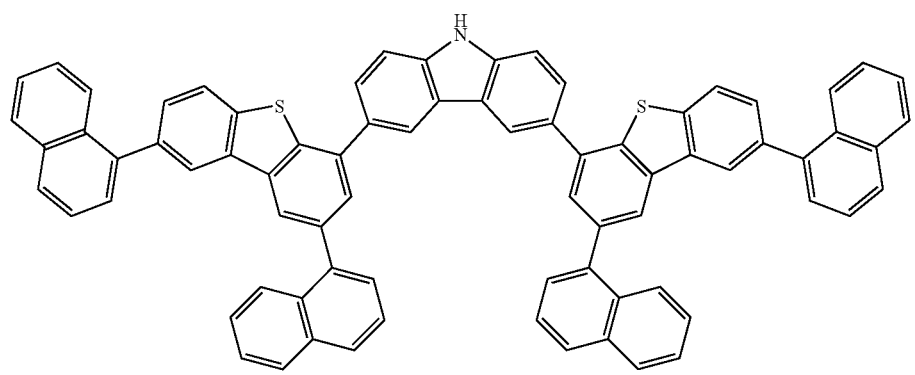
(UT-95)
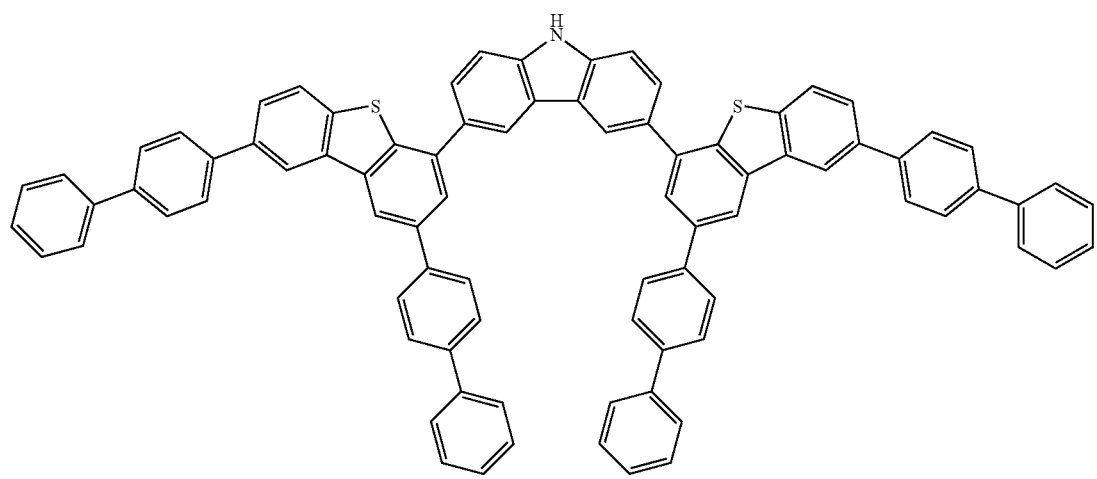

-continued
(UT-96)
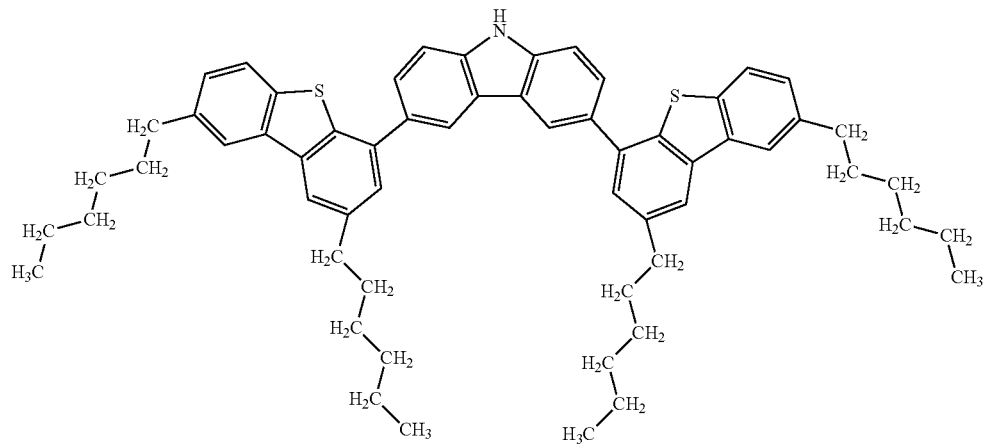
(UT-97)
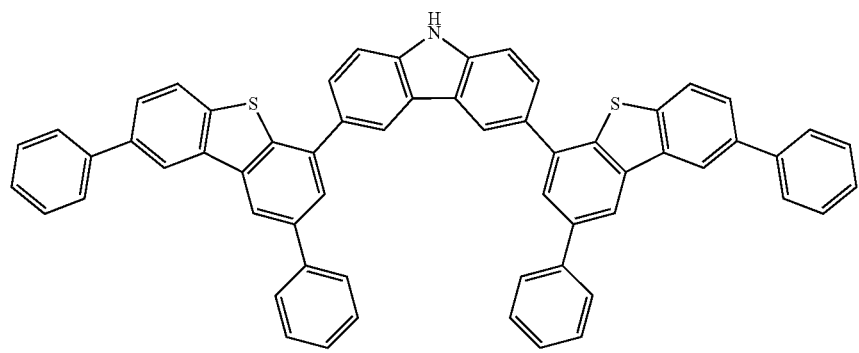
(UT-98)
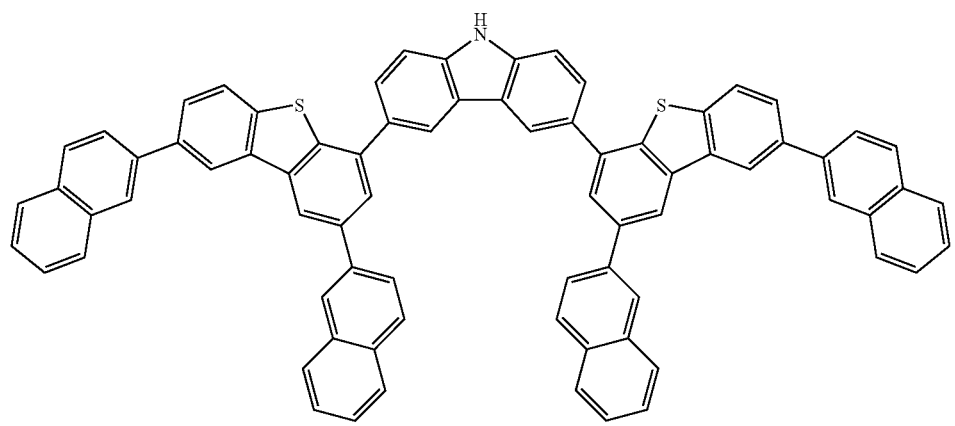
(UT-99)
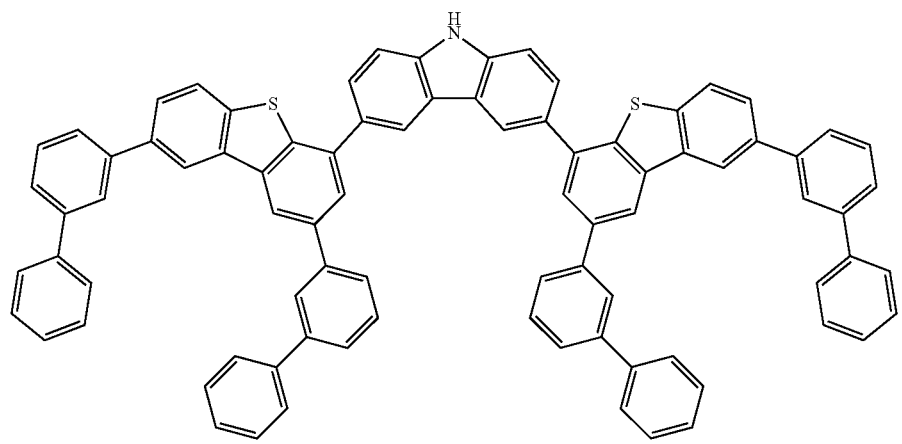

-continued
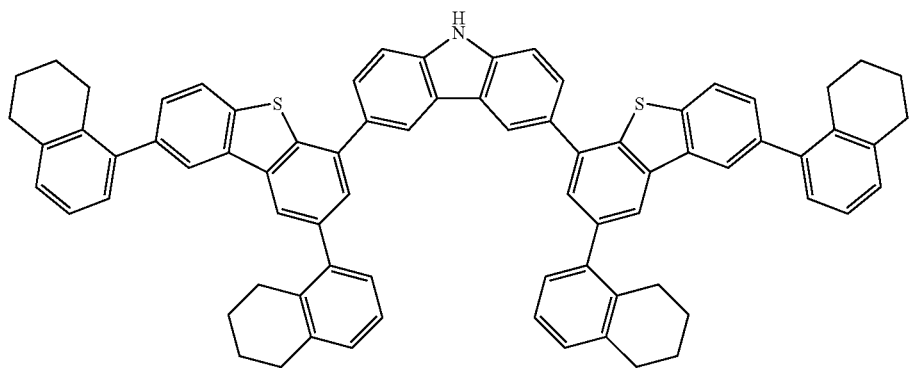
(UT-100)
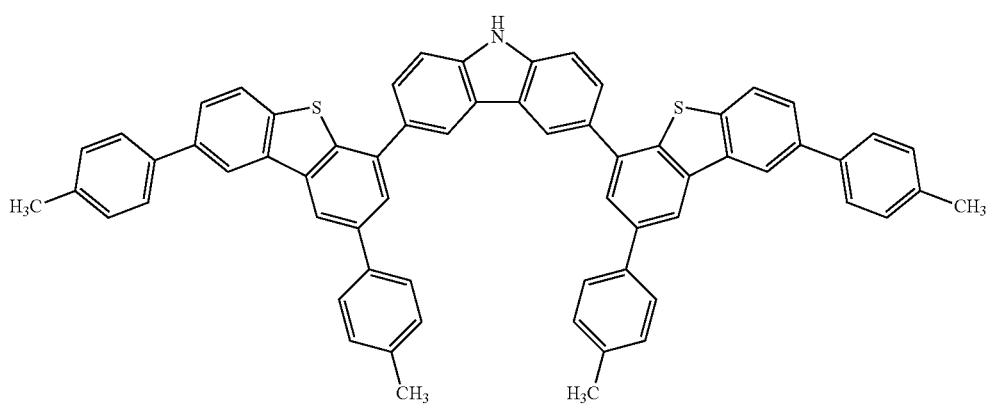
(UT-101)
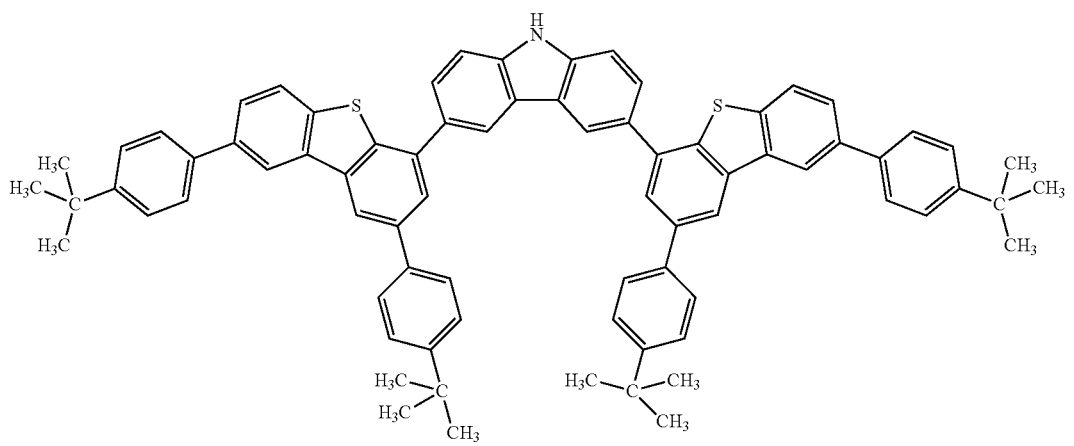
(UT-102)
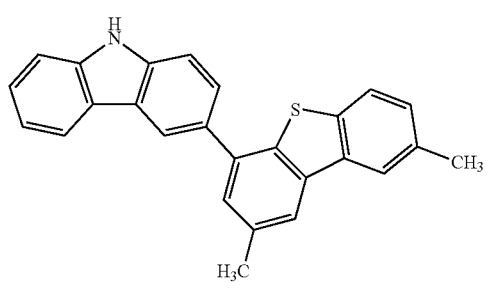
(UT-103)
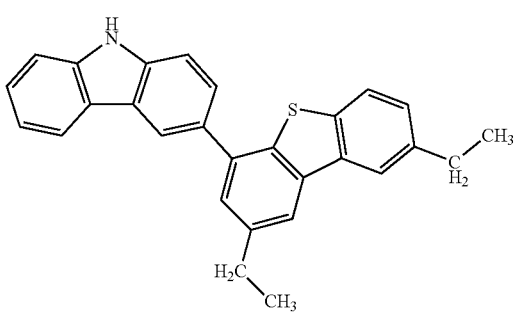
(UT-104)

-continued
(UT-105)
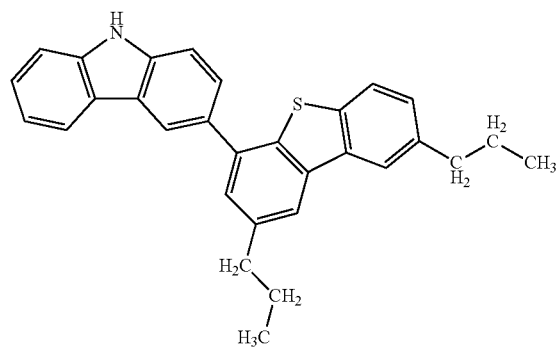
(UT-106)
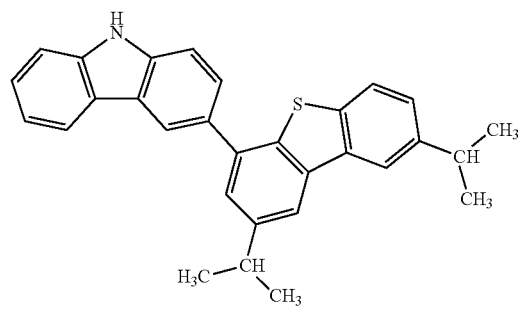
(UT-107)
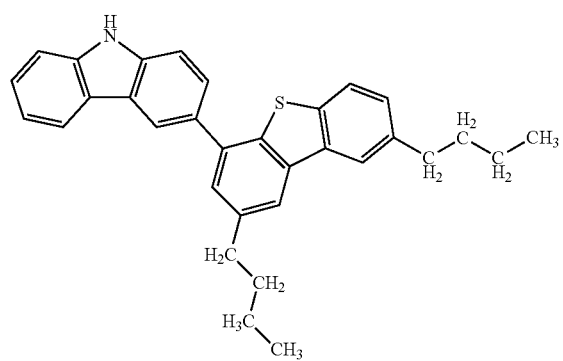
(UT-108)
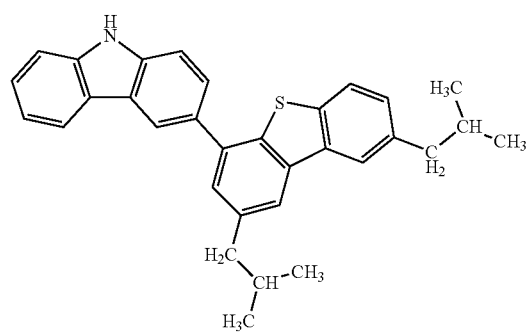
(UT-109)
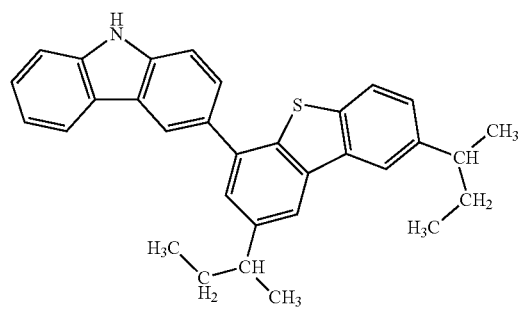
(UT-110)
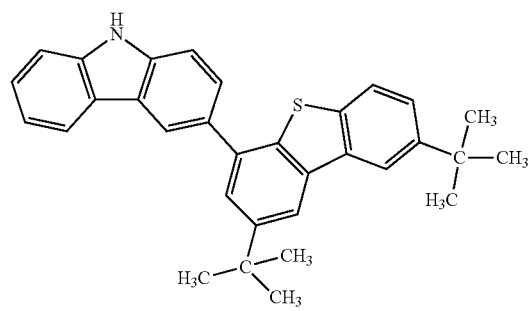
(UT-114)
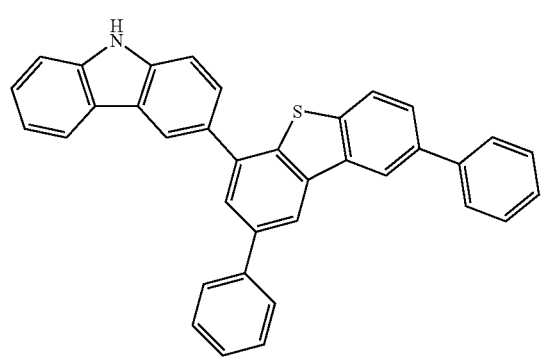
(UT-115)
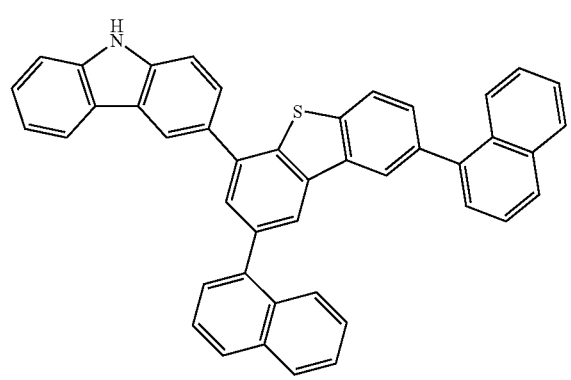

-continued
(UT-116)
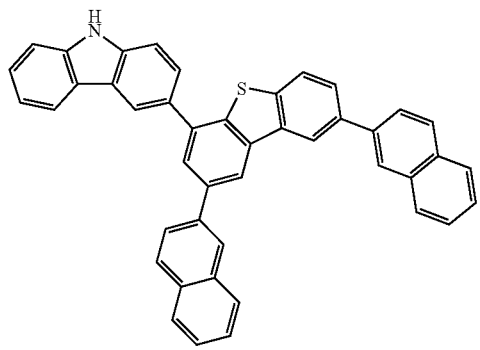
(UT-117)
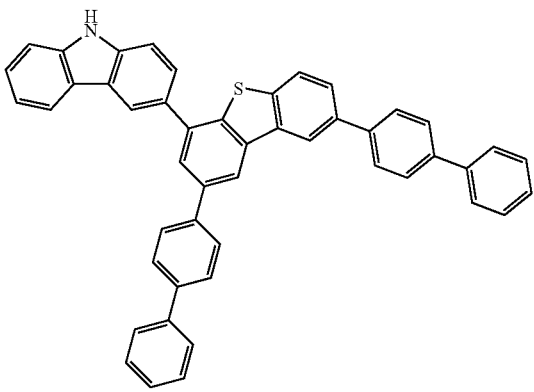
(UT-118)
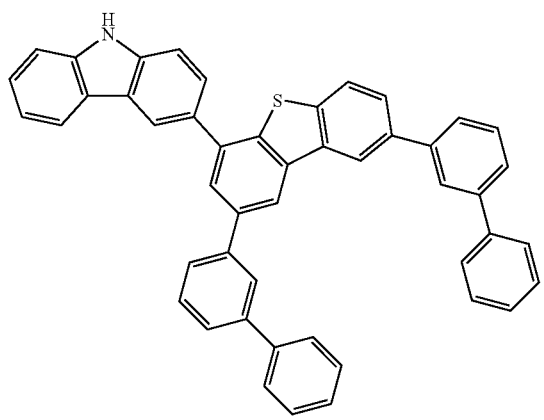
(UT-119)
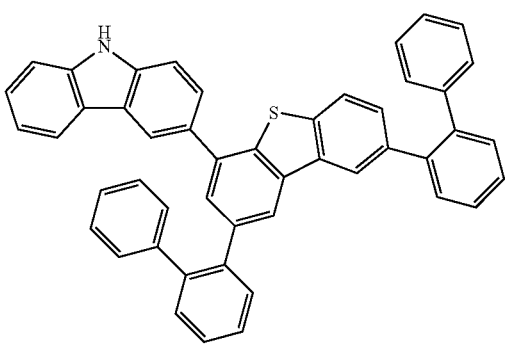
(UT-120)
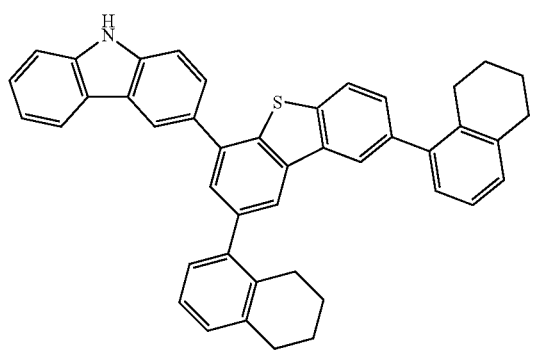
(UT-121)
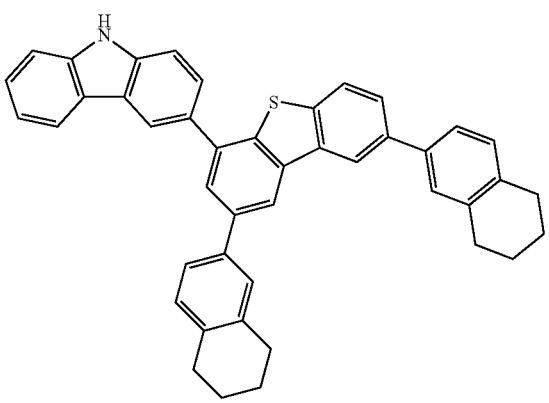
(UT-122)
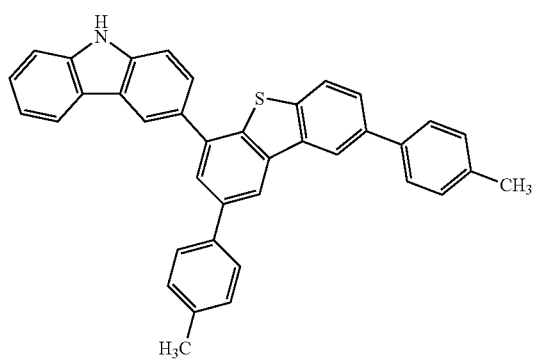
(UT-123)
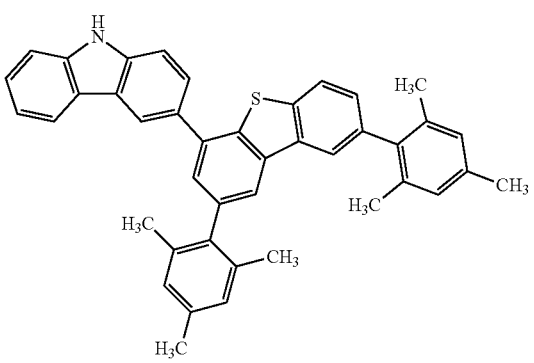

-continued
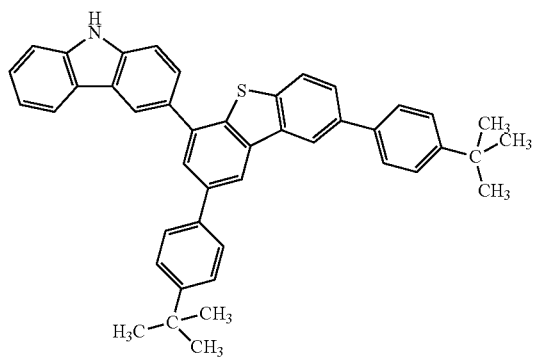
(UT-124)
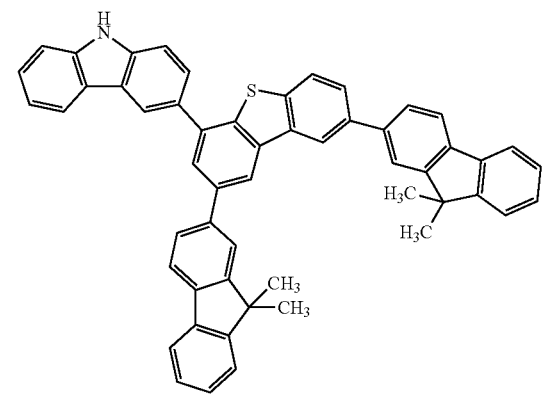
(UT-125)
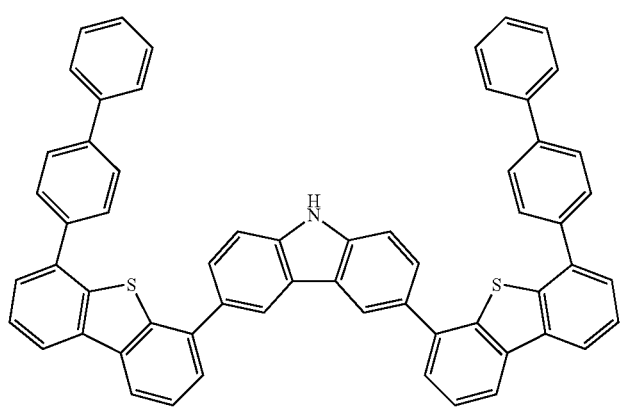
(UT-126)
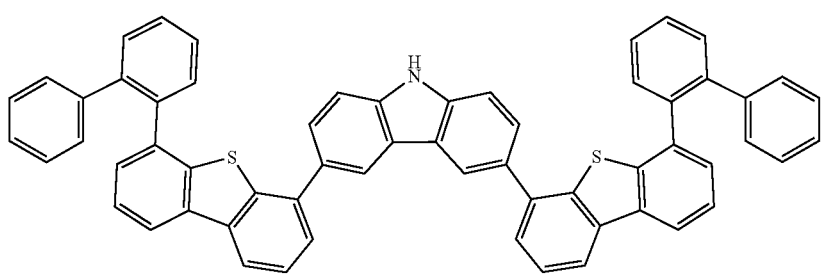
(UT-127)
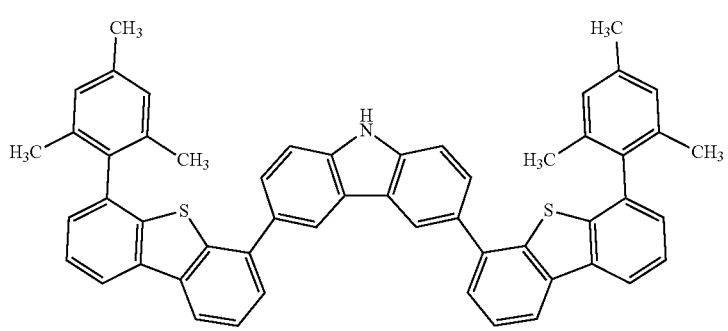
(UT-128)

-continued
(UT-129)
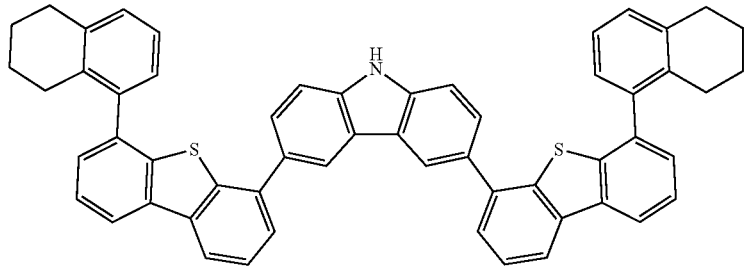
(UT-130)
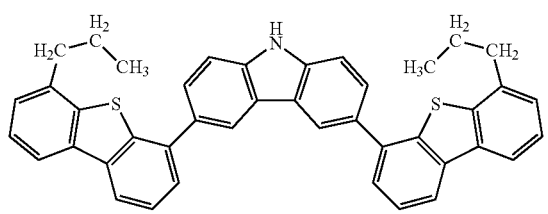
(UT-131)
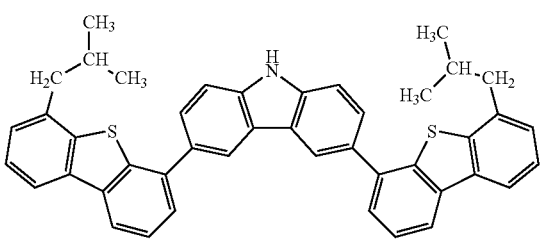
(UT-132)
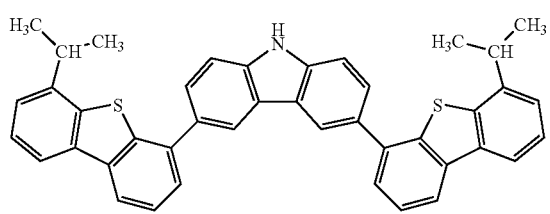
(UT-133)
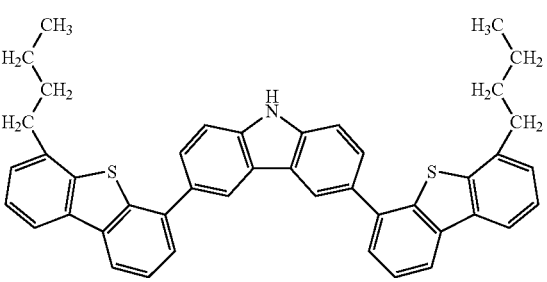
(UT-135)
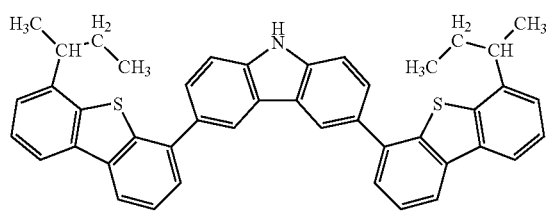
(UT-137)
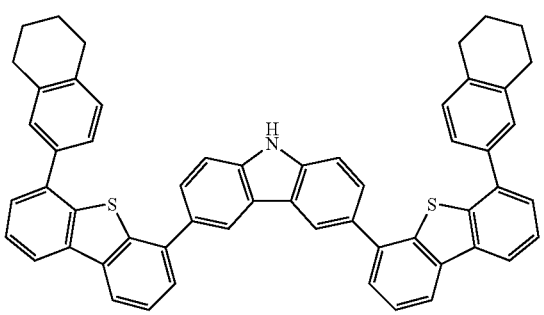
(UF-1)
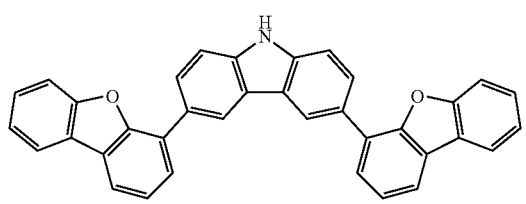
(UF-2)
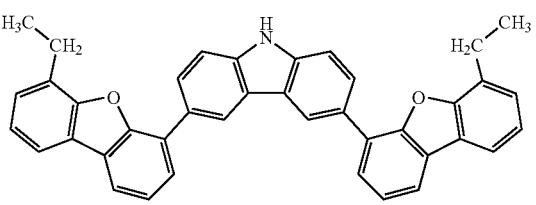
(UF-3)
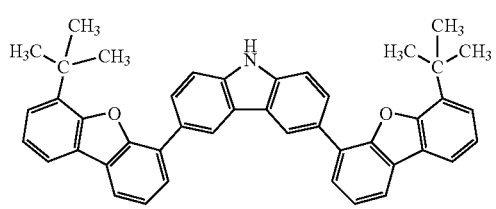
(UF-4)
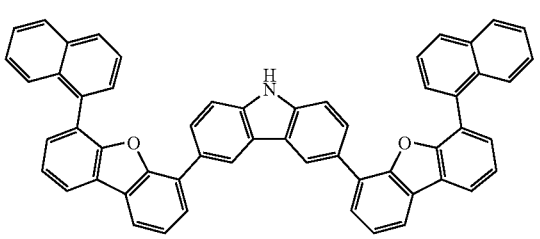

-continued
(UF-5)
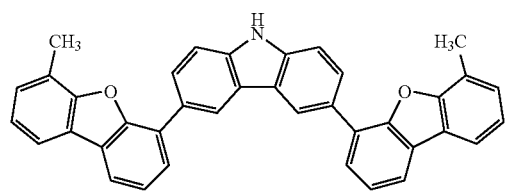
(UF-7)
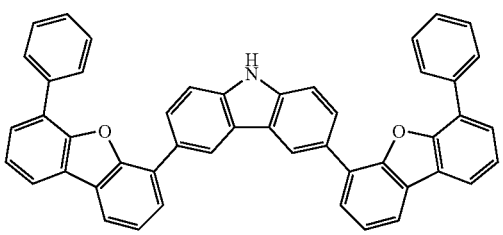
(UF-8)
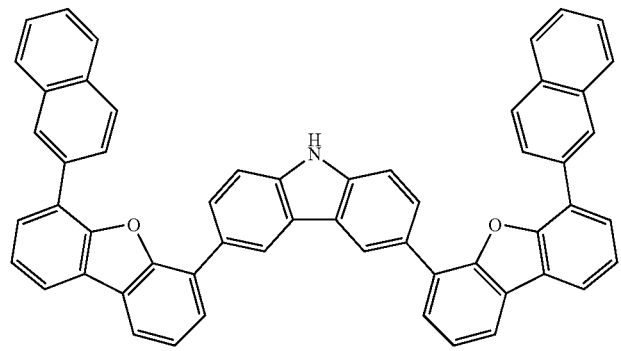
(UF-9)
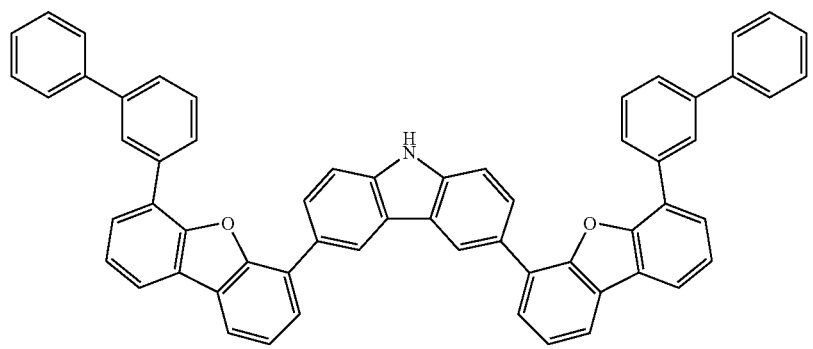
(UF-10)
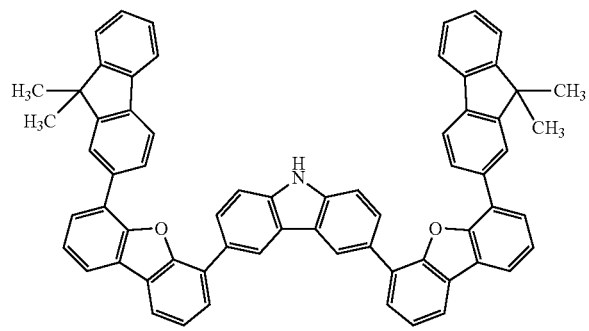
(UF-11)
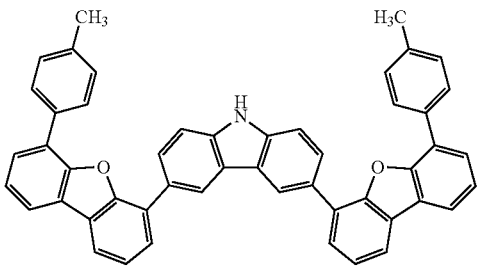
(UF-12)
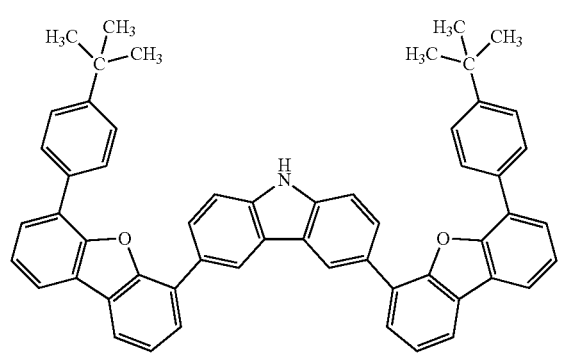
(UF-13)
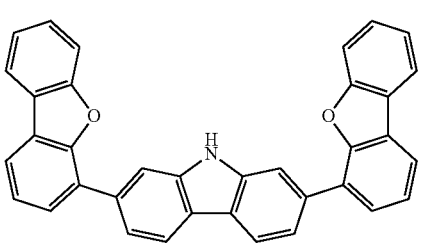

-continued
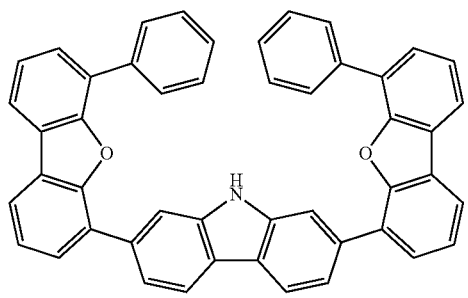
(UF-14)
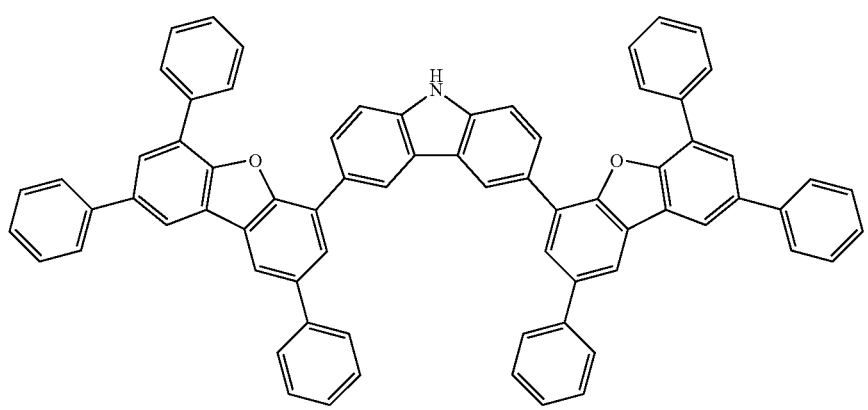
(UF-15)
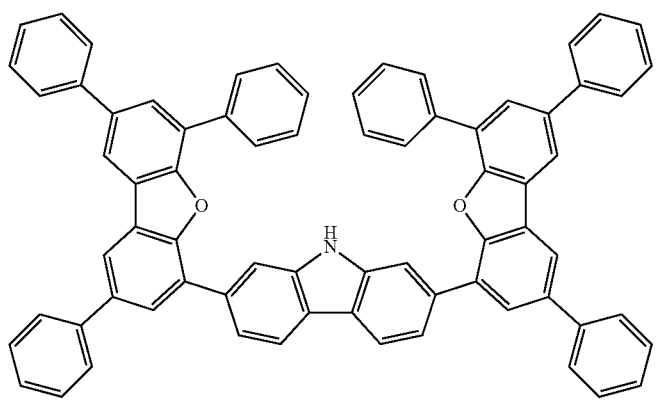
(UF-16)
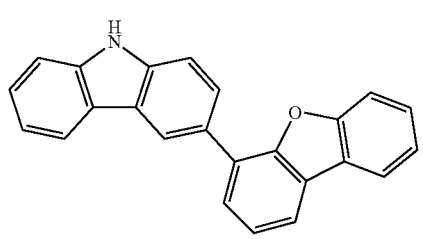
(UF-17)
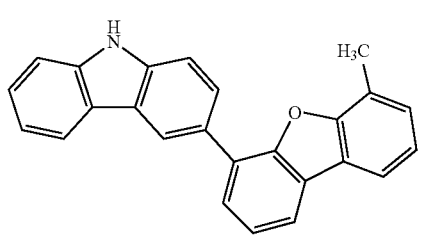
(UF-18)
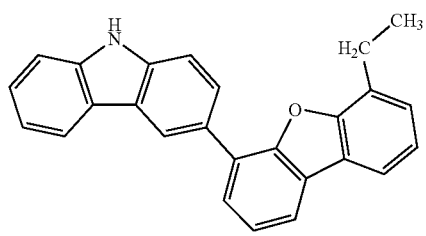
(UF-19)
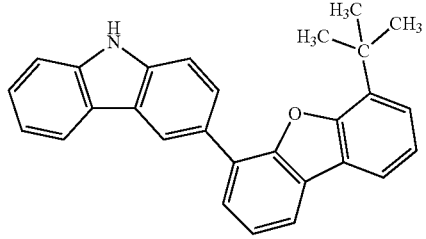
(UF-21)

393                                     394
-continued
(UF-22) 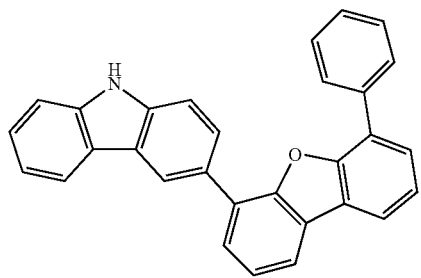
(UF-23) 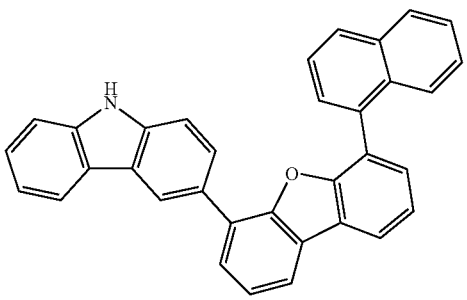
(UF-24) 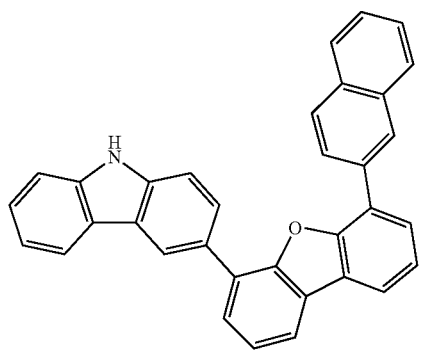
(UF-25) 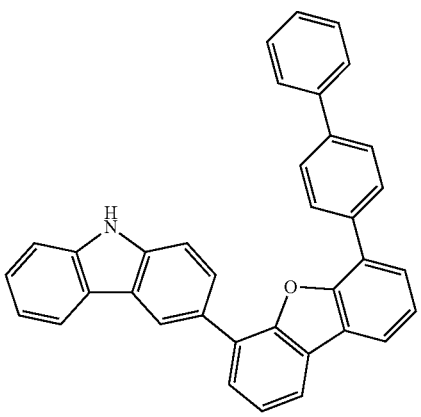
(UF-26) 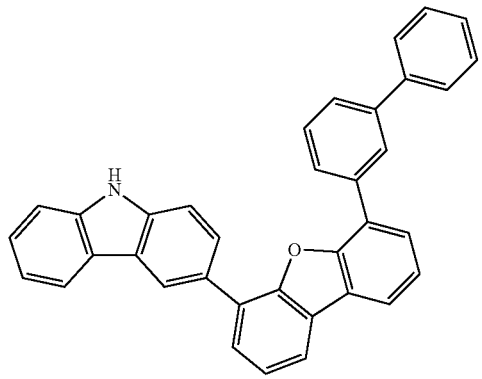
(UF-27) 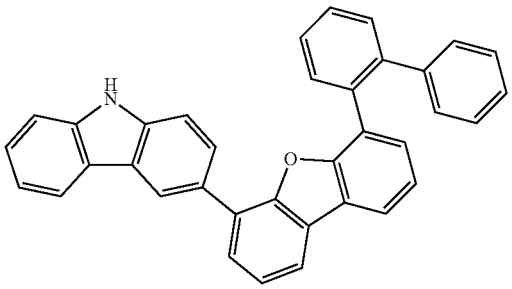
(UF-28) 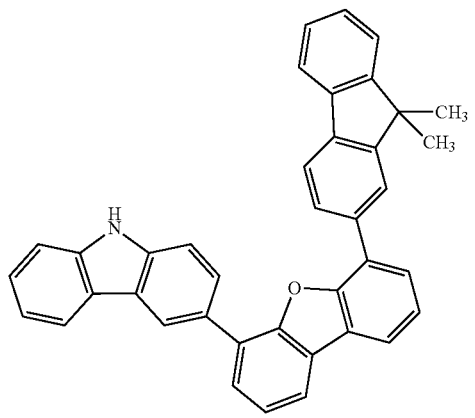
(UF-29) 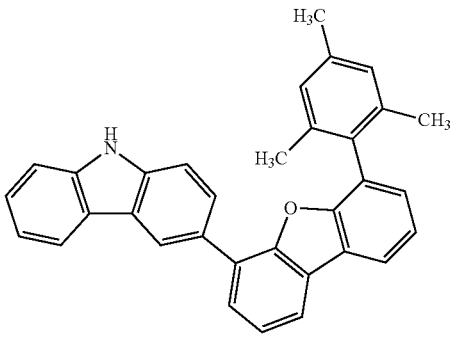

-continued
(UF-30)
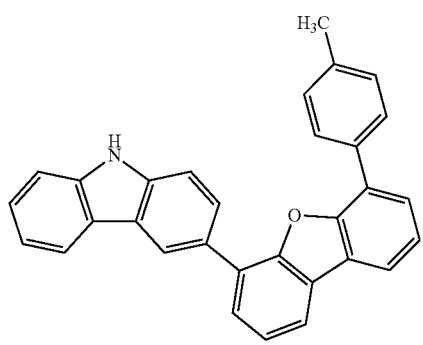
(UF-31)
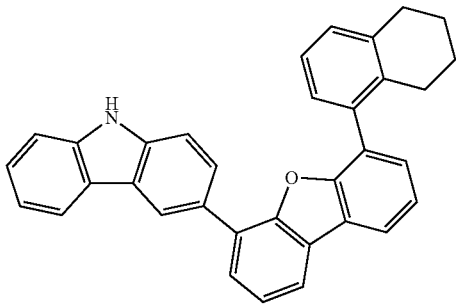
(UF-32)
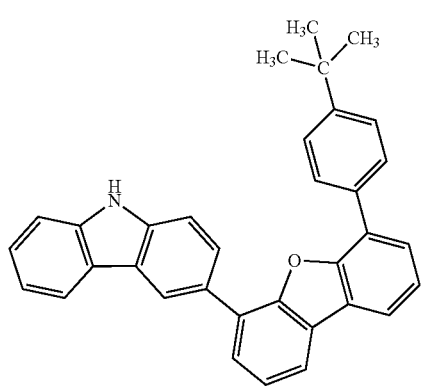
(UF-33)
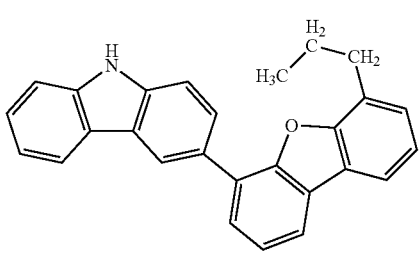
(UF-35)
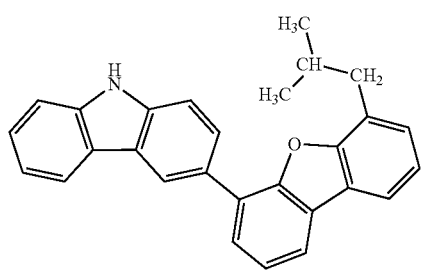
(UF-36)
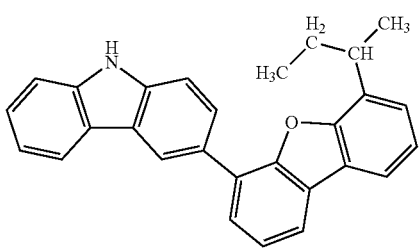
(UF-37)
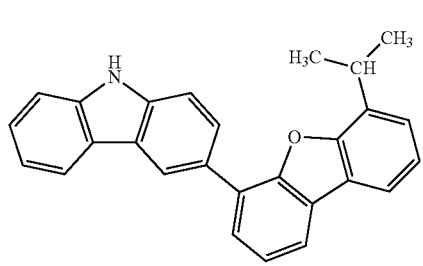
(UF-39)
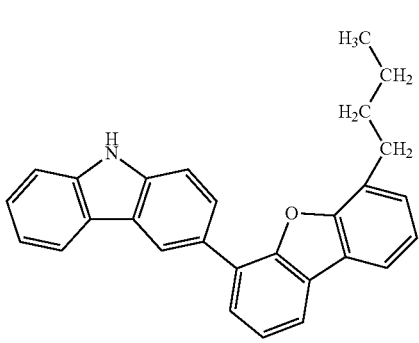

-continued
(UF-40)
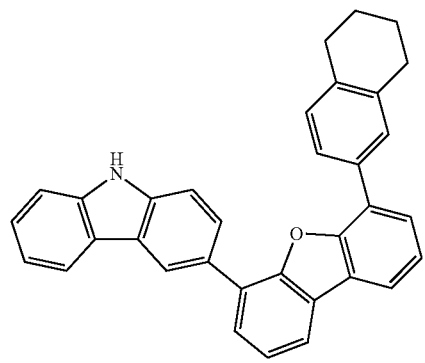
(UF-41)
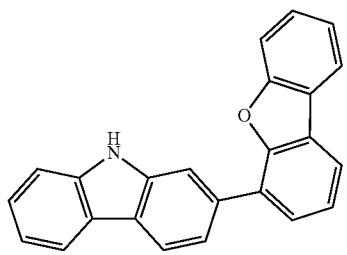
(UF-42)
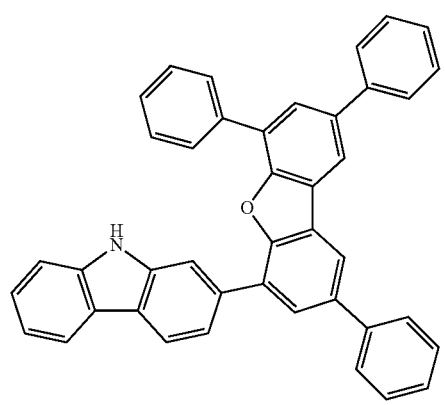
(UF-43)
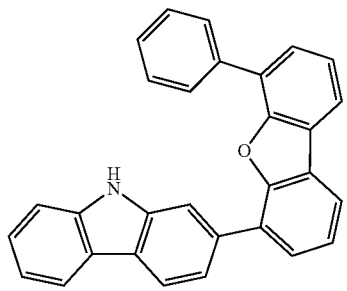
(UF-44)
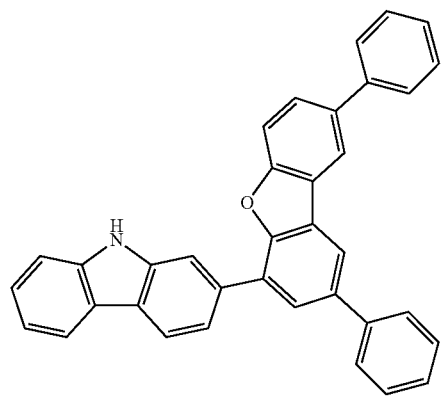
(UF-45)
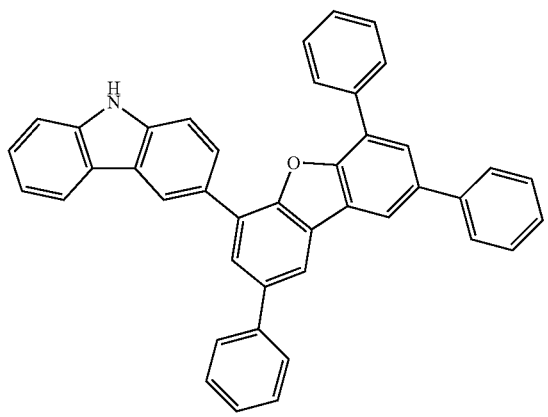
(UF-46)
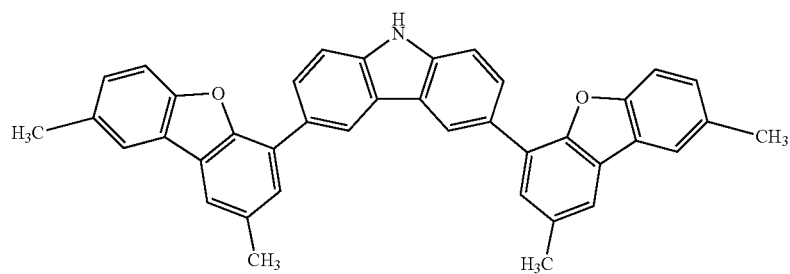

-continued
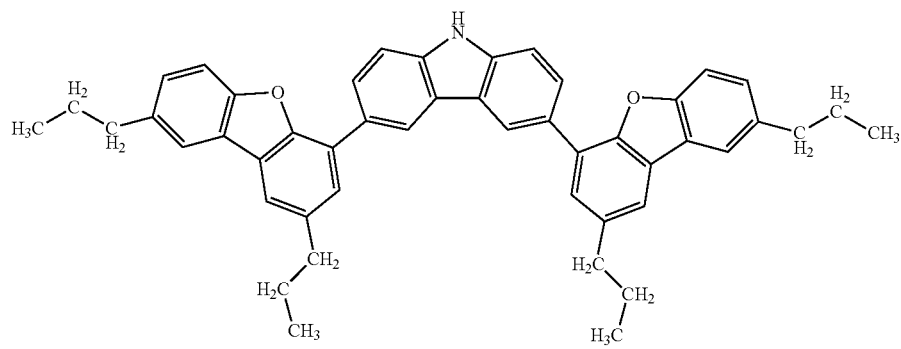
(UF-47)
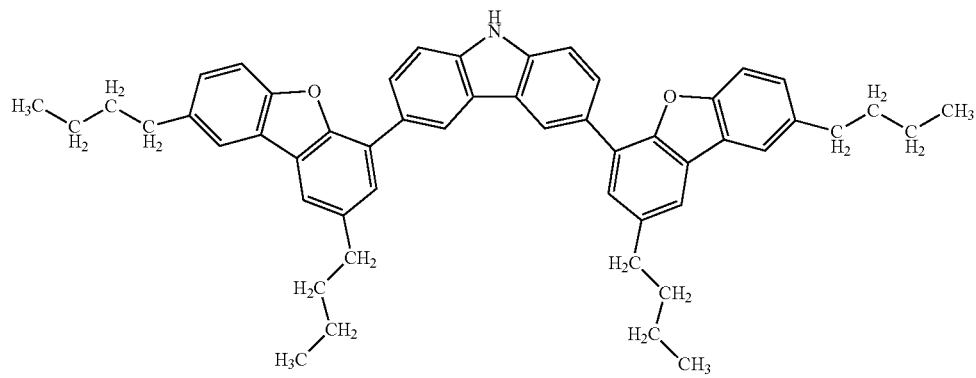
(UF-48)
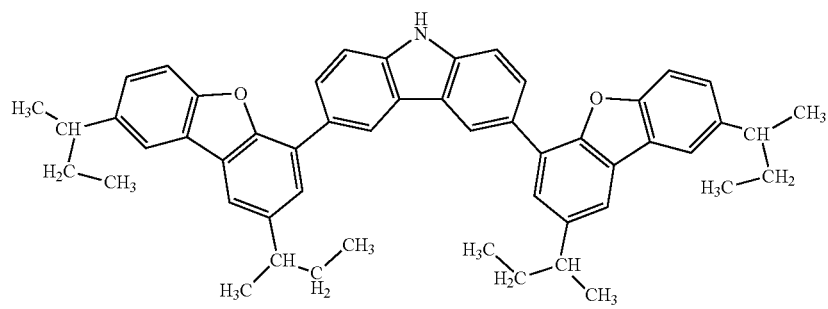
(UF-49)
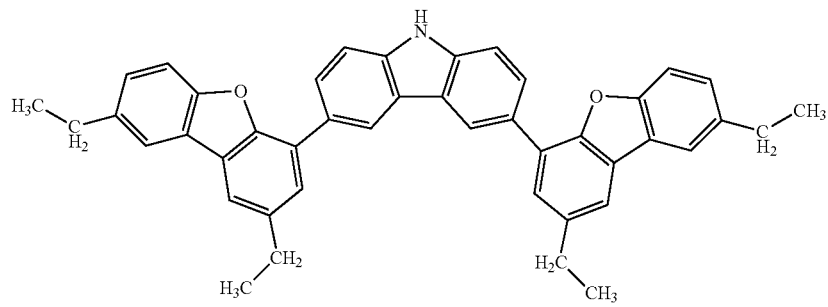
(UF-50)
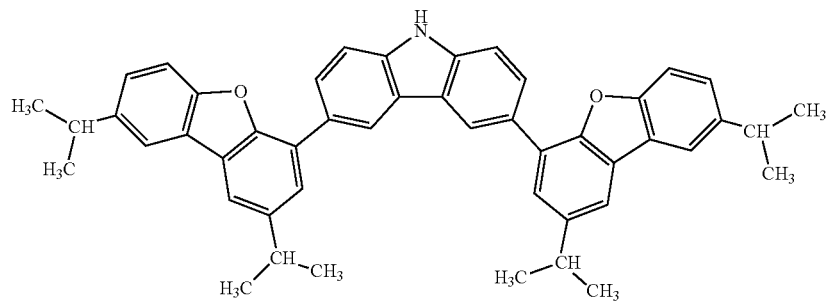
(UF-51)

-continued
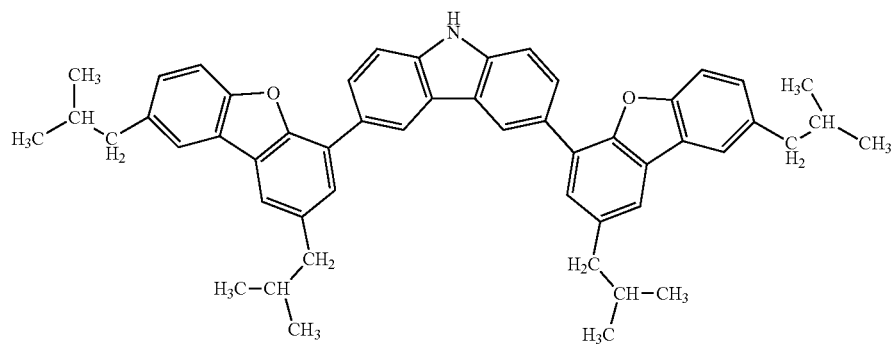
(UF-52)
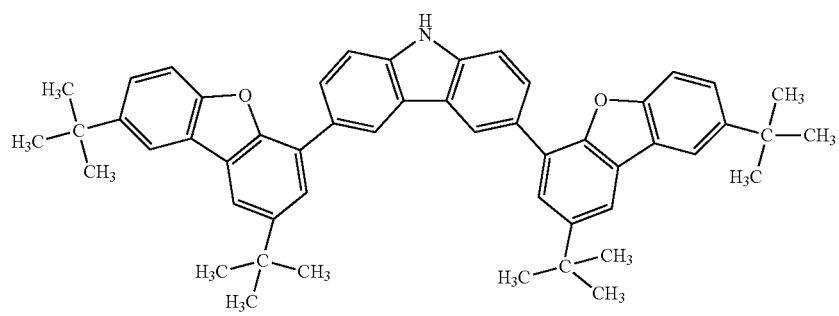
(UF-53)
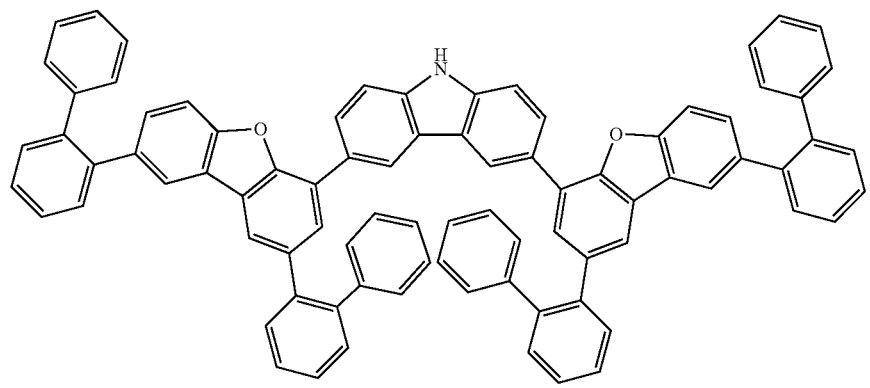
(UF-54)
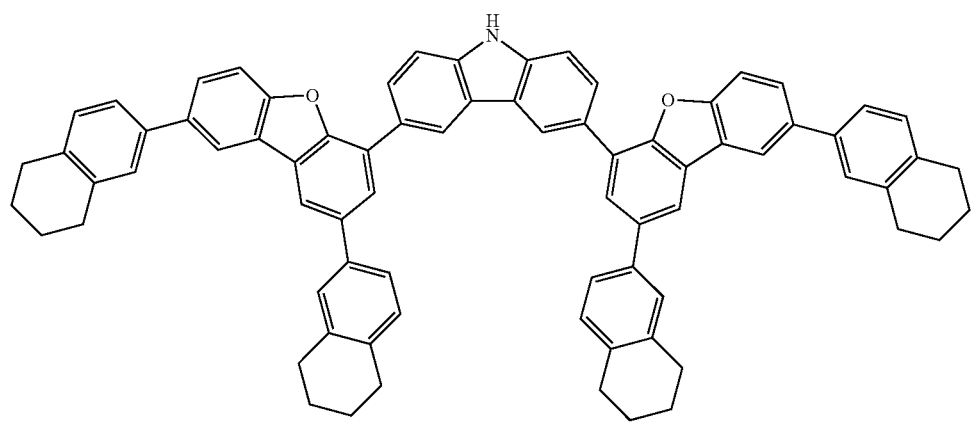
(UF-55)

-continued
(UF-56)
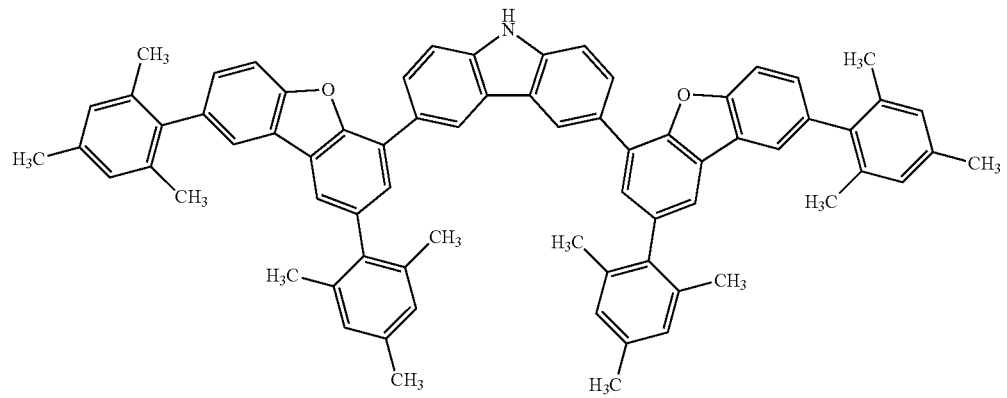
(UF-57)
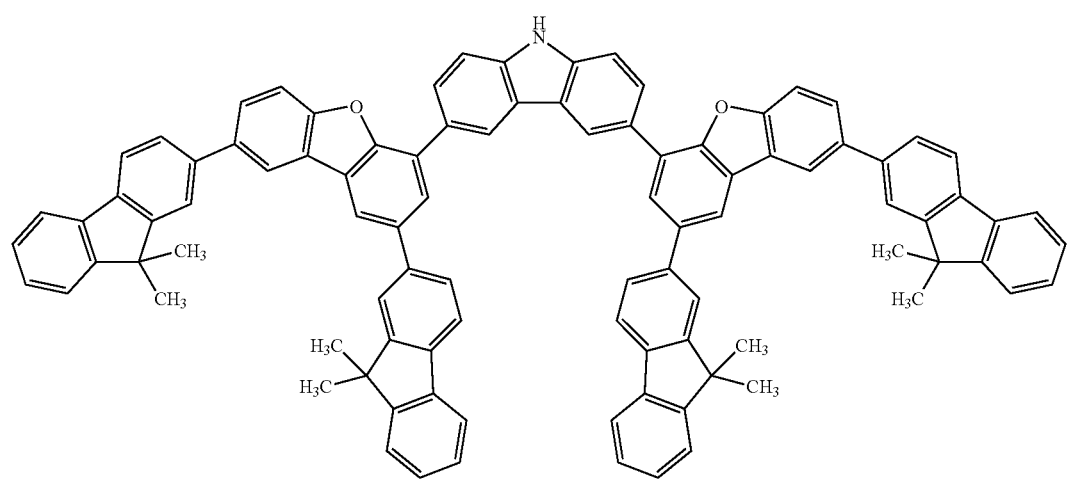
(UF-58)
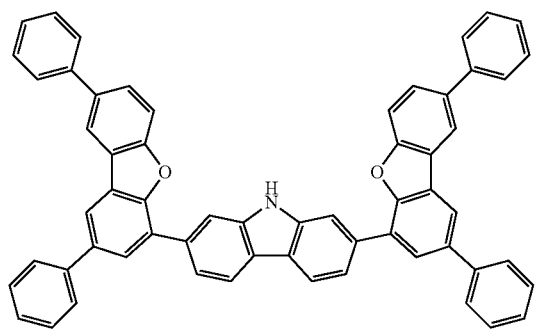
(UF-59)
(UF-60)
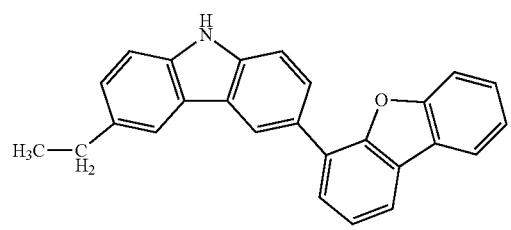
(UF-61)
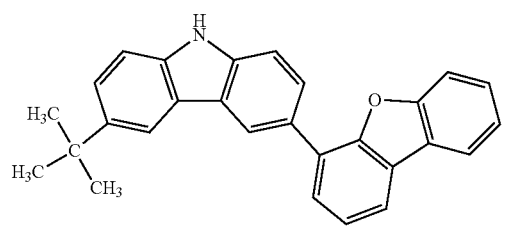

-continued
(UF-62)
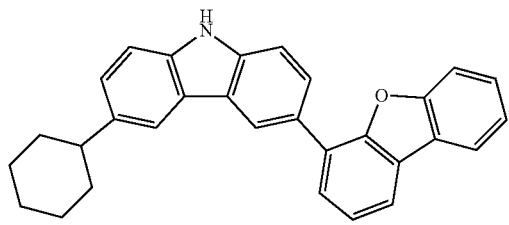
(UF-63)
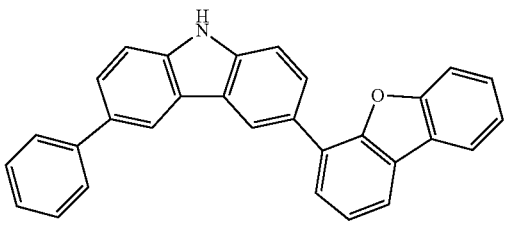
(UF-64)
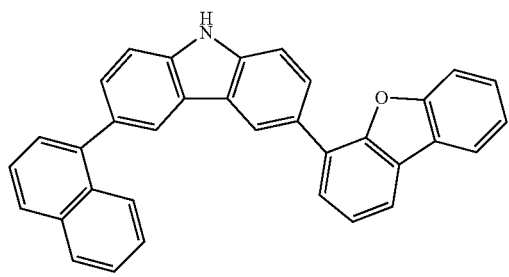
(UF-65)
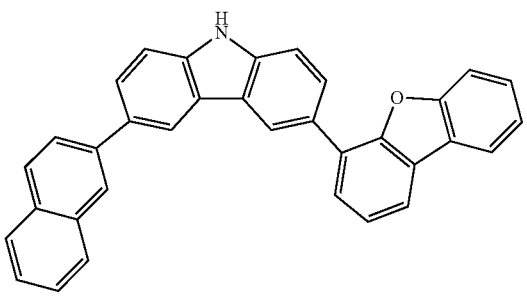
(UF-66)
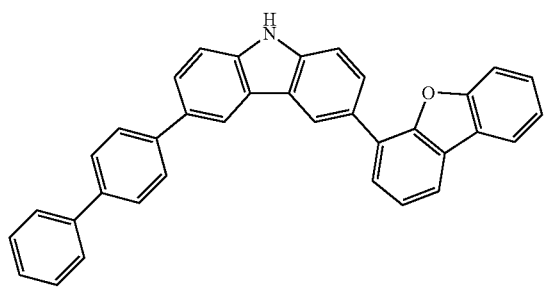
(UF-77)
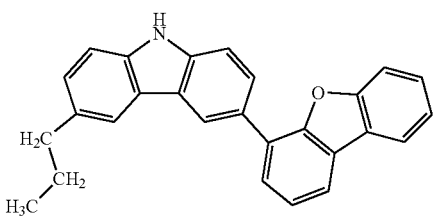
(UF-78)
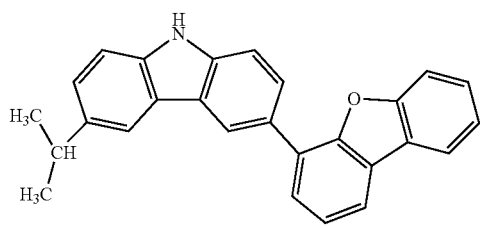
(UF-79)
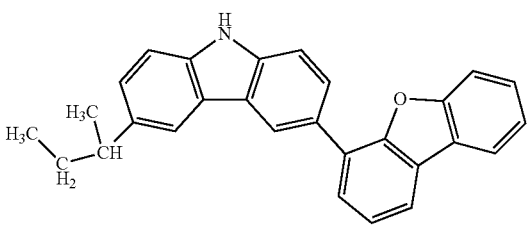
(UF-80)
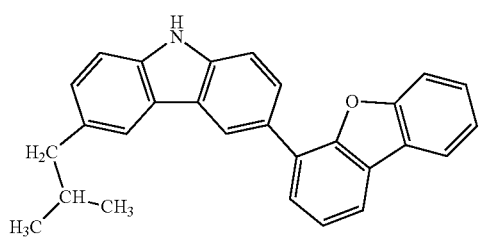
(UF-83)
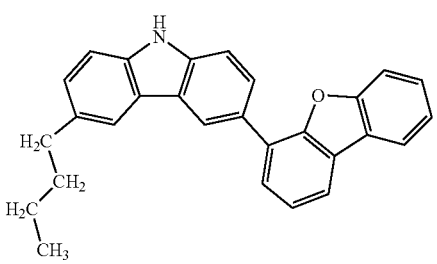

-continued
(UF-84)
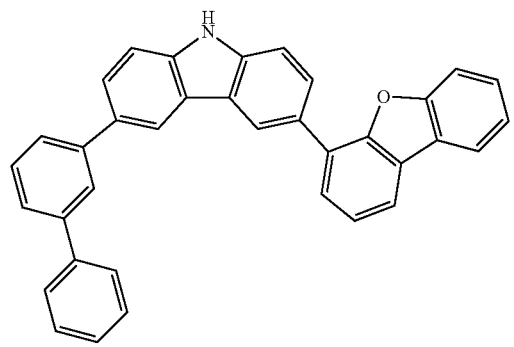
(UF-85)
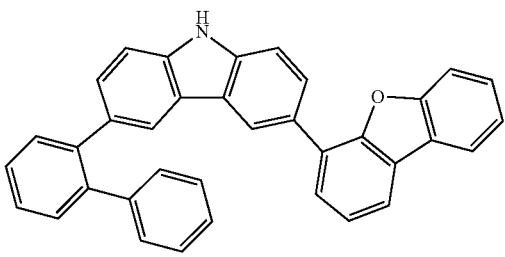
(UF-86)
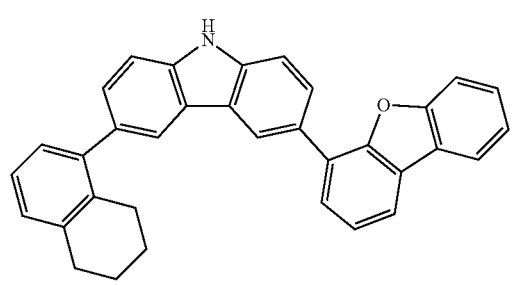
(UF-87)
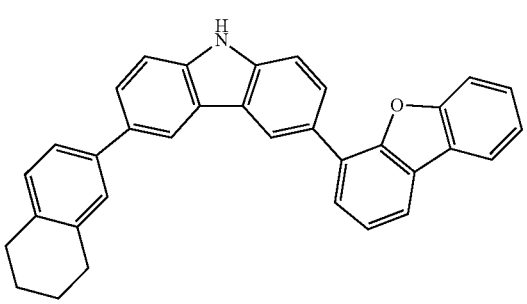
(UF-88)
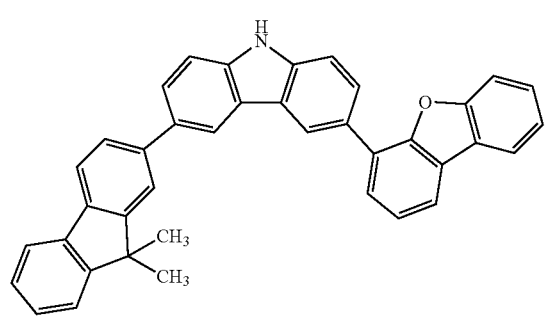
(UF-89)
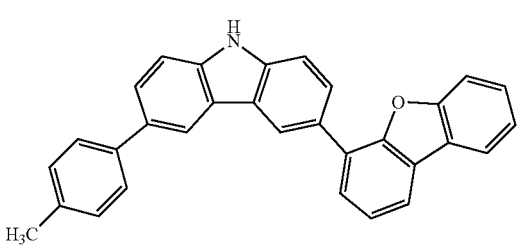
(UF-90)
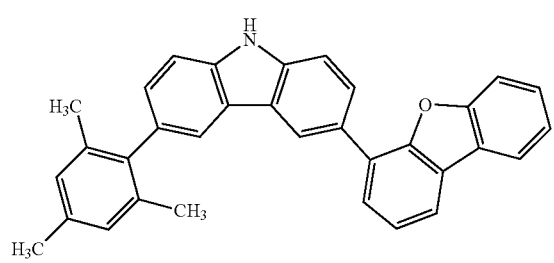
(UF-91)
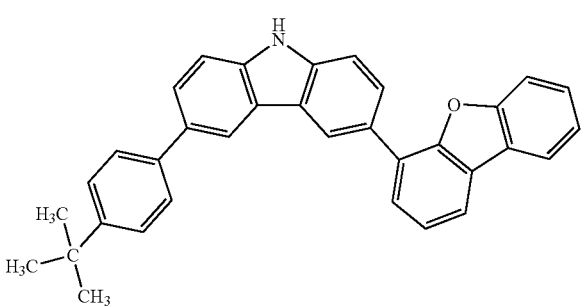

(UF-94)
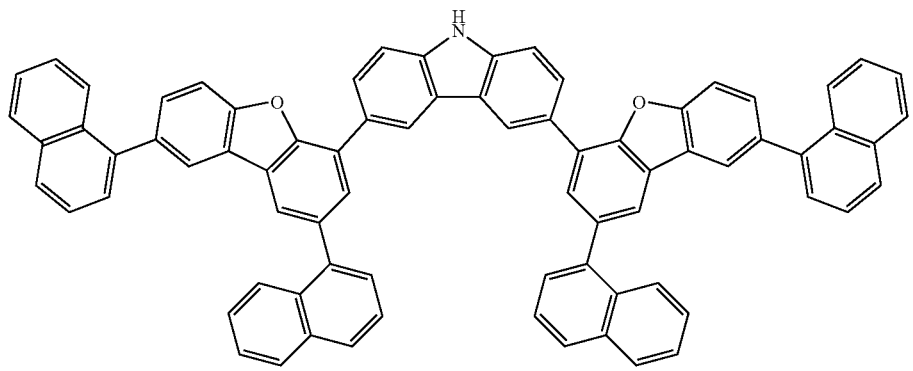
(UF-95)
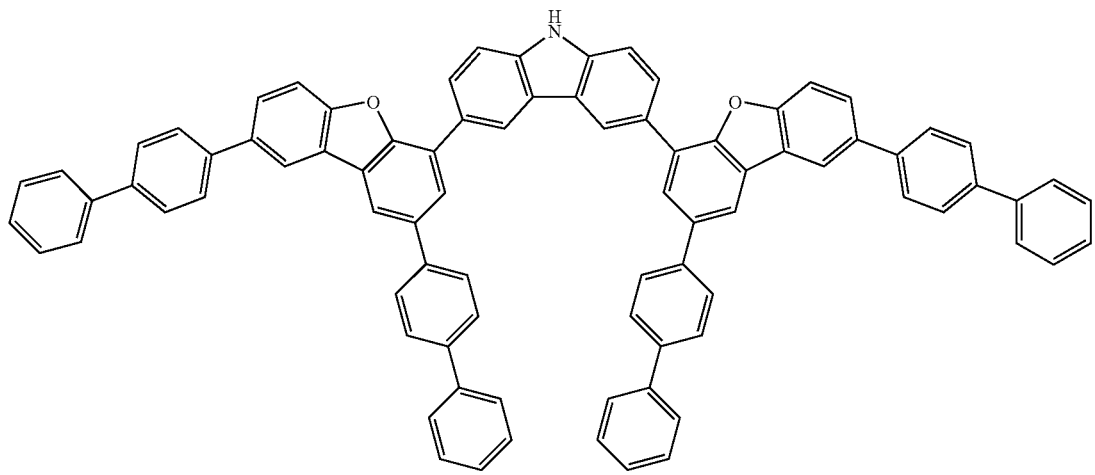
(UF-97)
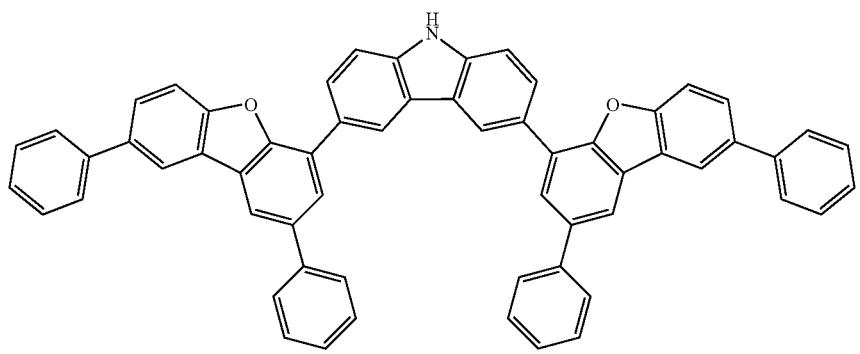
(UF-98)
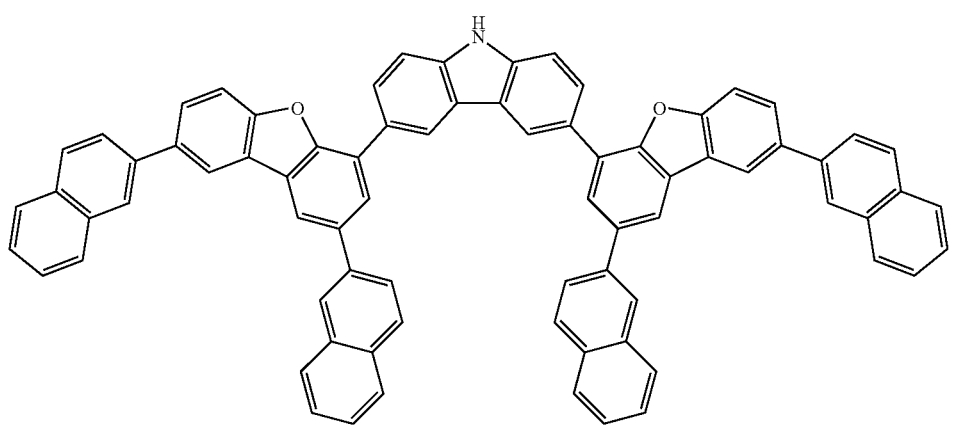

-continued
(UF-99)
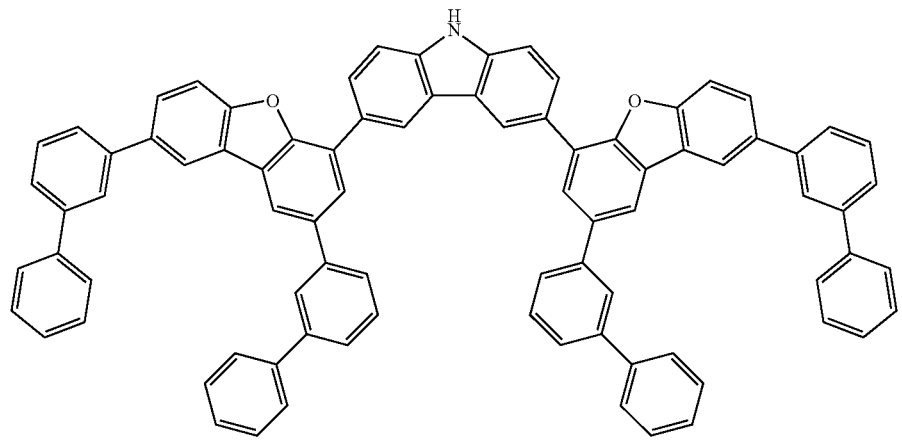
(UF-100)
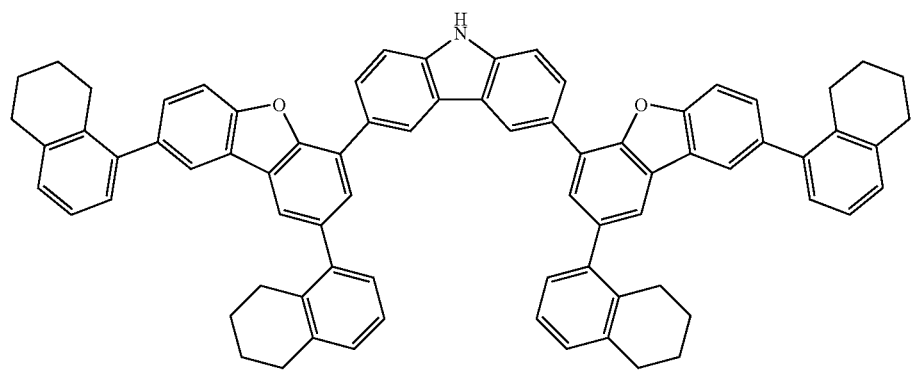
(UF-101)
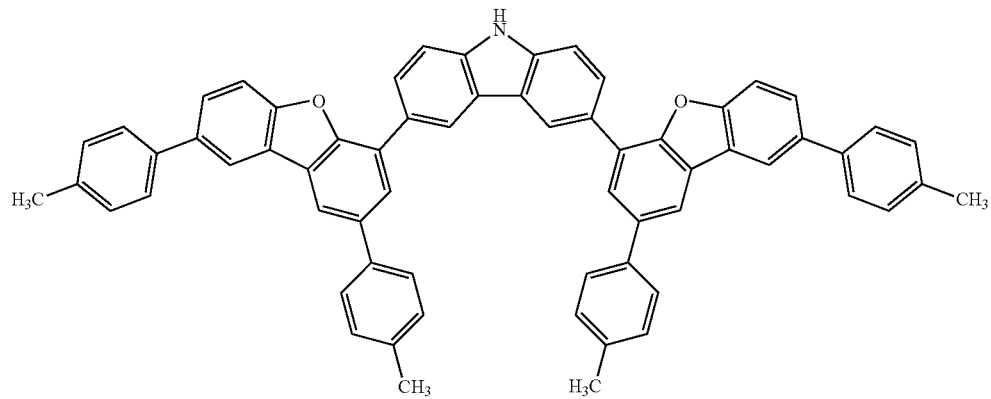
(UF-102)
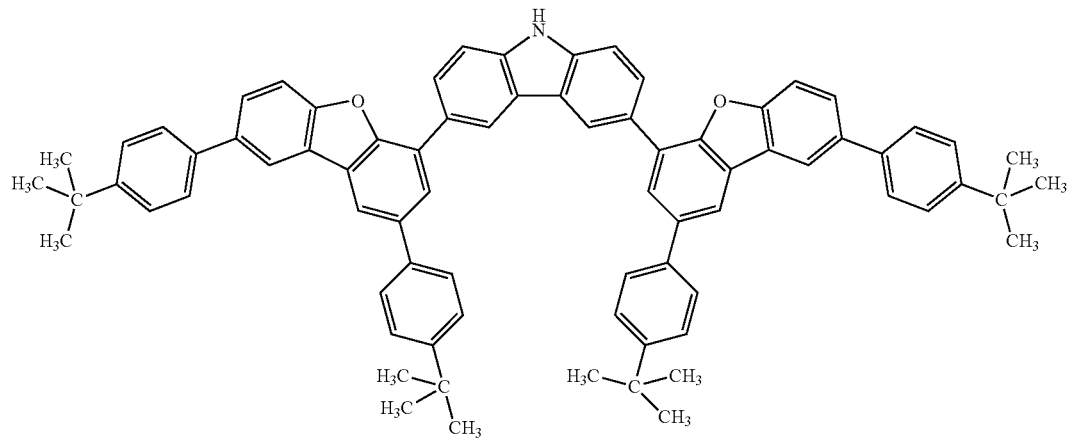

-continued
(UF-103)
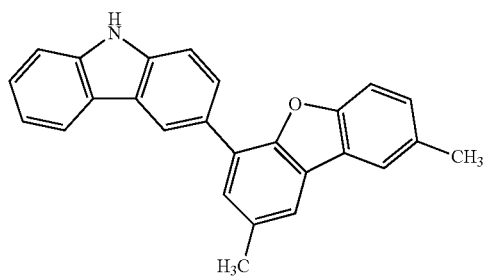
(UF-104)
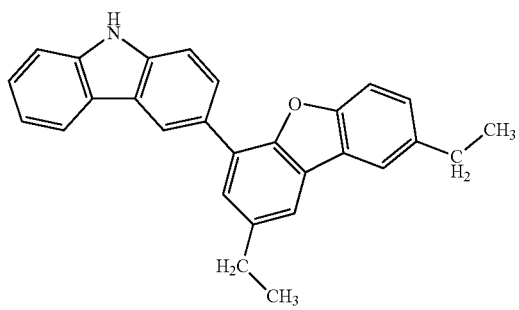
(UF-105)
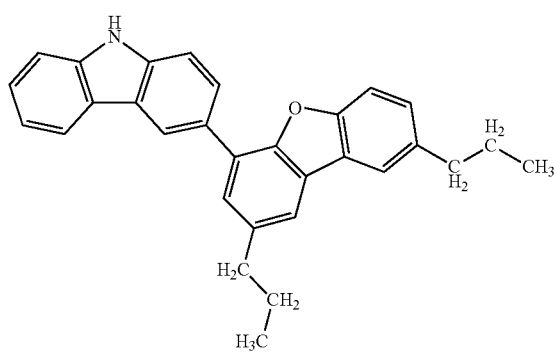
(UF-106)
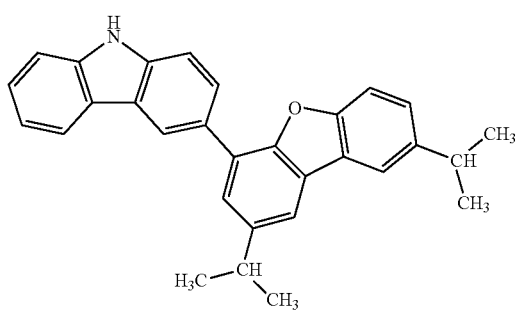
(UF-107)
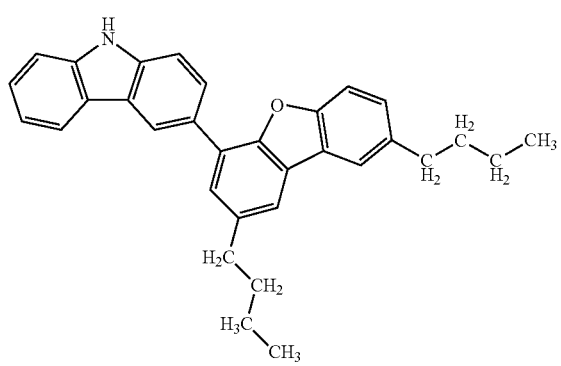
(UF-108)
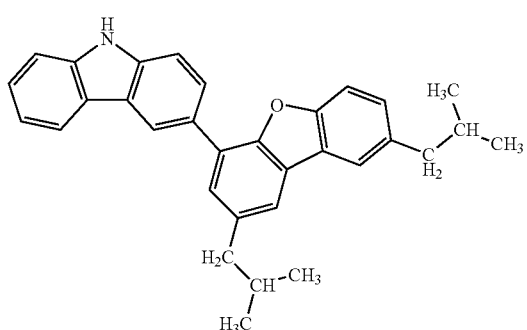
(UF-109)
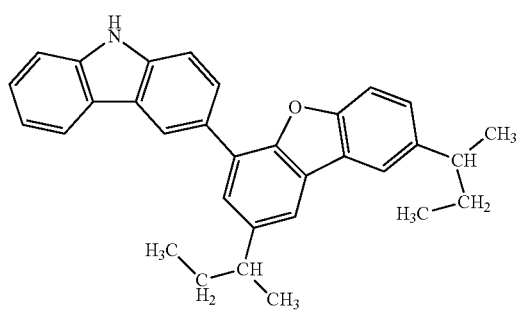
(UF-110)
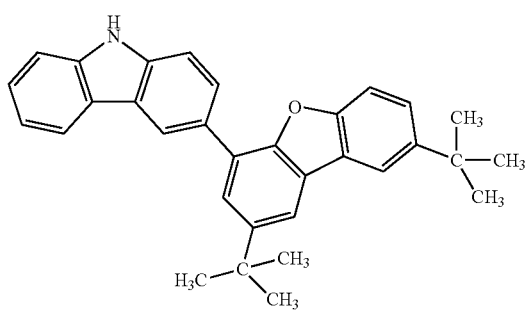

-continued
(UF-114)
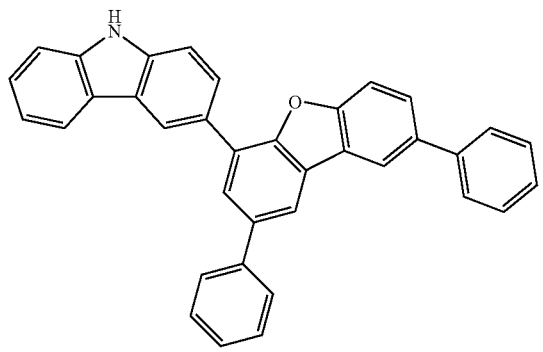
(UF-115)
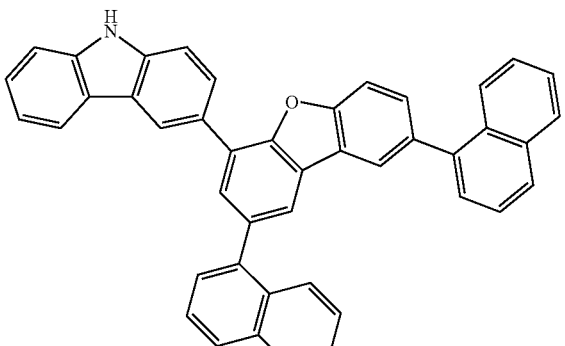
(UF-116)
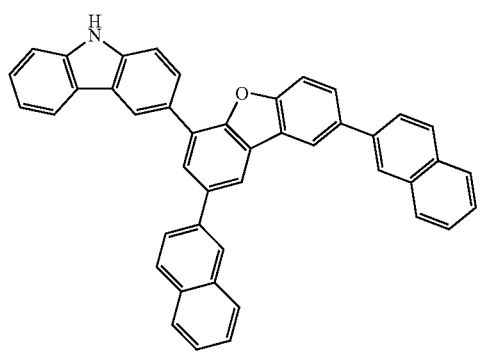
(UF-117)
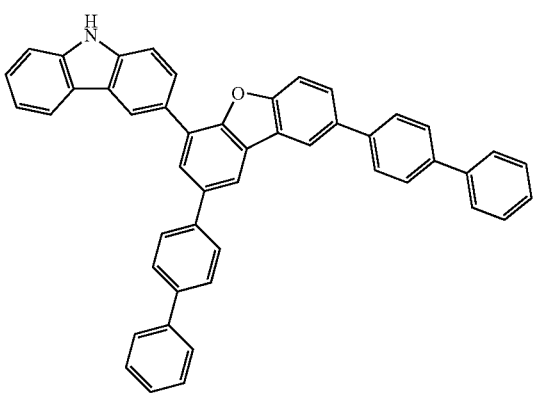
(UF-118)
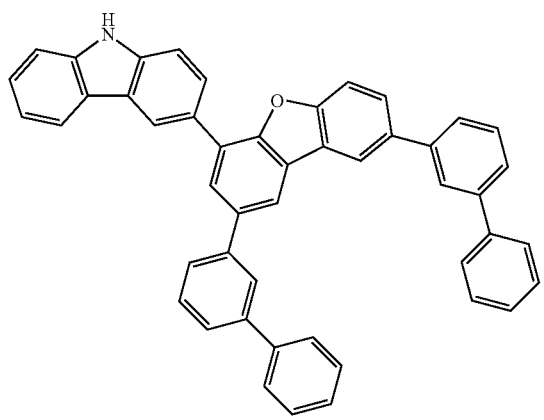
(UF-119)
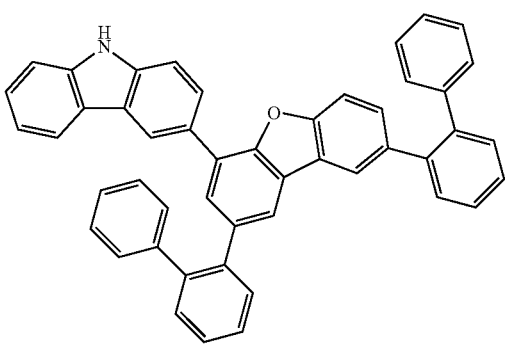
(UF-120)
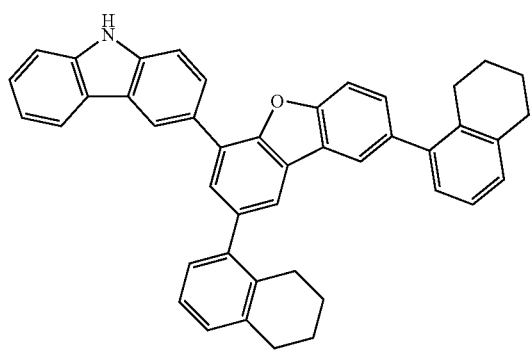
(UF-121)
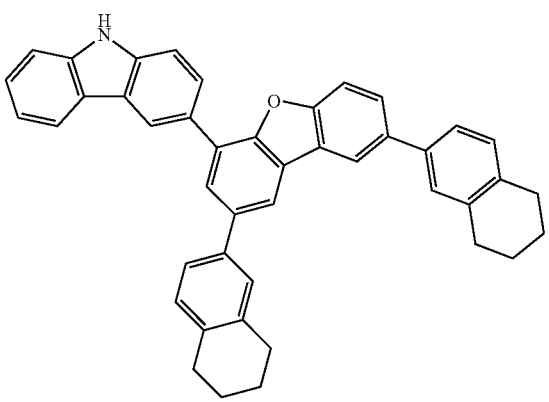

-continued
(UF-122)
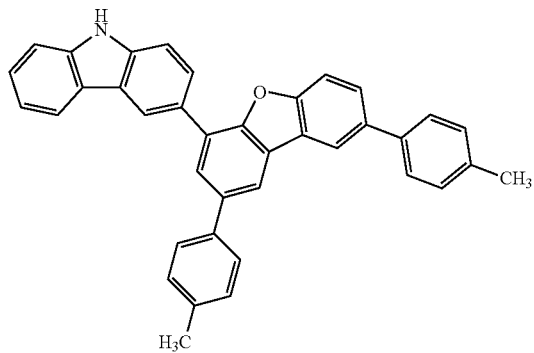
(UF-123)
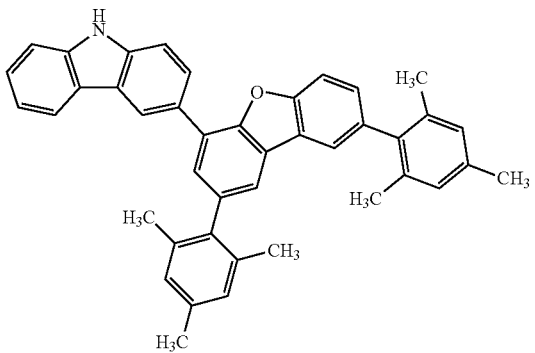
(UF-124)
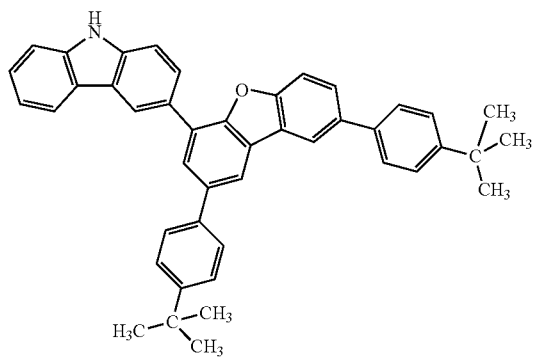
(UF-125)
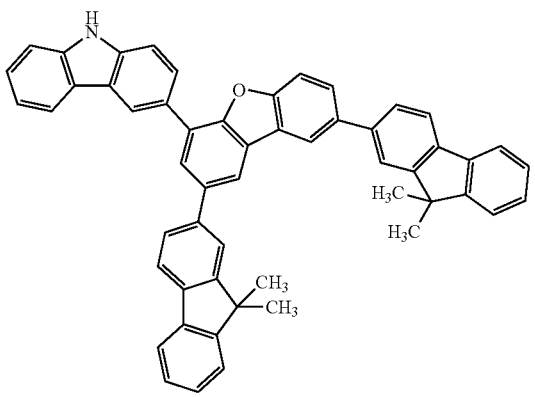
(UF-126)
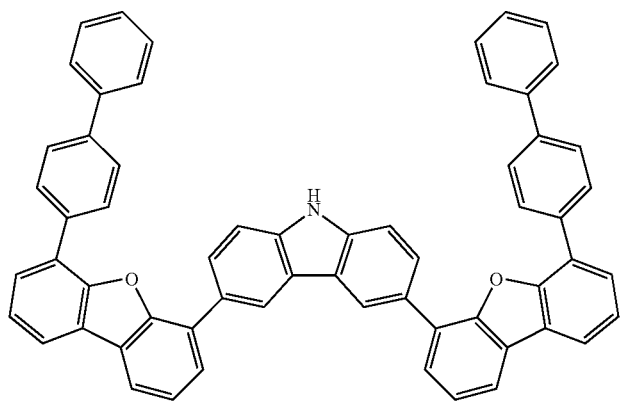
(UF-127)
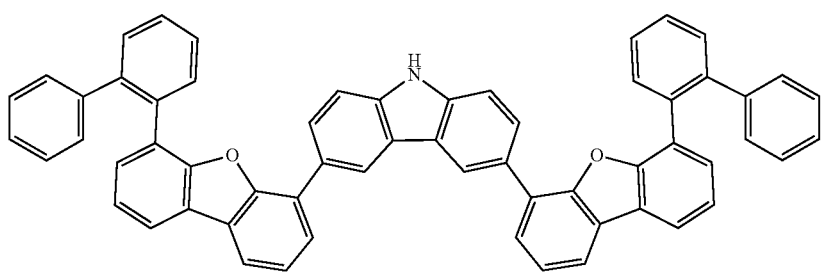

-continued
(UF-128)
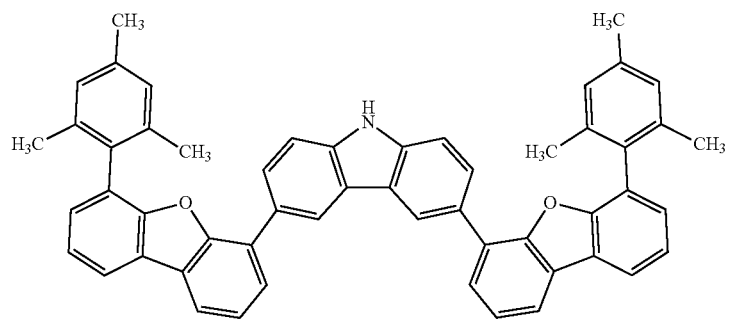
(UF-129)
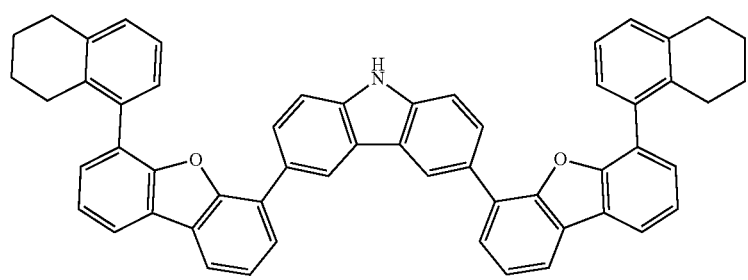
(UF-130)
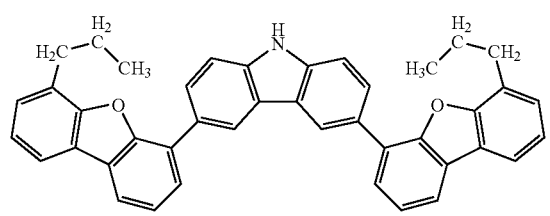
(UF-131)
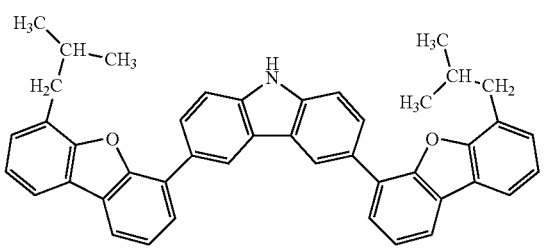
(UF-132)
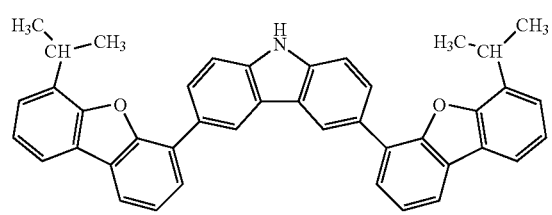
(UF-133)
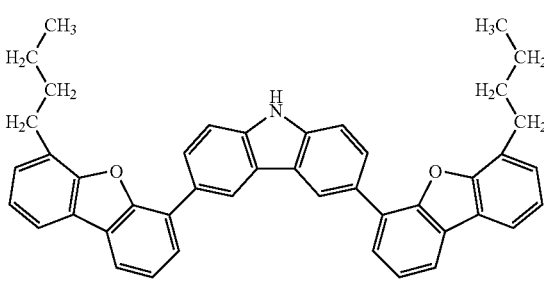
(UF-135)
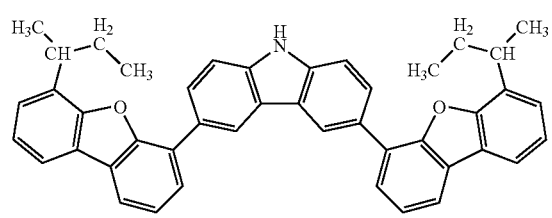
(UF-137)
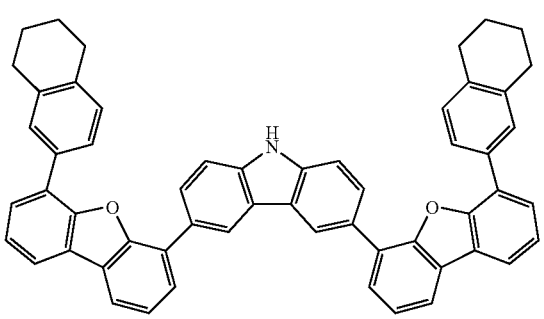

Embodiment 3

This embodiment shows an example in which any of the carbazole derivatives described in Embodiment 1 is used for an active layer of a vertical transistor (SIT), which is a kind of an organic semiconductor element.

Figure 2:
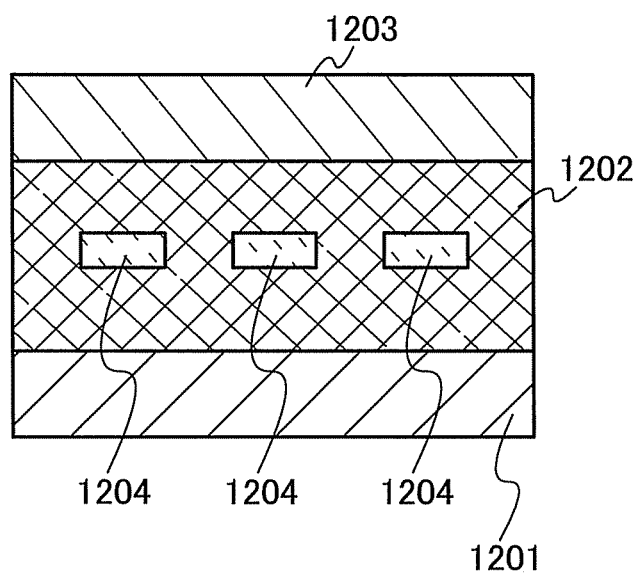
FIG. 2 is a conceptual diagram of an organic semiconductor element.

The element has a structure in which a thin-film active layer 1202 containing the carbazole derivative described in Embodiment 1 is interposed between a source electrode 1201 and a drain electrode 1203, and a gate electrode 1204 is embedded in the active layer 1202, as illustrated in FIG. 2. The gate electrode 1204 is electrically connected to a unit to apply a gate voltage, and the source electrode 1201 and the drain electrode 1203 are electrically connected to a unit to control a voltage between the source and the drain.

In such an element structure, when a voltage is applied between the source and the drain under the condition where a gate voltage is not applied, a current flows (an ON state). Then, when a gate voltage is applied in this state, a depletion layer is generated in the periphery of the gate electrode 1204, and thus a current does not flow (an OFF state). With such a mechanism, the element operates as a transistor.

In a vertical transistor, a material which has both a carrier-transport property and favorable film quality is required for an active layer like in a light-emitting element. The carbazole derivative described in Embodiment 1 can be suitably used because it sufficiently meets these requirements.

Embodiment 4

In this embodiment, one embodiment of a light-emitting element using any of the carbazole derivatives described in Embodiment 1 is described with reference to FIG. 1A.

A light-emitting element of this embodiment includes a plurality of layers between a pair of electrodes. In this embodiment, the light-emitting element includes a first electrode 102, a second electrode 104, and a layer 103 containing an organic compound provided between the first electrode 102 and the second electrode 104. In addition, in this embodiment, the first electrode 102 functions as an anode and the second electrode 104 functions as a cathode. In other words, when a voltage is applied between the first electrode 102 and the second electrode 104 such that the potential of the first electrode 102 is higher than that of the second electrode 104, light emission can be obtained.

The substrate 101 is used as a support of the light-emitting element. As the substrate 101, glass, plastic or the like can be used, for example. Note that a material other than glass or plastic can be used as long as it can function as a support of a light-emitting element.

The first electrode 102 is preferably formed using a metal, an alloy, a conductive compound, a mixture of them, or the like having a high work function (specifically, a work function of 4.0 eV or higher). Specifically, for example, indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide (IWZO), and the like can be given. Films of these conductive metal oxides are usually formed by sputtering; however, a sol-gel method or the like may also be used. For example, indium oxide-zinc oxide (IZO) can be formed by a sputtering method using a target in which zinc oxide is added to indium oxide at 1 wt % to 20 wt %. Moreover, indium oxide containing tungsten oxide and zinc oxide (IWZO) can be formed by a sputtering method using a target in which tungsten oxide is added to indium oxide at 0.5 wt % to 5 wt % and zinc oxide is added to indium oxide at 0.1 wt % to 1 wt %. Besides, gold (Au), platinum (Pt), nickel (Ni), tungsten (W), chromium (Cr), molybdenum (Mo), iron (Fe), cobalt (Co), copper (Cu), palladium (Pd), graphene, nitride of a metal material (e.g., titanium nitride), and the like can be given.

There is no particular limitation on a stacked structure of the layer 103 containing an organic compound. The layer 103 containing an organic compound may be formed as appropriate by combining a layer that contains a substance having a high electron-transport property, a layer that contains a substance having a high hole-transport property, a layer that contains a substance having a high electron-injection property, a layer that contains a substance having a high hole-injection property, a layer that contains a bipolar substance (a substance having a high electron- and hole-transport property), and the like. For example, the layer 103 containing an organic compound can be formed as appropriate by combining a hole-injection layer, a hole-transport layer, a light-emitting layer, an electron-transport layer, an electron-injection layer, and the like. In this embodiment, described is a structure in which the layer 103 containing an organic compound includes a hole-injection layer 111, a hole-transport layer 112, a light-emitting layer 113, and an electron-transport layer 114 stacked in that order over the first electrode 102. Specific materials to form each of the layers are given below.

The hole-injection layer 111 contains a substance having a high hole-injection property. Molybdenum oxide, vanadium oxide, ruthenium oxide, tungsten oxide, manganese oxide, or the like can be used. Alternatively, the hole-injection layer 111 can be formed using a phthalocyanine-based compound such as phthalocyanine (abbreviation: $H_2Pc$) or copper phthalocyanine (abbreviation: CuPc), an aromatic amine compound such as 4,4'-bis[N-(4-diphenylaminophenyl)-N-phenylamino]biphenyl (abbreviation: DPAB) or N,N'-bis[4-[bis (3-methylphenyl)amino]phenyl]-N,N'-diphenyl-[1,1'-biphenyl]-4,4'-diamine (abbreviation: DNTPD), a high molecular compound such as poly(ethylenedioxythiophene)/ poly(styrenesulfonic acid) (PEDOT/PSS), or the like.

Alternatively, the hole-injection layer 111 can be formed using a composite material in which a substance having an acceptor property is mixed into a substance having a high hole-transport property. Note that, by using such a substance having an acceptor property into which a substance having a high hole-transport property is mixed, a material used to form an electrode may be selected regardless of its work function. In other words, besides a material having a high work function, a material having a low work function can also be used for the first electrode 102. As the acceptor substance, 7,7,8, 8-tetracyano-2,3,5,6-tetrafluoroquinodimethane (abbreviation: $F_4$-TCNQ), chloranil, and the like can be given. In addition, a transition metal oxide can be given. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable because their electron-accepting property is high. Among these, molybdenum oxide is especially preferable because it is stable in the air and its hygroscopic property is low and is easily treated.

As the substance having a high hole-transport property used for the composite material, any of various compounds such as an aromatic amine compound, a carbazole derivative, aromatic hydrocarbon, and a high molecular compound (e.g., an oligomer, a dendrimer, or a polymer) can be used. The organic compound used for the composite material is preferably an organic compound having a high hole-transport property. Specifically, a substance having a hole mobility of $10^{-6}$ cm$^2$/Vs or higher is preferably used. However, another substance whose hole-transport property is higher than the electron-transport property may also be used. An organic compound which can be used as a substance having a high hole-transport property in the composite material is specifically given below.

Examples of the aromatic amine compound include N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis[4-[bis(3-methylphenyl)amino]phenyl]-N,N'-diphenyl-[1,1'-biphenyl]-4,4'-diamine (abbreviation: DNTPD), 1,3,5-tris[N-(4-diphenylaminophenyl)-N-phenylamino]benzene (abbreviation: DPA3B), and the like.

Examples of the carbazole derivative which can be used for the composite material specifically include 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Examples of the carbazole derivative which can be used for the composite material also include 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 1,4-bis[4-(N-carbazolyl)phenyl]-2,3,5,6-tetraphenylbenzene, and the like.

Examples of the aromatic hydrocarbon which can be used for the composite material include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Besides, pentacene, coronene, or the like can also be used. Thus, aromatic hydrocarbon having a hole mobility of 1×10$^{-6}$ cm$^2$/Vs or higher and having 14 to 42 carbon atoms is more preferably used.

The aromatic hydrocarbon which can be used for the composite material may have a vinyl skeleton. Examples of the aromatic hydrocarbon having a vinyl group include 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

Moreover, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: poly-TPD) can also be used.

Note that any of the carbazole derivatives described in Embodiment 1 can also be used as the organic compound in the composite material. The carbazole derivative described in Embodiment 1 is preferably contained in the hole-transport layer of the light-emitting element of this embodiment because in this case injection of holes from the hole-injection layer to the hole-transport layer can be smoothly performed, and thus, the driving voltage can be reduced. For the same reason, in the case where the carbazole derivative described in Embodiment 1 is used as an organic compound in the composite material, it is more preferable that the carbazole derivative and the carbazole derivative used for the hole-transport layer be the same substance.

The hole-transport layer 112 contains a substance having a high hole-transport property. In this embodiment, the carbazole derivative described in Embodiment 1 is used for the hole-transport layer.

The light-emitting layer 113 contains a light-emitting substance. The light-emitting layer 113 may be formed using a film containing only a light-emitting substance or a film in which an emission center substance is dispersed in a host material.

There is no particular limitation on a material that can be used as the light-emitting substance or the emission center substance in the light-emitting layer 113, and light emitted from the material may be either fluorescence or phosphorescence. Examples of the light-emitting substance or the emission center substance include the following. Examples of a fluorescent substance include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4- ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM). Examples of a phosphorescent substance include bis[2-(3',5'-bistrifluoromethylphenyl)pyridinato-N,$C^{2'}$]iridium(III) picolinate (abbreviation: Ir($CF_3$ppy)$_2$(pic)), bis[2-(4',6'-difluorophenyl)pyridinato-N,$C^{2'}$]iridium(III)acetylacetonate (abbreviation: FIracac), tris(2-phenylpyridinato)iridium(III) (abbreviation: Ir(ppy)$_3$), bis(2-phenylpyridinato)iridium(III) acetylacetonate (abbreviation: Ir(ppy)$_2$(acac)), tris(acetylacetonato)(monophenanthroline)terbium(III) (abbreviation: Tb(acac)$_3$(Phen)) bis(benzo[h]quinolinato)iridium(III) acetylacetonate (abbreviation: Ir(bzq)$_2$(acac)), bis(2,4-diphenyl-1,3-oxazolato-N,$C^{2'}$)iridium(III)acetylacetonate (abbreviation: Ir(dpo)$_2$(acac)), bis[2-(4'-perfluorophenylphenyl)pyridinato]iridium(III)acetylacetonate (abbreviation: Ir(p-PF-ph)$_2$(acac)), bis(2-phenylbenzothiazolato-N,$C^{2'}$)iridium(III)acetylacetonate (abbreviation: Ir(bt)$_2$(acac)), bis[2-(2'-benzo[4,5-c]thienyl)pyridinato-N,$C^{3'}$]iridium (acetylacetonate) (abbreviation: Ir(btp)$_2$(acac)), bis(1-phenylisoquinolinato-N,$C^{2'}$)iridium(III)acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(2,3,5-triphenylpyrazinato)iridium(III) (abbreviation: Ir(tppr)$_2$(acac)), 2,3,7,8,12,13,17,18-octaethyl-21H,23H-porphine platinum (II) (abbreviation: PtOEP), tris(1,3-diphenyl-1,3-propanedionato)(monophenanthroline)europium(III) (abbreviation: Eu(DBM)$_3$(Phen)), and tris[1-(2-thenoyl)-3,3,3-trifluoroacetonato](monophenanthroline)europium(III) (abbreviation: Eu(TTA)$_3$(Phen)).

There is no particular limitation on a material that can be used as the above host material, and for example, a metal complex, a heterocyclic compound, or an aromatic amine compound can be used. Examples of the metal complex include tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), bis[2-(2-benzothiazolyl)phenolato]zinc(II) (abbreviation: ZnBTZ), and the like. Examples of the heterocyclic compounds include 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), bathophenanthroline (abbreviation: BPhen), bathocuproine (abbreviation: BCP), 9-[4-(5-phenyl-1,3,4-oxadiazol-2-yl)phenyl]-9H-carbazole (abbreviation: CO11), and the like. Examples of the aromatic amine compound include 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), and the like. In addition, a condensed polycyclic aromatic compound such as an anthracene derivative, a phenanthrene derivative, a pyrene derivative, a chrysene derivative, and a dibenzo[g,p]chrysene derivative can be used. Specific examples of the condensed polycyclic aromatic compound include 9,10-diphenylanthracene (abbreviation: DPAnth), N,N-diphenyl-9-[4-(10-phenyl-9-anthryl)phenyl]-9H-carbazol-3-amine (abbreviation: CzAlPA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N,9-diphenyl-N-(9,10-diphenyl-2-anthryl)-9H-carbazol-3-amine (abbreviation: 2PCAPA), 6,12-dimethoxy-5,11-diphenylchrysene, N,N,N',N',N'',N''',N''',N''''-octaphenyldibenzo[g,p]chrysene-2,7,10,15-tetramine (abbreviation: DBC1), 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3''-(benzene-1,3,5-triyl)tripyrene (abbreviation: TPB3), and the like. One or more substances having a wider energy gap than the above-described emission center substance may be selected from these substances and known substances. Moreover, in the case where the emission center substance emits phosphorescence, a substance having higher triplet excitation energy (energy difference between a ground state and a triplet excitation state) than the emission center substance may be selected as the host material.

The light-emitting layer 113 may be a stack of two or more layers. For example, in the case where the light-emitting layer 113 is formed by stacking a first light-emitting layer and a second light-emitting layer in that order over the hole-transport layer, for example, the first light-emitting layer is formed using a substance having a hole-transport property as the host material and the second light-emitting layer is formed using a substance having an electron-transport property as the host material.

In the case where the light-emitting layer having the above-described structure is formed using a plurality of materials, the light-emitting layer can be formed using co-evaporation by a vacuum evaporation method; or an inkjet method, a spin coating method, a dip coating method, or the like as a method for mixing a solution.

The electron-transport layer 114 contains a substance having a high electron-transport property. For example, a layer containing a metal complex having a quinoline skeleton or a benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h]quinolinato)beryllium (abbreviation: BeBq$_2$), or bis(2-methyl-8-quinolinolato)(4-phenylphenolato)aluminum (abbreviation: BAlq), or the like can be used. Alternatively, a metal complex having an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$), or the like can be used. Besides the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances mentioned here mainly have an electron mobility of $10^{-6}$ $cm^2$/Vs or higher. However, another substance whose electron-transport property is higher than the hole-transport property may also be used for the electron-transport layer.

Furthermore, the electron-transport layer is not limited to a single layer, and two or more layers containing the above-described substances may be stacked.

Further, a layer that controls transport of electron carriers may be provided between the electron-transport layer and the light-emitting layer. Specifically, the layer that controls transport of electron carriers is a layer formed by adding a small amount of substance having a high electron-trapping property to the material having a high electron-transport property as described above, so that carrier balance can be adjusted. Such a structure is very effective in suppressing a problem (such as shortening of element lifetime) caused when electrons pass through the light-emitting layer.

In addition, an electron-injection layer may be provided between the electron-transport layer and the second electrode 104, in contact with the second electrode 104. As the electron-injection layer, an alkali metal, an alkaline earth metal, or a compound thereof such as lithium fluoride (LiF), cesium fluoride (CsF), or calcium fluoride ($CaF_2$) can be used. For example, a layer that is formed using a substance having an electron-transport property and contains an alkali metal, an alkaline earth metal, or a compound thereof, such as an Alq layer containing magnesium (Mg), may be used. A layer that is formed using a substance having an electron-transport property and contains an alkali metal or an alkaline earth metal is more preferably used as the electron-injection layer because electrons from the second electrode 104 is efficiently injected.

The second electrode 104 can be formed using a metal, an alloy, an electrically conductive compound, a mixture of them, or the like having a low work function (specifically, a work function of 3.8 eV or lower). Specific examples of such a cathode material include an element belonging to Group 1 or 2 in the periodic table, i.e., an alkali metal such as lithium (Li) or cesium (Cs), or an alkaline earth metal such as magnesium (Mg), calcium (Ca), or strontium (Sr); an alloy containing any of them (e.g., MgAg or AlLi); a rare earth metal such as europium (Eu) or ytterbium (Yb); an alloy containing such a rare earth metal; and the like. However, when the electron-injection layer is provided between the second electrode 104 and the electron-transport layer, the second electrode 104 can be formed using any of a variety of conductive materials such as Al, Ag, ITO, or indium oxide-tin oxide containing silicon or silicon oxide regardless of its work function. Films of these conductive materials can be formed by a sputtering method, an inkjet method, a spin coating method, or the like.

Further, any of a variety of methods can be employed for forming the layer 103 containing an organic compound regardless of a dry process or a wet process. For example, a vacuum evaporation method, an inkjet method, a spin coating method or the like may be used. A different formation method may be employed for each electrode or each layer.

In addition, the electrode may be formed by a wet method using a sol-gel method, or by a wet method using paste of a metal material. Alternatively, the electrode may be formed by a dry method such as a sputtering method or a vacuum evaporation method.

In the light-emitting element having the above-described structure, a current flows due to a potential difference made between the first electrode 102 and the second electrode 104, a hole and an electron are recombined in the light-emitting layer 113, which contains a substance having a high light-emitting property, and light is emitted. That is, a light-emitting region is formed in the light-emitting layer 113.

The emitted light is extracted out through one or both of the first electrode 102 and the second electrode 104. Therefore, one or both of the first electrode 102 and the second electrode 104 are light-transmitting electrodes. In the case where only the first electrode 102 is a light-transmitting electrode, the emitted light is extracted from the substrate side through the first electrode 102. In the case where only the second electrode 104 is a light-transmitting electrode, the emitted light is extracted from the side opposite to the substrate side through the second electrode 104. In a case where each of the first electrode 102 and the second electrode 104 is a light-transmitting electrode, the emitted light is extracted from both the substrate side and the side opposite to the substrate through the first electrode 102 and the second electrode 104.

The structure of the layers provided between the first electrode 102 and the second electrode 104 is not limited to the above-described structure. However, a structure in which a light-emitting region for recombination of holes and electrons is positioned away from the first electrode 102 and the second electrode 104 so as to prevent quenching due to the proximity of the light-emitting region and a metal used for electrodes and carrier-injection layers is preferable. The order of stacking the layers is not limited thereto, and the following order, which is opposite to that in FIG. 1A, may be employed: the second electrode, the electron-injection layer, the electron-transport layer, the light-emitting layer, the hole-transport layer, the hole-injection layer, and the first electrode over the substrate.

In addition, as for the hole-transport layer or the electron-transport layer in direct contact with the light-emitting layer, particularly a carrier-transport layer in contact with a side closer to a light-emitting region in the light-emitting layer 113, in order to suppress energy transfer from an exciton which is generated in the light-emitting layer, it is preferable that the energy gap thereof be wider than the energy gap of the light-emitting substance contained in the light-emitting layer or the energy gap of the emission center substance contained in the light-emitting layer.

Since the light-emitting element of this embodiment uses the carbazole derivative described in Embodiment 1, which has a wide energy gap, for the hole-transport layer, light emission can be obtained efficiently even when the light-emitting substance or the emission center substance is a substance that has a wide energy gap and emits blue fluorescence or a substance that has high triplet excitation energy (energy difference between a ground state and a triplet excited state) and emits green phosphorescence; thus, a light-emitting element with high emission efficiency can be provided. Accordingly, a light-emitting element having lower power consumption can be provided. In addition, a light-emitting element that emits light with high color purity can be provided. Further, the carbazole derivative described in Embodiment 1 has an excellent carrier-transport property; therefore, a light-emitting element driven with a low driving voltage can be provided.

In this embodiment, the light-emitting element is formed over a substrate formed of glass, plastic, or the like. By fabricating a plurality of such light-emitting elements over one substrate, a passive matrix light-emitting device can be fabricated. In addition, for example, a thin film transistor (TFT) may be formed over a substrate formed of glass, plastic, or the like, and a light-emitting element may be fabricated over an electrode electrically connected to the TFT. In this manner, an active matrix light-emitting device in which the TFT controls the drive of the light-emitting element can be fabricated. Note that there is no particular limitation on the structure of the TFT. Either a staggered TFT or an inverted staggered TFT may be employed. In addition, crystallinity of a semiconductor used for the TFT is not particularly limited either; an amorphous semiconductor or a crystalline semiconductor may be used. In addition, a driver circuit formed over a TFT substrate may be Constructed from both n-channel and p-channel TFTs or from one of n-channel and p-channel TFTs.

Embodiment 5

In this embodiment, a light-emitting element having a different structure from that described in Embodiment 4 is described.

Described is a structure in which light is emitted from an emission center substance having a light-emitting property by forming a light-emitting layer 113 described in Embodiment 4 in such a manner that the emission center substance is dispersed into any of the carbazole derivatives described in Embodiment 1, i.e., a structure in which the carbazole derivative described in Embodiment 1 is used as a host material of the light-emitting layer 113.

The carbazole derivative described in Embodiment 1 has a wide energy gap or high triplet excitation energy (energy difference between a ground state and a triplet excited state), and thus can make another light-emitting substance excited and emit light effectively; therefore, the carbazole derivative described in Embodiment 1 can be suitably used as the host material and light emission that originates from the light-emitting substance can be obtained. Thus, a light-emitting element having high emission efficiency with small energy loss can be provided. In addition, a light-emitting element that can easily provide light emission of a desired color that originates from the emission center substance can be provided. Accordingly, a light-emitting element capable of easily emitting light with high color purity can be provided. Further, the carbazole derivative described in Embodiment 1 has an excellent carrier-transport property; therefore, a light-emitting element driven with a low driving voltage can also be provided.

Here, there is no particular limitation on the emission center substance dispersed into the carbazole derivative described in Embodiment 1, and any of various materials can be used. Specifically, it is possible to use 4-(dicyanomethylene)-2-methyl-6-(p-dimethylaminostyryl)-4H-pyran (abbreviation: DCM1), 4-(dicyanomethylene)-2-methyl-6-(julolidin-4-yl-vinyl)-4H-pyran (abbreviation: DCM2), N,N-dimethylquinacridone (abbreviation: DMQd), 9,10-diphenylanthracene (abbreviation: DPA), 5,12-diphenyltetracene (abbreviation: DPT), coumarin 6, perylene, rubrene, N,N'-bis[4-(9-phenyl-9H-fluoren-9-yl)phenyl]-N,N'-diphenylpyrene-1,6-diamine (abbreviation: 1,6FLPAPrn), or another known fluorescent substance that emits fluorescence. Alternatively, it is possible to use bis(2-phenylbenzothiazolato-N,C$^{2'}$)iridium(III)acetylacetonate (abbreviation: Ir(bt)$_2$(acac)), tris(2-phenylquinolinato-N,C$^{2'}$)iridium(III) (abbreviation: Ir(pq)$_3$), bis(2-phenylquinolinato-N,C$^{2'}$)iridium(III)(acetylacetonate) (abbreviation: Ir(pq)$_2$(acac)), bis[2-(2'-benzo[4,5-a]thienyl)pyridinato-N,C$^{3'}$]iridium(III)acetylacetonate (abbreviation: Ir(btp)$_2$(acac)), bis(1-phenylisoquinolinato-N,C$^{2'}$)iridium(III)acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), tris(2-phenylpyridinato-N,C$^{2'}$)iridium(III) (abbreviation: Ir(ppy)$_3$), or 2,3,7,8,12,13,17,18-octaethyl-21H,23H-porphine platinum(II) (abbreviation: PtOEP), or another known phosphorescent substance that emits phosphorescence. In the case where the carbazole derivative described in Embodiment 1 has a light-emitting property, the carbazole derivative can be used as the emission center substance. In that case, the carbazole derivative used as the host material is preferably different from the carbazole derivative used as the emission center substance. Among the above-described substances or known substances, a substance that has a narrower band gap or lower triplet excitation energy than the carbazole derivative described in Embodiment 1, which is used as the host material, is selected as the emission center substance.

Further, another organic compound may be dispersed at the same time in the light-emitting layer, in addition to the carbazole derivative described in Embodiment 1 and the emission center substance dispersed into the carbazole derivative. In this case, a substance that improves carrier balance of the light-emitting layer is preferably used, such as the above-described substances having a high electron-transport property.

Note that, regarding the layers other than the light-emitting layer 113, the structure described in Embodiment 4 can be applied as appropriate. Further, the hole-transport layer 112 can be formed using any of the materials given as the substances having a high hole-transport property which can be used in a composite material in Embodiment 4. Besides, the hole-transport layer 112 can be formed using a substance having a high hole-transport property such as the following aromatic amine compounds: 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), or 4,4'-bis[N-(spiro-9,9'-bifluoren-2-yl)-N-phenylamino]biphenyl (abbreviation: BSPB); or the like. Needless to say, the carbazole derivative described in Embodiment 1 can also be used. The substances mentioned here mainly have a hole mobility of 10$^{-6}$ cm$^2$/Vs or higher. However, another substance whose hole-transport property is higher than the electron-transport property may also be used. Note that the layer containing a substance having a high hole-transport property is not limited to a single layer, and two or more layers containing the above-described substances may be stacked.

Alternatively, a high molecular compound such as poly(N-vinylcarbazole) (abbreviation: PVK) or poly(4-vinyltriphenylamine) (abbreviation: PVTPA) can be used for the hole-transport layer 112.

Embodiment 6

In this embodiment, an embodiment of a light-emitting element with a structure in which a plurality of light-emitting units are stacked (hereinafter this type of light-emitting element is also referred to as a stacked element) is described with reference to FIG. 1B. This light-emitting element includes a plurality of light-emitting units between a first electrode and a second electrode. Each light-emitting unit can have a structure similar to that of a layer 103 containing an organic compound described in Embodiment 4 or 5. That is, a light-emitting element described in Embodiment 4 or includes a single light-emitting unit; the light-emitting element in this embodiment includes a plurality of light-emitting units.

Figure 1B:
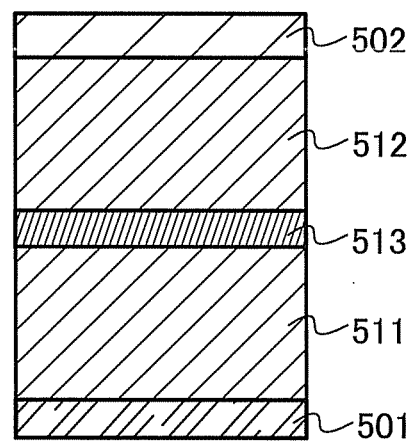

In FIG. 1B, a first light-emitting unit 511 and a second light-emitting unit 512 are stacked between a first electrode 501 and a second electrode 502, and a charge generation layer 513 is provided between the first light-emitting unit 511 and the second light-emitting unit 512. The first electrode 501 and the second electrode 502 correspond to a first electrode 102 and a second electrode 104 in Embodiment 4, respectively, and electrodes similar to those described in Embodiment 4 can be applied to the first electrode 501 and the second electrode 502. Further, the first light-emitting unit 511 and the second light-emitting unit 512 may have the same structure or different structures.

The charge generation layer 513 contains a composite material of an organic compound and a metal oxide. This composite material of an organic compound and a metal oxide is described in Embodiment 4 and contains an organic compound and a metal oxide such as vanadium oxide, molybdenum oxide, or tungsten oxide. As the organic compound, any of various compounds such as an aromatic amine compound, a carbazole derivative, aromatic hydrocarbon, and a high molecular compound (e.g., oligomer, dendrimer, or polymer) can be used. As the organic compound, an organic compound having a hole-transport property and a hole mobility of $10^{-6}$ cm$^2$/Vs or higher is preferably used. However, another substance whose hole-transport property is higher than the electron-transport property may also be used. The composite of an organic compound and a metal oxide has excellent carrier-injection property and carrier-transport property, and hence, low-voltage driving and low-current driving can be achieved.

The charge generation layer 513 may be formed by combining a layer containing the composite material of an organic compound and metal oxide with a layer containing another material. For example, the layer containing the composite material of an organic compound and a metal oxide may be combined with a layer containing a compound of a substance selected from substances having an electron-donating property and a compound having a high electron-transport property. Moreover, the layer containing the composite material of an organic compound and a metal oxide may be combined with a transparent conductive film.

The charge generation layer 513 interposed between the first light-emitting unit 511 and the second light-emitting unit 512 may have any structure as long as electrons can be injected to a light-emitting unit on one side and holes can be injected to a light-emitting unit on the other side when a voltage is applied between the first electrode 501 and the second electrode 502. For example, in FIG. 1B, any layer can be employed as the charge generation layer 513 as long as the layer injects electrons into the first light-emitting unit 511 and holes into the second light-emitting unit 512 when a voltage is applied such that the potential of the first electrode is higher than that of the second electrode.

Although the light-emitting element having two light-emitting units is described in this embodiment, the present invention can be similarly applied to a light-emitting element in which three or more light-emitting units are stacked. A plurality of light-emitting units which are partitioned by the charge generation layer are arranged between a pair of electrodes, as in the light-emitting element of this embodiment, whereby the element can emit light in a high luminance region while current density is kept low. Since the current density can be kept low, the element can have a long lifetime. When the light-emitting element is applied for illumination, voltage drop due to resistance of an electrode material can be reduced, thereby achieving homogeneous light emission in a large area. Moreover, the light-emitting device can be driven with a low driving voltage and consume less power.

By making emission colors of the light-emitting units different from each other, light of a desired color can be obtained from the light-emitting element as a whole. For example, in a light-emitting element including two light-emitting units, the emission colors of the first light-emitting unit and the second light-emitting unit are made complementary, so that the light-emitting element which emits white light as the whole element can be obtained. Note that the word "complementary" means color relationship in which an achromatic color is obtained when colors are mixed. In other words, when light of complementary colors is mixed, white light emission can be obtained. The same can be applied to a light-emitting element including three light-emitting units. For example, when the first light-emitting unit emits red light, the second light-emitting unit emits green light, and the third light-emitting unit emits blue light, white light can be emitted from the light-emitting element as a whole.

Since the light-emitting element of this embodiment contains the carbazole derivative described in Embodiment 1, a light-emitting element having high emission efficiency can be provided. In addition, a light-emitting element driven with a low driving voltage can be provided. Further, a light-emitting element having a long lifetime can be provided. In addition, the light-emitting unit containing the carbazole derivative can provide light that originates from the emission center substance with high color purity; therefore, it is easy to adjust the color of light emitted from the light-emitting element as a whole.

Note that this embodiment can be combined with any of the other embodiments as appropriate.

Embodiment 7

In this embodiment, a light-emitting device including a light-emitting element containing any of the carbazole derivatives described in Embodiment 1 is described.

In this embodiment, the light-emitting device including a light-emitting element containing any of the carbazole derivatives described in Embodiment 1 is described with reference to FIGS. 3A and 3B. Note that FIG. 3A is a top view illustrating the light-emitting device and FIG. 3B is a cross-sectional view of FIG. 3A taken along lines A-A' and B-B'. The light-emitting device includes a driver circuit portion (source-side driver circuit) 601, a pixel portion 602, and a driver circuit portion (gate-side driver circuit) 603 which are illustrated with dotted lines. These units control light emission of the light-emitting element. Moreover, a reference numeral 604 denotes a sealing substrate; 605, a sealing material; and 607, a space surrounded by the sealing material 605.

Reference numeral 608 denotes a wiring for transmitting signals to be inputted into the source-side driver circuit portion 601 and the gate-side driver circuit portion 603 and receiving signals such as a video signal, a clock signal, a start signal, and a reset signal from an FPC (flexible printed circuit) 609 serving as an external input terminal. Although only the FPC is illustrated here, a printed wiring board (PWB) may be attached to the FPC. The light-emitting device in the present specification includes, in its category, not only the light-emitting device itself but also the light-emitting device provided with the FPC or the PWB.

Next, the cross-sectional structure is described with reference to FIG. 3B. Although the driving circuit portion and the pixel portion are formed on an element substrate 610, the source-side driving circuit 601 that is the driving circuit portion, and one of the pixels in the pixel portion 602 are illustrated here.

In the source-side driver circuit 601, a CMOS circuit is formed in which an n-channel TFT 623 and a p-channel TFT 624 are combined. Such a driver circuit may be formed by using various circuits such as a CMOS circuit, a PMOS circuit, or an NMOS circuit. Although this embodiment shows a driver-integrated type where the driver circuit is formed over the substrate, the present invention is not limited to this, and the driver circuit may be formed outside the substrate, not over the substrate.

The pixel portion 602 is formed with a plurality of pixels including a switching TFT 611, a current controlling TFT 612, and a first electrode 613 electrically connected to a drain of the current controlling TFT. An insulator 614 is formed so as to cover the end portions of the first electrode 613. Here, the insulator 614 is formed using a positive type photosensitive acrylic resin film.

In order to improve the coverage, the insulator 614 is formed to have a curved surface with curvature at its upper or lower end portion. For example, in the case of using positive photosensitive acrylic for the insulator 614, only the upper end portion of the insulator 614 preferably has a curved surface with a radius of curvature of 0.2 µm to 3 µm. As the insulator 614, either a negative type which becomes insoluble in etchant by irradiation with light or a positive type which becomes soluble in etchant by irradiation with light can be used.

A layer 616 containing an organic compound and a second electrode 617 are formed over the first electrode 613. As a material used for the first electrode 613 functioning as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like can be used. Alternatively, a stack of a titanium nitride film and a film containing aluminum as its main component, a stack of three layers of a titanium nitride film, a film containing aluminum as its main component, and a titanium nitride film, or the like can be used. Note that when a stacked structure is employed, the first electrode 613 has low resistance as a wiring, forms a favorable ohmic contact, and can function as an anode.

In addition, the layer 616 containing an organic compound is formed by any of a variety of methods such as an evaporation method using an evaporation mask, an inkjet method, and a spin coating method. The layer 616 containing an organic compound contains the carbazole derivative described in Embodiment 1. Further, the layer 616 containing an organic compound may be formed using another material such as a low molecular compound or a high molecular compound (the category of the high molecular compound includes an oligomer and a dendrimer).

As a material used for the second electrode 617, which is formed over the layer 616 containing an organic compound and functions as a cathode, a material having a low work function (e.g., Al, Mg, Li, Ca, or an alloy or compound thereof, such as MgAg, MgIn, AlLi, LiF, or $CaF_2$) is preferably used. In the case where light generated in the layer 616 containing an organic compound passes through the second electrode 617, the second electrode 617 is preferably formed using a stack of a thin metal film and a transparent conductive film (ITO, indium oxide containing zinc oxide at 2 wt % to 20 wt %, indium tin oxide containing silicon, zinc oxide (ZnO), or the like).

Note that the light-emitting element is formed by the first electrode 613, the layer 616 containing an organic compound, and the second electrode 617. The light-emitting element has any of the structures described in Embodiments 4 to 6. The pixel portion, which includes a plurality of light-emitting elements, in the light-emitting device of this embodiment may include both the light-emitting element with any of the structures described in Embodiments 4 to 6 and the light-emitting element with a structure other than those.

Further, a light-emitting element 618 is provided in the space 607 surrounded by the element substrate 610, the sealing substrate 604, and the sealing material 605 by pasting the sealing substrate 604 and the element substrate 610 using the sealing material 605. The space 607 may be filled with filler, and may be filled with an inert gas (such as nitrogen or argon), the sealing material 605, or the like.

An epoxy based resin is preferably used for the sealing material 605. It is desirable that such a material do not transmit moisture or oxygen as much as possible. As a material for the sealing substrate 604, a plastic substrate formed of FRP (fiberglass-reinforced plastics), PVF (polyvinyl fluoride), polyester, acrylic, or the like can be used besides a glass substrate or a quartz substrate.

In this manner, the light-emitting device manufactured using the light-emitting element containing the carbazole derivative described in Embodiment 1 can be obtained.

Since the light-emitting device in this embodiment uses the light-emitting element containing the carbazole derivative described in Embodiment 1, a light-emitting device having favorable characteristics can be provided. Specifically, since the carbazole derivative described in Embodiment 1 has a wide energy gap and high triplet excitation energy and can suppress energy transfer from a light-emitting substance, a light-emitting element having high emission efficiency can be provided; thus, a light-emitting device having less power consumption can be provided. In addition, since a light-emitting element driven with a low driving voltage can be provided, a light-emitting device driven with a low driving voltage can be provided. Further, since the light-emitting element using the carbazole derivative described in Embodiment 1 has a long lifetime, a light-emitting device having high reliability can be provided.

Figure 4A:
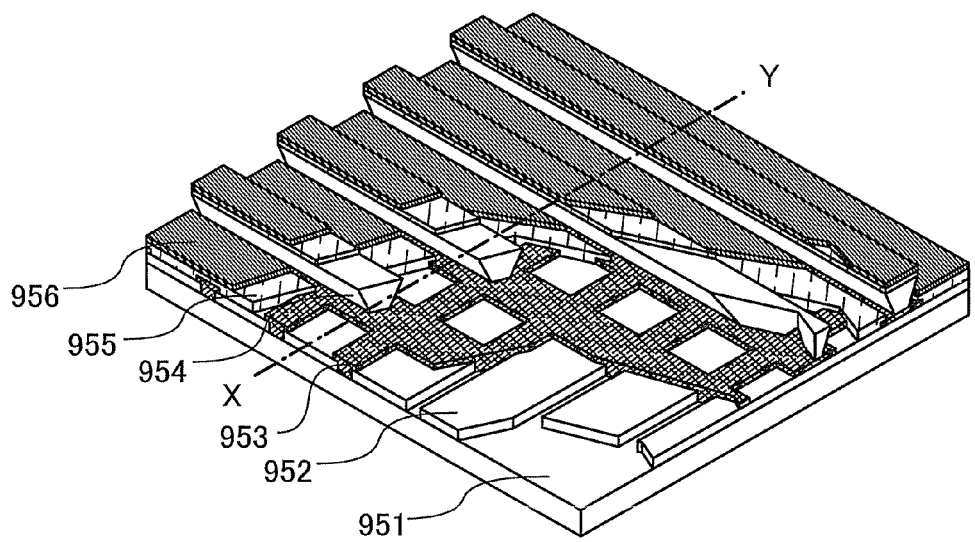
FIGS. 4A and 4B are conceptual diagrams of a passive matrix light-emitting device.
Figure 4B:
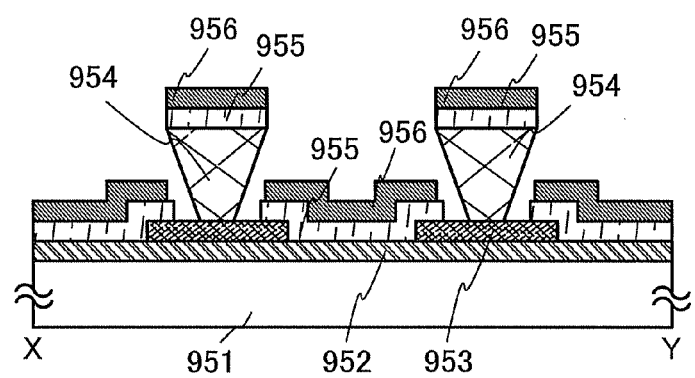

Although an active matrix light-emitting device is described in this embodiment as described above, a passive matrix light-emitting device may be alternatively fabricated. FIGS. 4A and 4B illustrate a passive matrix light-emitting device fabricated according to the present invention. FIG. 4A is a perspective view of the light-emitting device, and FIG. 4B is a cross-sectional view taken along line X-Y in FIG. 4A. In FIGS. 4A and 4B, an electrode 952 and an electrode 956 are provided over a substrate 951, and a layer 955 containing an organic compound is provided between the electrodes 952 and 956. An end portion of the electrode 952 is covered with an insulating layer 953. A partition layer 954 is provided over the insulating layer 953. The sidewalls of the partition layer 954 are aslope such that the distance between both sidewalls is gradually narrowed toward the surface of the substrate. That is, a cross section taken along the direction of the short side of the partition wall layer 954 is trapezoidal, and the lower side (a side which is in the same direction as a plane direction of the insulating layer 953 and in contact with the insulating layer 953) is shorter than the upper side (a side which is in the same direction as the plane direction of the insulating layer 953 and not in contact with the insulating layer 953). By providing the partition layer 954 in this manner, defects of the light-emitting element due to static charge and the like can be prevented. The passive matrix light-emitting device can also be driven with low power consumption by including the light-emitting element according to any of Embodiments 4 to 6 which contains the carbazole derivative described in Embodiment 1 and is operated with a low driving voltage. In addition, the light-emitting device can be driven with low power consumption by including the light-emitting element according to any of Embodiments 4 to 6 which contains the carbazole derivative described in Embodiment 1 and accordingly has high emission efficiency. Further, the light-emitting device can have high reliability by including the light-emitting element according to any of Embodiments 4 to 6 which contains the carbazole derivative described in Embodiment 1.

Embodiment 8

In this embodiment, electronic devices of one embodiment of the present invention, each including the light-emitting device described in Embodiment 7, are described. The electronic devices in this embodiment each include a light-emitting element containing any of the carbazole derivative described in Embodiment 1 and thus electronic devices each having a display portion which consumes less power can be obtained. In addition, electronic devices driven with a low driving voltage can be provided. Further, electronic devices having high reliability can be provided.

As examples of the electronic devices each containing the carbazole derivative described in Embodiment 1, the following can be given: cameras such as video cameras and digital cameras, goggle type displays, navigation systems, audio replay devices (e.g., car audio systems and audio systems), computers, game machines, portable information terminals (e.g., mobile computers, mobile phones, portable game machines, and electronic book readers), image replay devices in which a recording medium is provided (specifically, devices that are capable of replaying recording media, such as digital versatile discs (DVDs), and equipped with a display device that can display an image), and the like. Specific examples of these electronic devices are illustrated in FIGS. 5A to 5D.

FIG. 5A illustrates a television device which includes a housing 9101, a support 9102, a display portion 9103, speaker portions 9104, video input terminals 9105, and the like. In the display portion 9103 of this television device, light-emitting elements similar to those described in any of Embodiments 4 to 6 are arranged in matrix. The light-emitting elements can have high emission efficiency because each light-emitting element contains the carbazole derivative described in Embodiment 1. In addition, a light-emitting element driven with a low driving voltage can be provided. Further, a light-emitting element having high reliability can be provided. Therefore, this television device having the display portion 9103 which is formed using the light-emitting elements consumes less power. In addition, a television device driven with a low driving voltage can be provided. Further, a television device having high reliability can be provided.

FIG. 5B illustrates a computer according to one embodiment of the present invention. The computer includes a main body 9201, a housing 9202, a display portion 9203, a keyboard 9204, an external connection port 9205, a pointing device 9206, and the like. In the display portion 9203 of this computer, light-emitting elements similar to those described in any of Embodiments 4 to 6 are arranged in matrix. The light-emitting elements can have high emission efficiency because each light-emitting element contains the carbazole derivative described in Embodiment 1. In addition, a light-emitting element driven with a low driving voltage can be provided. Further, a light-emitting element having high reliability can be provided. Therefore, this computer having the display portion 9203 which is formed using the light-emitting elements consumes less power. In addition, a computer driven with a low driving voltage can be provided. Further, a computer having high reliability can be provided.

FIG. 5C illustrates a mobile phone according to one embodiment of the present invention. The mobile phone includes a main body 9401, a housing 9402, a display portion 9403, an audio input portion 9404, an audio output portion 9405, operation keys 9406, an external connection port 9407, an antenna 9408, and the like. In the display portion 9403 of this mobile phone, light-emitting elements similar to those described in any of Embodiments 4 to 6 are arranged in matrix. The light-emitting elements can have high emission efficiency because each light-emitting element contains the carbazole derivative described in Embodiment 1. In addition, a light-emitting element driven with a low driving voltage can be provided. Further, a light-emitting element having high reliability can be provided. Therefore, this mobile phone having the display portion 9403 which is formed using the light-emitting elements consumes less power. In addition, a mobile phone driven with a low driving voltage can be provided. Further, a mobile phone having high reliability can be provided.

FIG. 5D illustrates a camera according to one embodiment of the present invention which includes a main body 9501, a display portion 9502, a housing 9503, an external connection port 9504, a remote control receiving portion 9505, an image receiving portion 9506, a battery 9507, an audio input portion 9508, operation keys 9509, an eye piece portion 9510, and the like. In the display portion 9502 of this camera, light-emitting elements similar to those described in any of Embodiments 4 to 6 are arranged in matrix. The light-emitting elements can have high emission efficiency because each light-emitting element contains the carbazole derivative described in Embodiment 1. In addition, a light-emitting element driven with a low driving voltage can be provided. Further, a light-emitting element having high reliability can be provided. Therefore, this camera having the display portion 9502 which is formed using the light-emitting elements consumes less power. In addition, a camera driven with a low driving voltage can be provided. Further, a camera having high reliability can be provided.

As described above, the application range of the light-emitting device described in Embodiment 7 is so wide that the light-emitting device can be applied to electronic devices of every field. An electronic device which consumes less power can be obtained by using the carbazole derivative described in Embodiment 1. In addition, an electronic device having a display portion capable of providing high-quality display with excellent color reproducibility can be obtained.

The light-emitting device described in Embodiment 7 can also be used as a lighting device. One embodiment in which the light-emitting device described in Embodiment 7 is used as a lighting device is described with reference to FIG. 6.

Figure 6:
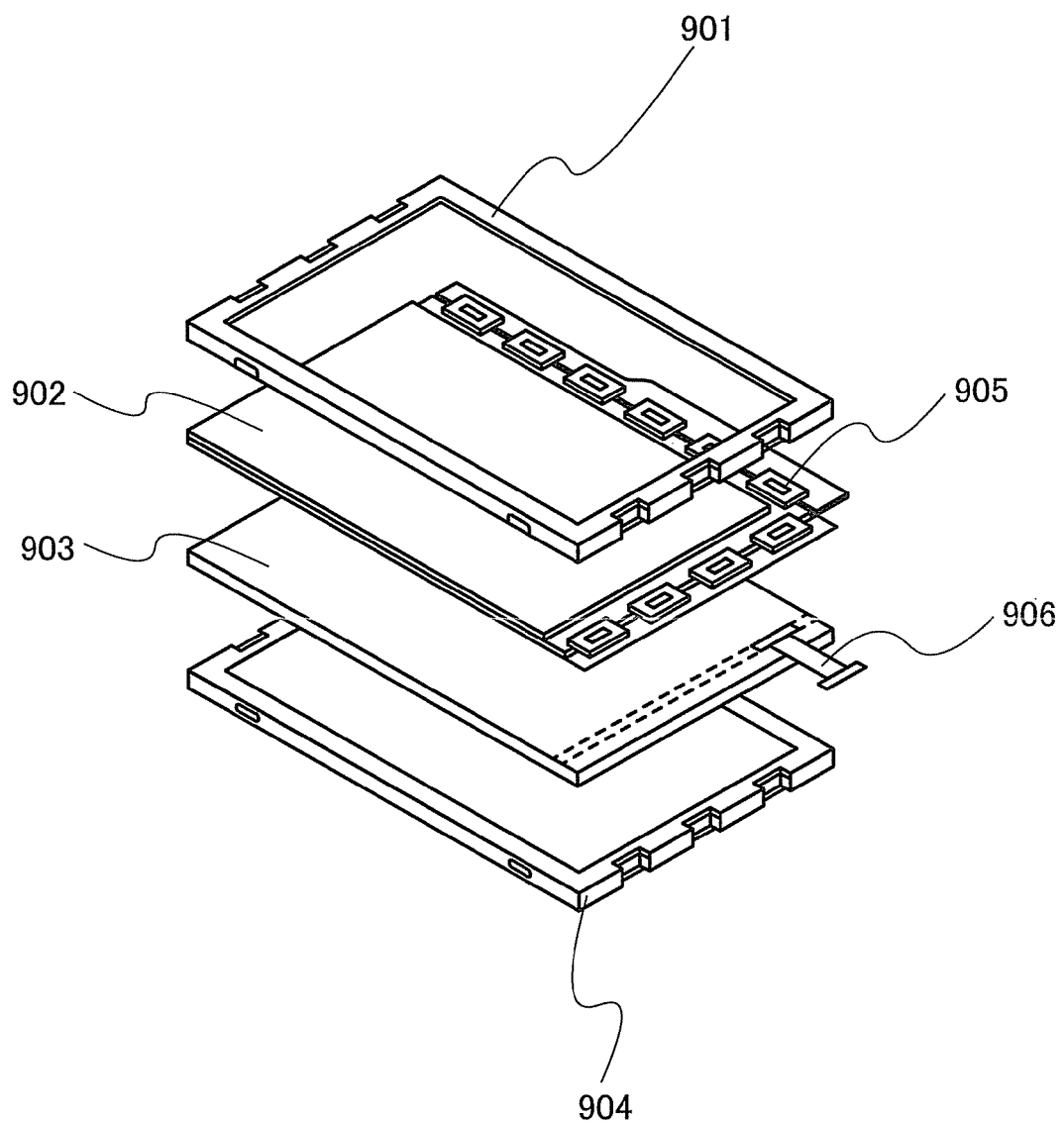
FIG. 6 illustrates an electronic device.

FIG. 6 illustrates an example of a liquid crystal display device using the light-emitting device described in Embodiment 7 as a backlight. The liquid crystal display device illustrated in FIG. 6 includes a housing 901, a liquid crystal layer 902, a backlight 903, and a housing 904. The liquid crystal layer 902 is connected to a driver IC 905. The light-emitting device described in Embodiment 7 is used as the backlight 903, to which a current is supplied through a terminal 906.

With the use of the light-emitting device described in Embodiment 7 as the backlight of the liquid crystal display device, a backlight having less power consumption can be provided. Further, the light-emitting device described in Embodiment 7 is a lighting device with plane light emission and can have a large area. Therefore, the backlight can have a large area, and a liquid crystal display device having a large area can be obtained. Furthermore, since the light-emitting device described in Embodiment 7 is thin, it becomes possible to reduce the thickness of a display device.

Figure 7:
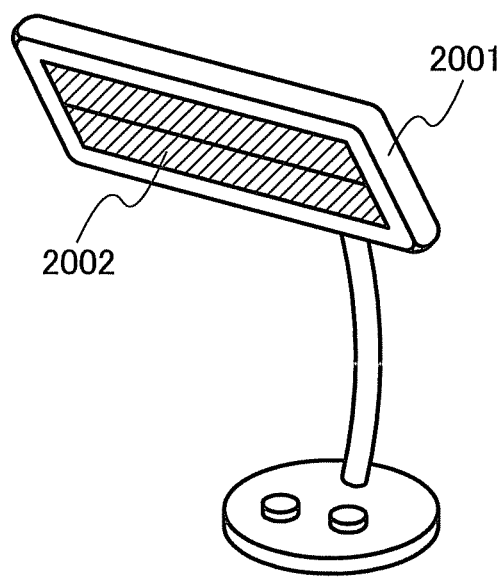
FIG. 7 illustrates a lighting device.

FIG. 7 illustrates an example in which the light-emitting device described in Embodiment 7 is used as a table lamp which is a lighting device. The table lamp illustrated in FIG. 7 includes a housing 2001 and a light source 2002, and the light-emitting device described in Embodiment 7 is used as the light source 2002.

Figure 8:
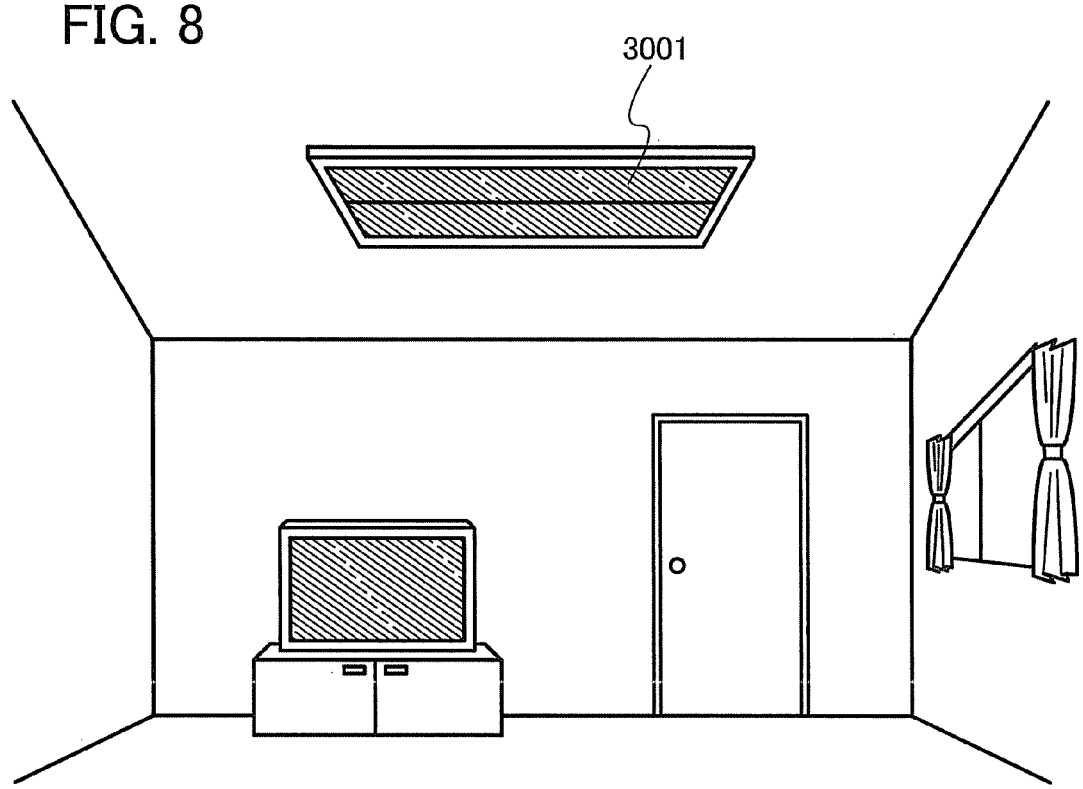
FIG. 8 illustrates lighting devices.

FIG. 8 illustrates an example in which the light-emitting device described in Embodiment 7 is used as an indoor lighting device 3001. Since the light-emitting device described in Embodiment 7 consumes less power, a lighting device that consumes less power can be obtained. Further, since the light-emitting device described in Embodiment 7 can have a large area, the light-emitting device can be used as a large-area lighting device. Further, since the light-emitting device described in Embodiment 7 is thin, the light-emitting device can be used for a lighting device having reduced thickness.

Example 1

Synthesis Example 1

In this example is described a method of synthesizing 3-(dibenzothiophen-4-yl)-9-[4-(10-phenyl-9-anthryl)phenyl]-9H-carbazole (abbreviation: DBTCzPA-II), which is the carbazole derivative represented by the structural formula (358) in Embodiment 1. A structure of DBTCzPA-II is illustrated in the following structural formula.

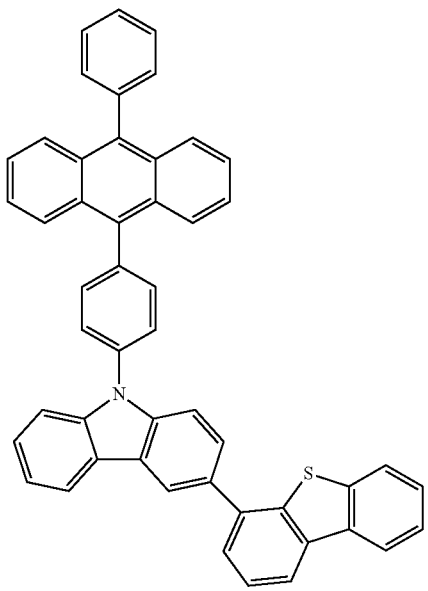

First, a method of synthesizing 3-(dibenzothiophen-4-yl)-9H-carbazole (abbreviation: DBTCz-II), which is a synthetic intermediate of DBTCzPA-II, is described. DBTCz-II is a carbazole derivative represented by the following structural formula. A structure of DBTCz-II is illustrated in the following structural formula.

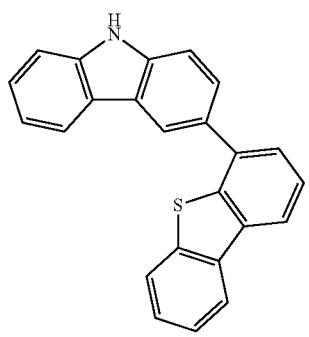 [SMILES: c1ccc2c(c1)[nH]c1ccc(-c3cccc4c3sc3ccccc34)cc12]

Step 1: Synthesis of
3-(Dibenzothiophen-4-yl)-9H-carbazole
(abbreviation: DBTCz-II)

In a 200-mL three-neck flask were put 3.0 g (12 mmol) of 3-bromocarbazole, 2.8 g (12 mmol) of dibenzothiophene-4-boronic acid, and 150 mg (0.5 mol) of tri(ortho-tolyl)phosphine, and the air in the flask was replaced with nitrogen. To this mixture were added 40 mL of toluene, 40 mL of ethanol, and 15 mL (2.0 mol/L) of an aqueous potassium carbonate solution. In the flask, the mixture was degassed by being stirred under reduced pressure. After the degassing, replacement with nitrogen was performed, and 23 mg (0.10 mmol) of palladium(II) acetate was added to this mixture, and then the mixture was refluxed at 110° C. for 3 hours. After the reflux, the mixture was cooled to room temperature, and then the precipitated solid was collected by suction filtration. The collected solid was dissolved in 100 mL of toluene, and this solution was filtered through Celite (produced by Wako Pure Chemical Industries, Ltd., Catalog No. 531-16855), Florisil (produced by Wako Pure Chemical Industries, Ltd., Catalog No. 540-00135), and alumina. The solid obtained by concentration of the obtained filtrate was recrystallized from toluene/hexane, so that 1.4 g of a white solid, which was the object of the synthesis, was obtained in 32% yield. The synthesis scheme of Step 1 is illustrated in (a-1).

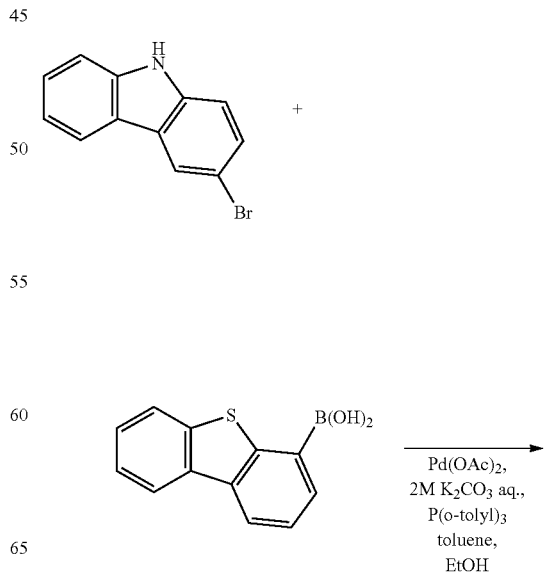

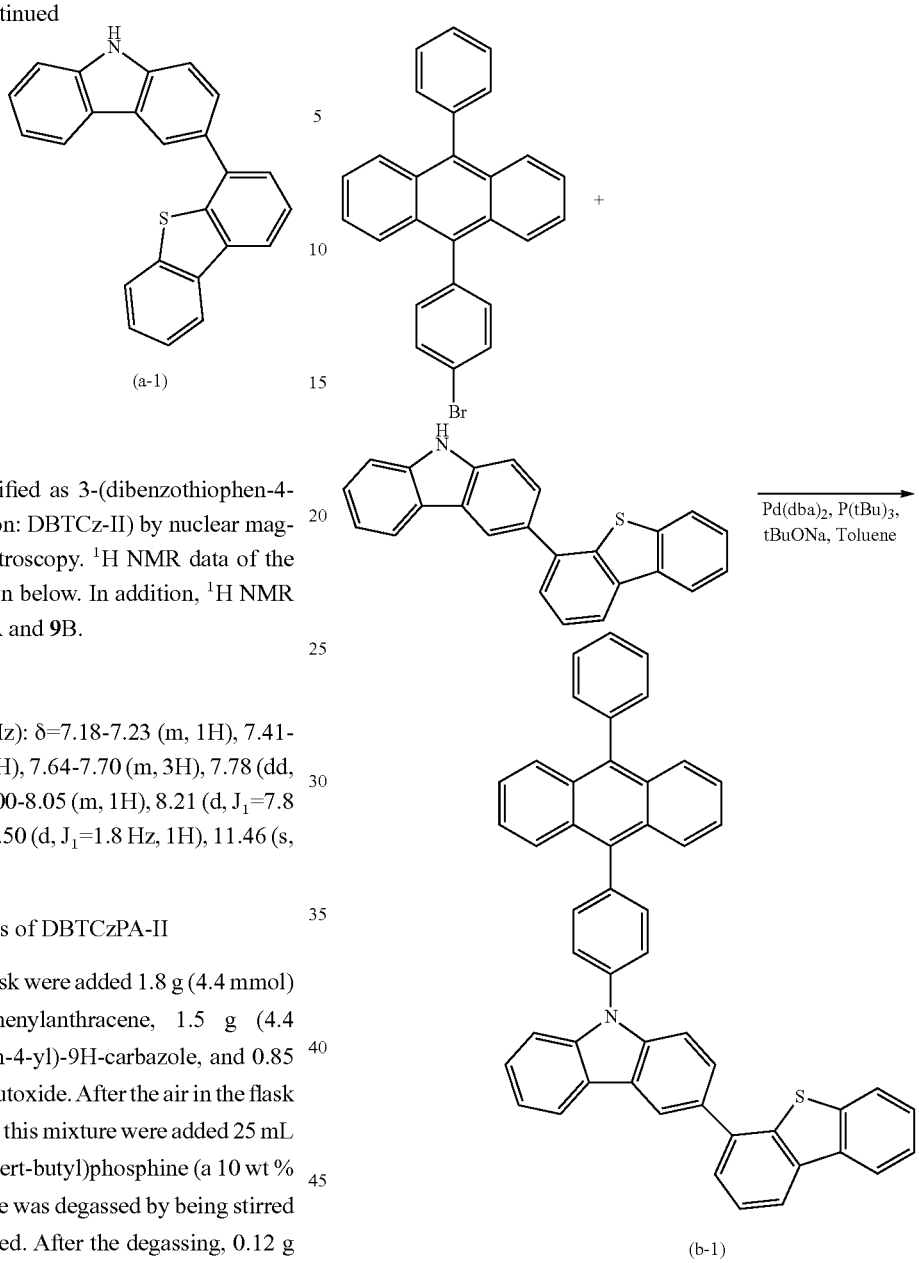

(a-1)

Figure 9A:
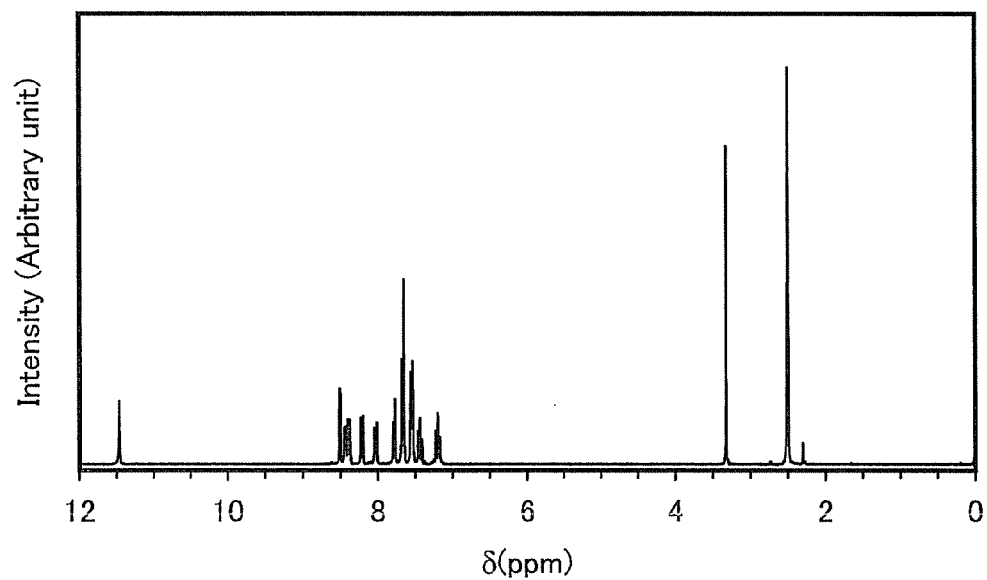
FIGS. 9A and 9B are $^1$H NMR charts of DBTCz-II.
Figure 9B:
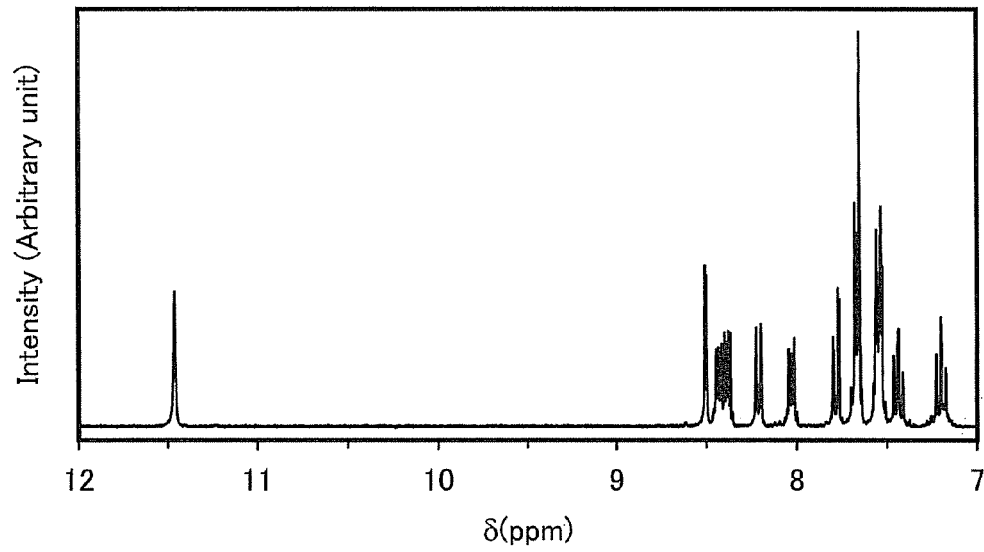

This compound was identified as 3-(dibenzothiophen-4-yl)-9H-carbazole (abbreviation: DBTCz-II) by nuclear magnetic resonance (NMR) spectroscopy. $^1$H NMR data of the obtained compound are shown below. In addition, $^1$H NMR charts are shown in FIGS. 9A and 9B.

$^1$H NMR (DMSO, 300 MHz): δ=7.18-7.23 (m, 1H), 7.41-7.46 (m, 1H), 7.51-7.53 (m, 3H), 7.64-7.70 (m, 3H), 7.78 (dd, $J_1$=1.8 Hz, $J_2$=8.1 Hz, 1H), 8.00-8.05 (m, 1H), 8.21 (d, $J_1$=7.8 Hz, 1H), 8.35-8.46 (m, 2H), 8.50 (d, $J_1$=1.8 Hz, 1H), 11.46 (s, 1H)

Step 2: Synthesis of DBTCzPA-II

To a 100-mL three-neck flask were added 1.8 g (4.4 mmol) of 9-(4-bromophenyl)-10-phenylanthracene, 1.5 g (4.4 mmol) of 3-(dibenzothiophen-4-yl)-9H-carbazole, and 0.85 g (8.8 mmol) of sodium tert-butoxide. After the air in the flask was replaced with nitrogen, to this mixture were added 25 mL of toluene and 2.2 mL of tri-(tert-butyl)phosphine (a 10 wt % hexane solution). This mixture was degassed by being stirred while the pressure was reduced. After the degassing, 0.12 g (0.22 mmol) of bis(dibenzylideneacetone)palladium(0) was added to the mixture. This mixture was stirred at 110° C. for 18 hours under a nitrogen stream, so that a solid was precipitated. After the stirring, this mixture was cooled to room temperature, and the precipitated solid was collected by suction filtration. The collected solid was dissolved in about 60 mL of toluene, and the obtained solution was suction-filtered through Celite (produced by Wako Pure Chemical Industries, Ltd., Catalog No. 531-16855), Florisil (produced by Wako Pure Chemical Industries, Ltd., Catalog No. 540-00135), and alumina. The obtained filtrate was concentrated to give a solid and the solid was recrystallized from toluene, so that 1.1 g of a white powder was obtained in 36% yield. The synthesis scheme of Step 2 is illustrated in (b-1).

Then, 1.1 g of the obtained white powder was purified. Using a train sublimation method, the purification was conducted by heating of the white powder at 300° C. under a pressure of 3.0 Pa with a flow rate of argon gas of 4.0 mL/min. After the purification, 1.0 g of a pale yellow solid was obtained in 90% yield.

The pale yellow solid after the above purification was subjected to nuclear magnetic resonance (NMR) spectroscopy. The measurement data are shown below.

$^1$H NMR (CDCl$_3$, 300 MHz): δ=7.36-7.68 (m, 15H), 7.72-7.93 (m, 12H), 8.19-8.286 (m, 3H), 8.57 (sd, $J_1$=1.5 Hz, 1H)

Figure 10:
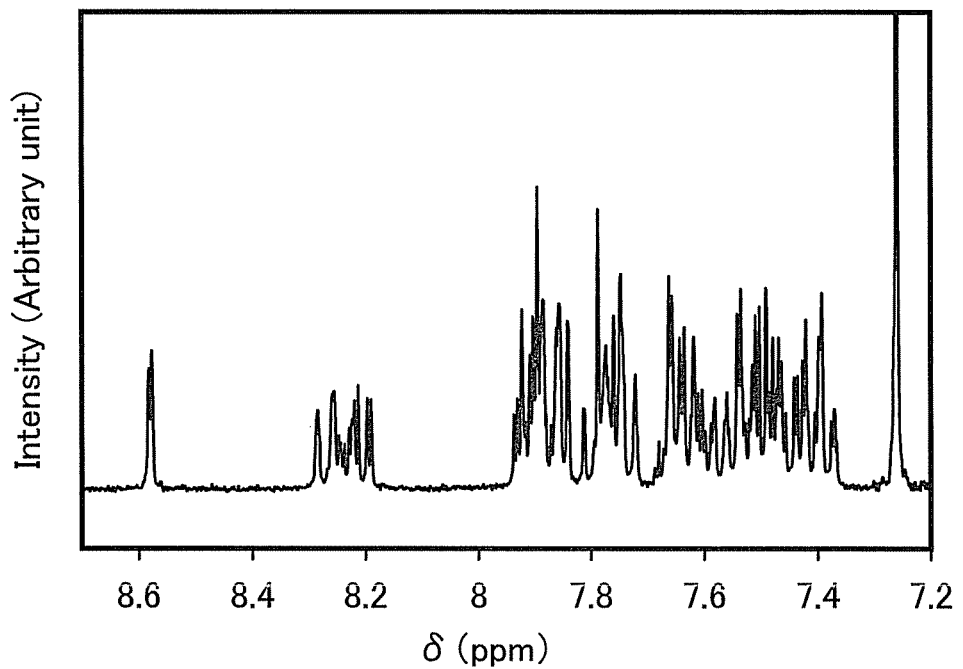
FIG. 10 is a $^1$H NMR chart of DBTCzPA-II.

Further, a $^1$H NMR chart is shown in FIG. 10. The measurement results showed that DBTCzPA-II, which is the carbazole derivative represented by the above structural formula, was obtained.

Figure 11A:
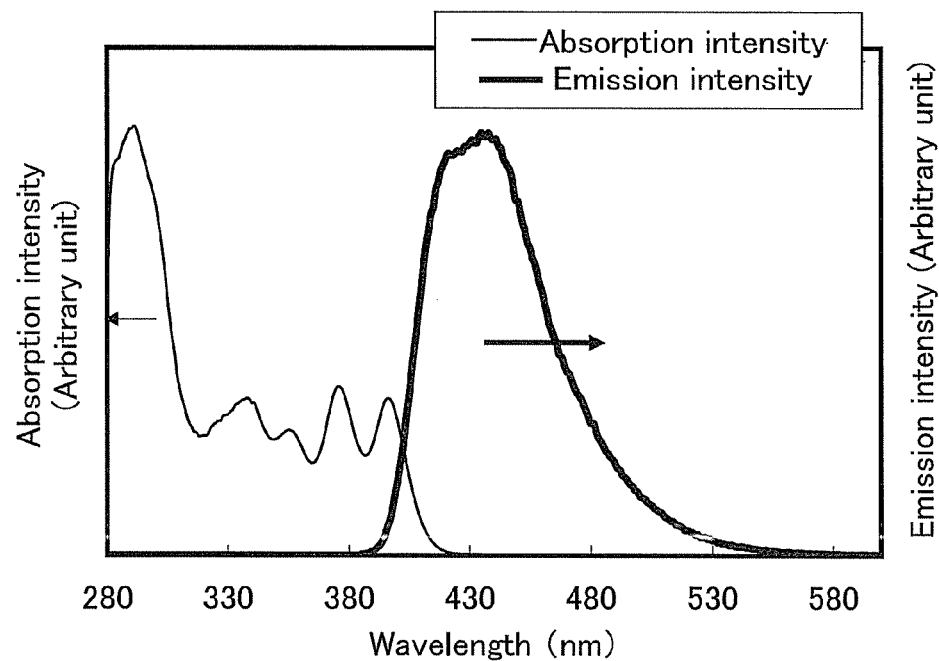
FIGS. 11A and 11B show absorption spectra and emission spectra of DBTCzPA-II.
Figure 11B:
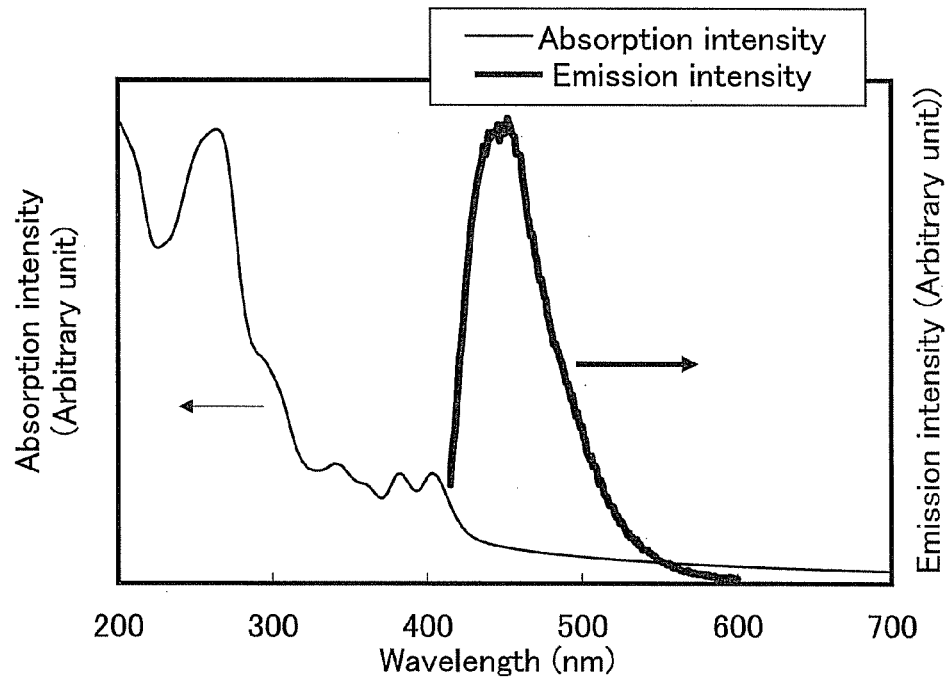

Next, an absorption and emission spectra of DBTCzPA-II in a toluene solution of DBTCzPA-II are shown in FIG. 11A, and an absorption and emission spectra of a thin film of DBTCzPA-II are shown in FIG. 11B. An ultraviolet-visible spectrophotometer (V-550, manufactured by JASCO Corporation) was used for the measurements of the absorption spectra. In the case of the toluene solution, the measurements were made with the toluene solution of DBTCzPA-II put in a quartz cell, and the absorption spectrum obtained by subtraction of absorption spectra of the quartz cell and toluene from the measured spectrum is shown in the drawing. In addition, as for the absorption spectrum of the thin film, a sample was prepared by evaporation of DBTCzPA-II on a quartz substrate, and the absorption spectrum obtained by subtraction of an absorption spectrum of quartz from the absorption spectrum of this sample is shown in the drawing. As in the measurements of the absorption spectra, an ultraviolet-visible spectrophotometer (V-550, manufactured by JASCO Corporation) was used for the measurements of the emission spectra. The emission spectrum of the toluene solution was measured with the toluene solution of DBTCzPA-II put in a quartz cell, and the emission spectrum of the thin film was measured with a sample prepared by evaporation of DBTCzPA-II on a quartz substrate. Thus, it was found that the greatest emission wavelength of DBTCzPA-II in the toluene solution of DBTCzPA-II was around 436 nm (at an excitation wavelength of 376 nm), and that the greatest emission wavelength of the thin film of DBTCzPA-II was around 447 nm (at an excitation wavelength of 400 nm).

Further, the ionization potential of DBTCzPA-II in a thin film state was measured by a photoelectron spectrometer (AC-2, manufactured by Riken Keiki, Co., Ltd.) in air. The obtained value of the ionization potential was converted to a negative value, so that the HOMO level of DBTCzPA-II was −5.73 eV. From the data of the absorption spectra of the thin film in FIG. 11B, the absorption edge of DBTCzPA-II, which was obtained from Tauc plot with an assumption of direct transition, was 2.92 eV. Therefore, the optical energy gap of DBTCzPA-II in the solid state was estimated at 2.92 eV; from the values of the HOMO level obtained above and this energy gap, the LUMO level of DBTCzPA-II was able to be estimated at −2.81 eV. It was thus found that DBTCzPA-II had a wide energy gap of 2.92 eV in the solid state.

Further, the oxidation reaction characteristics of DBTCzPA-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from −0.05 V to 1.10 V and then changed from 1.10 V to −0.05 V was one cycle, and 100 cycles were performed.

The measurement results revealed that DBTCzPA-II showed properties effective against repetition of redox reactions between an oxidized state and a neutral state without a large variation in oxidation peak even after the 100 cycles in the measurements.

Further, the HOMO level of DBTCzPA-II was determined also by calculation from the CV measurement results.

First, the potential energy of the reference electrode with respect to the vacuum level used was found to be −4.94 eV. The oxidation peak potential $E_{pa}$ of DBTCzPA-II was 1.01 V. In addition, the reduction peak potential $E_{pc}$ thereof was 0.86 V. Therefore, a half-wave potential (an intermediate potential between $E_{pa}$ and $E_{pc}$) can be calculated at 0.94 V. This means that DBTCzPA-II is oxidized by an electric energy of 0.94 [V vs. Ag/Ag$^+$], and this energy corresponds to the HOMO level. Here, since the potential energy of the reference electrode, which was used in this example, with respect to the vacuum level is −4.94 [eV] as described above, the HOMO level of DBTCzPA-II was calculated as follows: −4.94−0.94=−5.88 [eV].

Note that the potential energy of the reference electrode (Ag/Ag$^+$ electrode) with respect to the vacuum level corresponds to the Fermi level of the Ag/Ag$^+$ electrode, and should be calculated from a value obtained by measuring a substance whose potential energy with respect to the vacuum level is known, with the use of the reference electrode (Ag/Ag$^+$ electrode).

How the potential energy (eV) of the reference electrode (Ag/Ag$^+$ electrode), which was used in this example, with respect to the vacuum level is determined by calculation is specifically described. It is known that the oxidation-reduction potential of ferrocene in methanol is +0.610 [V vs. SHE] with respect to a standard hydrogen electrode (Reference: Christian R. Goldsmith et al., *J. Am. Chem. Soc.*, Vol. 124, No. 1, pp. 83-96, 2002). In contrast, using the reference electrode used in this example, the oxidation-reduction potential of ferrocene in methanol was calculated at +0.11 [V vs. Ag/Ag$^+$]. Thus, it was found that the potential energy of the reference electrode used in this example was lower than that of the standard hydrogen electrode by 0.50 [eV].

Here, it is known that the potential energy of the standard hydrogen electrode with respect to the vacuum level is −4.44 eV (Reference: Toshihiro Ohnishi and Tamami Koyama, *High molecular EL material*, Kyoritsu shuppan, pp. 64-67). Therefore, the potential energy of the reference electrode used in this example with respect to the vacuum level can be calculated at −4.44−0.50=−4.94 [eV].

Example 2

Synthesis Example 2

In this example is described a method of synthesizing 3-(dibenzofuran-4-yl)-9-[4-(10-phenyl-9-anthryl)phenyl]-9'1'-carbazole (abbreviation: DBFCzPA-II), which is the carbazole derivative represented by the structural formula (758) in Embodiment 1. A structure of DBFCzPA-II is illustrated in the following structural formula.

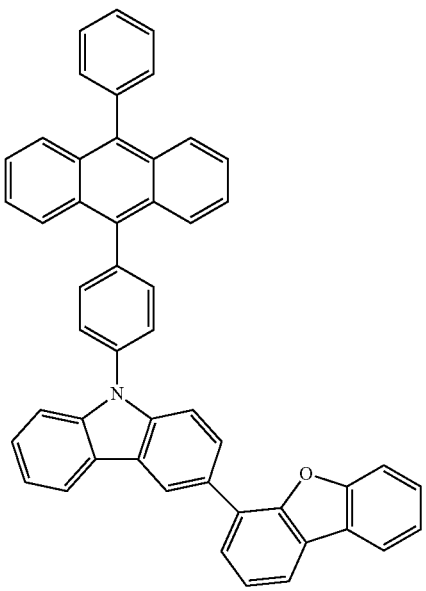 [SMILES: c1ccc(-c2c3ccccc3c(-c3ccc(-n4c5ccccc5c5cc(-c6cccc7c6oc6ccccc67)ccc54)cc3)c3ccccc23)cc1]

First, a method of synthesizing 3-(dibenzofuran-4-yl)-9H-carbazole (abbreviation: DBFCz-II), which is a synthetic intermediate of DBFCzPA-II, is described. 3-(Dibenzo furan-4-yl)-9H-carbazole is a carbazole derivative represented by the following structural formula.

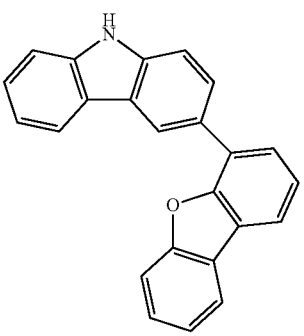 [SMILES: c1ccc2c(c1)[nH]c1ccc(-c3cccc4c3oc3ccccc34)cc12]

Step 1: Synthesis of 3-(Dibenzofuran-4-yl)-9H-carbazole (abbreviation: DBFCz-II)

In a 200-mL three-neck flask were put 2.0 g (8.1 mmol) of 3-bromocarbazole, 1.7 g (8.1 mmol) of dibenzofuran-4-boronic acid, and 150 mg (0.5 mol) of tri(ortho-tolyl)phosphine, and the air in the flask was replaced with nitrogen. To this mixture were added 20 mL of toluene, 20 mL of ethanol, and 15 mL (0.2 mol) of an aqueous potassium carbonate solution (2.0 mol/L). In the flask, the mixture was degassed by being stirred under reduced pressure. Then, 23 mg (0.10 mmol) of palladium(II) acetate was added to this mixture, and then the mixture was refluxed at 80° C. After the reflux, the mixture was cooled to room temperature, and then the obtained solid was collected by suction filtration. The collected solid was dissolved in 100 mL of toluene, and this solution was filtered through Celite (produced by Wako Pure Chemical Industries, Ltd., Catalog No. 531-16855), Florisil (produced by Wako Pure Chemical Industries, Ltd., Catalog No. 540-00135), and alumina. The solid obtained by concentration of the obtained filtrate was recrystallized from toluene/hexane, so that 2.3 g of a white solid was obtained in 85% yield. The synthesis scheme of Step 1 is illustrated in (a-2).

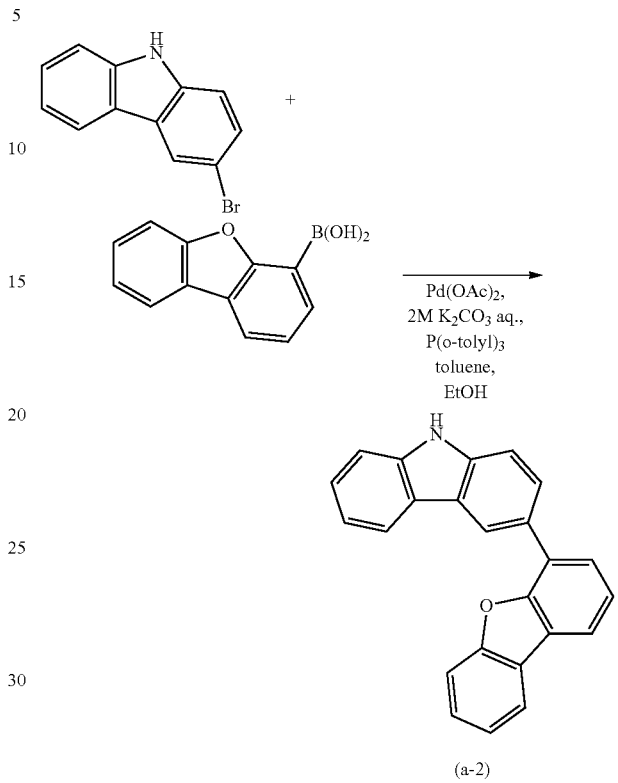

(a-2)

Figure 12A:
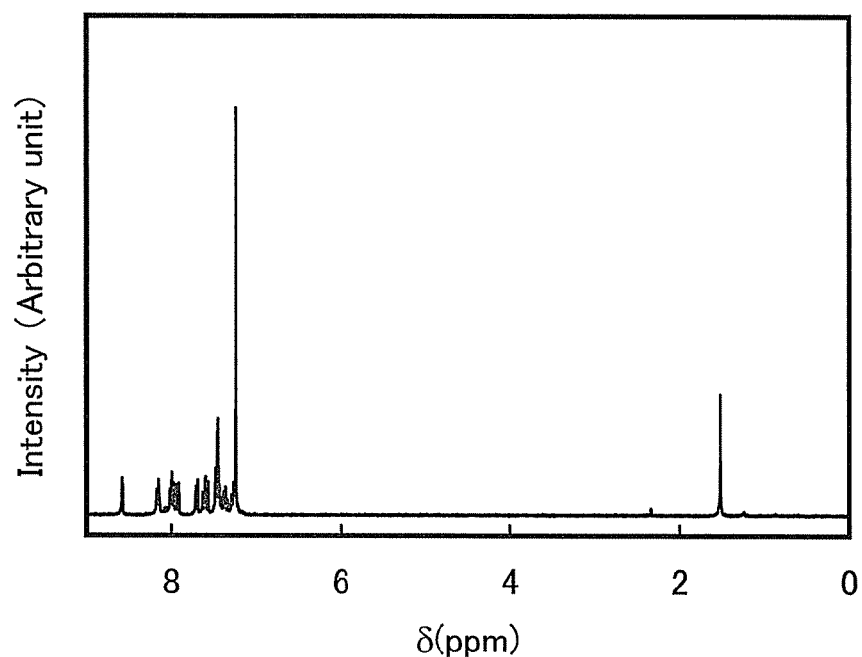
FIGS. 12A and 12B are $^1$H NMR charts of DBFCz-II.
Figure 12B:
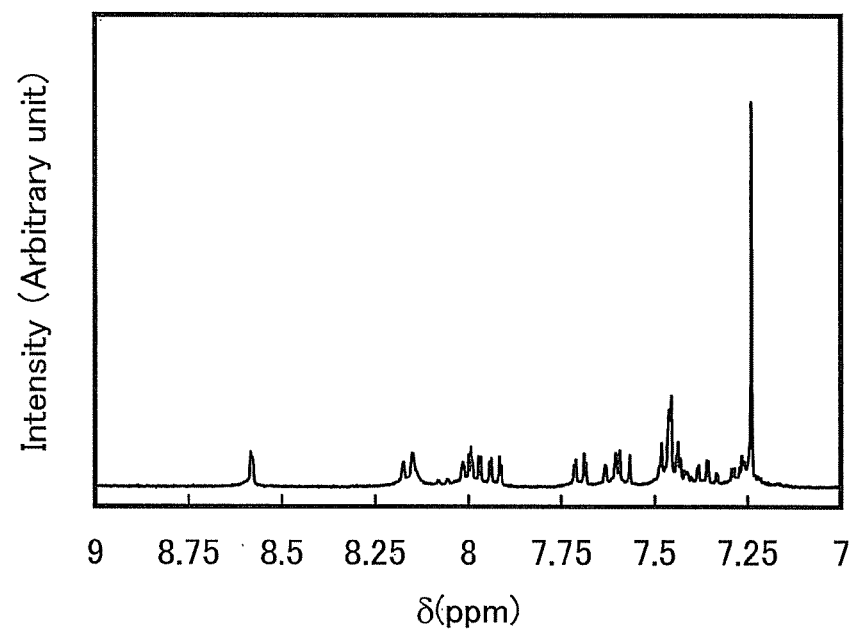

This compound was identified as 3-(dibenzofuran-4-yl)-9H-carbazole (abbreviation: DBFCz-II) by nuclear magnetic resonance (NMR) spectroscopy. $^1$H NMR data of the obtained compound is shown below. In addition, $^1$H NMR charts are shown in FIGS. 12A and 12B.

$^1$H NMR (CDCl$_3$, 300 MHz): δ=7.26-7.29 (m, 1H), 7.33-7.48 (m, 5H), 7.58 (d, J=8.4 Hz, 1H), 7.62 (d, J=8.4 Hz, 1H), 7.70 (dd, J$_1$=1.2 Hz, J$_1$=7.8 Hz, 1H), 7.93 (dd, J$_1$=1.5 Hz, J$_1$=7.5 Hz, 1H), 7.97-8.02 (m, 2H), 8.16 (d, J=7.5 Hz, 2H), 8.58 (d, J=1.5 Hz, 1H)

Step 2: Synthesis of DBFCzPA-II

To a 50-mL three-neck flask were added 0.61 g (1.5 mmol) of 9-(4-bromophenyl)-10-phenylanthracene, 0.50 g (1.5 mmol) of 3-(dibenzofuran-4-yl)-9H-carbazole, and 0.29 g (3.0 mmol) of sodium tert-butoxide. After the air in the flask was replaced with nitrogen, to this mixture were added 8.0 mL of toluene and 0.76 mL of tri-(tert-butyl)phosphine (a 10 wt % hexane solution). This mixture was degassed by being stirred while the pressure was reduced. After the degassing, 43 mg (0.075 mmol) of bis(dibenzylideneacetone)palladium (0) was added to the mixture. This mixture was stirred at 110° C. for 10 hours under a nitrogen stream. After the stirring, the obtained mixture was suction-filtered through Celite (produced by Wako Pure Chemical Industries, Ltd., Catalog No. 531-16855), Florisil (produced by Wako Pure Chemical Industries, Ltd., Catalog No. 540-00135), and alumina. An oily substance obtained by concentration of the obtained filtrate was purified by silica gel column chromatography (developing solvent, hexane:toluene=5:1). The obtained solid was recrystallized from toluene/hexane, so that 0.63 g of a white powder was obtained in 63% yield. The synthesis scheme of Step 2 is illustrated in (b-2).

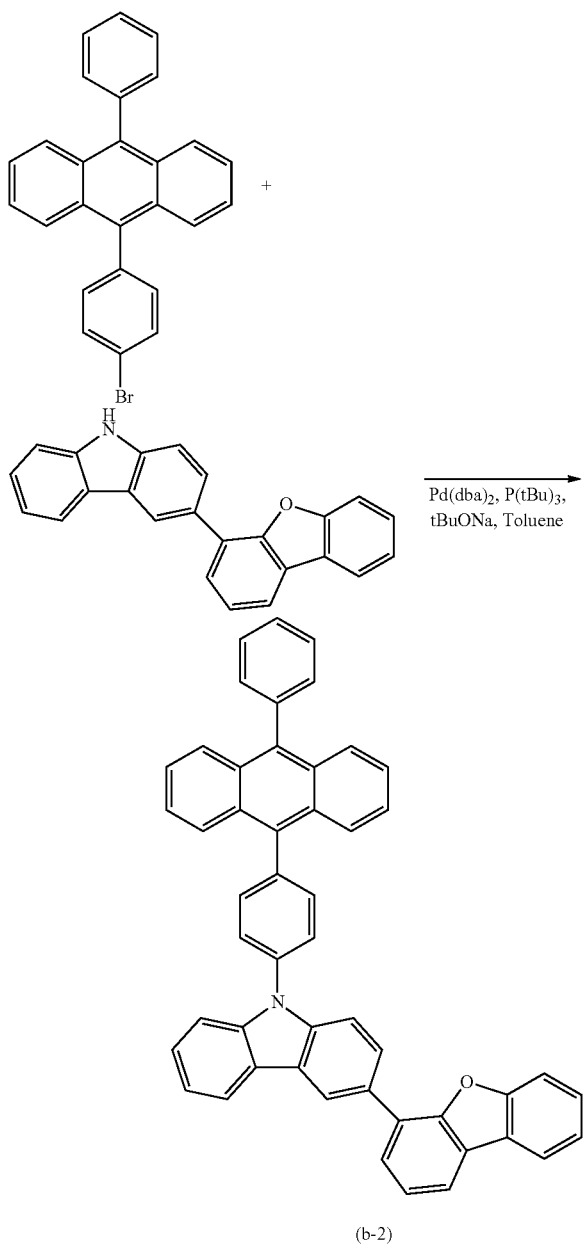

(b-2)

Then, 0.63 g of the obtained white powder was purified. Using a train sublimation method, the purification was conducted by heating of the white powder at 300° C. under a pressure of 3.0 Pa with a flow rate of argon gas of 4.0 mL/min. After the purification, 0.55 g of a pale yellow solid was obtained in 87% yield.

The pale yellow solid after the above purification was subjected to nuclear magnetic resonance (NMR) spectroscopy. The measurement data are shown below.

$^1$H NMR (CDCl$_3$, 300 MHz): δ=7.30-7.66 (m, 15H), 7.71-7.79 (m, 6H), 7.83-7.91 (m, 5H), 7.97 (dd, J$_1$=1.2 Hz, J$_2$=7.2 Hz, 1H), 8.04 (dd, J$_1$=0.90 Hz, J$_2$=7.8 Hz, 1H), 8.10 (dd, J$_1$=1.8 Hz, J$_2$=8.4 Hz, 1H), 8.31 (d, J$_1$=7.5 Hz, 1H), 8.72 (sd, J$_1$=0.90 Hz, 1H)

Figure 13:
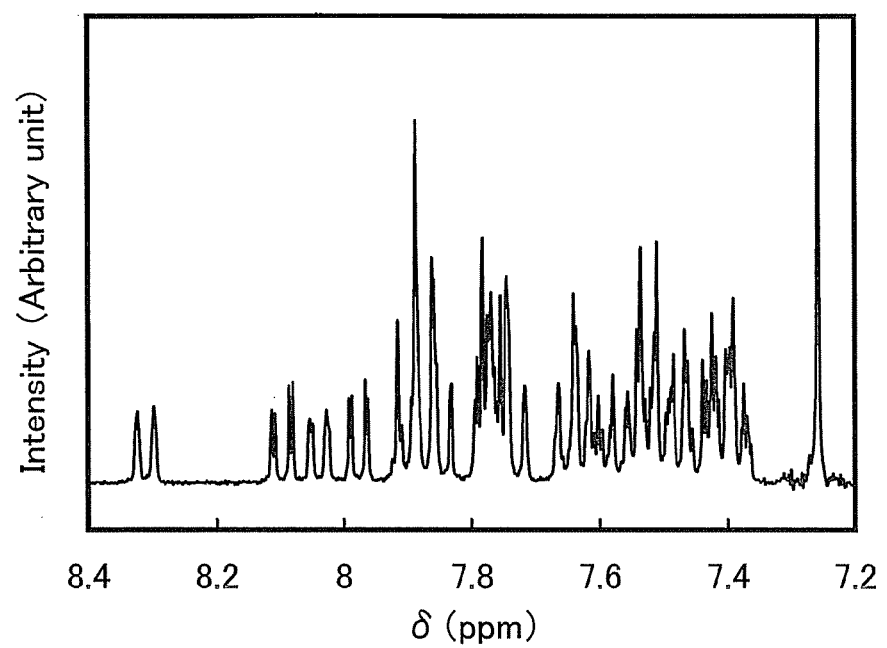
FIG. 13 is a $^1$H NMR chart of DBFCzPA-II.

Further, a $^1$H NMR chart is shown in FIG. 13. The measurement results showed that DBFCzPA-II, which is the carbazole derivative represented by the above structural formula, was obtained.

Figure 14A:
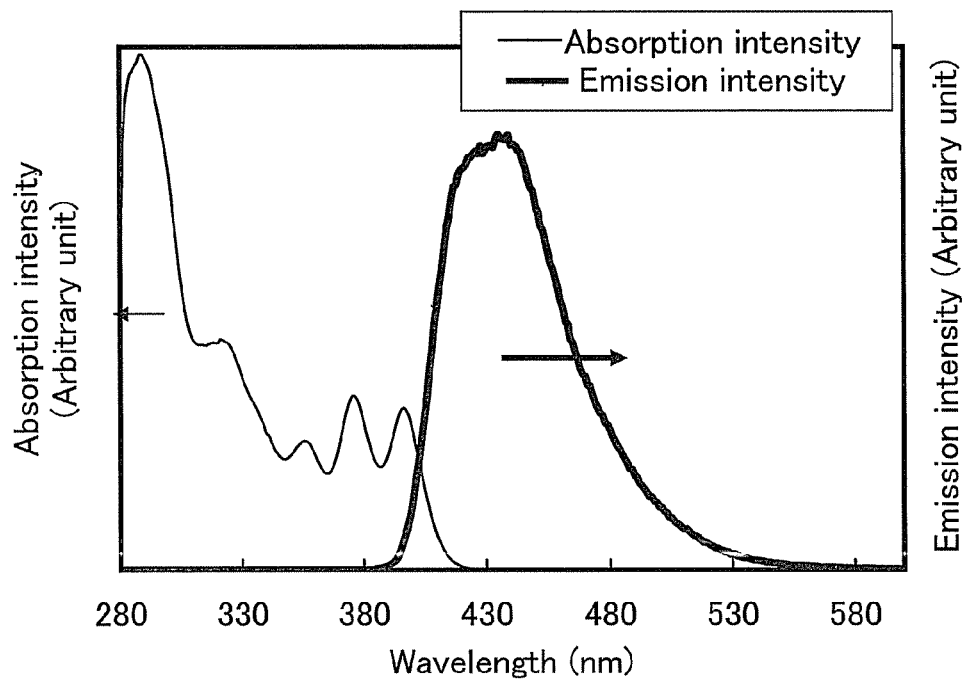
FIGS. 14A and 14B show absorption spectra and emission spectra of DBFCzPA-II.
Figure 14B:
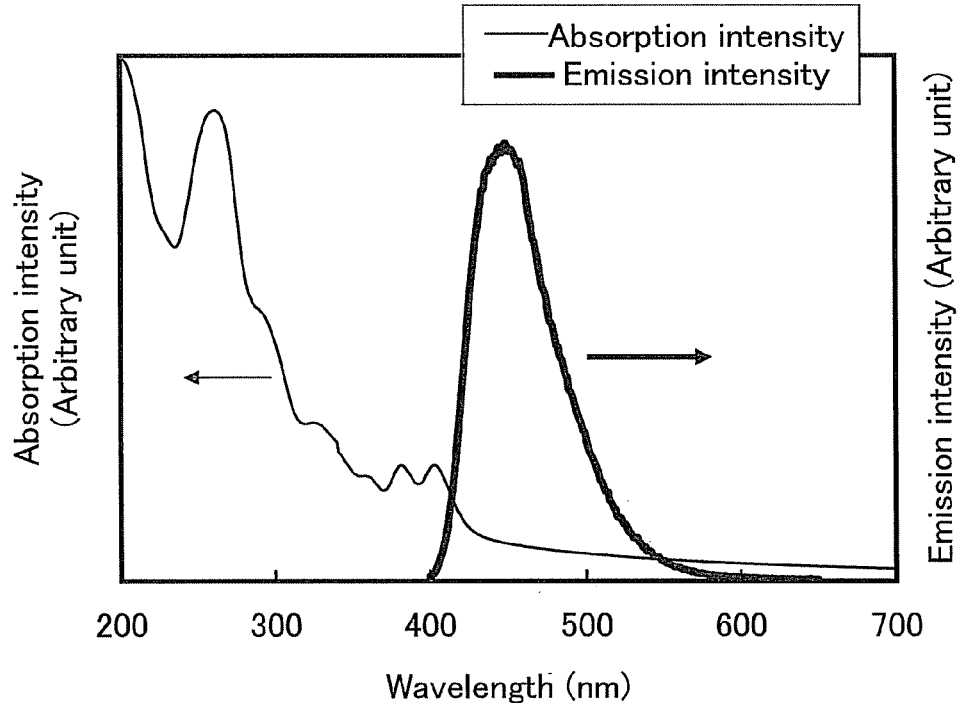

Next, an absorption and emission spectra of DBFCzPA-II in a toluene solution of DBFCzPA-II are shown in FIG. 14A, and an absorption and emission spectra of a thin film of DBFCzPA-II are shown in FIG. 14B. An ultraviolet-visible spectrophotometer (V-550, manufactured by JASCO Corporation) was used for the measurements of the absorption spectra. In the case of the toluene solution, the measurements were made with the toluene solution of DBFCzPA-II put in a quartz cell, and the absorption spectrum obtained by subtraction of absorption spectra of the quartz cell and toluene from the measured spectrum is shown in the drawing. In addition, as for the absorption spectrum of the thin film, a sample was prepared by evaporation of DBFCzPA-II on a quartz substrate, and the absorption spectrum obtained by subtraction of an absorption spectrum of quartz from the absorption spectrum of this sample is shown in the drawing. As in the measurements of the absorption spectra, an ultraviolet-visible spectrophotometer (V-550, manufactured by JASCO Corporation) was used for the measurements of the emission spectra. The emission spectrum of the toluene solution was measured with the toluene solution of DBFCzPA-II put in a quartz cell, and the emission spectrum of the thin film was measured with a sample prepared by evaporation of DBFCzPA-II on a quartz substrate. Thus, it was found that the greatest emission wavelength of DBFCzPA-II in the toluene solution of DBFCzPA-II was around 435 nm (at an excitation wavelength of 376 nm), and that the greatest emission wavelength of the thin film of DBFCzPA-II was around 449 nm (at an excitation wavelength of 380 nm).

Further, the ionization potential of DBFCzPA-II in a thin film state was measured by a photoelectron spectrometer (AC-2, manufactured by Riken Keiki, Co., Ltd.) in air. The obtained value of the ionization potential was converted to a negative value, so that the HOMO level of DBFCzPA-II was −5.64 eV. From the data of the absorption spectra of the thin film in FIG. 14B, the absorption edge of DBFCzPA-II, which was obtained from Tauc plot with an assumption of direct transition, was 2.93 eV. Therefore, the optical energy gap of DBFCzPA-II in the solid state was estimated at 2.93 eV; from the values of the HOMO level obtained above and this energy gap, the LUMO level of DBFCzPA-II was able to be estimated at −2.71 eV. It was thus found that DBFCzPA-II had a wide energy gap of 2.93 eV in the solid state.

Further, the oxidation reaction characteristics of DBFCzPA-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich. Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from 0.35 V to 0.95 V and then changed from 0.95 V to 0.35 V was one cycle, and 100 cycles were performed.

The measurement results revealed that DBFCzPA-II showed properties effective against repetition of redox reactions between an oxidized state and a neutral state without a large variation in oxidation peak even after the 100 cycles in the measurements.

Further, the HOMO level of DBFCzPA-II was determined also by calculation from the CV measurement results.

First, the potential energy of the reference electrode with respect to the vacuum level used was found to be −4.94 eV, as determined in Example 1. The oxidation peak potential $E_{pa}$ of DBFCzPA-II was 0.91 V. In addition, the reduction peak potential $E_{pc}$ thereof was 0.78 V. Therefore, a half-wave potential (an intermediate potential between $E_{pa}$ and $E_{pc}$) can be calculated at 0.85 V. This means that DBFCzPA-II is oxidized by an electric energy of 0.85 [V vs. Ag/Ag$^+$], and this energy corresponds to the HOMO level. Here, since the potential energy of the reference electrode, which was used in this example, with respect to the vacuum level is −4.94 [eV] as described above, the HOMO level of DBFCzPA-II was calculated as follows: −4.94−0.85=−5.79 [eV].

Example 3

Synthesis Example 3

In this example is described a method of synthesizing 3-(dibenzothiophen-4-yl)-9-(triphenylen-2-yl)-9H-carbazole (abbreviation: DBTCzTp-II), which is the carbazole derivative represented by the structural formula (287) in Embodiment 1. A structure of DBTCzTp-II is illustrated in the following structural formula (5).

Step 1: Synthesis of 3-(Dibenzothiophen-4-yl)-9H-carbazole

This was synthesized as in Step 1 in Synthesis Example 1.

Step 2: Synthesis of DBTCzTp-II

In a 100-mL three-neck flask were put 1.0 g (2.9 mmol) of 2-bromotriphenylene and 0.88 g (2.9 mmol) of 3-(dibenzothiophen-4-yl)-9H-carbazole, and the air in the flask was replaced with nitrogen. To this mixture were added 15 mL of toluene, 0.10 mL of tri(tert-butyl)phosphine (a 10 wt % hexane solution), 0.45 g (4.3 mmol) of sodium tert-butoxide. This mixture was degassed while being stirred under reduced pressure. After the degassing, replacement with nitrogen was performed, this mixture was heated to 80° C., and then 14 mg (0.025 mmol) of bis(dibenzylideneacetone)palladium(0) was added thereto. This mixture was stirred at 80° C. for 4 hours. After the stirring, 15 mg (0.025 mmol) of bis(dibenzylideneacetone)palladium(0) was added to this mixture, and then it was further stirred at 110° C. for 8 hours. After the stirring, about 30 mL of toluene was added to the mixture, and then it was stirred at 80° C. The mixture was subjected to hot filtration through Celite (produced by Wako Pure Chemical Industries, Ltd., Catalog No. 531-16855), Florisil (produced by Wako Pure Chemical Industries, Ltd., Catalog No. 540-00135), and alumina. The obtained filtrate was concentrated to give a white solid. The obtained solid was purified by silica gel column chromatography (developing solvent, hexane:ethyl acetate=9:1), and further recrystallized from toluene/hexane, so that 0.50 g of a white solid was obtained in 27% yield. The synthesis scheme of Step. 2 is illustrated in (b-3).

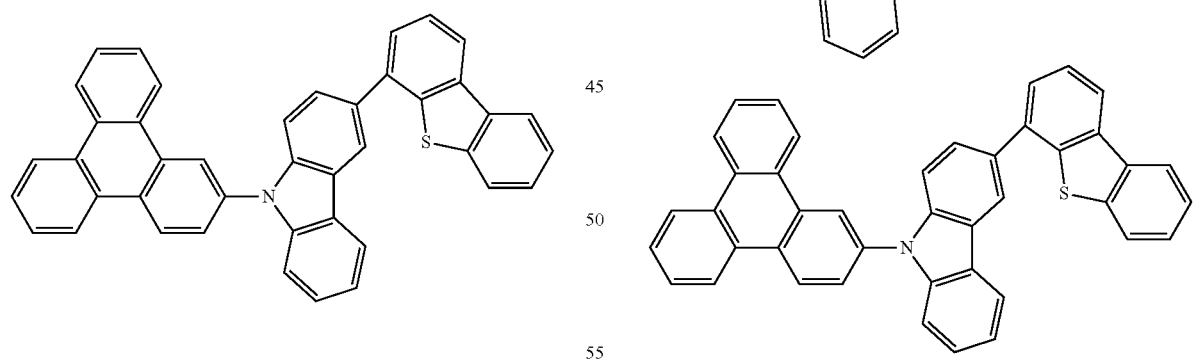

(b-3)

By a train sublimation method, 0.50 g of the obtained white solid was purified. In the purification, the pressure was 2.1 Pa, the flow rate of argon gas was 5.0 mL/min, and the temperature of the heating was 310° C. After the purification, 0.40 g of a colorless transparent solid was obtained in a yield of 78%.

Figure 15A:
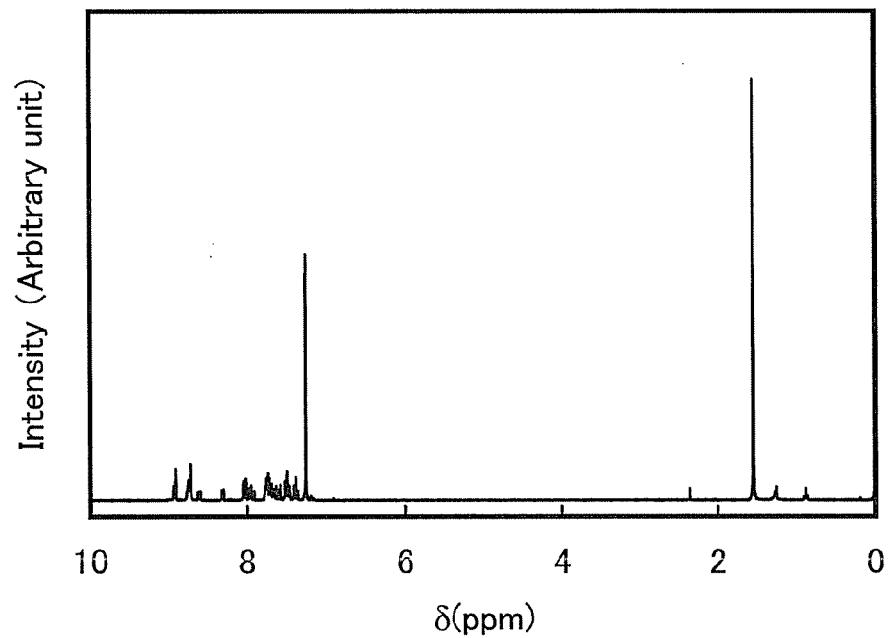
FIGS. 15A and 15B are $^1$H NMR charts of DBTCzTp-II.
Figure 15B:
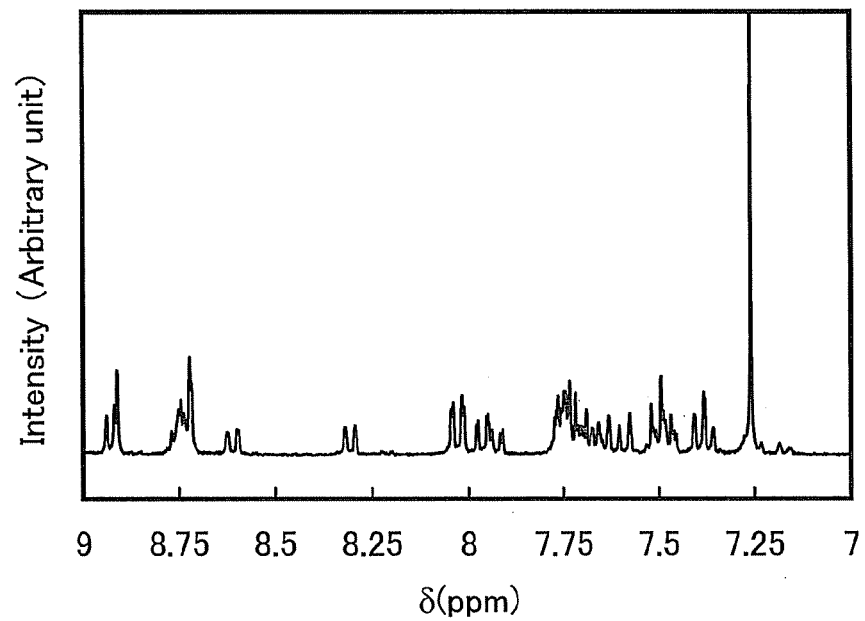

The colorless and transparent solid after the purification was subjected to nuclear magnetic resonance (NMR) spectroscopy. The measurement data are shown below. In addition, $^1$H NMR charts are shown in FIGS. 15A and 15B.

¹H NMR (CDCl₃, 300 MHz): δ=7.37-7.41 (m, 2H), 7.45-7.52 (m, 3H), 7.58-7.77 (m, 8H), 7.93 (dd, $J_1$=2.1 Hz, $J_1$=8.7 Hz, 1H), 7.96 (dd, $J_1$=1.5 Hz, $J_1$=7.8 Hz, 1H), 8.03 (dd, $J_1$=1.5 Hz, $J_1$=8.2 Hz, 2H), 8.31 (d, J=7.5 Hz, 1H), 8.61 (dd, $J_1$=1.5 Hz, $J_2$=8.0 Hz, 1H), 8.72-8.77 (m, 4H), 8.91-8.94 (m, 2H)

The measurement results showed that DBTCzTp-II, which is the carbazole derivative represented by the above structural formula (5), was obtained.

Figure 16A:
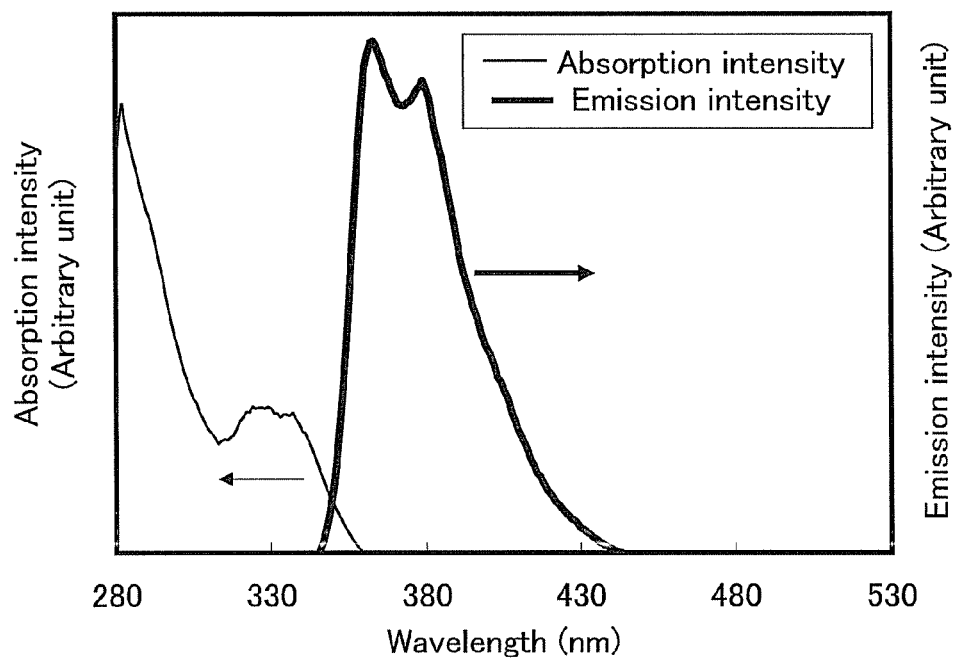
FIGS. 16A and 16B show absorption spectra and emission spectra of DBTCzTp-II.
Figure 16B:
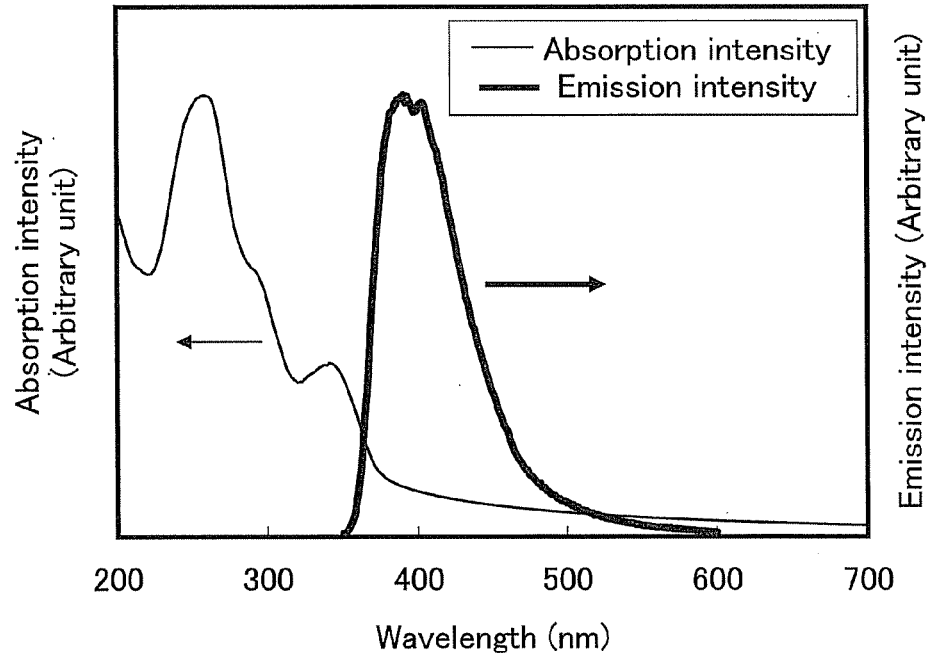

Next, an absorption and emission spectra of DBTCzTp-II in a toluene solution of DBTCzTp-II are shown in FIG. 16A, and an absorption and emission spectra of a thin film of DBTCzTp-II are shown in FIG. 16B. An ultraviolet-visible spectrophotometer (V-550, manufactured by JASCO Corporation) was used for the measurements of the absorption spectra. In the case of the toluene solution, the measurements were made with the toluene solution of DBTCzTp-II put in a quartz cell, and the absorption spectrum obtained by subtraction of absorption spectra of the quartz cell and toluene from the measured spectrum is shown in the drawing. In addition, as for the absorption spectrum of the thin film, a sample was prepared by evaporation of DBTCzTp-II on a quartz substrate, and the absorption spectrum obtained by subtraction of an absorption spectrum of quartz from the absorption spectrum of this sample is shown in the drawing. As in the measurements of the absorption spectra, an ultraviolet-visible spectrophotometer (V-550, manufactured by JASCO Corporation) was used for the measurements of the emission spectra. The emission spectrum of the toluene solution was measured with the toluene solution of DBTCzTp-II put in a quartz cell, and the emission spectrum of the thin film was measured with a sample prepared by evaporation of DBTCzTp-II on a quartz substrate. Thus, it was found that the greatest emission wavelengths of DBTCzTp-II in the toluene solution of DBTCzTp-II were around 363 nm and around 379 nm (at an excitation wavelength of 340 nm), and that the greatest emission wavelength of the thin film of DBTCzTp-II was around 390 nm (at an excitation wavelength of 336 nm).

Further, the ionization potential of DBTCzTp-II in a thin film state was measured by a photoelectron spectrometer (AC-2, manufactured by Riken Keiki, Co., Ltd.) in air. The obtained value of the ionization potential was converted to a negative value, so that the HOMO level of DBTCzTp-II was −5.84 eV. From the data of the absorption spectra of the thin film in FIG. 16B, the absorption edge of DBTCzTp-II, which was obtained from Tauc plot with an assumption of direct transition, was 3.34 eV. Therefore, the optical energy gap of DBTCzTp-II in the solid state was estimated at 3.34 eV; from the values of the HOMO level obtained above and this energy gap, the LUMO level of DBTCzTp-II was able to be estimated at −2.50 eV. It was thus found that DBTCzTp-II had a wide energy gap of 3.34 eV in the solid state.

Further, the oxidation reaction characteristics of DBTCzTp-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu₄NClO₄, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag⁺ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from −0.05 V to 1.10 V and then changed from 1.10 V to −0.05 V was one cycle, and 100 cycles were performed.

The measurement results revealed that DBTCzTp-II showed properties effective against repetition of redox reactions between an oxidized state and a neutral state without a large variation in oxidation peak even after the 100 cycles in the measurements.

Further, the HOMO level of DBTCzTp-II was determined also by calculation from the CV measurement results.

First, the potential energy of the reference electrode with respect to the vacuum level used was found to be −4.94 eV, as determined in Example 1. The oxidation peak potential $E_{pa}$ of DBTCzTp-II was 1.01 V. In addition, the reduction peak potential $E_{pc}$ thereof was 0.86 V. Therefore, a half-wave potential (an intermediate potential between $E_{pa}$ and $E_{pc}$) can be calculated at 0.94 V. This means that DBTCzTp-II is oxidized by an electric energy of 0.94 [V vs. Ag/Ag⁺], and this energy corresponds to the HOMO level. Here, since the potential energy of the reference electrode, which was used in this example, with respect to the vacuum level is −4.94 [eV] as described above, the HOMO level of DBTCzTp-II was calculated as follows: −4.94−0.94=−5.88 [eV].

Example 4

Synthesis Example 4

In this example is described a method of synthesizing 3-(dibenzofuran-4-yl)-9-(triphenylen-2-yl)carbazole (abbreviation: DBFCzTp-II), which is the carbazole derivative represented by the structural formula (687) in Embodiment 1. A structure of DBFCzTp-II is illustrated in the following structural formula (6).

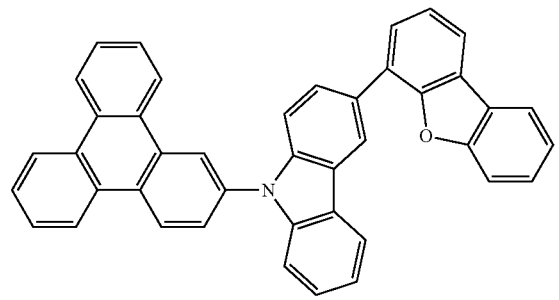 [SMILES: c1ccc2c(c1)oc1c(-c3ccc4c(c3)c3ccccc3n4-c3ccc4c5ccccc5c5ccccc5c4c3)cccc12]

Step 1: Synthesis of
3-(Dibenzofuran-4-yl)-9H-carbazole

This was synthesized as in Step 1 in Example 2.

Step 2: Synthesis of DBFCzTp-II

In a 50-mL three-neck flask were put 0.62 g (2.0 mmol) of 2-bromotriphenylene and 0.67 g (2.0 mmol) of 3-dibenzofuran-4-yl)-9H-carbazol, and the air in the flask was replaced with nitrogen. To this mixture were added 15 mL of toluene, 0.10 mL of tri(tert-butyl)phosphine (a 10 wt % hexane solution), 0.48 g (4.3 mmol) of sodium tert-butoxide. This mixture was degassed while being stirred under reduced pressure. After this mixture was heated at 80° C., 14 mg (0.025 mmol) of bis(dibenzylideneacetone)palladium(0) was added thereto. This mixture was stirred at 110° C. for 15.5 hours. After the stirring, the mixture was washed twice with about 30 mL of water, and the mixture was separated into an organic layer and a washed aqueous layer. Then, the aqueous layer was subjected to extraction twice with about 30 mL of toluene. The organic layer and the solution of the extract were combined and washed once with about 100 mL of saturated brine. The obtained organic layer was dried over magnesium sulfate, and this mixture was subjected to filtration through Celite (produced by Wako Pure Chemical Industries, Ltd., Catalog No. 531-16855), Florisil (produced by Wako Pure Chemical Industries, Ltd., Catalog No. 540-00135), and alumina. The obtained filtrate was concentrated to give a brown solid. The obtained brown solid was purified by silica gel column chromatography (developing solvent, hexane:toluene=2:1), and further recrystallized from hexane/toluene, so that 0.73 g of a white solid was obtained in 65% yield. The synthesis scheme of Step 2 is illustrated in (b-4).

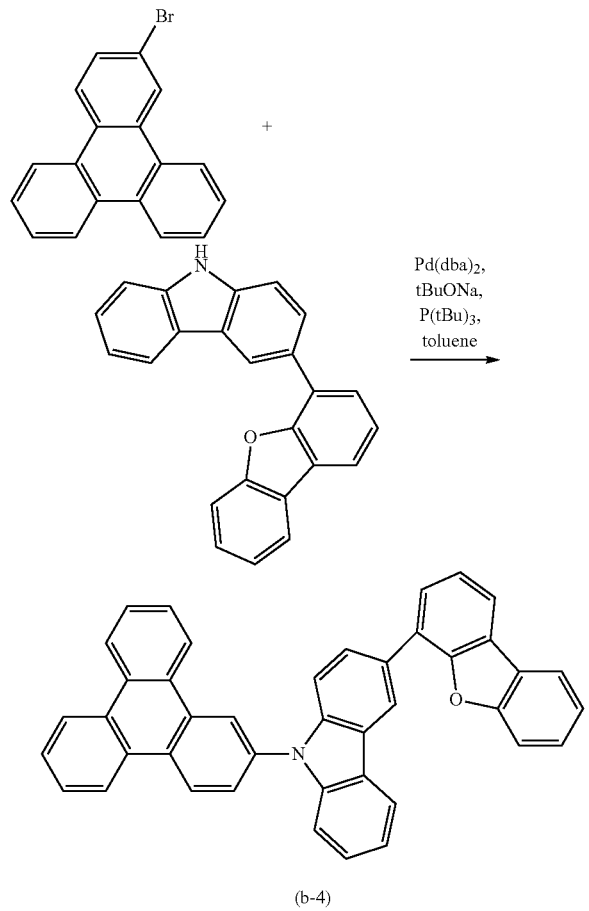

(b-4)

By a train sublimation method, 0.73 g of the obtained white solid was purified. In the purification, the pressure was 2.2 Pa, the flow rate of argon gas was 5.0 mL/min, and the temperature of the heating was 310° C. After the purification, 0.59 g of a colorless transparent solid was obtained in a yield of 81%.

Figure 17A:
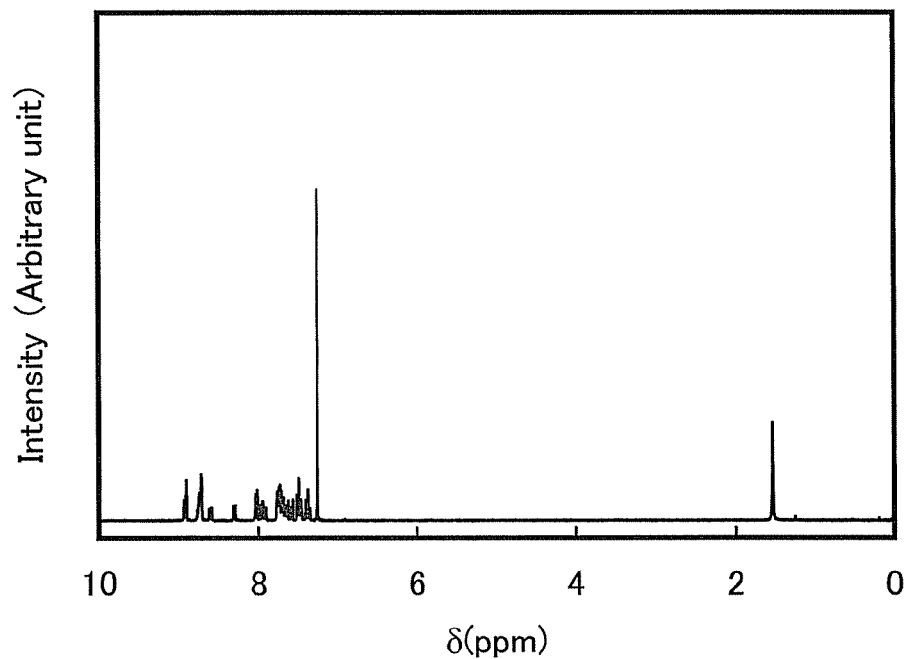
FIGS. 17A and 17B are $^1$H NMR charts of DBFCzTp-II.
Figure 17B:
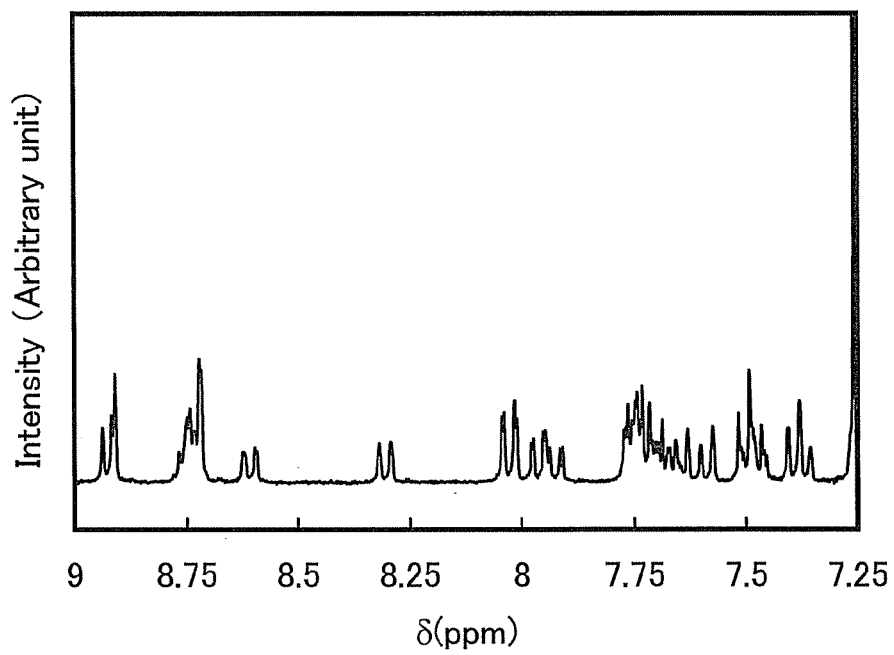

The colorless and transparent solid after the purification was subjected to nuclear magnetic resonance (NMR) spectroscopy. The measurement data are shown below. In addition, $^1$H NMR charts are shown in FIGS. 17A and 17B. Note that FIG. 17B is a chart where the range of from 7.25 ppm to 9 ppm in FIG. 17A is enlarged.

$^1$H NMR (CDCl$_3$, 300 MHz): δ=7.37-7.41 (m, 2H), 7.45-7.52 (m, 3H), 7.58-7.77 (m, 8H), 7.93 (dd, J$_1$=2.1 Hz, J$_1$=8.7 Hz, 1H), 7.96 (dd, J$_1$=1.5 Hz, J$_1$=7.8 Hz, 1H), 8.03 (dd, J$_1$=1.5 Hz, J$_1$=8.2 Hz, 2H), 8.31 (d, J=7.5 Hz, 1H), 8.61 (dd, J$_1$=1.5 Hz, J$_2$=8.0 Hz, 1H), 8.72-8.77 (m, 4H), 8.91-8.94 (m, 2H)

The measurement results showed that DBFCzTp-II, which is the carbazole derivative represented by the above structural formula, was obtained.

Figure 18A:
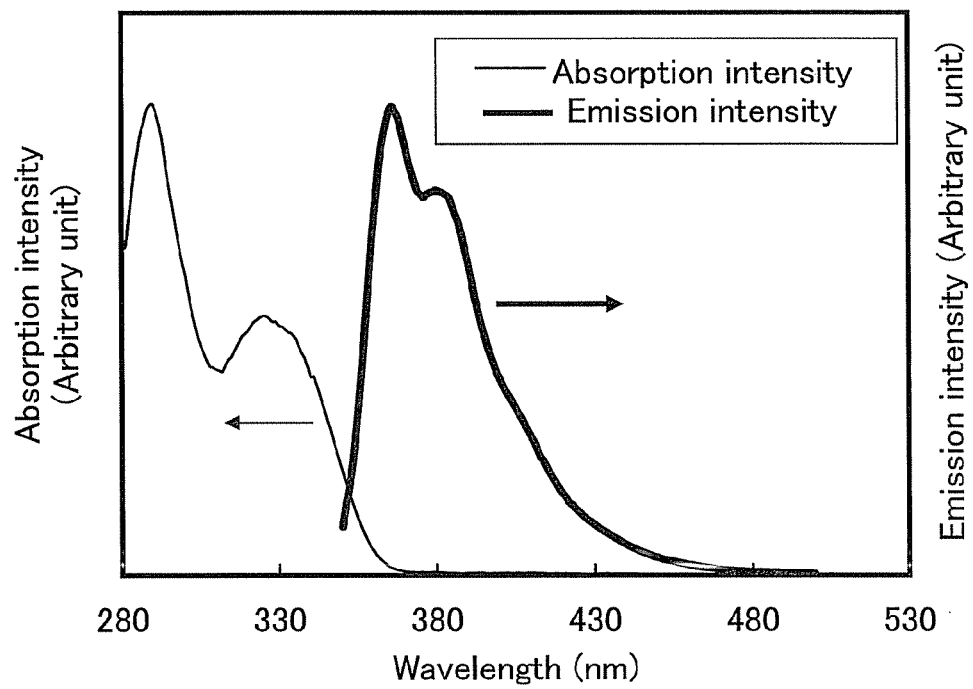
FIGS. 18A and 18B show absorption spectra and emission spectra of DBFCzTp-II.
Figure 18B:
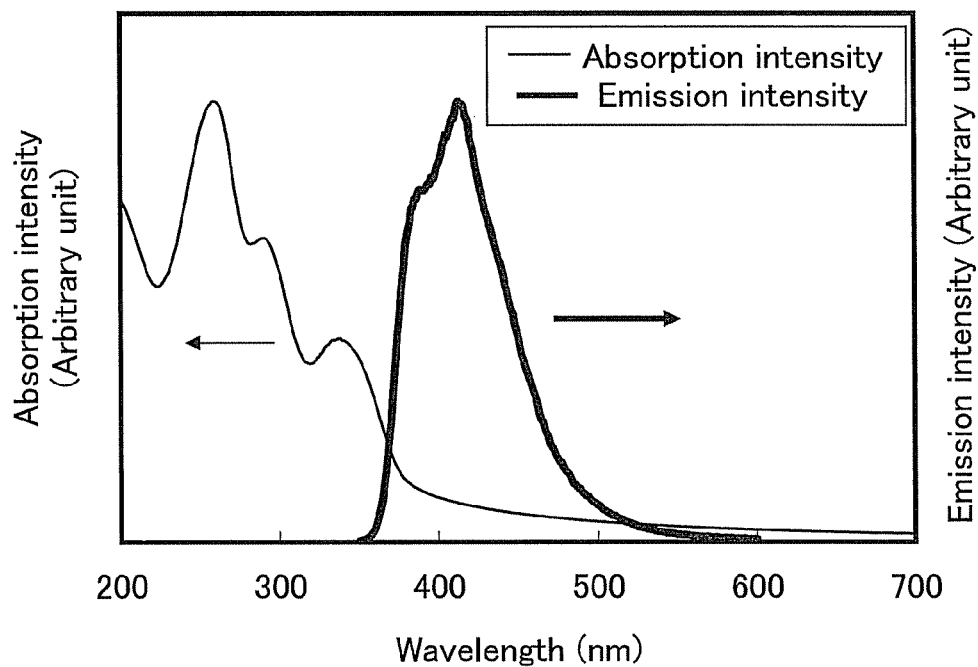

Next, an absorption and emission spectra of DBFCzTp-II in a toluene solution of DBFCzTp-II are shown in FIG. 18A, and an absorption and emission spectra of a thin film of DBFCzTp-II are shown in FIG. 18B. An ultraviolet-visible spectrophotometer (V-550, manufactured by JASCO Corporation) was used for the measurements of the absorption spectra. In the case of the toluene solution, the measurements were made with the toluene solution of DBFCzTp-II put in a quartz cell, and the absorption spectrum obtained by subtraction of absorption spectra of the quartz cell and toluene from the measured spectrum is shown in the drawing. In addition, as for the absorption spectrum of the thin film, a sample was prepared by evaporation of DBFCzTp-II on a quartz substrate, and the absorption spectrum obtained by subtraction of an absorption spectrum of quartz from the absorption spectrum of this sample is shown in the drawing. As in the measurements of the absorption spectra, an ultraviolet-visible spectrophotometer (V-550, manufactured by JASCO Corporation) was used for the measurements of the emission spectra. The emission spectrum of the toluene solution was measured with the toluene solution of DBFCzTp-II put in a quartz cell, and the emission spectrum of the thin film was measured with a sample prepared by evaporation of DBFCzTp-II on a quartz substrate. Thus, it was found that the maximum emission wavelengths of DBFCzTp-II in the toluene solution of DBFCzTp-II were around 380 nm and around 395 nm (at an excitation wavelength of 340 nm), and that the greatest emission wavelength of the thin film of DBFCzTp-II was around 413 nm (at an excitation wavelength of 334 nm).

Further, the ionization potential of DBFCzTp-II in a thin film state was measured by a photoelectron spectrometer (AC-2, manufactured by Riken Keiki, Co., Ltd.) in air. The obtained value of the ionization potential was converted to a negative value, so that the HOMO level of DBFCzTp-II was −5.79 eV. From the data of the absorption spectra of the thin film in FIG. 18B, the absorption edge of DBFCzTp-II, which was obtained from Tauc plot with an assumption of direct transition, was 3.33 eV. Therefore, the optical energy gap of DBFCzTp-II in the solid state was estimated at 3.33 eV; from the values of the HOMO level obtained above and this energy gap, the LUMO level of DBFCzTp-II was able to be estimated at −2.46 eV. It was thus found that DBFCzTp-II had a wide energy gap of 3.33 eV in the solid state.

Further, the oxidation reaction characteristics of DBFCzTp-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from 0.00 V to 1.10 V and then changed from 1.10 V to 0.00 V was one cycle, and 100 cycles were performed.

The measurement results revealed that DBFCzTp-II showed properties effective against repetition of redox reactions between an oxidized state and a neutral state without a large variation in oxidation peak even after the 100 cycles in the measurements.

Further, the HOMO level of DBFCzTp-II was determined also by calculation from the CV measurement results.

First, the potential energy of the reference electrode with respect to the vacuum level used was found to be −4.94 eV, as determined in Example 1. The oxidation peak potential $E_{pa}$ of DBFCzTp-II was 1.00 V. In addition, the reduction peak potential $E_{pc}$ thereof was 0.83 V. Therefore, a half-wave potential (an intermediate potential between $E_{pa}$ and $E_{pc}$) can be calculated at 0.92 V. This means that DBFCzTp-II is oxidized by an electric energy of 0.92 [V vs. Ag/Ag$^+$], and this energy corresponds to the HOMO level. Here, since the potential energy of the reference electrode, which was used in this example, with respect to the vacuum level is −4.94 [eV] as described above, the HOMO level of DBFCzTp-II was calculated as follows: −4.94−0.92=−5.86 [eV].

Example 5

Synthesis Example 5

In this example is described a method of synthesizing 3-(dibenzofuran-4-yl)-N-(9,10-diphenylanthracen-2-yl)-9H-carbazole (abbreviation: 2DBFCzPA-II), which is the carbazole derivative represented by the structural formula (728) in Embodiment 1. A structure of 2DBFCzPA-II is illustrated in the following structural formula.

Step 1: Synthesis of 3-(Dibenzofuran-4-yl)-9H-carbazole

This was synthesized as in Step 1 in Example 2.

Step 2: Synthesis of 2 DBFCzPA-II

To a 100-mL three-neck flask were added 1.00 g (3.00 mmol) of 2-bromo-9,10-diphenylanthracene, 1.23 g (3.00 mmol) of 3-(dibenzofuran-4-yl)-9H-carbazole, and 0.86 g (9.00 mmol) of sodium tert-butoxide. After the air in the flask was replaced with nitrogen, to this mixture were added 20 mL of toluene and 0.2 mL of tri-(tert-butyl)phosphine (a 10 wt % hexane solution). This mixture was degassed by being stirred while the pressure was reduced. After the degassing, 86 mg (0.15 mmol) of bis(dibenzylideneacetone)palladium(0) was added to the mixture. This mixture was stirred at 110° C. for 10 hours under a nitrogen stream. After the reflux, the mixture was cooled to room temperature, and then the obtained solid was collected by suction filtration. The collected solid was dissolved in 100 mL of toluene, and this solution was filtered through Celite (produced by Wako Pure Chemical Industries, Ltd., Catalog No. 531-16855), Florisil (produced by Wako Pure Chemical Industries, Ltd., Catalog No. 540-00135), and alumina. The obtained filtrate was concentrated to give an orange solid. The obtained solid was purified by silica gel column chromatography. In the column chromatography, a solution of toluene:hexane=1:5 was used as a developing solvent. The obtained fraction was concentrated to give a pale yellow solid. The obtained solid was recrystallized from toluene/hexane, so that 1.27 g of a pale yellow solid was obtained in 64% yield. The synthesis scheme of Step 2 is illustrated in (b-5).

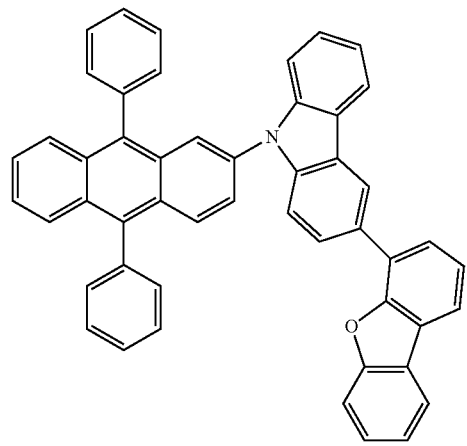 [SMILES: c1ccc(-c2c3ccccc3c(-c3ccccc3)c3cc(-n4c5ccccc5c5cc(-c6cccc7c6oc6ccccc67)ccc54)ccc23)cc1]

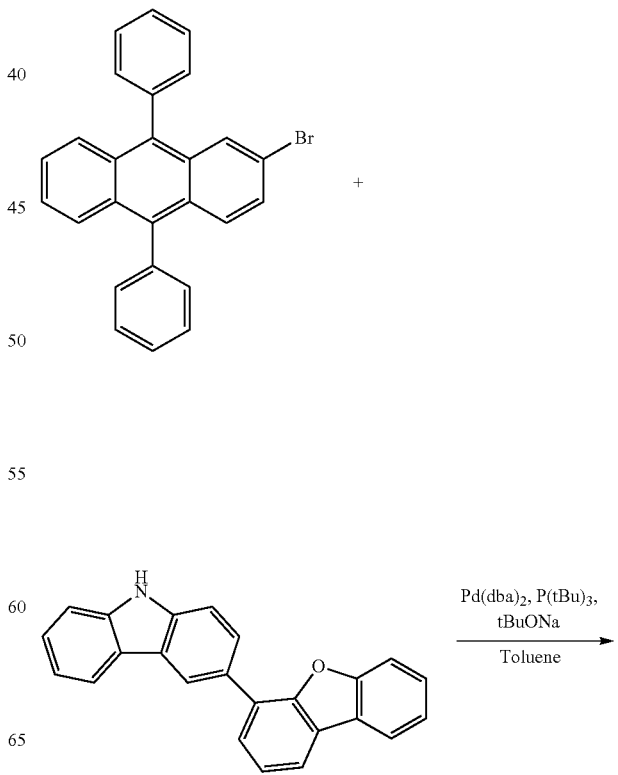

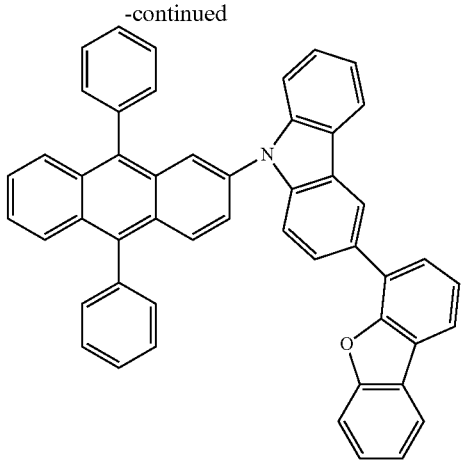

(b-5)

Figure 19A:
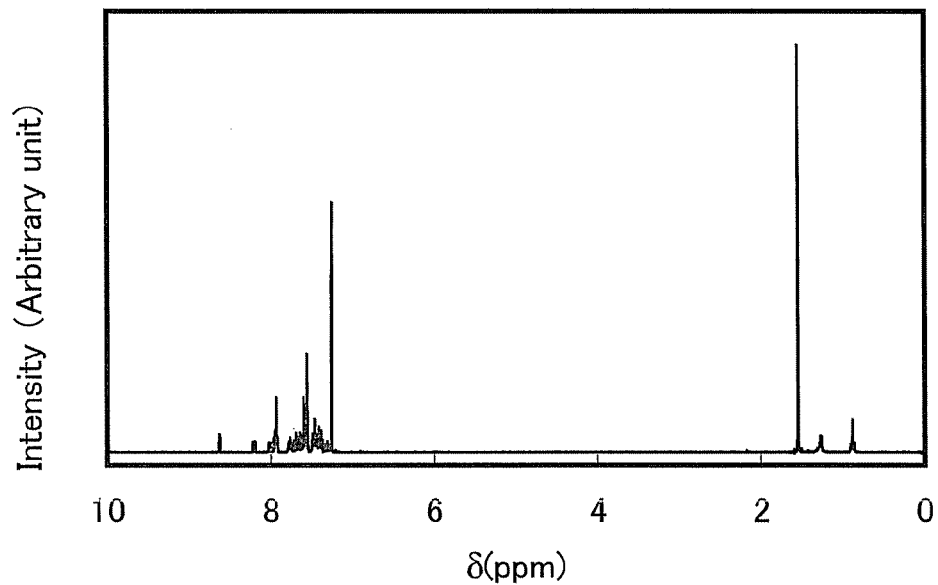
FIGS. 19A and 19B are $^1$H NMR charts of 2DBFCzPA-II.
Figure 19B:
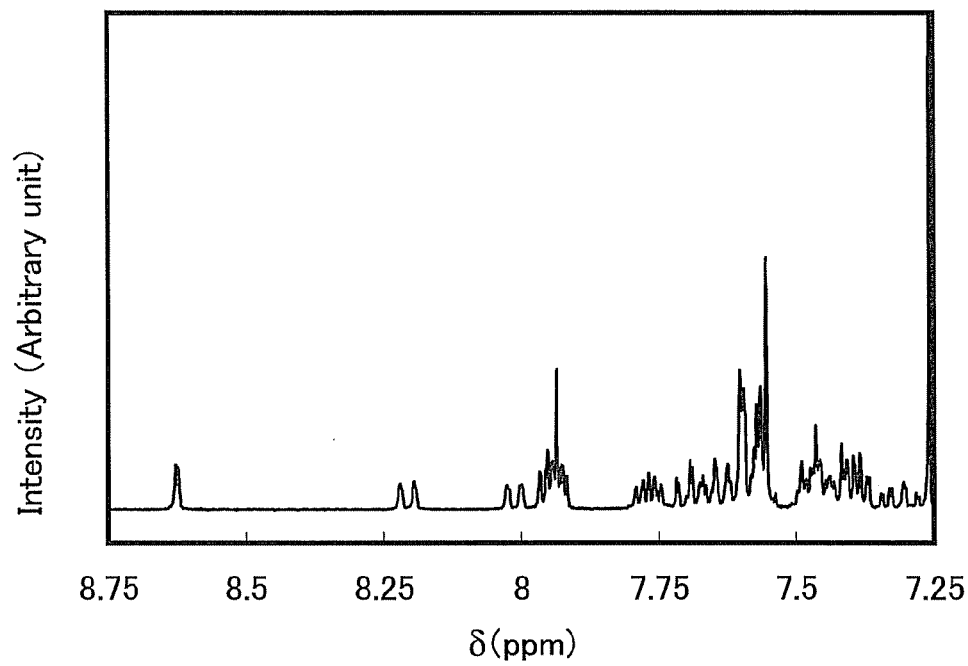

This compound was identified as 3-(dibenzofuran-4-yl)-N-(9,10-diphenylanthracen-2-yl)-9H-carbazole (abbreviation: 2 DBFCz-II) by nuclear magnetic resonance (NMR) spectroscopy. $^1$H NMR. data of the obtained compound is shown below. In addition, $^1$H NMR charts are shown in FIGS. 19A and 19B.

$^1$H NMR (CDCl$_3$, 300 MHz): δ=7.26-7.49 (m, 9H), 7.54-7.72 (m, 13H), 7.75-7.79 (m, 2H), 7.92-7.97 (m, 4H), 8.01 (d, J=8.1 Hz, 1H), 8.21 (d, J=7.5 Hz, 1H), 8.63 (d, J=0.9 Hz, 1H)

[Example 6]

Synthesis Example 6

In this example is described a method of synthesizing 3,6-bis(dibenzothiophen-4-yl)-9-[4-(10-phenyl-9-anthryl)phenyl]-9H-carbazole (abbreviation: DBT2CzPA-II), which is the carbazole derivative represented by the structural formula (201) in Embodiment 1. A structure of 3,6-bis(dibenzothiophen-4-yl)-9-[4-(10-phenyl-9-anthryl)phenyl]-9H-carbazole is illustrated in the following structural formula.

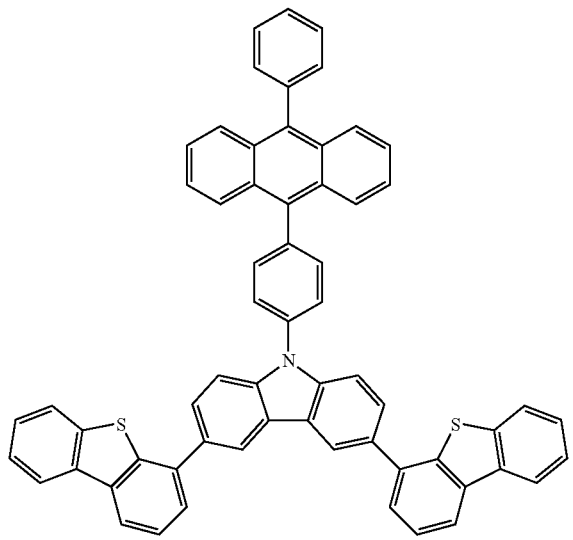 [SMILES: c1ccc(-c2c3ccccc3c(-c3ccc(-n4c5ccc(-c6cccc7c6sc6ccccc67)cc5c5cc(-c6cccc7c6sc6ccccc67)ccc54)cc3)c3ccccc23)cc1]

First, a method of synthesizing 3,6-di(benzothiophen-4-yl)-9H-carbazole (abbreviation: DBT2Cz-II), which is a synthetic intermediate of DBT2CzPA-II, is described. DBT2Cz-II is illustrated in the following structural formula.

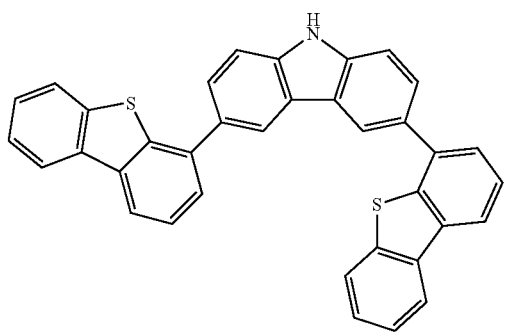 [SMILES: c1ccc2c(c1)sc1c(-c3ccc4[nH]c5ccc(-c6cccc7c6sc6ccccc67)cc5c4c3)cccc12]

Step 1: Synthesis of 3,6-(Dibenzothiophen-4-yl)-9H-carbazole

In a 200-mL three-neck flask were put 3.3 g (10 mmol) of 3,6-dibromocarbazole, 4.6 g (20 mmol) of dibenzothiophene-4-boronic acid, and 156 mg (0.5 mol) of tri(ortho-tolyl)phosphine, and the air in the flask was replaced with nitrogen. To this mixture were added 25 mL of toluene, 25 mL of ethanol, and 15 mL (2.0 mol/L) of an aqueous potassium carbonate solution. In the flask, the mixture was degassed by being stirred under reduced pressure. After the degassing, replacement with nitrogen was performed, and 22 mg (0.10 mmol) of palladium(II) acetate was added to this mixture, and then the mixture was refluxed at 80° C. for 2 hours. After the reflux, since a white solid was precipitated, about 450 mL of toluene was added to this mixture and the white solid was dissolved. The obtained suspension was filtered through Celite (produced by Wako Pure Chemical Industries, Ltd., Catalog No. 531-16855), Florisil (produced by Wako Pure Chemical Industries, Ltd., Catalog No. 540-00135), and alumina. The solid obtained by concentration of the obtained filtrate was recrystallized from about 200 mL of toluene, so that 2.0 g of a white solid, which was the object of the synthesis, was obtained in 38% yield. The synthesis scheme of Step 1 is illustrated in (a-1).

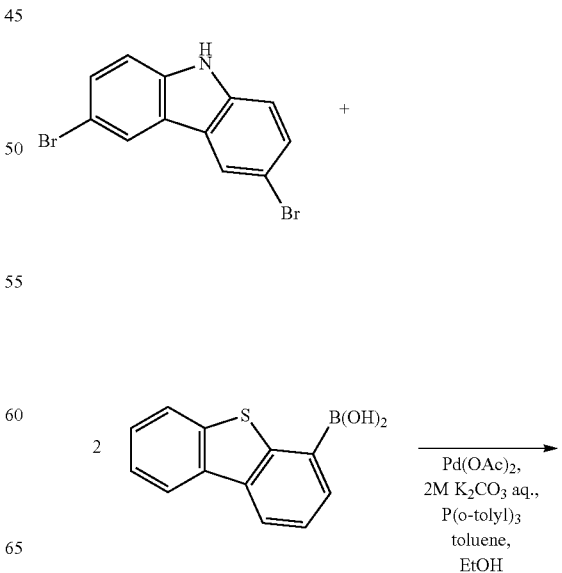

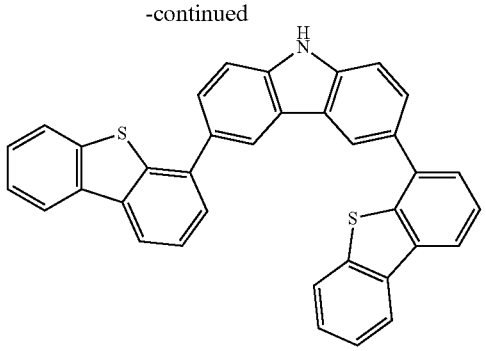

Figure 20A:
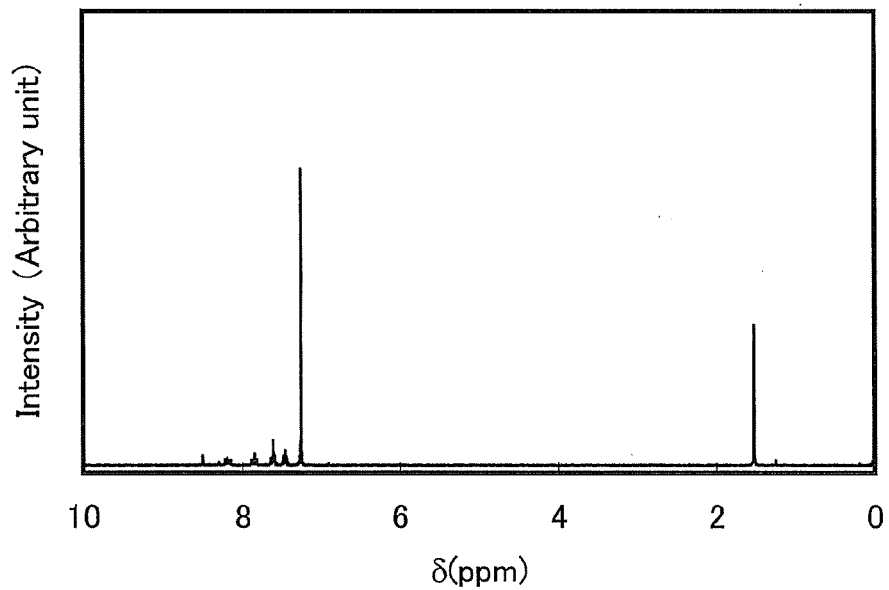
FIGS. 20A and 20B are $^1$H NMR charts of DBT2Cz-II.
Figure 20B:
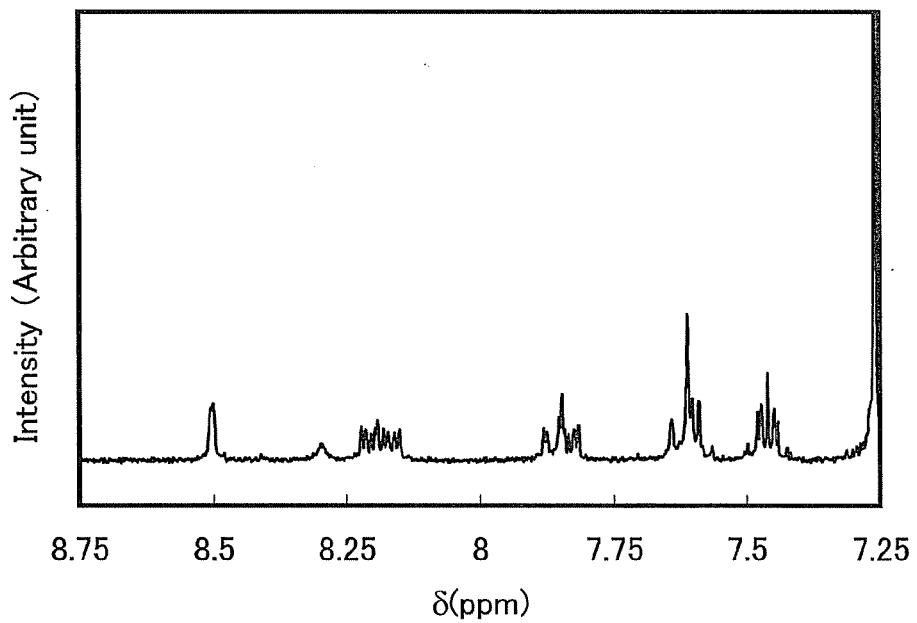

This compound was identified as 3,6-di(benzothiophen-4-yl)-9H-carbazole (abbreviation: DBT2Cz-II) by nuclear magnetic resonance (NMR) spectroscopy. $^1$H NMR data of the obtained compound is shown below. In addition, $^1$H NMR charts are shown in FIGS. 20A and 20B.

$^1$H NMR (CDCl$_3$, 300 MHz): δ=7.44-7.50 (m, 4H), 7.57-7.64 (m, 6H), 7.82-7.88 (m, 4H), 8.15-8.22 (m, 4H), 8.90 (d, J=0.9 Hz, 1H), 8.50 (d, J=1.2 Hz, 2H)

Step 2: Synthesis of DBTCzPA-II

To a 100-mL three-neck flask were added 0.95 g (2.32 mmol) of 9-(4-bromophenyl)-10-phenylanthracene, 1.23 g (2.32 mmol) of 3,6-di(benzothiophen-4-yl)-9H-carbazole, and 0.67 g (6.96 mmol) of sodium tert-butoxide. After the air in the flask was replaced with nitrogen, to this mixture were added 20 mL of toluene and 0.1 mL of tri-tert-butyl-phosphine (a 10 wt % hexane solution). This mixture was degassed by being stirred while the pressure was reduced. After the degassing, 24 g (0.11 mmol) of bis(dibenzylideneacetone)palladium(0) was added to the mixture. This mixture was stirred at 110° C. for 10 hours under a nitrogen stream. After the stirring, 100 mL of toluene was added to the obtained mixture, and this suspension was suction-filtered through Celite (produced by Wako Pure Chemical Industries, Ltd., Catalog No. 531-16855), Florisil (produced by Wako Pure Chemical Industries, Ltd., Catalog No. 540-00135), and alumina. The oily substance obtained by concentration of the obtained filtrate was recrystallized from toluene, so that 0.75 g of a pale yellow solid, which was the object of the synthesis, was obtained in 38% yield. The synthesis scheme of Step 2 is illustrated in (b-6).

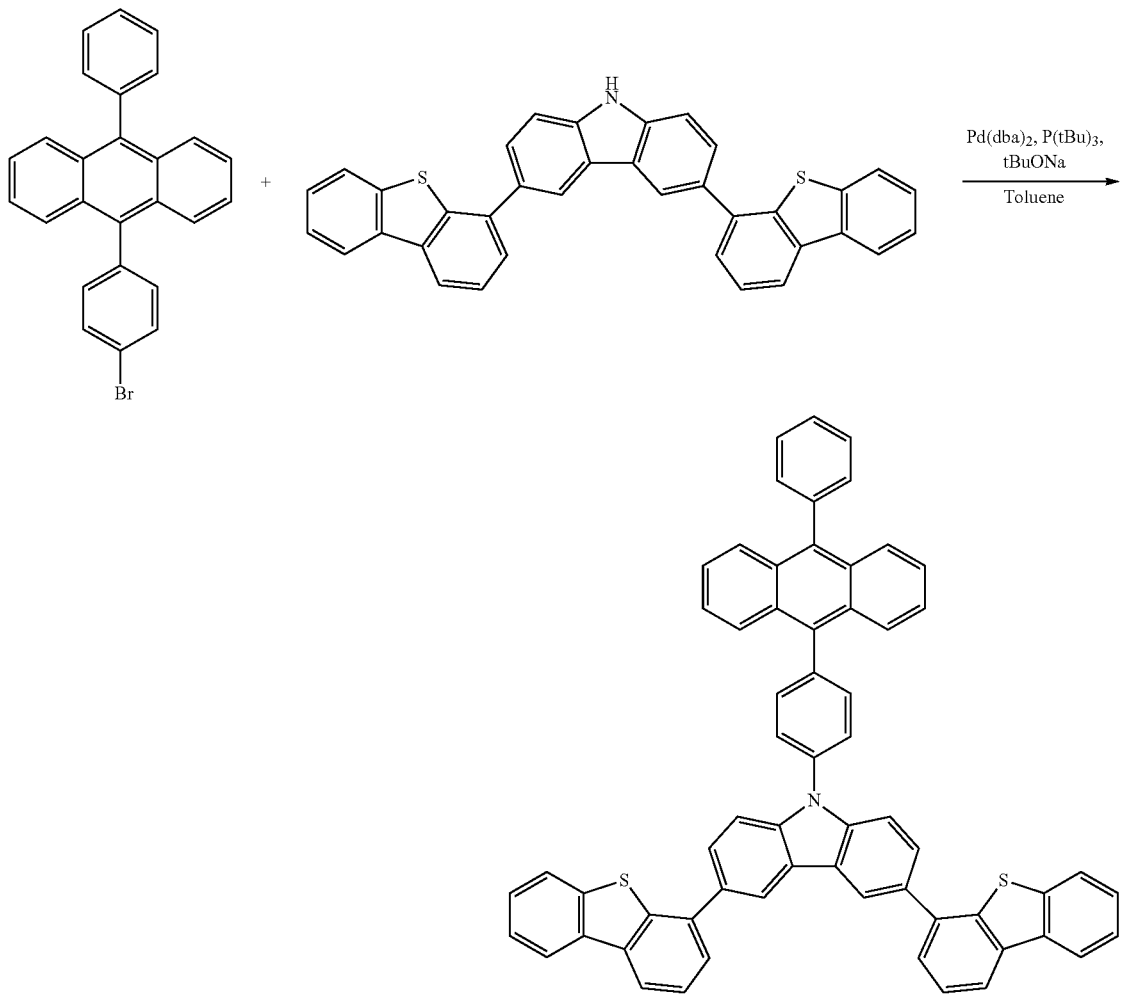

(b-6)

Figure 21A:
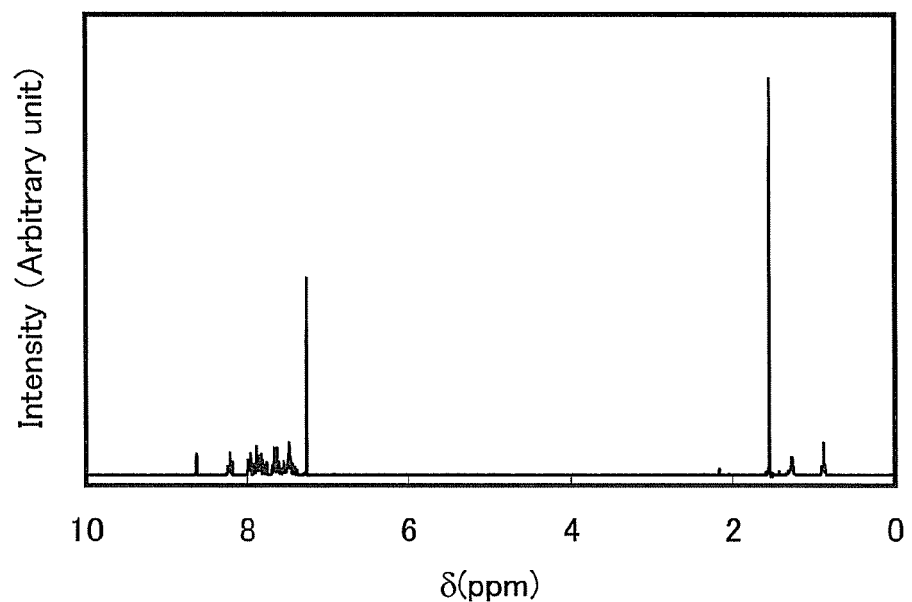
FIGS. 21A and 21B are $^1$H NMR charts of DBT2CzPA-II.
Figure 21B:
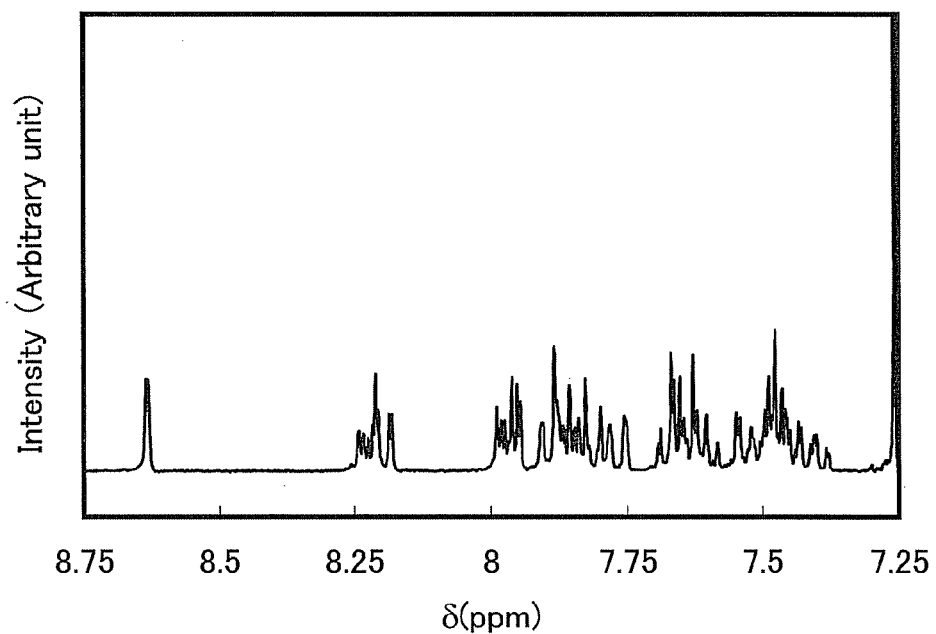

This compound was identified as 3,6-bis(dibenzothiophen-4-yl)-9-[4-(10-phenyl-9-anthryl)phenyl]-9H-carbazole (abbreviation: DBT2CzPA-II) by nuclear magnetic resonance (NMR) spectroscopy. $^1$H NMR data of the obtained compound is shown below. In addition, $^1$H NMR charts are shown in FIGS. 21A and 21B.

$^1$H NMR (CDCl$_3$, 300 MHz): δ=7.38-7.69 (m, 17H), 7.76-7.91 (m, 10H), 7.95-7.99 (m, 4H), 8.18-8.24 (m, 4H), 8.63 (d, J=0.9 Hz, 1H)

Example 7

Synthesis Example 7

In this example is described a method of synthesizing 3,6-di(benzofuran-4-yl)-9H-carbazole (abbreviation: DBF2Cz-II), which is the carbazole derivative represented by the general formula (G5) in Embodiment 2, which can be used as a synthetic intermediate of the carbazole derivative described in Embodiment 1. A structure of DBF2Cz-II is illustrated in the following structural formula.

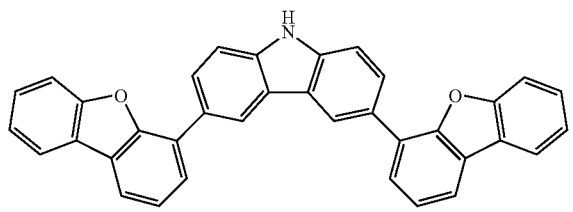

In a 200-mL three-neck flask were put 3.00 g (9.23 mmol) of 3,6-dibromocarbazole, 3.91 g (18.5 mmol) of dibenzothiophene-4-boronic acid, and 140 mg (0.46 mol) of tri(ortho-tolyl)phosphine, and the air in the flask was replaced with nitrogen. To this mixture were added 35 mL of toluene, 10 mL of ethanol, and 20 mL (2.0 mol/L) of an aqueous potassium carbonate solution. In the flask, the mixture was degassed by being stirred under reduced pressure. After the degassing, replacement with nitrogen was performed, and 21 mg (92.3 μmol) of palladium(II) acetate was added to this mixture, and then the mixture was refluxed at 80° C. for 3 hours. After the reflux, about 200 mL of toluene was added to this mixture and then the mixture was stirred at about 110° C. While this suspension was kept hot, it was filtered through Celite (produced by Wako Pure Chemical Industries, Ltd., Catalog No. 531-16855), Florisil (produced by Wako Pure Chemical Industries, Ltd., Catalog No. 540-00135), and alumina. The solid obtained by concentration of the obtained filtrate was recrystallized from toluene, so that 1.40 g of a white solid was obtained in 30% yield. The synthesis scheme is illustrated in (c-1).

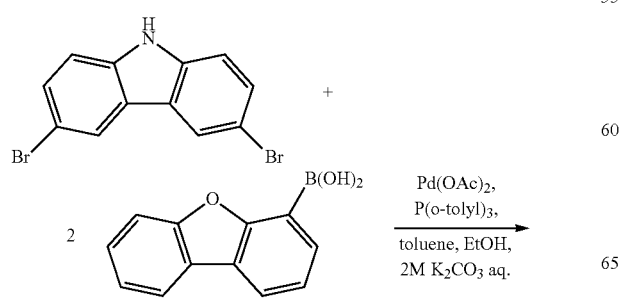

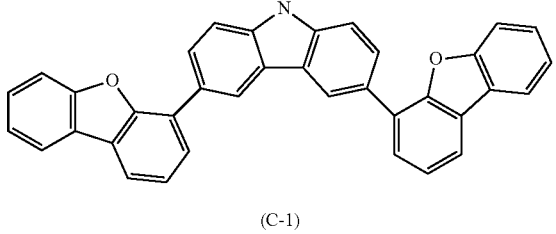

(C-1)

Figure 22A:
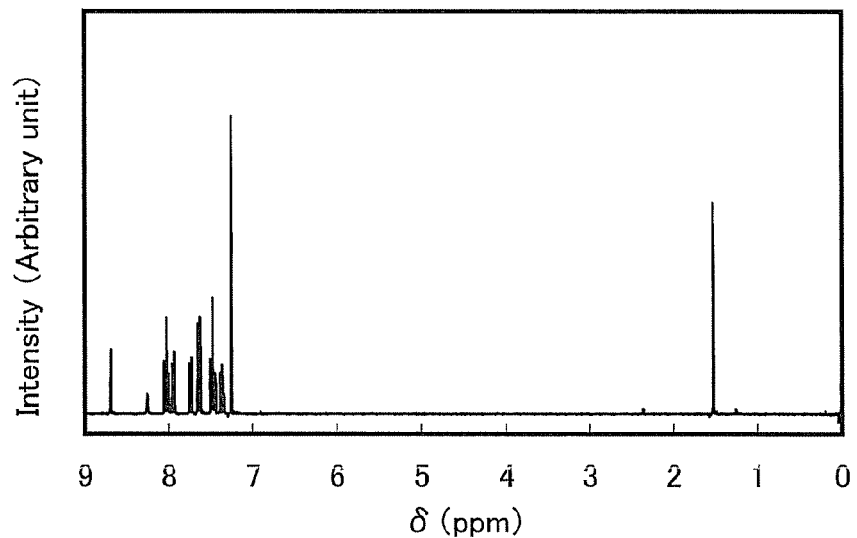
FIGS. 22A and 22B are $^1$H NMR charts of DBF2Cz-II.
Figure 22B:
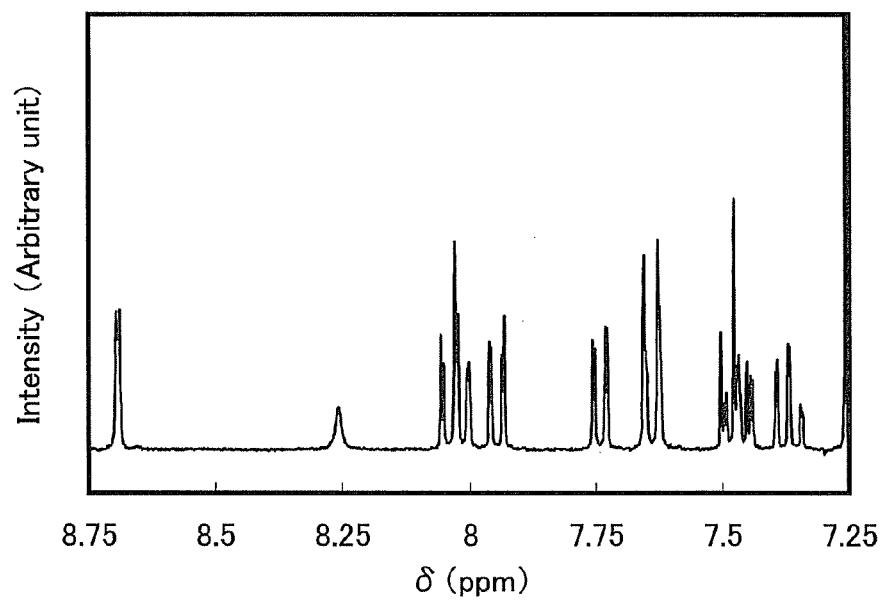

This white solid was identified as 3,6-bis(dibenzofuran-4-yl)-9H-carbazole (abbreviation: DBF2Cz-II) by nuclear magnetic resonance (NMR) spectroscopy. $^1$H NMR data of the obtained compound is shown below. In addition, $^1$H NMR charts are shown in FIGS. 22A and 22B.

$^1$H NMR (CDCl$_3$, 300 MHz): δ=7.37 (dt, J$_1$=0.9 Hz, J$_2$=7.2 Hz, 2H), 7.44-7.50 (m, 4H), 7.64 (d, J=8.1 Hz, 4H), 7.74 (dd, J$_1$=0.9 Hz, J$_2$=7.7 Hz, 2H), 7.95 (dd, J$_1$=0.9 Hz, J$_2$=7.5 Hz, 2H), 8.03 (dt, J=1.8 Hz, J$_2$=8.4 Hz, 4H), 8.26 (br, 1H), 8.69 (d, J=2.1 Hz, 1H)

Example 8

In this example are described light-emitting elements in which 3-(dibenzothiophen-4-yl)-9-[4-(10-phenyl-9-anthryl)phenyl]-9H-carbazole (abbreviation: DBTCzPA-II) and 3-(dibenzofuran-4-yl)-9-[4-(10-phenyl-9-anthryl)phenyl]-9H-carbazole (abbreviation: DBFCzPA-II), which are carbazole derivatives described in Embodiment 1, are respectively used as host materials in light-emitting layers in which emission center substances that emit blue fluorescence are used.

The molecular structures of organic compounds used in this example are illustrated in the following structural formulas (Iv) to (vi). In the element structure in FIG. 1A, an electron-injection layer is provided between an electron-transport layer 114 and a second electrode 104 was employed.

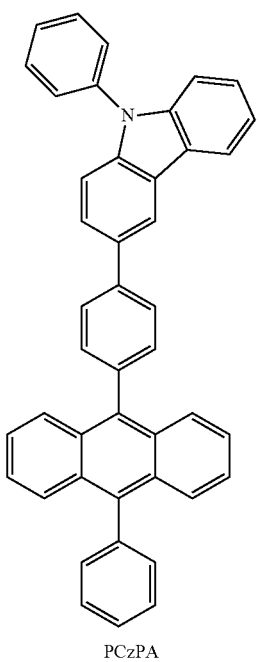

(v)

PCzPA

-continued

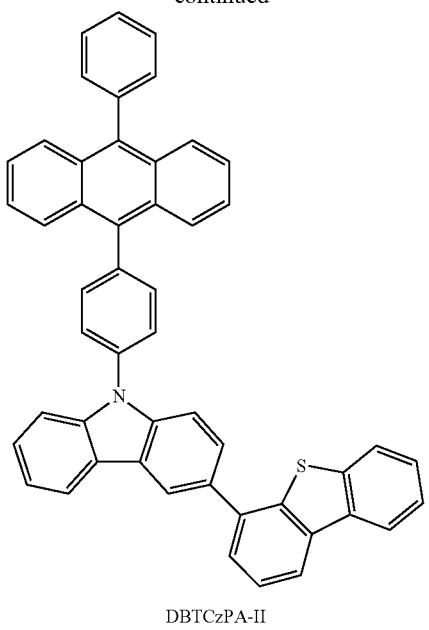

DBTCzPA-II

-continued

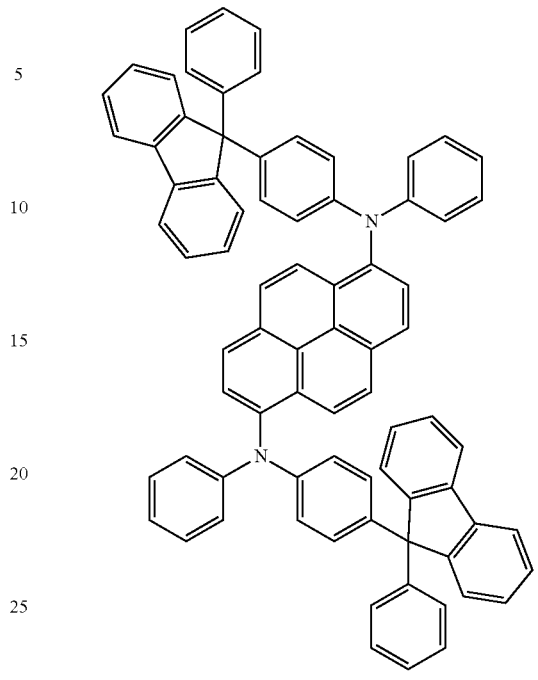

(vi)

1,6FLPAPrn

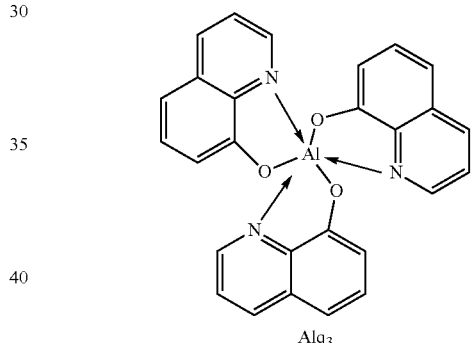

(vii)

Alq₃

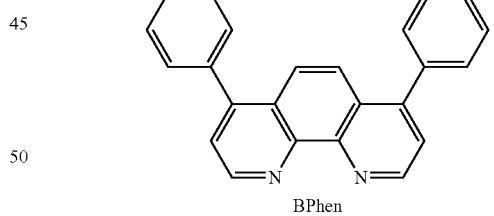

(iv)

BPhen

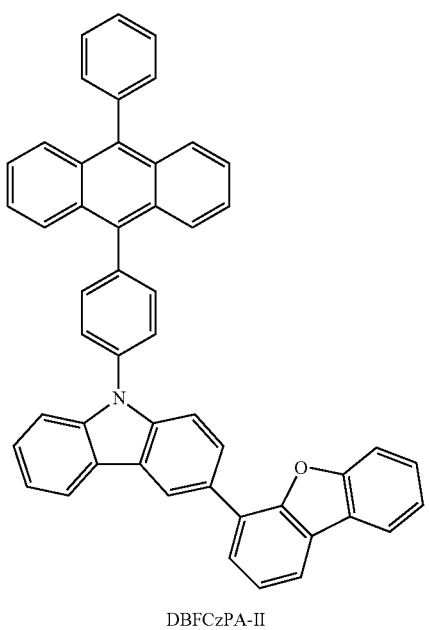 [SMILES: c1ccc(-c2c3ccccc3c(-c3ccc(-n4c5ccccc5c5cc(-c6cccc7c6oc6ccccc67)ccc54)cc3)c3ccccc23)cc1]

DBFCzPA-II

<<Fabrication of Light-Emitting Element 1 and Light-Emitting Element 2>>

First, a glass substrate 101 over which indium tin oxide containing silicon (ITSO) with a thickness of 110 nm was formed as a first electrode 102 was prepared. A surface of the ITSO was covered with a polyimide film so that an area of 2 mm×2 mm of the surface was exposed. The electrode area was 2 mm×2 mm. As a pretreatment for forming the light-emitting element over the substrate, the surface of the substrate was washed with water and baked at 200° C. for one hour, and then a UV ozone treatment was performed for 370 seconds. After that, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate 101 was fixed on a holder provided in the vacuum evaporation apparatus such that the surface of the substrate 101 provided with ITSO faced downward.

After the pressure in the vacuum evaporation apparatus was reduced to $10^{-4}$ Pa, 9-[4-(9-phenylcarbazol-3-yl)]phenyl-10-phenylanthracene (abbreviation: PCzPA) represented by the above structural formula (v), and molybdenum(VI) oxide were co-evaporated with a mass ratio of PCzPA to molybdenum(VI) oxide being 2:1, whereby a hole-injection layer 111 was formed. The thickness thereof was 50 nm. Note that the co-evaporation is an evaporation method in which a plurality of different substances are concurrently vaporized from the respective different evaporation sources.

Next, PCzPA was evaporated to a thickness of 10 nm, whereby a hole-transport layer 112 was formed.

Further, in the light-emitting element 1, on the hole-transport layer 112, DBTCzPA-II, which is the carbazole derivative represented by the above structural formula in Embodiment 1, and N,N'-bis[4-(9-phenyl-9H-fluoren-9-yl)phenyl]-N,N''-diphenylpyrene-1,6-diamine (abbreviation: 1,6FLPAPrn) were evaporated to a thickness of 30 nm with a mass ratio of DBTCzPA-II to 1,6FLPAPrn being 1:0.05, whereby a light-emitting layer 113 was formed.

In the light-emitting element 2, on the hole-transport layer 112, DBFCzPA-II which is the carbazole derivative represented by the above structural formula, and 1,6FLPAPrn were evaporated to a thickness of 30 nm with a mass ratio of DBFCzPA-II to 1,6FLPAPrn being −1:0.05, whereby a light-emitting layer 113 was formed.

Then, on the light-emitting layer 113, tris(8-quinolinolato)aluminum(III) represented by the above structural formula (vii) was evaporated to a thickness of 10 nm, and bathophenanthroline (abbreviation: BPhen) represented by the above structural formula (iv) was evaporated to a thickness of 15 nm, whereby the electron-transport layer 114 was formed. Further, lithium fluoride was evaporated to a thickness of 1 nm on the electron-transport layer 114, whereby the electron-injection layer was formed. Lastly, an aluminum film was formed to a thickness of 200 nm as the second electrode 104 which serves as a cathode, whereby the light-emitting elements 1 and 2 were completed. Note that in the above evaporation process, evaporation was all performed by a resistance heating method.

<<Operation Characteristics of Light-Emitting Elements 1 and 2>>

The light-emitting elements 1 and 2 thus obtained were sealed in a glove box under a nitrogen atmosphere without being exposed to air. Then, the operation characteristics of these light-emitting elements were measured. Note that the measurements were carried out at room temperature (in an atmosphere kept at 25° C.).

Figure 23:
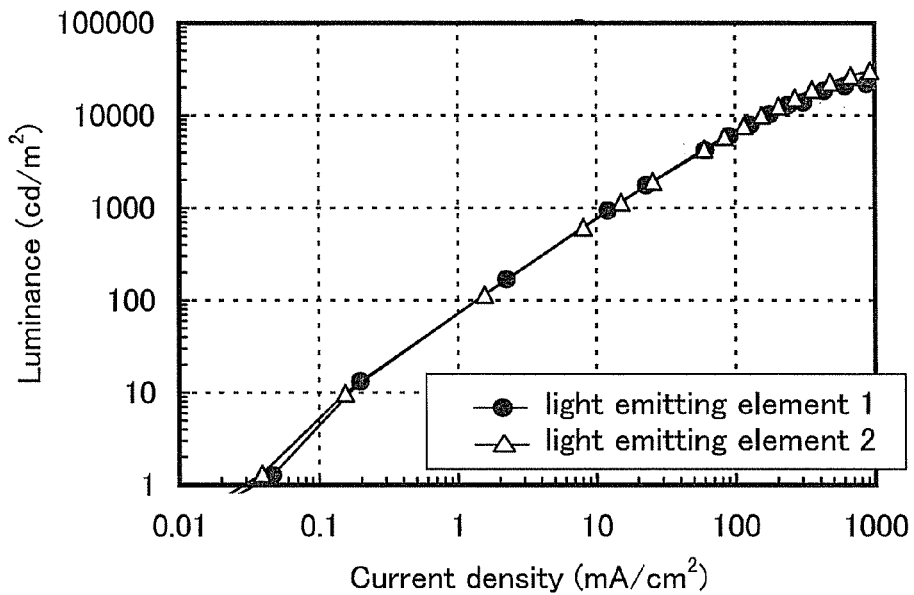
FIG. 23 is a graph showing luminance vs. current density characteristics of a light-emitting element 1 and a light-emitting element 2.
Figure 24:
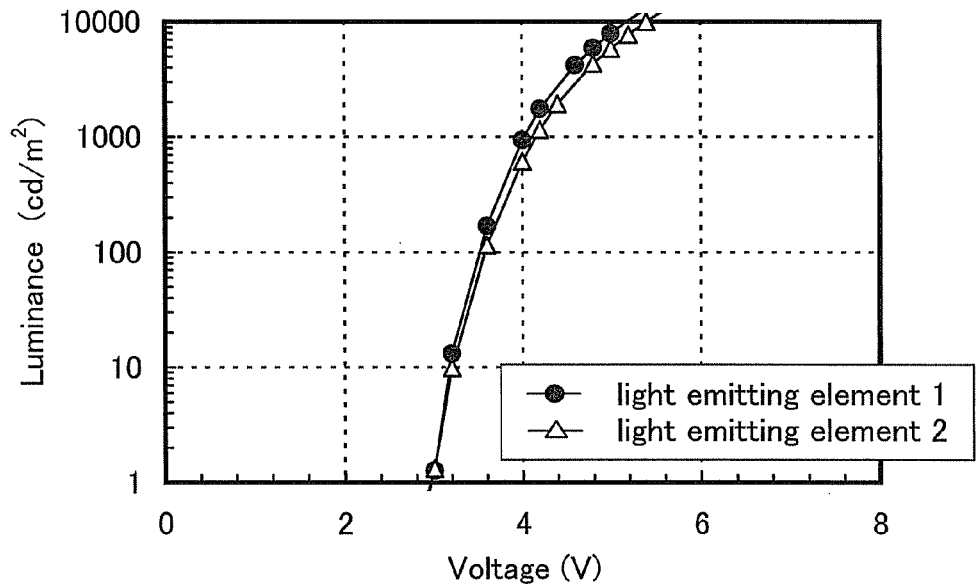
FIG. 24 is a graph showing luminance vs. voltage characteristics of the light-emitting element 1 and the light-emitting element 2.
Figure 25:
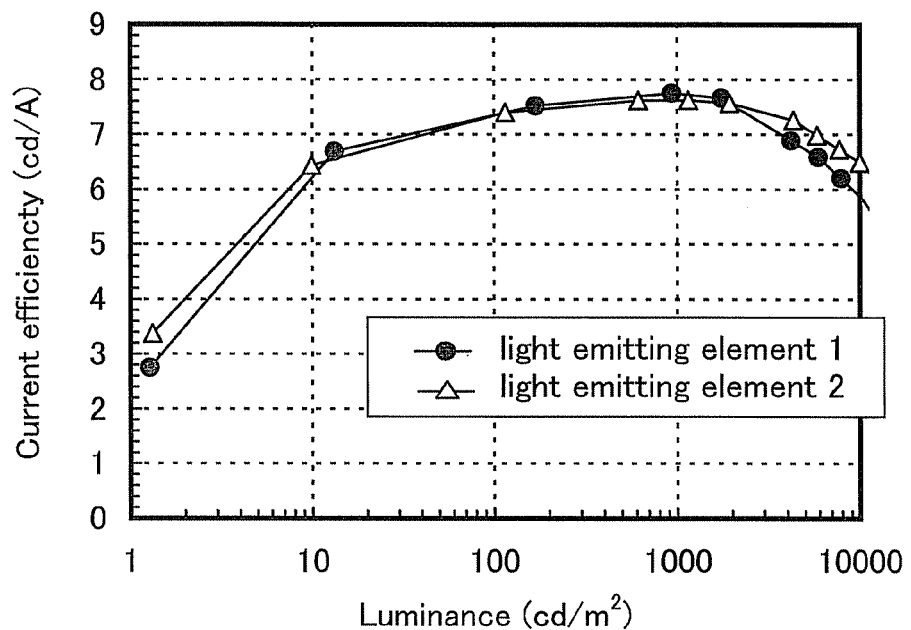
FIG. 25 is a graph showing current efficiency vs. luminance characteristics of the light-emitting element 1 and the light-emitting element 2.

FIG. 23 shows luminance vs. current density characteristics of the light-emitting elements, FIG. 24 shows luminance vs. voltage characteristics thereof, and FIG. 25 shows current efficiency vs. luminance characteristics thereof. In FIG. 23, the vertical axis represents luminance (cd/m$^2$), and the horizontal axis represents current density (mA/cm$^2$). In FIG. 24, the vertical axis represents luminance (cd/m$^2$), and the horizontal axis represents voltage (V). In FIG. 25, the vertical axis represents current efficiency (cd/A), and the horizontal axis represents luminance (cd/m$^2$).

From FIG. 25, it is found that the light-emitting elements in each of which the carbazole derivative described in Embodiment 1 is used as a host material in a light-emitting layer of the light-emitting element that emits blue fluorescence show favorable luminance vs. emission efficiency characteristics and high emission efficiency. This is because the carbazole derivatives described in Embodiment 1 have a wide energy gap, and thus even a light-emitting substance that emits blue fluorescence and has a wide energy gap can be effectively excited. In addition, from FIG. 23, it is found that the light-emitting elements in each of which the carbazole derivative described in Embodiment 1 is used as a host material in a light-emitting layer of the light-emitting element that emits blue fluorescence show favorable luminance vs. voltage characteristics and are driven with a low driving voltage. This indicates that the carbazole derivatives described in Embodiment 1 have an excellent carrier-transport property.

Figure 26:
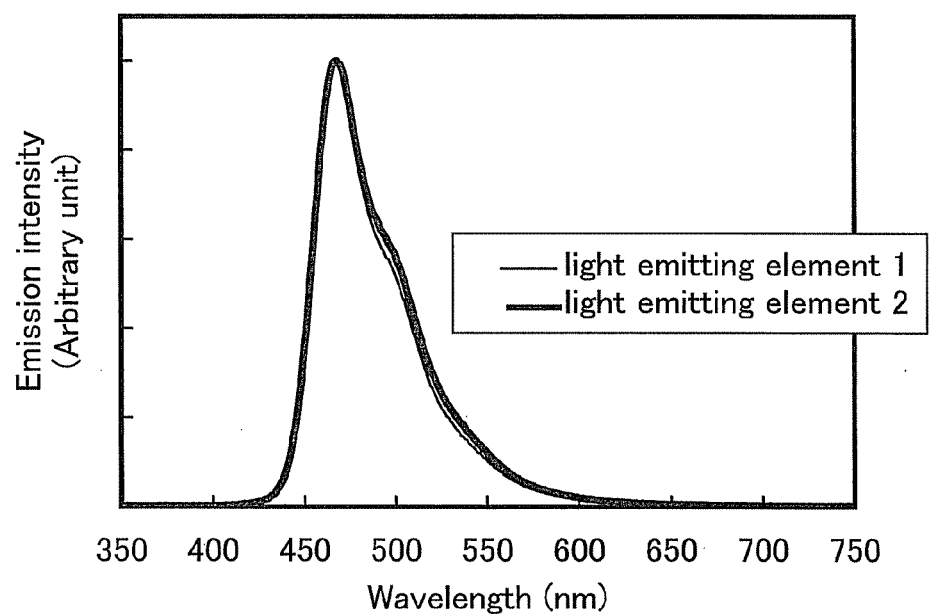
FIG. 26 shows emission spectra of the light-emitting element 1 and the light-emitting element 2.

FIG. 26 shows emission spectra when a current of 1 mA was made to flow in the fabricated light-emitting elements. In FIG. 26, the vertical axis represents emission wavelength (nm), and the horizontal axis represents emission intensity. The emission intensity is shown as a value relative to the maximum emission intensity assumed to be 1. From FIG. 26, it is found that each of the light-emitting elements 1 and 2 emits blue light which originates from 1,6FLPAPrn, which is the emission center substance.

Figure 27:
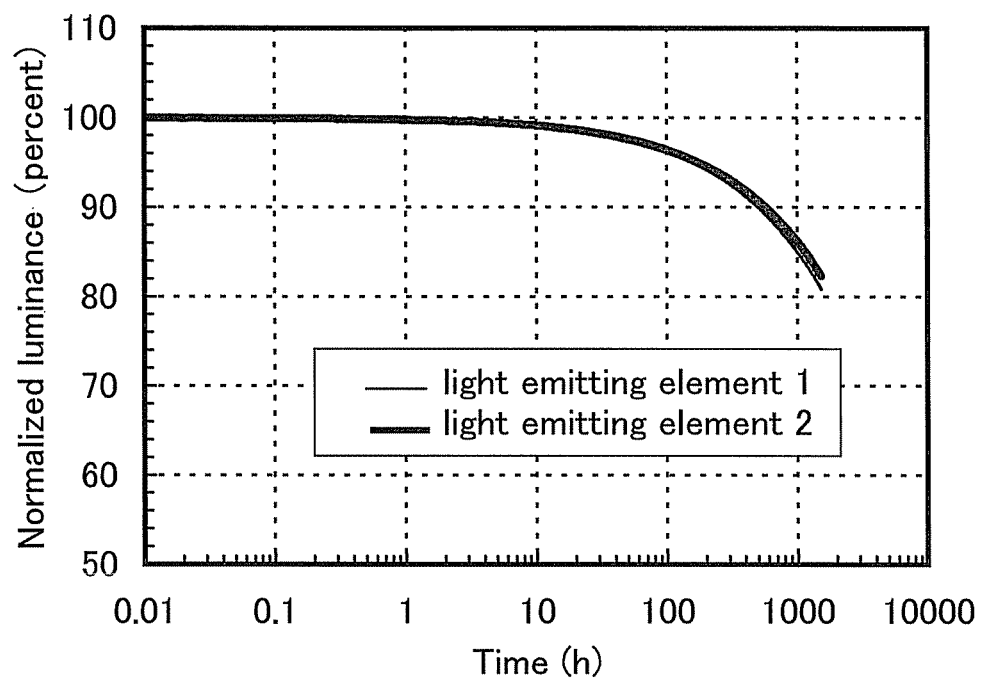
FIG. 27 is a graph showing change of normalized luminance vs. time characteristics of the light-emitting element 1 and the light-emitting element 2.

Next, the initial luminance is set at 1000 cd/m$^2$, these elements were driven under a condition where the current density was constant, and changes in luminance with respect to the driving time were examined. FIG. 27 shows normalized luminance vs. time characteristics of the light-emitting elements. From FIG. 27, it is found that each of the light-emitting elements 1 and 2 shows favorable characteristics and has high reliability.

Example 9

In this example are described light-emitting elements described in Embodiment 1 in which 3-(dibenzothiophen-4-yl)-9-(triphenylen-2-yl)-9H-carbazole (abbreviation: DBTCzTp-II) and 3-(dibenzofuran-4-yl)-9-(triphenylen-2-yl)carbazole (abbreviation: DBFCzTp-II), which are carbazole derivatives, are respectively used as host materials in light-emitting layers in which emission center substances that emit green phosphorescence are used.

The molecular structures of organic compounds used in this example are illustrated in the following structural formulas (i), (iii), and (iv). In the element structure in FIG. 1A, an electron-injection layer is provided between an electron-transport layer 114 and a second electrode 104 was employed.

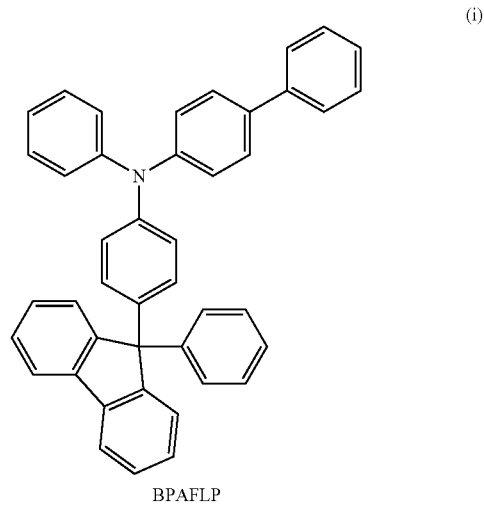

BPAFLP (i)

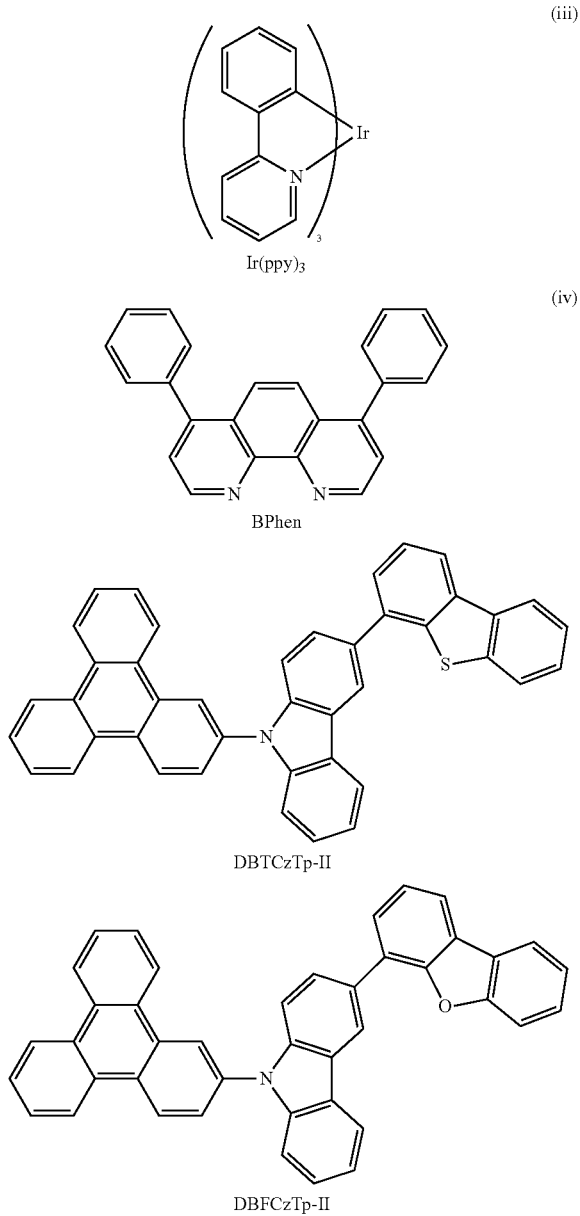

<<Fabrication of Light-Emitting Element 3 and Light-Emitting Element 4>>

First, a glass substrate 101 over which indium tin oxide containing silicon (ITSO) with a thickness of 110 nm was formed as a first electrode 102 was prepared. A surface of the ITSO was covered with a polyimide film so that an area of 2 mm×2 mm of the surface was exposed. The electrode area was 2 mm×2 mm. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate 101 was fixed on a holder provided in the vacuum evaporation apparatus such that the surface of the substrate 101 provided with ITSO faced downward.

After the pressure in the vacuum evaporation apparatus was reduced to $10^{-4}$ Pa, 4-phenyl-4'-(9-phenylfluoren-9-yl)triphenylamine (abbreviation: BPAFLP) represented by the above structural formula (1), and molybdenum(VI) oxide were co-evaporated with a mass ratio of BPAFLP to molybdenum(VI) oxide being 2:1, whereby a hole-injection layer 111 was formed. The thickness thereof was 50 nm. Note that the co-evaporation is an evaporation method in which a plurality of different substances are concurrently vaporized from the respective different evaporation sources.

Next, BPAFLP was evaporated to a thickness of 10 nm, whereby a hole-transport layer 112 was formed.

Further, in the light-emitting element 3, on the hole-transport layer 112, DBTCzTp-II, which is the carbazole derivative represented by the above structural formula in Embodiment 1, and tris(2-phenylpyridinato-N,C$^{2'}$)iridium(III) (abbreviation: Ir(ppy)$_3$) were evaporated to a thickness of 40 nm with a mass ratio of DBTCzTp-II to Ir(ppy)$_3$ being 1:0.06, and then DBTCzTp-II was evaporated to a thickness of 15 nm, whereby a light-emitting layer 113 was formed.

In the light-emitting element 4, on the hole-transport layer 112, DBFCzTp-II which is the carbazole derivative represented by the above structural formula, and Ir(ppy)$_3$ were evaporated to a thickness of 40 nm with a mass ratio of DBFCzTp-II to Ir(ppy)$_3$ being 1:0.06, whereby a light-emitting layer 113 was formed.

Then, on the light-emitting layer 113, bathophenanthroline (abbreviation: BPhen) represented by the above structural formula (iv) was evaporated to a thickness of 15 nm, whereby the electron-transport layer 114 was formed. Further, lithium fluoride was evaporated to a thickness of 1 nm on the electron-transport layer 114, whereby the electron-injection layer was formed. Lastly, an aluminum film was formed to a thickness of 200 nm as the second electrode 104 which serves as a cathode, whereby the light-emitting elements 3 and 4 were completed. Note that in the above evaporation process, evaporation was all performed by a resistance heating method.

<<Operation Characteristics of Light-Emitting Elements 3 and 4>>

The light-emitting elements 3 and 4 thus obtained were sealed in a glove box under a nitrogen atmosphere without being exposed to air. Then, the operation characteristics of these light-emitting elements were measured. Note that the measurements were carried out at room temperature (in an atmosphere kept at 25° C.).

Figure 28:
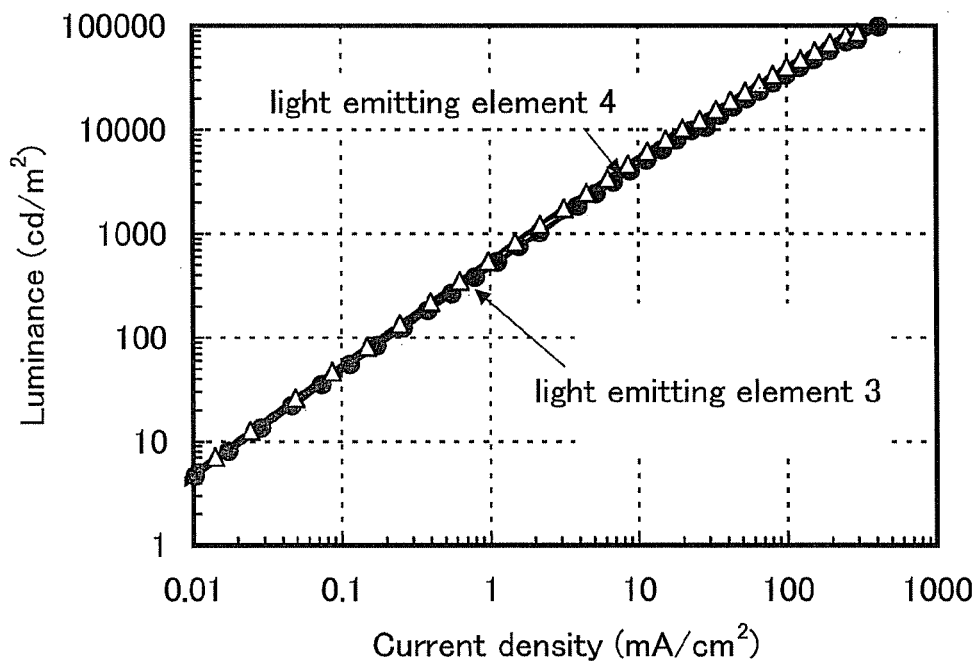
FIG. 28 is a graph showing luminance vs. current density characteristics of a light-emitting element 3 and a light-emitting element 4.
Figure 29:
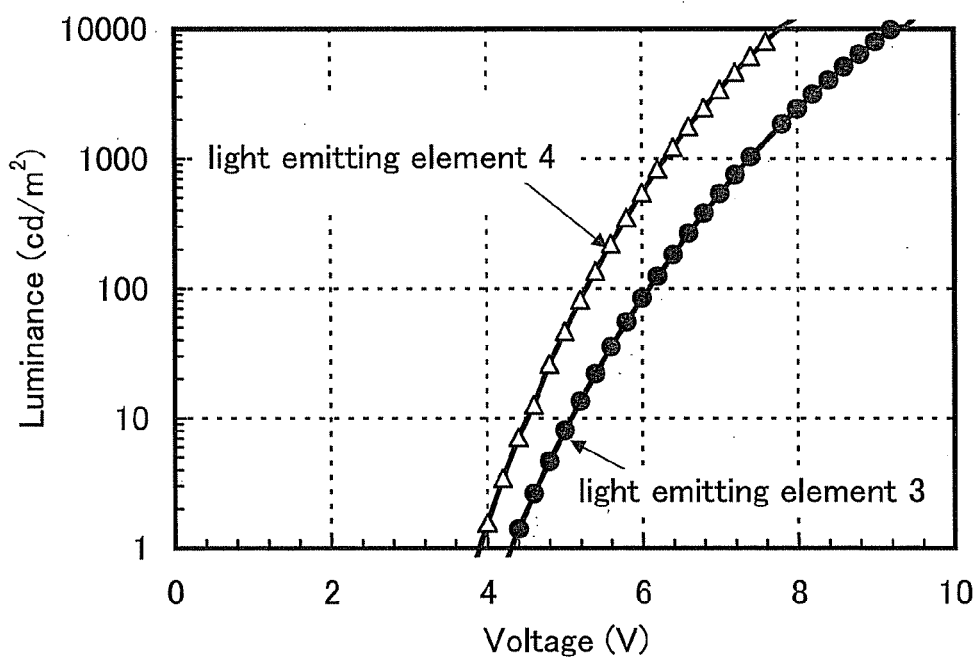
FIG. 29 is a graph showing luminance vs. voltage characteristics of the light-emitting element 3 and the light-emitting element 4.
Figure 30:
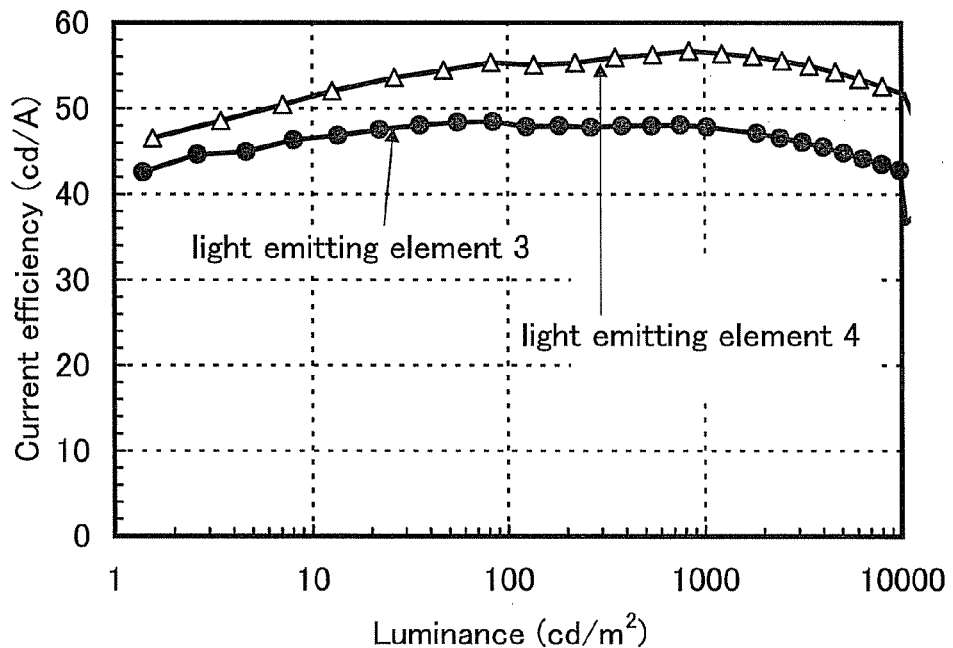
FIG. 30 is a graph showing current efficiency vs. luminance characteristics of the light-emitting element 3 and the light-emitting element 4.

FIG. 28 shows luminance vs. current density characteristics of the light-emitting elements, FIG. 29 shows luminance vs. voltage characteristics thereof, and FIG. 30 shows current efficiency vs. luminance characteristics thereof. In FIG. 28, the vertical axis represents luminance (cd/m$^2$), and the horizontal axis represents current density (mA/cm$^2$). In FIG. 29, the vertical axis represents luminance (cd/m$^2$), and the horizontal axis represents voltage (V). In FIG. 30, the vertical axis represents current efficiency (cd/A), and the horizontal axis represents luminance (cd/m$^2$).

From FIG. 30, it is found that the light-emitting elements in each of which the carbazole derivative described in Embodiment 1 is used as a host material in a light-emitting layer of the light-emitting element that emits green phosphorescence show favorable luminance vs. emission efficiency characteristics and high emission efficiency. This is because the carbazole derivatives described in Embodiment 1 have a wide energy gap, and thus has high triplet excitation energy; as a result, even a light-emitting substance that emits green phosphorescence can be effectively excited. In addition, from FIG. 28, it is found that the light-emitting elements in each of which the carbazole derivative described in Embodiment 1 is used as a host material in a light-emitting layer of the light-emitting element that emits green phosphorescence show favorable luminance vs. voltage characteristics and are driven, with a low driving voltage. This indicates that the carbazole derivatives described in Embodiment 1 have an excellent carrier-transport property.

Figure 31:
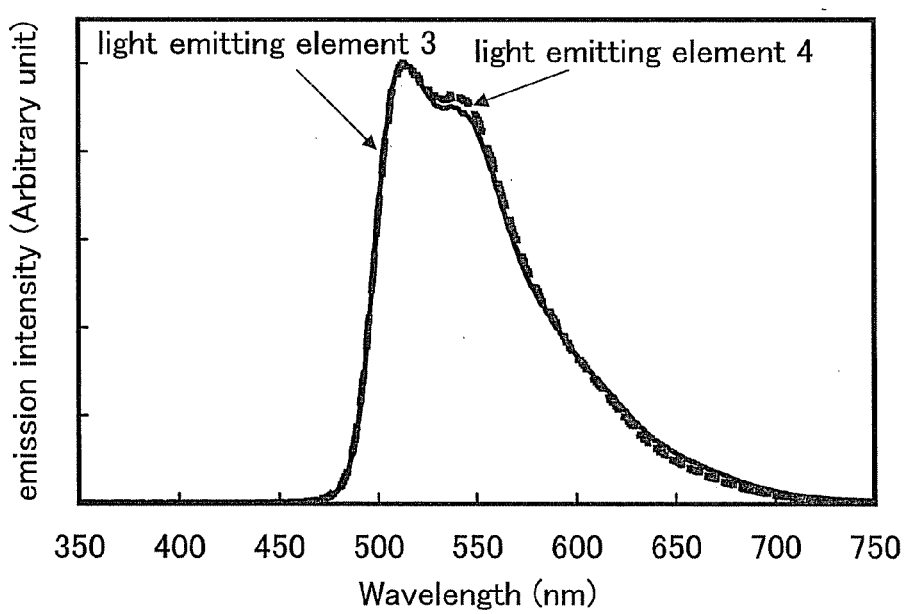
FIG. 31 shows emission spectra of the light-emitting element 3 and the light-emitting element 4.

FIG. 31 shows emission spectra when a current of 1 mA was made to flow in the fabricated light-emitting elements 3 and 4. In FIG. 31, the vertical axis represents emission wavelength (nm), and the horizontal axis represents emission intensity. The emission intensity is shown as a value relative to the maximum emission intensity assumed to be 1. From FIG. 31, it is found that each of the light-emitting elements 3 and 4 emits green light which originates from Ir(ppy)$_3$, which is the emission center substance.

Figure 32:
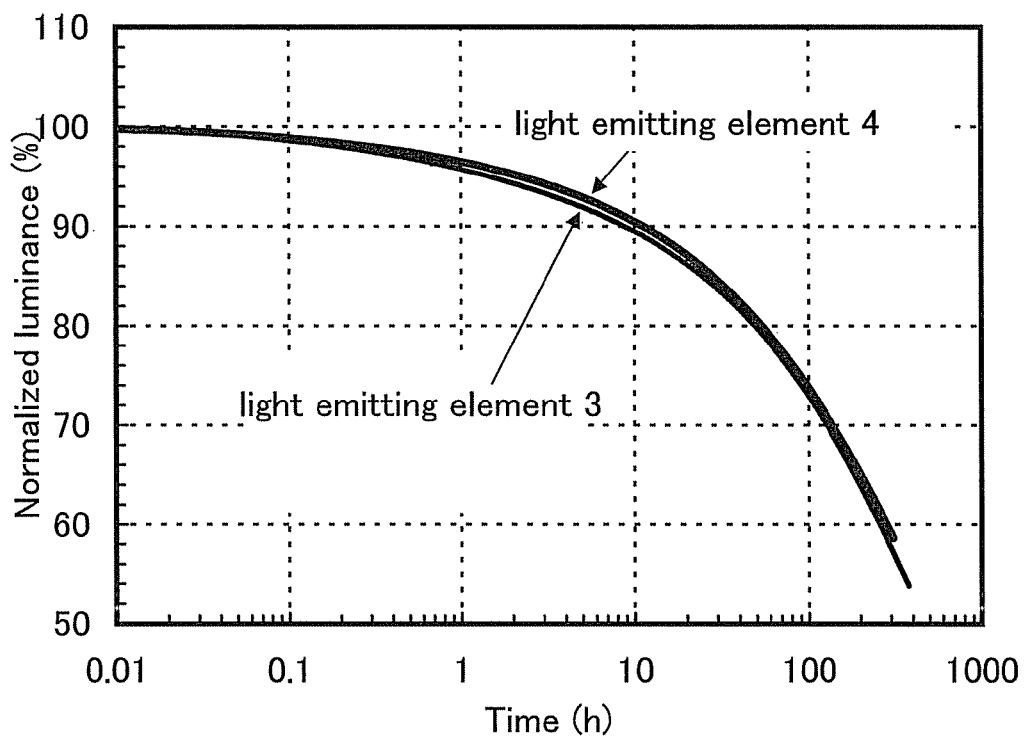
FIG. 32 is a graph showing change of normalized luminance vs. time characteristics of the light-emitting element 3 and the light-emitting element 4.

Next, the initial luminance is set at 1000 cd/m$^2$, these elements were driven under a condition where the current density was constant, and changes in luminance with respect to the driving time were examined. FIG. 32 shows normalized luminance vs. time characteristics of the light-emitting elements. From FIG. 32, it is found that each of the light-emitting elements 3 and 4 shows favorable characteristics and has high reliability.

Example 10

Synthesis Example 8

In this example is described a method of synthesizing 3-(dibenzothiophen-4-yl)-9-(9,10-diphenyl-2-anthryl)-9H-carbazole (abbreviation: 2DBTCzPA-II), which is the carbazole derivative represented by the structural formula (328) in Embodiment 1. A structure of 2DBTCzPA-II is illustrated in the following structural formula.

Step 1: Synthesis of 3-(Dibenzothiophen-4-yl)-9H-carbazole (abbreviation: DBTCz-II)

This was synthesized as in Step 1 in Example 1.

Step 2: Synthesis of 3-(dibenzothiophen-4-yl)-9-(9, 10-diphenyl-2-anthryl)-9H-carbazole (abbreviation: 2DBTCzPA-II)

To a 100-mL three-neck flask were added 1.4 g (3.0 mmol) of 2-iodo-9,10-diphenylanthracene, 1.1 g (3.0 mmol) of 3-(dibenzothiophen-4-yl)-9H-carbazole, and 0.86 g (9.0 mmol) of sodium tert-butoxide. After the air in the flask was replaced with nitrogen, to this mixture were added 20 mL of toluene and 0.2 mL of tri(tert-butyl)phosphine (a 10 wt % hexane solution). This mixture was degassed by being stirred while the pressure was reduced. After the degassing, 86 mg (0.15 mmol) of bis(dibenzylideneacetone)palladium(0) was added to the mixture. This mixture was stirred at 110° C. for 4 hours under a nitrogen stream. After the stirring, the obtained mixture was suction-filtered through Celite (produced by Wako Pure Chemical Industries, Ltd., Catalog No. 531-16855), alumina, and Florisil (produced by Wako Pure Chemical Industries, Ltd., Catalog No. 540-00135). The filtrate was concentrated to give a yellow solid. The obtained solid was purified by silica gel column chromatography (developing solvent, hexane:toluene=5:1). The obtained fraction was concentrated to give a yellow solid. The obtained yellow solid was recrystallized from toluene/hexane, so that 1.5 g of a yellow solid was obtained in 76% yield. The synthesis scheme of Step 2 is illustrated in (b-7).

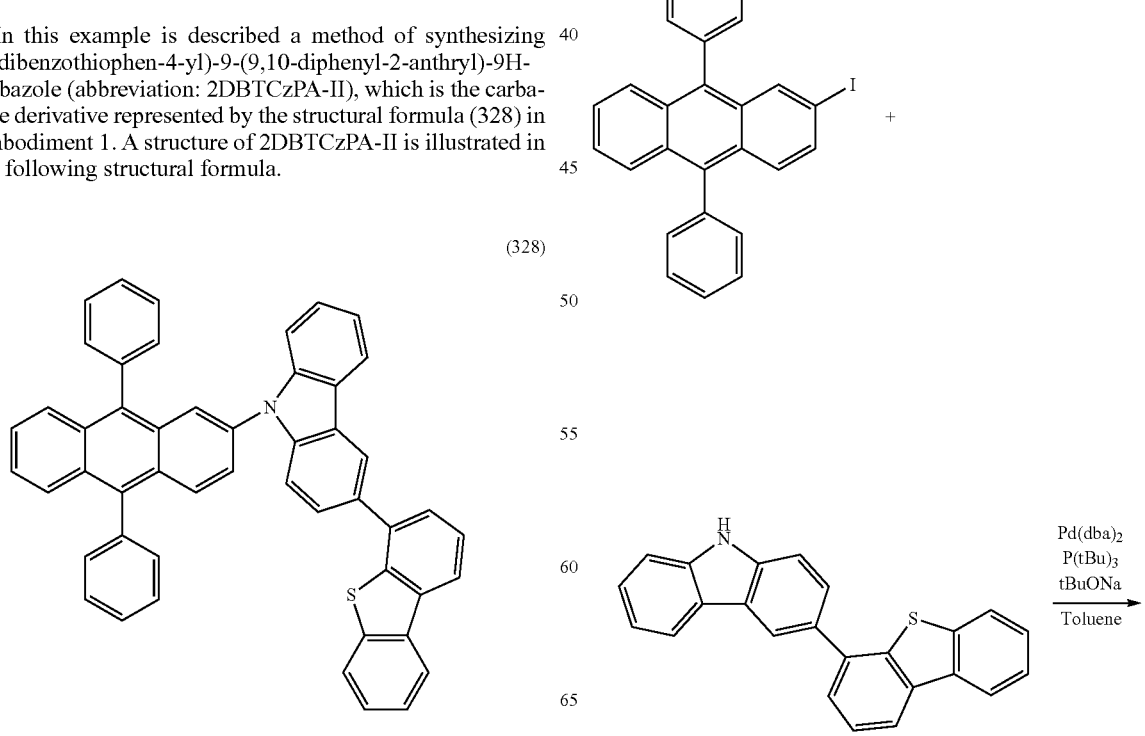

(328)

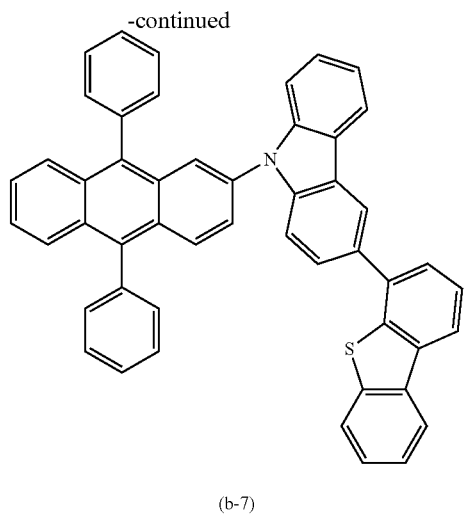

(b-7)

By a train sublimation method, the obtained yellow solid was purified. The purification was conducted by heating of 1.5 g of the yellow solid at 300° C. under a pressure of 2.2 Pa with a flow rate of argon gas of 5 mL/min. After the purification, 1.3 g of a yellow solid was obtained in 87% yield.

The yellow solid after the above purification was subjected to nuclear magnetic resonance (NMR) spectroscopy. The measurement result is described below.

$^1$H NMR (CDCl$_3$, 300 MHz): δ=7.29-7.51 (m, 8H), 7.54-7.69 (m, 13H), 7.74-7.79 (m, 3H), 7.81-7.86 (m, 1H), 7.94 (s, 1H), 7.96 (d, J$_1$=5.7 Hz, 1H), 8.13-8.22 (m, 3H), 8.49 (d, J$_1$=1.5 Hz, 1H)

Figure 33A:
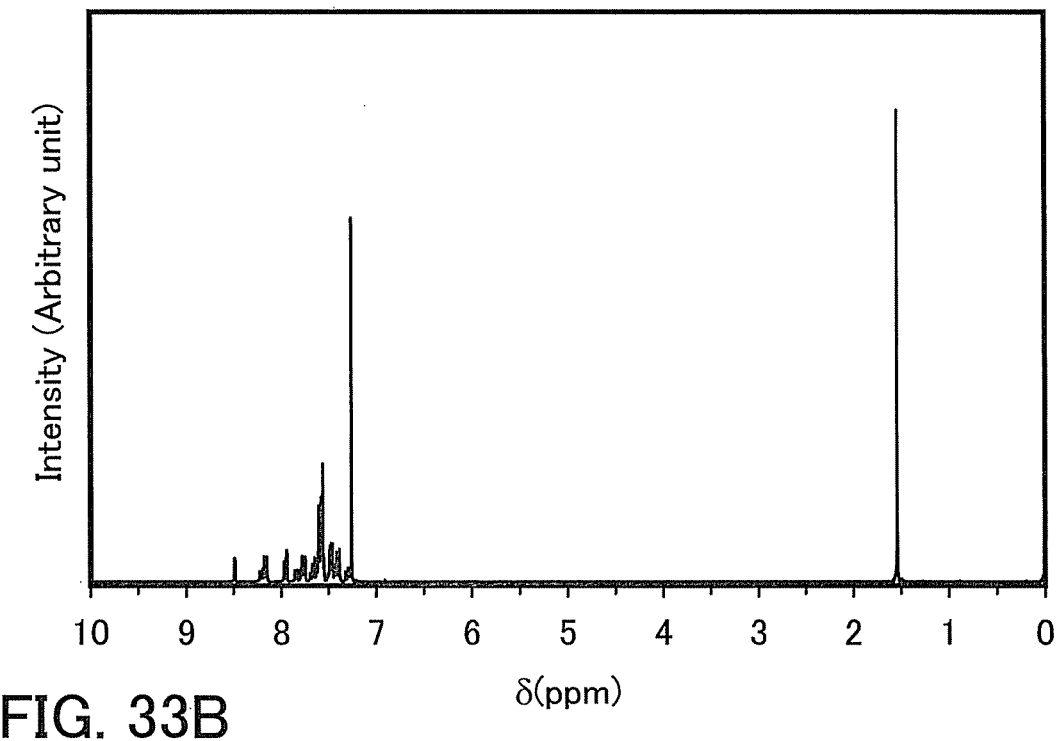
FIGS. 33A and 33B are $^1$H NMR charts of 2DBTCzPA-II.
Figure 33B:
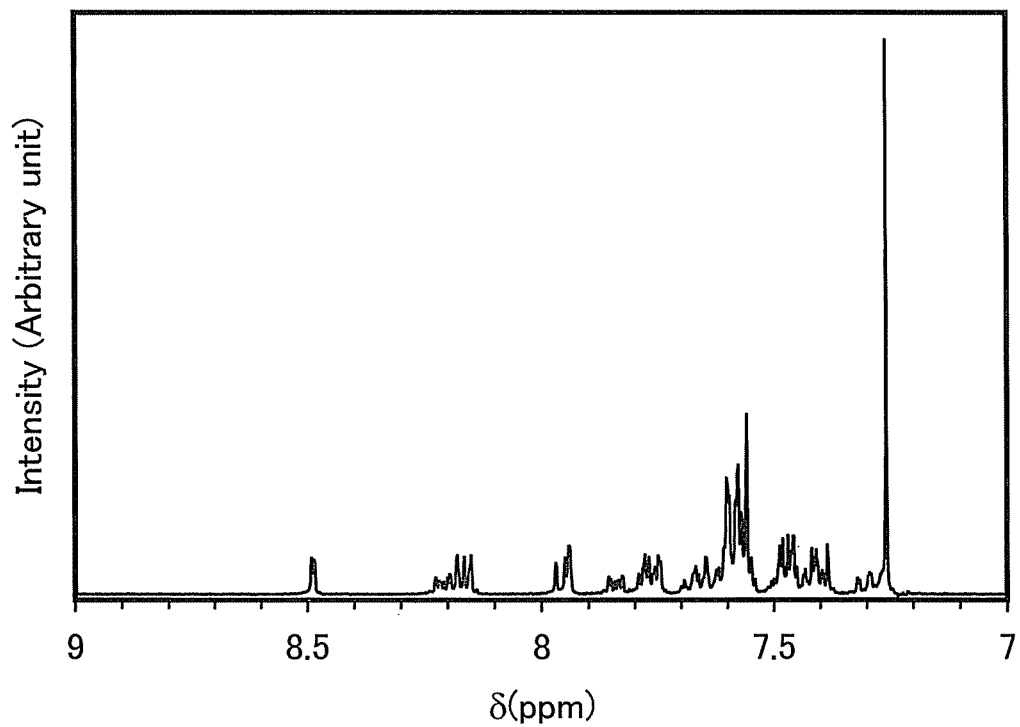

In addition, $^1$H NMR charts are shown in FIGS. 33A and 33B. The measurement results showed that 2DBTCzPA-II, which is the carbazole derivative represented by the above structural formula, was obtained.

Figure 34A:
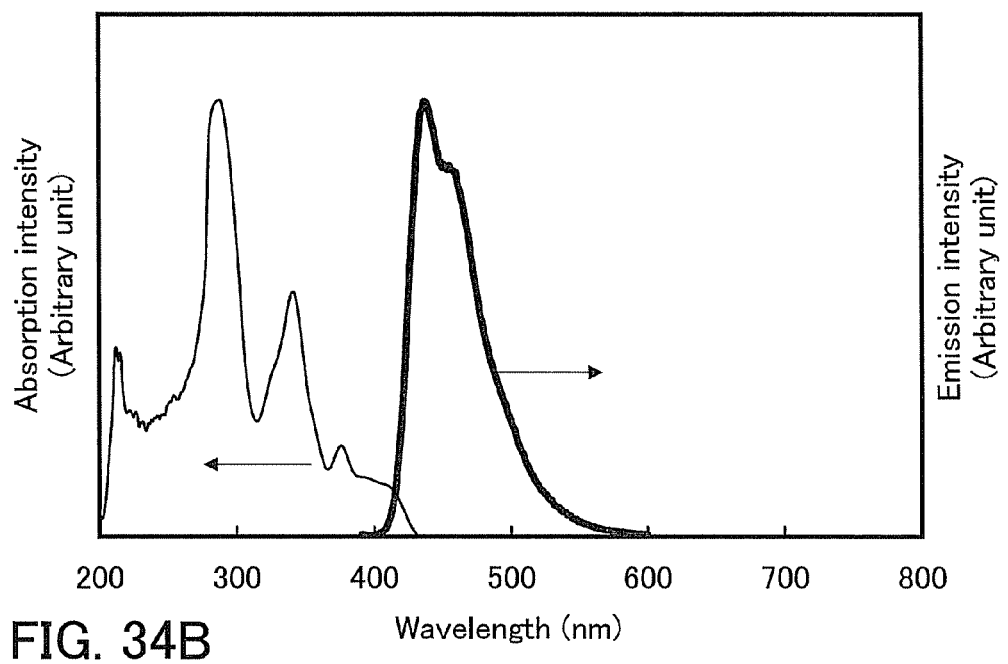
FIGS. 34A and 34B show absorption spectra and emission spectra of 2DBTCzPA-II.
Figure 34B:
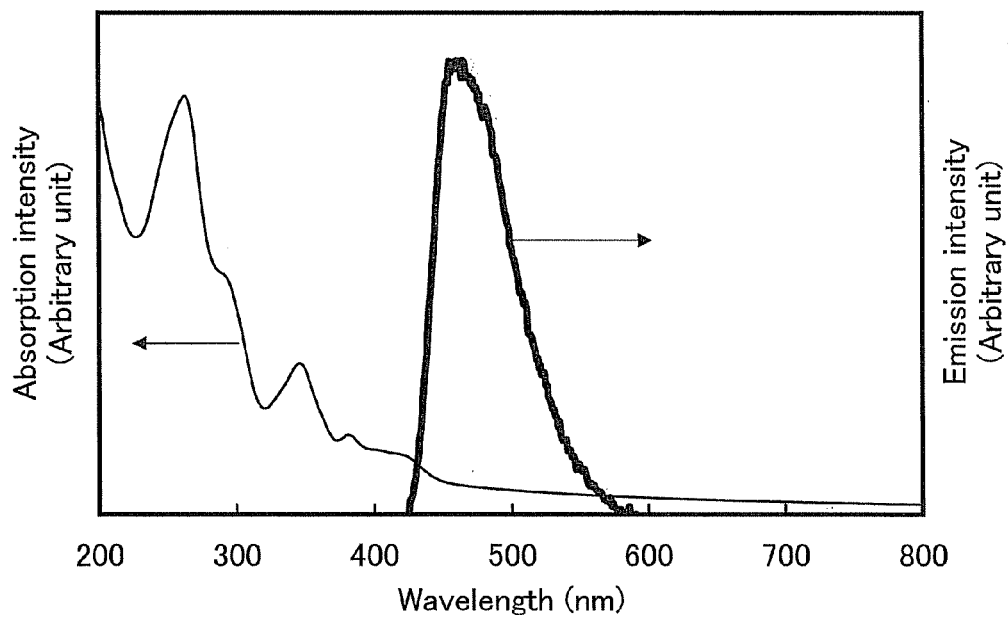

Next, an absorption and emission spectra of 2DBTCzPA-II in a toluene solution of 2DBTCzPA-II are shown in FIG. 34A, and an absorption and emission spectra of a thin film of 2DBTCzPA-II are shown in FIG. 34B. An ultraviolet-visible spectrophotometer (V-550, manufactured by JASCO Corporation) was used for the measurements of the absorption spectra. In the case of the toluene solution, the measurements were made with the toluene solution of 2DBTCzPA-II put in a quartz cell, and the absorption spectrum obtained by subtraction of absorption spectra of the quartz cell and toluene from the measured spectrum is shown in the drawing. In addition, as for the absorption spectrum of the thin film, a sample was prepared by evaporation of 2DBTCzPA-II on a quartz substrate, and the absorption spectrum obtained by subtraction of an absorption spectrum of quartz from the absorption spectrum of this sample is shown in the drawing. As in the measurements of the absorption spectra, an ultraviolet-visible spectrophotometer (V-550, manufactured by JASCO Corporation) was used for the measurements of the emission spectra. The emission spectrum of toluene was measured with the toluene solution of 2DBTCzPA-II put in a quartz cell, and the emission spectrum of the thin film was measured with a sample prepared by evaporation of 2DBTCzPA-II on a quartz substrate. Thus, it was found that the absorption peak wavelengths of 2DBTCzPA-II in the toluene solution of 2DBTCzPA-II were around 376 nm, around 341 nm, and around 288 nm, and the emission peak wavelengths thereof were around 438 nm and around 460 nm (at an excitation wavelength of 377 nm), and that the absorption peak wavelengths of the thin film of 2DBTCzPA-II were around 423 nm, around 381 nm, around 346 nm, and around 263 mm and the greatest emission wavelength thereof was around 460 nm (at an excitation wavelength of 420 nm).

Further, the ionization potential of 2DBTCzPA-II in a thin film state was measured by a photoelectron spectrometer (AC-2, manufactured by Riken Keiki, Co., Ltd.) in air. The obtained value of the ionization potential was converted to a negative value, so that the HOMO level of 2DBTCzPA-II was −5.59 eV. From the data of the absorption spectra of the thin film in FIG. 34B, the absorption edge of 2DBTCzPA-II, which was obtained from Tauc plot with an assumption of direct transition, was 2.75 eV. Therefore, the optical energy gap of 2DBTCzPA-II in the solid state was estimated at 2.75 eV; from the values of the HOMO level obtained above and this energy gap, the LUMO level of 2DBTCzPA-II was able to be estimated at −2.84 eV. It was thus found that 2DBTCzPA-II had a wide energy gap of 2.75 eV in the solid state.

Further, the oxidation reaction characteristics of 2DBTCzPA-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from 0.37 V to 0.90 V and then changed from 0.90 V to 0.36 V was one cycle, and 100 cycles were performed.

The measurement results revealed that 2DBTCzPA-II showed properties effective against repetition of redox reactions between an oxidized state and a neutral state without a large variation in oxidation peak even after the 100 cycles in the measurements.

Further, the HOMO level of 2DBTCzPA-II was determined also by calculation from the CV measurement results.

First, the potential energy of the reference electrode with respect to the vacuum level used was found to be −4.94 eV, as determined in Example 1. The oxidation peak potential E$_{pa}$ of 2DBTCzPA-II was 0.87 V. In addition, the reduction peak potential E$_{pc}$ thereof was 0.74 V. Therefore, a half-wave potential (an intermediate potential between E$_{pa}$ and E$_{pc}$) can be calculated at 0.81 V. This means that 2DBTCzPA-II is oxidized by an electric energy of 0.81 [V vs. Ag/Ag$^+$], and this energy corresponds to the HOMO level. Here, since the potential energy of the reference electrode, which was used in this example, with respect to the vacuum level is −4.94 [eV] as described above, the HOMO level of 2DBTCzPA-II was calculated as follows: −4.94−0.81=−5.75 [eV].

Example 11

Synthesis Example 9

In this example is described a method of synthesizing 3,6-bis(dibenzofuran-4-yl)-9-[4-(10-phenyl-9-anthryl)phenyl]-9H-carbazole (abbreviation: DBF2CzPA-II), which is the carbazole derivative represented by the structural formula (601) in Embodiment 1. A structure of DBF2CzPA-II is illustrated in the following structural formula.

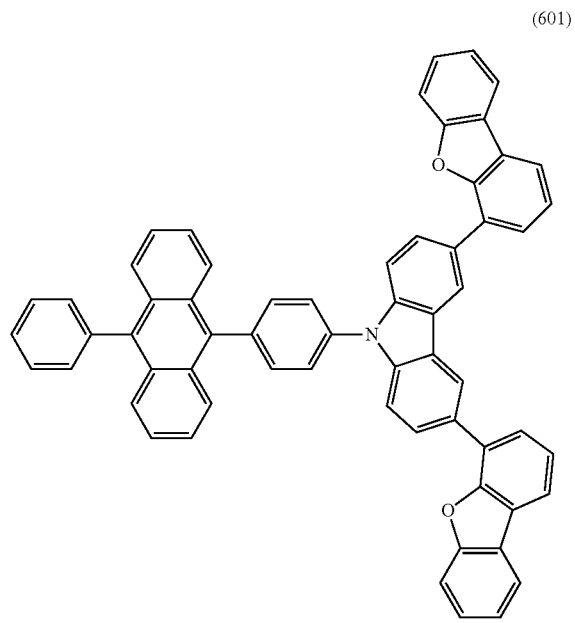 [SMILES: c1ccc(-c2c3ccccc3c(-c3ccc(-n4c5ccc(-c6cccc7c6oc6ccccc67)cc5c5cc(-c6cccc7c6oc6ccccc67)ccc54)cc3)c3ccccc23)cc1]

(601)

Step 1: Synthesis of 3,6-Di(benzofuran-4-yl)-9H-carbazole (abbreviation: DBF2Cz-II)

This was synthesized as in Example 7.

Step 2: Synthesis of 3,6-Bis(dibenzofuran-4-yl)-9-[4-(10-phenyl-9-anthryl)phenyl]-9H-carbazole (abbreviation: DBF2CzPA-II)

To a 100-mL three-neck flask were added 0.99 g (2.4 mmol) of 9-(4-bromophenyl)-10-phenylanthracene, 1.2 g (2.4 mmol) of 3,6-bis(dibenzofuran-4-yl)-9H-carbazole, and 0.62 g (6.4 mmol) of sodium tert-butoxide. After the air in the flask was replaced with nitrogen, to this mixture were added 20 mL of toluene and 0.2 mL of tri(tert-butyl)phosphine (a 10 wt % hexane solution). This mixture was degassed by being stirred while the pressure was reduced. After the degassing, 62 mg (0.11 mmol) of bis(dibenzylideneacetone)palladium (0) was added to the mixture. This mixture was stirred at 110° C. for 20 hours under a nitrogen stream. After the stirring, 100 mL of toluene was added to the obtained mixture, and the mixture was suction-filtered through Celite (produced by Wako Pure Chemical Industries, Ltd., Catalog No. 531-16855), alumina, and Florisil (produced by Wako Pure Chemical Industries, Ltd., Catalog No. 540-00135). The oily substance obtained by concentration of the filtrate was recrystallized from toluene/hexane, so that 1.2 g of a yellow solid was obtained in 59% yield. The synthesis scheme of Step 2 is illustrated in (b-8).

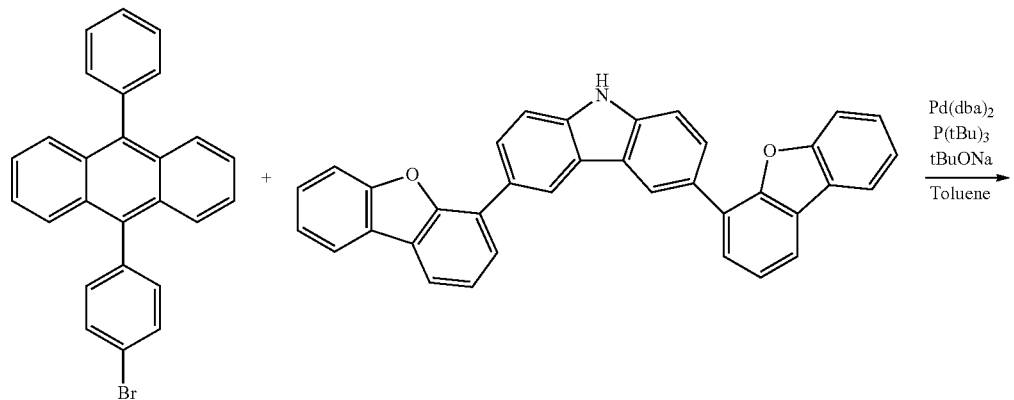

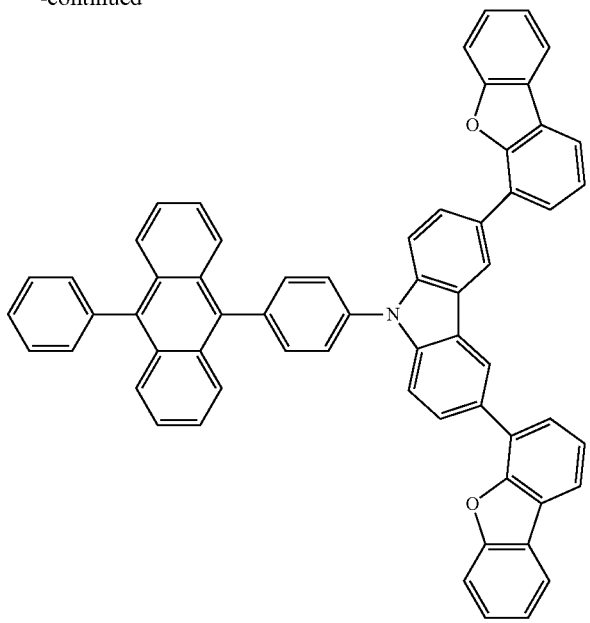

(b-8)

By a train sublimation method, the obtained yellow solid was purified. The purification was conducted by heating of 1.2 g of the yellow solid at 385° C. under a pressure of 2.6 Pa with a flow rate of argon gas of 5 mL/min. After the purification, 0.73 g of a yellow solid was obtained in 61% yield.

The yellow solid after the above purification was subjected to nuclear magnetic resonance (NMR) spectroscopy. The measurement result is described below.

$^1$H NMR(CDCl$_3$, 300 MHz): δ=7.36-7.55 (m, 12H), 7.58-7.67 (m, 5H), 7.76-7.82 (m, 6H), 7.89 (d, J$_1$=8.4 Hz, 4H), 7.95-8.00 (m, 4H), 8.02-8.05 (m, 2H), 8.28 (dd, J$_1$=1.5 Hz, J$_2$=8.7 Hz, 2H), 8.81 (d, J$_1$=1.5 Hz, 2H)

Figure 35A:
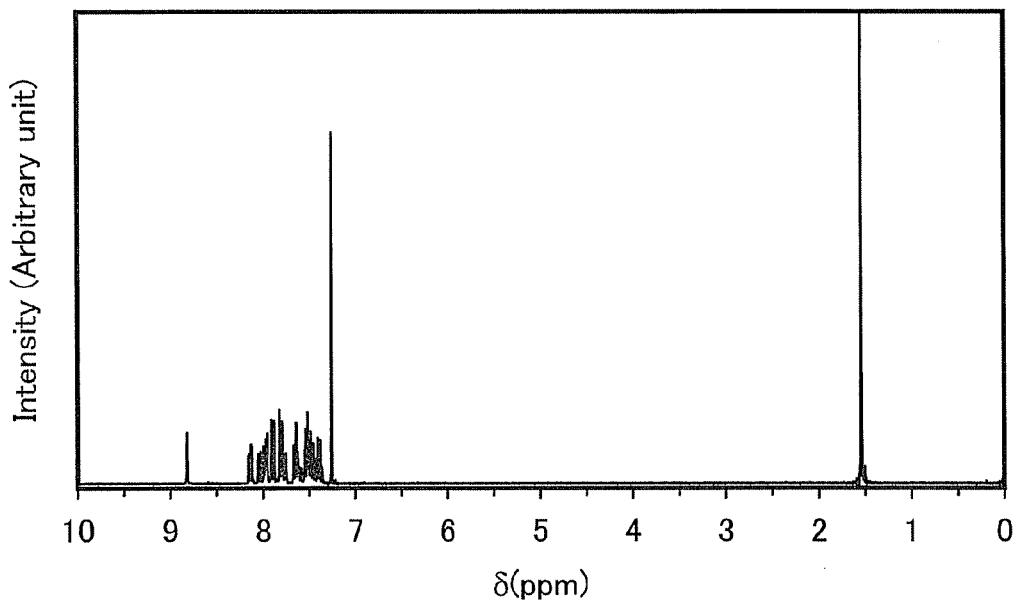
FIGS. 35A and 35B are $^1$H NMR charts of 2DBFCzPA-II.
Figure 35B:
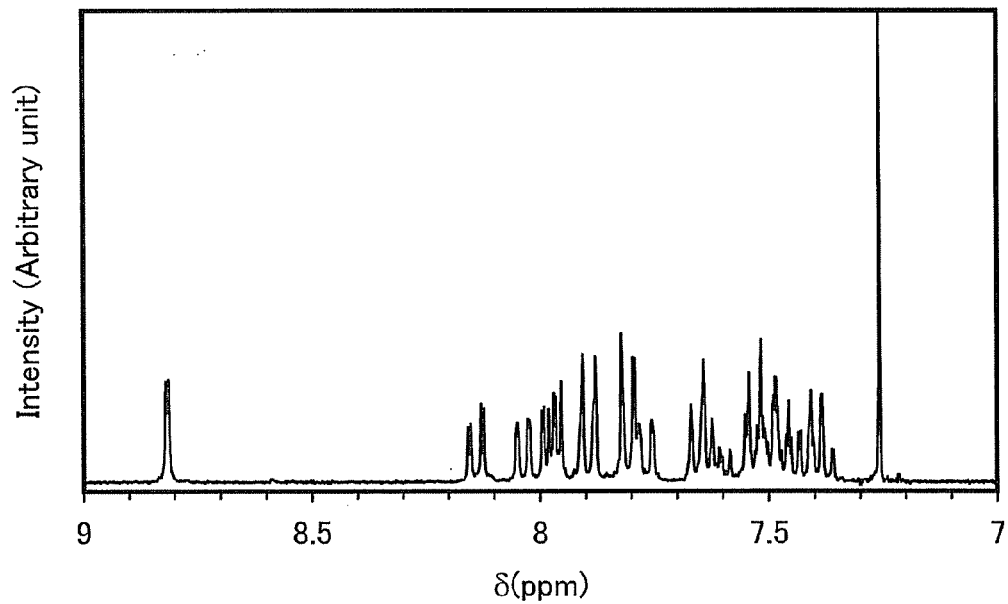

In addition, $^1$H NMR charts are shown in FIGS. 35A and 35B. Note that FIG. 35B is a chart where the range of from 7 ppm to 9 ppm in FIG. 35A is enlarged. The measurement results showed that DBF2CzPA-II, which is the carbazole derivative represented by the above structural formula, was obtained.

Figure 36A:
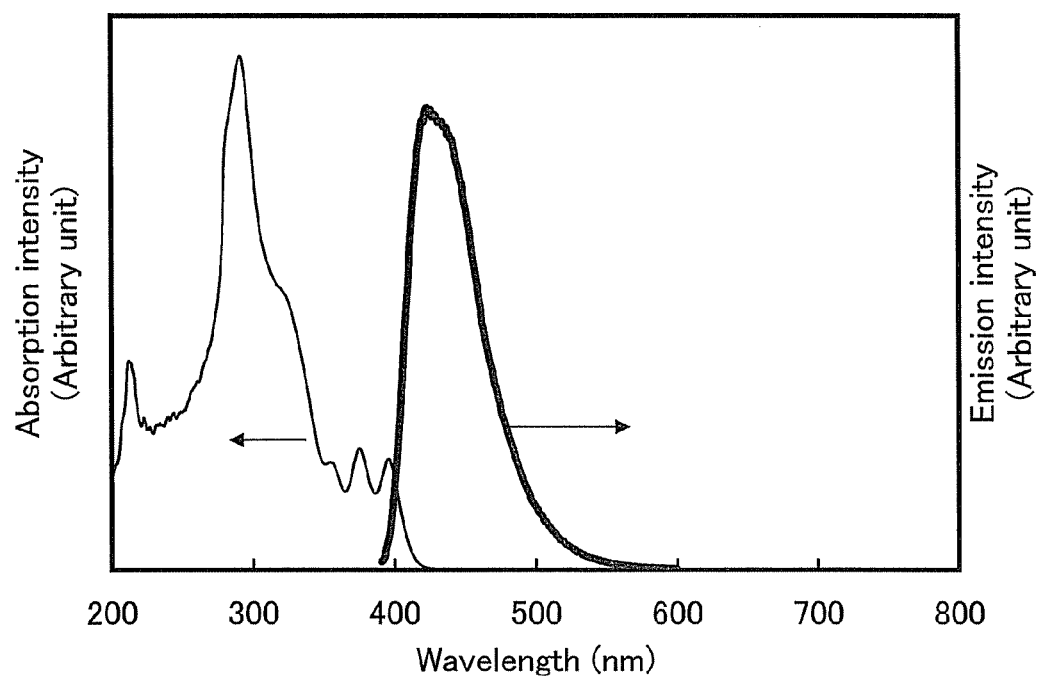
FIGS. 36A and 36B show absorption spectra and emission spectra of 2DBFCzPA-II.
Figure 36B:
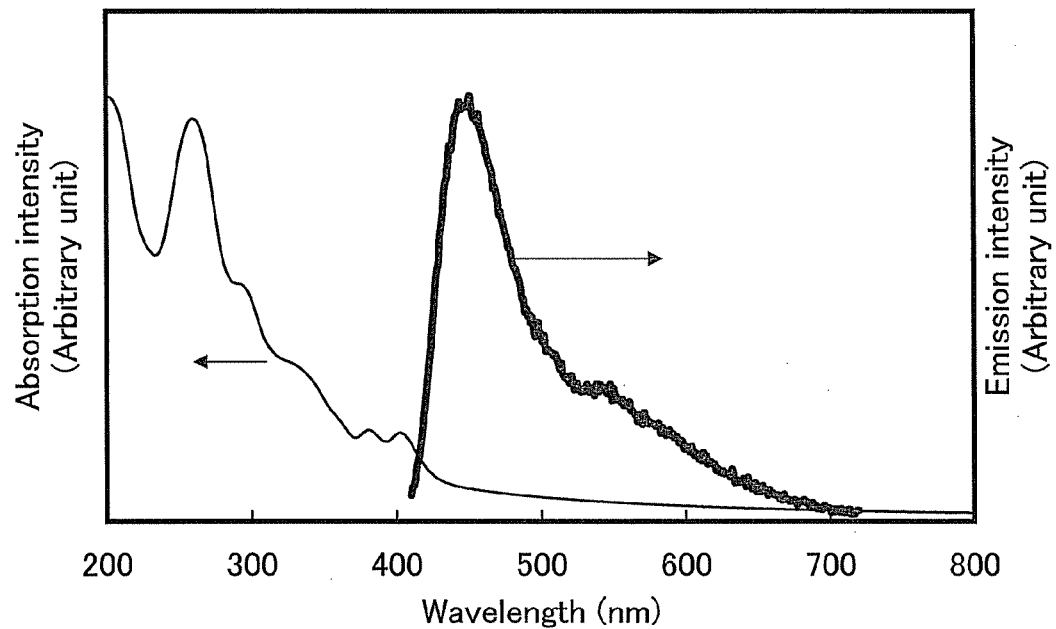

Next, an absorption and emission spectra of DBF2CzPA-II in a toluene solution of DBF2CzPA-II are shown in FIG. 36A, and an absorption and emission spectra of a thin film of DBF2CzPA-II are shown in FIG. 36B. An ultraviolet-visible spectrophotometer (V-550, manufactured by JASCO Corporation) was used for the measurements of the absorption spectra. In the case of the toluene solution, the measurements were made with the toluene solution of DBF2CzPA-II put in a quartz cell, and the absorption spectrum obtained by subtraction of absorption spectra of the quartz cell and toluene from the measured spectrum is shown in the drawing. In addition, as for the absorption spectrum of the thin film, a sample was prepared by evaporation of DBF2CzPA-II on a quartz substrate, and the absorption spectrum obtained by subtraction of an absorption spectrum of quartz from the absorption spectrum of this sample is shown in the drawing. As in the measurements of the absorption spectra, an ultraviolet-visible spectrophotometer (V-550, manufactured by JASCO Corporation) was used for the measurements of the emission spectra. The emission spectrum of toluene was measured with the toluene solution of DBF2CzPA-II put in a quartz cell, and the emission spectrum of the thin film was measured with a sample prepared by evaporation of DBF2CzPA-II on a quartz substrate. Thus, it was found that the absorption peak wavelengths of DBF2CzPA-II in the toluene solution of DBF2CzPA-II were around 396 nm, around 376 nm, around 357 nm, around 326 nm, and around 291 nm, and the emission peak wavelength thereof was around 424 nm (at an excitation wavelength of 376 nm), and that the absorption peak wavelengths of the thin film of DBF2CzPA-II were around 402 nm, around 381 nm, around 357 nm, around 325 nm, around 293 nm, and around 260 nm and the emission peak wavelengths thereof were around 542 nm and around 447 nm (at an excitation wavelength of 403 nm).

Further, the ionization potential of DBF2CzPA-II in a thin film state was measured by a photoelectron spectrometer (AC-2, manufactured by Riken Keiki, Co., Ltd.) in air. The obtained value of the ionization potential was converted to a negative value, so that the HOMO level of DBF2CzPA-II was −5.74 eV. From the data of the absorption spectra of the thin film in FIG. 36B, the absorption edge of DBF2CzPA-II, which was obtained from Tauc plot with an assumption of direct transition, was 2.91 eV. Therefore, the optical energy gap of DBF2CzPA-II in the solid state was estimated at 2.91 eV; from the values of the HOMO level obtained above and this energy gap, the LUMO level of DBF2CzPA-II was able to be estimated at −2.83 eV. It was thus found that DBF2CzPA-II had a wide energy gap of 2.91 eV in the solid state.

Further, the oxidation reaction characteristics of DBF2CzPA-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated. N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from 0.08 V to 0.90 V and then changed from 0.90 V to 0.08 V was one cycle, and 100 cycles were performed.

The measurement results revealed that DBF2CzPA-II showed properties effective against repetition of redox reactions between an oxidized state and a neutral state without a large variation in oxidation peak even after the 100 cycles in the measurements.

Further, the HOMO level of DBF2CzPA-II was determined also by calculation from the CV measurement results.

First, the potential energy of the reference electrode with respect to the vacuum level used was found to be −4.94 eV, as determined in Example 1. The oxidation peak potential $E_{pa}$ of DBF2CzPA-II was 0.87 V. In addition, the reduction peak potential $E_{pc}$ thereof was 0.73 V. Therefore, a half-wave potential (an intermediate potential between $E_{pa}$ and $E_{pc}$) can be calculated at 0.80 V. This means that DBF2CzPA-II is oxidized by an electric energy of 0.80 [V vs. Ag/Ag$^+$], and this energy corresponds to the HOMO level. Here, since the potential energy of the reference electrode, which was used in this example, with respect to the vacuum level is −4.94 [eV] as described above, the HOMO level of DBF2CzPA-II was calculated as follows: −4.94−0.80=−5.74 [eV].

Example 12

Synthesis Example 10

In this example is described a method of synthesizing 3-(dibenzothiophen-4-yl)-9-[3-(10-phenyl-9-anthryl)phenyl]-9H-carbazole (abbreviation: mDBTCzPA-II), which is the carbazole derivative represented by the structural formula (335) in Embodiment 1. A structure of mDBTCzPA-II is illustrated in the following structural formula.

Step 1: Synthesis of 3-(Dibenzothiophen-4-yl)-9H-carbazole (abbreviation: DBTCz-II)

This was synthesized as in Step 1 in Example 1.

Step 2: Synthesis of 3-(Dibenzothiophen-4-yl)-9-[3-(10-phenyl-9-anthryl)phenyl]-9H-carbazole (abbreviation: mDBTCzPA-II)

In a 50-mL three-neck flask were put 1.2 g (3.0 mmol) of 9-(3-bromophenyl)-10-phenylanthracene, 1.1 g (3.0 mmol) of 3-(dibenzothiophen-4-yl)-9H-carbazole, and 0.87 g (9.1 mmol) of sodium tert-butoxide. After the air in the flask was replaced with nitrogen, to this mixture were added 20 mL of toluene and 0.2 mL of tri(tert-butyl)phosphine (a 10 wt % hexane solution). This mixture was degassed by being stirred while the pressure was reduced. After the degassing, 87 mg (0.15 mmol) of bis(dibenzylideneacetone)palladium(0) was added to this mixture. This mixture was stirred at 110° C. for 5 hours under a nitrogen stream. After the stirring, the obtained mixture was suction-filtered through Celite (produced by Wako Pure Chemical Industries, Ltd., Catalog No. 531-16855), alumina, and Florisil (produced by Wako Pure Chemical Industries, Ltd., Catalog No. 540-00135). The filtrate was concentrated to give a yellow solid. The obtained solid was recrystallized from toluene. The obtained crystal was purified by high performance liquid column chromatography (abbreviation: HPLC) (developing solvent: chloroform). The obtained fraction was concentrated to give 1.5 g of a pale yellow solid in 72% yield. The synthesis scheme of Step 2 is illustrated in (b-9).

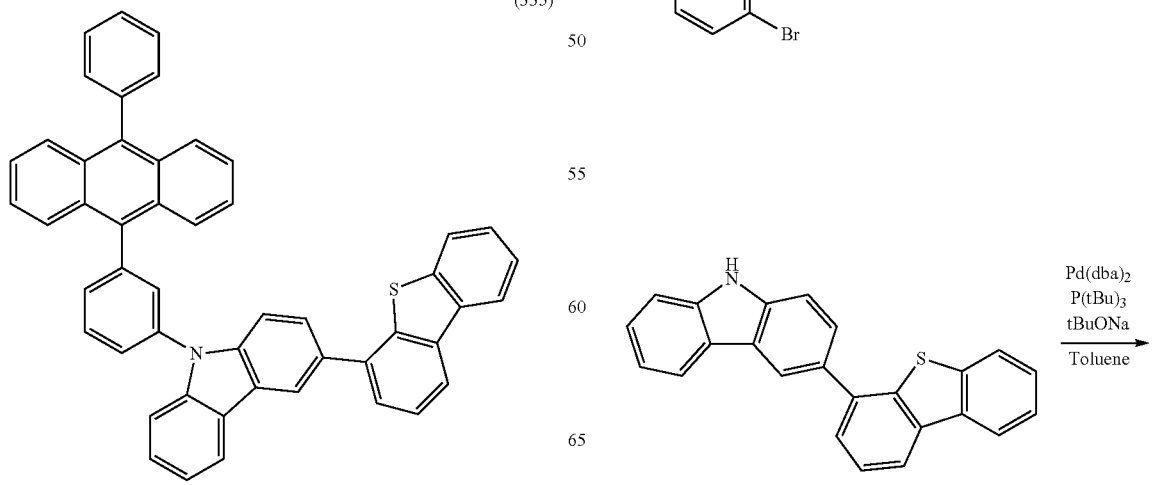

(335)

-continued

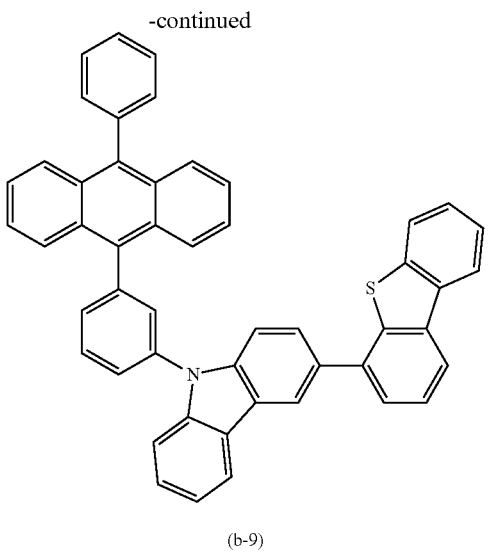

(b-9)

By a train sublimation method, the obtained pale yellow solid was purified. The purification was conducted by heating of 1.0 g of the pale yellow solid at 300° C. under a pressure of 2.6 Pa with a flow rate of argon gas of 5 mL/min. After the purification, 0.79 g of a white solid was obtained in a yield of 79%.

The pale yellow solid after the above purification was subjected to nuclear magnetic resonance (NMR) spectroscopy. The measurement data are shown below.

$^1$H NMR (CDCl$_3$, 300 MHz): δ=7.30-7.52 (m, 10H), 7.55-7.68 (m, 7H), 7.71-7.77 (m, 3H), 7.81-7.92 (m, 7H), 8.14-8.23 (m, 3H), 8.51 (d, J$_1$=0.90 Hz, 1H)

Figure 37A:
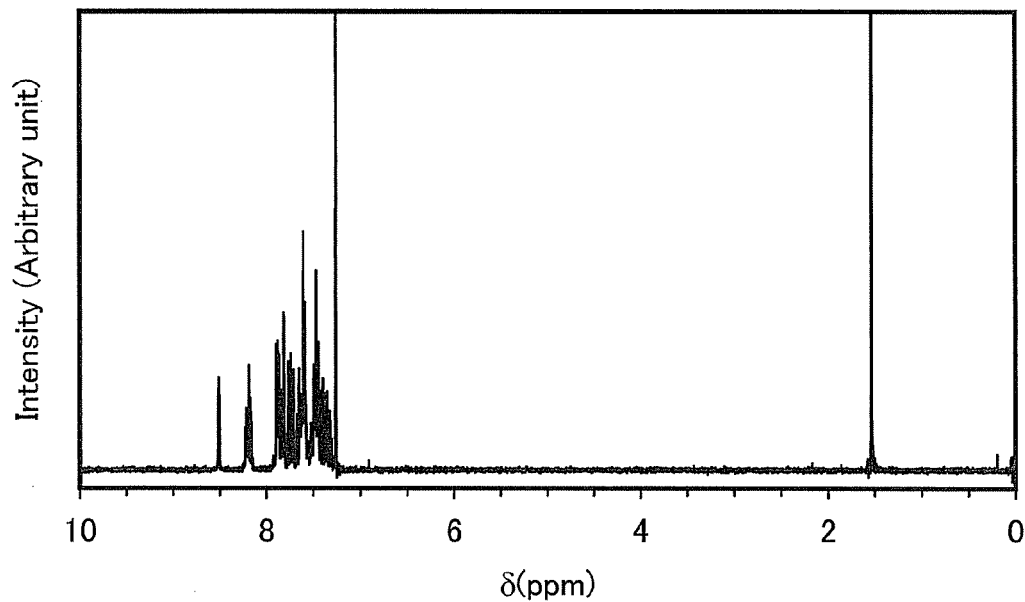
FIGS. 37A and 37B are $^1$H NMR charts of mDBTCzPA-II.
Figure 37B:
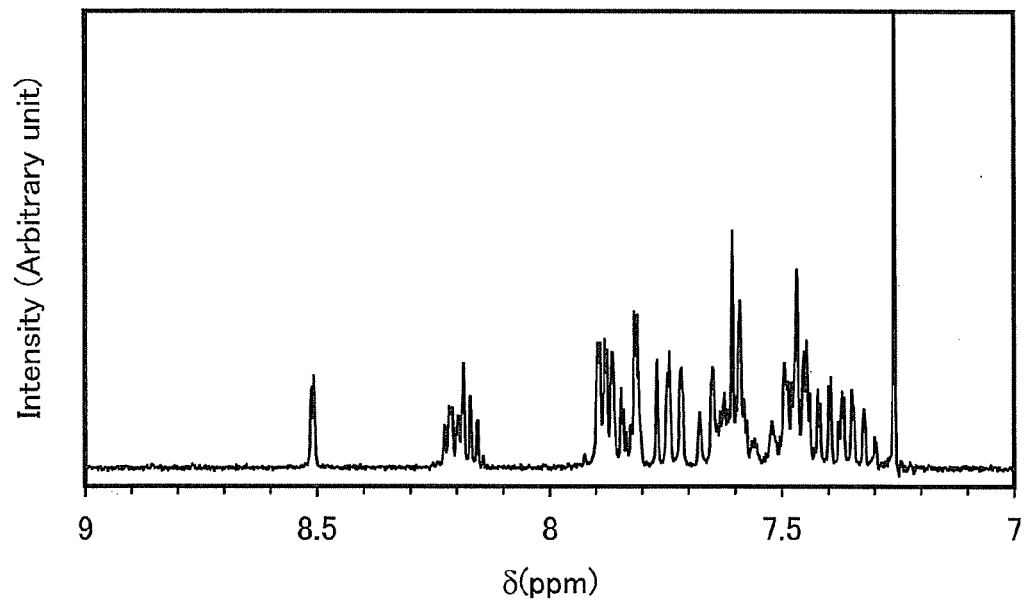

In addition, $^1$H NMR charts are shown in FIGS. 37A and 37B. Note that FIG. 37B is a chart where the range of from 7 ppm to 9 ppm in FIG. 37A is enlarged. The measurement results showed that mDBTCzPA-II, which is the carbazole derivative represented by the above structural formula, was obtained.

Figure 38A:
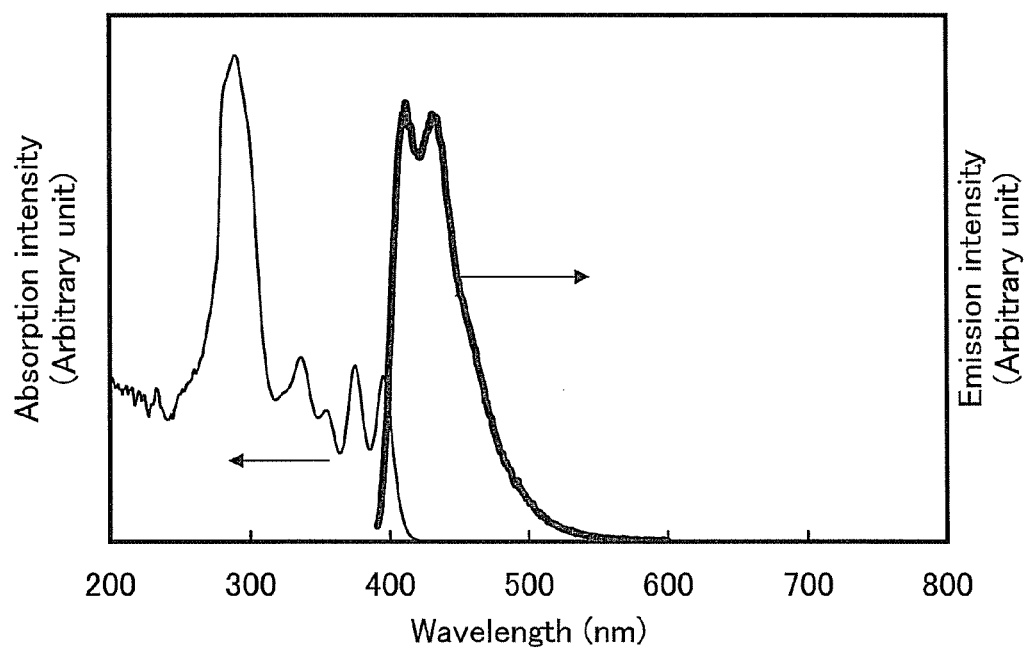
FIGS. 38A and 38B show absorption spectra and emission spectra of mDBTCzPA-II.
Figure 38B:
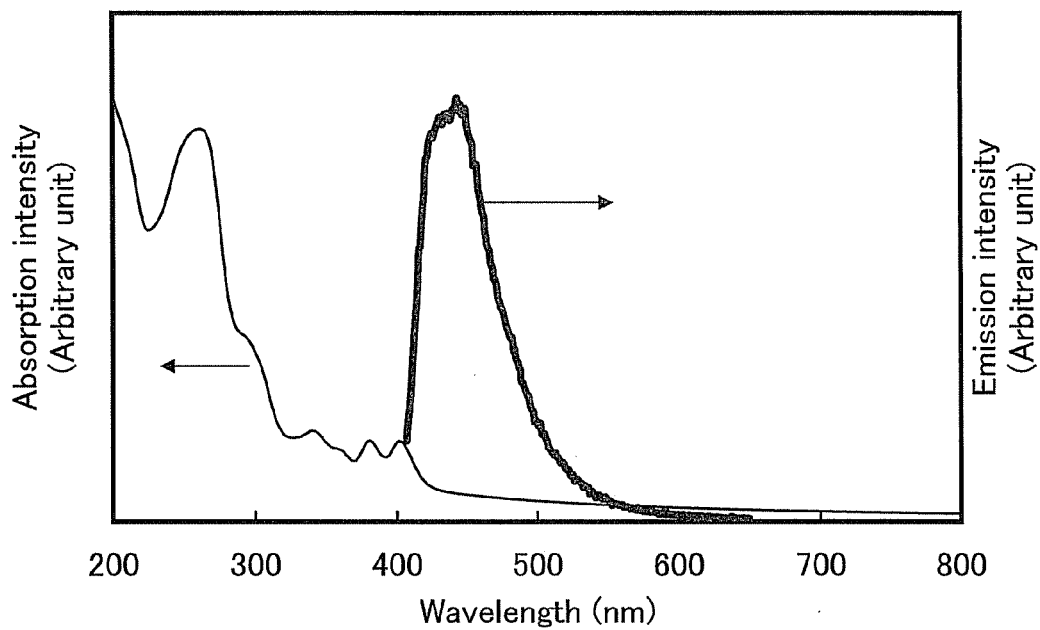

Next, an absorption and emission spectra of mDBTCzPA-II in a toluene solution of mDBTCzPA-II are shown in FIG. 38A, and an absorption and emission spectra of a thin film of mDBTCzPA-II are shown in FIG. 38B. An ultraviolet-visible spectrophotometer (V-550, manufactured by JASCO Corporation) was used for the measurements of the absorption spectra. In the case of the toluene solution, the measurements were made with the toluene solution of mDBTCzPA-II put in a quartz cell, and the absorption spectrum obtained by subtraction of the absorption spectra of the quartz cell and toluene from the measured spectrum is shown in the drawing. In addition, as for the absorption spectrum of the thin film, a sample was prepared by evaporation of mDBTCzPA-II on a quartz substrate, and the absorption spectrum obtained by subtraction of an absorption spectrum of quartz from the absorption spectrum of this sample is shown in the drawing. As in the measurements of the absorption spectra, an ultraviolet-visible spectrophotometer (V-550, manufactured by JASCO Corporation) was used for the measurements of the emission spectra. The emission spectrum of toluene was measured with the toluene solution of mDBTCzPA-II put in a quartz cell, and the emission spectrum of the thin film was measured with a sample prepared by evaporation of mDBTCzPA-II on a quartz substrate. Thus, it was found that the absorption peak wavelengths of mDBTCzPA-II in the toluene solution of mDBTCzPA-II were around 396 nm, around 375 nm, around 354 nm, around 336 nm, and around 290 nm and the emission peak wavelengths thereof were around 412 nm and around 433 nm (at an excitation wavelength of 376 nm), and that the absorption peak wavelengths of the thin film of mDBTCzPA-II were around 402 nm, around 381 nm, around 359 nm, around 340 nm, around 291 nm, around 261 nm, and around 207 nm and the greatest emission wavelength thereof was around 443 nm (at an excitation wavelength of 402 nm).

Further, the ionization potential of mDBTCzPA-II in a thin film state was measured by a photoelectron spectrometer (AC-2, manufactured by Riken Keiki, Co., Ltd.) in air. The obtained value of the ionization potential was converted to a negative value, so that the HOMO level of mDBTCzPA-II was −5.77 eV. From the data of the absorption spectra of the thin film in FIG. 38B, the absorption edge of mDBTCzPA-II, which was obtained from Tauc plot with an assumption of direct transition, was 2.95 eV. Therefore, the optical energy gap of mDBTCzPA-II in the solid state was estimated at 2.95 eV; from the values of the HOMO level obtained above and this energy gap, the LUMO level of mDBTCzPA-II was able to be estimated at −2.82 eV. It was thus found that mDBTCzPA-II had a wide energy gap of 2.95 eV in the solid state.

Further, the oxidation reaction characteristics of mDBTCzPA-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from −0.04 V to 1.15 V and then changed from 1.15 V to −0.04 V was one cycle, and 100 cycles were performed.

The measurement results revealed that mDBTCzPA-II showed properties effective against repetition of redox reactions between an oxidized state and a neutral state without a large variation in oxidation peak even after the 100 cycles in the measurements.

Further, the HOMO level of mDBTCzPA-II was determined also by calculation from the CV measurement results.

First, the potential energy of the reference electrode with respect to the vacuum level used was found to be −4.94 eV, as determined in Example 1. The oxidation peak potential E$_{pa}$ of mDBTCzPA-II was 0.95 V. In addition, the reduction peak potential E$_{pc}$ thereof was 0.83 V. Therefore, a half-wave potential (an intermediate potential between E$_{pa}$ and E$_{pc}$) can be calculated at 0.89 V. This means that mDBTCzPA-II is oxidized by an electric energy of 0.89 [V versus Ag/Ag$^+$], and this energy corresponds to the HOMO level. Here, since the potential energy of the reference electrode, which was used in

Example 13

Synthesis Example 11

In this example is described a method of synthesizing 3-(dibenzofuran-4-yl)-9-[3-(10-phenyl-9-anthryl)phenyl]-9H-carbazole (abbreviation: mDBFCzPA-II), which is the carbazole derivative represented by the structural formula (734) in Embodiment 1. A structure of mDBFCzPA-II is illustrated in the following structural formula.

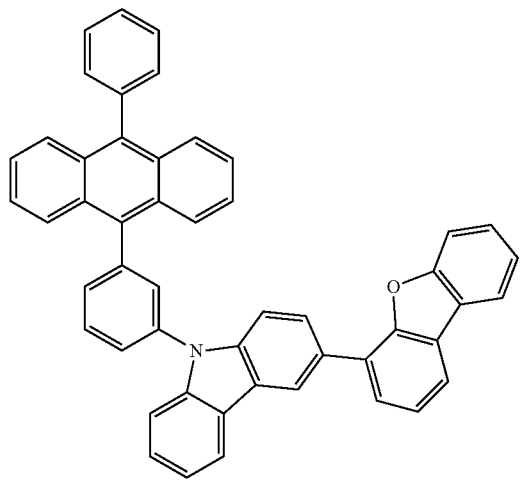

(734)

Step 1: Synthesis of 3-(Dibenzofuran-4-yl)-9H-carbazole (abbreviation: DBFCz-II)

This was synthesized as in Step 1 in Example 2.

Step 2: Synthesis of 3-(Dibenzofuran-4-yl)-9-[3-(10-phenyl-9-anthryl)phenyl]-9H-carbazole (abbreviation: mDBFCzPA-II)

In a 100-mL three-neck flask were put 1.2 g (3.0 mmol) of 9-(3-bromophenyl)-10-phenylanthracene, 1.0 g (3.0 mmol) of 3-(dibenzofuran-4-yl)-9H-carbazole, and 0.87 g (9.1 mmol) of sodium tert-butoxide. After the air in the flask was replaced with nitrogen, to this mixture were added 20 mL of toluene and 0.2 mL of tri(tert-butyl)phosphine (a 10 wt % hexane solution). This mixture was degassed by being stirred while the pressure was reduced. After the degassing, 87 mg (0.15 mmol) of bis(dibenzylideneacetone)palladium(0) was added to this mixture. This mixture was stirred at 110° C. for 6 hours under a nitrogen stream. After the stirring, the obtained mixture was suction-filtered through Celite (produced by Wako Pure Chemical Industries, Ltd., Catalog No. 531-16855), alumina, and Florisil (produced by Wako Pure Chemical Industries, Ltd., Catalog No. 540-00135). The filtrate was concentrated to give a yellow solid. The obtained solid was recrystallized from toluene to give 1.8 g of a white solid which was the object of the synthesis in 88% yield. The synthesis scheme of Step 2 is illustrated in (b-10).

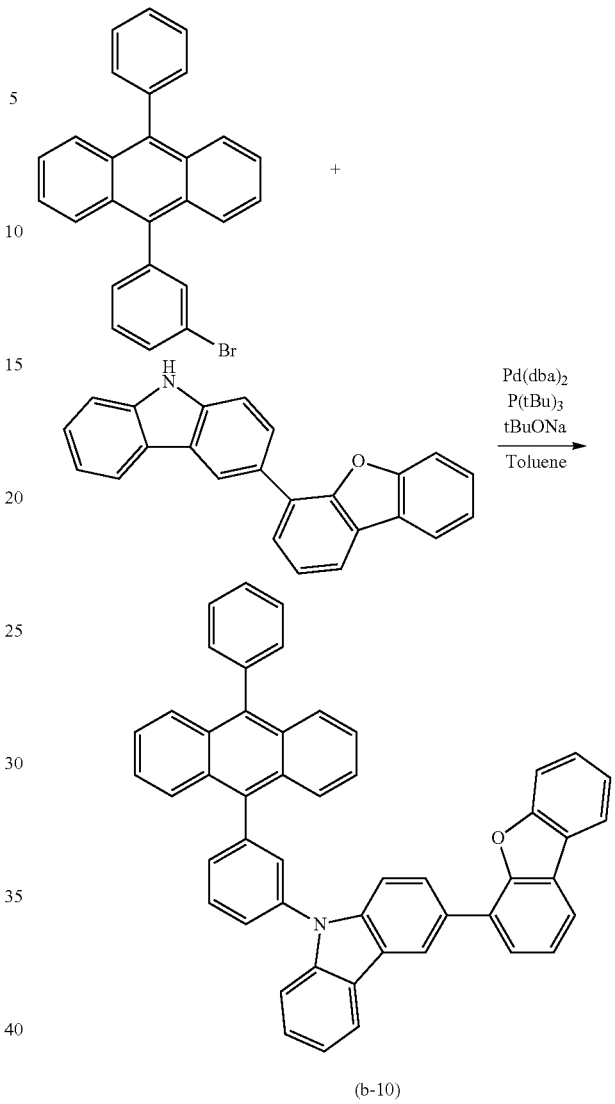

(b-10)

By a train sublimation method, the obtained white solid was purified. The purification was conducted by heating of 1.2 g of the white solid at 300° C. under a pressure of 2.6 Pa with a flow rate of argon gas of 5 mL/min. After the purification, 1.1 g of a white solid was obtained in a yield of 89%.

The white solid after the above purification was subjected to nuclear magnetic resonance (NMR) spectroscopy. The measurement data are shown below.

$^1$H NMR (CDCl$_3$, 300 MHz): δ=7.31-7.40 (m, 4H), 7.42-7.67 (m, 13H), 7.70-7.81 (m, 5H), 7.85-7.92 (m, 4H), 7.95 (dd, $J_1$=1.5 Hz, $J_2$=7.8 Hz, 1H), 7.99-8.03 (m, 2H), 8.24 (d, $J_1$=7.8 Hz, 1H), 8.65 (d, $J_1$=1.5 Hz, 1H)

Figure 39A:
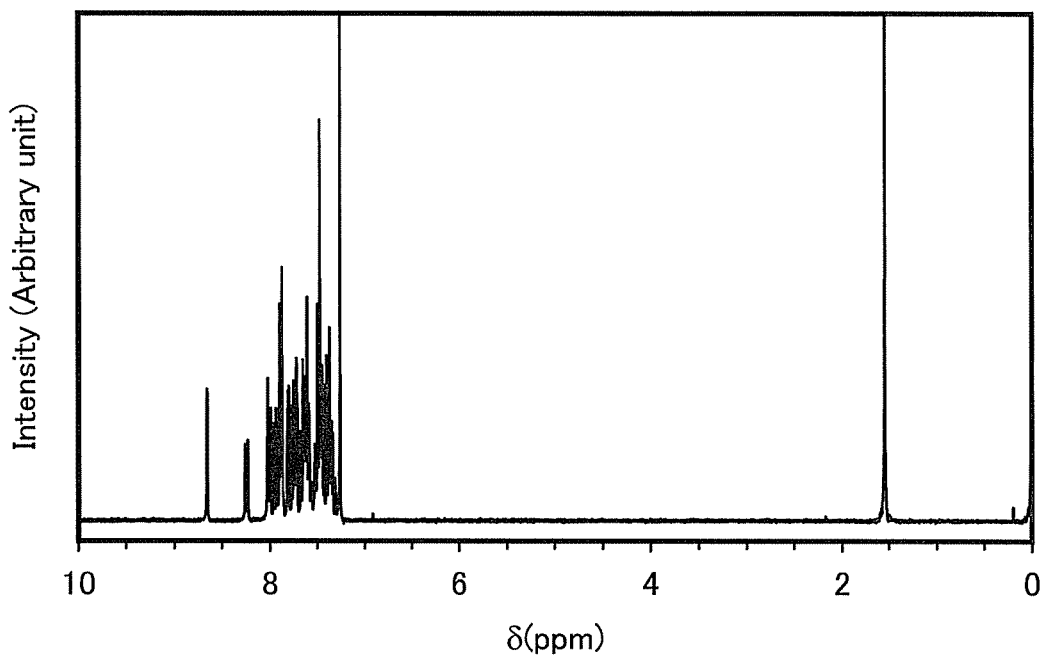
FIGS. 39A and 39B are $^1$H NMR charts of mDBFCzPA-II.
Figure 39B:
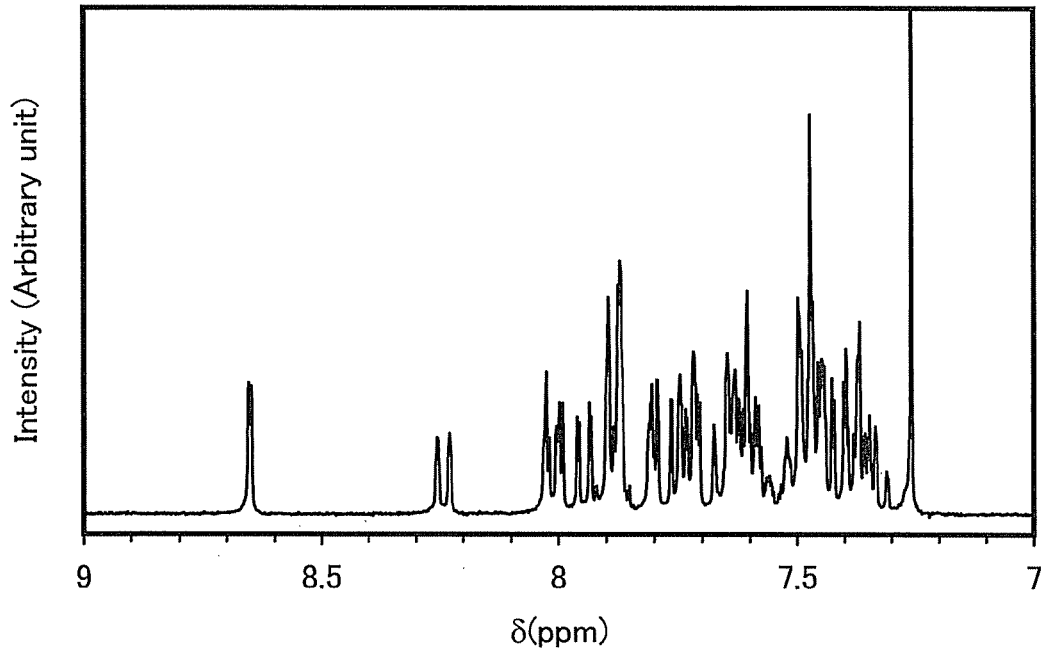

In addition, $^1$H NMR charts are shown in FIGS. 39A and 39B. Note that FIG. 39B is a chart where the range of from 7 ppm to 9 ppm in FIG. 39A is enlarged. The measurement results showed that mDBFCzPA-II, which is the carbazole derivative represented by the above structural formula, was obtained.

Figure 40A:
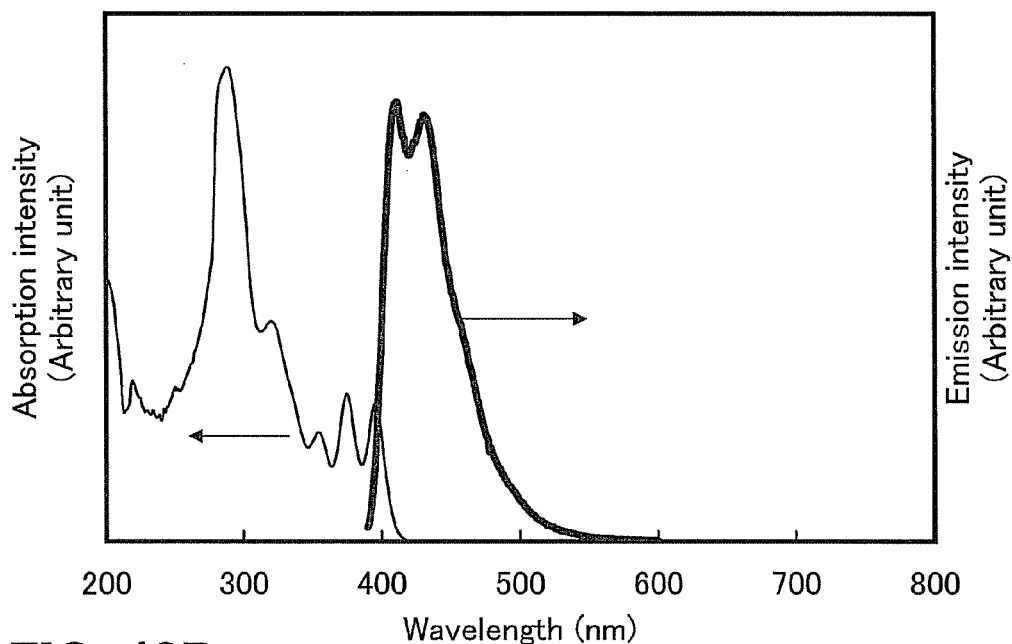
FIGS. 40A and 40B show absorption spectra and emission spectra of mDBFCzPA-II.
Figure 40B:
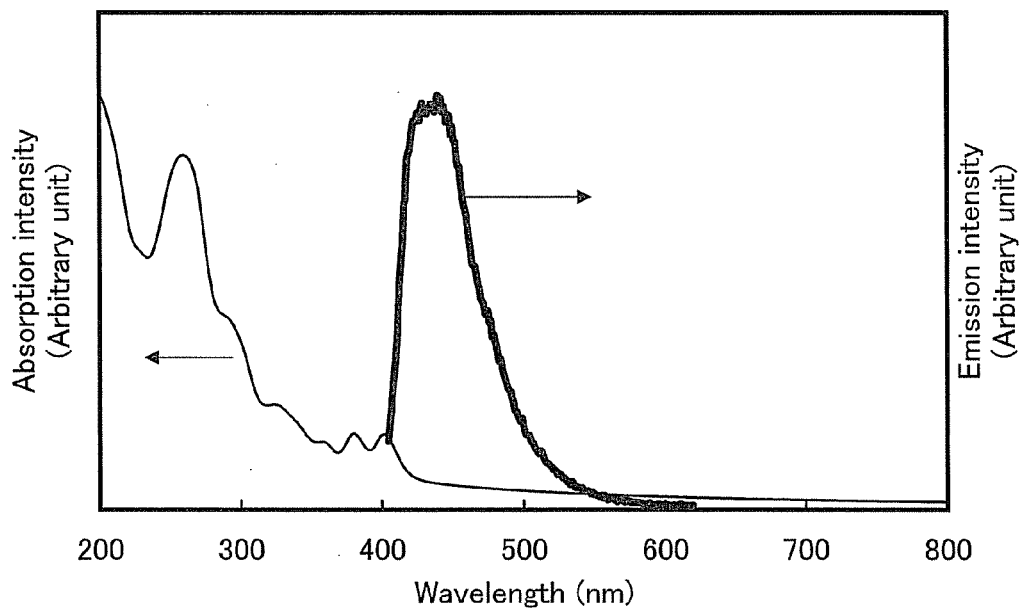

Next, an absorption and emission spectra of mDBFCzPA-II in a toluene solution of mDBFCzPA-II are shown in FIG. 40A, and an absorption and emission spectra of a thin film of mDBFCzPA-II are shown in FIG. 40B. An ultraviolet-visible spectrophotometer (V-550, manufactured by JASCO Corporation) was used for the measurements of the absorption spectra. In the case of the toluene solution, the measurements were made with the toluene solution of mDBFCzPA-II put in a quartz cell, and the absorption spectrum obtained by subtraction of the absorption spectra of the quartz cell and toluene from the measured spectrum is shown in the drawing. In addition, as for the absorption spectrum of the thin film, a sample was prepared by evaporation of mDBFCzPA-II on a quartz substrate, and the absorption spectrum obtained by subtraction of an absorption spectrum of quartz from the absorption spectrum of this sample is shown in the drawing. As in the measurements of the absorption spectra, an ultraviolet-visible spectrophotometer (V-550, manufactured by JASCO Corporation) was used for the measurements of the emission spectra. The emission spectrum of toluene was measured with the toluene solution of mDBFCzPA-II put in a quartz cell, and the emission spectrum of the thin film was measured with a sample prepared by evaporation of mDBFCzPA-II on a quartz substrate. Thus, it was found that the absorption peak wavelengths of mDBFCzPA-II in the toluene solution of mDBFCzPA-II were around 396 nm, around 375 nm, around 354 nm, around 336 nm, and around 290 nm and the emission peak wavelengths thereof were around 412 nm and around 433 nm (at an excitation wavelength of 375 nm), and that the absorption peak wavelengths of the thin film of mDBFCzPA-II were around 402 nm, around 381 nm, around 359 nm, around 340 nm, around 291 nm, around 261 nm, and around 207 nm and the greatest emission wavelength thereof was around 443 nm (at an excitation wavelength of 402 nm).

Further, the ionization potential of mDBFCzPA-II in a thin film state was measured by a photoelectron spectrometer (AC-2, manufactured by Riken Keiki, Co., Ltd.) in air. The obtained value of the ionization potential was converted to a negative value, so that the HOMO level of mDBFCzPA-II was −5.77 eV. From the data of the absorption spectra of the thin film in FIG. 40B, the absorption edge of mDBFCzPA-II, which was obtained from Tauc plot with an assumption of direct transition, was 2.95 eV. Therefore, the optical energy gap of mDBFCzPA-II in the solid state was estimated at 2.95 eV; from the values of the HOMO level obtained above and this energy gap, the LUMO level of mDBFCzPA-II was able to be estimated at −2.82 eV. It was thus found that mDBFCzPA-II had a wide energy gap of 2.95 eV in the solid state.

Further, the oxidation reaction characteristics of mDBFCzPA-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from −0.04 V to 1.15 V and then changed from 1.15 V to −0.04 V was one cycle, and 100 cycles were performed.

The measurement results revealed that mDBFCzPA-II showed properties effective against repetition of redox reactions between an oxidized state and a neutral state without a large variation in oxidation peak even after the 100 cycles in the measurements.

Further, the HOMO level of mDBFCzPA-II was determined also by calculation from the CV measurement results.

First, the potential energy of the reference electrode with respect to the vacuum level used was found to be −4.94 eV, as determined in Example 1. The oxidation peak potential $E_{pa}$ of mDBFCz-PA-II was 0.95 V. In addition, the reduction peak potential $E_{pc}$ thereof was 0.83 V. Therefore, a half-wave potential (an intermediate potential between $E_{pa}$ and $E_{pc}$) can be calculated at 0.89 V. This means that mDBFCzPA-II is oxidized by an electric energy of 0.89 [V versus Ag/Ag$^+$], and this energy corresponds to the HOMO level. Here, since the potential energy of the reference electrode, which was used in this example, with respect to the vacuum level is −4.94 [eV] as described above, the HOMO level of mDBFCzPA-II was calculated as follows: −4.94−0.89=−5.83 [eV].

Example 14

Synthesis Example 12

In this example is described a method of synthesizing 3-(6-phenyldibenzothiophen-4-yl)-9-[4-(10-phenyl-9-anthryl)phenyl]-9H-carbazole (abbreviation: DBTCzPA-IV), which is the carbazole derivative represented by the structural formula (203) in Embodiment 1. A structure of DBTCzPA-IV is illustrated in the following structural formula.

(203)

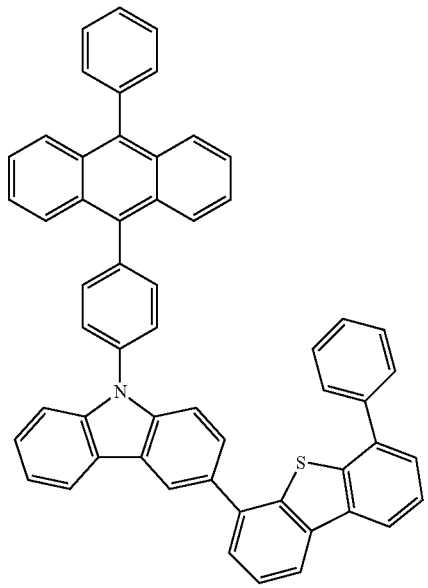

Step 1: Synthesis of 3-(6-Phenyldibenzothiophen-4-yl)-9H-carbazole (abbreviation: DBTCz-IV)

In a 50-mL three-neck flask were put 1.0 g (4.1 mmol) of 3-bromocarbazole, 1.2 g (4.1 mmol) of 6-phenyl-4-dibenzothienylboronic acid, and 62 mg (0.20 mmol) of tris(2-methylphenyl)phosphine. To this mixture were added 15 mL of toluene, 5 mL of ethanol, and 5 mL of a 2.0 M aqueous sodium carbonate solution. This mixture was degassed by being stirred while the pressure was reduced. To this mixture was added 9 mg (0.041 mmol) of palladium(II)acetate, and the mixture was stirred at 80° C. for 3 hours under a nitrogen stream. After the stirring, the aqueous layer of this mixture was subjected to extraction with toluene, and the solution of the extract and the organic layer were combined and washed with saturated brine. The organic layer was dried over magnesium sulfate. This mixture was separated by gravity filtration, and the filtrate was concentrated to give a solid. This solid was purified by silica gel column chromatography (developing solvent, toluene:hexane=1:2 and then toluene:hexane=3:2). Addition of ethyl acetate/hexane to the obtained solid was followed by irradiation with ultrasonic waves, and the solid was collected by suction filtration, so that 1.0 g of a white solid which was the object of the synthesis in 59% yield. The synthesis scheme of Step 1 is illustrated in (a-11).

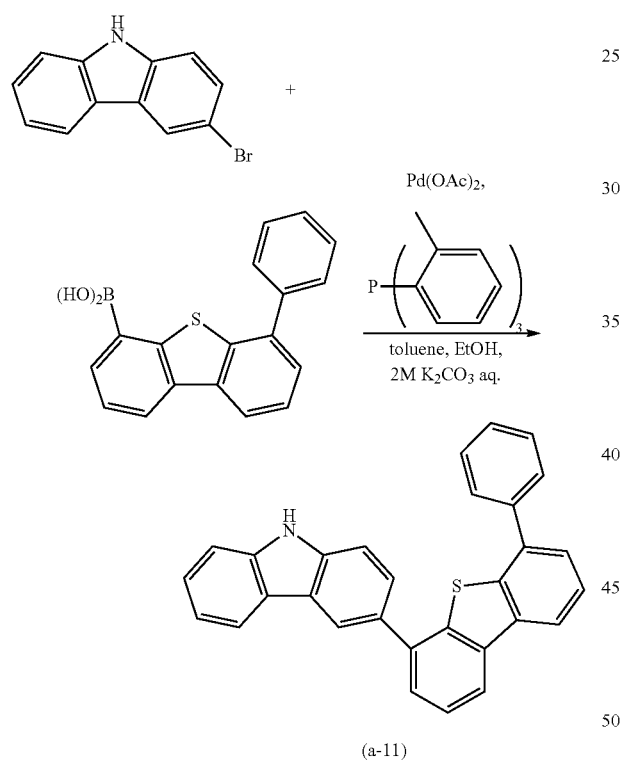

(a-11)

The obtained white solid was subjected to nuclear magnetic resonance (NMR) spectroscopy. The measurement data are shown below.

$^1$H NMR (CDCl$_3$, 300 MHz): δ=7.34-7.55 (m, 7H), 7.56 (d, J$_1$=4.2 Hz, 1H), 7.58-7.64 (m, 3H), 7.68-7.72 (m, 2H), 7.78 (dd, J$_1$=1.8 Hz, J$_2$=8.4 Hz, 1H), 8.10 (dd, J$_1$=0.90 Hz, J$_2$=1.8 Hz, 1H), 8.15 (s, 1H), 8.19-8.23 (m, 2H), 8.36 (d, J$_1$=1.5 Hz, 1H)

Figure 41A:
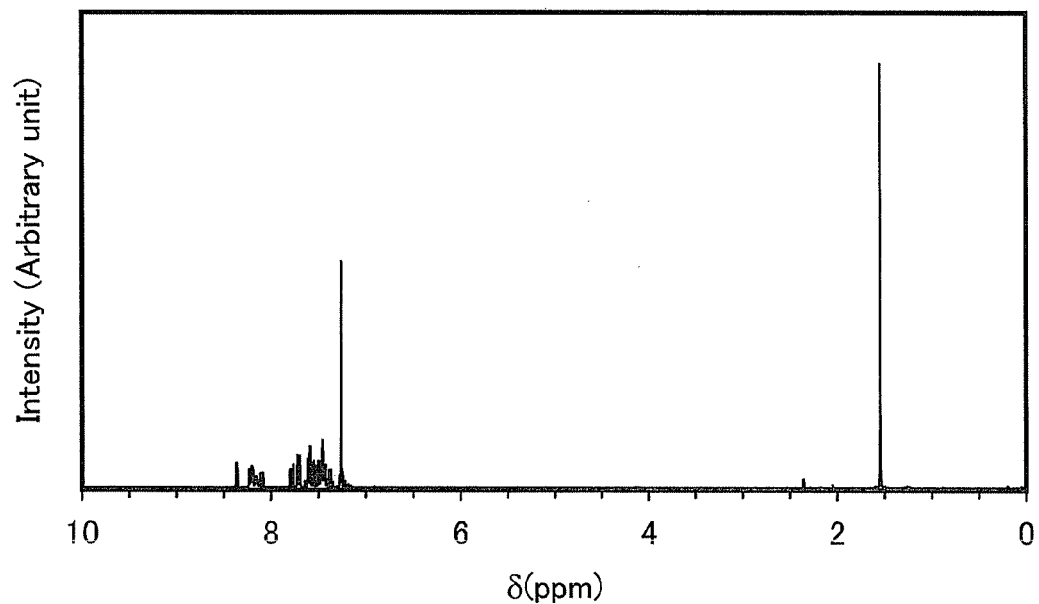
FIGS. 41A and 41B are $^1$H NMR charts of DBTCz-IV.
Figure 41B:
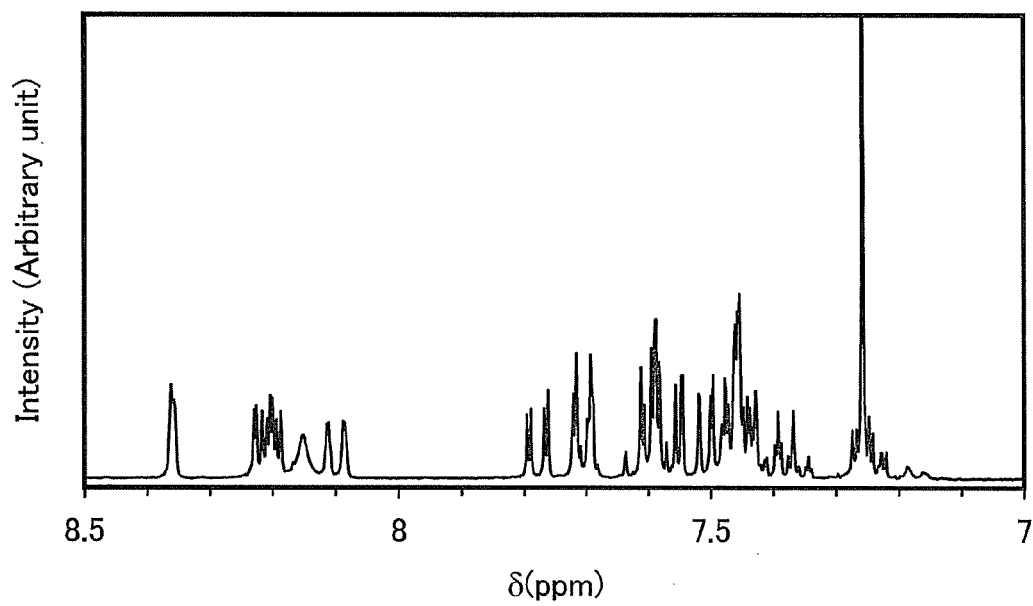

In addition, $^1$H NMR charts are shown in FIGS. 41A and 41B. Note that FIG. 41B is a chart where the range of from 7 ppm to 8.5 ppm in FIG. 41A is enlarged. The measurement results showed that DBTCz-IV, which is the carbazole derivative represented by the above structural formula, was obtained.

Step 2: Synthesis of 3-(6-Phenyldibenzothiophen-4-yl)-9-[4-(10-phenyl-9-anthryl)phenyl]-9H-carbazole (abbreviation: DBTCzPA-IV)

In a 50-mL three-neck flask were put 1.3 g (3.3 mmol) of 9-(4-bromophenyl)-10-phenylanthracene, 1.0 g (2.4 mmol) of 3-(6-phenyldibenzothiophen-4-yl)-9H-carbazole, and 0.95 g (9.9 mmol) of sodium tert-butoxide. After the air in the flask was replaced with nitrogen, to this mixture were added 20 mL of toluene and 0.2 mL of tri(tert-butyl)phosphine (a 10 wt % hexane solution). This mixture was degassed by being stirred while the pressure was reduced. After the degassing, 11 mg (0.18 mmol) of bis(dibenzylideneacetone)palladium (0) was added to this mixture. This mixture was stirred at 110° C. for 6 hours under a nitrogen stream. After the stirring, the aqueous layer of this mixture was subjected to extraction with toluene, and the solution of the extract and the organic layer were combined and washed with saturated brine. The organic layer was dried over magnesium sulfate. This mixture was gravity-filtered, and the filtrate was concentrated to give a solid. The obtained solid was purified by silica gel column chromatography (developing solvent, toluene:hexane=1:9 and then toluene:hexane=3:7). The obtained solid was recrystallized from toluene/hexane to give 1.4 g of a pale yellow solid which was the object of the synthesis in a yield of 80%. The synthesis scheme of Step 2 is illustrated in (b-11).

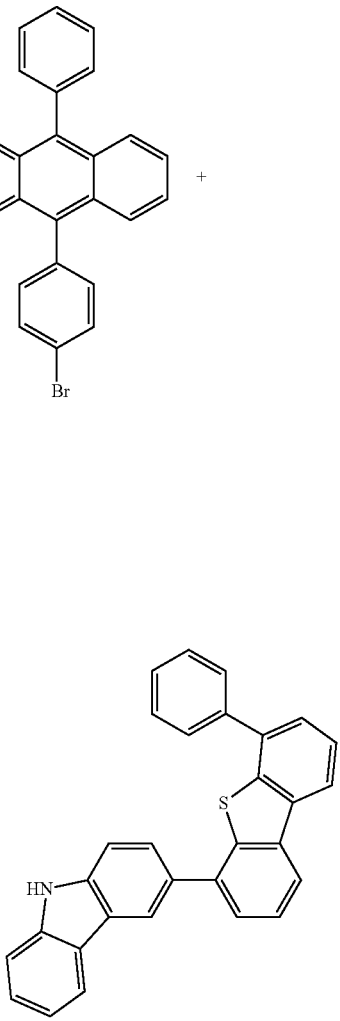

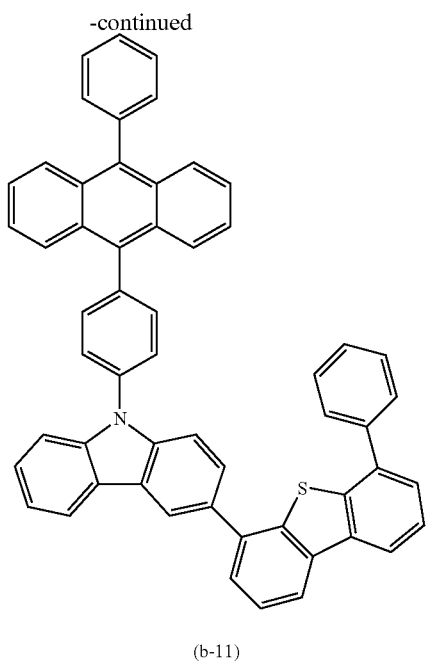

(b-11)

By a train sublimation method, 1.4 g of the obtained pale yellow solid was purified. The purification was conducted by heating of the pale yellow solid at 360° C. under a pressure of 2.9 Pa with a flow rate of argon gas of 5 ml/min. After the purification, 1.2 g of a pale yellow solid was obtained in a yield of 86%.

The pale yellow solid after the above purification was subjected to nuclear magnetic resonance (NMR) spectroscopy. The measurement data are shown below.

$^1$H NMR (CDCl$_3$, 300 MHz): δ=7.34-7.49 (m, 9H), 7.51-7.54 (m, 3H), 7.57 (t, J$_1$=1.5 Hz, 1H), 7.59-7.66 (m, 5H), 7.67-7.80 (m, 8H), 7.84-7.90 (m, 5H), 8.22-8.25 (m, 3H), 8.49 (d, J$_1$=1.5 Hz, 1H)

Figure 42A:
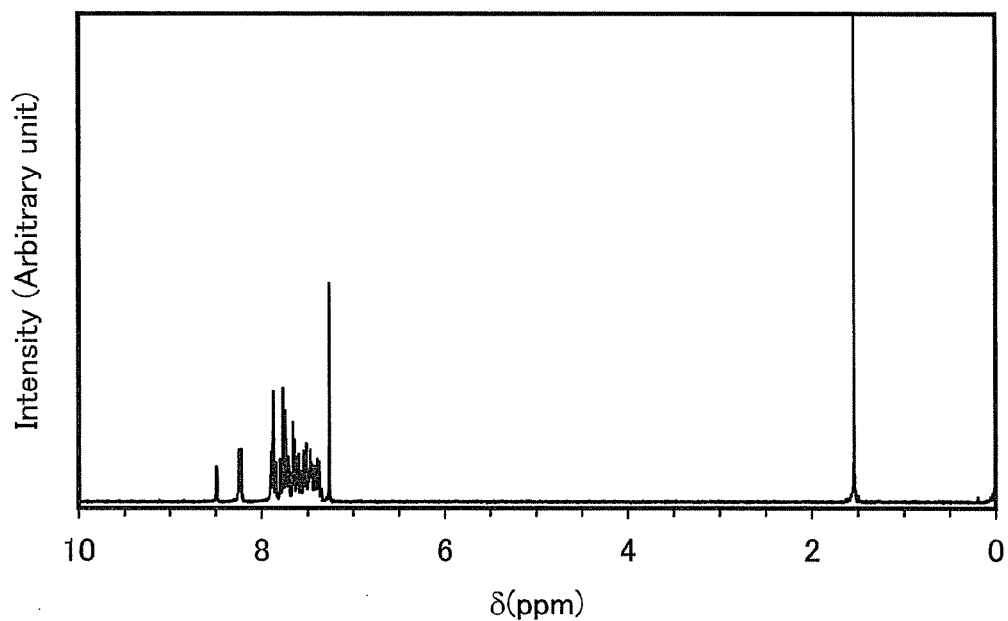
FIGS. 42A and 42B are $^1$H NMR charts of DBTCzTp-IV.
Figure 42B:
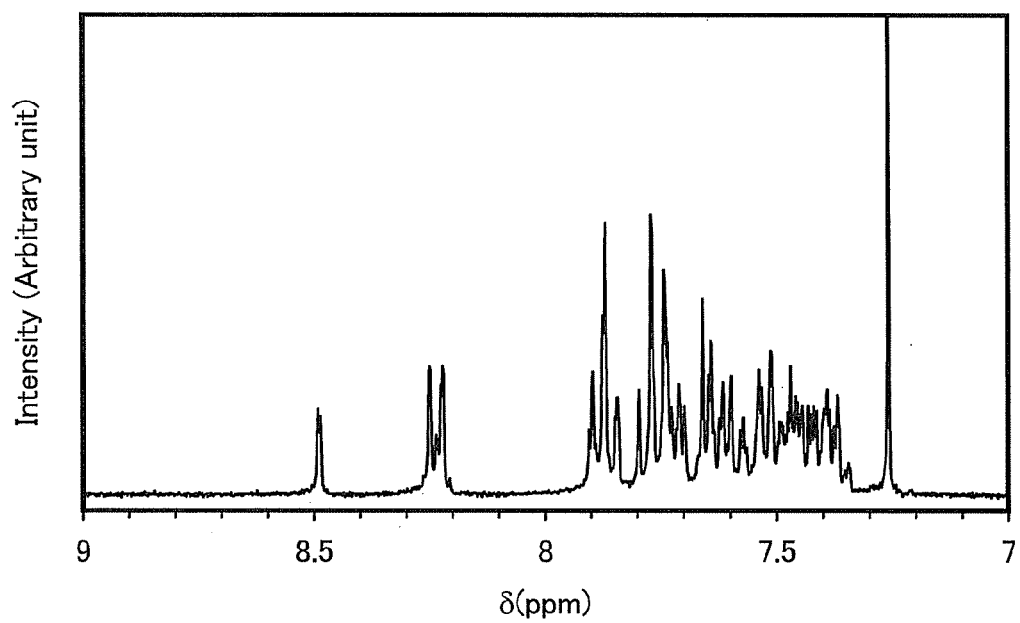

In addition, $^1$H NMR charts are shown in FIGS. 42A and 42B. Note that FIG. 42B is a chart where the range of from 7 ppm to 9 ppm in FIG. 42A is enlarged. The measurement results showed that DBTCzPA-IV, which is the carbazole derivative represented by the above structural formula, was obtained.

Figure 43A:
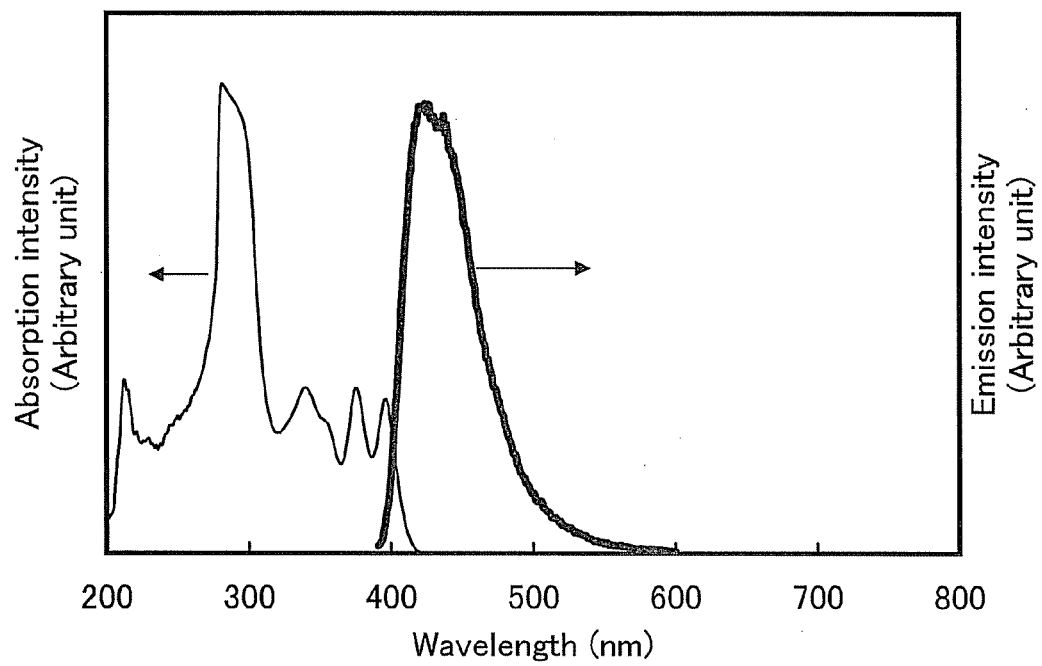
FIGS. 43A and 43B show absorption spectra and emission spectra of DBTCzTp-IV.
Figure 43B:
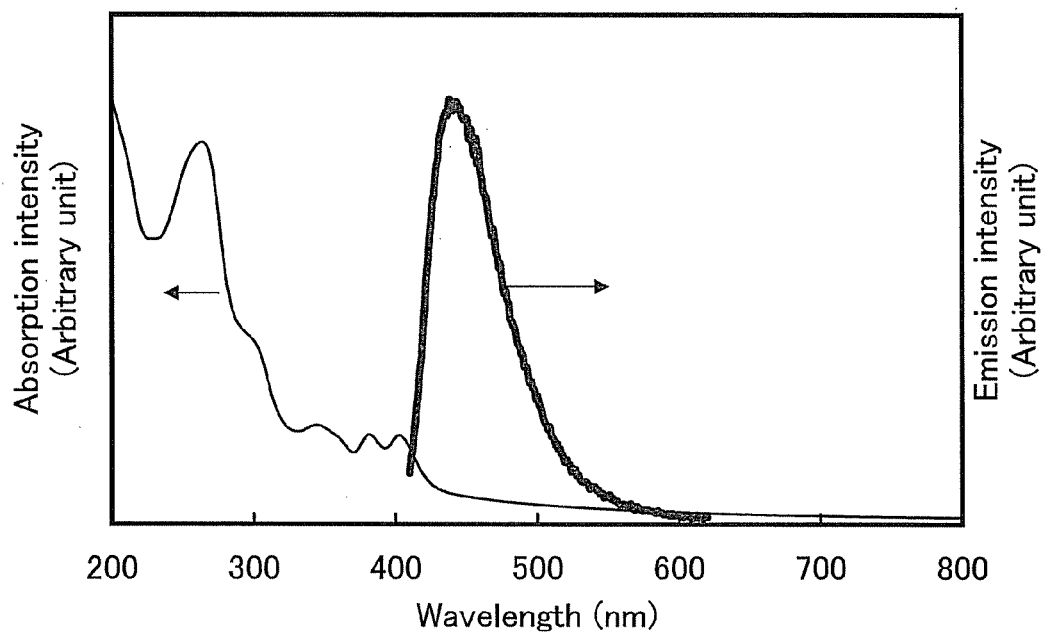

Next, an absorption and emission spectra of DBTCzPA-IV in a toluene solution of DBTCzPA-IV are shown in FIG. 43A, and an absorption and emission spectra of a thin film of DBTCzPA-IV are shown in FIG. 43B. An ultraviolet-visible spectrophotometer (V-550, manufactured by JASCO Corporation) was used for the measurements of the absorption spectra. In the case of the toluene solution, the measurements were made with the toluene solution of DBTCzPA-IV put in a quartz cell, and the absorption spectrum obtained by subtraction of the absorption spectra of the quartz cell and toluene from the measured spectrum is shown in the drawing. In addition, as for the absorption spectrum of the thin film, a sample was prepared by evaporation of DBTCzPA-IV on a quartz substrate, and the absorption spectrum obtained by subtraction of an absorption spectrum of quartz from the absorption spectrum of this sample is shown in the drawing. As in the measurements of the absorption spectra, an ultraviolet-visible spectrophotometer (V-550, manufactured by JASCO Corporation) was used for the measurements of the emission spectra. The emission spectrum of toluene was measured with the toluene solution of DBTCzPA-IV put in a quartz cell, and the emission spectrum of the thin film was measured with a sample prepared by evaporation of DBTCzPA-IV on a quartz substrate. Thus, it was found that the absorption peak wavelengths of DBTCzPA-IV in the toluene solution of DBTCzPA-IV were around 396 nm, around 376 nm, around 340 nm, and around 281 nm and the emission peak wavelengths thereof were around 423 nm and around 437 nm (at an excitation wavelength of 376 nm), and that the absorption peak wavelengths of the thin film of DBTCzPA-IV were around 403 nm, around 382 nm, around 356 nm, around 345 nm, around 296 nm, and around 264 nm and the greatest emission wavelength thereof was around 443 nm (at an excitation wavelength of 403 nm).

Further, the ionization potential of DBTCzPA-IV in a thin film state was measured by a photoelectron spectrometer (AC-2, manufactured by Riken Keiki, Co., Ltd.) in air. The obtained value of the ionization potential was converted to a negative value, so that the HOMO level of DBTCzPA-IV was −5.80 eV. From the data of the absorption spectra of the thin film in FIG. 43B, the absorption edge of DBTCzPA-IV, which was obtained from Tauc plot with an assumption of direct transition, was 2.93 eV. Therefore, the optical energy gap of DBTCzPA-IV in the solid state was estimated at 2.93 eV; from the values of the HOMO level obtained above and this energy gap, the LUMO level of DBTCzPA-IV was able to be estimated at −2.87 eV. It was thus found that DBTCzPA-IV had a wide energy gap of 2.93 eV in the solid state.

Further, the oxidation reaction characteristics of DBTCzPA-IV were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from −0.02 V to 0.93 V and then changed from 0.93 V to −0.02 V was one cycle, and 100 cycles were performed.

The measurement results revealed that DBTCzPA-IV showed properties effective against repetition of redox reactions between an oxidized state and a neutral state without a large variation in oxidation peak even after the 100 cycles in the measurements.

Further, the HOMO level of DBTCzPA-IV was determined also by calculation from the CV measurement results.

First, the potential energy of the reference electrode with respect to the vacuum level used was found to be −4.94 eV, as determined in Example 1. The oxidation peak potential E$_{pa}$ of DBTCzPA-IV was 0.89 V. In addition, the reduction peak potential E$_{pc}$ thereof was 0.79 V. Therefore, a half-wave

487 potential (an intermediate potential between $E_{pa}$ and $E_{pc}$) can be calculated at 0.84 V. This means that DBTCzPA-IV is oxidized by an electric energy of 0.84 [V versus Ag/Ag$^+$], and this energy corresponds to the HOMO level. Here, since the potential energy of the reference electrode, which was used in this example, with respect to the vacuum level is −4.94 [eV] as described above, the HOMO level of DBTCzPA-IV was calculated as follows: −4.94−0.84=−5.78.

Example 15

Synthesis Example 13

In this example is described a method of synthesizing 3-(dibenzothiophen-4-yl)-9-[4-(9,10-diphenyl-2-anthryl)phenyl]-9H-carbazole (abbreviation: 2DBTCzPPA-II), which is the carbazole derivative represented by the structural formula (323) in Embodiment 1. A structure of 2DBTCzPPA-II is illustrated in the following structural formula.

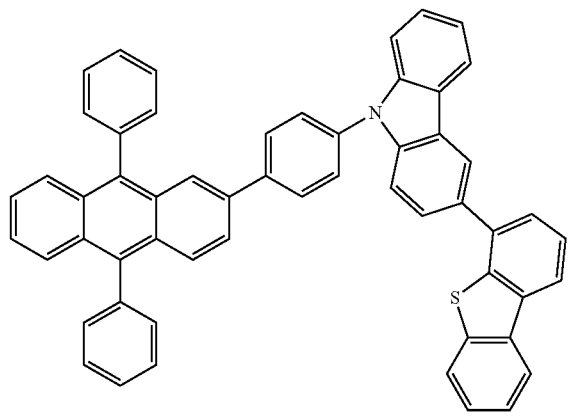

(323)

Step 1: Synthesis of
3-(Dibenzothiophen-4-yl)-9H-carbazole
(abbreviation: DBTCz-II)

This was synthesized as in Step 1 in Example 1.

Step 2: Synthesis of 3-(Dibenzothiophen-4-yl)-9-[4-(9,10-diphenyl-2-anthryl)phenyl]-9H-carbazole (abbreviation: 2DBTCzPPA-II)

In a 50-mL three-neck flask were put 1.3 g (2.7 mmol) of 2-(4-bromophenyl)-9,10-diphenylanthracene, 0.93 g (2.7 mmol) of 3-(dibenzothiophen-4-yl)-9H-carbazole, and 0.76 g (8.0 mmol) of sodium tert-butoxide. After the air in the flask was replaced with nitrogen, to this mixture were added 20 mL of toluene and 0.2 mL of tri(tert-butyl)phosphine (a 10 wt % hexane solution). This mixture was degassed by being stirred while the pressure was reduced. After the degassing, 76 mg (0.13 mmol) of bis(dibenzylideneacetone)palladium(0) was added to this mixture. This mixture was stirred at 110° C. for 4 hours under a nitrogen stream. After the stirring, the obtained mixture was suction-filtered through Celite (produced by Wako Pure Chemical Industries, Ltd., Catalog No. 531-16855), alumina, and Florisil (produced by Wako Pure Chemical Industries, Ltd., Catalog No. 540-00135), and the filtrate was concentrated to give a solid. The obtained solid was purified by silica gel column chromatography (developing solvent, hexane:toluene=5:1). A suspension was formed by addition of toluene/hexane to the obtained solid, and the suspension was irradiated with ultrasonic waves. Then, a solid was collected by suction filtration, so that 1.2 g of a yellow solid which was the object of the synthesis was obtained in a yield of 61%. The synthesis scheme of Step 2 is illustrated in (b-12).

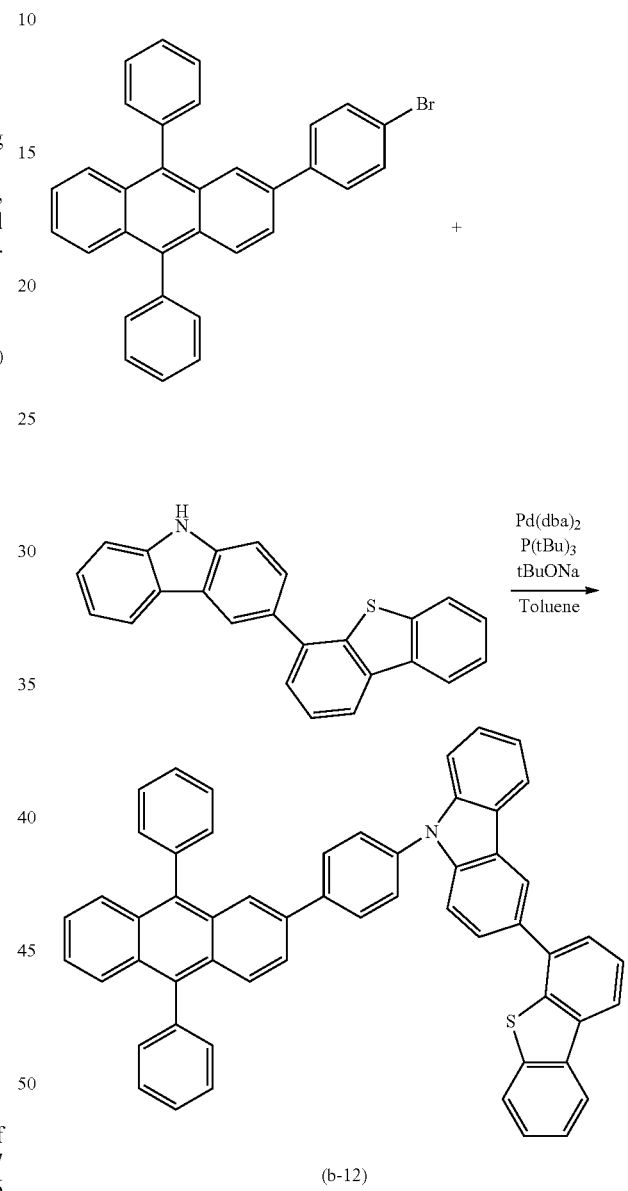

(b-12)

By a train sublimation method, the obtained yellow solid was purified. The purification was conducted by heating of 1.2 g of the yellow solid at 335° C. under a pressure of 2.6 Pa with a flow rate of argon gas of 5 mL/min. After the purification, 1.01 g of a yellow solid was obtained in a yield of 83%.

The yellow solid after the above purification was subjected to nuclear magnetic resonance (NMR) spectroscopy. The measurement data are shown below.

$^1$H NMR (CDCl$_3$, 300 MHz): δ=7.29-7.39 (m, 3H), 7.41-7.51 (m, 4H), 7.52-7.75 (m, 18H), 7.78-7.88 (m, 5H), 8.03 (d, J$_1$=1.5 Hz, 1H), 8.15-8.23 (m, 3H), 8.51 (d, J$_1$=0.90 Hz, 1H)

Figure 44A:
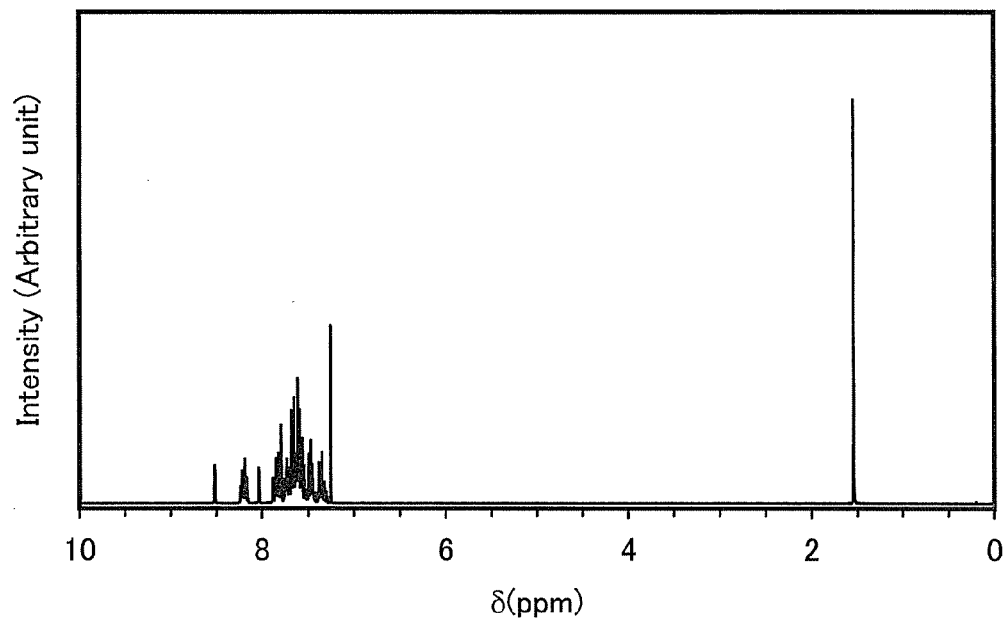
FIGS. 44A and 44B are $^1$H NMR charts of 2DBTCzPPA-II.
Figure 44B:
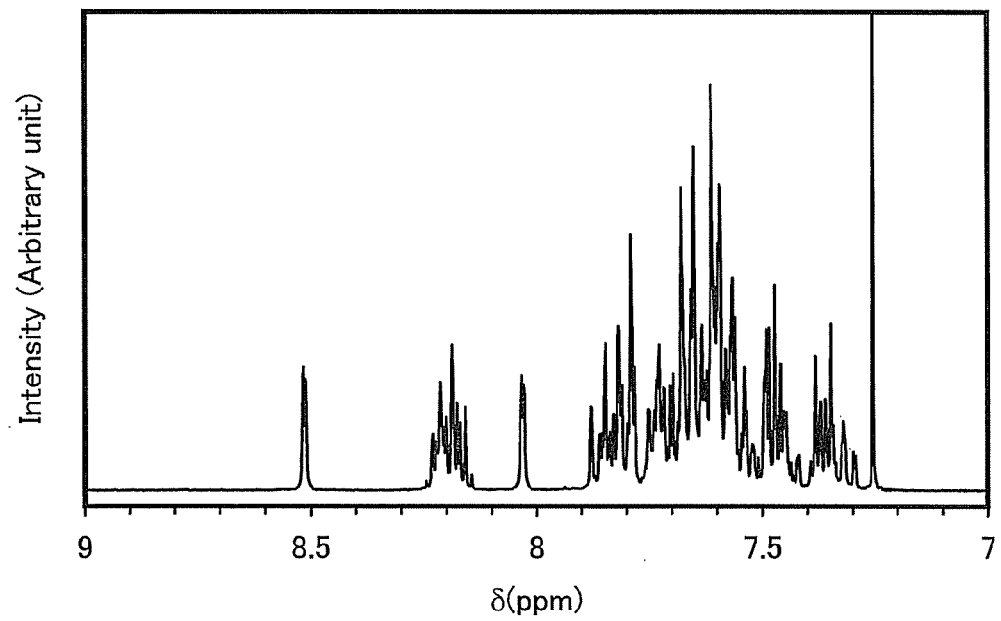

In addition, ¹H NMR charts are shown in FIGS. 44A and 44B. Note that FIG. 44B is a chart where the range of from 7 ppm to 9 ppm in FIG. 44A is enlarged. The measurement results showed that 2DBTCzPPA-II, which is the carbazole derivative represented by the above structural formula, was obtained.

Figure 45A:
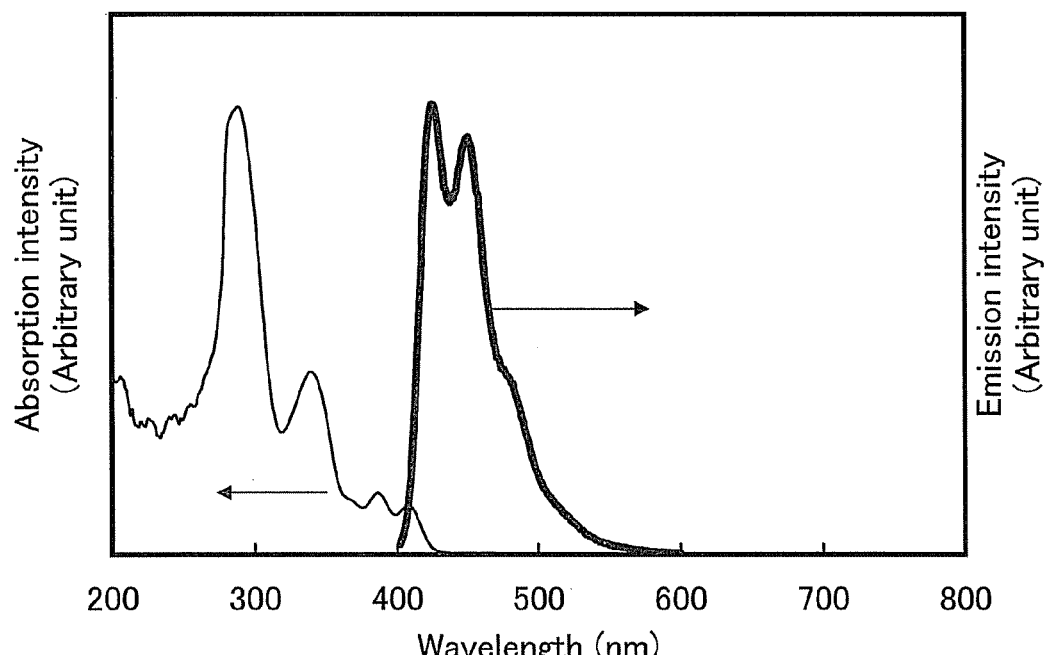
FIGS. 45A and 45B show absorption spectra and emission spectra of 2DBTCzPPA-II.
Figure 45B:
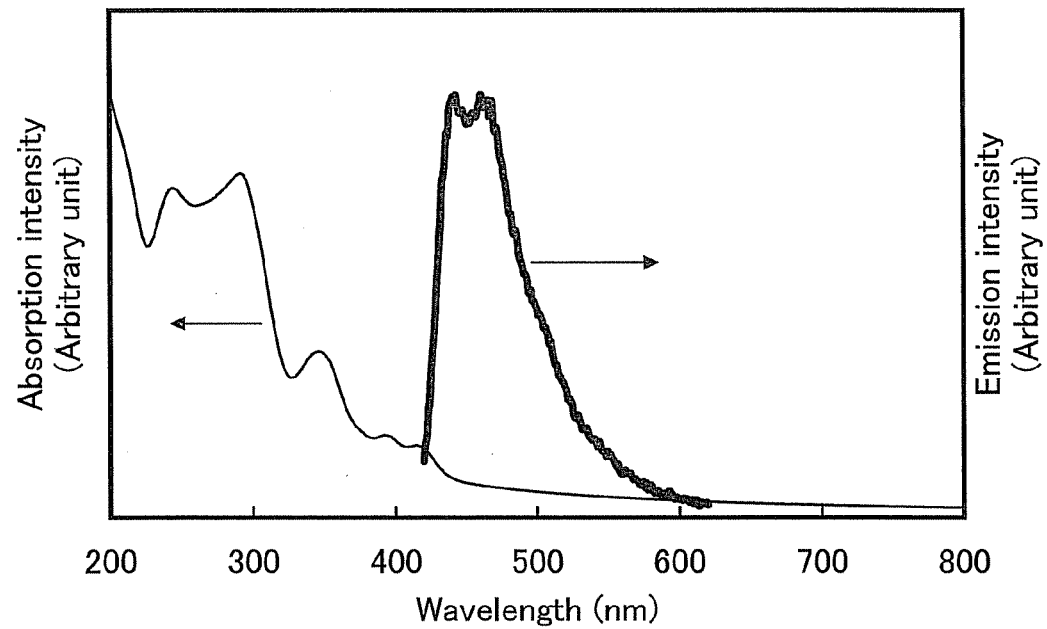

Next, an absorption and emission spectra of 2DBTCzPPA-II in a toluene solution of 2DBTCzPPA-II are shown in FIG. 45A, and an absorption and emission spectra of a thin film of 2DBTCzPPA-II are shown in FIG. 45B. An ultraviolet-visible spectrophotometer (V-550, manufactured by JASCO Corporation) was used for the measurements of the absorption spectra. In the case of the toluene solution, the measurements were made with the toluene solution of 2DBTCzPPA-II put in a quartz cell, and the absorption spectrum obtained by subtraction of the absorption spectra of the quartz cell and toluene from the measured spectrum is shown in the drawing. In addition, as for the absorption spectrum of the thin film, a sample was prepared by evaporation of 2DBTCzPPA-II on a quartz substrate, and the absorption spectrum obtained by subtraction of an absorption spectrum of quartz from the absorption spectrum of this sample is shown in the drawing. As in the measurements of the absorption spectra, an ultraviolet-visible spectrophotometer (V-550, manufactured by JASCO Corporation) was used for the measurements of the emission spectra. The emission spectrum of toluene was measured with the toluene solution of 2DBTCzPPA-II put in a quartz cell, and the emission spectrum of the thin film was measured with a sample prepared by evaporation of 2DBTCzPPA-II on a quartz substrate. Thus, it was found that the absorption peak wavelengths of 2DBTCzPPA-II in the toluene solution of 2DBTCzPPA-II were around 404 nm, around 382 nm, around 336 nm, and around 285 nm and the emission peak wavelengths thereof were around 483 nm, around 452 nm, and around 427 nm (at an excitation wavelength of 387 nm), and that the absorption peak wavelengths of the thin film of 2DBTCzPPA-II were around 415 nm, around 393 nm, around 346 nm, around 291 nm, and around 244 nm and the emission peak wavelengths thereof were around 461 nm and around 442 nm (at an excitation wavelength of 415 nm).

Further, the ionization potential of 2DBTCzPPA-II in a thin film state was measured by a photoelectron spectrometer (AC-2, manufactured by Riken Keiki, Co., Ltd.) in air. The obtained value of the ionization potential was converted to a negative value, so that the HOMO level of 2DBTCzPPA-II was −5.70 eV. From the data of the absorption spectra of the thin film in FIG. 45B, the absorption edge of 2DBTCzPPA-II, which was obtained from Tauc plot with an assumption of direct transition, was 2.81 eV. Therefore, the optical energy gap of 2DBTCzPPA-II in the solid state was estimated at 2.81 eV; from the values of the HOMO level obtained above and this energy gap, the LUMO level of 2DBTCzPPA-II was able to be estimated at −2.89 eV. It was thus found that 2DBTCzPPA-II had a wide energy gap of 2.81 eV in the solid state.

Further, the oxidation reaction characteristics of 2DBTCzPPA-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L.

Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from 0.31 V to 0.92 V and then changed from 0.92 V to 0.31 V was one cycle, and 100 cycles were performed.

The measurement results revealed that 2DBTCzPPA-II showed properties effective against repetition of redox reactions between an oxidized state and a neutral state without a large variation in oxidation peak even after the 100 cycles in the measurements.

Further, the HOMO level of 2DBTCzPPA-II was determined also by calculation from the CV measurement results.

First, the potential energy of the reference electrode with respect to the vacuum level used was found to be −4.94 eV, as determined in Example 1. The oxidation peak potential $E_{pa}$ of 2DBTCzPPA-II was 0.88 V. In addition, the reduction peak potential $E_{pc}$ thereof was 0.80 V. Therefore, a half-wave potential (an intermediate potential between $E_{pa}$ and $E_{pc}$) can be calculated at 0.84 V. This means that 2DBTCzPPA-II is oxidized by an electric energy of 0.84 [V versus Ag/Ag$^+$], and this energy corresponds to the HOMO level. Here, since the potential energy of the reference electrode, which was used in this example, with respect to the vacuum level is −4.94 [eV] as described above, the HOMO level of 2DBTCzPPA-II was calculated as follows: −4.94−0.84=−5.78 [eV].

Example 16

Synthesis Example 14

In this example is described a method of synthesizing 3-(dibenzofuran-4-yl)-9-[4-(9,10-diphenyl-2-anthryl)phenyl]-9H-carbazole (abbreviation: 2DBFCzPPA-II), which is the carbazole derivative represented by the structural formula (719) in Embodiment 1. A structure of 2DBFCzPPA-II is illustrated in the following structural formula.

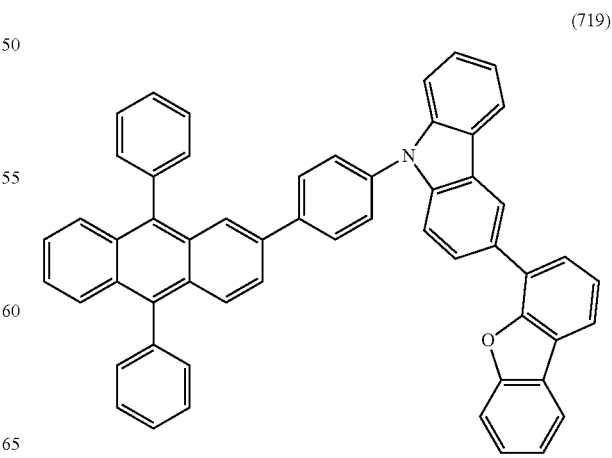

(719)

Step 1: Synthesis of 3-(Dibenzofuran-4-yl)-9H-carbazole (abbreviation: DBFCz-II)

This was synthesized as in Step 1 in Example 2.

Step 2: Synthesis of 3-(Dibenzofuran-4-yl)-9-[4-(9,10-diphenyl-2-anthryl)phenyl]-9H-carbazole (abbreviation: 2DBFCzPPA-II)

In a 50-mL three-neck flask were put 1.3 g (2.7 mmol) of 2-(4-bromophenyl)-9,10-diphenylanthracene, 0.88 g (2.7 mmol) of 3-(dibenzofuran-4-yl)-9H-carbazole, and 0.76 g (8.0 mmol) of sodium tert-butoxide. After the air in the flask was replaced with nitrogen, to this mixture were added 20 mL of toluene and 0.2 mL of tri(tert-butyl)phosphine (a 10 wt % hexane solution). This mixture was degassed by being stirred while the pressure was reduced. After the degassing, 76 mg (0.13 mmol) of bis(dibenzylideneacetone)palladium(0) was added to this mixture. This mixture was stirred at 110° C. for 4 hours under a nitrogen stream. After the stirring, the obtained mixture was suction-filtered through Celite (produced by Wako Pure Chemical Industries, Ltd., Catalog No. 531-16855), alumina, and Florisil (produced by Wako Pure Chemical Industries, Ltd., Catalog No. 540-00135), and the filtrate was concentrated to give a solid. This solid was purified by silica gel column chromatography (developing solvent, hexane:toluene=5:1). This solid was purified by high performance liquid column chromatography (abbreviation: HPLC) (developing solvent: chloroform). The obtained fraction was concentrated to give 1.4 g of a yellow solid which was the object of the synthesis in 71% yield. The synthesis scheme of Step 2 is illustrated in (b-13).

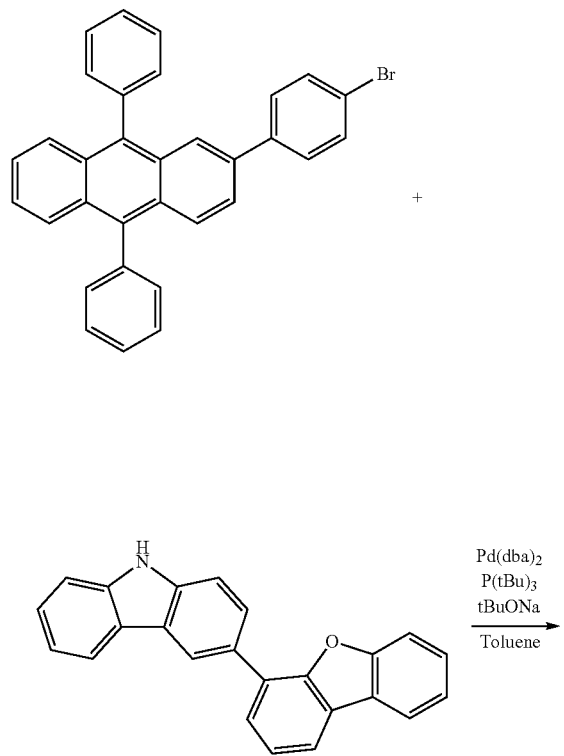

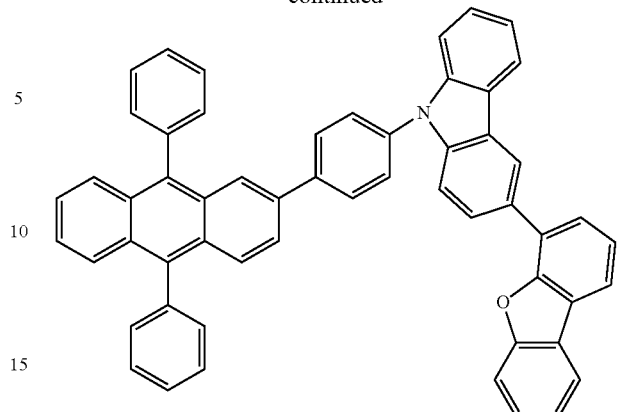

(b-13)

By a train sublimation method, the obtained yellow solid was purified. The purification was conducted by heating of 0.90 g of the yellow solid at 360° C. under a pressure of 2.6 Pa with a flow rate of argon gas of 5 mL/min. After the purification, 0.73 g of a yellow solid was obtained in a yield of 81%.

The yellow solid after the above purification was subjected to nuclear magnetic resonance (NMR) spectroscopy. The measurement data are shown below.

$^1$H NMR (CDCl$_3$, 300 MHz): δ=7.30-7.42 (m, 4H), 7.45-7.52 (m, 4H), 7.53-7.75 (m, 18H), 7.78-7.88 (m, 3H), 7.93-8.03 (m, 4H), 8.24 (d, J$_1$=7.5 Hz, 1H), 8.66 (d, J$_1$=1.5 Hz, 1H)

Figure 46A:
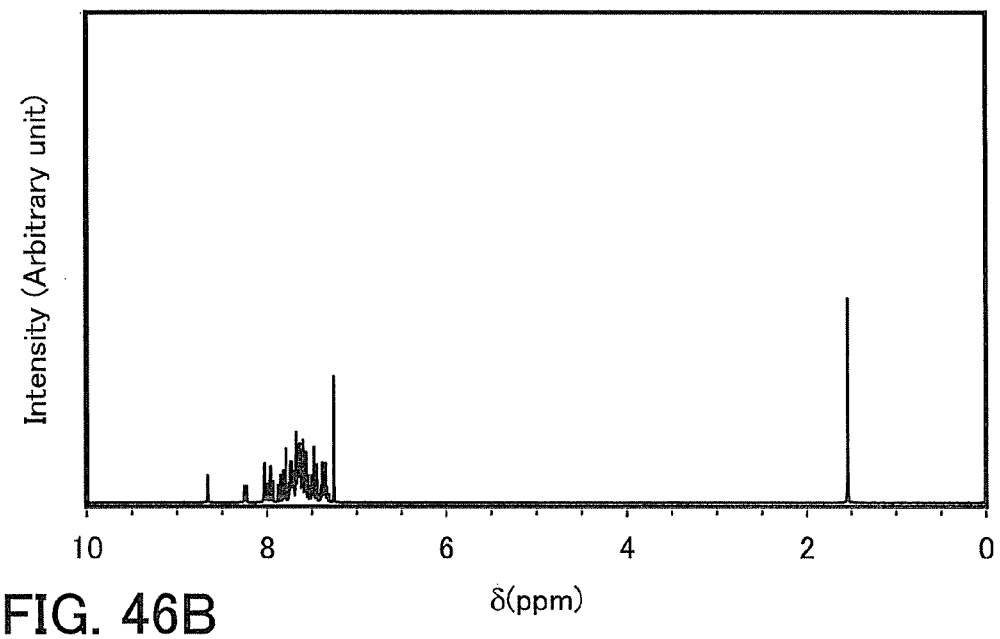
FIGS. 46A and 46B are $^1$H NMR charts of 2DBFCzPPA-II.
Figure 46B:
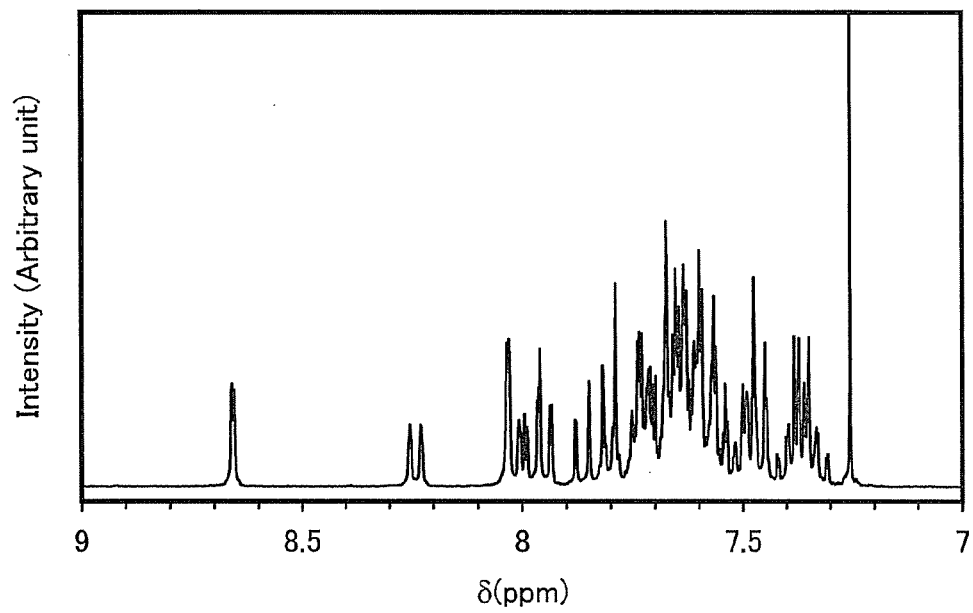

In addition, $^1$H NMR charts are shown in FIGS. 46A and 46B. Note that FIG. 46B is a chart where the range of from 7 ppm to 9 ppm in FIG. 46A is enlarged. The measurement results showed that 2DBFCzPPA-II, which is the carbazole derivative represented by the above structural formula, was obtained.

Figure 47A:
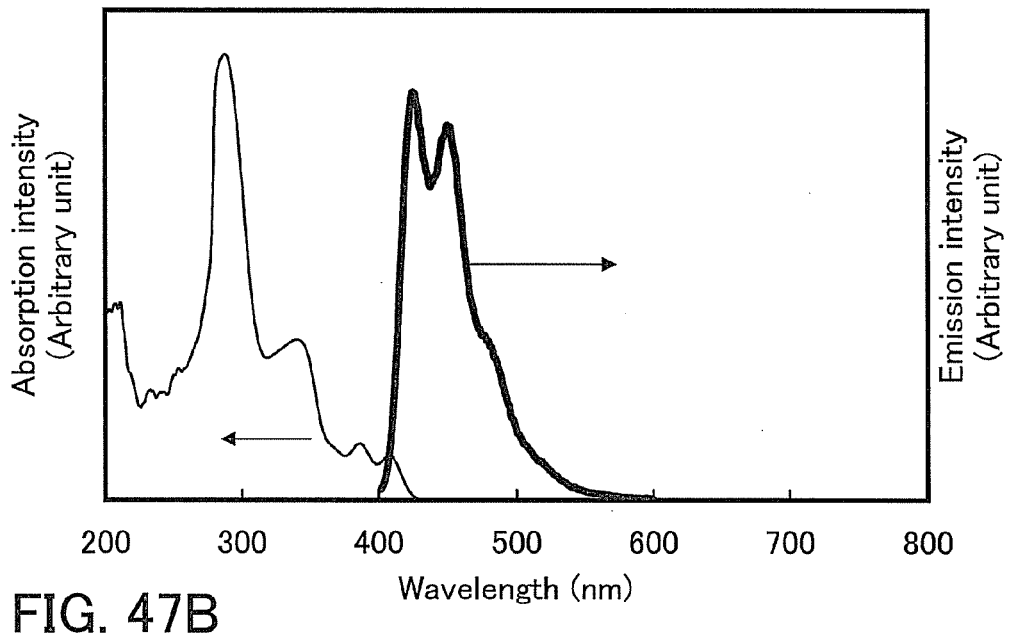
FIGS. 47A and 47B show absorption spectra and emission spectra of 2DBFCzPPA-II.
Figure 47B:
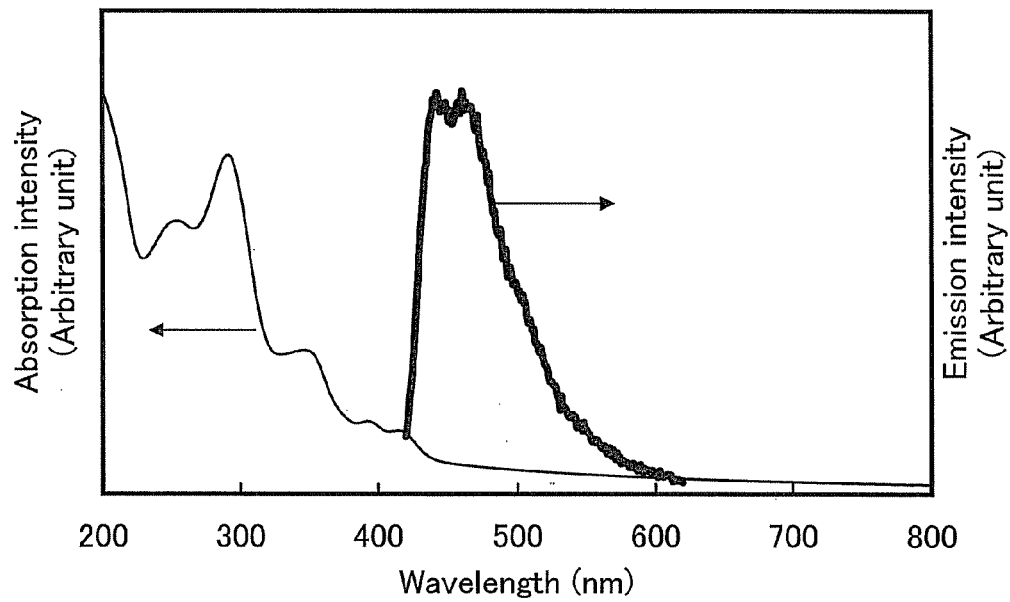

Next, an absorption and emission spectra of 2DBFCzPPA-II in a toluene solution of 2DBFCzPPA-II are shown in FIG. 47A, and an absorption and emission spectra of a thin film of 2DBFCzPPA-II are shown in FIG. 47B. An ultraviolet-visible spectrophotometer (V-550, manufactured by JASCO Corporation) was used for the measurements of the absorption spectra. In the case of the toluene solution, the measurements were made with the toluene solution of 2DBFCzPPA-II put in a quartz cell, and the absorption spectrum obtained by subtraction of the absorption spectra of the quartz cell and toluene from the measured spectrum is shown in the drawing. In addition, as for the absorption spectrum of the thin film, a sample was prepared by evaporation of 2DBFCzPPA-II on a quartz substrate, and the absorption spectrum obtained by subtraction of an absorption spectrum of quartz from the absorption spectrum of this sample is shown in the drawing. As in the measurements of the absorption spectra, an ultraviolet-visible spectrophotometer (V-550, manufactured by JASCO Corporation) was used for the measurements of the emission spectra. The emission spectrum of toluene was measured with the toluene solution of 2DBFCzPPA-II put in a quartz cell, and the emission spectrum of the thin film was measured with a sample prepared by evaporation of 2DBFCzPPA-II on a quartz substrate. Thus, it was found that the absorption peak wavelengths of 2DBFCzPPA-II in the toluene solution of 2DBFCzPPA-II were around 403 nm, around 381 nm, around 336 nm, and around 284 nm and the emission peak wavelengths thereof were around 453 nm and around 427 nm (at an excitation wavelength of 387 nm), and that the absorption peak wavelengths of the thin film of 2DBFCzPPA-II were around 415 nm, around 392 nm, around 347 nm, around 291 nm, and around 254 nm and the greatest emission wavelengths thereof were around 461 nm and around 443 nm (at an excitation wavelength of 415 nm).

Further, the ionization potential of 2DBFCzPPA-II in a thin film state was measured by a photoelectron spectrometer (AC-2, manufactured by Riken Keiki, Co., Ltd.) in air. The obtained value of the ionization potential was converted to a negative value, so that the HOMO level of 2DBFCzPPA-II was −5.68 eV. From the data of the absorption spectra of the thin film in FIG. 47B, the absorption edge of 2DBFCzPPA-II, which was obtained from Tauc plot with an assumption of direct transition, was 2.81 eV. Therefore, the optical energy gap of 2DBFCzPPA-II in the solid state was estimated at 2.81 eV; from the values of the HOMO level obtained above and this energy gap, the LUMO level of 2DBFCzPPA-II was able to be estimated at −2.87 eV. It was thus found that 2DBFCz-PPA-II had a wide energy gap of 2.81 eV in the solid state.

Further, the oxidation reaction characteristics of 2DBFCzPPA-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from 0.27 V to 0.90 V and then changed from 0.90 V to 0.26 V was one cycle, and 100 cycles were performed.

The measurement results revealed that 2DBFCzPPA-II showed properties effective against repetition of redox reactions between an oxidized state and a neutral state without a large variation in oxidation peak even after the 100 cycles in the measurements.

Further, the HOMO level of 2DBFCzPPA-II was determined also by calculation from the CV measurement results.

First, the potential energy of the reference electrode with respect to the vacuum level used was found to be −4.94 eV, as determined in Example 1. The oxidation peak potential $E_{pa}$ of 2DBFCzPPA-II was 0.89 V. In addition, the reduction peak potential $E_{pc}$ thereof was 0.75 V. Therefore, a half-wave potential (an intermediate potential between $E_{pa}$ and $E_{pc}$) can be calculated at 0.82 V. This means that 2DBFCzPPA-II is oxidized by an electric energy of 0.82 [V versus Ag/Ag$^+$], and this energy corresponds to the HOMO level. Here, since the potential energy of the reference electrode, which was used in this example, with respect to the vacuum level is −4.94 [eV] as described above, the HOMO level of 2DBFCzPPA-II was calculated as follows: −4.94−0.82=−5.76 [eV].

Example 17

Synthesis Example 15

In this example is described a method of synthesizing 3-(dibenzothiophen-4-yl)-9-[3-(9,10-diphenyl-2-anthryl)phenyl]-9H-carbazole (abbreviation: 2mDBTCzPPA-II), which is the carbazole derivative represented by the structural formula (324) in Embodiment 1. A structure of 2mDBTCz-PPA-II is illustrated in the following structural formula.

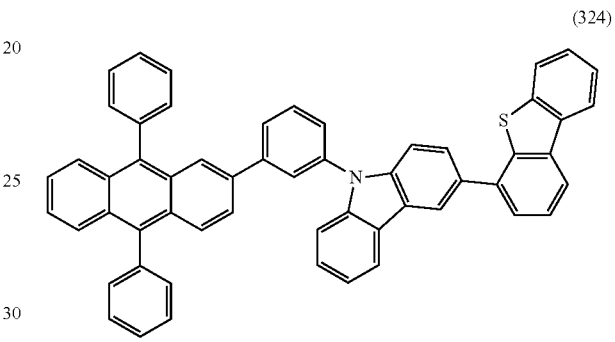

(324)

Step 1: Synthesis of 3-(Dibenzothiophen-4-yl)-9H-carbazole (abbreviation: DBTCz-II)

This was synthesized as in Step 1 in Example 1.

Step 2: Synthesis of 3-(Dibenzothiophen-4-yl)-9-[3-(9,10-diphenyl-2-anthryl)phenyl]-9H-carbazole (abbreviation: 2mDBTCzPPA-II)

In a 100-mL three-neck flask were put 1.0 g (2.1 mmol) of 2-(3-bromophenyl)-9,10-diphenylanthracene, 0.72 g (2.1 mmol) of 3-(dibenzothiophen-4-yl)-9H-carbazole, and 0.59 g (6.2 mmol) of sodium tert-butoxide. After the air in the flask was replaced with nitrogen, to this mixture were added 20 mL of toluene and 0.2 mL of tri(tert-butyl)phosphine (a 10 wt % hexane solution). This mixture was degassed by being stirred while the pressure was reduced. After the degassing, 59 mg (0.10 mmol) of bis(dibenzylideneacetone)palladium(0) was added to this mixture. This mixture was stirred at 110° C. for 5 hours under a nitrogen stream. After the stirring, the obtained mixture was suction-filtered through Celite (produced by Wako Pure Chemical Industries, Ltd., Catalog No. 531-16855), alumina, and Florisil (produced by Wako Pure Chemical Industries, Ltd., Catalog No. 540-00135). The filtrate was concentrated to give a yellow solid. This solid was purified by silica gel column chromatography (developing solvent, hexane:toluene=5:1). The obtained solid was recrystallized from toluene/hexane to give 1.1 g of a yellow solid in 70% yield. The synthesis scheme of Step 2 is illustrated in (b-14).

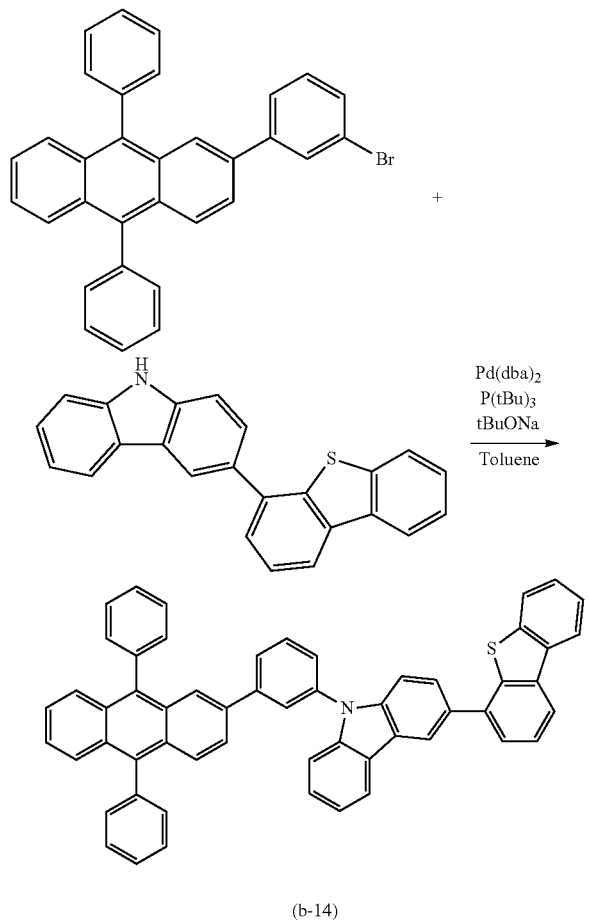

(b-14)

By a train sublimation method, the obtained yellow solid was purified. The purification was conducted by heating of 1.1 g of the yellow solid at 330° C. under a pressure of 2.9 Pa with a flow rate of argon gas of 5 mL/min. After the purification, 0.89 g of a yellow solid was obtained in a yield of 84%.

The yellow solid after the above purification was subjected to nuclear magnetic resonance (NMR) spectroscopy. The measurement data are shown below.

$^1$H NMR (CDCl$_3$, 300 MHz): δ=7.30-7.38 (m, 3H), 7.40-7.76 (m, 23H), 7.77-7.87 (m, 4H), 8.01 (d, J$_1$=0.90 Hz, 1H), 8.16-8.24 (m, 3H), 8.52 (d, J=1.2 Hz, 1H)

Figure 48A:
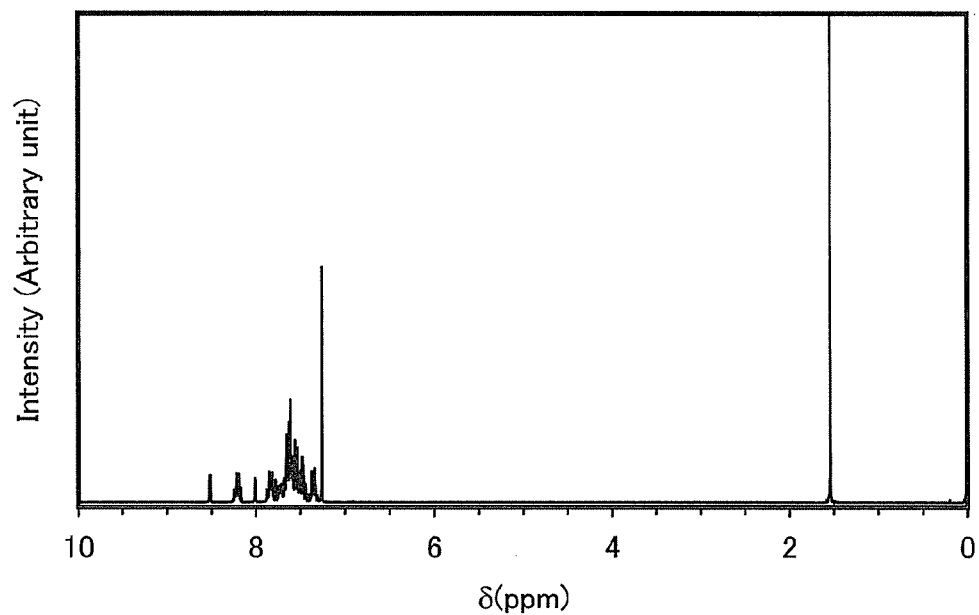
FIGS. 48A and 48B are $^1$H NMR charts of 2mDBTCzPPA-II.
Figure 48B:
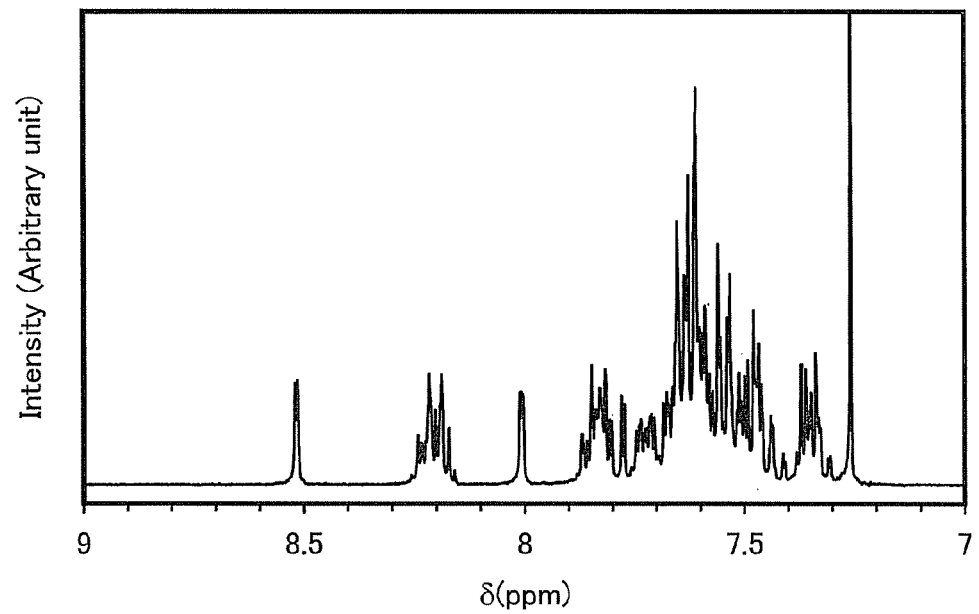

In addition, $^1$H NMR charts are shown in FIGS. 48A and 48B. Note that FIG. 48B is a chart where the range of from 7 ppm to 9 ppm in FIG. 48A is enlarged. The measurement results showed that 2mDBTCzPPA-II, which is the carbazole derivative represented by the above structural formula, was obtained.

Figure 49A:
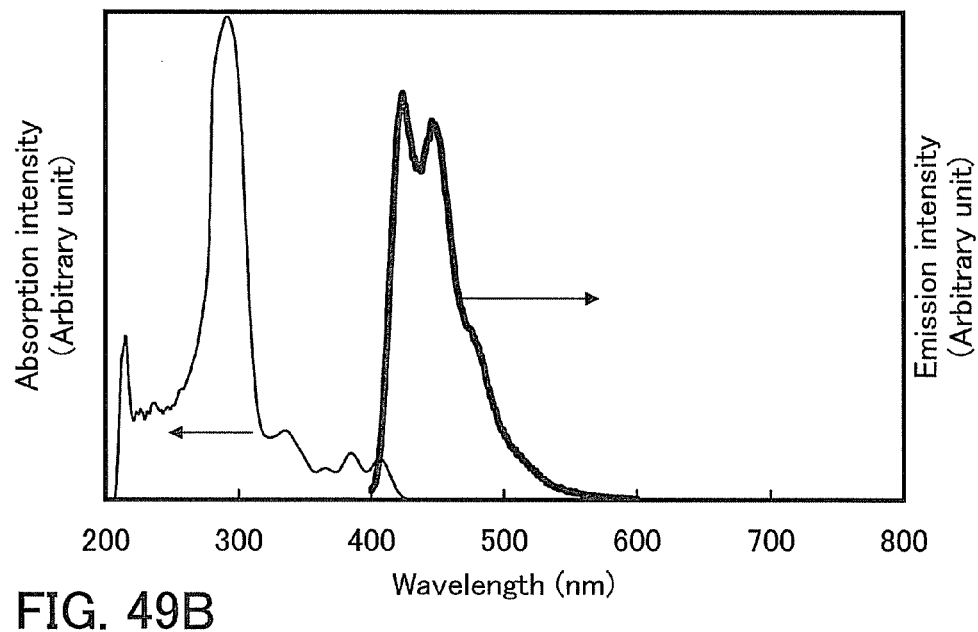
FIGS. 49A and 49B show absorption spectra and emission spectra of 2mDBTCzPPA-II.
Figure 49B:
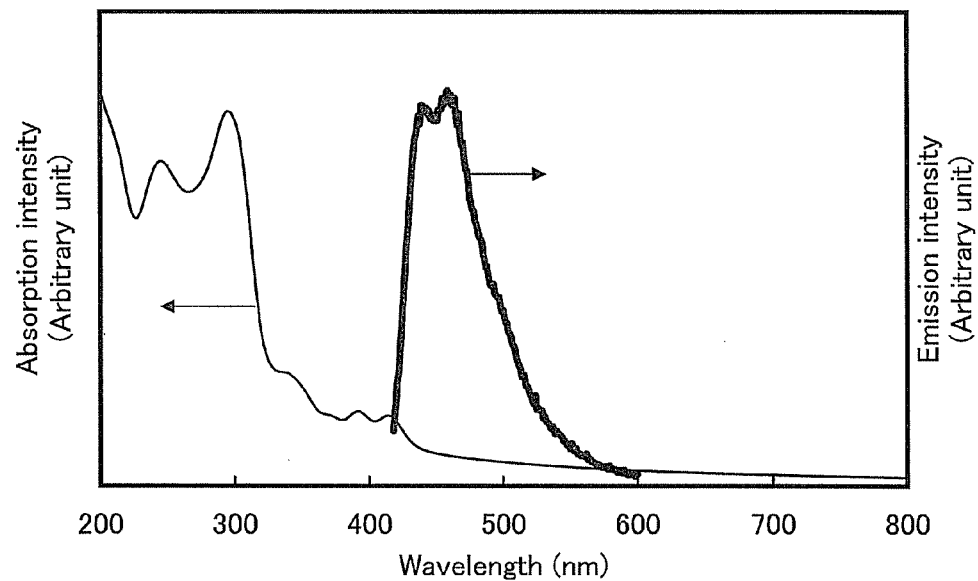

Next, an absorption and emission spectra of 2mDBTCz-PPA-II in a toluene solution of 2mDBTCzPPA-II are shown in FIG. 49A, and an absorption and emission spectra of a thin film of 2mDBTCzPPA-II are shown in FIG. 49B. An ultraviolet-visible spectrophotometer (V-550, manufactured by JASCO Corporation) was used for the measurements of the absorption spectra. In the case of the toluene solution, the measurements were made with the toluene solution of 2mDBTCzPPA-II put in a quartz cell, and the absorption spectrum obtained by subtraction of the absorption spectra of the quartz cell and toluene from the measured spectrum is shown in the drawing. In addition, as for the absorption spectrum of the thin film, a sample was prepared by evaporation of 2mDBTCzPPA-II on a quartz substrate, and the absorption spectrum obtained by subtraction of an absorption spectrum of quartz from the absorption spectrum of this sample is shown in the drawing. As in the measurements of the absorption spectra, an ultraviolet-visible spectrophotometer (V-550, manufactured by JASCO Corporation) was used for the measurements of the emission spectra. The emission spectrum of toluene was measured with the toluene solution of 2mDBTC-zPPA-II put in a quartz cell, and the emission spectrum of the thin film was measured with a sample prepared by evaporation of 2mDBTCzPPA-II on a quartz substrate. Thus, it was found that the absorption peak wavelengths of 2mDBTCz-PPA-II in the toluene solution of 2mDBTCzPPA-II were around 406 nm, around 385 nm, around 365 nm, around 335 nm, and around 292 nm and the emission peak wavelengths thereof were around 424 nm and around 437 nm (at an excitation wavelength of 385 nm), and that the absorption peak wavelengths of the thin film of 2mDBTCzPPA-II were around 414 nm, around 392 nm, around 370 nm, around 339 nm, around 295 nm, around 245 nm, and around 208 nm and the emission peak wavelengths thereof were around 492 nm, around 459 nm, and around 440 nm (at an excitation wavelength of 403 nm).

Further, the ionization potential of 2mDBTCzPPA-II in a thin film state was measured by a photoelectron spectrometer (AC-2, manufactured by Riken Keiki, Co., Ltd.) in air. The obtained value of the ionization potential was converted to a negative value, so that the HOMO level of 2mDBTCzPPA-II was −5.74 eV. From the data of the absorption spectra of the thin film in FIG. 49B, the absorption edge of 2mDBTCzPPA-II, which was obtained from Tauc plot with an assumption of direct transition, was 2.84 eV. Therefore, the optical energy gap of 2mDBTCzPPA-II in the solid state was estimated at 2.84 eV; from the values of the HOMO level obtained above and this energy gap, the LUMO level of 2mDBTCzPPA-II was able to be estimated at −2.90 eV. It was thus found that 2mDBTCzPPA-II had a wide energy gap of 2.84 eV in the solid state.

Further, the oxidation reaction characteristics of 2mDBTCzPPA-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from 0.06 V to 1.05 V and then changed from 1.05 V to 0.06 V was one cycle, and 100 cycles were performed.

The measurement results revealed that 2mDBTCzPPA-II showed properties effective against repetition of redox reactions between an oxidized state and a neutral state without a large variation in oxidation peak even after the 100 cycles in the measurements.

Further, the HOMO level of 2mDBTCzPPA-II was determined also by calculation from the CV measurement results.

First, the potential energy of the reference electrode with respect to the vacuum level used was found to be −4.94 eV, as determined in Example 1. The oxidation peak potential $E_{pa}$ of 2mDBTCzPPA-II was 0.91 V. In addition, the reduction peak potential $E_{pc}$ thereof was 0.82 V. Therefore, a half-wave potential (an intermediate potential between $E_{pa}$ and $E_{pc}$) can be calculated at 0.87 V. This means that 2mDBTCzPPA-II is oxidized by an electric energy of 0.87 [V versus Ag/Ag⁺], and this energy corresponds to the HOMO level. Here, since the potential energy of the reference electrode, which was used in this example, with respect to the vacuum level is −4.94 [eV] as described above, the HOMO level of 2mDBTCzPPA-II was calculated as follows: −4.94−0.87=−5.81 [eV].

Example 18

Synthesis Example 16

In this example is described a method of synthesizing 3-(dibenzofuran-4-yl)-9-[3-(9,10-diphenyl-2-anthryl)phenyl]-9H-carbazole (abbreviation: 2mDBFCzPPA-II), which is the carbazole derivative represented by the structural formula (727) in Embodiment 1. A structure of 2mDBFCzPPA-II is illustrated in the following structural formula.

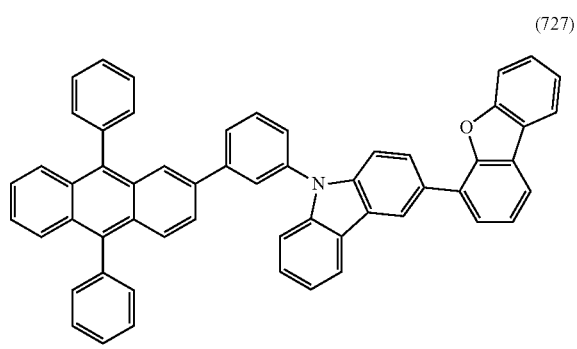 [SMILES: c1ccc(-c2c3ccccc3c(-c3ccccc3)c3cc(-c4cccc(-n5c6ccccc6c6cc(-c7cccc8c7oc7ccccc78)ccc65)c4)ccc23)cc1]

(727)

Step 1: Synthesis of 3-(Dibenzofuran-4-yl)-9H-carbazole (abbreviation: DBFCz-II)

This was synthesized as in Step 1 in Example 2.

Step 2: Synthesis of 3-(Dibenzofuran-4-yl)-9-[3-(9,10-diphenyl-2-anthryl)phenyl]-9H-carbazole (abbreviation: 2mDBFCzPPA-II)

In a 100-mL three-neck flask were put 1.0 g (2.1 mmol) of 2-(3-bromophenyl)-9,10-diphenylanthracene, 0.69 g (2.1 mmol) of 3-(dibenzofuran-4-yl)-9H-carbazole, and 0.59 g (6.2 mmol) of sodium tert-butoxide. After the air in the flask was replaced with nitrogen, to this mixture were added 20 mL of toluene and 0.2 mL of tri(tert-butyl)phosphine (a 10 wt % hexane solution). This mixture was degassed by being stirred while the pressure was reduced. After the degassing, 59 mg (0.10 mmol) of bis(dibenzylideneacetone)palladium(0) was added to this mixture. This mixture was stirred at 110° C. for 5 hours under a nitrogen stream. After the stirring, the obtained mixture was suction-filtered through Celite (produced by Wako Pure Chemical Industries, Ltd., Catalog No. 531-16855), alumina, and Florisil (produced by Wako Pure Chemical Industries, Ltd., Catalog No. 540-00135). The filtrate was concentrated to give a yellow solid. The obtained solid was recrystallized from toluene, and the obtained crystal was purified by high performance liquid column chromatography (abbreviation: HPLC) (developing solvent: chloroform). The obtained fraction was concentrated to give 0.91 g of a pale yellow solid in 60% yield. The synthesis scheme of Step 2 is illustrated in (b-15).

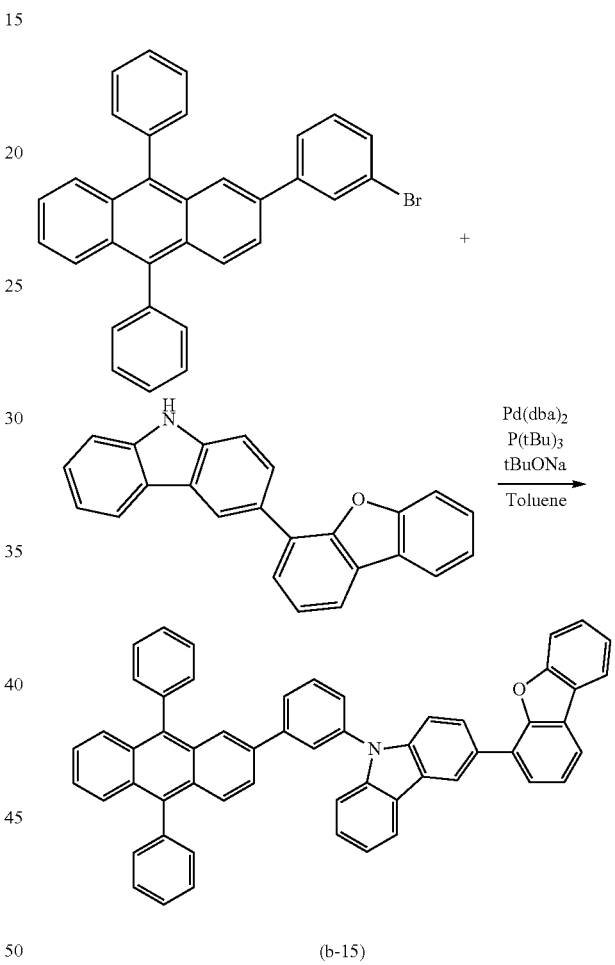

(b-15)

By a train sublimation method, the obtained pale yellow solid was purified. The purification was conducted by heating of 0.90 g of the pale yellow solid at 335° C. under a pressure of 2.7 Pa with a flow rate of argon gas of 5 mL/min. After the purification, 0.78 g of a pale yellow solid was obtained in a yield of 87%.

The yellow solid after the above purification was subjected to nuclear magnetic resonance (NMR) spectroscopy. The measurement data are shown below.

¹H NMR (CDCl₃, 300 MHz): δ=7.30-7.41 (m, 4H), 7.44-7.76 (m, 23H), 7.81-7.85 (m, 2H), 7.95-8.05 (m, 4H), 8.25 (d, $J_1$=7.5 Hz, 1H), 8.66 (d, $J_1$=1.5 Hz, 1H)

Figure 50A:
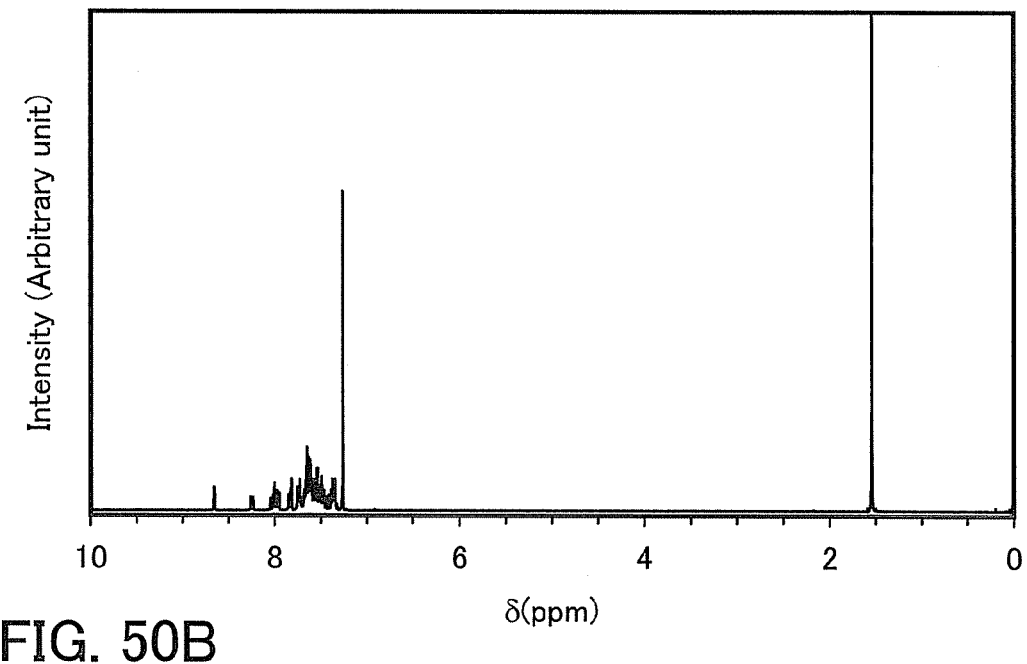
FIGS. 50A and 50B are $^1$H NMR charts of 2mDBFCzPPA-II.
Figure 50B:
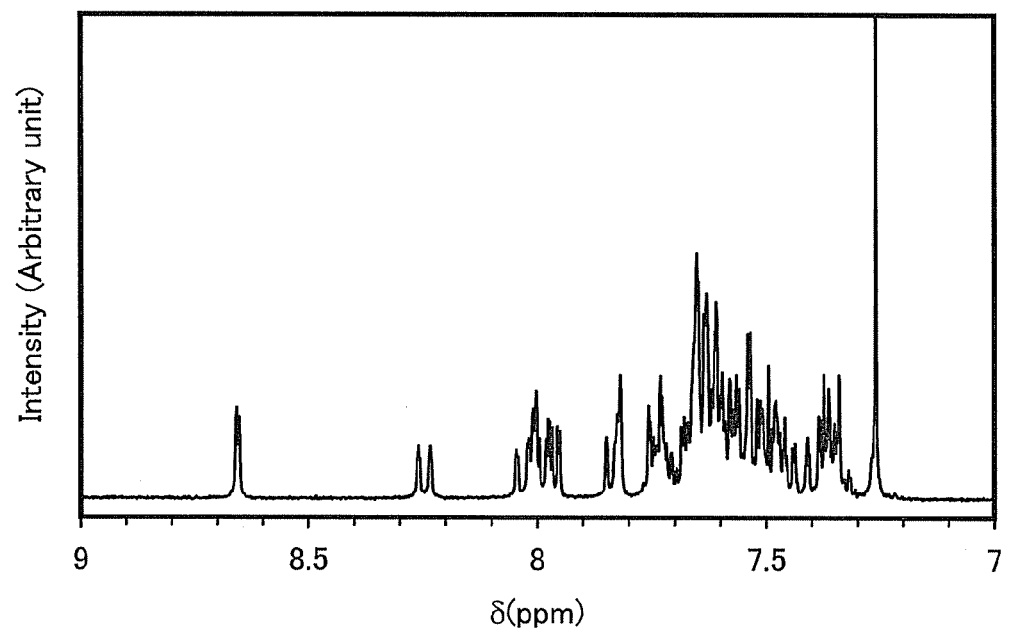

In addition, ¹H NMR charts are shown in FIGS. 50A and 50B. Note that FIG. 50B is a chart where the range of from 7 ppm to 9 ppm in FIG. 50A is enlarged. The measurement results showed that 2mDBFCzPPA-II, which is the carbazole derivative represented by the above structural formula, was obtained.

Figure 51A:
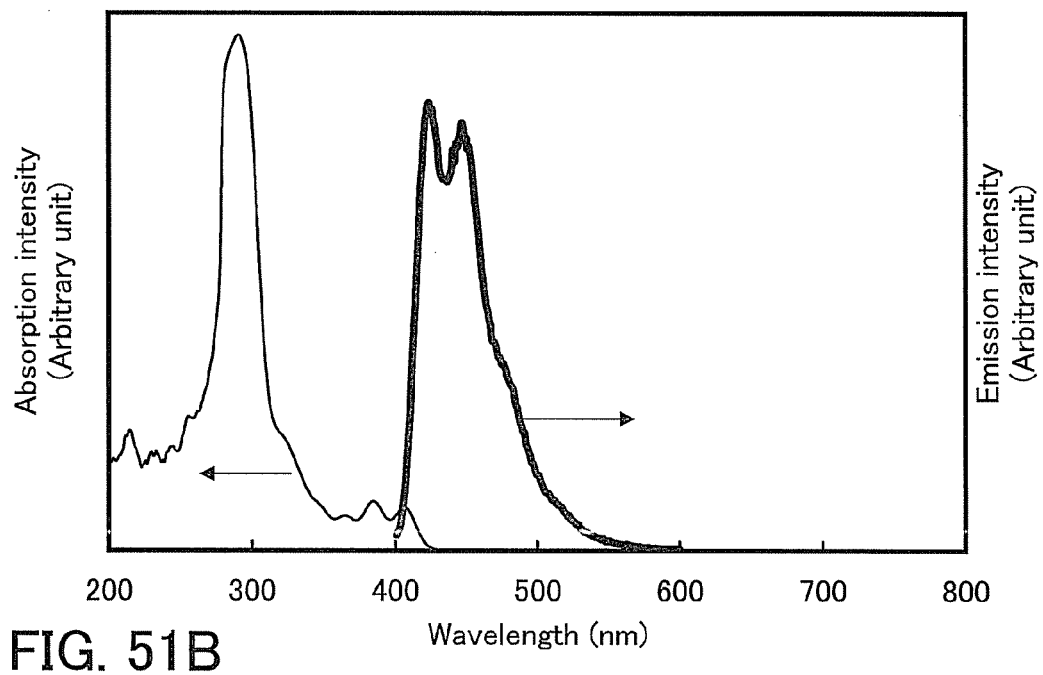
FIGS. 51A and 51B show absorption spectra and emission spectra of 2mDBFCzPPA-II.
Figure 51B:
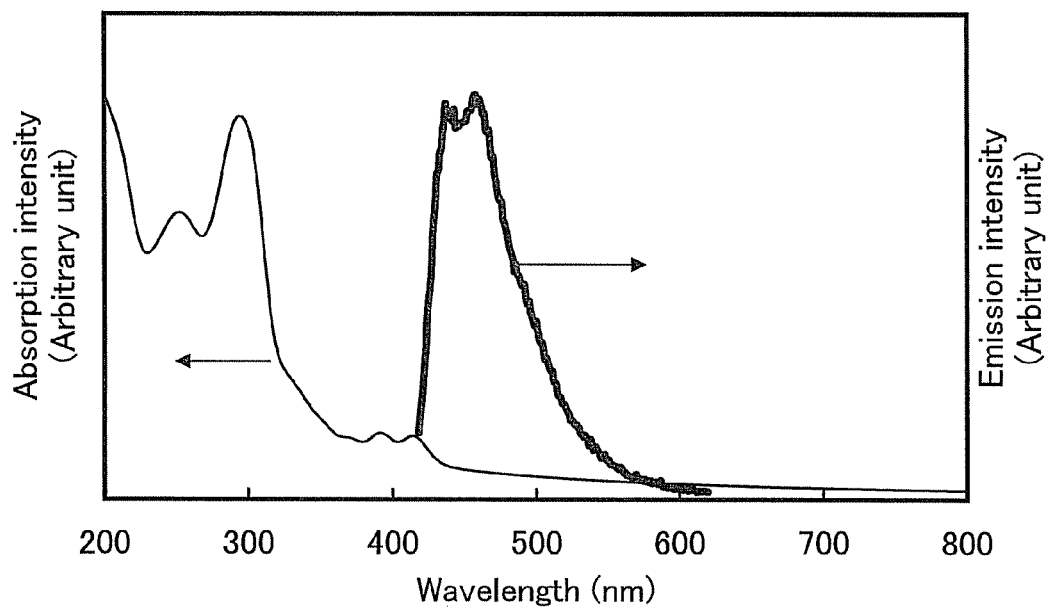

Next, an absorption and emission spectra of 2mDBFCz-PPA-II in a toluene solution of 2mDBFCzPPA-II are shown in FIG. 51A, and an absorption and emission spectra of a thin film of 2mDBFCzPPA-II are shown in FIG. 51B. An ultraviolet-visible spectrophotometer (V-550, manufactured by JASCO Corporation) was used for the measurements of the absorption spectra. In the case of the toluene solution, the measurements were made with the toluene solution of 2mDBFCzPPA-II put in a quartz cell, and the absorption spectrum obtained by subtraction of the absorption spectra of the quartz cell and toluene from the measured spectrum is shown in the drawing. In addition, as for the absorption spectrum of the thin film, a sample was prepared by evaporation of 2mDBFCzPPA-II on a quartz substrate, and the absorption spectrum obtained by subtraction of an absorption spectrum of quartz from the absorption spectrum of this sample is shown in the drawing. As in the measurements of the absorption spectra, an ultraviolet-visible spectrophotometer (V-550, manufactured by JASCO Corporation) was used for the measurements of the emission spectra. The emission spectrum of toluene was measured with the toluene solution of 2mDBFCzPPA-II put in a quartz cell, and the emission spectrum of the thin film was measured with a sample prepared by evaporation of 2mDBFCzPPA-II on a quartz substrate. Thus, it was found that the absorption peak wavelengths of 2mDBFCzPPA-II in the toluene solution of 2mDBFCzPPA-II were around 406 nm, around 385 nm, around 365 nm, and around 291 nm and the emission peak wavelengths thereof were around 436 nm and around 424 nm (at an excitation wavelength of 386 nm), and that the absorption peak wavelengths of the thin film of 2mDBFCzPPA-II were around 414 nm, around 391 nm, around 369 nm, around 328 nm, around 294 nm, and around 252 nm and the emission peak wavelengths thereof were around 488 nm, around 457 nm, and around 438 nm (at an excitation wavelength of 413 nm).

Further, the ionization potential of 2mDBFCzPPA-II in a thin film state was measured by a photoelectron spectrometer (AC-2, manufactured by Riken Keiki, Co., Ltd.) in air. The obtained value of the ionization potential was converted to a negative value, so that the HOMO level of 2mDBFCzPPA-II was −5.75 eV. From the data of the absorption spectra of the thin film in FIG. 51B, the absorption edge of 2mDBFCzPPA-II, which was obtained from Tauc plot with an assumption of direct transition, was 2.84 eV. Therefore, the optical energy gap of 2mDBFCzPPA-II in the solid state was estimated at 2.84 eV; from the values of the HOMO level obtained above and this energy gap, the LUMO level of 2mDBFCzPPA-II was able to be estimated at −2.91 eV. It was thus found that 2mDBFCzPPA-II had a wide energy gap of 2.84 eV in the solid state.

Further, the oxidation reaction characteristics of 2mDBFCzPPA-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from −0.41 V to 1.05 V and then changed from 1.05 V to −1.41 V was one cycle, and 100 cycles were performed.

The measurement results revealed that 2mDBFCzPPA-II showed properties effective against repetition of redox reactions between an oxidized state and a neutral state without a large variation in oxidation peak even after the 100 cycles in the measurements.

Further, the HOMO level of 2mDBFCzPPA-II was determined also by calculation from the CV measurement results.

First, the potential energy of the reference electrode with respect to the vacuum level used was found to be −4.94 eV, as determined in Example 1. The oxidation peak potential $E_{pa}$ of 2mDBFCzPPA-II was 0.93 V. In addition, the reduction peak potential $E_{pc}$ thereof was 0.82 V. Therefore, a half-wave potential (an intermediate potential between $E_{pa}$ and $E_{pc}$) can be calculated at 0.88 V. This means that 2mDBFCzPPA-II is oxidized by an electric energy of 0.88 [V versus Ag/Ag$^+$], and this energy corresponds to the HOMO level. Here, since the potential energy of the reference electrode, which was used in this example, with respect to the vacuum level is −4.94 [eV] as described above, the HOMO level of 2mDBFCzPPA-II was calculated as follows: −4.94−0.88=−5.82 [eV].

Reference Example 1

A method of synthesizing N,N'-bis[4-(9-phenyl-9H-fluoren-9-yl)phenyl]-N,N'-diphenyl-pyrene-1,6-diamine (abbreviation: 1,6FLPAPrn) (structural formula (vi)) used in the above Examples is specifically described. A structure of 1,6FLPAPrn is illustrated below.

(vi)

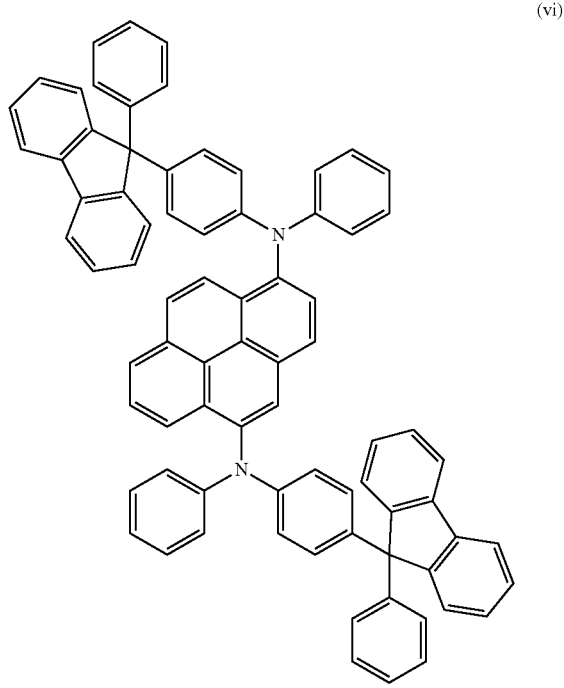

1,6FLPAPrn

Step 1: Method of Synthesizing 9-(4-Bromophenyl)-9-phenylfluorene

In a 100-mL three-neck flask, 1.2 g (50 mmol) of magnesium was heated and stirred for 30 minutes under reduced pressure to be activated. The activated magnesium was cooled to room temperature, and the flask was made to contain a nitrogen atmosphere. Then, several drops of dibromoethane were added, so that form formation and heat generation were confirmed. After 12 g (50 mmol) of 2-bromobiphenyl dissolved in 10 mL of diethyl ether was slowly added dropwise to this mixture, the mixture was heated and stirred under reflux for 2.5 hours, so that a Grignard reagent was prepared.

Into a 500-mL three-neck flask were placed 10 g (40 mmol) of 4-bromobenzophenone and 100 mL of diethyl ether, and the air in the flask was replaced with nitrogen. After the Grignard reagent which was synthesized in advance was slowly added dropwise to this mixture, the mixture was heated and stirred under reflux for 9 hours.

After reaction, this mixture solution was filtered to give a residue. The obtained residue was dissolved in 150 mL of ethyl acetate, and 1 M hydrochloric acid was added thereto until acidification, and then stirring was performed for 2 hours. The organic layer of this mixture was washed with water, and dried by addition of magnesium sulfate. This mixture was filtered, and the obtained filtrate was concentrated to give an oily substance.

Into a 500-mL recovery flask were placed this oily substance, 50 mL of glacial acetic acid, and 1.0 mL of hydrochloric acid. The mixture was stirred and heated at 130° C. for 1.5 hours under a nitrogen atmosphere.

After the reaction, this reaction mixture was filtered to give a residue. The obtained residue was washed with water, an aqueous sodium hydroxide solution, water, and methanol in this order. Then, the mixture was dried, so that the substance which was the object of the synthesis was obtained as 11 g of a white powder in 69% yield. The synthesis scheme of the above Step 1 is illustrated in (E1-1) below.

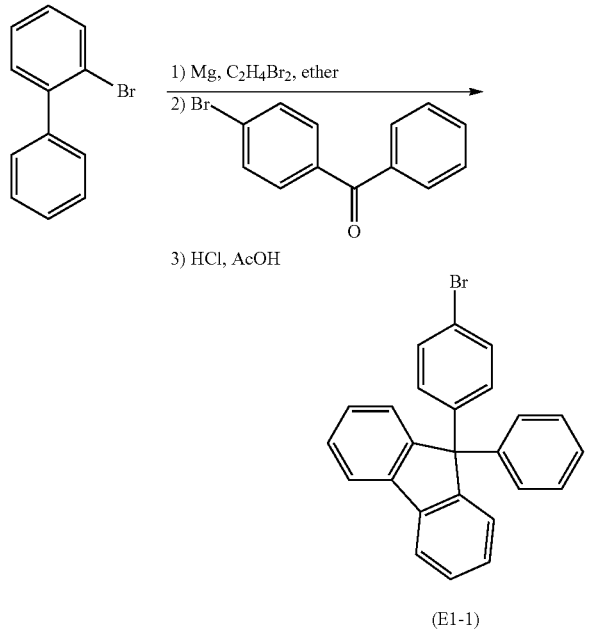

(E1-1)

Step 2: Method of Synthesizing 4-(9-Phenyl-9H-fluoren-9-yl)diphenylamine (abbreviation: FLPA)

In a 200-mL three-neck flask were put 5.8 g (14.6 mmol) of 9-(4-bromophenyl)-9-phenylfluorene, 1.7 mL (18.6 mmol) of aniline, and 4.2 g (44.0 mmol) of sodium tert-butoxide. The air in the flask was replaced with nitrogen. To this mixture were added 147.0 mL of toluene and 0.4 mL of a 10% hexane solution of tri(tert-butyl)phosphine. The temperature of this mixture was set to 60° C., and 66.1 mg (0.1 mmol) of bis(dibenzylideneacetone)palladium(0) was added to the mixture, followed by stirring for 3.5 hours. After the stirring, the mixture was suction-filtered through Florisil (produced by Wako Pure Chemical Industries, Ltd., Catalog No. 540-00135), Celite (produced by Wako Pure Chemical Industries, Ltd., Catalog No. 531-16855), and alumina. The obtained filtrate was concentrated. The solid obtained by concentration of the obtained filtrate was purified by silica gel column chromatography (developing solvent, hexane:toluene=2:1). The obtained fraction was concentrated to give 6.0 g of a white solid in 99% yield, which was the object of the synthesis. The synthesis scheme of Step 2 is illustrated in (E1-2) below.

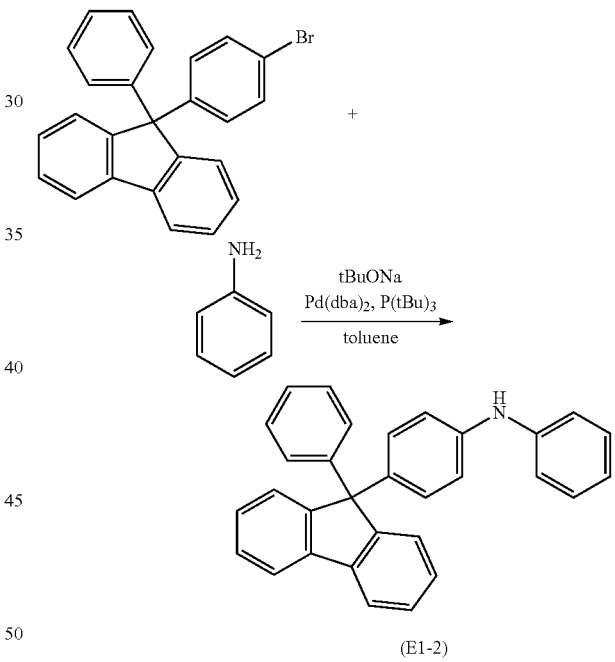

(E1-2)

Step 3: Method of Synthesizing N,N'-Bis[4-(9-phenyl-9H-fluoren-9-yl)phenyl]-N,N-diphenyl-pyrene-1,6-diamine (abbreviation: 1,6FLPAPrn)

In a 50-mL three-neck flask were put 0.4 g (1.2 mmol) of 1,6-dibromopyrene, 1.0 g (2.4 mmol) of 4-(9-phenyl-9H-fluoren-9-yl)diphenylamine (abbreviation: FLPA), which was obtained in Step 2 in Reference Example 1, and 0.3 g (3.6 mmol) of sodium tert-butoxide. The air in the flask was replaced with nitrogen. To this mixture were added 11.5 mL of toluene and 0.20 mL of a 10% hexane solution of tri(tert-butyl)phosphine. The temperature of this mixture was set to 70° C., and 31.1 mg (0.05 mmol) of bis(dibenzylideneacetone)palladium(0) was added to the mixture, followed by stirring for 4.0 hours. After the stirring, the mixture was suction-filtered through Florisil, Celite, and alumina, and a filtrate was obtained. The obtained filtrate was concentrated. The solid obtained by concentration of the obtained filtrate was purified by silica gel column chromatography (developing solvent: chloroform). The obtained fraction was concentrated to give a yellow solid. The obtained solid was washed with a mixed solvent of toluene and hexane, and then the mixture was suction-filtered to give a yellow solid. The obtained yellow solid was washed with a mixed solvent of chloroform and hexane, so that 0.8 g of a pale yellow powdered solid was obtained in 68% yield.

By a train sublimation method, 0.8 g of the obtained pale yellow solid was purified. Under a pressure of 2.7 Pa with a flow rate of argon gas at 5.0 mL/min, the sublimation purification was carried out at 360° C. After the purification, 0.4 g of the object of the synthesis was obtained in a yield of 56%. The synthesis scheme of Step 3 is illustrated in (E2-A) below.

A nuclear magnetic resonance (NMR) method and a mass spectrometry identified the obtained compound as N,N'-bis[4-(9-phenyl-9H-fluoren-9-yl)phenyl]-N,N'-diphenyl-pyrene-1,6-diamine (abbreviation: 1,6FLPAPrn). The $^1$H NMR data is shown below.

$^1$H NMR (CDCl$_3$, 300 MHz): δ=6.88-6.91 (m, 6H), 7.00-7.03 (m, 8H), 7.13-7.40 (m, 26H), 7.73-7.80 (m, 6H), 7.87 (d, J=9.0 Hz, 2H), 8.06-8.09 (m, 4H)

Reference Example 2

A method of synthesizing 4-phenyl-4'-(9-phenylfluoren-9-yl)triphenylamine (abbreviation: BPAFLP) (structural formula (i)) used in the above Example is specifically described. A structure of BPAFLP is illustrated below.

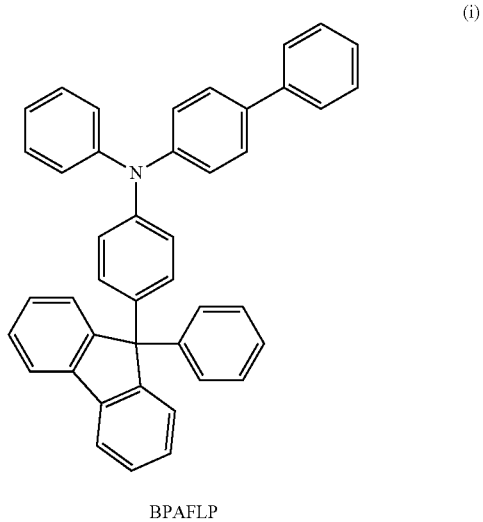 [SMILES: c1ccc(-c2ccc(N(c3ccccc3)c3ccc(C4(c5ccccc5)c5ccccc5-c5ccccc54)cc3)cc2)cc1]

BPAFLP

Step 1: Synthesis of 9-(4-Bromophenyl)-9-phenylfluorene

This was synthesized as in Step 1 in Reference Example 1.

Step 2: Synthesis of 4-Phenyl-4'-(9-phenylfluoren-9-yl)triphenylamine (abbreviation: BPAFLP)

Into a 100-mL three-neck flask were placed 3.2 g (8.0 mmol) of 9-(4-bromophenyl)-9-phenylfluorene, 2.0 g (8.0 mmol) of 4-phenyl-diphenylamine, 1.0 g (10 mmol) of sodium tert-butoxide, and 23 mg (0.04 mmol) of bis(dibenzylideneacetone)palladium(0), and the air in the flask was replaced with nitrogen. Then, 20 mL of dehydrated xylene was added to this mixture. After the mixture was degassed by being stirred under reduced pressure, 0.2 mL (0.1 mmol) of tri(tert-butyl)phosphine (a 10 wt % hexane solution) was added to the mixture. This mixture was stirred and heated at 110° C. for 2 hours under a nitrogen atmosphere.

After the reaction, 200 mL of toluene was added to this reaction mixture, and this suspension was filtered through Florisil (produced by Wako Pure Chemical Industries, Ltd., Catalog No. 540-00135) and Celite (produced by Wako Pure Chemical Industries, Ltd., Catalog No. 531-16855). The obtained filtrate was concentrated, and the resulting substance was purified by silica gel column chromatography (developing solvent, toluene:hexane=1:4). The obtained fraction was concentrated, and the resulting substance was

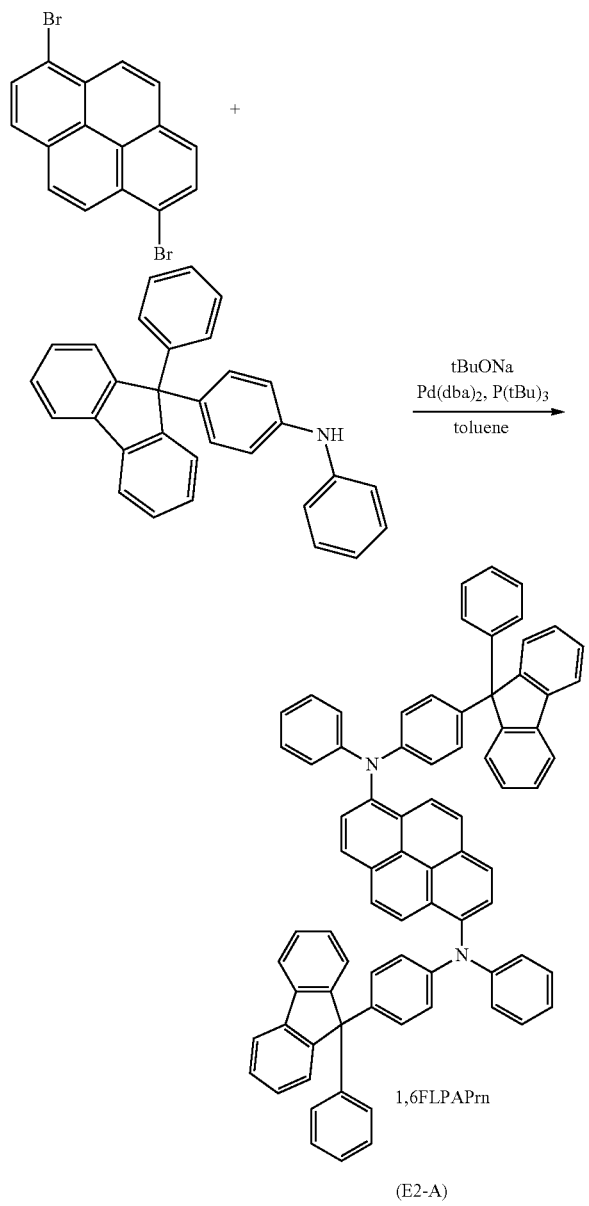

(E2-A)

recrystallized from acetone/methanol, so that the substance which was the object of the synthesis was obtained as 4.1 g of a white powder in 92% yield. A reaction scheme of the above synthesis method is illustrated in (J-4) below.

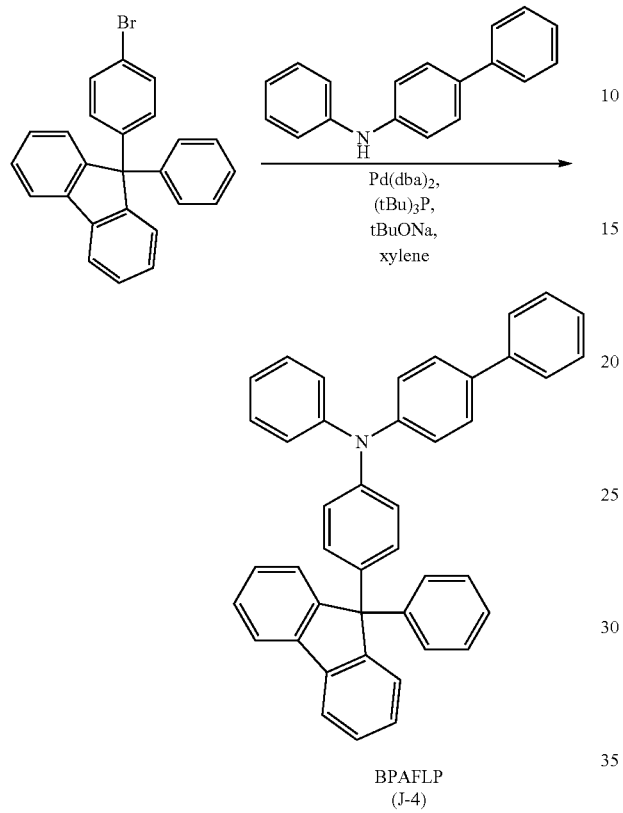

BPAFLP
(J-4)

The Rf values of the substance that was the object of the synthesis, 9-(4-bromophenyl)-9-phenylfluorene, and 4-phenyl-diphenylamine were respectively 0.41, 0.51, and 0.27, which were found by silica gel thin layer chromatography (TLC) (developing solvent, ethyl acetate:hexane=1:10).

The compound obtained in the above Step 2 was subjected to nuclear magnetic resonance (NMR) spectroscopy. The measurement data are shown below. The measurement results indicate that the obtained compound was BPAFLP, which is a fluorene derivative.

$^1$H NMR (CDCl$_3$, 300 MHz): δ (ppm)=6.63-7.02 (m, 3H), 7.06-7.11 (m, 6H), 7.19-7.45 (m, 18H), 7.53-7.55 (m, 2H), 7.75 (d, J=6.9, 2H)

REFERENCE NUMERALS

101: substrate, 102: first electrode, 103: layer containing organic compound, 104: second electrode, 111: hole-injection layer, 112: hole-transport layer, 113: light-emitting layer, 114: electron-transport layer, 501: first electrode, 502: second electrode, 511: first light-emitting unit, 512: second light-emitting unit, 513: charge generation layer, 601: driver circuit portion: (source-side driver circuit), 602: pixel portion, 603: driver circuit portion: (gate-side driver circuit), 604: sealing substrate, 605: sealing material, 607: space, 608: wiring, 609: FPC (flexible printed circuit), 610: element substrate, 611: switching TFT, 612: current controlling TFT, 613: first electrode, 614: insulator, 616: layer containing organic compound, 617: second electrode, 618: light-emitting element, 623: n-channel TFT, 624: p-channel TFT, 901: housing, 902: liquid crystal layer, 903: backlight, 904: housing, 905: driver IC, 906: terminal, 951: substrate, 952: electrode, 953: insulating layer, 954: partition layer, 955: a layer containing organic compound, 956: electrode, 1201: source electrode, 1202: active layer, 1203: drain electrode, 1204: gate electrode, 2001: housing, 2002: light source, 3001: lighting device, 9101: housing, 9102: support, 9103: display portion, 9104: speaker portion, 9105: video input terminal, 9201: main body, 9202: housing, 9203: display portion, 9204: keyboard, 9205: external connection port, 9206: pointing device, 9401: main body, 9402: housing, 9403: display portion, 9404: audio input portion, 9405: audio output portion, 9406: operation key, 9407: external connection port, 9408: antenna, 9501: main body, 9502: display portion, 9503: housing, 9504: external connection port, 9505: remote control receiving portion, 9506: image receiving portion, 9507: battery, 9508: audio input portion, 9509: operation key, 9510: eye piece portion.

This application is based on Japanese Patent Application serial no. 2010-211184 filed with Japan Patent Office on Sep. 21, 2010, and Japanese Patent Application serial no. 2011-182368 filed with Japan Patent Office on Aug. 24, 2011, the entire contents of which are hereby incorporated by reference.

The invention claimed is:
1. A carbazole derivative represented by a general formula (G1),

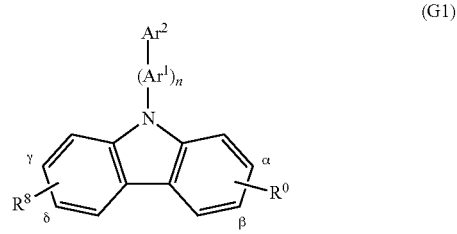

(G1)

wherein Ar$^1$ represents a phenylene group, a naphthylene group, or a biphenylene group,
wherein Ar$^2$ represents an aryl group that has 14 to 30 carbon atoms and comprises a condensed tricyclic ring, a condensed tetracyclic ring, a condensed pentacyclic ring, a condensed hexacyclic ring, or a condensed heptacyclic ring,
wherein R$^0$ represents a group represented by a general formula (g1),
wherein R$^8$ represents hydrogen, an alkyl group having 1 to 4 carbon atoms, an aryl group having 6 to 15 carbon atoms, or a group represented by a general formula (g2),
wherein a substitution site of R$^0$ is a carbon atom represented by either α or β,
wherein a substitution site of R$^8$ is a carbon atom represented by either γ or δ,
wherein n is either 0 or 1,
wherein Ar$^1$ has no substituent or a first substituent, and the first substituent is an alkyl group having 1 to 4 carbon atoms,
wherein Ar$^2$ has no substituent or a second substituent, and the second substituent is of an alkyl group having 1 to 4 carbon atoms, or an aryl group having 6 to 15 carbon atoms, (g1)

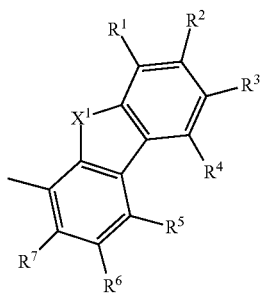

wherein $X^1$ represents oxygen or sulfur, and $R^1$ to $R^7$ individually represent hydrogen, an alkyl group having 1 to 4 carbon atoms, or an aryl group having 6 to 15 carbon atoms, and (g2)

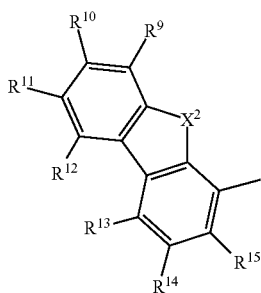

wherein $X^2$ represents oxygen or sulfur, and $R^9$ to $R^{15}$ individually represent hydrogen, an aryl group having 6 to 15 carbon atoms, or an alkyl group having 1 to 4 carbon atoms.

2. The carbazole derivative according to claim 1,
wherein $R^8$ is a substituent represented by the general formula (g2), and
wherein in the case where the $R^0$ is bonded to a position of the α, the $R^8$ is bonded to a position of the γ, and in the case where the $R^0$ is bonded to a position of the β, the $R^8$ is bonded to a position of the δ.

3. The carbazole derivative according to claim 1,
wherein $R^0$ is a substituent represented by a general formula (g3), (g3)

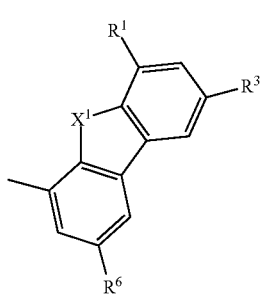

wherein $X^1$ represents oxygen or sulfur, and $R^1$, $R^3$, and $R^6$ individually represent of hydrogen, an aryl group having 6 to 15 carbon atoms, or an alkyl group having 1 to 4 carbon atoms, wherein $R^8$ is a substituent represented by a general formula (g4), and (g4)

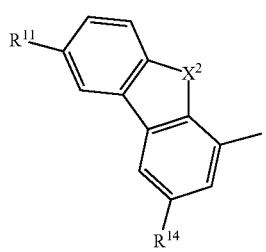

wherein $X^2$ represents oxygen or sulfur, and $R^{11}$ and $R^{14}$ individually represent hydrogen, an aryl group having 6 to 15 carbon atoms, or an alkyl group having 1 to 4 carbon atoms.

4. The carbazole derivative according to claim 3,
wherein the $R^8$ is a substituent represented by a general formula (g4), and
wherein in the case where the $R^0$ is bonded to a position of the α, the $R^8$ is bonded to a position of the γ, and in the case where the $R^0$ is bonded to a position of the β, the $R^8$ is bonded to a position of the δ.

5. The carbazole derivative according to claim 3,
wherein $R^0$ is a substituent represented by a general formula (g5), (g5)

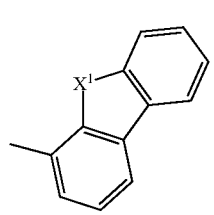

wherein $X^1$ represents oxygen or sulfur,
wherein $R^8$ is a substituent represented by a general formula (g6), and (g6)

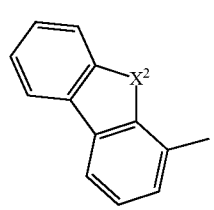

wherein $X^2$ represents oxygen or sulfur.

6. The carbazole derivative according to claim 5,
wherein $R^8$ is a substituent represented by the general formula (g6), and
wherein in the case where the $R^0$ is bonded to a position of the α, the $R^8$ is bonded to a position of the γ, and in the case where the $R^0$ is bonded to a position of the β, the $R^8$ is bonded to a position of the δ.

7. A carbazole derivative represented by a structural formula selected from the group consisting of:
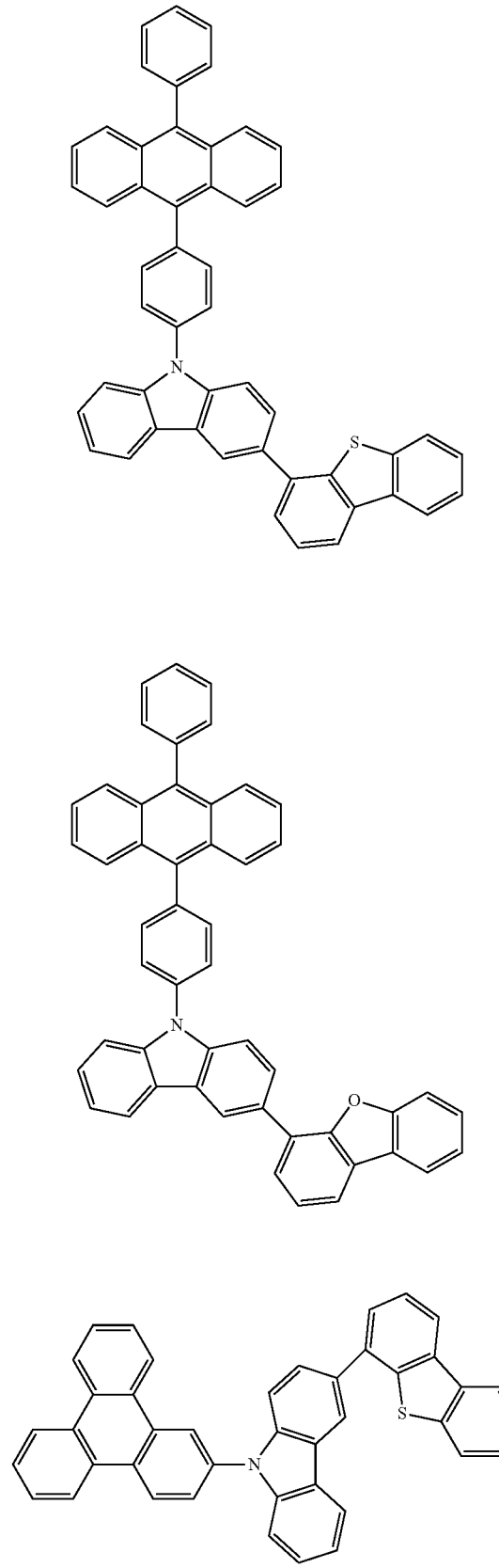
-continued
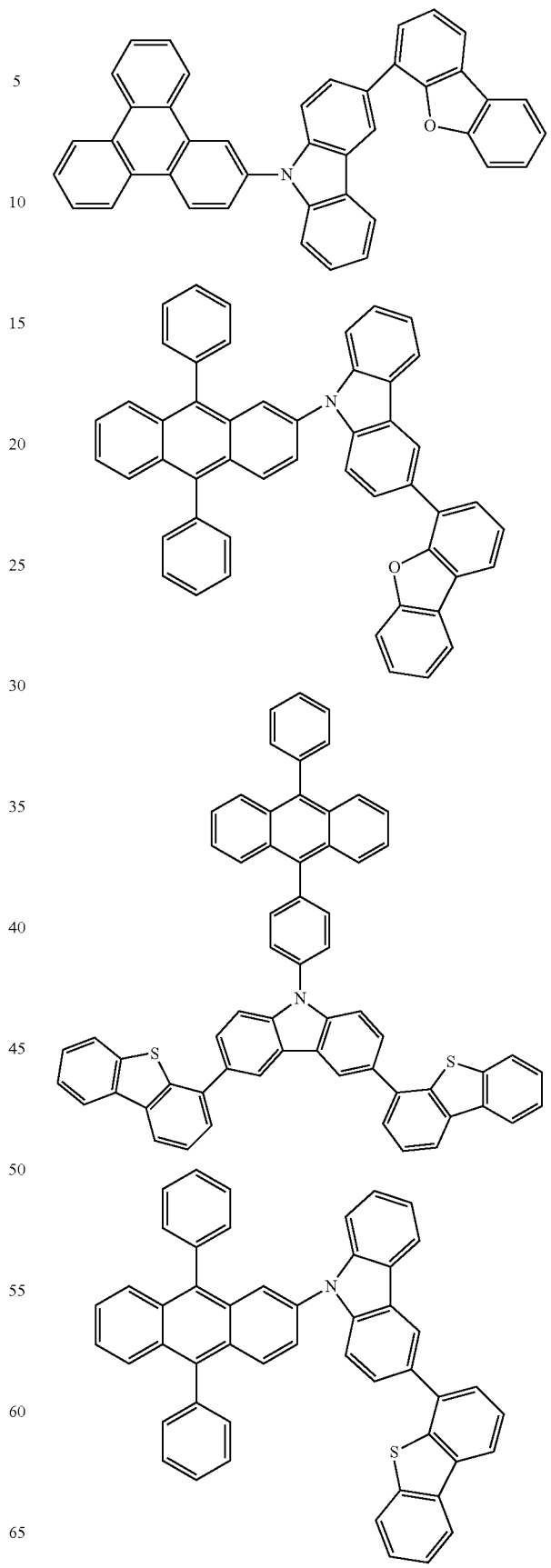

511
-continued
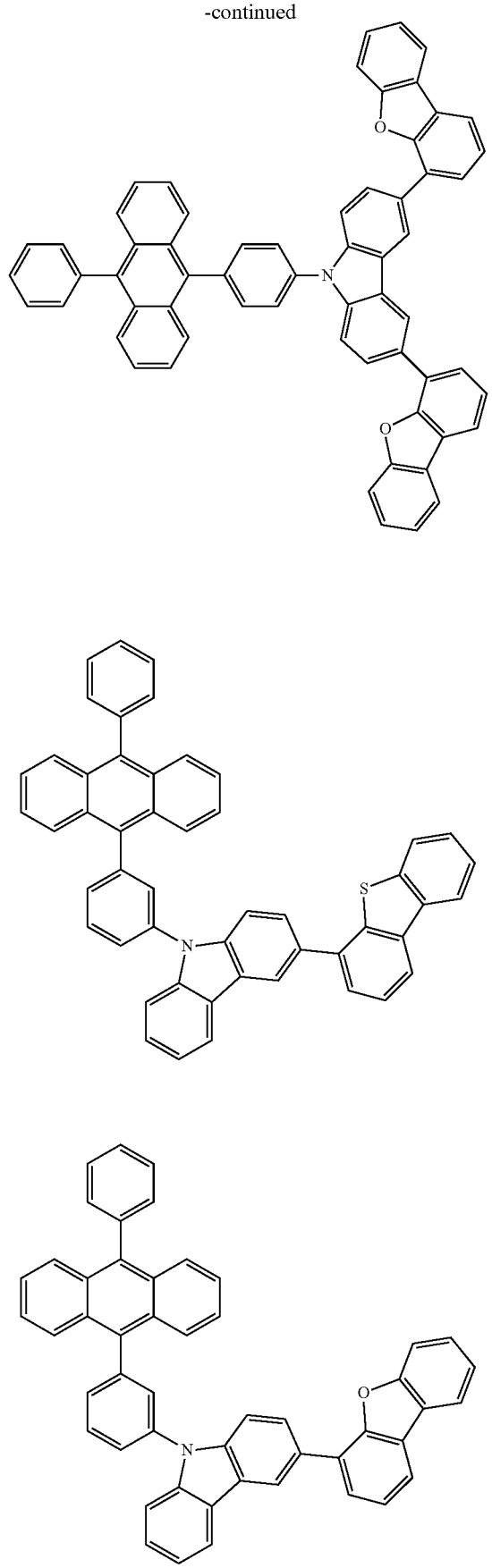
512
-continued
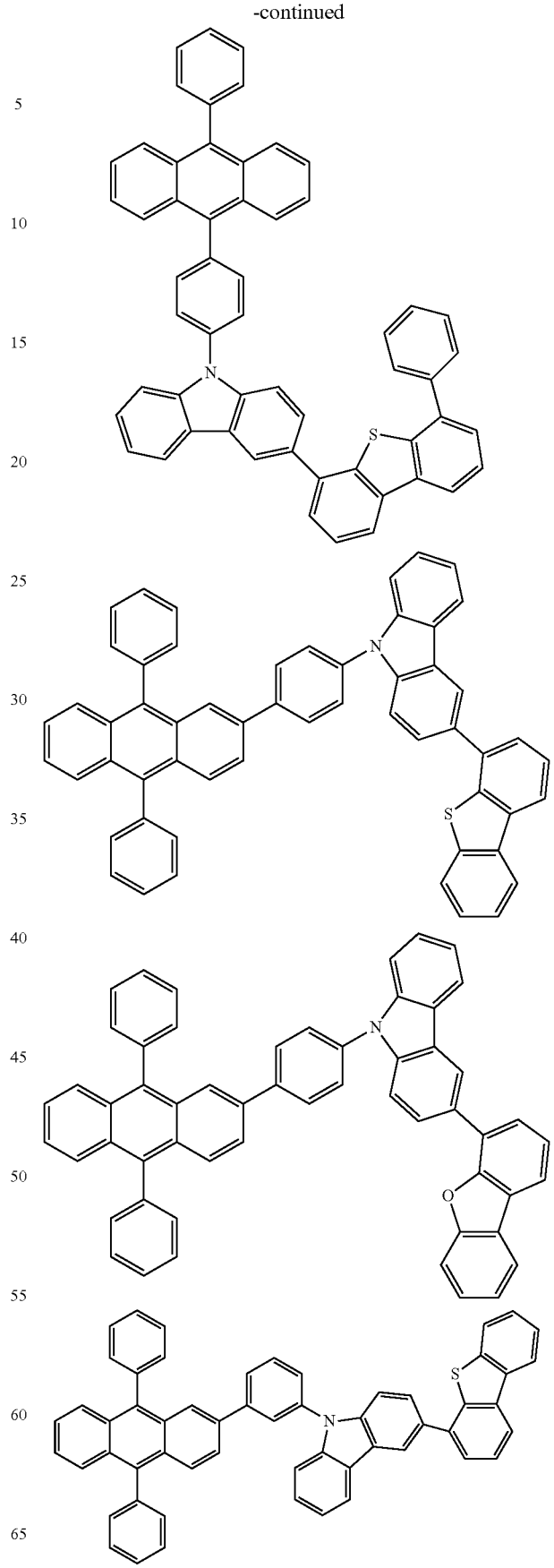

513
-continued

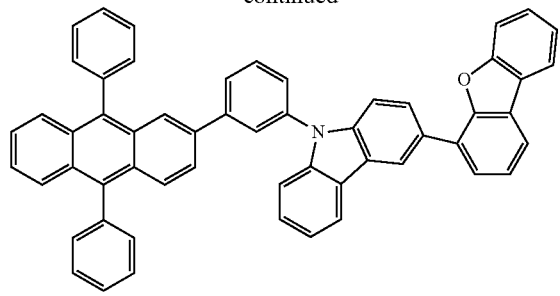

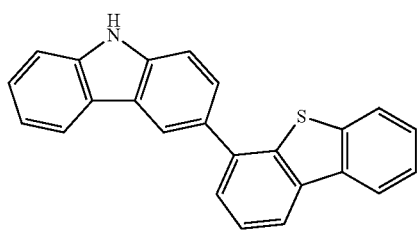

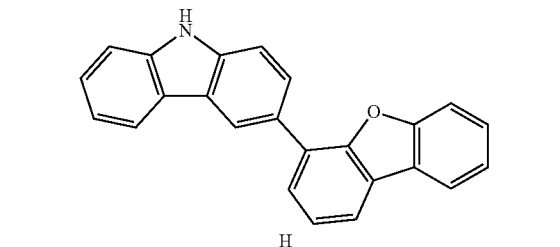

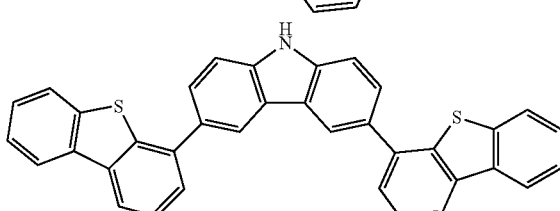

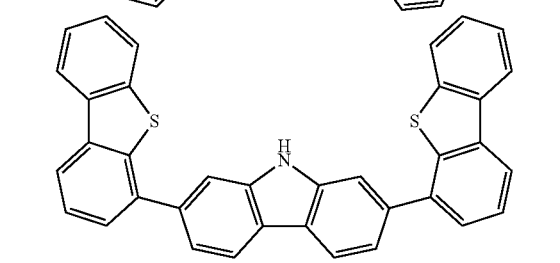

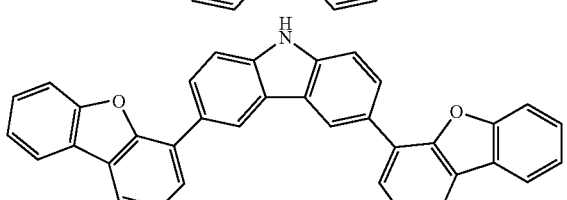

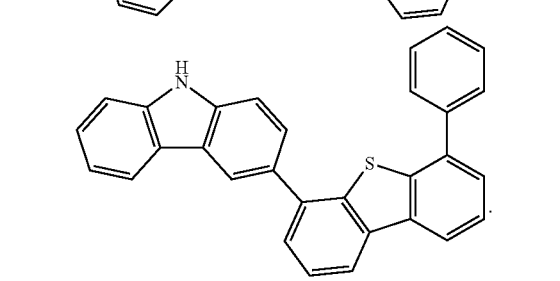

514

8. A carbazole derivative represented by a general formula (G5),

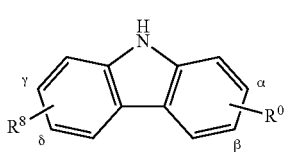
(G5)

wherein $R^0$ represents a group represented by a general formula (g1),
wherein $R^8$ represents hydrogen, an alkyl group having 1 to 4 carbon atoms, an aryl group having 6 to 15 carbon atoms, or a group represented by a general formula (g2),
wherein a substitution site of $R^0$ is a carbon atom represented by either α or β,
wherein a substitution site of $R^8$ is a carbon atom represented by either γ or δ,

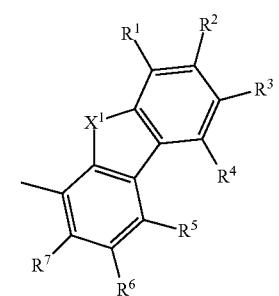
(g1)

wherein $X^1$ represents oxygen or sulfur, and $R^1$ to $R^7$ individually represent hydrogen, an alkyl group having 1 to 4 carbon atoms, or an aryl group having 6 to 15 carbon atoms, and

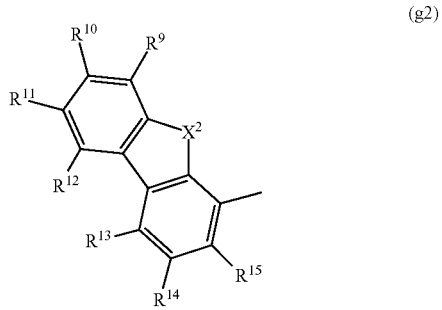
(g2)

wherein $X^2$ represents oxygen or sulfur, and $R^9$ to $R^{15}$ individually represent hydrogen, an aryl group having 6 to 15 carbon atoms, or an alkyl group having 1 to 4 carbon atoms.

9. The carbazole derivative according to claim 8,
wherein $R^8$ is a substituent represented by the general formula (g2), and
wherein in the case where the $R^0$ is bonded to a position of the α, the $R^8$ is bonded to a position of the γ, and in the case where the $R^0$ is bonded to a position of the β, the $R^8$ is bonded to a position of the δ.

10. The carbazole derivative according to claim 8,
wherein $R^0$ is a substituent represented by a general formula (g3),

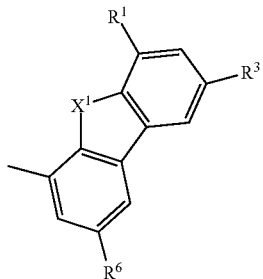

(g3)

wherein $X^1$ represents oxygen or sulfur, and $R_1$, $R^3$, and $R^6$ individually represent hydrogen, an aryl group having 6 to 15 carbon atoms, or an alkyl group having 1 to 4 carbon atoms,
wherein $R^8$ is a substituent represented by a general formula (g4),

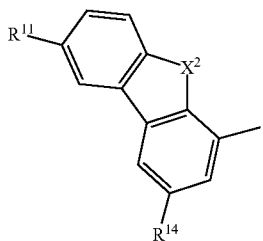

(g4)

wherein $X^2$ represents oxygen or sulfur, and $R^{11}$, and $R^{14}$ individually represent hydrogen, an aryl group having 6 to 15 carbon atoms, or an alkyl group having 1 to 4 carbon atoms.

11. The carbazole derivative according to claim 10,
wherein the $R^8$ is a substituent represented by the general formula (g4), and
wherein in the case where the $R^0$ is bonded to a position of the α, the $R^8$ is bonded to a position of the γ, and in the case where the $R^0$ is bonded to a position of the β, the $R^8$ is bonded to a position of the δ.

12. The carbazole derivative according to claim 8,
wherein $R^0$ is a substituent represented by a general formula (g5),

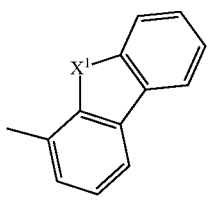

(g5)

wherein $X^1$ represents oxygen or sulfur,
wherein $R^8$ is a substituent represented by a general formula (g6), and

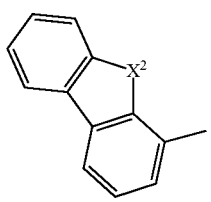

(g6)

wherein $X^2$ represents oxygen or sulfur.

13. The carbazole derivative according to claim 12,
wherein the $R^8$ is a substituent represented by the general formula (g6), and
wherein in the case where the $R^0$ is bonded to a position of the α, the $R^8$ is bonded to a position of the γ, and in the case where the $R^0$ is bonded to a position of the 13, the $R^8$ is bonded to a position of the δ.

* * * * *

UNITED STATES PATENT AND TRADEMARK OFFICE
CERTIFICATE OF CORRECTION

PATENT NO.       : 8,642,782 B2
APPLICATION NO.  : 13/228672
DATED            : February 4, 2014
INVENTOR(S)      : Hiroki Suzuki et al.

It is certified that error appears in the above-identified patent and that said Letters Patent is hereby corrected as shown below:

In the Specification:

Column 353, line 48; Change "$R^9, R^1\%$ or $R^{14}$" to --$R^9$, $R^{11}$, or $R^{14}$--.

Column 424, line 62; Change "p-rnPhAFD" to --p-mPhAFD--.

Column 425, line 22; Change "[4,5-c]" to --[4,5-α]--.

Column 429, line 4; Change "Constructed" to --constructed--.

Column 430, line 58; Change "4 or includes" to --4 or 5 includes--.

Column 442, line 64; Change "91'-carbazole" to --9H-carbazole--.

Column 450, line 27; Change "$Ag/Ag^4$]," to --$Ag/Ag^+$],--.

Column 454, line 8; Change "2BFCzPA-II" to --2DBFCzPA-II--.

Column 455, line 24; Change "2 DBFCz-II" to --2DBFCz-II--.

Column 460, line 36; Change "(Iv)" to --(iv)--.

Column 463, line 24; Change "N,N"-diphenylpyrene-1," to --N,N'-diphenylpyrene-1,--.

Column 466, line 7; Change "(1)" to --(i)--.

Column 467, line 13; Change "driven, with" to --driven with--.

Column 470, line 1; Change "263 mm" to --263 nm--.

Column 501, line 9; Change "form" to --foam--.

Column 502, line 55; Change "]-N,N-diphenyl" to --]-N,N'-diphenyl--.

Column 506, line 65; Change "is of an" to --is an--.

Signed and Sealed this
Seventeenth Day of June, 2014

Michelle K. Lee
*Deputy Director of the United States Patent and Trademark Office*

CERTIFICATE OF CORRECTION (continued)
U.S. Pat. No. 8,642,782 B2

In the Claims:

Column 507, line 65, Claim 3; Change "represent of hydrogen," to --represent hydrogen,--.

Column 516, line 42, Claim 13; Change "the 13," to --the β,--.